(12) United States Patent
Byun et al.

(10) Patent No.: US 11,878,965 B2
(45) Date of Patent: *Jan. 23, 2024

(54) INHIBITORS OF PEPTIDYLARGININE DEIMINASES

(71) Applicant: Gilead Sciences, Inc., Foster City, CA (US)

(72) Inventors: Daniel H. Byun, Foster City, CA (US); Zhenhong R. Cai, Palo Alto, CA (US); Eda Y. Canales, San Mateo, CA (US); Laurent P. Debien, San Francisco, CA (US); Timothy R. Hansen, San Francisco, CA (US); Richard Huang, San Mateo, CA (US); Petr Jansa, Foster City, CA (US); Rick A. Lee, Livermore, CA (US); Jennifer A. Loyer-Drew, Seattle, WA (US); Ryan McFadden, Foster City, CA (US); Michael L. Mitchell, Castro Valley, CA (US); Hyung-Jung Pyun, Fremont, CA (US); Roland D. Saito, San Mateo, CA (US); Michael S. Sangi, San Mateo, CA (US); Adam J. Schrier, Redwood City, CA (US); Marina E. Shatskikh, Irvine, CA (US); James G. Taylor, Burlingame, CA (US); Joshua J. Van Veldhuizen, Seattle, WA (US); Lianhong Xu, Palo Alto, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/557,860

(22) Filed: Dec. 21, 2021

(65) Prior Publication Data
US 2023/0090053 A1    Mar. 23, 2023

Related U.S. Application Data

(60) Provisional application No. 63/129,416, filed on Dec. 22, 2020.

(51) Int. Cl.
| | | |
|---|---|---|
| *C07D 401/04* | (2006.01) |
| *A61K 31/437* | (2006.01) |
| *A61K 31/454* | (2006.01) |
| *A61K 31/501* | (2006.01) |
| *A61K 31/506* | (2006.01) |
| *A61K 31/5355* | (2006.01) |
| *A61K 31/5383* | (2006.01) |
| *A61K 45/06* | (2006.01) |
| *C07D 401/14* | (2006.01) |
| *C07D 519/00* | (2006.01) |

(52) U.S. Cl.
CPC .......... *C07D 401/04* (2013.01); *A61K 31/437* (2013.01); *A61K 31/454* (2013.01); *A61K 31/501* (2013.01); *A61K 31/506* (2013.01); *A61K 31/5355* (2013.01); *A61K 31/5383* (2013.01); *A61K 45/06* (2013.01); *C07D 401/14* (2013.01); *C07D 519/00* (2013.01)

(58) Field of Classification Search
CPC ........ A61P 19/00; A61P 35/02; C07D 401/14; C07D 471/04; C07D 519/00; C07D 401/04; A61K 31/437; A61K 31/454; A61K 31/501; A61K 31/5383; A61K 31/5355; A61K 45/06; A61K 31/506
See application file for complete search history.

(56) References Cited

FOREIGN PATENT DOCUMENTS

| | | |
|---|---|---|
| WO | WO-2014015905 A1 | 1/2014 |
| WO | WO-2016185279 A1 | 11/2016 |
| WO | WO-2017100594 A1 | 6/2017 |
| WO | WO-2017100601 A1 | 6/2017 |
| WO | WO-2017147102 A1 | 8/2017 |
| WO | WO-2018022897 A1 | 2/2018 |
| WO | WO-2018049296 A1 | 3/2018 |
| WO | WO-2019058393 A1 | 3/2019 |
| WO | WO-2019077631 A1 | 4/2019 |
| WO | WO-2019152883 A1 | 8/2019 |
| WO | WO-2019161803 A1 | 8/2019 |
| WO | WO-2020033488 A1 | 2/2020 |
| WO | WO-2020033490 A1 | 2/2020 |
| WO | WO-2020033514 A1 | 2/2020 |
| WO | WO-2020033520 A1 | 2/2020 |
| WO | WO-2021057910 A1 | 4/2021 |
| WO | WO-2021158840 A1 | 8/2021 |
| WO | WO-2021163254 A1 | 8/2021 |
| WO | WO-2021222353 A1 | 11/2021 |
| WO | WO-2022034616 A1 | 2/2022 |

OTHER PUBLICATIONS

International Preliminary Report on Patentability dated Jul. 6, 2023 for International Application No. PCT/US2021/064618.
International Search Report and Written Opinion in corresponding International Application No. PCT/US2021/064618, dated Apr. 25, 2022, 23 pages.

*Primary Examiner* — Kortney L. Klinkel
*Assistant Examiner* — Padmaja S Rao

(57) ABSTRACT

The present disclosure relates to novel compounds for use in therapeutic treatment of a disease associated with peptidylarginine deiminases (PADs), such as peptidylarginine deiminase type 4 (PAD4). The present disclosure also relates to processes and intermediates for the preparation of such compounds, methods of using such compounds and pharmaceutical compositions comprising the compounds described herein.

20 Claims, No Drawings
Specification includes a Sequence Listing.

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcccagggga cattgatccg t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic

```
primer
<400> SEQUENCE: 2
tcagggcacc atgttccacc a                                           21
```

INHIBITORS OF PEPTIDYLARGININE DEIMINASES

CROSS REFERENCE TO RELATED APPLICATIONS

This application claims priority to U.S. Provisional Application No. 63/129,416, filed Dec. 22, 2020, which is incorporated herein in its entireties for all purposes.

SEQUENCE LISTING

The instant application contains a Sequence Listing which has been submitted electronically in ASCII format and is hereby incorporated by reference in its entirety. Said ASCII copy, created on Dec. 2, 2021, is named 1248-US-NP_SL.txt and is 702 bytes in size.

FIELD

The present disclosure relates to novel compounds for use in therapeutic treatment of a disease associated with peptidylarginine deiminases (PADs). The present disclosure also relates to processes and intermediates for the preparation of such compounds, methods of using such compounds and pharmaceutical compositions comprising the compounds described herein.

BACKGROUND

Peptidylarginine deiminases catalyze the posttranslational modification of peptidyl arginine to peptidyl citrulline. There are five known PAD isozymes with 45% to 58% amino acid sequence identity between human isozymes and at least 70% identity across each vertebrate orthologue. PADs have diverse tissue distribution, different putative physiological functions, and reported associations with various disease states. PAD6 is thought to be the only catalytically inactive PAD and is expressed mainly in oocyte, ovary and early embryo; it is proposed to be involved in oocyte cytoskeletal sheet formation and female fertility. PAD1 and PAD3 are expressed in epidermis and hair follicles and are proposed to be involved in cornification of epidermal tissues, hair growth and maintenance of the stratum corneum. PAD2 is expressed more broadly and can be found in multiple tissues and cell types including brain, spinal cord, skeletal muscles, pituitary glands, spleen, neutrophils and macrophages. It is proposed to be involved in plasticity of CNS, transcription regulation, chemokine signaling, and female reproduction. Expression of PAD4 is restricted to cells of the myeloid lineage, in particular: neutrophils, eosinophils and monocyte/macrophages. PAD4 is hypothesized to be involved in an array of functions, including regulation of transcription, cell cycle, apoptosis, formation of neutrophil extracellular tarps (NETs), and tumorgenesis. Accordingly, there is a need for inhibitors of PADs that have therapeutic potential in treatment of disease linked to pathological consequences of citrullination and NETosis including, for example, rheumatoid arthritis, systemic lupus erythematous, antiphospholipid antibody syndrome, small vessels vasculitis, colitis, thrombosis, atherosclerosis, sepsis, diabetes and certain types of cancer.

SUMMARY

Provided herein are compounds for inhibiting peptidylarginine deiminase type 4 (PAD4). The present disclosure provides a compound of Formula I:

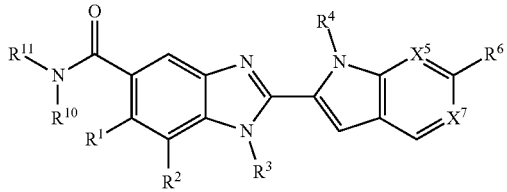

or a pharmaceutically acceptable salt thereof, wherein:

$X^5$ is N or C—$R^5$;

$X^7$ is N or C—$R^7$;

$R^1$ is hydrogen, halo, —CN, —$OR^{12}$, —$N(R^{12})_2$, —$SR^{12}$, —$C_{1-8}$ alkyl optionally substituted with 1 to 3 $Z^1$, $C_{3-6}$ cycloalkyl optionally substituted with 1 to 3 $Z^1$, or 4-6 membered heterocyclyl optionally substituted with 1 to 3 $Z^1$;

$R^2$ is hydrogen, halo, —CN, —$OR^{12}$, —$N(R^{12})_2$, —$SR^{12}$, —$C_{1-8}$ alkyl optionally substituted with 1 to 3 $Z^1$, $C_{3-6}$ cycloalkyl optionally substituted with 1 to 3 $Z^1$, or 4-6 membered heterocyclyl optionally substituted with 1 to 3 $Z^1$;

$R^3$ is hydrogen, $C_{1-8}$ alkyl optionally substituted with 1 to 3 $Z^1$, $C_{3-10}$ alkenyl optionally substituted with 1 to 3 $Z^1$, $C_{3-10}$ alkynyl optionally substituted with 1 to 3 $Z^1$, $C_{3-10}$ cycloalkyl optionally substituted with 1 to 3 $Z^1$, or 4-10 membered heterocyclyl optionally substituted with 1 to 3 $Z^1$; or $R^2$ and $R^3$ are taken together with the atoms to which they are attached to form an optionally substituted 6 to 8 membered heterocyclyl ring;

$R^4$ is hydrogen, $C_{1-8}$ alkyl optionally substituted with 1 to 3 $Z^1$, $C_{3-10}$ alkenyl optionally substituted with 1 to 3 $Z^1$, $C_{3-10}$ alkynyl optionally substituted with 1 to 3 $Z^1$, $C_{3-10}$ cycloalkyl optionally substituted with 1 to 3 $Z^1$, or 4-10 membered heterocyclyl optionally substituted with 1 to 3 $Z^1$;

$R^5$ is hydrogen, halo, —CN, or —$OR^{12}$;

$R^6$ is

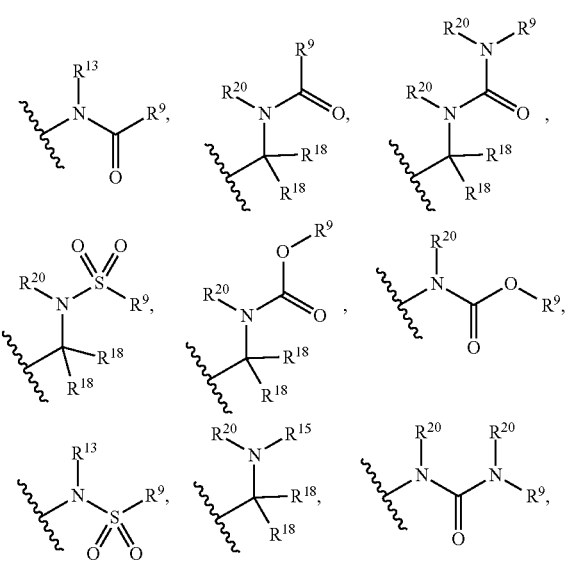

-continued

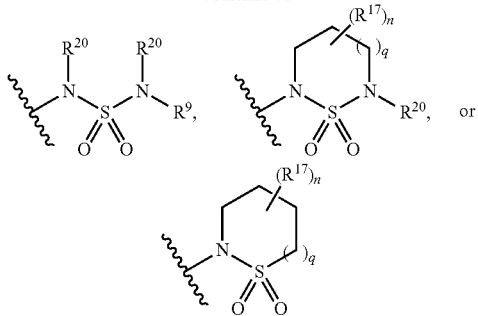

where q is 0, 1 or 2, and n is 0, 1, 2, 3, 4, 5, or 6;

$R^7$ is hydrogen, halo, —CN, or —OR$^{12}$;

$R^9$ is $C_{1-8}$ alkyl optionally substituted with 1 to 3 $Z^1$, $C_{2-8}$ alkenyl optionally substituted with 1 to 3 $Z^1$, $C_{2-8}$ alkynyl optionally substituted with 1 to 3 $Z^1$, $C_{3-10}$ cycloalkyl optionally substituted with 1 to 3 $Z^1$, 4-10 membered heterocyclyl optionally substituted with 1 to 3 $Z^1$, $C_{6-10}$ aryl optionally substituted with 1 to 3 $Z^1$, or 5-10 membered heteroaryl optionally substituted with 1 to 3 $Z^1$;

$R^{10}$ is hydrogen, $C_{1-8}$ alkyl optionally substituted with 1 to 3 $Z^{10}$, or $C_{3-6}$ cycloalkyl optionally substituted with 1 to 3 $Z^{10}$;

$R^{11}$ is hydrogen, $C_{1-8}$ alkyl optionally substituted with 1 to 4 $Z^{10}$, $C_{3-8}$ cycloalkyl optionally substituted with 1 to 4 $Z^{10}$, or 4-12-membered heterocyclyl optionally substituted with 1 to 4 $Z^{10}$; or $R^{10}$ and $R^{11}$ are taken together with the nitrogen to which they are attached to form a 4 membered heterocyclyl optionally substituted with 1 to 4 $Z^{10}$;

each $R^{12}$ is independently hydrogen, $C_{1-8}$ alkyl optionally substituted with 1 to 3 $Z^{1b}$, $C_{3-8}$ alkenyl optionally substituted with 1 to 3 $Z^{1b}$, $C_{3-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$;

$R^{13}$ is $C_{1-8}$ alkyl optionally substituted with 1 to 3 $Z^{1b}$, $C_{3-8}$ alkenyl optionally substituted with 1 to 3 $Z^{1b}$, $C_{3-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$;

$R^{15}$ is $C_{6-10}$ aryl optionally substituted with 1 to 3 $Z^1$ or 5-10 membered heteroaryl optionally substituted with 1 to 3 $Z^1$;

each $R^{17}$ is independently hydrogen, halo, —NO$_2$, —N$_3$, —CN, $C_{1-8}$ alkyl optionally substituted by 1 to 3 $Z^{1a}$, $C_{2-8}$ alkenyl optionally substituted by 1 to 3 $Z^{1a}$, $C_{2-8}$ alkynyl optionally substituted by 1 to 3 $Z^{1a}$, $C_{3-8}$ cycloalkyl optionally substituted by 1 to 3 $Z^{1a}$, 6-10 membered aryl optionally substituted by 1 to 3 $Z^{1a}$, 4-10 membered heterocyclyl optionally substituted by 1 to 3 $Z^{1a}$, 5-10 membered heteroaryl optionally substituted with 1 to 3 $Z^{1a}$, —OR$^{20}$, —C(O)R$^{20}$, —C(O)OR$^{20}$, —C(O)N(R$^{20}$)$_2$, —N(R$^{20}$)$_2$, —N(R$^{20}$)$_3$$^+$, —N(R$^{20}$)C(O)R$^{20}$, —N(R$^{20}$)C(O)OR$^{20}$, —N(R$^{20}$)C(O)N(R$^{20}$)$_2$, —N(R$^{20}$)S(O)$_2$(R$^{20}$), —NR$^{20}$S(O)$_2$N(R$^{20}$)$_2$, —NR$^{20}$S(O)$_2$O(R$^{20}$), —NS(O)(R$^{20}$)$_2$, —OC(O)R$^{20}$, —OC(O)OR$^{20}$, —OC(O)N(R$^{20}$)$_2$, —Si(R$^{20}$)$_3$, —SR$^{20}$, —S(O)R$^{20}$, —SF$_5$, —S(O)(NR$^{20}$)R$^{20}$, —S(NR$^{20}$)(NR$^{20}$)R$^{20}$, —S(O)(NR$^{20}$)N(R$^{20}$)$_2$, —S(O)(NCN)R$^{20}$, —S(O)$_2$R$^{20}$, —S(O)$_2$N(R$^{20}$)$_2$, —C(O)N(R$^{20}$)S(O)$_2$R$^{20}$, or —S(O)$_2$N(R$^{20}$)C(O)R$^{20}$; or two R$^{17}$ on the same or different carbon atoms are taken together to form a 3-8-membered ring optionally substituted with 1 to 4 $Z^1$;

each $R^{18}$ is independently hydrogen, halo, —NO$_2$, —N$_3$, —CN, $C_{1-8}$ alkyl optionally substituted by 1 to 3 $Z^{1a}$, $C_{2-8}$ alkenyl optionally substituted by 1 to 3 $Z^{1a}$, $C_{2-8}$ alkynyl optionally substituted by 1 to 3 $Z^{1a}$, $C_{3-8}$ cycloalkyl optionally substituted by 1 to 3 $Z^{1a}$, 6-10 membered aryl optionally substituted by 1 to 3 $Z^{1a}$, 4-10 membered heterocyclyl optionally substituted by 1 to 3 $Z^{1a}$, 5-10 membered heteroaryl optionally substituted with 1 to 3 $Z^{1a}$, —OR$^{20}$, —C(O)R$^{20}$, —C(O)OR$^{20}$, —C(O)N(R$^{20}$)$_2$, —N(R$^{20}$)$_2$, —N(R$^{20}$)$_3$$^+$, —N(R$^{20}$)C(O)R$^{20}$, —N(R$^{20}$)C(O)OR$^{20}$, —N(R$^{20}$)C(O)N(R$^{20}$)$_2$, —N(R$^{20}$)S(O)$_2$(R$^{20}$), —NR$^{20}$S(O)$_2$N(R$^{20}$)$_2$, —NR$^{20}$S(O)$_2$O(R$^{20}$), —NS(O)(R$^{20}$)$_2$, —OC(O)R$^{20}$, —OC(O)OR$^{20}$, —OC(O)N(R$^{20}$)$_2$, —Si(R$^{20}$)$_3$, —SR$^{20}$, —S(O)R$^{20}$, —SF$_5$, —S(O)(NR$^{20}$)R$^{20}$, —S(NR$^{20}$)(NR$^{20}$)R$^{20}$, —S(O)(NR$^{20}$)N(R$^{20}$)$_2$, —S(O)(NCN)R$^{20}$, —S(O)$_2$R$^{20}$, —S(O)$_2$N(R$^{20}$)$_2$, —C(O)N(R$^{20}$)S(O)$_2$R$^{20}$, or —S(O)$_2$N(R$^{20}$)C(O)R$^{20}$;

each $Z^1$ is independently halo, —NO$_2$, —N$_3$, —CN, $C_{1-8}$ alkyl optionally substituted by 1 to 3 $Z^{1a}$, $C_{2-8}$ alkenyl optionally substituted by 1 to 3 $Z^{1a}$, $C_{2-8}$ alkynyl optionally substituted by 1 to 3 $Z^{1a}$, $C_{3-8}$ cycloalkyl optionally substituted by 1 to 3 $Z^{1a}$, 6-10 membered aryl optionally substituted by 1 to 3 $Z^{1a}$, 4-10 membered heterocyclyl optionally substituted by 1 to 3 $Z^{1a}$, 5-10 membered heteroaryl optionally substituted with 1 to 3 $Z^{1a}$, —OR$^{20}$, —C(O)R$^{20}$, —C(O)OR$^{20}$, —C(O)N(R$^{20}$)$_2$, —N(R$^{20}$)$_2$, —N(R$^{20}$)$_3$$^+$, —N(R$^{20}$)C(O)R$^{20}$, —N(R$^{20}$)C(O)OR$^{20}$, —N(R$^{20}$)C(O)N(R$^{20}$)$_2$, —N(R$^{20}$)S(O)$_2$(R$^{20}$), —NR$^{20}$S(O)$_2$N(R$^{20}$)$_2$, —NR$^{20}$S(O)$_2$O(R$^{20}$), —NS(O)(R$^{20}$)$_2$, —OC(O)R$^{20}$, —OC(O)OR$^{20}$, —OC(O)N(R$^{20}$)$_2$, —Si(R$^{20}$)$_3$, —SR$^{20}$, —S(O)R$^{20}$, —SF$_5$, —S(O)(NR$^{20}$)R$^{20}$, —S(NR$^{20}$)(NR$^{20}$)R$^{20}$, —S(O)(NR$^{20}$)N(R$^{20}$)$_2$, —S(O)(NCN)R$^{20}$, —S(O)$_2$R$^{20}$, —S(O)$_2$N(R$^{20}$)$_2$, —C(O)N(R$^{20}$)S(O)$_2$R$^{20}$, or —S(O)$_2$N(R$^{20}$)C(O)R$^{20}$;

each $Z^{1a}$ is independently oxo, halo, —NO$_2$, —N$_3$, —CN, $C_{1-8}$ alkyl optionally substituted by 1 to 3 $Z^{1b}$, $C_{2-8}$ alkenyl optionally substituted by 1 to 3 $Z^{1b}$, $C_{2-8}$ alkynyl optionally substituted by 1 to 3 $Z^{1b}$, $C_{3-8}$ cycloalkyl optionally substituted by 1 to 3 $Z^{1b}$, 6-10 membered aryl optionally substituted by 1 to 3 $Z^{1b}$, 4-10 membered heterocyclyl optionally substituted by 1 to 3 $Z^{1b}$, 5-10 membered heteroaryl optionally substituted with 1 to 3 $Z^{1b}$, —OR$^{21}$, —C(O)R$^{21}$, —C(O)OR$^{21}$, —C(O)N(R$^{21}$)$_2$, —N(R$^{21}$)$_2$, —N(R$^{21}$)$_3$$^+$, —N(R$^{21}$)C(O)R$^{21}$, —N(R$^{21}$)C(O)OR$^{21}$, —N(R$^{21}$)C(O)N(R$^{21}$)$_2$, —N(R$^{21}$)S(O)$_2$(R$^{21}$), —NR$^{21}$S(O)$_2$N(R$^{21}$)$_2$, —NR$^{21}$S(O)$_2$O(R$^{21}$), —NS(O)(R$^{21}$)$_2$, —OC(O)R$^{21}$, —OC(O)OR$^{21}$, —OC(O)N(R$^{21}$)$_2$, —Si(R$^{21}$)$_3$, —SR$^{21}$, —S(O)R$^{21}$, —SF$_5$, —S(O)(NR$^{21}$)R$^{21}$, —S(NR$^{21}$)(NR$^{21}$)R$^{21}$, —S(O)(NR$^{21}$)N(R$^{21}$)$_2$, —S(O)(NCN)R$^{21}$, —S(O)$_2$R$^{21}$, —S(O)$_2$N(R$^{21}$)$_2$, —C(O)N(R$^{21}$)S(O)$_2$R$^{21}$, or —S(O)$_2$N(R$^{21}$)C(O)R$^{21}$;

each $Z^{10}$ is independently selected from oxo, halo, —CN, $C_{1-8}$ alkyl optionally substituted by 1 to 3 $Z^{1b}$, $C_{3-8}$ cycloalkyl optionally substituted by 1 to 3 $Z^{1b}$, aryl optionally substituted by 1 to 3 $Z^{1b}$, 4-10 membered heterocyclyl optionally substituted by 1 to 3 $Z^{1b}$, 5-10 membered heteroaryl optionally substituted with 1 to 3 $Z^{1b}$, —$OR^{22}$, —$C(O)R^{22}$, —$C(O)OR^{22}$, —$C(O)N(R^{22})_2$, —$N(R^{22})_2$, —$N(R^{22})_3^+$, —$N(R^{22})C(O)R^{22}$, —$N(R^{22})C(O)OR^{22}$, —$N(R^{22})C(O)N(R^{22})_2$, —$N(R^{22})S(O)_2R^{22}$, $OC(O)R^{22}$, —$OC(O)OR^{22}$, —$OC(O)$—$N(R^{22})_2$, and —$S$—$R^{22}$; and each $R^{20}$, $R^{21}$ and $R^{22}$ is independently hydrogen, $C_{1-8}$ alkyl optionally substituted with 1 to 3 $Z^{1b}$, $C_{2-8}$ alkenyl optionally substituted with 1 to 3 $Z^{1b}$, $C_{2-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$;

each $Z^{1b}$ is independently oxo, hydroxy, halo, —$NO_2$, —$N_3$, —$CN$, $C_{1-9}$ alkyl, $C_{2-6}$ alkenyl, $C_{2-6}$ alkynyl, $C_{3-15}$ cycloalkyl, $C_{1-8}$ haloalkyl, $C_{6-10}$ aryl, 5-10 membered heteroaryl heteroaryl, 4-10 membered heterocyclyl, —$O(C_{1-9}$ alkyl), —$O(C_{2-6}$ alkenyl), —$O(C_{2-6}$ alkynyl), —$O(C_{3-15}$ cycloalkyl), —$O(C_{1-8}$ haloalkyl), —$O(aryl)$, —$O(heteroaryl)$, —$O(heterocyclyl)$, —$OC(O)(C_{1-9}$ alkyl), —$OC(O)(C_{2-6}$ alkenyl), —$OC(O)(C_{2-6}$ alkenyl), —$OC(O)(C_{2-6}$ alkynyl), —$OC(O)(C_{3-15}$ cycloalkyl), —$OC(O)(C_{1-8}$ haloalkyl), —$OC(O)(aryl)$, —$OC(O)(heteroaryl)$, —$OC(O)(heterocyclyl)$, —$NH_2$, —$NH(C_{1-9}$ alkyl), —$NH(C_{2-6}$ alkenyl), —$NH(C_{2-6}$ alkynyl), —$NH(C_{3-15}$ cycloalkyl), —$NH(C_{1-8}$ haloalkyl), —$NH(aryl)$, —$NH(heteroaryl)$, —$NH(heterocyclyl)$, —$N(C_{1-9}$ alkyl)$_2$, —$N(C_{3-15}$ cycloalkyl)$_2$, —$N(C_{2-6}$ alkenyl)$_2$, —$N(C_{2-6}$ alkynyl)$_2$, —$N(C_{3-15}$ cycloalkyl)$_2$, —$N(C_{1-8}$ haloalkyl)$_2$, —$N(aryl)_2$, —$N(heteroaryl)_2$, —$N(heterocyclyl)_2$, —$N(C_{1-9}$ alkyl)$(C_{3-15}$ cycloalkyl), —$N(C_{1-9}$ alkyl)$(C_{2-6}$ alkenyl), —$N(C_{1-9}$ alkyl)$(C_{2-6}$ alkynyl), —$N(C_{1-9}$ alkyl)$(C_{3-15}$ cycloalkyl), —$N(C_{1-9}$ alkyl)$(C_{1-8}$ haloalkyl), —$N(C_{1-9}$ alkyl)(aryl), —$N(C_{1-9}$ alkyl)(heteroaryl), —$N(C_{1-9}$ alkyl)(heterocyclyl), —$C(O)(C_{1-9}$ alkyl), —$C(O)(C_{2-6}$ alkenyl), —$C(O)(C_{2-6}$ alkynyl), —$C(O)(C_{3-15}$ cycloalkyl), —$C(O)(C_{1-8}$ haloalkyl), —$C(O)(aryl)$, —$C(O)(heteroaryl)$, —$C(O)(heterocyclyl)$, —$C(O)O(C_{1-9}$ alkyl), —$C(O)O(C_{2-6}$ alkenyl), —$C(O)O(C_{2-6}$ alkynyl), —$C(O)O(C_{3-15}$ cycloalkyl), —$C(O)O(C_{1-8}$ haloalkyl), —$C(O)O(aryl)$, —$C(O)O(heteroaryl)$, —$C(O)O(heterocyclyl)$, —$C(O)NH_2$, —$C(O)NH(C_{1-9}$ alkyl), —$C(O)NH(C_{2-6}$ alkenyl), —$C(O)NH(C_{2-6}$ alkynyl), —$C(O)NH(C_{3-15}$ cycloalkyl), —$C(O)NH(C_{1-8}$ haloalkyl), —$C(O)NH(aryl)$, —$C(O)NH(heteroaryl)$, —$C(O)NH(heterocyclyl)$, —$C(O)N(C_{1-9}$ alkyl)$_2$, —$C(O)N(C_{3-15}$ cycloalkyl)$_2$, —$C(O)N(C_{2-6}$ alkenyl)$_2$, —$C(O)N(C_{2-6}$ alkynyl)$_2$, —$C(O)N(C_{1-8}$ haloalkyl)$_2$, —$C(O)N(aryl)_2$, —$C(O)N(heteroaryl)_2$, —$C(O)N(heterocyclyl)_2$, —$NHC(O)(C_{1-9}$ alkyl), —$NHC(O)(C_{2-6}$ alkenyl), —$NHC(O)(C_{2-6}$ alkynyl), —$NHC(O)(C_{3-15}$ cycloalkyl), —$NHC(O)(C_{1-8}$ haloalkyl), —$NHC(O)(aryl)$, —$NHC(O)(heteroaryl)$, —$NHC(O)(heterocyclyl)$, —$NHC(O)O(C_{1-9}$ alkyl), —$NHC(O)O(C_{2-6}$ alkenyl), —$NHC(O)O(C_{2-6}$ alkynyl), —$NHC(O)O(C_{3-15}$ cycloalkyl), —$NHC(O)O(C_{1-8}$ haloalkyl), —$NHC(O)O(aryl)$, —$NHC(O)O(heteroaryl)$, —$NHC(O)O(heterocyclyl)$, —$NHC(O)NH(C_{1-9}$ alkyl), —$NHC(O)NH(C_{2-6}$ alkenyl), —$NHC(O)NH(C_{2-6}$ alkynyl), —$NHC(O)NH(C_{3-15}$ cycloalkyl), —$NHC(O)NH(C_{1-8}$ haloalkyl), —$NHC(O)NH(aryl)$, —$NHC(O)NH(heteroaryl)$, —$NHC(O)NH(heterocyclyl)$, —$SH$, —$S(C_{1-9}$ alkyl), —$S(C_{2-6}$ alkenyl), —$S(C_{2-6}$ alkynyl), —$S(C_{3-15}$ cycloalkyl), —$S(C_{1-8}$ haloalkyl), —$S(aryl)$, —$S(heteroaryl)$, —$S(heterocyclyl)$, —$NHS(O)(C_{1-9}$ alkyl), —$N(C_{1-9}$ alkyl)$(S(O)(C_{1-9}$ alkyl), —$S(O)N(C_{1-9}$ alkyl)$_2$, —$S(O)(C_{1-9}$ alkyl), —$S(O)(NH)(C_{1-9}$ alkyl), —$S(O)(C_{2-6}$ alkenyl), —$S(O)(C_{2-6}$ alkynyl), —$S(O)(C_{3-15}$ cycloalkyl), —$S(O)(C_{1-8}$ haloalkyl), —$S(O)(aryl)$, —$S(O)(heteroaryl)$, —$S(O)(heterocyclyl)$, —$S(O)_2(C_{1-9}$ alkyl), —$S(O)_2(C_{2-6}$ alkenyl), —$S(O)_2(C_{2-6}$ alkynyl), —$S(O)_2(C_{3-15}$ cycloalkyl), —$S(O)_2(C_{1-8}$ haloalkyl), —$S(O)_2(aryl)$, —$S(O)_2(heteroaryl)$, —$S(O)_2(heterocyclyl)$, —$S(O)_2NH(C_{1-9}$ alkyl), or —$S(O)_2N(C_{1-9}$ alkyl)$_2$;

wherein any alkyl, cycloalkyl, aryl, heteroaryl, or heterocyclyl of $Z^{1b}$ is optionally substituted with one or more halo, $C_{1-9}$ alkyl, $C_{1-8}$ haloalkyl, —$OH$, —$NH_2$, —$NH(C_{1-9}$ alkyl), —$NH(C_{3-15}$ cycloalkyl), —$NH(C_{1-8}$ haloalkyl), —$NH(aryl)$, —$NH(heteroaryl)$, —$NH(heterocyclyl)$, —$N(C_{1-9}$ alkyl)$_2$, —$N(C_{3-15}$ cycloalkyl)$_2$, —$NHC(O)(C_{3-15}$ cycloalkyl), —$NHC(O)(C_{1-8}$ haloalkyl), —$NHC(O)(aryl)$, —$NHC(O)(heteroaryl)$, —$NHC(O)(heterocyclyl)$, —$NHC(O)O(C_{1-9}$ alkyl), —$NHC(O)O(C_{2-6}$ alkynyl), —$NHC(O)O(C_{3-15}$ cycloalkyl), —$NHC(O)O(C_{1-8}$ haloalkyl), —$NHC(O)O(aryl)$, —$NHC(O)O(heteroaryl)$, —$NHC(O)O(heterocyclyl)$, —$NHC(O)NH(C_{1-9}$ alkyl), —$S(O)(NH)(C_{1-9}$ alkyl), —$S(O)_2(C_{1-9}$ alkyl), —$S(O)_2(C_{3-15}$ cycloalkyl), —$S(O)_2(C_{1-8}$ haloalkyl), —$S(O)_2(aryl)$, —$S(O)_2(heteroaryl)$, —$S(O)_2(heterocyclyl)$, —$S(O)_2NH(C_{1-9}$ alkyl), —$S(O)_2N(C_{1-9}$ alkyl)$_2$, —$O(C_{3-15}$ cycloalkyl), —$O(C_{1-8}$ haloalkyl), —$O(aryl)$, —$O(heteroaryl)$, —$O(heterocyclyl)$, or —$O(C_{1-9}$ alkyl).

Also provided herein are compounds of Table 1, Table 2, Table 3, and Table 4, or a pharmaceutically acceptable salt thereof.

The present disclosure provides a method of inhibiting peptidylarginine deiminase type 4 (PAD4) comprising contacting an effective amount of a compound of Formula I, or any formula described herein, or a pharmaceutically acceptable salt thereof, with a cell.

The present disclosure provides a method of inhibiting peptidylarginine deiminase type 4 (PAD4) comprising administering an effective amount of a compound of Formula I, or any formula described herein, or a pharmaceutically acceptable salt thereof, to a patient in need thereof.

The present disclosure provides a method for treating a disease or disorder mediated by peptidylarginine deiminase type 4 (PAD4), comprising administering an effective amount of a compound of Formula I, or any formula described herein, or a pharmaceutically acceptable salt thereof, to a patient in need thereof.

The present disclosure provides a method for treating acute lymphocytic leukemia, ankylosing spondylitis, cancer, chronic lymphocytic leukemia, colitis, lupus, systemic lupus erythematosus, cutaneous lupus erythematosus, rheumatoid arthritis, multiple sclerosis, or ulcerative colitis, comprising administering an effective amount of a compound of Formula I, or any formula described herein, or a pharmaceutically acceptable salt thereof, to a patient in need thereof.

In one embodiment, the present disclosure provides a pharmaceutical composition comprising a compound of Formula I, or any formula described herein, or a pharmaceutically acceptable salt thereof, and a pharmaceutically acceptable carrier or excipient.

In one embodiment, the present disclosure provides a pharmaceutical composition comprising a compound of Formula I, or any formula described herein, or a pharmaceutically acceptable salt thereof, and at least one additional therapeutic agent and at least one pharmaceutically acceptable carrier or excipient.

In one embodiment, the present disclosure provides a pharmaceutical composition comprising a compound of Formula I, or any formula described herein, or a pharmaceutically acceptable salt thereof, at least one additional therapeutic agent suitable for treating rheumatoid arthritis, and at least one pharmaceutically acceptable carrier or excipient.

In one embodiment, the present disclosure provides a kit that includes a compound of Formula I, or any formula described herein, or a pharmaceutically acceptable salt thereof, a label and/or instructions for use of the compound in the treatment of rheumatoid arthritis or a disease or condition mediated by peptidylarginine deiminase type 4 (PAD4).

In one embodiment, the present disclosure provides a compound of Formula I, or any formula described herein, or a pharmaceutically acceptable salt thereof, for use in therapy.

In another embodiment, the present disclosure provides a compound of Formula I, or any formula described herein, or a pharmaceutically acceptable salt thereof, for use in the manufacture of a medicament for treating rheumatoid arthritis or a disease or condition mediated by peptidylarginine deiminase type 4 (PAD4).

DETAILED DESCRIPTION

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. Unless chemically or structurally required, no directionality is indicated or implied by the order in which a chemical group is written or named.

A wavy line on a chemical group as shown below, for example,

indicates a point of attachment, i.e., it shows the broken bond by which the group is connected to another described group.

The prefix "C$_{u-v}$" indicates that the following group has from u to v carbon atoms. For example, "C$_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., C$_{1-20}$ alkyl), 1 to 12 carbon atoms (i.e., C$_{1-12}$ alkyl), 1 to 10 carbon atoms (i.e., C$_{1-10}$ alkyl), 1 to 8 carbon atoms (i.e., C$_{1-8}$ alkyl), 1 to 6 carbon atoms (i.e., C$_{1-6}$ alkyl), or 1 to 4 carbon atoms (i.e., C$_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

"Alkenyl" refers to any group derived from a straight or branched hydrocarbon with at least one carbon-carbon double bond. Unless otherwise specified, alkenyl groups have from 2 to 20 carbon atoms (i.e., C$_{2-20}$ alkenyl), 2 to 12 carbon atoms (i.e., C$_{2-12}$ alkenyl), 2 to 10 carbon atoms (i.e., C$_{2-10}$ alkenyl), 2 to 8 carbon atoms (i.e., C$_{2-8}$ alkenyl), 2 to 6 carbon atoms (i.e., C$_{2-6}$ alkenyl), or 2 to 4 carbon atoms (i.e., C$_{2-4}$ alkenyl). Examples of alkenyl groups include ethenyl, propenyl, butadienyl (including 1,2-butadienyl, and 1,3-butadienyl).

"Alkynyl" refers to any group derived from a straight or branched hydrocarbon with at least one carbon-carbon triple bond. Unless otherwise specified, alkynyl groups have from 2 to 20 carbon atoms (i.e., C$_{2-20}$ alkynyl), 2 to 12 carbon atoms (i.e., C$_{2-12}$ alkynyl), 2 to 10 carbon atoms (i.e., C$_{2-10}$ alkynyl), 2 to 8 carbon atoms (i.e., C$_{2-8}$ alkynyl), 2 to 6 carbon atoms (i.e., C$_{2-6}$ alkynyl), or 2 to 4 carbon atoms (i.e., C$_{2-4}$ alkynyl). The term "alkynyl" also includes those groups having one triple bond and one double bond. Examples of alkynyl groups include, but are not limited to, ethynyl (—C≡C—), propargyl (—CH$_2$C≡C—), (E)-pent-3-en-1-ynyl, and the like.

The term "aryl" as used herein refers to a single all carbon aromatic ring or a multiple condensed all carbon ring system wherein at least one of the rings is aromatic. For example, in certain embodiments, an aryl group 6 to 20 ring carbon atoms (i.e., C$_{6-20}$ aryl), 6 to 14 carbon ring atoms (i.e., C$_{6-14}$ aryl), 6 to 12 carbon ring atoms (i.e., C$_{6-12}$ aryl), or 6 to 10 carbon ring atoms (i.e., C$_{6-10}$ aryl). Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. Aryl, however, does not encompass or overlap in any way with heteroaryl defined below. If one or more aryl groups are fused with a heteroaryl ring, the resulting ring system is heteroaryl. It is also to be understood that when reference is made to a certain atom-range membered aryl (e.g., $C_{6-10}$ aryl), the atom range is for the total ring atoms of the aryl. For example, a 6-membered aryl would include phenyl and a 10-membered aryl would include naphthyl and 1,2,3,4-tetrahydronaphthyl. Aryl groups include, but are not limited to, those groups derived from acenaphthylene, anthracene, azulene, benzene, chrysene, a cyclopentadienyl anion, naphthalene, fluoranthene, fluorene, indane, perylene, phenalene, phenanthrene, pyrene, and the like. Non-limiting examples of aryl groups include, but are not limited to, phenyl, indenyl, naphthyl, 1,2,3,4-tetrahydronaphthyl, anthracenyl, and the like.

The term "cycloalkyl" refers to a single saturated or partially unsaturated all carbon ring having 3 to 20 annular carbon atoms (i.e., $C_{3-20}$ cycloalkyl), 3 to 14 ring carbon atoms (i.e., $C_{3-14}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). As used herein the term "cycloalkenyl" refers to the non-aromatic carbocyclic (partially saturated cyclic alkyl) group having at least one double bond. Accordingly, cycloalkyl includes multicyclic carbocycles such as a bicyclic carbocycles (e.g., bicyclic carbocycles having about 6 to 12 annular carbon atoms such as bicyclo[3.1.0]hexane, bicyclo[2.1.1]hexane), bicyclo[1.1.1]pentane, and polycyclic carbocycles (e.g., tricyclic and tetracyclic carbocycles with up to about 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, spiro[3.3]heptane, and 1-cyclohex-3-enyl.

"Halo" and "halogen" refer to fluoro, chloro, bromo and iodo.

"Haloalkyl" refers to an alkyl group as defined herein, wherein one or more hydrogen atoms (e.g., 1-5, or 1-3) are replaced by a halogen. Examples include, but are not limited to, —CH$_2$Cl, —CH$_2$F, —CH$_2$Br, —CFClBr, —CH$_2$CH$_2$Cl, —CH$_2$CH$_2$F, —CF$_3$, —CH$_2$CF$_3$, —CH$_2$CCl$_3$, and the like, as well as alkyl groups such as perfluoroalkyl in which all hydrogen atoms are replaced by fluorine atoms.

"Heteroalkyl" refers to an alkyl in which one or more of the carbon atoms (and any associated hydrogen atoms) are each independently replaced with the same or different heteroatom or heteroatomic group. Heteroatoms include, but are not limited to, N, P, O, S, etc. Heteroatomic groups include, but are not limited to, —NR—, —O—, —S—, —PH—, —P(O)$_2$—, —S(O)—, —S(O)$_2$—, and the like, where R is H, alkyl, aryl, cycloalkyl, heteroalkyl, heteroaryl or cycloheteroalkyl. Heteroalkyl groups include, but are not limited to, —OCH$_3$, —CH$_2$OCH$_3$, —SCH$_3$, —CH$_2$SCH$_3$, —NRCH$_3$, —CH$_2$NRCH$_3$, —CH$_2$OH and the like, where R is hydrogen, alkyl, aryl, arylalkyl, heteroalkyl, or heteroaryl. As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to a monoradical or diradical aromatic group having a single ring, multiple rings, or multiple fused rings, with one or more ring heteroatoms independently selected from nitrogen, oxygen, and sulfur. The term includes fused ring systems wherein one or more (e.g., one, two, or three) fused rings is/are fully or partially unsaturated. As used herein, heteroaryl include 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Non-limiting examples of heteroaryl groups include, but are not limited to, groups derived from acridine, benzimidazole, benzothiophene, benzofuran, benzoxazole, benzothiazole, carbazole, carboline, cinnoline, furan, imidazole, imidazopyridine, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyridone, pyrimidine, pyrrole, pyrrolizine, quinazoline, quinoline, quinolizine, quinoxaline, tetrazole, thiadiazole, thiazole, thiophene, triazole, xanthene, and the like.

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms, 2 to 12 ring carbon atoms, 2 to 10 ring carbon atoms, 2 to 8 ring carbon atoms, 3 to 12 ring carbon atoms, 3 to 8 ring carbon atoms, or 3 to 6 ring carbon atoms; and having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. A heterocyclyl may contain one or more oxo and/or thioxo groups. Examples of heterocyclyl groups include, but are not limited to, groups derived from azetidine, aziridine, imidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, tetrahydro-2H-thiopyran 1,1-dioxide, quinuclidine, N-bromopyrrolidine, N-chloropiperidine, and the like. Heterocycles include spirocycles, such as, for example, aza or oxo-spiroheptanes. As used herein, the term "bridged-heterocyclyl" refers to a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, bridged-heterocyclyl includes bicyclic and tricyclic ring systems. Non-limiting examples of bridged-heterocyclyl include 8-azabicyclo[3.2.1]octan-8-yl, 2-azabicyclo[3.2.1] octan-2-yl, 2-azabicyclo[2.2.1]heptan-2-yl, and 7-azabicyclo[2.2.1]heptan-7-yl. Also used herein, the term "spiroheterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro[3.5]nonanyl, 2-oxa-6-azaspiro[3.4]octanyl, 5-azaspiro[2.4]heptanyl, and 6-oxa-1-azaspiro[3.3]heptanyl. Examples of the fused-heterocyclyl rings include, but are not limited to, 3-azabicyclo[3.1.0]hexanyl, 1,2,3,4-tetrahydroisoquinolinyl, 1-oxo-1,2,3,4-tetrahydroisoquinolinyl, 1-oxo-1,2-dihydroisoquinolinyl, 4,5,6,7-tetrahydrothieno[2,3-c]pyridinyl, indolinyl, and isoindolinyl, where the heterocyclyl can be bound via either ring of the fused system. Additional examples, but are not limited to, groups derived from include dihydroquinolines, e.g., 3,4-dihydroquinoline, dihydroisoquinolines, e.g., 1,2-dihydroisoquinoline, dihydroimidazole, tetrahydroimidazole, etc., indoline, isoindoline, isoindolones (e.g., isoindolin-1-one), isatin, dihydrophthalazine, quinolinone, spiro[cyclopropane-1,1'-isoindolin]-3'-one, and the like. Additional examples of heterocycles include, but are not limited to, groups derived from 2-azabicyclo[2.2.1]heptane, 8-azabicyclo[3.2.1]octane, 3-azabicyclo[4.1.0]heptane, octahydro-2H-pyrido[4,3-b][1,4]oxazine, hexahydropyridazine, 3,8-diazabicyclo[3.2.1]octane, 2,5-diazabicyclo[2.2.1]heptane, 3,6-diazabicyclo[3.1.1]heptane, 3-oxa-7,9-diazabicyclo[3.3.1]nonane, 7-azabicyclo[2.2.1]heptane, 2-azabicyclo[2.2.2]octane, 6-oxa-2-azabicyclo[3.2.1]octane, and hexahydropyrazino[2,1-c][1,4]oxazine, for example, where the heterocycle can be bound via either ring of the fused system.

"Bridged" refers to a ring fusion wherein non-adjacent atoms on a ring are joined by a divalent substituent, such as an alkylene or heteroalkylene group or a single heteroatom. Quinuclidinyl and adamantyl are examples of bridged ring systems.

"Spiro" refers to a ring substituent which is joined by two bonds at the same carbon atom. Examples of spiro groups include 1,1-diethylcyclopentane, dimethyl-dioxolane, and 4-benzylmethylpiperidine, wherein the cyclopentane and piperidine, respectively, are the spiro substituents. When substituents bound to the same atom join together (e.g., two $Z^8$ groups join together) they may be taken from the same point of attachment to form a spiro ring.

The term "fused" refers to a ring which is bound to an adjacent ring.

"Oxo" refers to =O or —O⁻. "Hydroxyl" and "hydroxy" are used interchangeably and refer to —OH. Where tautomeric forms of the compound exist, hydroxyl and oxo groups are interchangeable.

It is understood that combinations of chemical groups may be used and will be recognized by persons of ordinary skill in the art. For instance, the group "hydroxyalkyl" would refer to a hydroxyl group attached to an alkyl group. A great number of such combinations may be readily envisaged. Additional examples of substituent combinations used herein include: $C_{1-6}$ alkylamiocarbonyl (e.g., $CH_3CH_2NHC(O)$—), $C_{1-6}$ alkoxycarbonyl (e.g., $CH_3O$—C(O)—), 5-7 membered heterocyclyl-$C_{1-6}$ alkyl (e.g., piperazinyl-$CH_2$—), $C_{1-6}$ alkylsulfonyl-5-7 membered heterocyclyl (e.g., $CH_3S(O)_2$-morpholinyl-), 5-7 membered heterocyclyl $C_{1-6}$ alkoxy, 5-7 membered heterocyclyloxy, (4-7 membered heterocyclyl)-4-7 membered heterocyclyl (e.g., oxetanyl-pyrrolidinyl-), $C_{3-6}$ cycloalkylaminocarbonyl (e.g., cyclopropyl-NH—C(O)—), 5-7 membered heterocyclyl-$C_{2-6}$ alkynyl (e.g., N-piperazinyl-$CH_2C≡CCH_2$—), and $C_{6-10}$ arylaminocarbonyl (e.g., phenyl-NH—C(O)—).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. The suffix "ene" is often used to refer to a group that has two single bond points of attachments to other groups. For example, methylene refers to —$CH_2$—. Similarly, alkylene, alkenylene, alkynylene, cycloalkylene, heterocyclene, arylene, and heteroarylene refer to respective alkyl, alkenyl, alkynyl, cycloalkyl, heterocyclyl, aryl, and heteroaryl groups as defined herein having two single bond points of attachments to other groups. Also, unless indicated explicitly otherwise, where combinations of groups are referred to herein as one moiety, e.g., arylalkyl, the last-mentioned group contains the atom by which the moiety is attached to the rest of the molecule.

The compounds described herein include isomers, stereoisomers, tautomers, and the like. As used herein, the term "isomers" refers to different compounds that have the same molecular formula but differ in arrangement and configuration of the atoms. Also as used herein, the term "a stereoisomer" refers to any of the various stereo isomeric configurations which may exist for a given compound disclosed herein and includes geometric isomers. It is understood that a substituent may be attached at a chiral center of a carbon atom. Therefore, the compound disclosed herein includes enantiomers, diastereomers or racemates of the compound.

"Enantiomers" are a pair of stereoisomers that are non-superimposable mirror images of each other. A 1:1 mixture of a pair of enantiomers is a "racemic" mixture.

The term is used to designate a racemic mixture where appropriate. "Diastereoisomers" are stereoisomers that have at least two stereocenters, but which are not mirror-images of each other.

The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present disclosure is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included. To the extent that compounds depicted herein are represented as having a particular stereochemistry, it is understood by one of skill in the art that such compounds may contain some detectable or undetectable levels of compounds sharing the same structure, but having different stereochemistry.

"$IC_{95}$" or "$EC_{95}$" refers to the inhibitory concentration required to achieve 95% of the maximum desired effect, which in many cases herein is the inhibition of the PAD4 enzyme.

"$IC_{50}$" or "$EC_{50}$" refers to the inhibitory concentration required to achieve 50% of the maximum desired effect, which in many cases herein is the inhibition of the PAD4 enzyme.

"Pharmaceutically acceptable" refers to compounds, salts, compositions, dosage forms and other materials which are useful in preparing a pharmaceutical composition that is suitable for veterinary or human pharmaceutical use.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, PA, (2005), at p. 732, Table 38-5, both of which are hereby incorporated by reference herein.

Compounds disclosed herein include isotopically labeled, solvates, hydrates, tautomers, stereoisomers and salt forms thereof.

Provided are also compounds in which from 1 to n hydrogen atoms attached to a carbon atom may be replaced by deuterium atom or D, in which n is the number of hydrogen atoms in the molecule. As known in the art, the deuterium atom is a non-radioactive isotope of the hydrogen atom. Such compounds exhibit may increase resistance to metabolism, and thus may be useful for increasing the half-life of the compounds when administered to a mammal. See, e.g., Foster, "Deuterium Isotope Effects in Studies of Drug Metabolism," Trends Pharmacol. Sci., 5(12):524-527 (1984). Such compounds are synthesized by means well known in the art, for example by employing starting materials in which one or more hydrogen atoms have been replaced by deuterium.

Any formula or structure given herein, including Formula I, or any formula disclosed herein, is intended to represent unlabeled forms as well as isotopically labeled forms of the compounds. Isotopically labeled compounds have structures depicted by the formulas given herein except that one or more (e.g., one to three, or one to five) atoms are replaced by an isotope having a selected atomic mass or mass number. Examples of isotopes that can be incorporated into compounds of the disclosure include isotopes of hydrogen, carbon, nitrogen, oxygen, phosphorus, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present disclosure, for example those into which radioactive isotopes such as $^3$H and $^{14}$C are incorporated, are within the ambit of the present disclosure. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in treatment of patients. Such isotopically labeled analogs of compounds of the present disclosure may also be useful for treatment of diseases disclosed herein because they may provide improved pharmacokinetic and/or pharmacodynamic properties over the unlabeled forms of the same compounds. Such isotopically leveled forms of or analogs of compounds herein are within the ambit of the present disclosure. One of skill in the art is able to prepare and use such isotopically labeled forms following procedures for isotopically labeling compounds or aspects of compounds to arrive at isotopic or radiolabeled analogs of compounds disclosed herein.

The present disclosure also provides for prodrugs of the compounds disclosed herein. A "prodrug" is defined in the pharmaceutical field as a biologically inactive derivative of a drug that upon administration to the human body is converted to the biologically active parent drug according to some chemical or enzymatic pathway.

Compounds

Provided herein are compounds that function as inhibitors of peptidylarginine deiminase type 4 (PAD4), methods of using such compounds and compositions comprising such compounds optionally in combination with one or more additional agents or therapies. In all embodiments discussed herein where there is more than one occurrence of a group or variable, it is intended that the group or variable is independently selected the list that follows. All embodiments directed to compounds also include any salt, stereoisomer, mixture of stereoisomers, prodrug, isotopically labeled, solvate, hydrate, or tautomer thereof.

Provided is a compound of Formula I:

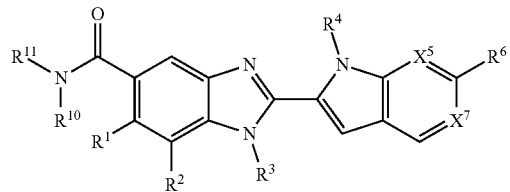

or a pharmaceutically acceptable salt thereof, wherein:

$X^5$ is N or C—$R^5$;

$X^7$ is N or C—$R^7$;

$R^1$ is hydrogen, halo, —CN, —OR$^{12}$, —N(R$^{12}$)$_2$, —SR$^{12}$, —C$_{1-8}$ alkyl optionally substituted with 1 to 3 $Z^1$, $C_{3-6}$ cycloalkyl optionally substituted with 1 to 3 $Z^1$, or 4-6 membered heterocyclyl optionally substituted with 1 to 3 $Z^1$;

$R^2$ is hydrogen, halo, —CN, —OR$^{12}$, —N(R$^{12}$)$_2$, —SR$^{12}$, —C$_{1-8}$ alkyl optionally substituted with 1 to 3 $Z^1$, $C_{3-6}$ cycloalkyl optionally substituted with 1 to 3 $Z^1$, or 4-6 membered heterocyclyl optionally substituted with 1 to 3 $Z^1$;

R³ is hydrogen, $C_{1-8}$ alkyl optionally substituted with 1 to 3 $Z^1$, $C_{3-10}$ alkenyl optionally substituted with 1 to 3 $Z^1$, $C_{3-10}$ alkynyl optionally substituted with 1 to 3 $Z^1$, $C_{3-10}$ cycloalkyl optionally substituted with 1 to 3 $Z^1$, or 4-10 membered heterocyclyl optionally substituted with 1 to 3 $Z^1$; or R² and R³ are taken together with the atoms to which they are attached to form an optionally substituted 6 to 8 membered heterocyclyl ring;

R⁴ is hydrogen, $C_{1-8}$ alkyl optionally substituted with 1 to 3 $Z^1$, $C_{3-10}$ alkenyl optionally substituted with 1 to 3 $Z^1$, $C_{3-10}$ alkynyl optionally substituted with 1 to 3 $Z^1$, $C_{3-10}$ cycloalkyl optionally substituted with 1 to 3 $Z^1$, or 4-10 membered heterocyclyl optionally substituted with 1 to 3 $Z^1$;

R⁵ is hydrogen, halo, —CN, or —OR¹²;

R⁶ is

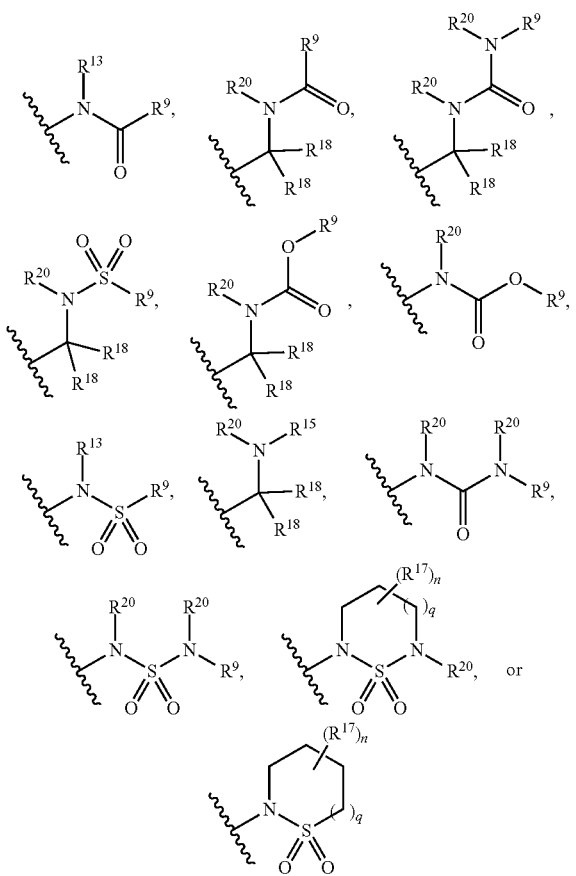

where q is 0, 1 or 2, and n is 0, 1, 2, 3, 4, 5, or 6;

R⁷ is hydrogen, halo, —CN, or —OR¹²;

R⁹ is $C_{1-8}$ alkyl optionally substituted with 1 to 3 $Z^1$, $C_{2-8}$ alkenyl optionally substituted with 1 to 3 $Z^1$, $C_{2-8}$ alkynyl optionally substituted with 1 to 3 $Z^1$, $C_{3-10}$ cycloalkyl optionally substituted with 1 to 3 $Z^1$, 4-10 membered heterocyclyl optionally substituted with 1 to 3 $Z^1$, $C_{6-10}$ aryl optionally substituted with 1 to 3 $Z^1$, or 5-10 membered heteroaryl optionally substituted with 1 to 3 $Z^1$;

R¹⁰ is hydrogen, $C_{1-8}$ alkyl optionally substituted with 1 to 3 $Z^{10}$, or $C_{3-6}$ cycloalkyl optionally substituted with 1 to 3 $Z^{10}$;

R¹¹ is hydrogen, $C_{1-8}$ alkyl optionally substituted with 1 to 4 $Z^{10}$, $C_{3-8}$ cycloalkyl optionally substituted with 1 to 4 $Z^{10}$, or 4-12-membered heterocyclyl optionally substituted with 1 to 4 $Z^{10}$; or R¹⁰ and R¹¹ are taken together to form a 4-12-membered heterocyclyl optionally substituted with 1 to 4 $Z^{10}$;

each R¹² is independently hydrogen, $C_{1-8}$ alkyl optionally substituted with 1 to 3 $Z^{1b}$, $C_{3-8}$ alkenyl optionally substituted with 1 to 3 $Z^{1b}$, $C_{3-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$;

R¹³ is $C_{1-8}$ alkyl optionally substituted with 1 to 3 $Z^{1b}$, $C_{3-8}$ alkenyl optionally substituted with 1 to 3 $Z^{1b}$, $C_{3-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$;

R¹⁵ is $C_{6-10}$ aryl optionally substituted with 1 to 3 $Z^1$ or 5-10 membered heteroaryl optionally substituted with 1 to 3 $Z^1$;

each R¹⁷ is independently hydrogen, halo, —NO₂, —N₃, —CN, $C_{1-8}$ alkyl optionally substituted by 1 to 3 $Z^{1a}$, $C_{2-8}$ alkenyl optionally substituted by 1 to 3 $Z^{1a}$, $C_{2-8}$ alkynyl optionally substituted by 1 to 3 Zia $C_{3-8}$ cycloalkyl optionally substituted by 1 to 3 $Z^{1a}$, 6-10 membered aryl optionally substituted by 1 to 3 $Z^{1a}$, 4-10 membered heterocyclyl optionally substituted by 1 to 3 $Z^{1a}$, 5-10 membered heteroaryl optionally substituted with 1 to 3 $Z^{1a}$, —OR²⁰, —C(O)R²⁰, —C(O)OR²⁰, —C(O)N(R²⁰)₂, —N(R²⁰)₂, —N(R²⁰)₃⁺, —N(R²⁰)C(O)R²⁰, —N(R²⁰)C(O)OR²⁰, —N(R²⁰)C(O)N(R²⁰)₂, —N(R²⁰)S(O)₂(R²⁰), —NR²⁰S(O)₂N(R²⁰)₂, —NR²⁰S(O)₂O(R²⁰), —NS(O)(R²⁰)₂, —OC(O)R²⁰, —OC(O)OR²⁰, —OC(O)N(R²⁰)₂, —Si(R²⁰)₃, —SR²⁰, —S(O)R²⁰, —SF₅, —S(O)(NR²⁰)R²⁰, —S(NR²⁰)(NR²⁰)R²⁰, —S(O)(NR²⁰)N(R²⁰)₂, —S(O)(NCN)R²⁰, —S(O)₂R²⁰, —S(O)₂N(R²⁰)₂, —C(O)N(R²⁰)S(O)₂R²⁰, or —S(O)₂N(R²⁰)C(O)R²⁰; or two R¹¹ on the same or different carbon atoms are taken together to form a 3-8-membered ring optionally substituted with 1 to 4 $Z^1$;

each R⁸ is independently hydrogen, halo, —NO₂, —N₃, —CN, $C_{1-8}$ alkyl optionally substituted by 1 to 3 $Z^{1a}$, $C_{2-8}$ alkenyl optionally substituted by 1 to 3 $Z^{1a}$, $C_{2-8}$ alkynyl optionally substituted by 1 to 3 $Z^{1a}$, $C_{3-8}$ cycloalkyl optionally substituted by 1 to 3 $Z^{1a}$, 6-10 membered aryl optionally substituted by 1 to 3 $Z^{1a}$, 4-10 membered heterocyclyl optionally substituted by 1 to 3 $Z^{1a}$, 5-10 membered heteroaryl optionally substituted with 1 to 3 $Z^{1a}$, —OR²⁰, —C(O)R²⁰, —C(O)OR²⁰, —C(O)N(R²⁰)₂, —N(R²⁰)₂, —N(R²⁰)₃⁺, —N(R²⁰)C(O)R²⁰, —N(R²⁰)C(O)OR²⁰, —N(R²⁰)C(O)N(R²⁰)₂, —N(R²⁰)S(O)₂(R²⁰), —NR²⁰S(O)₂N(R²⁰)₂, —NR²⁰S(O)₂O(R²⁰), —NS(O)(R²⁰)₂, —OC(O)R²⁰, —OC(O)OR²⁰, —OC(O)N(R²⁰)₂, —Si(R²⁰)₃, —SR²⁰, —S(O)R²⁰, —SF₅, —S(O)(NR²⁰)R²⁰, —S(NR²⁰)(NR²⁰)R²⁰, —S(O)(NR²⁰)N(R²⁰)₂, —S(O)(NCN)R²⁰, —S(O)₂R²⁰, —S(O)₂N(R²⁰)₂, —C(O)N(R²⁰)S(O)₂R²⁰, or —S(O)₂N(R²⁰)C(O)R²⁰;

each $Z^1$ is independently halo, —NO₂, —N₃, —CN, $C_{1-8}$ alkyl optionally substituted by 1 to 3 $Z^{1a}$, $C_{2-8}$ alkenyl optionally substituted by 1 to 3 $Z^{1a}$, $C_{2-8}$ alkynyl optionally substituted by 1 to 3 $Z^{1a}$, $C_{3-8}$ cycloalkyl optionally substituted by 1 to 3 $Z^{1a}$, 6-10 membered aryl optionally substituted by 1 to 3 $Z^{1a}$, 4-10 membered heterocyclyl optionally substituted by 1 to 3 $Z^{1a}$, 5-10 membered heteroaryl optionally substituted with 1 to 3 $Z^{1a}$, —$OR^{20}$, —$C(O)R^{20}$, —$C(O)OR^{20}$, —$C(O)N(R^{20})_2$, —$N(R^{20})_2$, —$N(R^{20})_3^+$, —$N(R^{20})C(O)R^{20}$, —$N(R^{20})C(O)OR^{20}$, —$N(R^{20})C(O)N(R^{20})_2$, —$N(R^{20})S(O)_2(R^{20})$, —$NR^{20}S(O)_2N(R^{20})_2$, —$NR^{20}S(O)_2O(R^{20})$, —$NS(O)(R^{20})_2$, —$OC(O)R^{20}$, —$OC(O)OR^{20}$, —$OC(O)N(R^{20})_2$, —$Si(R^{20})_3$, —$SR^{20}$, —$S(O)R^{20}$, —$SF_5$, —$S(O)(NR^{20})R^{20}$, —$S(NR^{20})(NR^{20})R^{20}$, —$S(O)(NR^{20})N(R^{20})_2$, —$S(O)(NCN)R^{20}$, —$S(O)_2R^{20}$, —$S(O)_2N(R^{20})_2$, —$C(O)N(R^{20})S(O)_2R^{20}$, or —$S(O)_2N(R^{20})C(O)R^{20}$;

each $Z^{1a}$ is independently oxo, halo, —$NO_2$, —$N_3$, —CN, $C_{1-8}$ alkyl optionally substituted by 1 to 3 $Z^{1b}$, $C_{2-8}$ alkenyl optionally substituted by 1 to 3 $Z^{1b}$, $C_{2-8}$ alkynyl optionally substituted by 1 to 3 $Z^{1b}$, $C_{3-8}$ cycloalkyl optionally substituted by 1 to 3 $Z^{1b}$, 6-10 membered aryl optionally substituted by 1 to 3 $Z^{1b}$, 4-10 membered heterocyclyl optionally substituted by 1 to 3 $Z^{1b}$, 5-10 membered heteroaryl optionally substituted with 1 to 3 $Z^{1b}$, —$OR^{21}$, —$C(O)R^{21}$, —$C(O)OR^{21}$, —$C(O)N(R^{21})_2$, —$N(R^{21})_2$, —$N(R^{21})_3^+$, —$N(R^{21})C(O)R^{21}$, —$N(R^{21})C(O)OR^{21}$, —$N(R^{21})C(O)N(R^{21})_2$, —$N(R^{21})S(O)_2(R^{21})$, —$NR^{21}S(O)_2N(R^{21})_2$, —$NR^{21}S(O)_2O(R^{21})$, —$NS(O)(R^{21})_2$, —$OC(O)R^{21}$, —$OC(O)OR^{21}$, —$OC(O)N(R^{21})_2$, —$Si(R^{21})_3$, —$SR^{21}$, —$S(O)R^{21}$, —$SF_5$, —$S(O)(NR^{21})R^{21}$, —$S(NR^{21})(NR^{21})R^{21}$, —$S(O)(NR^{21})N(R^{21})_2$, —$S(O)(NCN)R^{21}$, —$S(O)_2R^{21}$, —$S(O)_2N(R^{21})_2$, —$C(O)N(R^{21})S(O)_2R^{21}$, or —$S(O)_2N(R^{21})C(O)R^{21}$;

each $Z^{10}$ is independently selected from oxo, halo, —CN, $C_{1-8}$ alkyl optionally substituted by 1 to 3 $Z^{1b}$, $C_{3-8}$ cycloalkyl optionally substituted by 1 to 3 $Z^{1b}$, aryl optionally substituted by 1 to 3 $Z^{1b}$, 4-10 membered heterocyclyl optionally substituted by 1 to 3 $Z^{1b}$, 5-10 membered heteroaryl optionally substituted with 1 to 3 $Z^{1b}$, —$OR^{22}$, —$C(O)R^{22}$, —$C(O)OR^{22}$, —$C(O)N(R^{22})_2$, —$N(R^{22})_2$, —$N(R^{22})_3^+$, —$N(R^{22})C(O)R^{22}$, —$N(R^{22})C(O)OR^{22}$, —$N(R^{22})C(O)N(R^{22})_2$, —$N(R^{22})S(O)_2R^{22}$, —$OC(O)R^{22}$, —$OC(O)OR^{22}$, —$OC(O)$—$N(R^{22})_2$, and —$S$—$R^{22}$; and each $R^{20}$, $R^{21}$ and $R^{22}$ is independently hydrogen, $C_{1-8}$ alkyl optionally substituted with 1 to 3 $Z^{1b}$, $C_{2-8}$ alkenyl optionally substituted with 1 to 3 $Z^{1b}$, $C_{2-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$;

each $Z^{1b}$ is independently oxo, hydroxy, halo, —$NO_2$, —$N_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, $C_{6-10}$ aryl, 5-10 membered heteroaryl heteroaryl, 4-10 membered heterocyclyl, —$O(C_{1-9}$ alkyl), —$O(C_{2-6}$ alkenyl), —$O(C_{2-6}$ alkynyl), —$O(C_{3-15}$ cycloalkyl), —$O(C_{1-8}$ haloalkyl), —$O$(aryl), —$O$(heteroaryl), —$O$(heterocyclyl), —$OC(O)(C_{1-9}$ alkyl), —$OC(O)(C_{2-6}$ alkenyl), —$OC(O)(C_{2-6}$ alkenyl), —$OC(O)(C_{2-6}$ alkynyl), —$OC(O)(C_{3-15}$ cycloalkyl), —$OC(O)(C_{1-8}$ haloalkyl), —$OC(O)$(aryl), —$OC(O)$(heteroaryl), —$OC(O)$(heterocyclyl), —$NH_2$, —$NH(C_{1-9}$ alkyl), —$NH(C_{2-6}$ alkenyl), —$NH(C_{2-6}$ alkynyl), —$NH(C_{3-15}$ cycloalkyl), —$NH(C_{1-8}$ haloalkyl), —$NH$(aryl), —$NH$(heteroaryl), —$NH$(heterocyclyl), —$N(C_{1-9}$ alkyl)$_2$, —$N(C_{3-15}$ cycloalkyl)$_2$, —$N(C_{2-6}$ alkenyl)$_2$, —$N(C_{2-6}$ alkynyl)$_2$, —$N(C_{3-15}$ cycloalkyl)$_2$, —$N(C_{1-8}$ haloalkyl)$_2$, —$N$(aryl)$_2$, —$N$(heteroaryl)$_2$, —$N$(heterocyclyl)$_2$, —$N(C_{1-9}$ alkyl)$(C_{3-15}$ cycloalkyl), —$N(C_{1-9}$ alkyl)$(C_{2-6}$ alkenyl), —$N(C_{1-9}$ alkyl)$(C_{2-6}$ alkynyl), —$N(C_{1-9}$ alkyl)$(C_{3-15}$ cycloalkyl), —$N(C_{1-9}$ alkyl)$(C_{1-8}$ haloalkyl), —$N(C_{1-9}$ alkyl)(aryl), —$N(C_{1-9}$ alkyl)(heteroaryl), —$N(C_{1-9}$ alkyl)(heterocyclyl), —$C(O)(C_{1-9}$ alkyl), —$C(O)(C_{2-6}$ alkenyl), —$C(O)(C_{2-6}$ alkynyl), —$C(O)(C_{3-15}$ cycloalkyl), —$C(O)(C_{1-8}$ haloalkyl), —$C(O)$(aryl), —$C(O)$(heteroaryl), —$C(O)$(heterocyclyl), —$C(O)O(C_{1-9}$ alkyl), —$C(O)O(C_{2-6}$ alkenyl), —$C(O)O(C_{2-6}$ alkynyl), —$C(O)O(C_{3-15}$ cycloalkyl), —$C(O)O(C_{1-8}$ haloalkyl), —$C(O)O$(aryl), —$C(O)O$(heteroaryl), —$C(O)O$(heterocyclyl), —$C(O)NH_2$, —$C(O)NH(C_{1-9}$ alkyl), —$C(O)NH(C_{2-6}$ alkenyl), —$C(O)NH(C_{2-6}$ alkynyl), —$C(O)NH(C_{3-15}$ cycloalkyl), —$C(O)NH(C_{1-8}$ haloalkyl), —$C(O)NH$(aryl), —$C(O)NH$(heteroaryl), —$C(O)NH$(heterocyclyl), —$C(O)N(C_{1-9}$ alkyl)$_2$, —$C(O)N(C_{3-15}$ cycloalkyl)$_2$, —$C(O)N(C_{2-6}$ alkenyl)$_2$, —$C(O)N(C_{2-6}$ alkynyl)$_2$, —$C(O)N(C_{1-8}$ haloalkyl)$_2$, —$C(O)N$(aryl)$_2$, —$C(O)N$(heteroaryl)$_2$, —$C(O)N$(heterocyclyl)$_2$, —$NHC(O)(C_{1-9}$ alkyl), —$NHC(O)(C_{2-6}$ alkenyl), —$NHC(O)(C_{2-6}$ alkynyl), —$NHC(O)(C_{3-15}$ cycloalkyl), —$NHC(O)(C_{1-8}$ haloalkyl), —$NHC(O)$(aryl), —$NHC(O)$(heteroaryl), —$NHC(O)$(heterocyclyl), —$NHC(O)O(C_{1-9}$ alkyl), —$NHC(O)O(C_{2-6}$ alkenyl), —$NHC(O)O(C_{2-6}$ alkynyl), —$NHC(O)O(C_{3-15}$ cycloalkyl), —$NHC(O)O(C_{1-8}$ haloalkyl), —$NHC(O)O$(aryl), —$NHC(O)O$(heteroaryl), —$NHC(O)O$(heterocyclyl), —$NHC(O)NH(C_{1-9}$ alkyl), —$NHC(O)NH(C_{2-6}$ alkenyl), —$NHC(O)NH(C_{2-6}$ alkynyl), —$NHC(O)NH(C_{3-15}$ cycloalkyl), —$NHC(O)NH(C_{1-8}$ haloalkyl), —$NHC(O)NH$(aryl), —$NHC(O)NH$(heteroaryl), —$NHC(O)NH$(heterocyclyl), —SH, —$S(C_{1-9}$ alkyl), —$S(C_{2-6}$ alkenyl), —$S(C_{2-6}$ alkynyl), —$S(C_{3-15}$ cycloalkyl), —$S(C_{1-8}$ haloalkyl), —$S$(aryl), —$S$(heteroaryl), —$S$(heterocyclyl), —$NHS(O)(C_{1-9}$ alkyl), —$N(C_{1-9}$ alkyl)$(S(O)(C_{1-9}$ alkyl), —$S(O)N(C_{1-9}$ alkyl)$_2$, —$S(O)(C_{1-9}$ alkyl), —$S(O)(NH)(C_{1-9}$ alkyl), —$S(O)(C_{2-6}$ alkenyl), —$S(O)(C_{2-6}$ alkynyl), —$S(O)(C_{3-15}$ cycloalkyl), —$S(O)(C_{1-8}$ haloalkyl), —$S(O)$(aryl), —$S(O)$(heteroaryl), —$S(O)$(heterocyclyl), —$S(O)_2(C_{1-9}$ alkyl), —$S(O)_2(C_{2-6}$ alkenyl), —$S(O)_2(C_{2-6}$ alkynyl), —$S(O)_2(C_{3-15}$ cycloalkyl), —$S(O)_2(C_{1-8}$ haloalkyl), —$S(O)_2$(aryl), —$S(O)_2$(heteroaryl), —$S(O)_2$(heterocyclyl), —$S(O)_2NH(C_{1-9}$ alkyl), or —$S(O)_2N(C_{1-9}$ alkyl)$_2$;

wherein any alkyl, cycloalkyl, aryl, heteroaryl, or heterocyclyl of $Z^{1b}$ is optionally substituted with one or more halo, $C_{1-9}$ alkyl, $C_{1-8}$ haloalkyl, —OH, —$NH_2$, —$NH(C_{1-9}$ alkyl), —$NH(C_{3-15}$ cycloalkyl), —$NH(C_{1-8}$ haloalkyl), —$NH$(aryl), —$NH$(heteroaryl), —$NH$(heterocyclyl), —$N(C_{1-9}$ alkyl)$_2$, —$N(C_{3-15}$ cycloalkyl)$_2$, —$NHC(O)(C_{3-15}$ cycloalkyl), —$NHC(O)(C_{1-8}$ haloalkyl), —$NHC(O)$(aryl), —$NHC(O)$(heteroaryl), —$NHC(O)$(heterocyclyl), —$NHC(O)O(C_{1-9}$ alkyl), —$NHC(O)O(C_{2-6}$ alkynyl), —$NHC(O)O(C_{3-15}$ cycloalkyl), —$NHC(O)O(C_{1-8}$ haloalkyl), —$NHC(O)O$(aryl), —$NHC(O)O$(heteroaryl), —$NHC(O)O$(heterocyclyl), —$NHC(O)NH(C_{1-9}$ alkyl), —$S(O)(NH)(C_{1-9}$ alkyl), —$S(O)_2(C_{1-9}$ alkyl), —$S(O)_2(C_{3-15}$ cycloalkyl), —$S(O)_2(C_{1-8}$ haloalkyl), —$S(O)_2$(aryl), —$S(O)_2$(heteroaryl), —$S(O)_2$(heterocyclyl), —$S(O)_2NH(C_{1-9}$ alkyl), —$S(O)_2N(C_{1-9}$ alkyl)$_2$, —O($C_{3-15}$ cycloalkyl), —O($C_{1-8}$ haloalkyl), —O(aryl), —O(heteroaryl), —O(heterocyclyl), or —O($C_{1-9}$ alkyl).

In certain embodiments, $X^5$ is N. In certain embodiments, $X^5$ is C—$R^5$. In certain embodiments, $X^5$ is C—H or C—F.

In certain embodiments, $X^7$ is N. In certain embodiments, $X^7$ is C—$R^7$. In certain embodiments, $X^7$ is C—H or C—F.

In certain embodiments, $R^1$ is hydrogen, halo or —$C_{1-8}$ alkyl optionally substituted with 1 to 3 $Z^1$. In certain embodiments, $R^1$ is hydrogen, halo or —$C_{1-8}$ alkyl. In certain embodiments, $R^1$ is hydrogen or halo. In certain embodiments, $R^1$ is hydrogen, fluoro or methyl. In certain embodiments, $R^1$ is hydrogen or fluoro. In certain embodiments, $R^1$ is hydrogen.

In certain embodiments, $R^2$ and $R^3$ are taken together with the atoms to which they are attached to form an optionally substituted 6 to 8 membered heterocyclyl ring.

In certain embodiments, $R^2$ is hydrogen, halo, —CN, —$OR^{12}$, —$N(R^{12})_2$, —$SR^{12}$, —$C_{1-8}$ alkyl optionally substituted with 1 to 3 $Z^1$, $C_{3-6}$ cycloalkyl optionally substituted with 1 to 3 $Z^1$, or 4-6 membered heterocyclyl optionally substituted with 1 to 3 $Z^1$; and $R^3$ is hydrogen, $C_{1-8}$ alkyl optionally substituted with 1 to 3 $Z^1$, $C_{3-10}$ alkenyl optionally substituted with 1 to 3 $Z^1$, $C_{3-10}$ alkynyl optionally substituted with 1 to 3 $Z^1$, $C_{3-10}$ cycloalkyl optionally substituted with 1 to 3 $Z^1$, or 4-10 membered heterocyclyl optionally substituted with 1 to 3 $Z^1$.

In certain embodiments, $R^2$ is hydrogen, halo, or —O—$C_{1-8}$ alkyl. In certain embodiments, $R^2$ is hydrogen, fluoro, chloro, or methoxy. In certain embodiments, $R^2$ is fluoro, chloro, or methoxy. In certain embodiments, $R^2$ is —O—$C_{1-8}$ alkyl. In certain embodiments, $R^2$ is methoxy. In certain embodiments, $R^2$ is halo. In certain embodiments, $R^2$ is fluoro and chloro. In certain embodiments, $R^2$ is fluoro. In certain embodiments, $R^2$ is hydrogen or fluoro. In certain embodiments, $R^2$ is hydrogen.

In certain embodiments, $R^3$ is $C_{1-8}$ alkyl optionally substituted with 1 to 3 $Z^1$ or $C_{3-10}$ cycloalkyl optionally substituted with 1 to 3 $Z^1$. In certain embodiments, $R^3$ is $C_{1-8}$ alkyl optionally substituted with 1 to 3 $Z^1$. In certain embodiments, $R^3$ is $C_{3-10}$ cycloalkyl optionally substituted with 1 to 3 $Z^1$. In certain embodiments, $R^3$ is methyl,

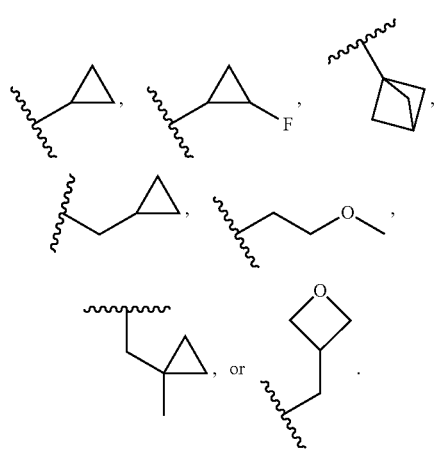

In certain embodiments, $R^3$ is methyl,

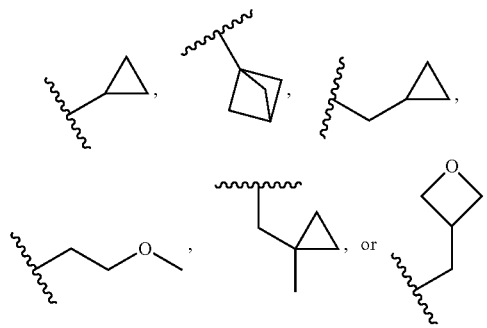

In certain embodiments, $R^3$ is methyl or

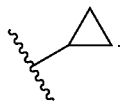

In certain embodiments, $R^4$ is $C_{1-8}$ alkyl optionally substituted with 1 to 3 $Z^1$ or $C_{3-10}$ cycloalkyl optionally substituted with 1 to 3 $Z^1$. In certain embodiments, $R^4$ is $C_{1-8}$ alkyl optionally substituted with 1 to 3 $Z^1$. In certain embodiments, $R^4$ is $C_{3-10}$ cycloalkyl optionally substituted with 1 to 3 $Z^1$. In certain embodiments, R is ethyl,

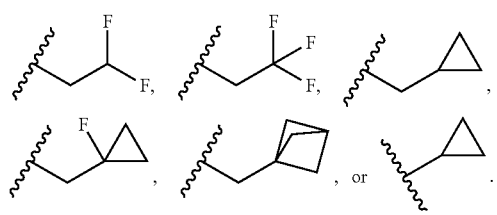

In certain embodiments, $R^4$ is

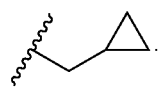 [SMILES: *CC1CC1]

In certain embodiments, $R^6$ is

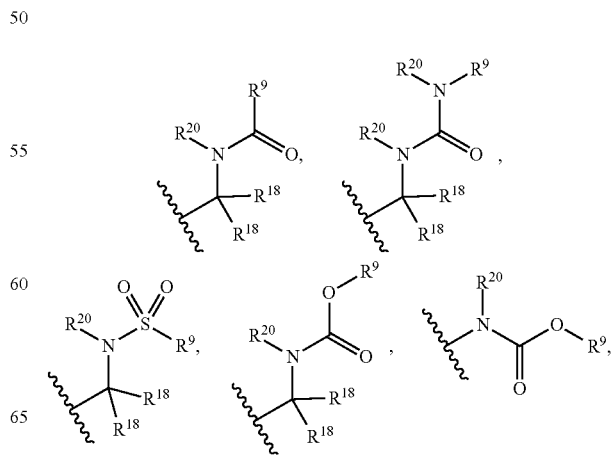

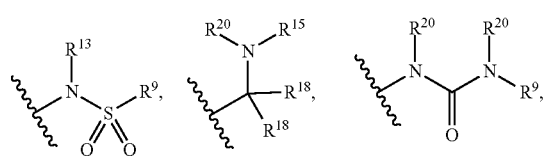
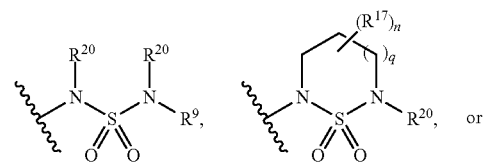
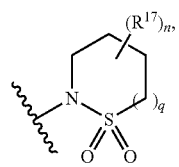
where q is 0, 1 or 2, and n is 0, 1, 2, 3, 4, 5, or 6. In certain embodiments, $R^6$ is
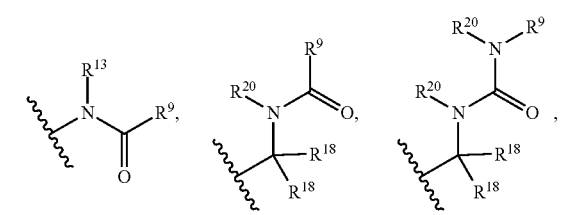
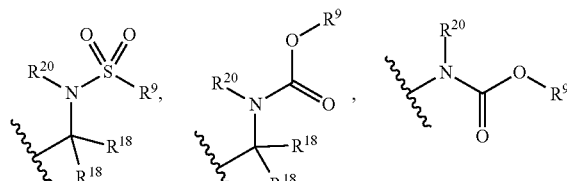
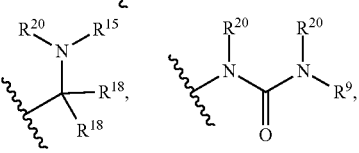
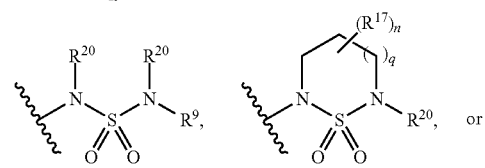
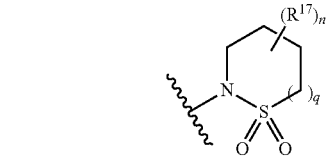
where q is 0, 1 or 2, and n is 0, 1, 2, 3, 4, 5, or 6. In certain embodiments, $R^6$ is
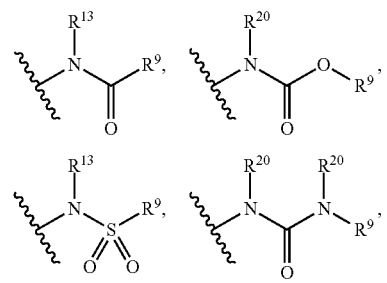
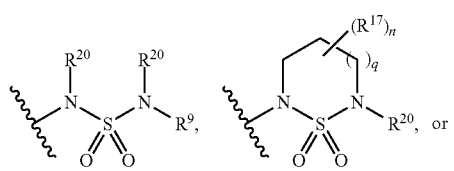
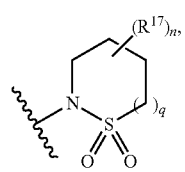
where q is 0, 1 or 2, and n is 0, 1, 2, 3, 4, 5, or 6. In certain embodiments, $R^6$ is
In certain embodiments, $R^6$ is
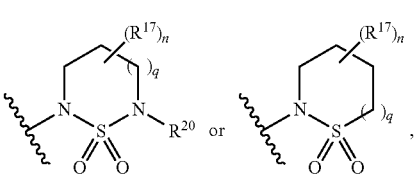
where q is 0, 1 or 2, and n is 0, 1, 2, 3, 4, 5, or 6.

In certain embodiments, $R^6$ is

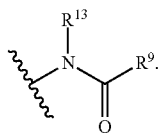

In certain embodiments, $R^6$ is

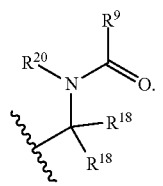

In certain embodiments, $R^6$ is

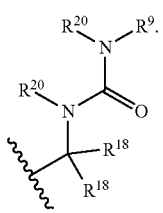

In certain embodiments, $R^6$ is

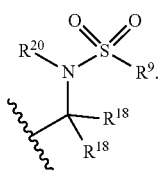

In certain embodiments, $R^6$ is

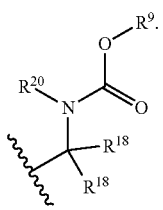

In certain embodiments, $R^6$ is

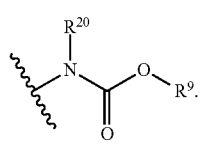

In certain embodiments, $R^6$ is

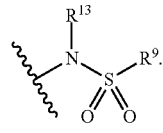

In certain embodiments, $R^6$ is

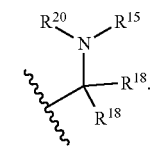

In certain embodiments, $R^6$ is

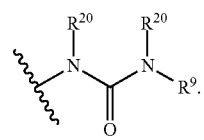

In certain embodiments, $R^6$ is

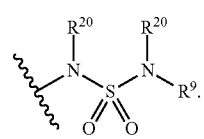

In certain embodiments, $R^6$ is

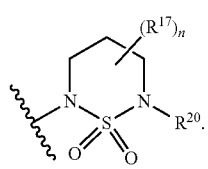

In certain embodiments, $R^6$ is

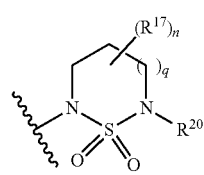

where q is 0, 1 or 2. In certain embodiments, $R^6$ is

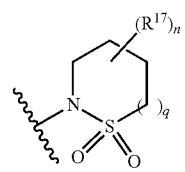

where q is 0, 1 or 2.

In certain embodiments, q is 0. In certain embodiments, q is 1. In certain embodiments, q is 2.

In certain embodiments, n is 0. In certain embodiments, n is 1. In certain embodiments, n is 2. In certain embodiments, n is 3. In certain embodiments, n is 4. In certain embodiments, n is 5. In certain embodiments, n is 6. In certain embodiments, n is 0, 1, 2, 3, or 4. In certain embodiments, n is 0, 1, or 2.

In certain embodiments, $R^6$ is

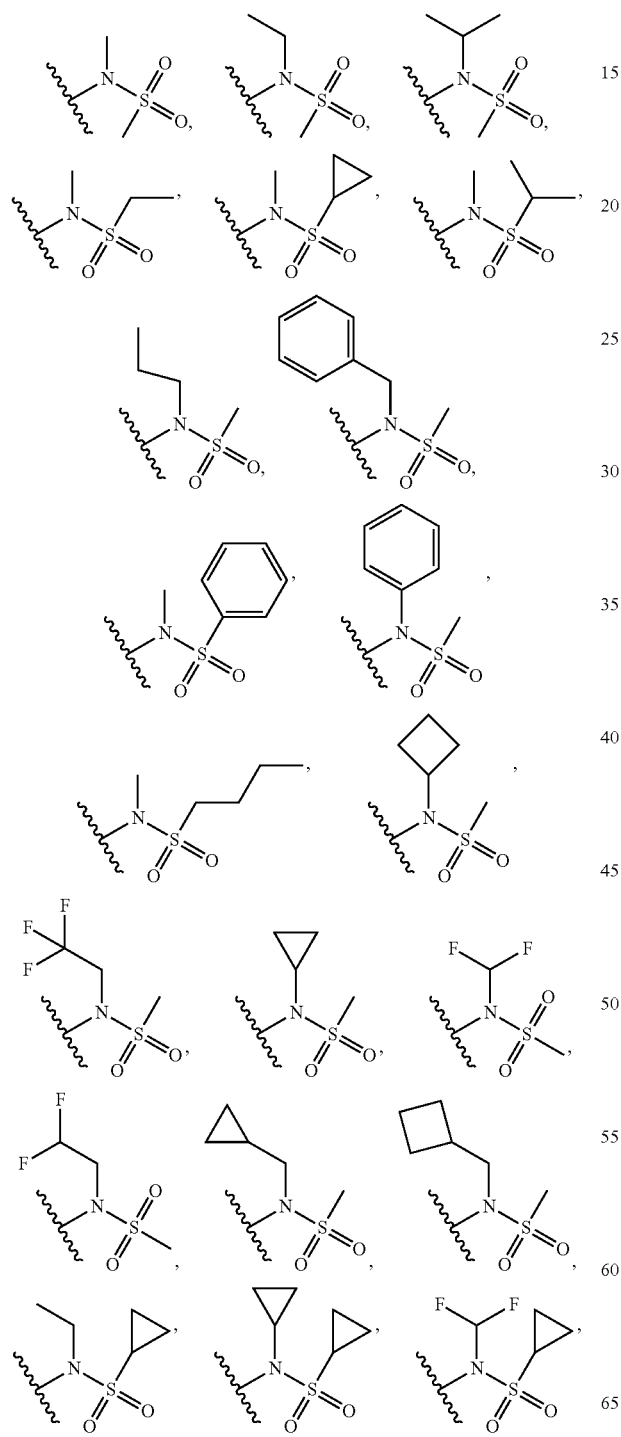

-continued

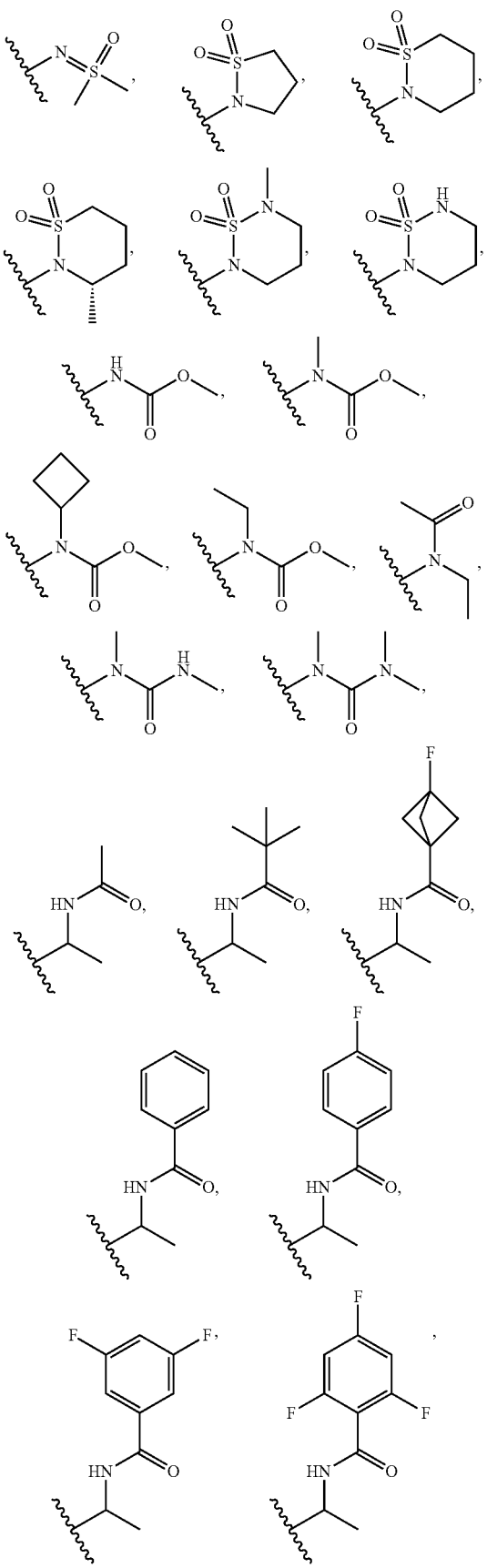

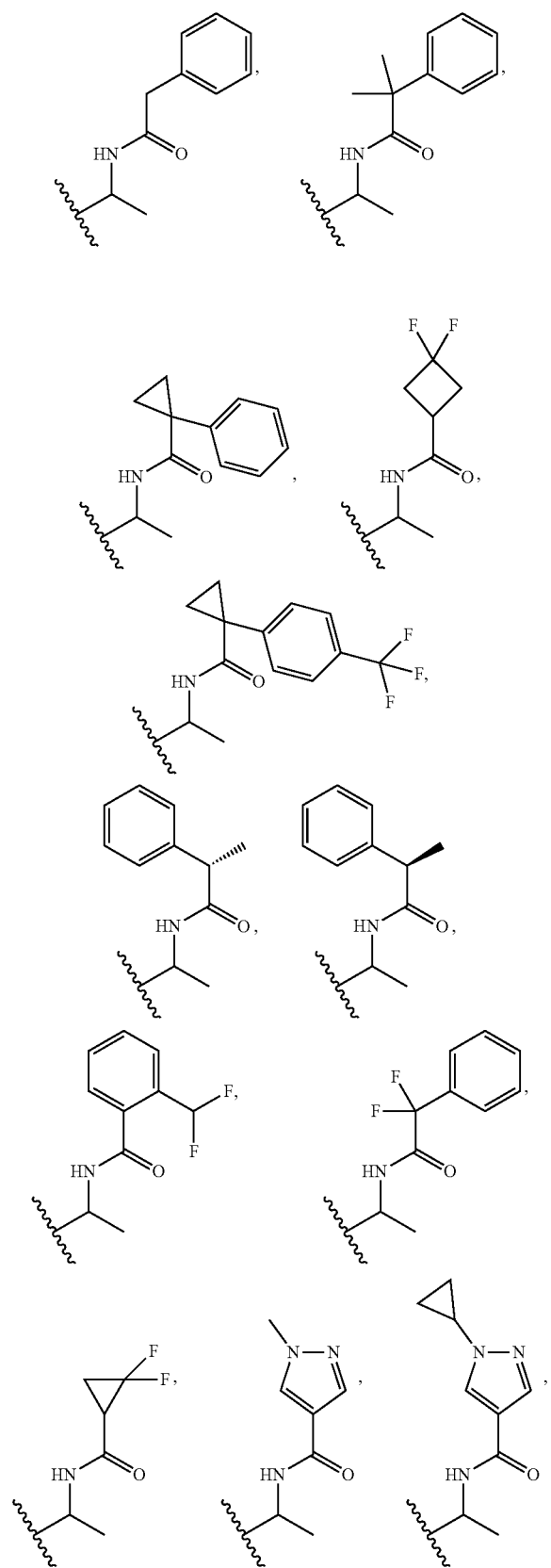
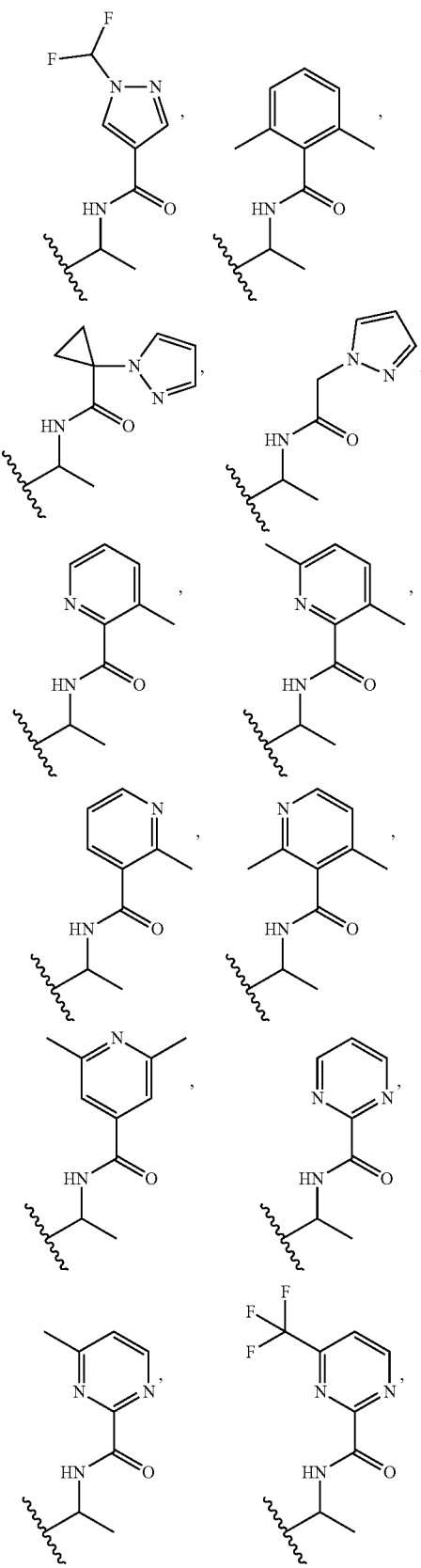

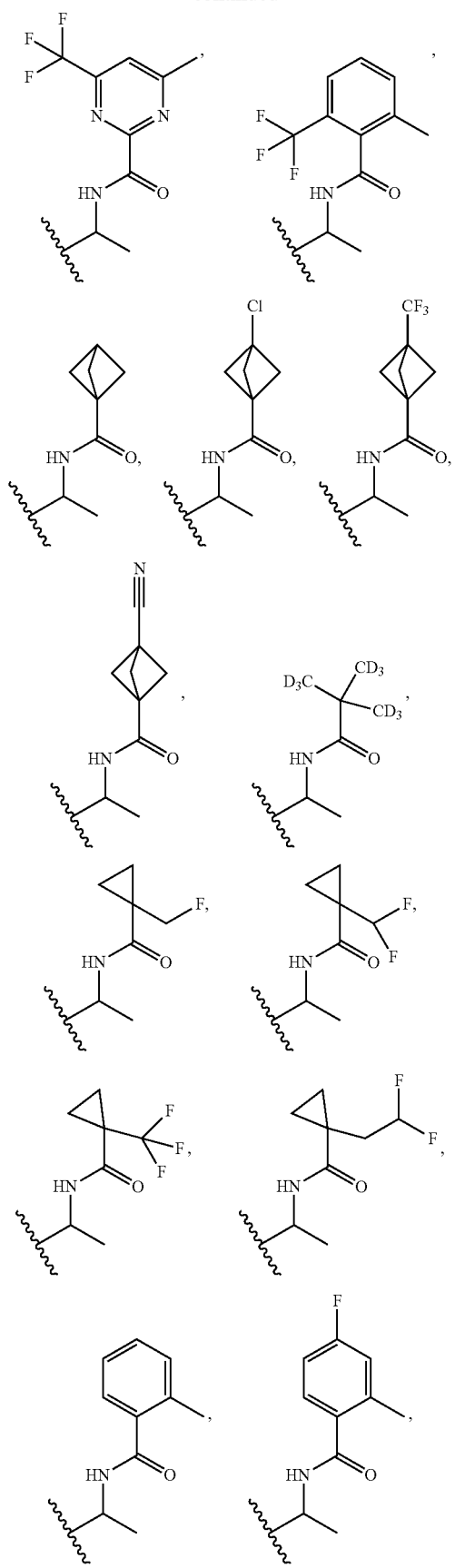
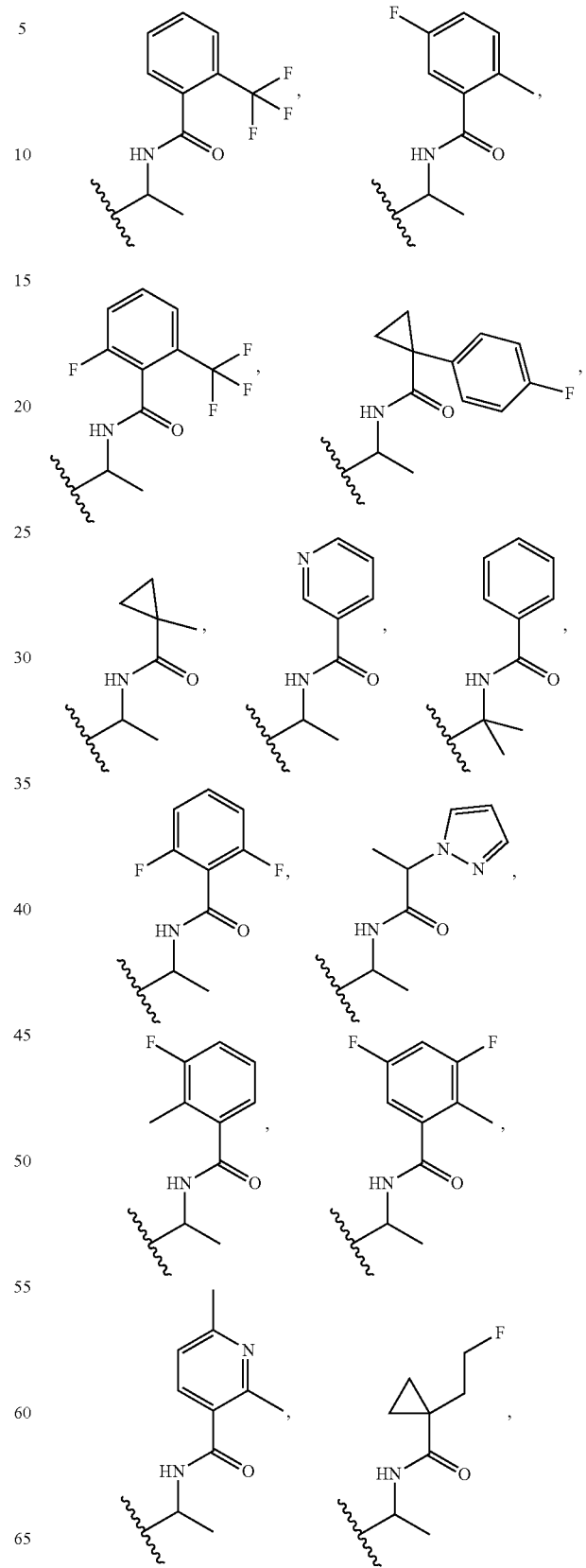

31
-continued
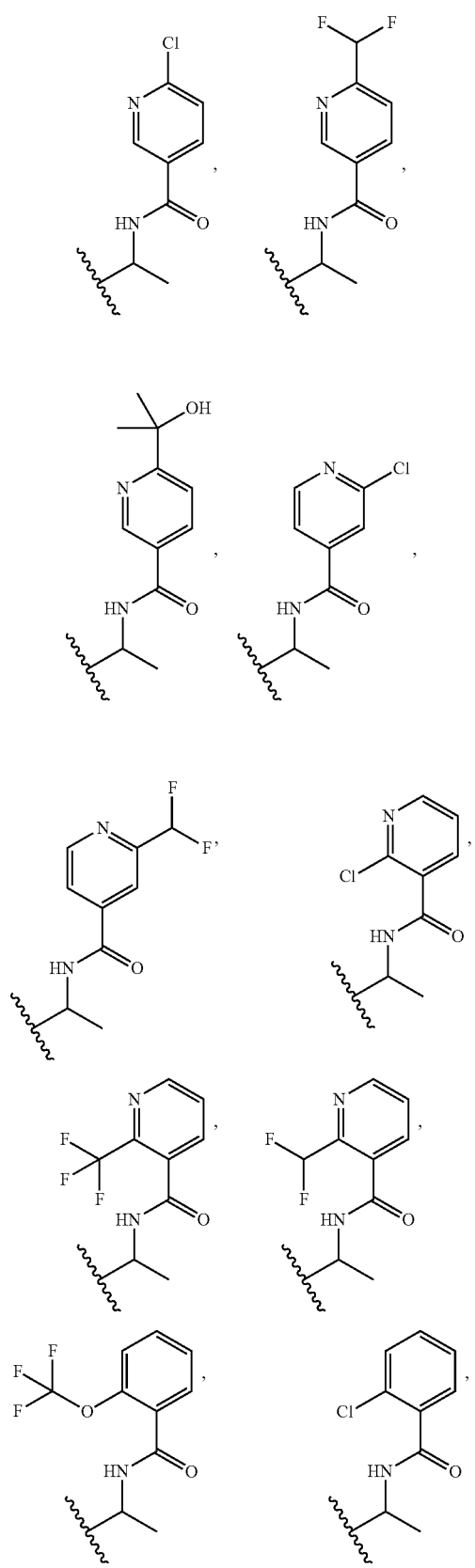
32
-continued
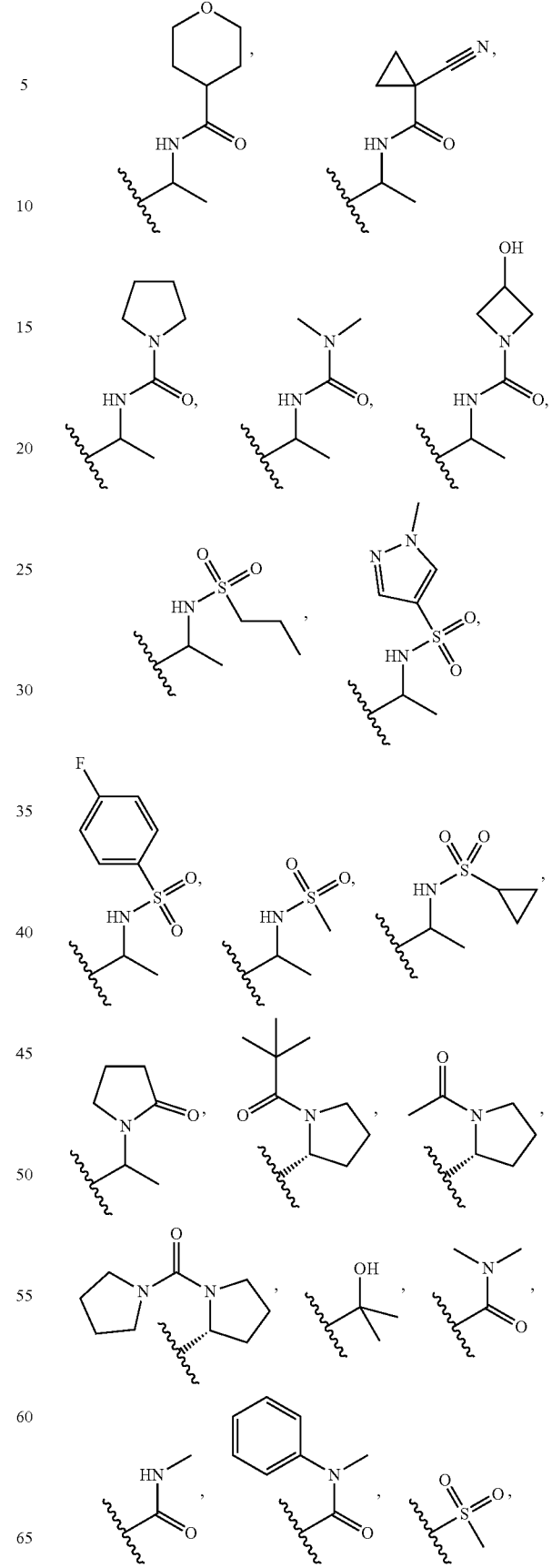

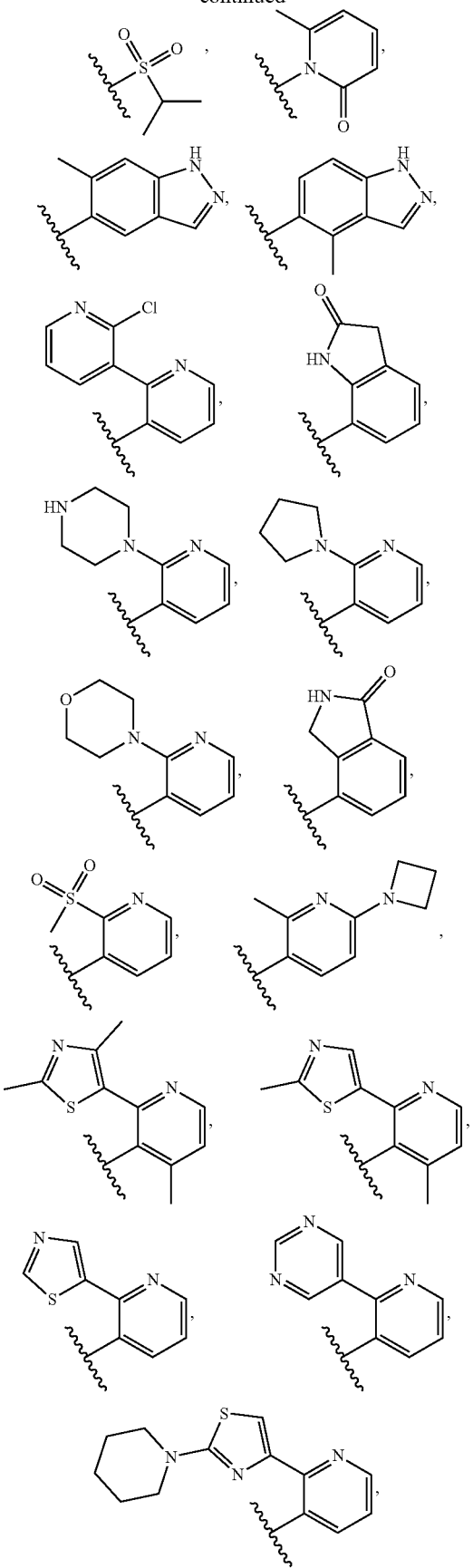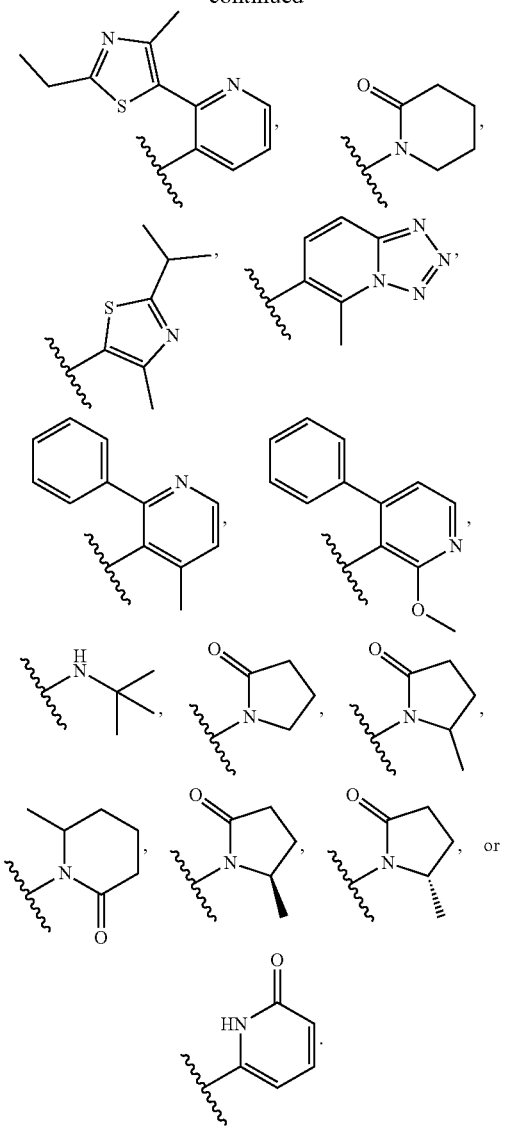
In certain embodiments, $R^6$ is
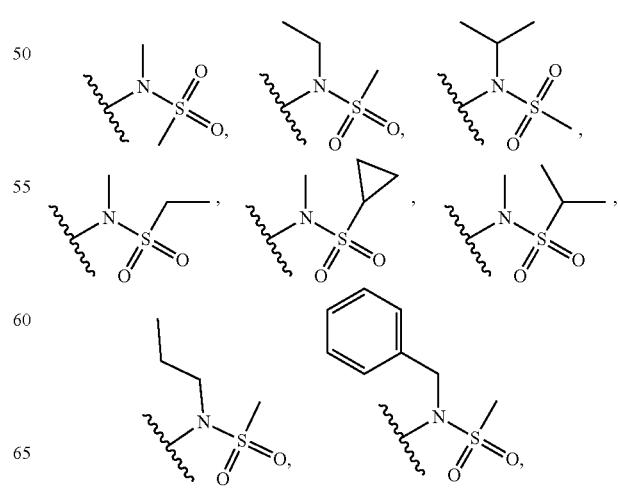

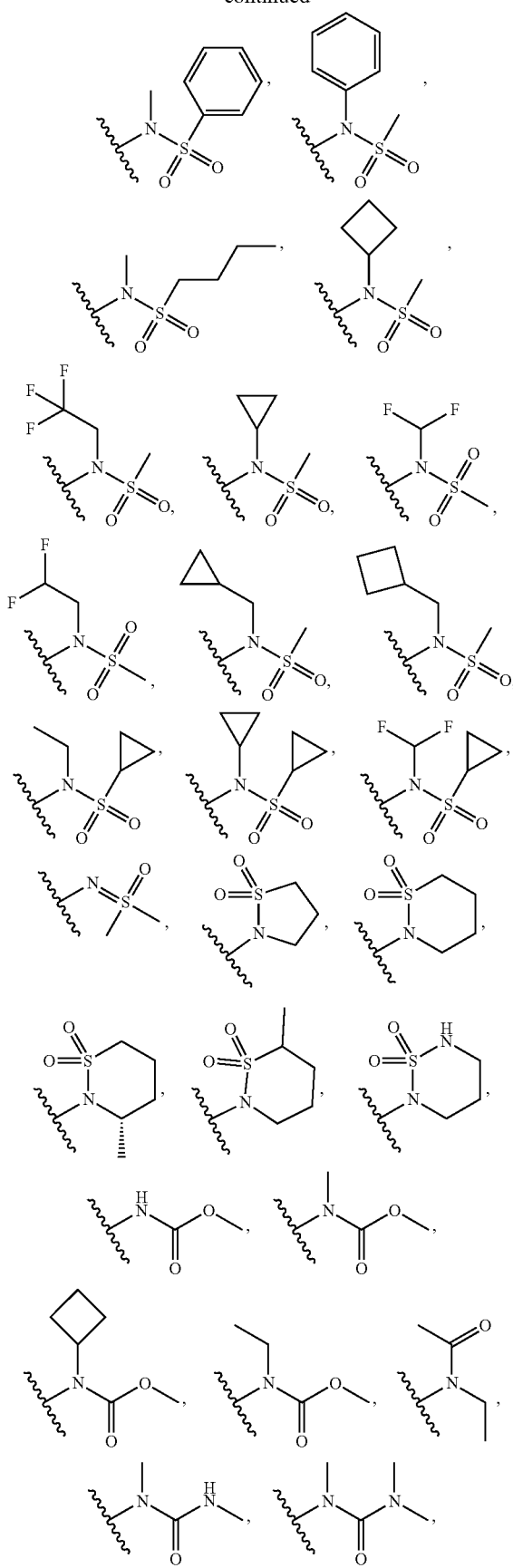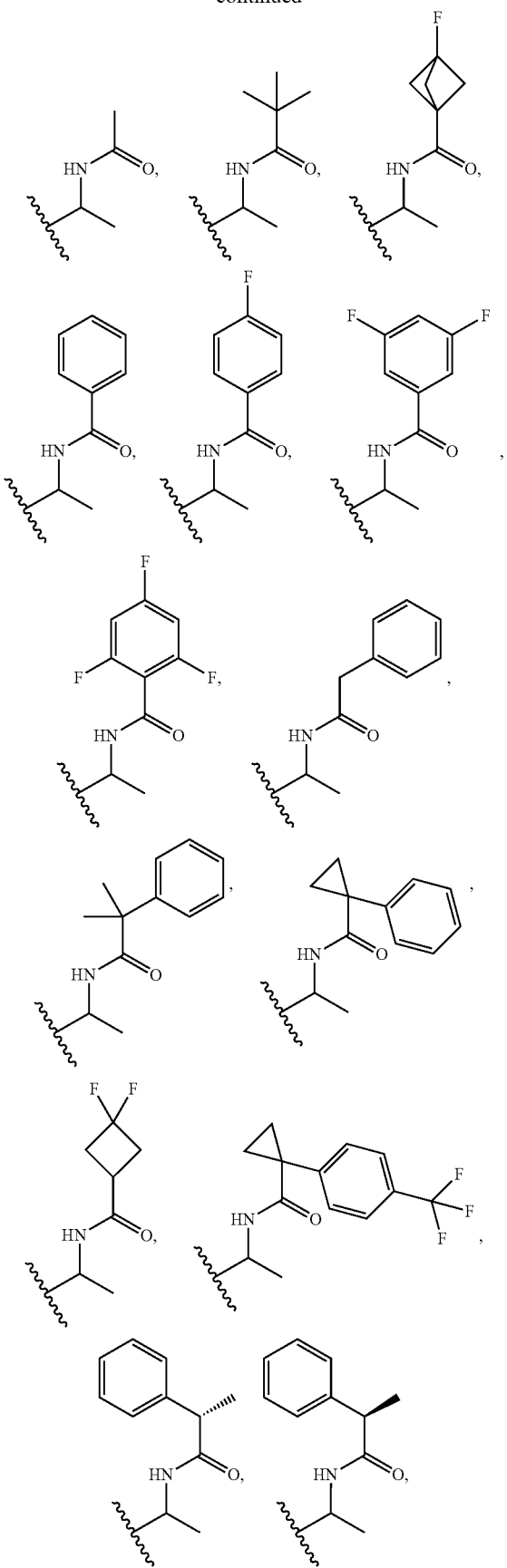

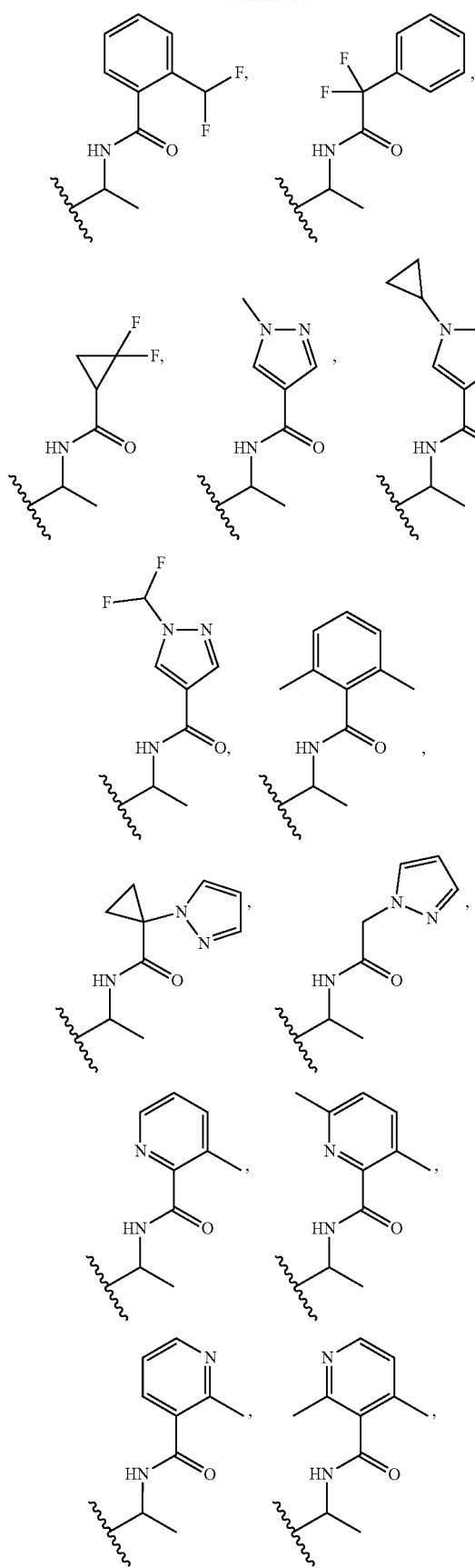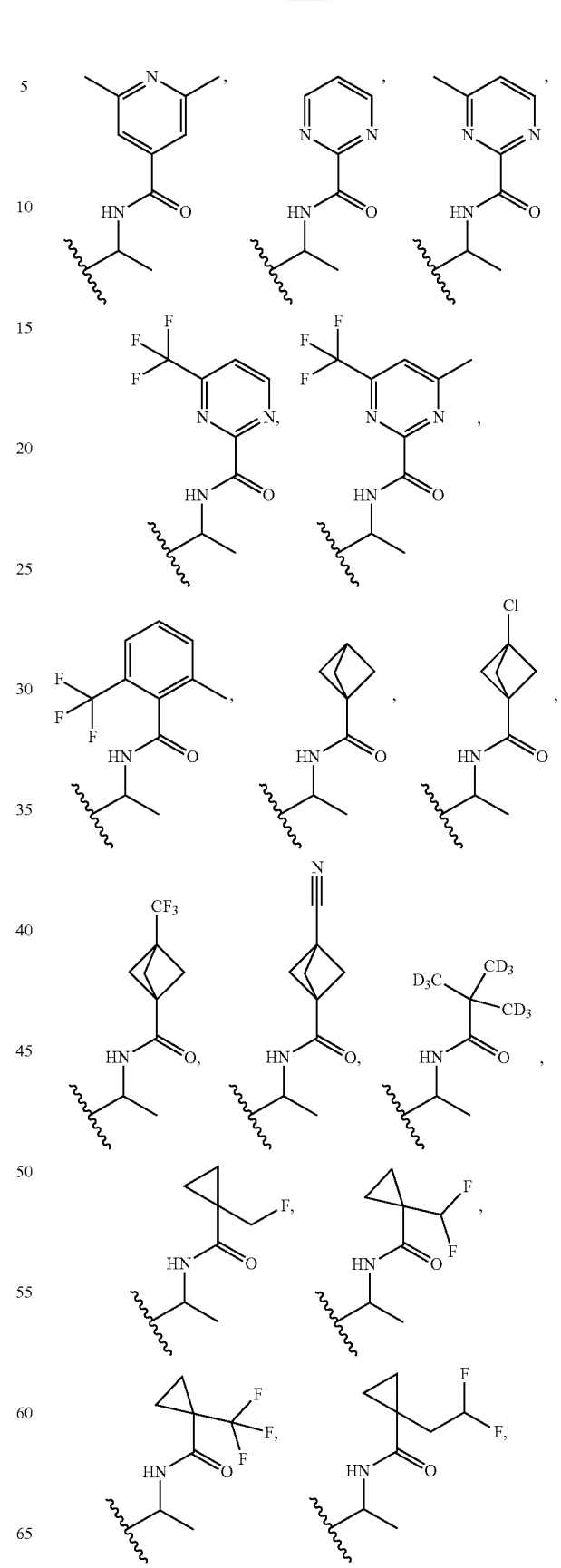

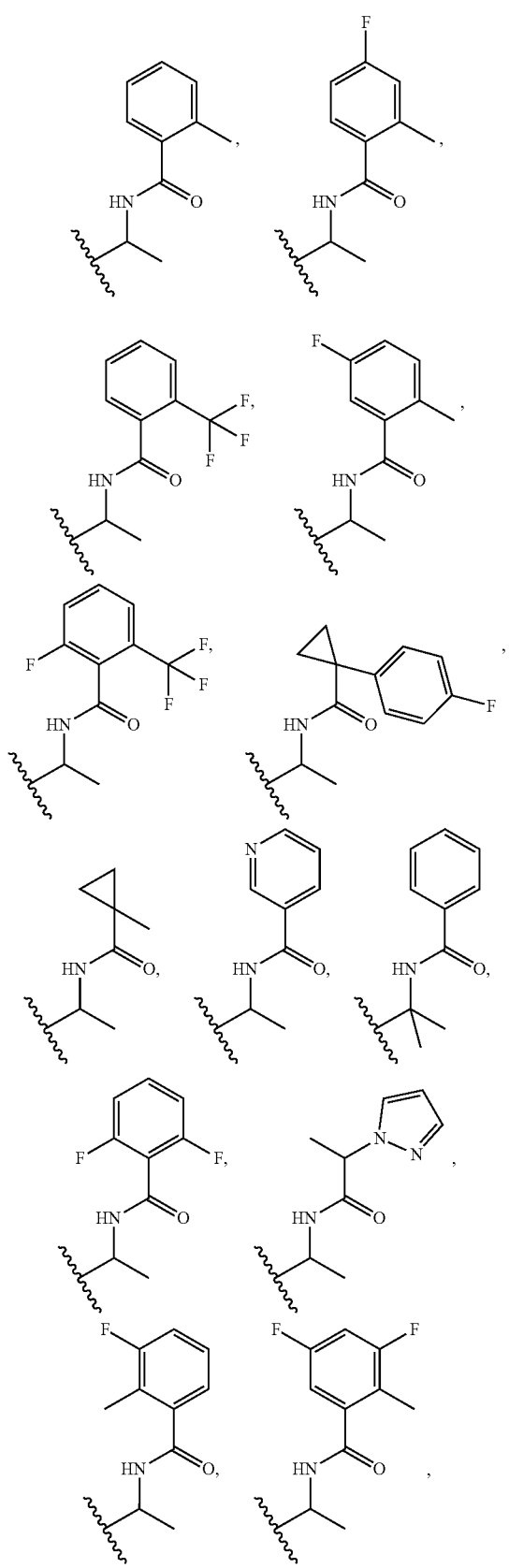
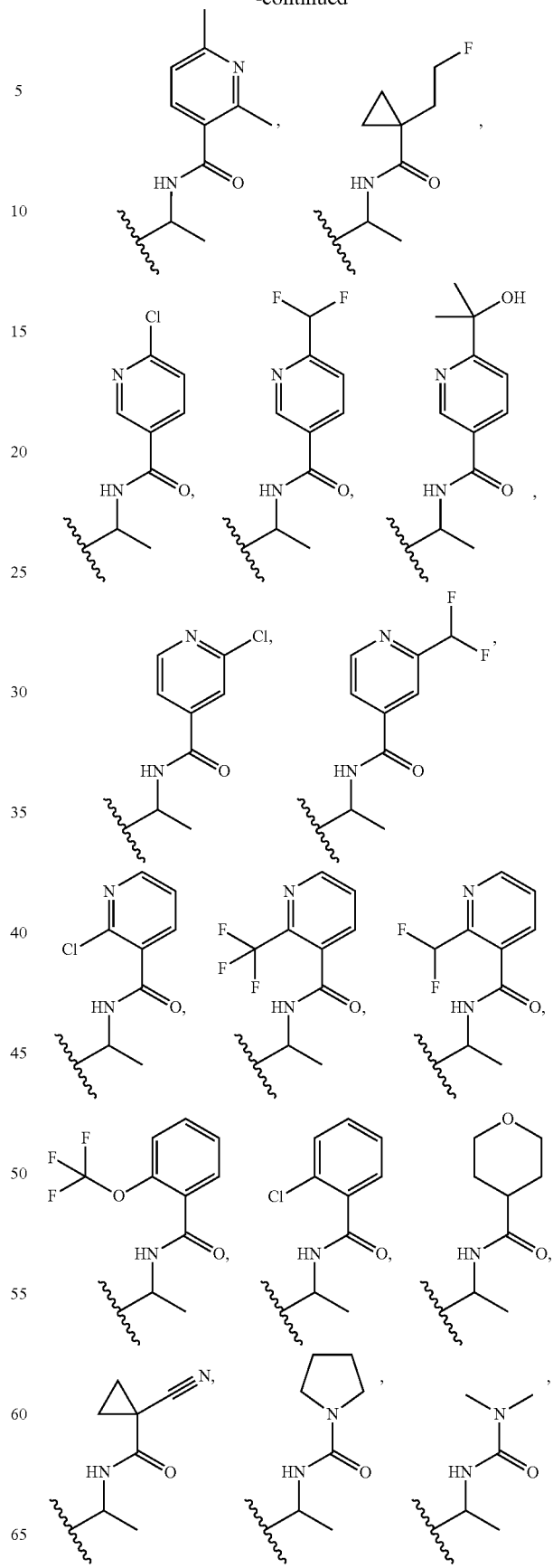

41
-continued
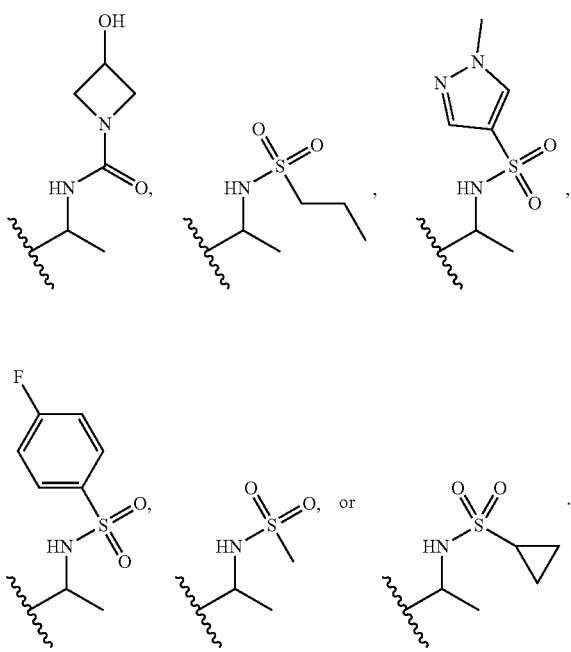
In certain embodiments, $R^6$ is
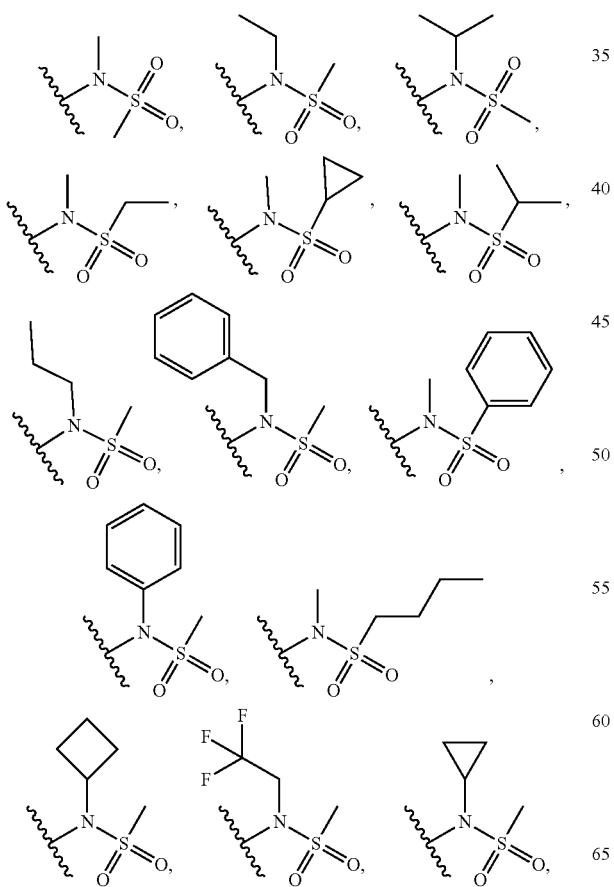
42
-continued
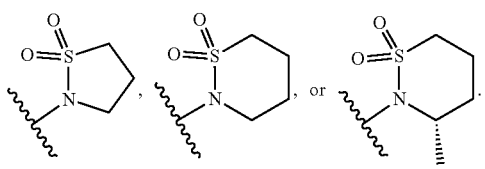
In certain embodiments, $R^6$ is
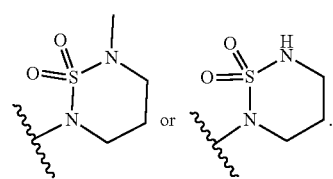
In certain embodiments, $R^6$ is
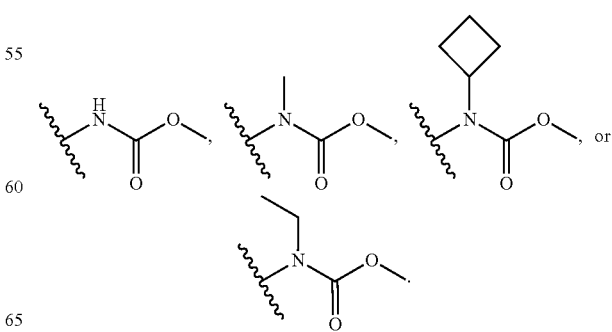
In certain embodiments, $R^6$ is In certain embodiments, $R^6$ is
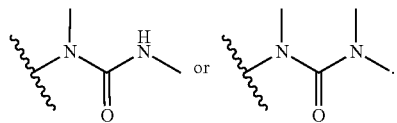 or
In certain embodiments, $R^6$ is
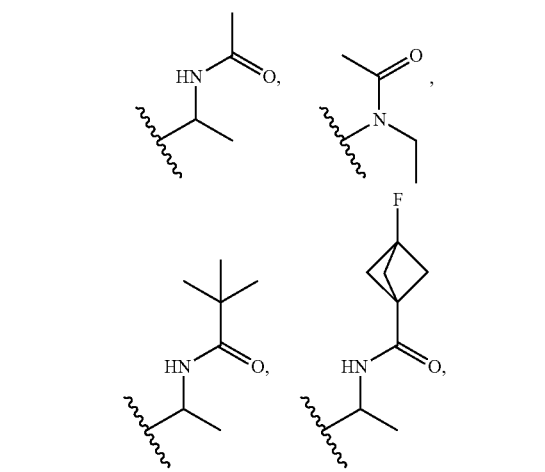
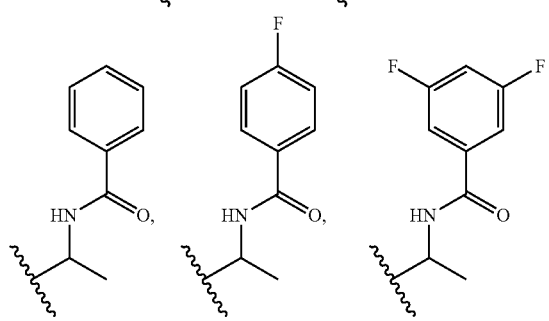
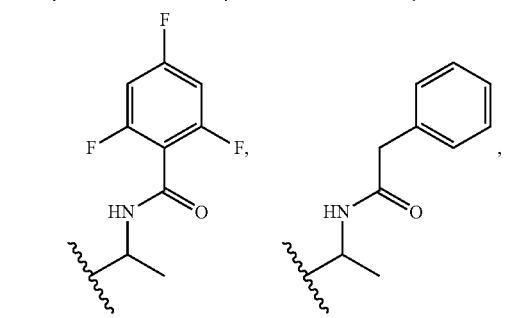
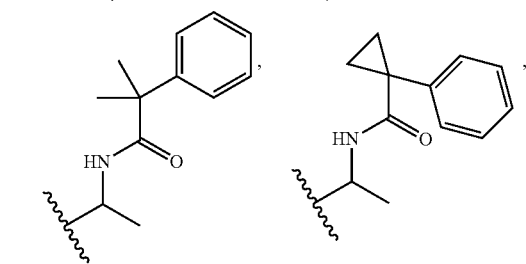
-continued
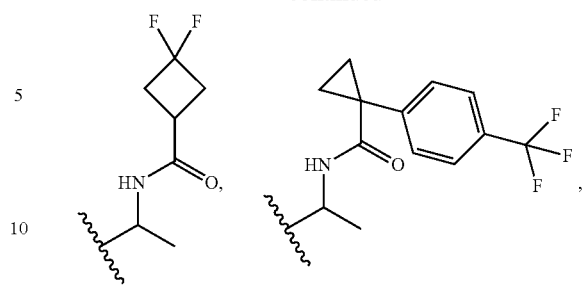
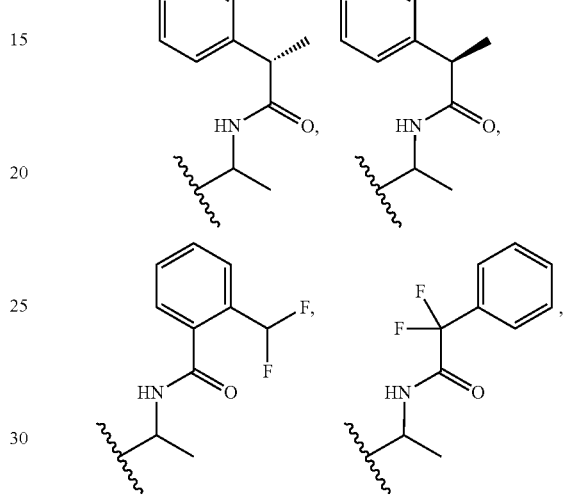
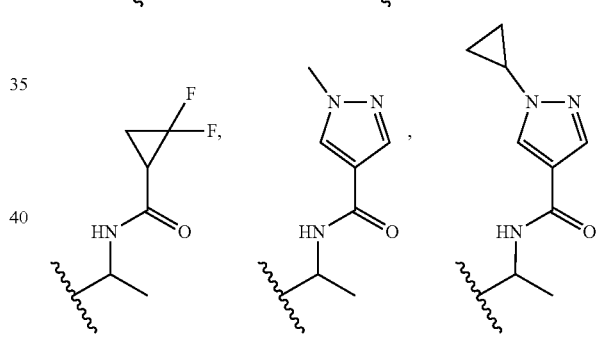
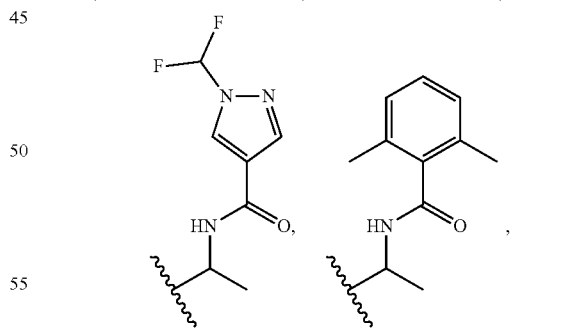
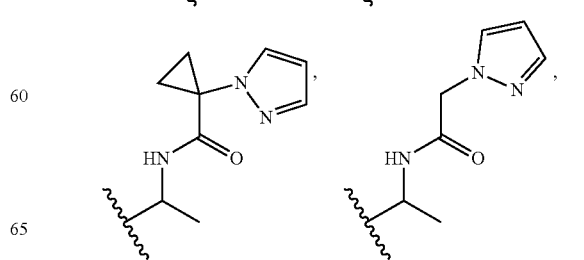

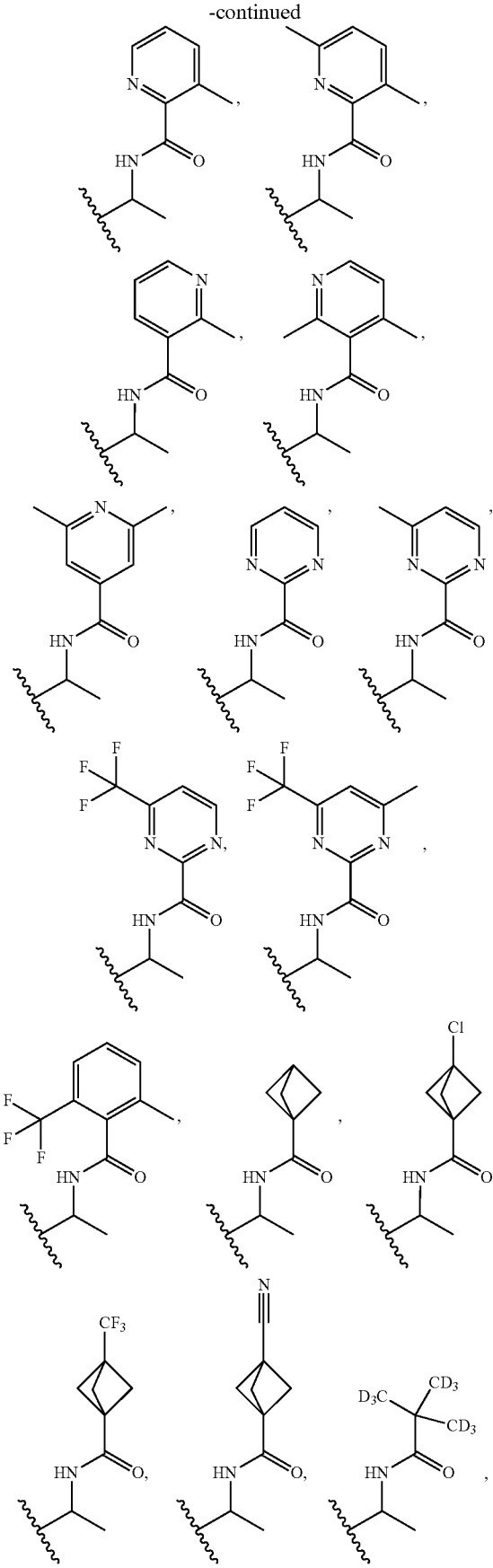
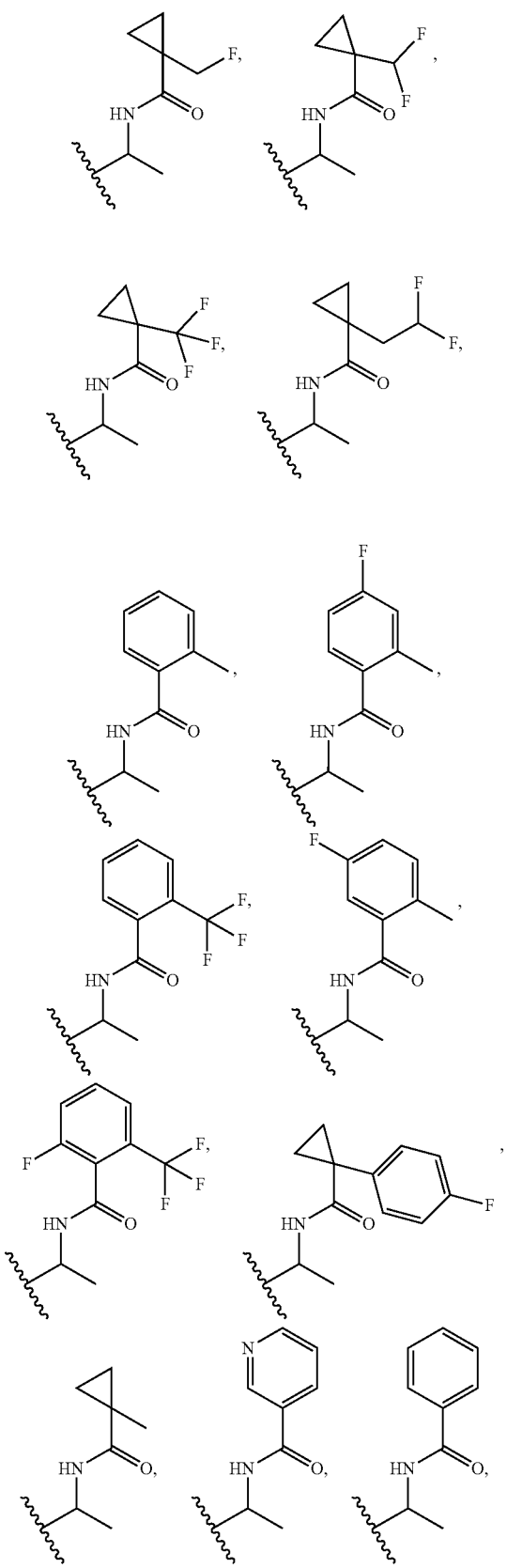

-continued
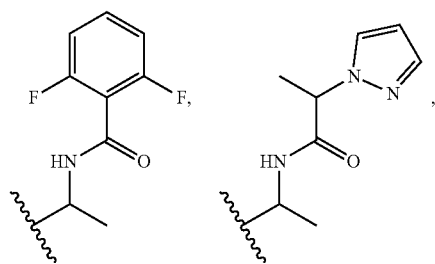
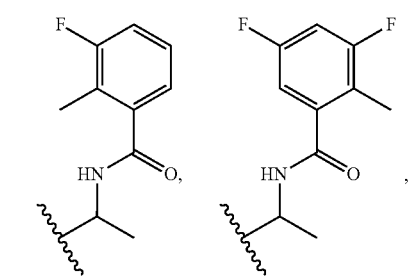
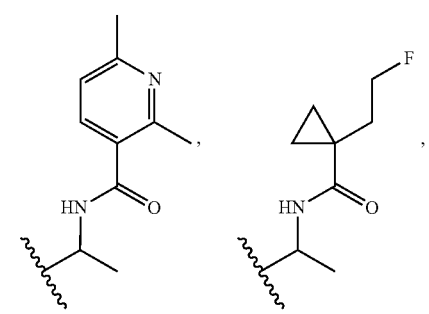
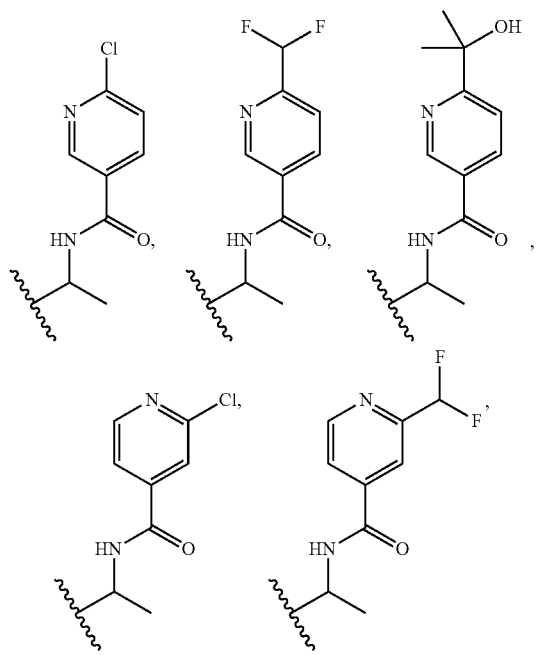
-continued
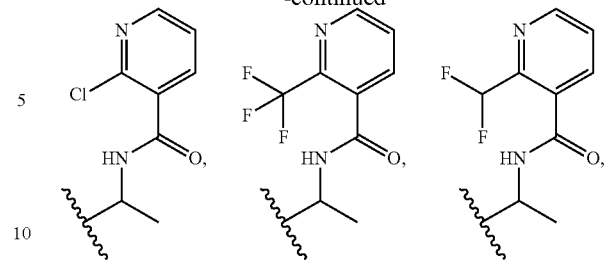
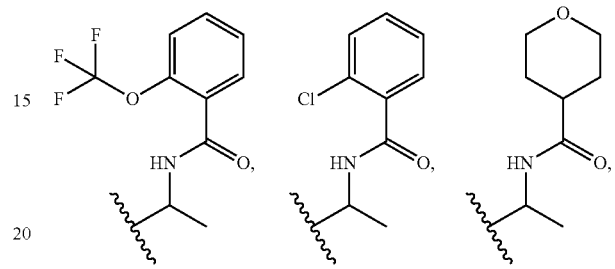
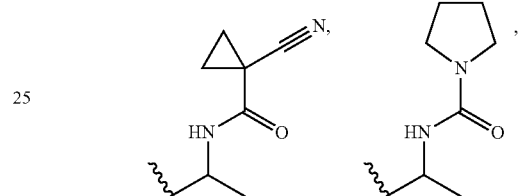
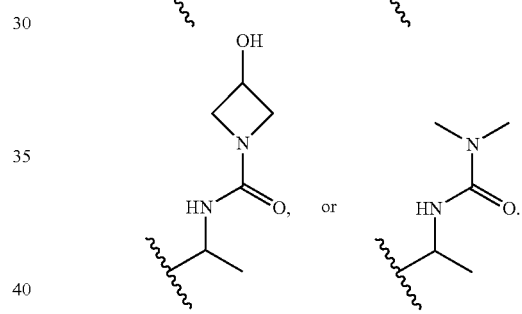
In certain embodiments, $R^6$ is
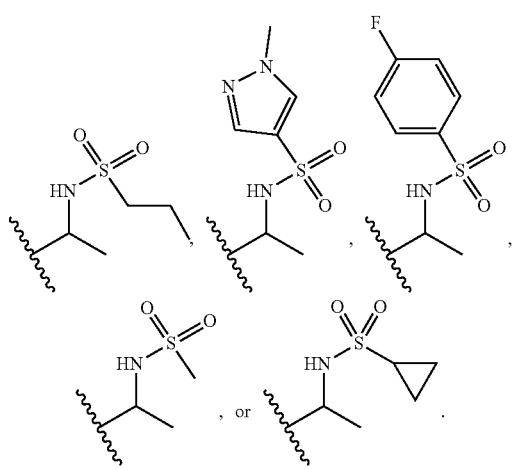
In certain embodiments, $R^{10}$ is hydrogen, $C_{1-8}$ alkyl optionally substituted with 1 to 3 $Z^{10}$, or $C_{3-6}$ cycloalkyl optionally substituted with 1 to 3 $Z^{10}$;

$R^{11}$ is $C_{1-8}$ alkyl optionally substituted with 1 to 4 $Z^{10}$, $C_{3-8}$ cycloalkyl optionally substituted with 1 to 4 $Z^{10}$, or 4-12-membered heterocyclyl optionally substituted with 1 to 4 $Z^{10}$; or $R^{10}$ and $R^{11}$ are taken together to form a 4-12-membered heterocyclyl optionally substituted with 1 to 4 $Z^{10}$.

In certain embodiments, $R^{10}$ is hydrogen or —CH$_3$, and $R^{11}$ is $C_{1-6}$ alkyl optionally substituted with 1 to 3 $Z^{10}$, $C_{3-6}$ cycloalkyl optionally substituted with 1 to 3 $Z^{10}$, or 4-12-membered heterocyclyl optionally substituted with 1 to 3 $Z^{10}$; or $R^{10}$ and $R^{11}$ taken together form a 4-10-membered heterocyclyl optionally substituted with 1 to 3 $Z^{10}$.

In certain embodiments, $R^{10}$ is hydrogen or —CH$_3$, and $R^{11}$ is 4-12 membered heterocyclyl optionally substituted with 1 to 3 $Z^{10}$.

In certain embodiments, $R^{10}$ and $R^{11}$ taken together form a 4-10 membered heterocyclyl optionally substituted with 1 to 3 $Z^{10}$.

In certain embodiments, the moiety

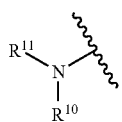

is

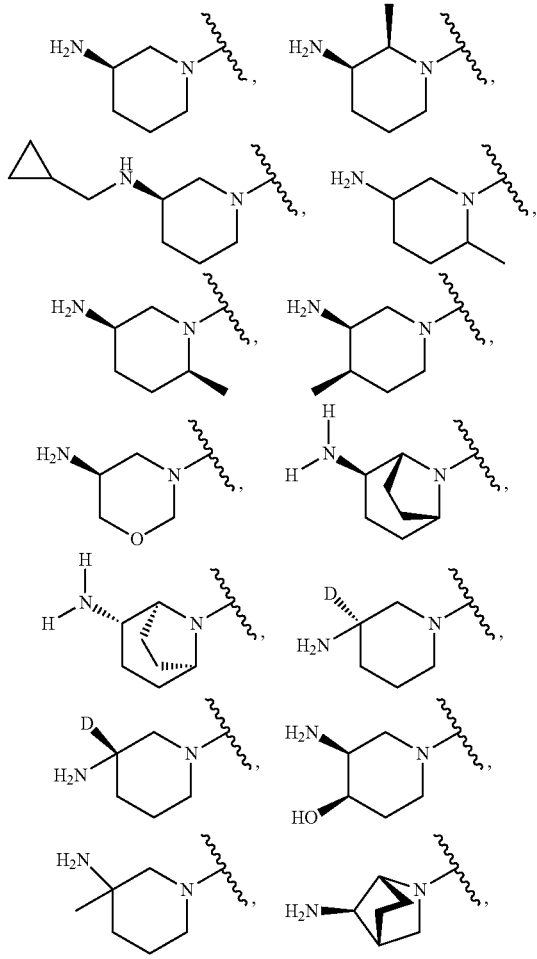

-continued

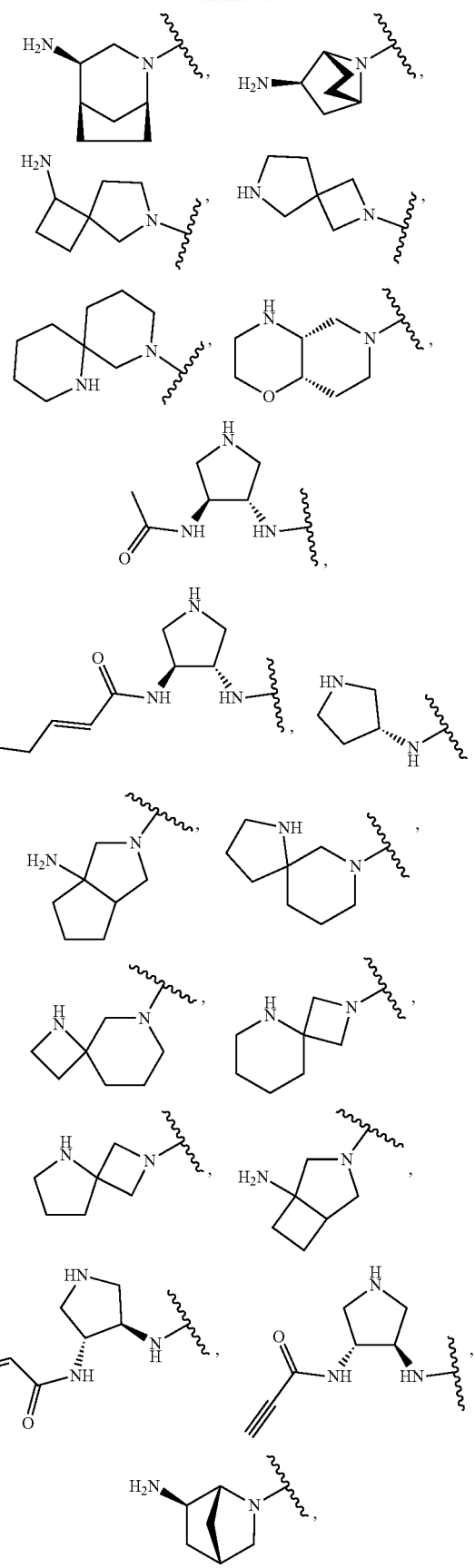

-continued
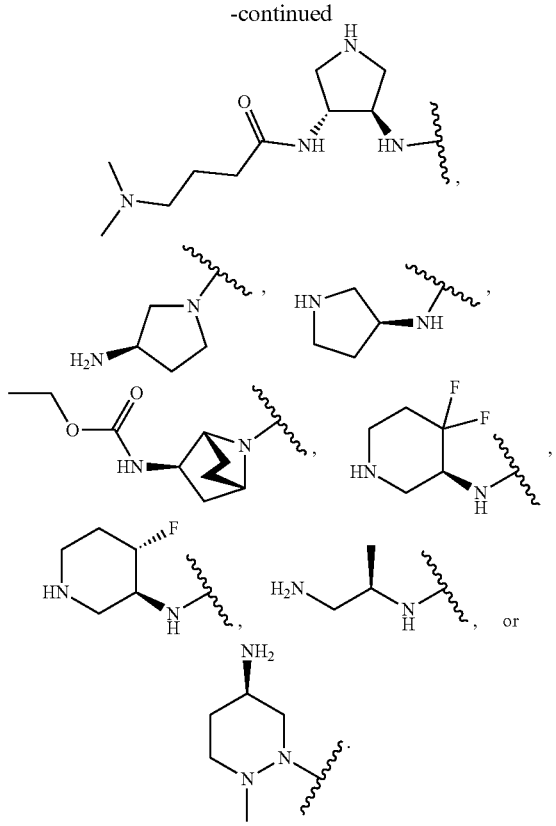
In certain embodiments, the moiety
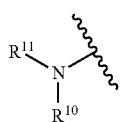
is
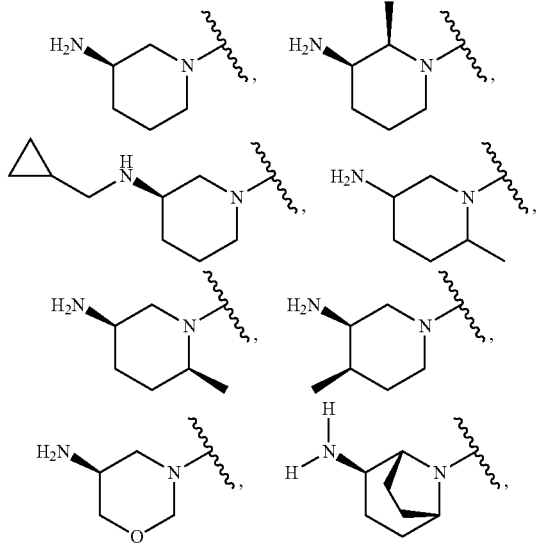
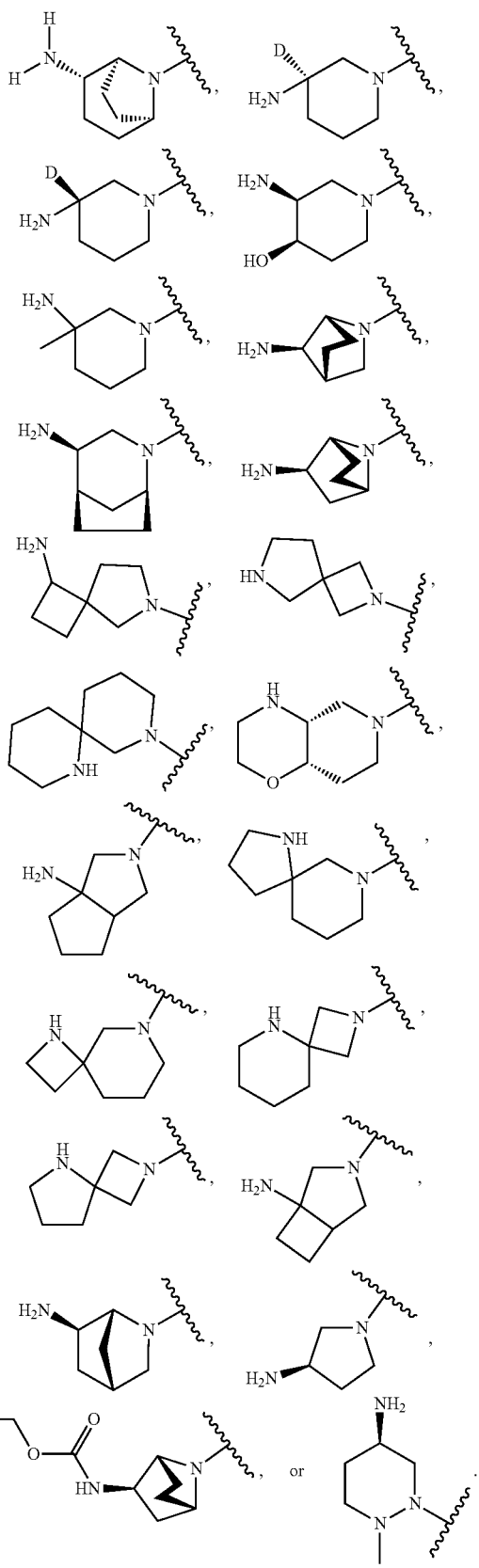

In certain embodiments, the moiety

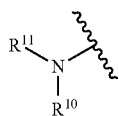

is

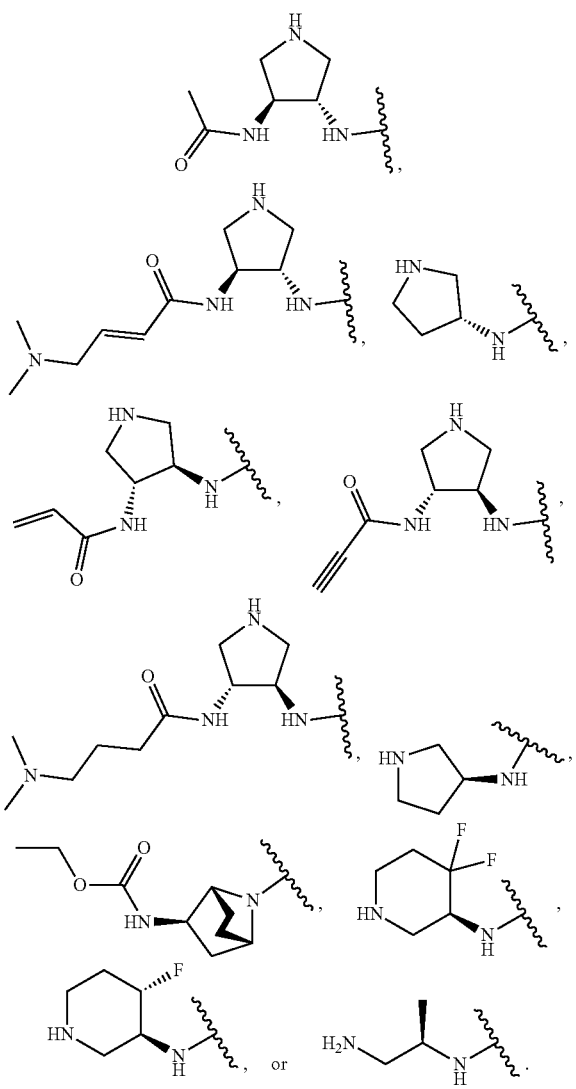

Also provided is a compound of Formula IA:

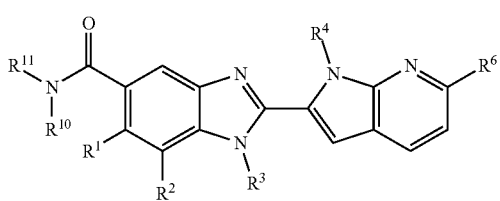

wherein each of $R^1$, $R^2$, $R^3$, $R^4$, $R^6$, $R^{10}$, and $R^{11}$ are independently as defined herein.

In certain embodiments, $R^1$ is hydrogen, halo or —$C_{1-8}$ alkyl optionally substituted with 1 to 3 $Z^1$. In certain embodiments, $R^1$ is hydrogen, fluoro, or methyl. In certain embodiments, $R^2$ is hydrogen, fluoro, chloro, or methoxy. In certain embodiments, $R^3$ is methyl,

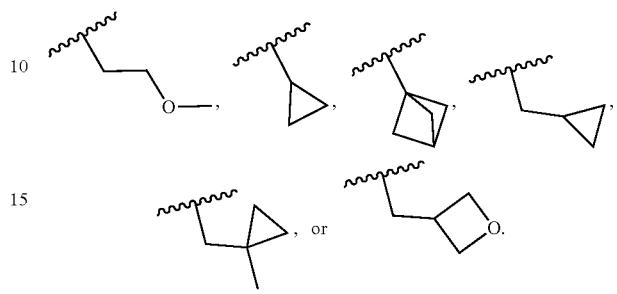

In certain embodiments, $R^4$ is

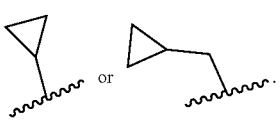

Also provided is a compound of Formula IB:

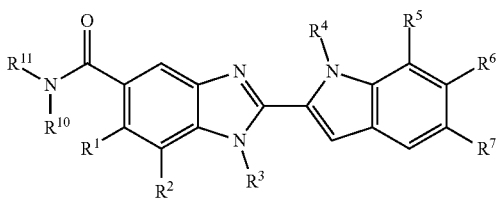

wherein each of $R^1$, $R^2$, $R^3$, $R^4$, $R^5$, $R^6$, $R^7$, $R^{10}$, and $R^{11}$ are independently as defined herein.

In certain embodiments, $R^1$ is hydrogen. In certain embodiments, $R^2$ is methoxy or fluoro. In certain embodiments, $R^2$ is methoxy. In certain embodiments, $R^3$ is methyl or cyclopropyl. In certain embodiments, $R^4$ is

In certain embodiments, $R^5$ is hydrogen.

In certain embodiments, $R^6$ is

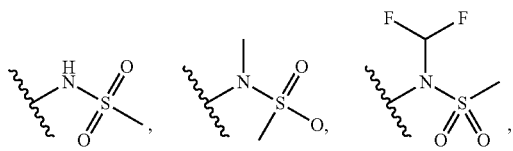

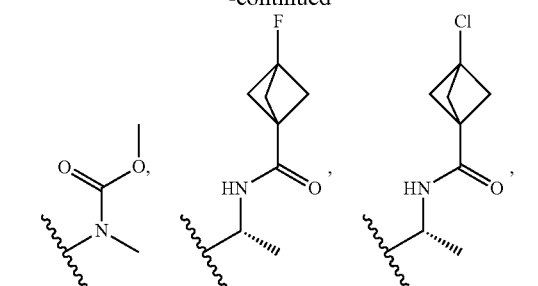
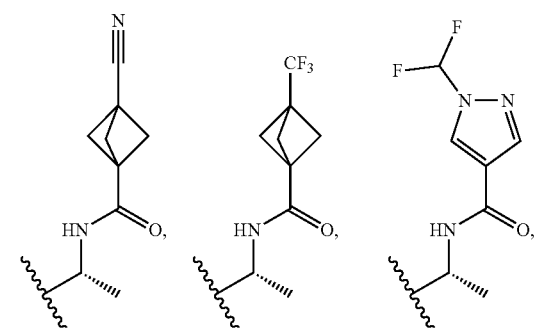
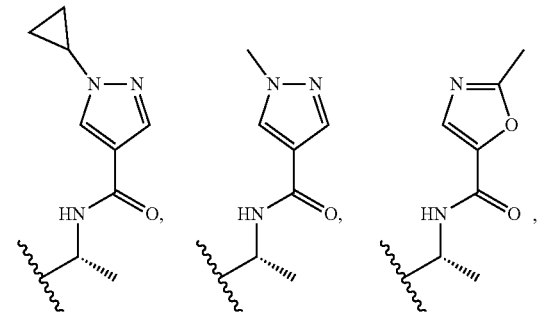
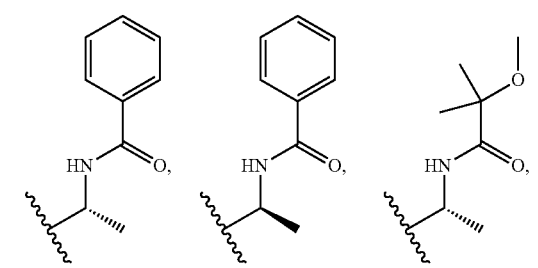
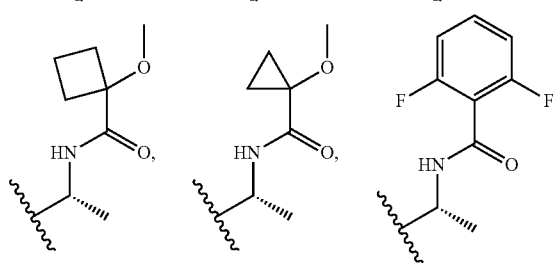
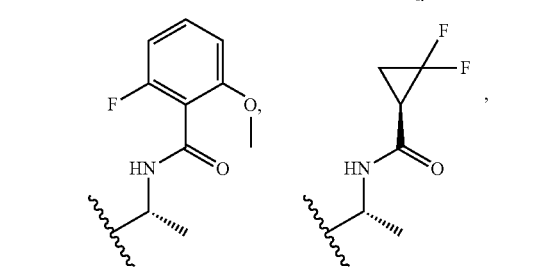
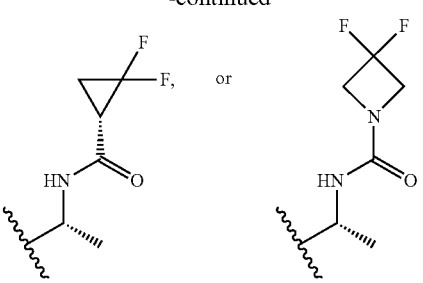
In certain embodiments, R⁷ is hydrogen.
In certain embodiments, the moiety
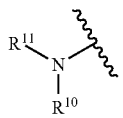
is
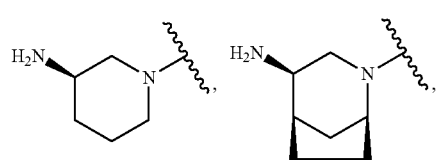
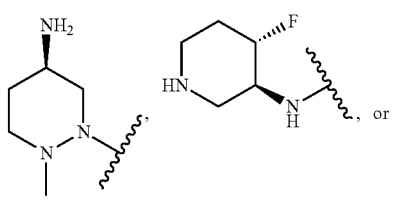
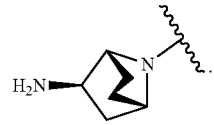
In certain embodiments, the moiety
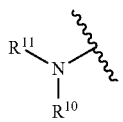
is
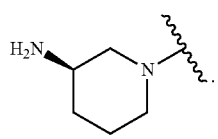

In certain embodiments, the moiety

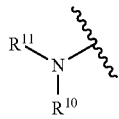

is

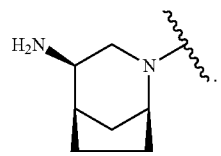

In certain embodiments, the moiety

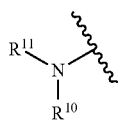

is

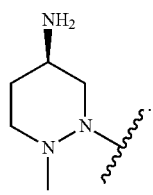 [SMILES: *N1C[C@H](N)CCN1C]

In certain embodiments, the moiety

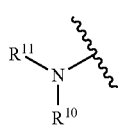

is

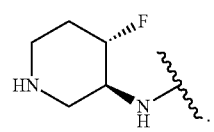

In certain embodiments, the moiety

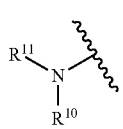

is

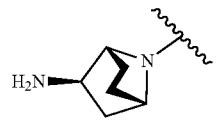

Also provided is a compound of Formula IC:

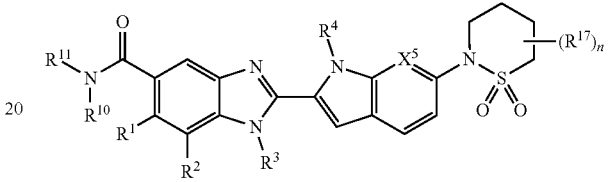

wherein each of n, $R^1$, $R^2$, $R^3$, $R^4$, $X^5$, $R^{17}$, $R^{10}$, $R^{11}$, and $R^{17}$ are independently as defined herein.

Also provided is a compound of Formula ID:

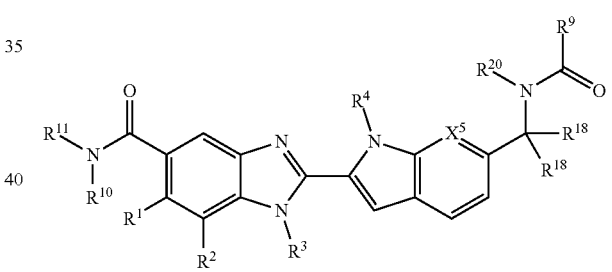

wherein each of $R^1$, $R^2$, $R^3$, $R^4$, $X^5$, $R^9$, $R^{10}$, $R^{11}$, $R^{18}$ and $R^{20}$ are independently as defined herein.

Also provided is a compound of Formula IE:

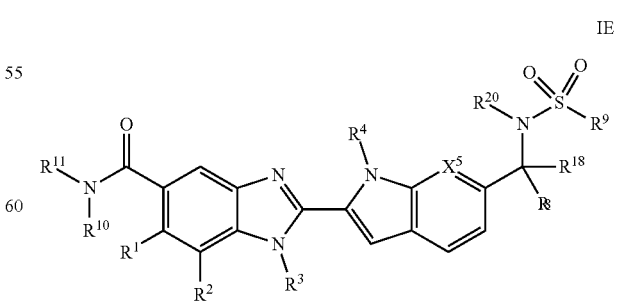

wherein each of $R^1$, $R^2$, $R^3$, $R^4$, $X^5$, $R^9$, $R^{10}$, $R^{11}$, $R^{18}$ and $R^{20}$ are independently as defined herein.

Also provided is a compound of Formula IF:

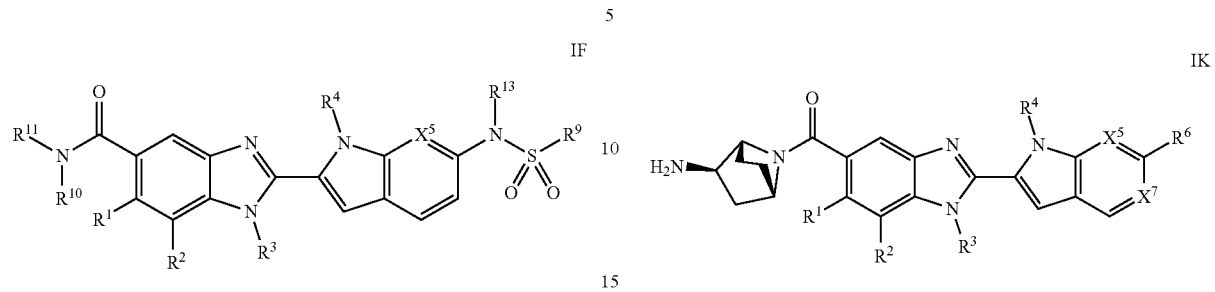

IF wherein each of $R^1$, $R^2$, $R^3$, $R^4$, $X^5$, $R^9$, $R^{10}$, $R^{11}$ and $R^{13}$ are independently as defined herein.

Also provided is a compound of Formula IG:

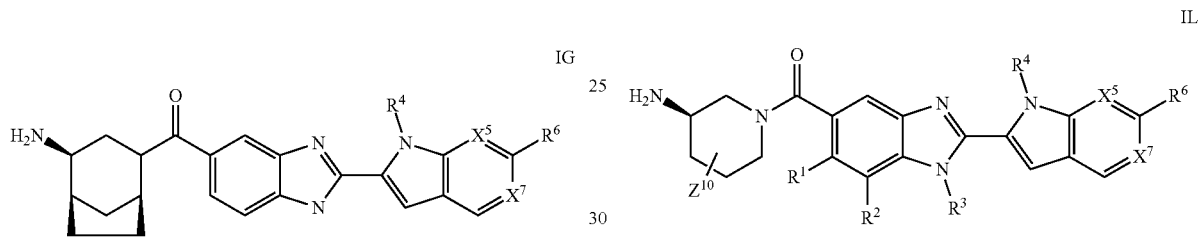

IG wherein each of $R^1$, $R^2$, $R^3$, $R^4$, $X^5$, $R^6$, and $X^7$ are independently as defined herein.

Also provided is a compound of Formula IH:

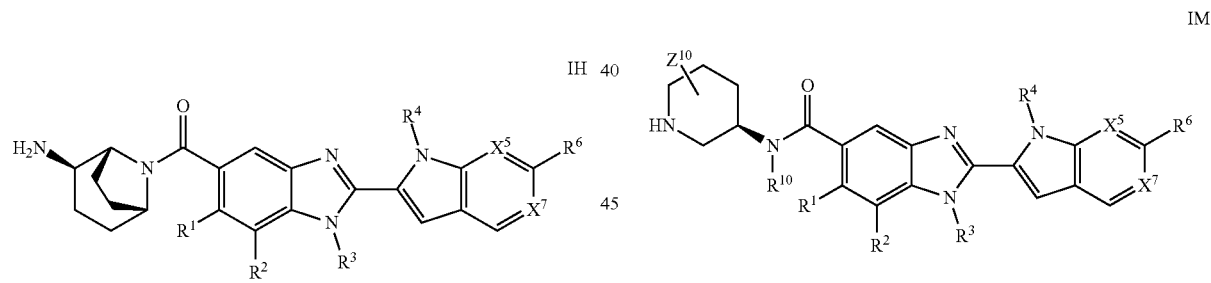

IH wherein each of $R^1$, $R^2$, $R^3$, $R^4$, $X^5$, $R^6$, and $X^7$ are independently as defined herein.

Also provided is a compound of Formula IJ:

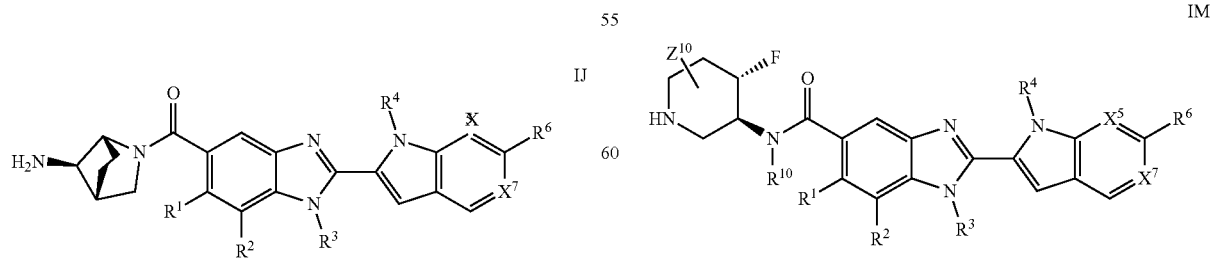

IJ wherein each of $R^1$, $R^2$, $R^3$, $R^4$, $X^5$, $R^6$, and $X^7$ are independently as defined herein.

Also provided is a compound of Formula IK:

IK wherein each of $R^1$, $R^2$, $R^3$, $R^4$, $X^5$, $R^6$, and $X^7$ are independently as defined herein.

Also provided is a compound of Formula IL:

IL wherein each of $Z^{10}$, $R^1$, $R^2$, $R^4$, $X^5$, $R^6$, and $X^7$ are independently as defined herein.

Also provided is a compound of Formula IM:

IM wherein each of $Z^{10}$, $R^1$, $R^2$, $R^4$, $X^5$, $R^6$, and $X^7$ are independently as defined herein.

Also provided is a compound of Formula IN:

IM wherein each of $Z^{10}$, $R^1$, $R^2$, $R^3$, $R^4$, $X^5$, $R^6$, and $X^7$ are independently as defined herein.

Also provided is a compound of Formula IO:

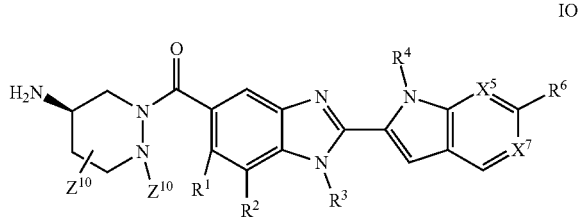

IO wherein each of $Z^{10}$, $R^1$, $R^2$, $R^3$, $R^4$, $X^5$, $R^6$, and $X^7$ are independently as defined herein.

In certain embodiments of a Formula IG-IO, $R^6$ is hydrogen, $C_{1-8}$ alkyl optionally substituted with 1 to 3 $Z^1$, $C_{3-10}$ alkenyl optionally substituted with 1 to 3 $Z^1$, $C_{3-10}$ alkynyl optionally substituted with 1 to 3 $Z^1$, $C_{3-10}$ cycloalkyl optionally substituted with 1 to 3 $Z^1$, or 4-10 membered heterocyclyl optionally substituted with 1 to 3 $Z^1$.

Also provided is a compound of Formula IP:

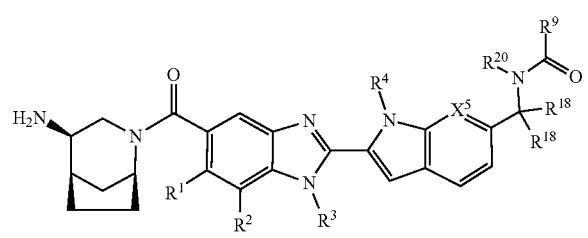

IP wherein each of $R^1$, $R^2$, $R^3$, $R^4$, $X^5$, $R^9$, $R^{18}$, and $R^{20}$ are independently as defined herein.

Also provided is a compound of Formula IQ:

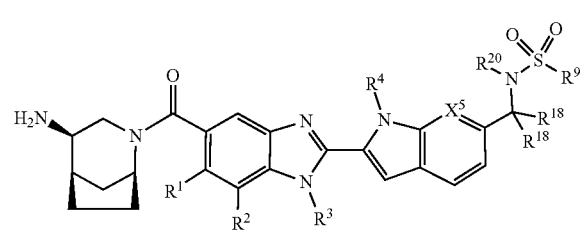

IQ wherein each of $R^1$, $R^2$, $R^3$, $R^4$, $X^5$, $R^9$, $R^{18}$, and $R^{20}$ are independently as defined herein.

Also provided is a compound of Formula IR:

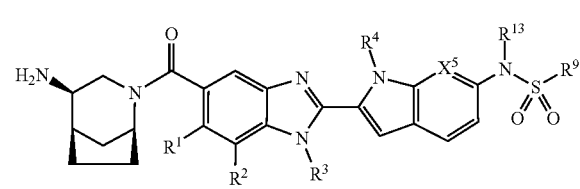

IR wherein each of $R^1$, $R^2$, $R^3$, $R^4$, $X^5$, $R^9$, and $R^{13}$ are independently as defined herein.

In certain embodiments, each of $R^1$, $R^2$, $R^3$, $R^4$, $X^5$, and $R^9$ are independently as defined herein, and $R^{13}$ is hydrogen, $C_{1-8}$ alkyl optionally substituted with 1 to 3 $Z^{1b}$, $C_{3-8}$ alkenyl optionally substituted with 1 to 3 $Z^{1b}$, $C_{3-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$.

Also provided is a compound of Formula IS:

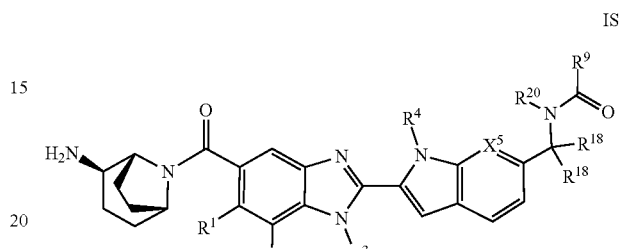

IS wherein each of $R^1$, $R^2$, $R^3$, $R^4$, $X^5$, $R^9$, $R^{18}$, and $R^{20}$ are independently as defined herein.

Also provided is a compound of Formula IT:


IT wherein each of $R^1$, $R^2$, $R^3$, $R^4$, $X^5$, $R^9$, $R^{18}$, and $R^{20}$ are independently as defined herein.

Also provided is a compound of Formula IU:

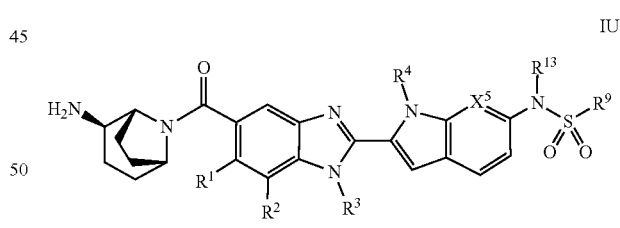

IU wherein each of $R^1$, $R^2$, $R^3$, $R^4$, $X^5$, $R^9$, and $R^{13}$ are independently as defined herein.

In certain embodiments, each of $R^1$, $R^2$, $R^3$, $R^4$, $X^5$, and $R^9$ are independently as defined herein, and $R^{13}$ is hydrogen, $C_{1-8}$ alkyl optionally substituted with 1 to 3 $Z^{1b}$, $C_{3-8}$ alkenyl optionally substituted with 1 to 3 $Z^{1b}$, $C_{3-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$.

In certain embodiments, each $Z^1$ is independently halo, $-NO_2$, $-N_3$, $-CN$, $C_{1-8}$ alkyl optionally substituted by 1 to 3 $Z^{1b}$, $C_{2-8}$ alkenyl optionally substituted by 1 to 3 $Z^{1b}$, $C_{2-8}$ alkynyl optionally substituted by 1 to 3 $Z^{1b}$, $C_{3-8}$ cycloalkyl optionally substituted by 1 to 3 $Z^{1b}$, 6-10 membered aryl optionally substituted by 1 to 3 $Z^{1b}$, 4-10 membered heterocyclyl optionally substituted by 1 to 3 $Z^{1b}$, 5-10 membered heteroaryl optionally substituted with 1 to 3 $Z^{1b}$, —$OR^{20}$, —$C(O)R^{20}$, —$C(O)OR^{20}$, —$C(O)N(R^{20})_2$, —$N(R^{20})_2$, —$N(R^{20})_3{}^+$, —$N(R^{20})C(O)R^{20}$, —$N(R^{20})C(O)OR^{20}$, —$N(R^{20})C(O)N(R^{20})_2$, —$N(R^{20})S(O)_2(R^{20})$, —$NR^{20}S(O)_2N(R^{20})_2$, —$NR^{20}S(O)_2O(R^{20})$, —$NS(O)(R^{20})_2$, —$OC(O)R^{20}$, —$OC(O)OR^{20}$, —$OC(O)N(R^{20})_2$, —$Si(R^{20})_3$, —$SR^{20}$, —$S(O)R^{20}$, —$SF_5$, —$S(O)(NR^{20})R^{20}$, —$S(NR^{20})(NR^{20})R^{20}$, —$S(O)(NR^{20})N(R^{20})_2$, —$S(O)(NCN)R^{20}$, —$S(O)_2R^{20}$, —$S(O)_2N(R^{20})_2$, —$C(O)N(R^{20})S(O)_2R^{20}$, or —$S(O)_2N(R^{20})C(O)R^{20}$;

each $Z^{10}$ is independently selected from oxo, halo, —CN, $C_{1-8}$ alkyl optionally substituted by 1 to 3 $Z^{1b}$, $C_{3-8}$ cycloalkyl optionally substituted by 1 to 3 $Z^{1b}$, aryl optionally substituted by 1 to 3 $Z^{1b}$, 4-10 membered heterocyclyl optionally substituted by 1 to 3 $Z^{1b}$, 5-10 membered heteroaryl optionally substituted with 1 to 3 $Z^{1b}$, —$OR^{22}$, —$C(O)R^{22}$, —$C(O)OR^{22}$, —$C(O)N(R^{22})_2$, —$N(R^{22})_2$, —$N(R^{22})_3{}^+$, —$N(R^{22})C(O)R^{22}$, —$N(R^{22})C(O)OR^{22}$, —$N(R^{22})C(O)N(R^{22})_2$, —$N(R^{22})S(O)_2R^{22}$, —$OC(O)R^{22}$, —$OC(O)OR^{22}$, —$OC(O)—N(R^{22})_2$, and —$S—R^{22}$; and each $R^{20}$ and $R^{22}$ is independently hydrogen, $C_{1-8}$ alkyl optionally substituted with 1 to 3 $Z^{1b}$, $C_{2-8}$ alkenyl optionally substituted with 1 to 3 $Z^{1b}$, $C_{2-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$.

In certain embodiments, each $Z^1$ is independently hydroxy, halo, —$NO_2$, —$N_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, $C_{6-10}$ aryl, 5-10 membered heteroaryl heteroaryl, 4-10 membered heterocyclyl, —$O(C_{1-9}$ alkyl), —$O(C_{2-6}$ alkenyl), —$O(C_{2-6}$ alkynyl), —$O(C_{3-15}$ cycloalkyl), —$O(C_{1-8}$ haloalkyl), —O(aryl), —O(heteroaryl), —O(heterocyclyl), —$OC(O)(C_{1-9}$ alkyl), —$OC(O)(C_{2-6}$ alkenyl), —$OC(O)(C_{2-6}$ alkenyl), —$OC(O)(C_{2-6}$ alkynyl), —$OC(O)(C_{3-15}$ cycloalkyl), —$OC(O)(C_{1-8}$ haloalkyl), —OC(O)(aryl), —OC(O)(heteroaryl), —OC(O)(heterocyclyl), —$NH_2$, —$NH(C_{1-9}$ alkyl), —$NH(C_{2-6}$ alkenyl), —$NH(C_{2-6}$ alkynyl), —$NH(C_{3-15}$ cycloalkyl), —$NH(C_{1-8}$ haloalkyl), —NH(aryl), —NH(heteroaryl), —NH(heterocyclyl), —$N(C_{1-9}$ alkyl)$_2$, —$N(C_{3-15}$ cycloalkyl)$_2$, —$N(C_{2-6}$ alkenyl)$_2$, —$N(C_{2-6}$ alkynyl)$_2$, —$N(C_{3-15}$ cycloalkyl)$_2$, —$N(C_{1-8}$ haloalkyl)$_2$, —N(aryl)$_2$, —N(heteroaryl)$_2$, —N(heterocyclyl)$_2$, —$N(C_{1-9}$ alkyl)($C_{3-15}$ cycloalkyl), —$N(C_{1-9}$ alkyl)($C_{2-6}$ alkenyl), —$N(C_{1-9}$ alkyl)($C_{2-6}$ alkynyl), —$N(C_{1-9}$ alkyl)($C_{3-15}$ cycloalkyl), —$N(C_{1-9}$ alkyl)($C_{1-8}$ haloalkyl), —$N(C_{1-9}$ alkyl)(aryl), —$N(C_{1-9}$ alkyl)(heteroaryl), —$N(C_{1-9}$ alkyl)(heterocyclyl), —$C(O)(C_{1-9}$ alkyl), —$C(O)(C_{2-6}$ alkenyl), —$C(O)(C_{2-6}$ alkynyl), —$C(O)(C_{3-15}$ cycloalkyl), —$C(O)(C_{1-8}$ haloalkyl), —C(O)(aryl), —C(O)(heteroaryl), —C(O)(heterocyclyl), —$C(O)O(C_{1-9}$ alkyl), —$C(O)O(C_{2-6}$ alkenyl), —$C(O)O(C_{2-6}$ alkynyl), —$C(O)O(C_{3-15}$ cycloalkyl), —$C(O)O(C_{1-8}$ haloalkyl), —C(O)O(aryl), —C(O)O(heteroaryl), —C(O)O(heterocyclyl), —$C(O)NH_2$, —$C(O)NH(C_{1-9}$ alkyl), —$C(O)NH(C_{2-6}$ alkenyl), —$C(O)NH(C_{2-6}$ alkynyl), —$C(O)NH(C_{3-15}$ cycloalkyl), —$C(O)NH(C_{1-8}$ haloalkyl), —C(O)NH(aryl), —C(O)NH(heteroaryl), —C(O)NH(heterocyclyl), —$C(O)N(C_{1-9}$ alkyl)$_2$, —$C(O)N(C_{3-15}$ cycloalkyl)$_2$, —$C(O)N(C_{2-6}$ alkenyl)$_2$, —$C(O)N(C_{2-6}$ alkynyl)$_2$, —$C(O)N(C_{1-8}$ haloalkyl)$_2$, —$C(O)N(aryl)_2$, —C(O)N(heteroaryl)$_2$, —C(O)N(heterocyclyl)$_2$, —$NHC(O)(C_{1-9}$ alkyl), —$NHC(O)(C_{2-6}$ alkenyl), —$NHC(O)(C_{2-6}$ alkynyl), —$NHC(O)(C_{3-15}$ cycloalkyl), —$NHC(O)(C_{1-8}$ haloalkyl), —NHC(O)(aryl), —NHC(O)(heteroaryl), —NHC(O)(heterocyclyl), —$NHC(O)O(C_{1-9}$ alkyl), —$NHC(O)O(C_{2-6}$ alkenyl), —$NHC(O)O(C_{2-6}$ alkynyl), —$NHC(O)O(C_{3-15}$ cycloalkyl), —$NHC(O)O(C_{1-8}$ haloalkyl), —NHC(O)O(aryl), —NHC(O)O(heteroaryl), —NHC(O)O(heterocyclyl), —$NHC(O)NH(C_{1-9}$ alkyl), —$NHC(O)NH(C_{2-6}$ alkenyl), —$NHC(O)NH(C_{2-6}$ alkynyl), —$NHC(O)NH(C_{3-15}$ cycloalkyl), —$NHC(O)NH(C_{1-8}$ haloalkyl), —NHC(O)NH(aryl), —NHC(O)NH(heteroaryl), —NHC(O)NH(heterocyclyl), —SH, —$S(C_{1-9}$ alkyl), —$S(C_{2-6}$ alkenyl), —$S(C_{2-6}$ alkynyl), —$S(C_{3-15}$ cycloalkyl), —$S(C_{1-8}$ haloalkyl), —S(aryl), —S(heteroaryl), —S(heterocyclyl), —$NHS(O)(C_{1-9}$ alkyl), —$N(C_{1-9}$ alkyl)($S(O)(C_{1-9}$ alkyl), —$S(O)N(C_{1-9}$ alkyl)$_2$, —$S(O)(C_{1-9}$ alkyl), —$S(O)(NH)(C_{1-9}$ alkyl), —$S(O)(C_{2-6}$ alkenyl), —$S(O)(C_{2-6}$ alkynyl), —$S(O)(C_{3-15}$ cycloalkyl), —$S(O)(C_{1-8}$ haloalkyl), —S(O)(aryl), —S(O)(heteroaryl), —S(O)(heterocyclyl), —$S(O)_2(C_{1-9}$ alkyl), —$S(O)_2(C_{2-6}$ alkenyl), —$S(O)_2(C_{2-6}$ alkynyl), —$S(O)_2(C_{3-15}$ cycloalkyl), —$S(O)_2(C_{1-8}$ haloalkyl), —$S(O)_2(aryl)$, —$S(O)_2(heteroaryl)$, —$S(O)_2(heterocyclyl)$, —$S(O)_2NH(C_{1-9}$ alkyl), or —$S(O)_2N(C_{1-9}$ alkyl)$_2$; wherein any alkyl, cycloalkyl, aryl, heteroaryl, or heterocyclyl of $Z^{1b}$ is optionally substituted with one or more halo, $C_{1-9}$ alkyl, $C_{1-8}$ haloalkyl, —OH, —$NH_2$, —$NH(C_{1-9}$ alkyl), —$NH(C_{3-15}$ cycloalkyl), —$NH(C_{1-8}$ haloalkyl), —NH(aryl), —NH(heteroaryl), —NH(heterocyclyl), —$N(C_{1-9}$ alkyl)$_2$, —$N(C_{3-15}$ cycloalkyl)$_2$, —$NHC(O)(C_{3-15}$ cycloalkyl), —$NHC(O)(C_{1-8}$ haloalkyl), —NHC(O)(aryl), —NHC(O)(heteroaryl), —NHC(O)(heterocyclyl), —$NHC(O)O(C_{1-9}$ alkyl), —$NHC(O)O(C_{2-6}$ alkynyl), —$NHC(O)O(C_{3-15}$ cycloalkyl), —$NHC(O)O(C_{1-8}$ haloalkyl), —NHC(O)O(aryl), —NHC(O)O(heteroaryl), —NHC(O)O(heterocyclyl), —$NHC(O)NH(C_{1-9}$ alkyl), —$S(O)(NH)(C_{1-9}$ alkyl), —$S(O)_2(C_{1-9}$ alkyl), —$S(O)_2(C_{3-15}$ cycloalkyl), —$S(O)_2(C_{1-8}$ haloalkyl), —$S(O)_2(aryl)$, —$S(O)_2(heteroaryl)$, —$S(O)_2(heterocyclyl)$, —$S(O)_2NH(C_{1-9}$ alkyl), —$S(O)_2N(C_{1-9}$ alkyl)$_2$, —$O(C_{3-15}$ cycloalkyl), —$O(C_{1-8}$ haloalkyl), —O(aryl), —O(heteroaryl), —O(heterocyclyl), or —$O(C_{1-9}$ alkyl).

In certain embodiments, $R^9$ is $C_{1-8}$ alkyl optionally substituted with 1 to 3 $Z^1$. In certain embodiments, $R^9$ is $C_{2-8}$ alkenyl optionally substituted with 1 to 3 $Z^1$. In certain embodiments, $R^9$ is $C_{2-8}$ alkynyl optionally substituted with 1 to 3 $Z^1$. In certain embodiments, $R^9$ is $C_{3-10}$ cycloalkyl optionally substituted with 1 to 3 $Z^1$. In certain embodiments, $R^9$ is 4-10 membered heterocyclyl optionally substituted with 1 to 3 $Z^1$. In certain embodiments, $R^9$ is $C_{6-10}$ aryl optionally substituted with 1 to 3 $Z^1$. In certain embodiments, $R^9$ is or 5-10 membered heteroaryl optionally substituted with 1 to 3 $Z^1$.

In certain embodiments, each $R^{12}$ is independently hydrogen, $C_{1-8}$ alkyl optionally substituted with 1 to 3 $Z^{1b}$, $C_{3-8}$ alkenyl optionally substituted with 1 to 3 $Z^{1b}$, or $C_{3-8}$ alkynyl optionally substituted with 1 to 3 $Z^{1b}$. In certain embodiments, each $R^{12}$ is independently hydrogen, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$. In certain embodiments, each $R^{12}$ is independently hydrogen, $C_{1-8}$ alkyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$.

In certain embodiments, each $R^{12}$ is independently hydrogen, $C_{1-8}$ alkyl optionally substituted with 1 to 3 $Z^{1b}$, $C_{3-10}$ cycloalkyl optionally substituted with 1 to 3 $Z^{1b}$, or 4-10 membered heterocyclyl optionally substituted with 1 to 3 $Z^{1b}$. In certain embodiments, at least one $R^{12}$ is hydrogen.

In certain embodiments, $R^{13}$ is $C_{1-8}$ alkyl optionally substituted with 1 to 3 $Z^{1b}$. In certain embodiments, $R^{13}$ is $C_{3-8}$ alkenyl optionally substituted with 1 to 3 $Z^{1b}$. In certain embodiments, $R^{13}$ is $C_{3-8}$ alkynyl optionally substituted with 1 to 3 $Z^{1b}$. In certain embodiments, $R^{13}$ is $C_{3-10}$ cycloalkyl optionally substituted with 1 to 3 $Z^{1b}$. In certain embodiments, $R^{13}$ is 4-10 membered heterocyclyl optionally substituted with 1 to 3 $Z^{1b}$. In certain embodiments, $R^{13}$ is $C_{6-10}$ aryl optionally substituted with 1 to 3 $Z^{1b}$. In certain embodiments, $R^{13}$ is 5-10 membered heteroaryl optionally substituted with 1 to 3 $Z^{1b}$. In certain embodiments, $R^{13}$ is methyl.

In certain embodiments, each $R^{17}$ is independently hydrogen, halo, —NO$_2$, —N$_3$, —CN, $C_{1-8}$ alkyl optionally substituted by 1 to 3 $Z^{1a}$, $C_{2-8}$ alkenyl optionally substituted by 1 to 3 $Z^{1a}$, $C_{2-8}$ alkynyl optionally substituted by 1 to 3 $Z^{1a}$, $C_{3-8}$ cycloalkyl optionally substituted by 1 to 3 $Z^{1a}$, 6-10 membered aryl optionally substituted by 1 to 3 $Z^{1a}$, 4-10 membered heterocyclyl optionally substituted by 1 to 3 $Z^{1a}$, or 5-10 membered heteroaryl optionally substituted with 1 to 3 $Z^{1a}$. In certain embodiments, each $R^{17}$ is independently hydrogen, $C_{1-8}$ alkyl optionally substituted by 1 to 3 $Z^{1a}$, or $C_{3-8}$ cycloalkyl optionally substituted by 1 to 3 $Z^{1a}$. In certain embodiments, each $R^{17}$ is independently hydrogen, $C_{1-8}$ alkyl optionally substituted by 1 to 3 halo, or $C_{3-8}$ cycloalkyl. In certain embodiments, each $R^{17}$ is independently hydrogen, $C_{1-8}$ alkyl, or $C_{3-8}$ cycloalkyl. In certain embodiments, each $R^{17}$ is independently hydrogen or $C_{1-8}$ alkyl optionally substituted by 1 to 3 $Z^{1a}$. In certain embodiments, each $R^{17}$ is independently hydrogen or $C_{1-8}$ alkyl. In certain embodiments, each $R^{17}$ is independently hydrogen or methyl. In certain embodiments, each $R^{17}$ is methyl. In certain embodiments, two $R^{17}$ on the same or different carbon atoms are taken together to form a 3-8-membered ring optionally substituted with 1 to 4 $Z^1$.

In certain embodiments, each $R^{18}$ is independently hydrogen, or $Z^1$. In certain embodiments, each $R^{18}$ is independently hydrogen, $C_{1-8}$ alkyl optionally substituted with 1 to 5 $Z^{1a}$, $C_{2-8}$ alkenyl optionally substituted with 1 to 5 $Z^{1a}$, $C_{2-8}$ alkynyl optionally substituted with 1 to 5 $Z^{1a}$, $C_{3-10}$ cycloalkyl optionally substituted with 1 to 5 $Z^{1a}$, 4-10 membered heterocyclyl optionally substituted with 1 to 5 $Z^{1a}$, $C_{6-10}$ aryl optionally substituted with 1 to 5 $Z^{1a}$, or 5-10 membered heteroaryl optionally substituted with 1 to 5 $Z^{1a}$. In certain embodiments, each $R^{18}$ is independently hydrogen or $C_{1-8}$ alkyl optionally substituted with 1 to 5 $Z^1$. In certain embodiments, each $R^{18}$ is independently hydrogen or $C_{1-8}$ alkyl optionally substituted with 1 to 5 halo. In certain embodiments, each $R^{18}$ is independently hydrogen or $C_{1-8}$ alkyl. In certain embodiments, each $R^{18}$ is independently hydrogen or methyl. In certain embodiments, one $R^{18}$ is hydrogen and the other is methyl. In certain embodiments, each $R^{18}$ is methyl. In certain embodiments, each $R^{18}$ is hydrogen.

In certain embodiments, $R^{20}$ is hydrogen or $C_{1-8}$ alkyl optionally substituted by 1 to 3 $Z^{1a}$. In certain embodiments, $R^{20}$ is hydrogen or $C_{1-8}$ alkyl. In certain embodiments, $R^{20}$ is hydrogen or methyl. In certain embodiments, $R^{20}$ is methyl. In certain embodiments, $R^{20}$ is hydrogen.

In certain embodiments, each $Z^1$ is independently oxo, hydroxy, fluoro, chloro, —CN, —CH$_3$, ethyl, isopropyl, tert-butyl, —CF$_3$, —CHF$_2$, cyclopropyl, cyclobutyl, —OCH$_3$, —O-ethyl, —O-isopropyl, —O-cyclopropyl, —OCF$_3$, —OCF$_2$H, —C(O)-alkyl, —C(O)-cycloalkyl, —C(O)-aryl, —C(O)-heteroaryl, or —NH$_2$.

In certain embodiments, each $Z^1$ is independently halo, oxo, —CN, $C_{1-6}$ alkyl optionally substituted by 1 to 3 $Z^{1a}$, $C_{3-6}$ cycloalkyl optionally substituted with 1 to 3 $Z^{1b}$, 4-6 membered heterocyclyl having 1 to 2 heteroatoms selected from O and N that is optionally substituted by 1 to 3 $Z^{1a}$, 5-6 membered heteroaryl having 1 to 4 heteroatoms selected from O and N and optionally substituted with 1 to 3 $Z^{1a}$, —OR$^{12}$, —N(R$^{12}$)$_2$, —C(O)R$^{12}$, N(R$^{12}$)C(O)R$^{12}$, —N(R$^{12}$)C(O)OR$^{12}$, —N(R$^{12}$)S(O)$_2$R$^{12}$, —OC(O)R$^{12}$, —OC(O)OR$^{12}$, —OC(O)N(R$^{12}$)$_2$, or —S(O)$_2$R$^{12}$.

In certain embodiments, each $Z^1$ is independently fluoro, chloro, —CN, $C_{1-6}$ alkyl optionally substituted with 1 to 3 $Z^{1b}$, $C_{3-6}$ cycloalkyl optionally substituted by 1 to 3 $Z^{1b}$, —OR$^{12}$, —N(R$^{12}$)$_2$, —C(O)R$^{12}$, N(R$^{12}$)C(O)R$^{12}$, —N(R$^{12}$)C(O)OR$^{12}$, —N(R$^{12}$)S(O)$_2$R$^{12}$, —OC(O)R$^{12}$, —OC(O)OR$^{12}$, —OC(O)N(R$^{12}$)$_2$, or —S(O)$_2$R$^{12}$.

In certain embodiments, each $Z^1$ is independently oxo, hydroxy, fluoro, chloro, —CN, —CH$_3$, ethyl, isopropyl, tert-butyl, —CF$_3$, —CHF$_2$, cyclopropyl, cyclobutyl, —OCH$_3$, —O-ethyl, —O-isopropyl, —O-cyclopropyl, —OCF$_3$, —OCF$_2$H, —C(O)-alkyl, —C(O)-cycloalkyl, —C(O)-aryl, —C(O)-heteroaryl, or —NH$_2$.

In certain embodiments, each $Z^1$ is independently fluoro, chloro, —CN, —OH, —OCH$_3$, —OCHF$_2$, —OCF$_3$, —CH$_3$, —CHF$_2$, —CF$_3$, —CH$_2$OH, —CH$_2$OCH$_3$, or —NH$_2$.

In certain embodiments, each $Z^1$ is independently halo, oxo, —CN, $C_{1-6}$ alkyl optionally substituted by 1 to 3 $Z^{1a}$, $C_{3-6}$ cycloalkyl optionally substituted with 1 to 3 $Z^{1b}$, 4-6 membered heterocyclyl having 1 to 2 heteroatoms selected from O and N that is optionally substituted by 1 to 3 $Z^{1a}$, 5-6 membered heteroaryl having 1 to 4 heteroatoms selected from O and N and optionally substituted with 1 to 3 $Z^{1a}$, —OR$^{12}$, —N(R$^{12}$)$_2$, —C(O)R$^{12}$, —N(R$^{12}$)C(O)R$^{12}$, —N(R$^{12}$)C(O)OR$^{12}$, —N(R$^{12}$)S(O)$_2$R$^{12}$, —OC(O)R$^{12}$, —OC(O)OR$^{12}$, —OC(O)N(R$^{12}$)$_2$, or —S(O)$_2$R$^{12}$.

In certain embodiments, each $Z^1$ is independently oxo, hydroxy, fluoro, chloro, —CN, —CH$_3$, ethyl, isopropyl, tert-butyl, —CF$_3$, —CHF$_2$, cyclopropyl, cyclobutyl, —OCH$_3$, —O-ethyl, —O-isopropyl, —O-cyclopropyl, —OCF$_3$, —OCF$_2$H, —C(O)-alkyl, —C(O)-cycloalkyl, —C(O)-aryl, —C(O)-heteroaryl, or —NH$_2$.

In certain embodiments, each $Z^1$ is independently halo, oxo, —CN, $C_{1-6}$ alkyl optionally substituted by 1 to 3 $Z^{1a}$, $C_{3-6}$ cycloalkyl optionally substituted with 1 to 3 $Z^{1b}$, 4-6 membered heterocyclyl having 1 to 2 heteroatoms selected from O and N that is optionally substituted by 1 to 3 $Z^{1a}$, 5-6 membered heteroaryl having 1 to 4 heteroatoms selected from O and N and optionally substituted with 1 to 3 $Z^{1a}$, —OR$^{12}$, —N(R$^{12}$)$_2$, —C(O)R$^{12}$, N(R$^{12}$)C(O)R$^{12}$, —N(R$^{12}$)C(O)OR$^{12}$, —N(R$^{12}$)S(O)$_2$R$^{12}$, —OC(O)R$^{12}$, —OC(O)OR$^{12}$, —OC(O)N(R$^{12}$)$_2$, or —S(O)$_2$R$^{12}$.

In certain embodiments, each $Z^1$ is independently oxo, hydroxy, fluoro, chloro, —CN, —CH$_3$, ethyl, isopropyl, tert-butyl, —CF$_3$, —CHF$_2$, cyclopropyl, cyclobutyl, —OCH$_3$, —O-ethyl, —O-isopropyl, —O-cyclopropyl, —OCF$_3$, —OCF$_2$H, —C(O)-alkyl, —C(O)-cycloalkyl, —C(O)-aryl, —C(O)-heteroaryl, or —NH$_2$.

In certain embodiments, each $Z^1$ is independently halo, oxo, —CN, $C_{1-6}$ alkyl optionally substituted by 1 to 3 $Z^{1a}$, $C_{3-6}$ cycloalkyl optionally substituted with 1 to 3 $Z^{1b}$, 4-6 membered heterocyclyl having 1 to 2 heteroatoms selected from O and N that is optionally substituted by 1 to 3 $Z^{1a}$, 5-6 membered heteroaryl having 1 to 4 heteroatoms selected from O and N optionally substituted with 1 to 3 $Z^{1a}$, —$OR^{12}$, —$N(R^{12})_2$, —$C(O)R^{12}$, $N(R^{12})C(O)R^{12}$, —$N(R^{12})C(O)OR^{12}$, —$N(R^{12})S(O)_2R^{12}$, —$OC(O)R^{12}$, —$OC(O)OR^{12}$, —$OC(O)N(R^{12})_2$, or —$S(O)_2R^{12}$.

In certain embodiments, each $Z^1$ is independently oxo, hydroxy, fluoro, chloro, —CN, —$CH_3$, ethyl, isopropyl, tert-butyl, —$CF_3$, —$CHF_2$, cyclopropyl, cyclobutyl, —$OCH_3$, —O-ethyl, —O-isopropyl, —O-cyclopropyl, —$OCF_3$, —$OCF_2H$, —C(O)-alkyl, —C(O)-cycloalkyl, —C(O)-aryl, —C(O)-heteroaryl, or —$NH_2$.

In certain embodiments, each $Z^1$ is independently halo, oxo, —CN, $C_{1-6}$ alkyl optionally substituted by 1 to 3 $Z^{1a}$, $C_{3-6}$ cycloalkyl optionally substituted with 1 to 3 $Z^{1b}$, 4-6 membered heterocyclyl having 1 to 2 heteroatoms selected from O and N that is optionally substituted by 1 to 3 $Z^{1a}$, 5-6 membered heteroaryl having 1 to 4 heteroatoms selected from O and N and optionally substituted with 1 to 3 $Z^{1a}$, —$OR^{12}$, —$N(R^{12})_2$, —$C(O)R^{12}$, $N(R^{12})C(O)R^{12}$, —$N(R^{12})C(O)OR^{12}$, —$N(R^{12})S(O)_2R^{12}$, —$OC(O)R^{12}$, —$OC(O)OR^{12}$, —$OC(O)N(R^{12})_2$, or —$S(O)_2R^{12}$.

In certain embodiments, each $Z^1$ is independently oxo, hydroxy, fluoro, chloro, —CN, —$CH_3$, ethyl, isopropyl, tert-butyl, —$CF_3$, —$CHF_2$, cyclopropyl, cyclobutyl, —$OCH_3$, —O-ethyl, —O-isopropyl, —O-cyclopropyl, —$OCF_3$, —$OCF_2H$, —C(O)-alkyl, —C(O)-cycloalkyl, —C(O)-aryl, —C(O)-heteroaryl, or —$NH_2$.

In certain embodiments, each $Z^1$ is independently halo, $C_{1-8}$ alkyl optionally substituted by 1 to 3 $Z^{1a}$, or —$OR^9$. In certain embodiments, each $Z^1$ is independently halo, $C_{1-8}$ alkyl, $C_{1-8}$ haloalkyl, or —O—$C_{1-8}$ alkyl. In certain embodiments, each $Z^1$ is independently fluoro, methyl, —$CF_3$, or —O—$CH_3$.

In certain embodiments, each $Z^{1a}$ is independently halo, —CN, $C_{1-6}$ alkyl optionally substituted by 1 to 3 $Z^{1b}$, $C_{3-6}$ cycloalkyl optionally substituted by 1 to 3 $Z^{1b}$, 6 membered aryl optionally substituted by 1 to 3 $Z^{1b}$, 4-6 membered heterocyclyl having 1 to 2 heteroatoms selected from O or N that is optionally substituted by 1 to 3 $Z^{1b}$, 5-6 membered heteroaryl having 1 to 2 heteroatoms selected from O and N and optionally substituted with 1 to 3 $Z^{1b}$, —$OR^{12}$, —$N(R^{12})_2$, —$C(O)R^{12}$, $N(R^{12})C(O)R^{12}$, —$N(R^{12})C(O)OR^{12}$, —$N(R^{12})S(O)_2R^{12}$, —$OC(O)R^{12}$, —$OC(O)OR^{12}$, —$OC(O)N(R^{12})_2$, or —$S(O)_2R^{12}$.

In certain embodiments, each $Z^{1a}$ is independently halo, —$CH_3$, cyclopropyl, or —$OCH_3$.

In certain embodiments, each $Z^{1b}$ is independently hydroxy, halo, —CN, $C_{1-6}$ alkyl, $C_{2-6}$ alkenyl, $C_{2-6}$ alkynyl, $C_{3-6}$ cycloalkyl, $C_{1-6}$ haloalkyl, $C_{6-10}$ aryl, 5-10 membered heteroaryl heteroaryl, 4-10 membered heterocyclyl, or —O($C_{1-6}$ alkyl).

In certain embodiments, provided is a compound as shown in Table 1, Table 2, Table 3, and Table 4, or a pharmaceutically acceptable salt thereof. In certain embodiments, provided is a compound as shown in Table 1, Table 2, Table 3, and Table 4, or a pharmaceutically acceptable salt thereof. In certain embodiments, provided is a compound as shown in Table 1, or a pharmaceutically acceptable salt thereof. In certain embodiments, provided is a compound as shown in Table 2, or a pharmaceutically acceptable salt thereof. In certain embodiments, provided is a compound as shown in Table 3, or a pharmaceutically acceptable salt thereof. In certain embodiments, provided is a compound as shown in Table 4, or a pharmaceutically acceptable salt thereof.

One of skill in the art is aware that each and every embodiment of a group (e.g., $R^1$) disclosed herein may be combined with any other embodiment of each of the remaining groups (e.g., $R^{10}$, $R^{11}$, $Z^1$, $Z^{10}$, etc.) to generate a complete compound of Formula I, or any Formula described herein or a pharmaceutically acceptable salt thereof, each of which is deemed within the ambit of the present disclosure.

Methods and Compositions

Peptidylarginine deiminase type 4 (PAD4) is hypothesized to be involved in an array of functions, including regulation of transcription, cell cycle, apoptosis, formation of neutrophil extracellular tarps (NETs), and tumorgenesis. Expression of PAD4 is restricted to cells of the myeloid lineage, such as: neutrophils, eosinophils and monocyte/macrophages.

The present disclosure provides compounds and compositions capable of inhibiting peptidylarginine deiminase type 4 (PAD4), and thus, the present disclosure provides a method for treating a disease or disorder mediated by peptidylarginine deiminase type 4 (PAD4), comprising administering an effective amount of a compound of Formula I, or any formula described herein, or a pharmaceutically acceptable salt thereof, to a patient in need thereof.

As used herein, "treatment" or "treating" is an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and/or c) relieving the disease or condition, e.g., causing the regression of clinical symptoms, ameliorating the disease state, delaying the progression of the disease, increasing the quality of life, and/or prolonging survival.

As used herein, "delaying" development of a disease or condition means to defer, hinder, slow, retard, stabilize and/or postpone development of the disease or condition. This delay can be of varying lengths of time, depending on the history of the disease and/or subject being treated.

As used herein, "prevention" or "preventing" refers to a regimen that protects against the onset of the disease or disorder such that the clinical symptoms of the disease do not develop. Thus, "prevention" relates to administration of a therapy (e.g., administration of a therapeutic substance) to a subject before signs of disease are detectable in the subject.

As used herein, the term "therapeutically effective amount" or "effective amount" refers to an amount that is effective to elicit the desired biological or medical response, including the amount of a compound that, when administered to a subject for treating a disease, is sufficient to effect such treatment for the disease or to an amount that is effective to protect against the contracting or onset of a disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment outcome. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Patient" and "subject" refer to humans, domestic animals (e.g., dogs and cats), farm animals (e.g., cattle, horses, sheep, goats and pigs), laboratory animals (e.g., mice, rats, hamsters, guinea pigs, pigs, pocket pets, rabbits, dogs, and monkeys), and the like. In certain embodiments, the patient is a human.

Protein arginine deiminases (PADs) have been contemplated to display some level of substrate specificity possibly related to their tissue specific expression pattern. For example, keratins are physiological substrates of PAD1 and PAD3, myelin basic protein, enolase are citrullinated by PAD2, whereas histones and transcription factors are citrullinated by PAD4. In vitro, PADs are capable of citrullinating various substrates including intracellular and extracellular arginine containing proteins, peptides and peptide mimetics such as benzoyl arginine ethyl ester, used frequently in biochemical assays. Hydrolysis of peptidyl arginine to citrulline removes positive charge, and therefore may affect protein folding, stability, activity, and ability to form hydrogen bonds. Moreover, citrullinated proteins in susceptible individuals such as rheumatoid arthritis (RA) patients become neo-antigens and elicit an autoimmune response leading to the production of anti-citrullinated protein antibodies known as ACPA. The immunogenic property of citrullinated epitopes appears to be specific to RA, with ACPA detectable in 75% of RA patients and displaying 98% specificity for the disease. RA is a disabling autoimmune disease characterized by chronic inflammation of the joints and synovial tissues, pain and progressive bone destruction. ACPA may appear years prior to the onset of clinical RA and their presence correlates with disease prognosis. ACPA are regarded not only as a useful biomarker for RA diagnosis and for predicting a severe disease course, but they have also been postulated to contribute to a disease pathogenesis. Although the antigens recognized by ACPA are diverse and differ between RA patients, a number of common autoantigens have been reported: citrullinated forms of vimentin, enolase, fibrinogen, collagen II, and histones. PAD4 and also PAD2 are contemplated to be responsible for the generation of citrullinated neo-epitopes in RA as their expression is elevated in the inflamed synovium. Neutrophils and macrophages are the main source of these enzymes. Neutrophils are the most abundant white blood cells in circulation. As critical players in the early innate immune response, they hone quickly to sites of inflammation, are abundant in RA synovial fluid and have been shown to be involved in disease pathology. Neutrophils are also short-lived and may undergo inflammatory forms of cell death, including NETosis and necroptosis, which have been implicated in driving inflammation in the RA synovium. Several lines of evidence point to a putative role for citrullination and ACPAs in driving RA. Genetic (HLA-DR-SE risk allele) and environmental (smoking, periodontitis) factors linked to RA are intimately associated with citrullination and ACPAs. Multiple intracellular and extracellular citrullinated proteins (for example enolase, vimentin, fibrinogen, histones, actin, and collagen) are present in RA synovial tissues but absent in healthy or non-RA synovial tissue. Moreover, PADI4 polymorphisms are linked to RA susceptibility and have been identified in large GWAS studies. PAD4 itself is a target of an autoimmune response and 13-18% of RA patients develop anti-PAD4 antibodies; these auto-antibodies have been shown to activate PAD4 by modulating the enzyme's requirement for calcium and are associated with increased risk of progressive joint damage, interstitial lung disease, and poorer response to SOC.

Currently, it is not fully understood what drives excessive citrullination in RA, or even RA "at risk" individuals. It is contemplated that stimulation of synovial protein citrullination might be linked to the neutrophil cell death/lysis that can occur via one of several proinflammatory mechanisms. Moreover, it is hypothesized that citrullinated proteins are not only acting as neo-epitopes, but are involved directly in disease pathology. PAD4 is postulated to contribute to inflammatory processes in RA via the generation of ACPA neo-epitopes and formation of ACPA-immune complexes which could promote further citrullination, inflammation and pathology through engagement of Fc receptors. Aberrant protein citrullination might also modify the function of critical processes in the RA synovium, either independently or upon association of with cognate ACPAs. For example, it was demonstrated that osteoclast differentiation is linked to the citrullination of proteins and that some ACPAs were able to bind to osteoclast precursor cells promoting differentiation and activation in vitro and stimulation of IL-8 production. Moreover, infusion of some ACPAs into mice causes IL-8 dependent bone loss and IL-8 mediated pain behavior and exaggerate bone erosion in a methylate bovine serum albumin induced arthritis.

Therefore, PAD4 inhibitors should be explored as novel therapeutics for treatment of ACPA positive RA (over 75% of all RA patients) where disease could be exaggerated by citrullination and ACPA immune complexes and other types of RA. Animal studies with the use of knockout (KO) animals or PAD inhibitors provided additional rationale for the use of PAD4 inhibitors in treatment of RA. For example, in a chronic joint inflammation models such as collagen induced arthritis (CIA) or glucose-6 phosphate isomerase induced arthritis, PAD4 KO (DBA/1J) mice display improved clinical (around 60% reduction), histological scores, reduced antibody titer, and reduction of some pro inflammatory cytokines. Similarly, prophylactic treatment with pan-PAD covalent inhibitors such as chloroamidine and BB-chloroamidine or reversible PAD4-specific inhibitor GSK199 in a murine CIA model led to improvement of clinical and histological scores, reduction of antibodies titer and epitope spreading, reduction of citrullinated proteins in joints and shift from pro-inflammatory to pro-resolution immunological responses.

Beyond RA, activated PAD4 was also shown to be necessary and sufficient for citrullination of a histone H3 on neutrophil extracellular traps (NETs). Therefore, it is thought that PAD4 might be involved in a formation of NETs and citrullination of additional proteins associated with these structures. NETs are composed of chromatin and nuclear, cytoplasmic and granules proteins extruded from neutrophils during programmed cell death known as NETosis. NETosis is often regarded as a doubled-edged sword, because although it is a part of a normal antimicrobial defense, excessive NETs formation and/or defective NETs clearance induce inflammatory responses. NETosis results in a release of citrullinated proteins, granules' enzymes, antimicrobial proteins and DNA-protein complexes that can become neo-antigens and fuel autoimmunity in susceptible individuals. Moreover, active PADs are released during NETosis and can citrullinate cellular proteins associated with NETs and extracellular proteins in synovium or vasculature. NETs were also contemplated to serve as scaffolds for thrombosis. For that reason, NETosis has been postulated to exacerbate autoimmune and other inflammatory diseases with neutrophil infiltration. Thus, it was contemplated that targeting PAD4 may have therapeutic potential in diseases associated with sterile inflammation. PAD4 KO mice show improved outcome, protection from tissue and organs injury, deceased disease parameters and attenuation of NETosis markers in several murine models of acute or chronic injury such as stenosis model of deep vein thrombosis, myocardial ischemia/reperfusion, LPS endotoxemic shock and cecal ligation puncture (CLP) sepsis. Moreover, pan-PAD covalent inhibitors such as BB-chloroamidine, chloroamidine, or YW3-56 resulted in reduction of clinical, inflammatory, histopathological and mechanical end points, attenuation of NETosis and improved outcome in various models of chronic and acute inflammatory diseases including MRL/lpr mouse model of lupus, hemorrhagic shock in rats, mouse CLP sepsis model, mouse DSS-colitis, mouse ApoE$^{-/-}$ and high fat diet arteriosclerosis model, mouse streptozotocin induced diabetic wound healing model. Therefore, PAD4 inhibitors may have therapeutic potential in treatment of disease linked to pathological consequences of NETosis beyond RA, such as systemic lupus erythematous, antiphospholipid antibody syndrome, small vessels vasculitis, colitis, thrombosis, atherosclerosis, sepsis, diabetes, among others.

In certain embodiments, the disease or disorder mediated by peptidylarginine deiminase type 4 (PAD4) is acute lymphocytic leukemia, ankylosing spondylitis, cancer, chronic lymphocytic leukemia, colitis, lupus, systemic lupus erythematosus, cutaneous lupus erythematosus, rheumatoid arthritis, multiple sclerosis, or ulcerative colitis. Accordingly, provided is a method for treating acute lymphocytic leukemia, ankylosing spondylitis, cancer, chronic lymphocytic leukemia, colitis, lupus, systemic lupus erythematosus, cutaneous lupus erythematosus, rheumatoid arthritis, multiple sclerosis, or ulcerative colitis, comprising administering an effective amount of a compound of Formula I, or any formula described herein, or a pharmaceutically acceptable salt thereof, to a patient in need thereof.

As PAD4 may contribute to the initiation and propagation of RA, PAD4 inhibitors can be envisioned as a prophylactic treatment for individuals that are at risk of developing clinical RA, as identified by ACPA positivity, family history of RA, exposure to environmental factors, genetic predisposition and presence of arthralgia.

In certain embodiments, the disease or disorder is inflammatory arthritis. In certain embodiments, the disease or disorder is rheumatoid arthritis. In certain embodiments, the disease or disorder is systemic lupus. In certain embodiments, the disease or disorder is vasculitis. In certain embodiments, the disease or disorder is cutaneous lupus erythematosus. In certain embodiments, the disease or disorder is psoriasis. In certain embodiments, the disease or disorder is a fibrotic lung disease, such as idiopathic pulmonary fibrosis (IPF). In certain embodiments, the disease or disorder is fibroproliferative lung disease. In certain embodiments, the disease or disorder is rheumatoid arthritis with joint and/or lung disease. In certain embodiments, the disease or disorder is inflammatory bowel disease.

In certain embodiments, the disease or disorder is acid-induced lung injury, acne (PAPA), acute lymphocytic leukemia, acute, respiratory distress syndrome, Addison's disease, adrenal hyperplasia, adrenocortical insufficiency, ageing, AIDS, alcoholic hepatitis, alcoholic hepatitis, alcoholic liver disease, allergen induced asthma, allergic bronchopulmonary, aspergillosis, allergic conjunctivitis, alopecia, Alzheimer's disease, amyloidosis, amyotrophic lateral sclerosis, and weight loss, angina pectoris, angioedema, anhidrotic ecodermal dysplasia-ID, ankylosing spondylitis, anterior segment, inflammation, antiphospholipid syndrome, aphthous stomatitis, appendicitis, arthritis, asthma, atherosclerosis, atopic dermatitis, autoimmune diseases, autoimmune hepatitis, bee sting-induced inflammation, Behcet's disease, Behcet's syndrome, Bells Palsy, berylliosis, Blau syndrome, bone pain, bronchiolitis, burns, bursitis, cancer, cardiac hypertrophy, carpal tunnel syndrome, catabolic disorders, cataracts, cerebral aneurysm, chemical irritant-induced inflammation, chorioretinitis, chronic heart failure, chronic lung disease of prematurity, chronic lymphocytic leukemia, chronic obstructive pulmonary disease, colitis, complex regional pain syndrome, connective tissue disease, corneal ulcer, Crohn's disease, cryopyrin-associated periodic syndromes, cyrptococcosis, cystic fibrosis, deficiency of the interleukin-1-receptor antagonist (DIRA), dermatitis, dermatitis endotoxemia, dermatomyositis, diffuse intrinsic pontine glioma, endometriosis, endotoxemia, epicondylitis, erythroblastopenia, familial amyloidotic polyneuropathy, familial cold urticarial, familial Mediterranean fever, fetal growth retardation, glaucoma, glomerular disease, glomerular nephritis, gout, gouty arthritis, graft-versus-host disease, gut diseases, head injury, headache, hearing loss, heart disease, hemolytic anemia, Henoch-Scholein purpura, hepatitis, hereditary periodic fever syndrome, herpes zoster and simplex, HIV-1, hypercalcemia, hypercholesterolemia, hyperimmunoglobulinemia D with recurrent fever (HIDS), hypoplastic and other anemias, hypoplastic anemia, idiopathic thrombocytopenic purpura, incontinentia pigmenti, infectious mononucleosis, inflammatory bowel disease, inflammatory lung disease, inflammatory neuropathy, inflammatory pain, insect bite-induced inflammation, iritis, irritant-induced inflammation, ischemia/reperfusion, juvenile rheumatoid arthritis, keratitis, kidney disease, kidney injury caused by parasitic infections, kidney injury caused by parasitic infections, kidney transplant rejection prophylaxis, leptospiriosis, leukemia, Loeffler's syndrome, lung injury, fibrotic lung disease, lupus, lupus nephritis, lymphoma, meningitis, mesothelioma, mixed connective tissue disease, Muckle-Wells syndrome (urticaria deafness amyloidosis), multiple sclerosis, muscle wasting, muscular dystrophy, myasthenia gravis, myocarditis, mycosis fungoides, mycosis fungoides, myelodysplastic syndrome, myositis, nasal sinusitis, necrotizing enterocolitis, neonatal onset multisystem inflammatory disease (NOMID), nephrotic syndrome, neuritis, neuropathological diseases, non-allergen induced asthma, obesity, ocular allergy, optic neuritis, organ transplant, osteoarthritis, otitis media, Paget's disease, pain, pancreatitis, Parkinson's disease, pemphigus, pericarditis, periodic fever, periodontitis, peritoneal endometriosis, pertussis, pharyngitis and adenitis (PFAPA syndrome), plant irritant-induced inflammation, pneumonia, pneumonitis, pneumocystis infection, poison ivy/urushiol oil-induced inflammation, polyarteritis nodosa, polychondritis, polycystic kidney disease, polymyositis, psoriasis, psoriasis, psoriasis, psoriasis, psychosocial stress diseases, pulmonary disease, pulmonary hypertension, pulmonary fibrosis, pyoderma gangrenosum, pyogenic sterile arthritis, renal disease, retinal disease, rheumatic carditis, rheumatic disease, rheumatoid arthritis, sarcoidosis, seborrhea, sepsis, severe pain, sickle cell, sickle cell anemia, silica-induced disease, Sjogren's syndrome, skin diseases, sleep apnea, solid tumors, spinal cord injury, Stevens-Johnson syndrome, stroke, subarachnoid haemorrhage, sunburn, temporal arteritis, tenosynovitis, thrombocytopenia, thyroiditis, tissue transplant, TNF receptor associated periodic syndrome (TRAPS), toxoplasmosis, transplant, traumatic brain injury, tuberculosis, type 1 diabetes, type 2 diabetes, ulcerative colitis, urticarial, uveitis, Wegener's granulomatosis, interstitial lung disease, psoriatic arthritis, juvenile idiopathic arthritis, Sjögren's syndrome, antineutrophil cytoplasmic antibody (ANCA)-associated Alzheimer's, scleroderma or CREST syndrome.

In certain embodiments, the disease or disorder is one or more of rheumatoid arthritis, systemic lupus erythematosus, multiple sclerosis, or cancer.

In certain embodiments, the present disclosure provides a method for treating anti-neutrophil cytoplasm antibodies (ANCA) vasculitis, antiphospholipid syndrome, psoriasis, lung inflammatory diseases, interstitial lung disease (ILD), idiopathic pulmonary fibrosis (IPF), acute lung injury (ALI), acute respiratory distress syndrome (ARDS), chronic obstructive pulmonary disease (COPD), cystic fibrosis (CF), or COVID 19 ARDS, comprising administering an effective amount of a compound of Formula I, or any formula described herein, or a pharmaceutically acceptable salt thereof, to a patient in need thereof.

Also provided is a pharmaceutical composition comprising a compound of Formula I, or any formula described herein, or a pharmaceutically acceptable salt thereof, and a pharmaceutically acceptable carrier or excipient. Also provided is a pharmaceutical composition comprising a compound of Table 1, or any formula described herein, or a pharmaceutically acceptable salt thereof, and a pharmaceutically acceptable carrier or excipient. Also provided is a pharmaceutical composition comprising a compound of Table 2, or any formula described herein, or a pharmaceutically acceptable salt thereof, and a pharmaceutically acceptable carrier or excipient. Also provided is a pharmaceutical composition comprising a compound of Table 3, or any formula described herein, or a pharmaceutically acceptable salt thereof, and a pharmaceutically acceptable carrier or excipient. Also provided is a pharmaceutical composition comprising a compound of Table 4, or any formula described herein, or a pharmaceutically acceptable salt thereof, and a pharmaceutically acceptable carrier or excipient.

The pharmaceutical compositions of compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

In one aspect, the compounds described herein may be administered orally. Oral administration may be via, for example, capsule or enteric coated tablets. In making the pharmaceutical compositions that include at least one compound of Formula I, or a pharmaceutically acceptable salt, is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions may, in some embodiments, be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. In some embodiments, for oral administration, each dosage unit contains from about 10 mg to about 1000 mg of a compound described herein, for example from about 50 mg to about 500 mg, for example about 50 mg, about 75 mg, about 100 mg, about 150 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg. In other embodiments, for parenteral administration, each dosage unit contains from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, and the severity of the subject's symptoms.

In certain embodiments, dosage levels of the compound of Formula I may be from 0.1 mg to 100 mg per kilogram of body weight per day, for example from about 1 mg to about 50 mg per kilogram, for example from about 5 mg to about 30 mg per kilogram. Such dosage levels may, in certain instances, be useful in the treatment of the above-indicated conditions. In other embodiments, dosage levels may be from about 10 mg to about 2000 mg per subject per day. The amount of active ingredient that may be combined with the vehicle to produce a single dosage form will vary depending upon the host treated and the particular mode of administration. Dosage unit forms may contain from 1 mg to 1000 mg of an active ingredient.

The compounds disclosed herein, or a pharmaceutically acceptable salt thereof, may be administered to a subject in accordance with an effective dosing regimen for a desired period of time or duration, such as at least about one day, at least about one week, at least about one month, at least about 2 months, at least about 3 months, at least about 4 months, at least about 6 months, or at least about 12 months or longer. In one variation, the compound is administered on a daily or intermittent schedule. In one variation, the compound is administered on a monthly schedule. In one variation, the compound is administered every two months. In one variation, the compound is administered every three months. In one variation, the compound is administered every four months. In one variation, the compound is administered every five months. In one variation, the compound is administered every 6 months.

The dosage or dosing frequency of a compound disclosed herein, or a pharmaceutically acceptable salt thereof, may be adjusted over the course of the treatment, based on the judgment of the administering physician. The compound may be administered to a subject (e.g., a human) in an effective amount. In certain embodiments, the compound is administered once daily.

For preparing solid compositions such as tablets, the principal active ingredient may be mixed with a pharmaceutical excipient to form a solid preformulation composition containing a homogeneous mixture of a compound of Formula I, or a pharmaceutically acceptable salt, thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

In certain embodiments, a method of treating or preventing rheumatoid arthritis (RA) comprising administering a therapeutically effective amount of a compound disclosed herein, or a pharmaceutically acceptable salt thereof, to a subject in need thereof, is provided. In certain embodiments, a method of treating RA comprising administering a therapeutically effective amount of a compound disclosed herein, or a pharmaceutically acceptable salt thereof, to a subject in need thereof, is provided. In certain embodiments, the method comprises administering a compound disclosed herein, or a pharmaceutically acceptable salt thereof, in combination with one, two, three, or four additional therapeutic agents. In certain embodiments, the subject may have not previously received prior treatment (treatment naïve) for RA. In certain embodiments, the subject may have previously received treatment (treatment experienced) for RA.

In certain embodiments, a compound disclosed herein, or a pharmaceutically acceptable salt thereof for use in the manufacture of a medicament for treating RA in a subject (e.g., a human) is disclosed.

Also disclosed herein is a compound disclosed herein, or a pharmaceutically acceptable salt thereof, for use in the therapeutic treatment or delaying the onset of RA.

Also disclosed herein is a compound disclosed herein, or a pharmaceutically acceptable salt thereof, for use in the therapeutic treatment of RA.

In certain embodiments, a compound disclosed herein, or a pharmaceutically acceptable salt thereof can be used as a research tool (e.g., to study the inhibition of PAD4 in a subject or in vitro).

Kits that include a compound of Formula I, or a pharmaceutically acceptable salt, thereof, and suitable packaging are provided. In one embodiment, a kit further includes instructions for use. In one aspect, a kit includes a compound of Formula I, or a pharmaceutically acceptable salt thereof, and instructions for use of the compounds in the treatment of the diseases or conditions described herein.

Articles of manufacture that include a compound of Formula I, or a pharmaceutically acceptable salt thereof, in a suitable container are provided. The container may be a vial, jar, ampoule, preloaded syringe, and intravenous bag.

Combination Therapy

In certain embodiments, a compound disclosed herein is administered with one or more additional therapeutic agents. In one embodiment, the present disclosure provides a pharmaceutical composition comprising a compound of Formula I, or any formula described herein, or a pharmaceutically acceptable salt thereof, and at least one additional therapeutic agent and at least one pharmaceutically acceptable carrier or excipient.

In one embodiment, the present disclosure provides a pharmaceutical composition comprising a compound of Formula I, or any formula described herein, or a pharmaceutically acceptable salt thereof, at least one additional therapeutic agent suitable for treating rheumatoid arthritis, and at least one pharmaceutically acceptable carrier or excipient.

Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and the one or more additional therapeutic agents are both present in the body of the patient. When administered sequentially, the combination may be administered in two or more administrations.

Co-administration includes administration of unit dosages of the compounds disclosed herein before or after administration of unit dosages of one or more additional therapeutic agents. For example, the compound disclosed herein may be administered within seconds, minutes, or hours of the administration of the one or more additional therapeutic agents. In some embodiments, a unit dose of a compound disclosed herein is administered first, followed within seconds or minutes by administration of a unit dose of one or more additional therapeutic agents. Alternatively, a unit dose of one or more additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments, a compound of Formula I is formulated as a tablet, which may optionally contain one or more other compounds useful for treating the target indication. In certain embodiments, such tablets are suitable for once daily dosing. In other embodiments, the tablets are suitable for twice a day dosing.

Combination Drugs

In one embodiment, a compound as disclosed herein, such as a compound of Formula I, Table 1, Table 2, Table 3, or Table 4, may be combined with one or more other active agents.

For example, in certain embodiments, a compound as disclosed herein, such as a compound of Formula I, Table 1, Table 2, Table 3, or Table 4, may be used in combination with conventional synthetic and targeted synthetic disease-modifying antirheumatic drugs (DMARDs) or biological DMARDs due to orthogonal or complementary mechanisms of action.

The one or more active agents may be chosen from 14-3-3 protein eta inhibitors, 5-Lipoxygenase inhibitors, Abl tyrosine kinase inhibitors, ACTH receptor agonists, Adenosine A3 receptor agonists, adenosine deaminase inhibitors, ADP ribosyl cyclase-1 inhibitors, ADP ribosyl cyclase-1 modulators, ADP ribosylation factor 6 inhibitors, Adrenocorticotrophic hormone ligands, Aggrecanase-2 inhibitors, Albumin modulators, AP1 transcription factor inhibitors, Basigin inhibitors, Bcr protein inhibitors, B-lymphocyte antigen CD19 inhibitors, B-lymphocyte antigen CD20 inhibitors, B-lymphocyte antigen CD20 modulators, B-lymphocyte stimulator ligand inhibitors, Bradykinin receptor modulators, BRAF gene inhibitors, branched amino acid aminotransferase 1 inhibitors, Bromodomain containing protein inhibitors, BTK tyrosine kinase inhibitors, Cadherin-11 antagonists, Calcineurin inhibitors, Calcium channel inhibitors, Carbonic anhydrase inhibitors, Cathepsin K inhibitors, Cathepsin S inhibitors, CCR1 chemokine antagonists, CCR2 chemokine antagonists, CCR3 gene modulators, CCR5 chemokine antagonists, CD126 antagonists, CD29 modulators, CD3 modulators, CD39 agonists, CD4 agonists, CD4 antagonists, CD40 ligand inhibitors, CD40 ligand receptor antagonists, CD40 ligand receptor modulators, CD52 antagonists, CD73 agonists, CD79b modulators, CD80 antagonists, CD86 antagonists, CD95 antagonists, Cell adhesion molecule inhibitors, Choline kinase inhibitors, Clusterin stimulators, Complement C5 factor inhibitors, Complement Factor stimulators, C-reactive protein inhibitors, CSF-1 antagonists, CXC10 chemokine ligand inhibitors, CXCR4 chemokine antagonists, Cyclin-dependent kinase inhibitor 1 inhibitors, Cyclin-dependent kinase-2 inhibitors, Cyclin-dependent kinase-4 inhibitors, Cyclin-dependent kinase-5 inhibitors, Cyclin-dependent kinase-6 inhibitors, Cyclin-dependent kinase-7 inhibitors, Cyclin-dependent kinase-9 inhibitors, Cyclooxygenase 2 inhibitors, Cyclooxygenase 2 modulators, Cyclooxygenase inhibitors, Cytosolic phospholipase A2 inhibitors, Cytotoxic T-lymphocyte protein-4 modulators, Cytotoxic T-lymphocyte protein-4 stimulators, DHFR inhibitors, Diamine acetyltransferase inhibitors, Dihydroorotate dehydrogenase inhibitors, Elongation factor 2 inhibitors, Eotaxin 2 ligand inhibitors, EP4 prostanoid receptor antagonists, Erythropoietin receptor agonists, Fas ligands, FGF-2 ligand inhibitors, FK506 binding protein-12 modulators, Folate antagonists, Folate receptor agonists, Folate receptor beta antagonists, Folate receptor modulators, Fractalkine ligand inhibitors, Fyn tyrosine kinase inhibitors, G protein coupled receptor 15 antagonists, GABA A receptor modulators, glucocorticoid agonists, Glucocorticoid antagonists, Glucocorticoid induced leucine zipper stimulators, GM-CSF ligand inhibitors, GM-CSF receptor antagonists, GM-CSF receptor modulators, growth regulated protein alpha ligand inhibitors, H+ K+ ATPase inhibitors, histamine H4 receptor antagonists, histone deacetylase inhibitors, histone deacetylase-6 inhibitors, HIV-1 gp120 protein inhibitors, HLA class II antigen DQ-2 alpha modulators, HLA class II antigen inhibitors, HLA class II antigen modulators, Hsp 70 family inhibitors, Hypoxia inducible factor-1 inhibitors, IFNB gene stimulators, I-kappa B kinase beta inhibitors, I-kappa B kinase inhibitors, IL-1 antagonists, IL-10 agonists, IL-11 agonists, IL-12 antagonists, IL-15 antagonists, IL-17 antagonists, IL-17 receptor modulators, IL-8 ligand inhibitors, IL-2 agonists, IL-2 antagonists, IL-21 antagonists, IL-23 antagonists, IL-3 antagonists, IL-4 agonists, IL-6 antagonists, IL-6 receptor modulators, IL-6 neutralizing human antibodies, anti-IL6 antibody, immunoglobulin antagonists, immunoglobulin G1 agonists, immunoglobulin G1 antagonists, Immunoglobulin G1 modulators, Immunoglobulin G2 antagonists, immunoglobulin G2 modulators, immunoglobulin gamma Fc receptor II modulators, immunoglobulin gamma Fc receptor IIB antagonists, immunoglobulin kappa modulators, immunoglobulin M antagonists, inducible nitric oxide synthase inhibitors, Inosine monophosphate dehydrogenase inhibitors, insulin sensitizers, integrin alpha-1/beta-1 antagonists, integrin alpha-4/beta-1 antagonists, integrin alpha-9 antagonist, integrin antagonists, interferon beta ligands, interferon gamma ligands, interleukin 17A ligand inhibitors, Interleukin 17F ligand inhibitors, Interleukin 23A inhibitors, Interleukin ligands, Interleukin receptor 17A antagonists, Interleukin-1 beta ligand inhibitors, Interleukin-10 ligands, Interleukin-2 ligands, Interleukin-4 ligands, Interleukin-6 ligand inhibitors, Itk tyrosine kinase inhibitors, JAK tyrosine kinase inhibitors, Jak1 tyrosine kinase inhibitors, Jak2 tyrosine kinase inhibitors, JAK3 gene inhibitors, Jak3 tyrosine kinase inhibitors, Jun N terminal kinase inhibitors, KCNA voltage-gated potassium channel-3 modulators, Kelch like ECH associated protein 1 modulators, Kit tyrosine kinase inhibitors, LanC like protein 2 modulators, Leukotriene BLT receptor antagonist, LITAF gene inhibitors, Lymphocyte function antigen-3 receptor antagonists, Lyn tyrosine kinase inhibitors, Macrophage mannose receptor 1 modulators, MAdCAM inhibitors, MAP kinase modulators, MAP3K2 gene inhibitors, MAPKAPK5 inhibitors, Matrix metalloprotease inhibitors, MCL1 gene inhibitors, MEK protein kinase inhibitors, MEK-1 protein kinase inhibitors, MEK-2 protein kinase inhibitors, Membrane copper amine oxidase inhibitors, Metalloprotease-2 inhibitors, Metalloprotease-9 inhibitors, methylprednisolone, Midkine ligand inhibitors, Mitochondrial 10 kDa heat shock protein stimulators, mTOR complex 1 inhibitors, mTOR inhibitors, NAD ADP ribosyltransferase stimulators, NAMPT gene inhibitors, NF kappa B inhibitor stimulators, NFAT gene inhibitors, NFE2L2 gene stimulators, Nicotinic acetylcholine receptor antagonists, NK cell receptor modulators, NKG2 A B activating NK receptor antagonists, NKG2 D activating NK receptor antagonists, Nuclear erythroid 2-related factor 2 stimulators, Nuclear factor kappa B inhibitors, Nuclear factor kappa B modulators, Nuclear factor kappa B p105 inhibitors, Opioid growth factor receptor agonists, Opioid receptor delta antagonists, Osteoclast differentiation factor antagonists, Osteoclast differentiation factor ligand inhibitors, Oxidoreductase inhibitors, P2X7 purinoceptor agonists, p38 MAP kinase alpha inhibitors, p38 MAP kinase inhibitors, PDE 4 inhibitors, PDE 5 inhibitors, PDGF receptor agonists, PDGF receptor antagonists, PDGF-B ligand inhibitors, PERK gene inhibitors, Phosphoinositide-3 kinase delta inhibitors, Phosphoinositide-3 kinase gamma inhibitors, Phospholipase A2 inhibitors, Platelet activating factor receptor antagonists, PPAR gamma agonists, Programmed cell death protein 1 modulators, Prostaglandin D synthase stimulators, peptidylarginine deiminase inhibitors, Protein tyrosine kinase inhibitors, PurH purine biosynthesis protein inhibitors, Rho associated protein kinase 2 inhibitors, Seprase inhibitors, Signal transducer CD24 modulators, Signal transduction inhibitors, Sodium glucose transporter-2 inhibitors, Sphingosine 1 phosphate phosphatase modulators, STAT3 gene inhibitors, Superoxide dismutase stimulators, SYK family tyrosine kinase inhibitors, Syk tyrosine kinase inhibitors, Syndecan-1 inhibitors, T cell receptor antagonists, T cell receptor modulators, T cell surface glycoprotein CD28 inhibitors, T cell surface glycoprotein CD28 stimulators, TAK1 binding protein modulators, Talin modulators, T-cell differentiation antigen CD6 inhibitors, T-cell surface glycoprotein CD8 inhibitors, Tenascin modulators, TGF beta agonists, Thymulin agonists, TLR-2 antagonists, TLR-4 antagonists, TLR-9 antagonists, TNF alpha ligand inhibitors, TNF alpha ligand modulators, TNF antagonists, TNF gene inhibitors, TNF receptor modulators, TNFSF11 gene inhibitors, Transcription factor p65 inhibitors, Transcription factor RelB inhibitors, Transferrin modulators, Tumor necrosis factor 13C receptor antagonists, Tumor necrosis factor 15 ligand inhibitors, Tumor necrosis factor ligand 13 inhibitors, Tumor necrosis factor ligand inhibitors, Type I IL-1 receptor antagonists, Type I TNF receptor antagonists, Type II TNF receptor modulators, Unspecified GPCR agonists, VEGF receptor antagonists, VEGF-2 receptor antagonists, VEGF-2 receptor modulators, VEGF-B ligand inhibitors, X-linked inhibitor of apoptosis protein inhibitors, or Zap70 tyrosine kinase inhibitors.

Examples of active agents that may be combined with the compounds described herein include 99mTc labelled annexin V-128, abatacept, abatacept biosimilar, ABBV-257, ABT-122, ABT-494, acalabrutinib, aceclofenac, actarit, AdMSCs, MS-392, adalimumab, adalimumab biosimilar, adalimumab follow-on biologic, AK-106, ALX-0061, aminopterin, anakinra, anakinra biosimilar, anakinra follow-on biologic, ARG-301, ASLAN-003, ASP-5094, AT-132, AZD-9567, baricitinib, BI-655064, bimekizumab, BiP (rheumatoid arthritis), BLHP-006, blisibimod, BMS-986104, BMS-986142, ABBV-105, BTT-1023, canakinumab, Cartistem, CCX-354, CD24-IgFc, celecoxib, cerdulatinib, certolizumab pegol, CF-101, CFZ-533, CHR-5154, cibinetide, ciclosporin, clazakizumab, CNTO-6785, corticotropin, CR-6086, CreaVax-RA, CWG-92, CWG-940, Cx-611, DE-098, DEN-181, deflazacort, Rheumavax, denosumab, diacerein, diclofenac, E-6011, eicosapentaenoic acid monoglycerides, etanercept, etanercept biosimilar, etanercept follow-on biologic, etodolac, etoricoxib, filgotinib, fosdagrocorat, gerilimzumab, ginsenoside C-K, givinostat, goat polyclonal antibodies, golimumab, GS-5745, GS-9876, GSK-3196165, HM-71224, HMPL-523, hyaluronate sodium, IB-RA (injectable, rheumatoid arthritis), IB-RA (oral, rheumatoid arthritis), ICP-022, iguratimod, IMD-2560, imidazole salicylate, infliximab, infliximab biobetter, infliximab biosimilar, CT-P13, INSIX RA, interferon gamma follow-on biologic, interleukin-2 (injectable), interleukin-2 follow-on biologic, INV-103, IR-501, itolizumab, JNJ-40346527, Ka Shu Ning, KD-025, ketoprofen+omeprazole, leflunomide, lenzilumab, LLDT-8, LNP-1955, lumiracoxib, LY-3090106, masitinib, mavrilimumab, MBS-2320, MEDI-5117, meloxicam, methotrexate, MGD-010, misoprostol+diclofenac, MM-A01-01, monalizumab, MORAb-022, MPC-300-IV, MRC-375, nabumetone, namilumab, naproxen+esomeprazole, naproxen+esomeprazole strontium, ocaratuzumab, ofatumumab, OHR-118, olokizumab, OM-89, once-daily naproxen (oral controlled release, pain), ONO-4059, Oralgam, ozoralizumab, peficitinib, pelubiprofen, PF-06687234, piperidone hydrochloridum, piroxicam, prednisolone, prednisone, Procell, Prosorba, PRT-2607, PRTX-100, PRX-167700, QBSAU, rabeximod, RCT-18, recombinant human CD22 monoclonal antibody (iv infusion), Lonn Ryonn Pharma/SinoMab Bioscience (Shenzhen), RA-Curcusome, recombinant human interleukin-1 receptor antagonist (rheumatoid arthritis), recombinant human interleukin-2 recombinant TNF receptor 2-Fc fusion protein mutant, RG-6125, RhuDex, rifabutin+clarithromycin+clofazimine, rituximab, rituximab biosimilar, Toritz, rituximab follow-on biologic, RPI-78, SAN-300, sarilumab, SBI-087, seliciclib, SHR-0302, sirukumab, spebrutinib, SSS-07, KDDF-201110-06, Syn-1002, T-5224, TAB-08, tacrolimus, TAK-020, TAK-079, tarenflurbil (transdermal spraygel, skin disease/rheumatoid arthritis), technetium Tc 99m tilmanocept, technetium[99Tc] methylenediphosphonate, tenoxicam, Debio-0512, tocilizumab, tofacitinib, tofacitinib citrate, *Trichuris suis* ova, umbilical cord-derived mesenchymal stem cells (iv, RA/liver disease), ustekinumab, VAY-736, VB-201, WF-10, XmAb-5871, YHB-1411-2, or YRA-1909.

In certain embodiments, a compound described herein may be combined with a 14-3-3 protein eta inhibitor, such as anti-AGX-020 mAbs (rheumatoid arthritis) or Augurex; a 5-Lipoxygenase inhibitor, such as darbufelone, tebufelone, ZD-2138, etalocib, PGV-20229, L-708780, T-0757, T-0799, ZM-216800, L-699333, BU-4601A, or SKF-104351; a 5-Lipoxygenase/Cyclooxygenase inhibitor, such as tenoxicam, licofelone, tenidap, tepoxalin, flobufen, SKF-86002, WY-28342, or CI-986; or a 5-Lipoxygenase/PPAR gamma agonist, such as etalocib; a Abl tyrosine kinase inhibitor/Bcr protein inhibitor/Kit tyrosine kinase inhibitor/PDGF receptor antagonist/or Signal transduction inhibitors, such as imatinib; a ACTH receptor agonist/Adrenocorticotrophic hormone ligand/Opioid growth factor receptor agonist, such as FAR-404, or metenkefalin acetate+tridecactide acetate; an adenosine A3 receptor agonist, such as CF-101 (piclidenoson); an adenosine deaminase inhibitor, such as cladribine, pentostatin, or FR-221647; a ADP ribosyl cyclase-1 inhibitor, such as daratumumab; a ADP ribosyl cyclase-1 modulator/Syndecan-1 inhibitor, such as indatuximab ravtansine; a ADP ribosylation factor 6 inhibitor, such as NAV-2729; a adrenocorticotrophic hormone ligand, such as corticotropin or Mallinckrodt; aggrecanase-2/TNF gene inhibitors, such as GIBH-R-001-2; albumin modulators, such as ONS-1210; albumin modulators/IL-6 antagonists, such as ALX-0061 (vobarilizumab); albumin modulators/TNF alpha ligand inhibitors, such as HOT-3010; a API transcription factor/Nuclear factor kappa B inhibitor, such astarenflurbil or SP-100030; anti-TNF steroid antibody-drug conjugates (anti-TNF-GRM), such as ABBV-3373; Basigin inhibitors/Branched amino acid aminotransferase 1/Metalloprotease-9 inhibitors/Metalloprotease-2 inhibitors, such as ERG-240; BET inhibitors such as GSK-3358699; Bispecic anti-CD86/IL-10, such as APVO-210; bispecific humanized monoclonal antibody targeted against BAFF and IL-17A, such as tibulizumab; bispecific antibody-peptide conjugate (BAFF/ICOSL), such as AMG-570; B-lymphocyte antigen CD19 inhibitors, such as MDX-1342; B-lymphocyte antigen CD19 inhibitors/Immunoglobulin gamma Fc receptor IIB antagonists, such as XmAb-5871; B-lymphocyte antigen CD20 inhibitors, such as ocrelizumab, ofatumumab, rituximab, ABP-798, Maball, Mabtas, Reditux, Zytux, veltuzumab, ocaratuzumab, BLX-301, IDEC-102, ABP-798, GP-2013, MK-8808, HLX-01, CT-P10, TL-011, PF-05280586, IBPM-001RX, IBI-301, AME-133v, BCD-020, BT-D004, SAIT-101, or JHL-1101; B-lymphocyte antigen CD20 modulators, such as SBI-087, TRU-015, DXL-625, or MabionCD20; B-lymphocyte stimulator ligand inhibitors, such as belimumab, RCT-18, blisibimod, tabalumab, or briobacept; B-lymphocyte stimulator ligand/Tumor necrosis factor ligand 13 inhibitors, such as atacicept; bradykinin receptor modulators/Histone deacetylase inhibitors/P2X7 purinoceptor agonists, such asgivinostat; BRAF gene/MEK protein kinase/PERK gene inhibitors, such as binimetinib; Bromodomain containing protein inhibitors, such as RVX-297 or ZEN-003694; Btk tyrosine kinase inhibitors, such as AC-0058, acalabrutinib, HM-71224, spebrutinib, BMS-986142, TAK-020, tirabrutinib (ONO-4059), TAS-5315, ABBV-105, GDC-0834, EBI-1459, BMS-986195, evobrutinib, or fenebrutinib; Btk tyrosine kinase inhibitors/Syk tyrosine kinase inhibitors/VEGF-2 receptor antagonists, such as CG-026806; Btk tyrosine kinase inhibitors/IL-6 antagonists, such as RN-486; Btk tyrosine kinase/Jak1 tyrosine kinase inhibitors, such as upadacitinib+ABBV-105; Btk tyrosine kinase/Jak3 tyrosine kinase inhibitors, such as AC-0025; cadherin-11 antagonists, such as RG-6125; calcineurin inhibitors, such as ciclosporin; calcineurin inhibitors/opioid receptor delta antagonists, such as HS-378; calcium channel inhibitors, such as RP-3128; carbonic anhydrase/Cyclooxygenase 2 inhibitors, such as polmacoxib; cathepsin K inhibitors, such as CRA-013783 or VEL-0230; cathepsin K/cathepsin S inhibitors, such as AM-3876 or NPI-2019; cathepsin S inhibitors, such as MIV-247 or RWJ-445380; CCR1 chemokine antagonists, such as BX-471, BMS-817399, BI-638683, CCX-354, MLN-3701, MLN-3897, CP-481715 or PS-375179; CCR2 chemokine antagonists, such as MK-0812 or AZD-6942; CCR3 gene modulators/Eotaxin 2 ligand inhibitors, such as CM-102; CCR5 chemokine antagonists, such as OHR-118, NIBR-6465, AZD-5672, or AZD-8566; CD29 modulators/Interleukin-10 ligands, such as PF-06687234; CD3 modulators, such as otelixizumab; CD39/CD73 agonists, such as AAV5-CD39/CD73 (rheumatoid arthritis), or Arthrogen; CCR5 chemokine antagonists/CD4 agonists/HIV-1 gp120 protein inhibitors, such as maraviroc; CD4 antagonists, such as zanolimumab, MTRX-1011A, BW-4162W94, EP-1645, or clenoliximab; CD40 ligand inhibitors, such as dapirolizumab pegol; CD40 ligand receptor antagonists, such as BI-655064, anti-CD40-XTEN, teneliximab, VIB-4920, or iscalimab; CD40 ligand receptor modulators/Immunoglobulin G1 modulators, such as CFZ-533; CD52 antagonists/Clusterin stimulators, such as alemtuzumab; bispecific CD32B/CD79B antibody, such as PRV-3279 (MGD-010); CD80 antagonists, such as abatacept biobetter; CD80 antagonists/T cell surface glycoprotein CD28 inhibitors, such as RhuDex; CD80 antagonists/CD86 antagonists, such as XENP-9523 or ASP-2408; CD86 antagonists, such as abatacept or biosuperior; CD86 antagonists/Cytotoxic T-lymphocyte protein-4 modulators, such as ES-210; CD95 antagonists, such as DE-098 or CS-9507; cell adhesion molecule inhibitors, such as alicaforsen, NPC-17923, TK-280 and PD-144795; chemokine receptor antagonists, such as PF-06835375; complement C5 factor inhibitors, such as eculizumab; complement C5 factor inhibitors/IL-1 antagonists, such as antisense oligonucleotides (rheumatoid arthritis); Leiden University Medical CenterComplement Factor stimulators, such as CM-101; C-reactive protein inhibitors, such as ISIS-353512; C-reactive protein inhibitors/Cyclooxygenase 2 inhibitors/Nuclear factor kappa B inhibitors/Immunoglobulin M antagonists/IL-2 receptor antagonists/PGE2 antagonists, such as IB-RACSF-1 antagonists: masitinib, FPA-008, JNJ-27301937, JNJ-40346527, PLX-5622, CT-1578, PD-360324, or JNJ-28312141; CSF-1 antagonists/Fyn tyrosine kinase inhibitors/Kit tyrosine kinase inhibitors/Lyn tyrosine kinase inhibitors/NK cell receptor modulators/PDGF receptor antagonists, such as masitinib; CXC10 chemokine ligand inhibitors, such as 946414-98-8 or BMS-936557; CXCR4 chemokine antagonists, such as plerixafor; CDK-2/7/9 inhibitors/MCL1 gene inhibitors, such as seliciclib; CDK-1/2/5/7/9 inhibitors, such as BP-14; cyclooxygenase 2 inhibitors, such as celecoxib, etoricoxib, meloxicam, or lumiracoxib; cyclooxygenase 2/Oxidoreductase inhibitors, such as etodolac; cyclooxygenase 2 modulators, such as DRGT-46; cyclooxygenase inhibitors, such as aceclofenac, diclofenac, naproxcinod, naproxen etemesil, nabumetone, Aleve, pelubiprofen, LY-210073, NS-398, bromfenac, L-746483, LY-255283, ibuprofen, flurbiprofen, SC-57666, or bermoprofen; cyclooxygenase inhibitors/H+ K+ ATPase inhibitors, such as naproxen+esomeprazole strontium; cyclooxygenase inhibitors/PGE1 agonists, such as misoprostol+diclofenac; cyclooxygenase inhibitors/Oxidoreductase inhibitors, such as imidazole salicylate; cytosolic phospholipase A2 inhibitors/Phospholipase A2 inhibitors, such as AVX-002; cytotoxic T-lymphocyte protein-4 stimulators/T cell surface glycoprotein CD28 inhibitors, such as abatacept, (BMS-188667) or belatacept; DHFR inhibitors, such as MPI-2505, Jylamvo, or ZeNEO-Methotrexate; DHFR inhibitors/Folate antagonists/Transferrin modulators, such as methotrexate; Diamine acetyltransferase inhibitors, such as diminazene aceturate; dihydroorotate dehydrogenase inhibitors, such as ASLAN-003, HWA-486, or ABR-224050; dihydroorotate dehydrogenase/Protein tyrosine kinase inhibitors, such as leflunomide; elongation factor 2 inhibitors/interleukin-2 ligands/NAD ADP ribosyltransferase stimulators, such as denileukin diftitox; EP4 prostanoid receptor antagonists, such as CR-6086; Erythropoietin receptor agonists, such as cibinetide; Fas ligands, such as AP-300; FGF-2 ligand inhibitors, such as RBM-007; FK506 binding protein-12 modulators/mTOR inhibitors, such as temsirolimus; folate antagonists/Transferrin modulators/DHFR inhibitors, such as MBP-Y003; folate receptor modulators, such as technetium (99mTc) etarfolatide; fractalkine ligand inhibitors, such as E-6011; Fyn tyrosine kinase inhibitors/GABA A receptor modulators/Cyclooxygenase 2 inhibitors/Dihydroorotate dehydrogenase inhibitors, such as laflunimus; Glucocorticoid agonists, such as prednisone, prednisolone, or fosdagrocorat; Glucocorticoid antagonists, such as REC-200; Glucocorticoid induced leucine zipper stimulators, such as ART-G01; GM-CSF ligand inhibitors, such as namilumab, gimsilumab (MORAb-022), or TJM-2; GM-CSF receptor antagonists, such as mavrilimumab; GM-CSF receptor modulators, such as GSK-3196165 or otilimab; growth regulated protein alpha ligand inhibitors/AP1 transcription factor; inhibitors/IL-6 antagonists/Interleukin-1 beta ligand inhibitors/Cathepsin K inhibitors/NFAT gene inhibitors, such as T-5224; H+ K+ ATPase inhibitors, such as naproxen+esomeprazole, ketoprofen+omeprazole, KEO-25001, HC-1004, or PN-40020; histamine H4 receptor antagonists, such as toreforant or GD-48; histone deacetylase inhibitors, such as CHR-5154 (GSK-3117391); histone deacetylase-6 inhibitors, such as CKD-506; HLA class II antigen DQ-2 alpha modulators, such as NexVax2; HLA class II antigen inhibitors, such as HLA-DR1/DR4 inhibitors (rheumatoid arthritis) or Provid; HLA class II antigen modulators, such as recombinant T-cell receptor ligand (rheumatoid arthritis) or Artielle; Hsp 70 family inhibitors, such as gusperimus trihydrochloride; hypoxia inducible factor-1 inhibitors/VEGF receptor antagonists, such as 2-methoxyestradiol; IFNB gene stimulators, such as ART-102; I-kappa B kinase beta inhibitors, such as IMD-2560; I-kappa B kinase beta inhibitors/Nuclear factor kappa B inhibitors, such as IMD-0560; I-kappa B kinase inhibitors/

NFE2L2 gene stimulators/Nuclear factor kappa B inhibitors/STAT3 gene inhibitors, such as bardoxolone methyl; IL-1 antagonists, such as recombinant human interleukin-1 receptor antagonist (rheumatoid arthritis), Shanghai Fudan-Zhangjiang Bio-Pharmaceutical; IL-1 antagonists/Interleukin-1 beta ligand inhibitors, such as rilonacept; IL-10 agonists, such as peg-ilodecakin; IL-1I agonists/PDGF receptor agonists, such as oprelvekin; IL-12 antagonists/IL-23 antagonists, such as ustekinumab or briakinumab; IL-15 antagonists, such as AMG-714; IL-17 antagonists, such as ixekizumab or secukinumab; IL-17 receptor modulators, such as CNTO-6785; IL-2 receptor agonists, such as interleukin-2 follow-on biologic (IL-2), Anteluke or Interking; IL-2/IL-21/IL-15 antagonists, such as BNZ-132-2; IL-21 antagonists, such as NN-8828; IL-4 agonists, such as SER-130-AMI; IL-6 antagonists, such as BCD-089, olokizumab, clazakizumab, sirukumab, SA-237, FB-704A, OP-R003, peptide IL-6 antagonist, MEDI-5117, AMG-220, FM-101, BLX-1025, esonarimod, TA-383, or sarilumab; IL-6 antagonists/Interleukin-1 beta ligand inhibitors/TNF alpha ligand inhibitors, such as K-832; IL-6 antagonists/Insulin sensitizers/Interleukin-1 beta ligand inhibitors, such as BLX-1002; IL-6 receptor antagonists/modulators, such as tocilizumab, HS-628, or LusiNEX; IL-6 receptor modulators, such as BAT-1806 or RO-4877533; immunoglobulin antagonists, such as iguratimod; immunoglobulin G1 agonists, such as BX-2922 and HF-1020; immunoglobulin G1 agonists/Interleukin-1 beta ligand inhibitors, such as canakinumab; immunoglobulin G1 agonists/TNF alpha ligand inhibitors, such as STI-002; immunoglobulin G1 antagonists/TNF alpha ligand inhibitors, such as YHB-1411-2; immunoglobulin G1 modulators/GM-CSF ligand inhibitors/immunoglobulin kappa modulators, such as lenzilumab; immunoglobulin G2 antagonists/NF kappa B inhibitor stimulators/Osteoclast differentiation factor antagonists/Osteoclast differentiation factor ligand inhibitors/TNFSF11 gene inhibitors, such as denosumab; immunoglobulin gamma Fc receptor II modulators, such as MGD-010; inducible nitric oxide synthase inhibitors/Cyclooxygenase 2 inhibitors/MAP kinase modulators/Nuclear factor kappa B inhibitors, such as SKLB-023; inosine monophosphate dehydrogenase inhibitors, such as mizoribine; insulin sensitizers/Nuclear factor kappa B inhibitors/interleukin ligand inhibitors, such as HE-3286; integrin alpha-1/beta-1 antagonists, such as SAN-300; integrin alpha-4/beta-1 antagonists/cell adhesion molecule inhibitors, such as natalizumab; integrin alpha-9 antagonist, such as ASP-5094; integrin antagonists, such as PEG-HM-3 or CY-9652; interferon beta ligands, such as recombinant interferon beta-1a; interferon beta ligands/IL-6 antagonists, such as TA-383; interferon gamma ligands, such as Li Zhu Yin De Fu or Clongamma; interleukin 17A ligand inhibitors/Tumor necrosis factor ligand inhibitors, such as ABT-122 or ABBV-257; interleukin 17F ligand inhibitors, such as bimekizumab; interleukin 18 ligand inhibitors, such as tadekinig alfa; interleukin 23A inhibitors, such as guselkumab; interleukin ligands/IL-1 antagonists, such as IBPB-007-IL; interleukin receptor 17A antagonists, such as brodalumab; interleukin-1 beta ligand inhibitors, such as gevokizumab, LY-2189102 or CDP-484; interleukin-1 beta ligand inhibitors/TNF alpha ligand inhibitors, such as PMI-001; interleukin-1 beta ligands/TNF alpha ligand modulators, such as PUR-0110; interleukin-2 ligands, such as recombinant interleukin-2; IL-2 modulators, such as AMG-592; interleukin-4 ligands/Tenascin modulators, such as Tetravil; interleukin-6 ligand inhibitors, such as gerilimzumab or PF-4236921; IRAK-4 protein kinase inhibitor, such as BAY-1830839, BAY-1834845, or PF-06650833; Itk tyrosine kinase inhibitors, such as JTE-051; Itk tyrosine kinase inhibitors/Jak3 tyrosine kinase inhibitors, such as ARN-4079; JAK tyrosine kinase inhibitors, such as deuterated tofacitinib analog or SD-900; JAK tyrosine kinase inhibitors/Syk tyrosine kinase inhibitors, such as cerdulatinib or CVXL-0074; Jak1 tyrosine kinase inhibitors, such as ABT-494 (upadacitinib), ruxolitinib, filgotinib, itacitinib, NIP-585, YJC-50018, GLPG-0555, MRK-12, or SHR-0302; Jak1/3 tyrosine kinase inhibitors, such as tofacitinib, tofacitinib citrate, peficitinib, CKD-374, or CS-944X; Jak1/2 tyrosine kinase inhibitors, such as baricitinib or ruxolitinib; Jak2 tyrosine kinase inhibitors/CSF-1 antagonists, such as CT-1578; JAK3 gene inhibitors, such as PF-06651600; Jak3 tyrosine kinase inhibitors, such as decernotinib, DNX-04042, MTF-003, or PS-020613; Jun N terminal kinase inhibitors, such as IQ-1S; KCNA voltage-gated potassium channel-3 modulators, such as MRAD-P1; Kelch like ECH associated protein 1 modulators/Nuclear erythroid 2-related factor 2 stimulators, such as dimethyl fumarate; LanC like protein 2 modulators, such as BT-11; LDL receptor related protein-1 stimulator, such as SP-16; Leukotriene BLT receptor antagonists/complement C5 factor inhibitors, such as nomacopan; LITAF gene inhibitors/JAK3 gene inhibitors/MAP3K2 gene inhibitors/TNF antagonists, such as GBL-5b; Lymphocyte function antigen-3 receptor antagonists, such as alefacept; Macrophage mannose receptor 1 modulators, such as technetium Tc 99m tilmanocept; MAdCAM inhibitors/Immunoglobulin G2 modulators, such as PF-547659; MAPKAPK5 inhibitors/matrix metalloprotease inhibitors, such as GLPG-0259; MEK protein kinase inhibitors, such as AD-GL0001; Membrane copper amine oxidase inhibitors, such as BTT-1023, PRX-167700, or vepalimomab; Metalloprotease-9 inhibitors, such as GS-5745; Microbiome modulator, such as EDP-1815; Midkine ligand inhibitors, such as CAB-102; Mitochondrial 10 kDa heat shock protein stimulators, such as INV-103; mTOR inhibitors, such as everolimus; NAMPT gene inhibitors, such as ART-D01; Nicotinic acetylcholine receptor antagonists, such as RPI-78 or RPI-MN; NKG2 A B activating NK receptor antagonists, such as monalizumab; NKG2 D activating NK receptor antagonists, such as NNC-0142-002; Nuclear factor kappa B inhibitors, such as dehydroxymethylepoxyquinomicin, MP-42, VGX-1027, SP-650003, MG-132, SIM-916, VGX-350, VGX-300, GIT-027, MLN-1145, or NVP-IKK-005; Nuclear factor kappa B modulators/Nuclear factor kappa B p105 inhibitors/Transcription factor RelB inhibitors/Transcription factor p65 inhibitors, such as REM-1086; Osteoclast differentiation factor antagonists, such as cyclic peptidomimetics (rheumatoid arthritis/osteoporosis), University of Michigan; p38 MAP kinase alpha inhibitors, such as VX-745, BMS-582949, or BMS-751324; p38 MAP kinase inhibitors, such as BCT-197, losmapimod, or ARRY-797; PDE 4 inhibitors, such as apremilast; PDE 5 inhibitors, such as PDE5 inhibitors (rheumatoid arthritis), University of Rochester; PDGF-B ligand inhibitors/VEGF receptor antagonists, such as SL-1026; Phosphoinositide-3 kinase delta inhibitors, such as CT-732, INK-007 or GNE-293; Phosphoinositide-3 kinase delta/gamma inhibitors, such as duvelisib or RP-6503; Phospholipase A2 inhibitors, such as AK-106, varespladib methyl, Ro-31-4493, BM-162353, Ro-23-9358, or YM-26734; Platelet activating factor receptor antagonists, such as piperidone hydrochloridum; PPAR gamma agonists, such as rosiglitazone XR; PPAR gamma agonists/Insulin sensitizers, such as rosiglitazone; Programmed cell death protein 1 modulators, such as INSIX RA; Prostaglandin D synthase stimulators, such as HF-0220; Protein tyrosine kinase inhibitors, such as tairuimide; PurH purine biosynthesis protein inhibitors/Inosine monophosphate dehydrogenase inhibitors, such as mycophenolate mofetil; Rev protein modulators, such as ABX-464; RIP-1 kinase inhibitors, such as GSK-2982772; IL-17 antagonist/Rho associated protein kinase 2 inhibitor, such as KD-025; Signal transducer CD24 modulators, such as CD24-IgFc; Sodium glucose transporter-2 inhibitors/PPAR gamma agonists/Insulin sensitizers, such as THR-0921; STAT3 gene inhibitors, such as vidofludimus; STAT-3 inhibitors, such as HL-237; Superoxide dismutase stimulators, such as imisopasem manganese; SYK family tyrosine kinase inhibitors/Zap70 tyrosine kinase inhibitors, such as MK-8457; Syk tyrosine kinase inhibitors, such as fostamatinib, entospletinib, KDDF-201110-06, HMPL-523, AB-8779, GS-9876, PRT-2607, CG-103065, or SKI-O-703; T cell receptor antagonists, such as TCR inhibiting SCHOOL peptides (systemic/topical, rheumatoid arthritis/dermatitis/scleroderma), SignaBlok, CII modified peptide (rheumatoid arthritis), or Peking University; T cell receptor modulators/HLA class II antigen modulators, such as ARG-301; T cell surface glycoprotein CD28 stimulators, such as TAB-08 or theralizumab; TAK1 binding protein modulators, such as epigallocatechin 3-gallate; Talin modulators, such as short-form talin regulators (rheumatoid arthritis) or KayteeBio; T-cell differentiation antigen CD6 inhibitors, such as itolizumab; T-cell surface glycoprotein CD8 inhibitors/TGF beta agonists/CD4 antagonists, such as tregalizumab; Thymulin agonists, such as Syn-1002; TLR-2/TLR-4 antagonists, such as VB-201; TLR-4 antagonists, such as NI-0101; TLR-2/4/9 antagonists, such as P-13; TNF agonists/TNF antagonists/Type II TNF receptor modulators, such as Lifmior; TNF alpha ligand inhibitors, such as Adfrar, FKB-327, Exemptia, Cinnora, Mabura, adalimumab, infliximab, Flixabi, PF-06438179, hadlima, recombinant humanized anti-TNF-alpha monoclonal antibody, CMAB-008, CT-P13, GB-242, golimumab (CNTO-148), ozoralizumab, AT-132, ISIS-104838, ISU-202, CT-P17, MB-612, Debio-0512, anti-TNF alpha human monoclonal antibody, UB-721, KN-002, DA-3113, BX-2922, R-TPR-015, BOW-050, PF-06410293, CKD-760, CHS-1420, GS-071, ABP-710, BOW-015, HLX-03, BI-695501, MYL-1401A, ABP-501, BAX-2923, SCH-215596, ABT-D2E7, BAT-1406, XPro-1595, Atsttrin, SSS-07, golimumab biosimilar, TA-101, BLX-1002, ABX-0401, TAQ-588, TeHL-1, placulumab, CYT-007-TNFQb, SSR-150106, PassTNF, Verigen, DOM-0200, DOM-0215, AME-527, anti-TNF-alpha mAb, GENZ-38167, BLX-1028, CYT-020-TNFQb, CC-1080, CC-1069, LBAL, GP-2017, Idacio, IBI-303, or HS-016; TNF alpha ligand inhibitors/TNF antagonists/Type II TNF receptor modulators, such as BAX-2200; TNF alpha ligand inhibitors/Type II TNF receptor modulators, such as Eucept, TNF alpha ligand modulators, such as MM-A01-01, CDP-571, camobucol, or JNJ-63823539; TNF antagonists, such as DNX-114, TNF antagonist+IL-12 antagonist (rheumatoid arthritis), University of Oxford, BN-006, pegsunercept, ACE-772, onercept, DE-096, PN-0615, lenercept, ITF-1779, MDL-201112, HD-203, Qiangke, or TNF a Fc; TNF antagonists/Type II TNF receptor modulators, such as Altebrel, Intacept, QL-0902, etanercept, Erelzi, opinercept, YISAIPU, Anbainuo, Benepali, YLB-113, SCB-808, DA-3853, or SCB-131; TNF antagonists/TNF alpha ligand inhibitors, such as certolizumab pegol; TNF receptor modulators, such as recombinant TNF receptor 2-Fc fusion protein mutant or T-0001; TNF receptor modulators/TNF alpha ligand inhibitors, such as tgAAV-TNFR:Fc; tumor necrosis factor 13C receptor antagonists, such as VAY-736; tumor necrosis factor 15 ligand inhibitors, such as anti-TL1A antibodies (rheumatoid arthritis/inflammatory bowel disease), or NIAMS; Tumor necrosis factor ligand inhibitors, such as etanercept biosimilar; Type I IL-1 receptor antagonists, such as anakinra, IL-1 Ra, anakinra follow-on biologic or AXXO; Type I TNF receptor antagonists, such as NM-9405; Type II TNF receptor modulators, such as LBEC-0101, DMB-3853, DWP-422, or BT-D001; Unspecified GPCR agonists, such as NCP-70X; VEGF receptor antagonists, such as NSC-650853; VEGF-2 receptor modulators, such as VEGFR2 neutralizing antibody (rheumatoid arthritis), University of Rochester; VEGF-B ligand inhibitors, such as CSL-346; X-linked inhibitor of apoptosis protein inhibitors, such as IAP inhibitors (oral) or Pharmascience; or Zap70 tyrosine kinase inhibitors, such as CT-5332.

In one embodiment, the compound of Formula I, or any formula described herein, or a pharmaceutically acceptable salt thereof, is useful for the treatment of cancer in combination with a JAK-1 inhibitor. An example of such JAK-1 inhibitor is a compound disclosed in WO2008/109943. Examples of other JAK inhibitors include, but are not limited to, AT9283, AZD1480, baricitinib, BMS-911543, fedratinib, filgotinib (GLPG0634), gandotinib (LY2784544), INCB039110 (itacitinib), lestaurtinib, momelotinib (CYT0387), NS-018, pacritinib (SB1518), peficitinib (ASP015K), ruxolitinib, tofacitinib (formerly tasocitinib), INCB052793, and XL019. In one embodiment, a compound as disclosed herein, such as a compound of Formula I or any formula described herein, or a pharmaceutically acceptable salt thereof, may be combined with filgotinib (GLPG0634).

Synthesis

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds of Formula I, e.g., compounds having structures described by one or more of Formula I, or other formulas or compounds disclosed herein, or a pharmaceutically acceptable salt thereof, may be accomplished as described in the following examples.

General Syntheses

Typical embodiments of compounds in accordance with the present disclosure may be synthesized using the general reaction schemes and/or examples described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Starting materials are typically obtained from commercial sources or synthesized using published methods for synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein.

Synthetic Reaction Parameters

The compounds of this disclosure can be prepared from readily available starting materials using, for example, the following general methods and procedures. It will be appreciated that where typical or specific process conditions (e.g., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting certain functional groups are well known in the art. For example, numerous protecting groups are described in T. W. Greene and G. M. Wuts (1999) *Protecting Groups in Organic Synthesis*, 3rd Edition, Wiley, New York, and references cited therein. Protective groups can be added or removed at any appropriate stage in order to enable the syntheses described herein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, such as nitrogen.

The following is a list of abbreviations and acronyms used throughout the application:

| Abbreviation | Meaning |
|---|---|
| ° C. | Degree Celsius |
| ATP | Adenosine-5'-triphosphate |
| AcOH | Acetic acid |
| Boc | Tert-butyloxycarbonyl |
| Bn | Benzyl |
| Bs | Benzenesulfonyl |
| CDI | 1,1'-Carbonyldiimidazole |
| d | Doublet |
| Dba | Dibenzylideneacetone |
| DBU | 1,8-Diazabicyclo[5.4.0]undec-7-ene |
| dd | Doublet of doublets |
| DCE | 1,2-dichloroethane |
| DCM | Dichloromethane |
| DEAD | Diethyl azodicarboxylate |
| Dess-Martin periodinane | 1,1,1-Tris(acetyloxy)-1,1-dihydro-1,2-benziodoxol-3-(1H)-one |
| DIAD | Diisopropyl azodicarboxylate |
| DIPEA, DIEA | N,N-diisopropylethylamine |
| DMAP | 4-Dimethylaminopyridine |
| DME | 1,2-dimethoxyethane |
| DMF | Dimethylformamide |
| DMSO | Dimethylsulfoxide |
| DMPU | 1,3-dimethyl-3,4,5,6-tetrahydro-2(1H)-pyrimidinone |
| Dppf | 1,1'-Bis(diphenylphosphino)ferrocene |
| DPPA | Diphenylphosphoryl azide |
| EDC | 1-Ethyl-3-(3-dimethylaminopropyl)carbodiimide |
| EDTA | Ethylenediaminetetraacetic acid |
| EGTA | Ethylene glycol tetraacetic acid |
| EtOAc | Ethyl acetate |
| equiv/eq | Equivalents |
| ESI | Electrospray ionization |
| Ac | Acetate |
| Et | Ethyl |
| g | Grams |
| HATU | 2-(7-Aza-1H-Benzotriazole-1-yl)-1,1,3,3-tetramethyluronium hexafluorophosphate |
| HCl | Hydrochloric acid |
| hERG | human Ether-à-go-go Related Gene |
| HPLC | High-performance liquid chromatography |
| h/hr | Hours |
| Hunig's Base | N,N-diisopropylethylamine |
| Hz | Hertz |
| IC$_{50}$ | The half maximal inhibitory concentration |
| IPTG | Isopropyl β-d-1-thiogalactopyranoside |

-continued

| Abbreviation | Meaning |
|---|---|
| Ir[dF(CF$_3$)ppy]$_2$(dtbbpy)PF$_6$ | [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate |
| J | Coupling constant |
| Jackiephos | 2-{Bis[3,5-bis(trifluoromethyl)phenyl]phosphino}-3,6-dimethoxy-2',4',6'-triisopropyl-1,1'-biphenyl |
| Jackiephos Pd G3 | [(2-{Bis[3,5-bis(trifluoromethyl)phenyl]phosphine}-3,6-dimethoxy-2',4',6'-triisopropyl-1,1'-biphenyl)-2-(2'-amino-1,1'-biphenyl)]palladium(II) methanesulfonate |
| kg | Kilogram |
| LC/MS, LCMS, LC-MS | Liquid chromatography mass spectrometry |
| LDA | Lithium diisopropylamide |
| LiHMDS | Lithium bis(trimethylsilyl)amide |
| L-selectride | Lithium tri-sec-butylborohydride solution |
| M | Molar |
| m | Multiplet |
| m/z | mass-to-charge ratio |
| M+ | Mass peak |
| M + H | Mass peak plus hydrogen |
| Me | Methyl |
| MeOH | Methyl alcohol/methanol |
| Mg | Milligram |
| MHz | Megahertz |
| min/m | Minute |
| ml/mL | Milliliter |
| mM | Millimolar |
| mmol | Millimole |
| MS | Mass spectroscopy |
| MTBE | Methyl tert-butyl ether |
| Mw | Microwave |
| N | Normal |
| Mol | Mole |
| NaHMDS | Sodium bis(trimethylsilyl)amide |
| NCS | N-chlorosuccinimide |
| NIS | N-iodosuccinimide |
| NMP | N-methylpyrrolidinone |
| NMR | Nuclear magnetic resonance |
| p | Pentuplet |
| PCR | Polymerase chain reaction |
| Ph | Phenyl |
| ppm | Parts per million |
| PPTS | Pyridinium para-toluenesulfonate |
| Prep | Preparative |
| Rf | Retention factor |
| RP | Reverse phase |
| RT/rt | Room temperature |
| s | Second |
| s | Singlet |
| SEM | Trimethylsilylethoxymethyl |
| SPhos | 2-Dicyclohexylphosphino-2',6'-dimethoxybiphenyl |
| SPhos Pd G4 | Methanesulfonato(2-dicyclohexylphosphino-2",6"-dimethoxy-1,1"-biphenyl)(2"-methylamino-1,1"-biphenyl-2-yl)palladium(II) dichloromethane adduct |
| SUMO | Small ubiquitin-like modifier |
| t | Triplet |
| TBAF | Tetrabutylammonium fluoride |
| TBAI | Tetrabutylammonium iodide |
| TBS | Tert-butyldimethylsilyl |
| TBDPS | Tert-butyldiphenylsilyl |
| tBuXPhos | 2-Di-tert-butylphosphino-2',4',6'-triisopropylbiphenyl |
| tBuXPhos Pd G1 | Chloro[2-(di-tert-butylphosphino)-2',4',6'-triisopropyl-1,1'-biphenyl][2-(2-aminoethyl)phenyl]]palladium(II) |
| tBuXPhos Pd G3 | [(2-Di-tert-butylphosphino-2',4',6'-triisopropyl-1,1'-biphenyl)-2-(2'-amino-1,1'-biphenyl)]palladium(II) methanesulfonate |
| TCEP | Tris(2-carboxyethyl)phosphine |
| TEA | Triethylamine |
| Tf | Trifluoromethylsulfonyl |
| TFA | Trifluoroacetic acid |
| THP | Tetrahydropyranyl |
| TLC | Thin layer chromatography |
| Trt/Trityl | Triphenylmethyl |
| TMS | Trimethylsilyl |
| Ts | Toluenesulfonyl |
| WT | Wild type |

| Abbreviation | Meaning |
|---|---|
| Xantphos | 4,5-Bis(diphenylphosphino)-9,9-dimethylxanthene |
| XPhos | 2-Dicyclohexylphosphino-2',4',6'-triisopropylbiphenyl |
| XPhos Pd G3 | (2-Dicyclohexylphosphino-2',4',6'-triisopropyl-1,1'-biphenyl)[2-(2'-amino-1,1'-biphenyl)]palladium(II) methanesulfonate |
| Zhan 1b | 1,3-Bis(2,4,6-trimethylphenyl)-4,5-dihydroimidazol-2-ylidene[2-(i-propoxy)-5-(N,N-dimethylaminosulfonyl)phenyl]methyleneruthenium (II) dichloride |
| δ | Chemical shift |
| μg | Microgram |
| μL/μl | Microliter |
| μM | Micromolar |
| μm | Micrometer |
| μmol | Micromole |

Compounds as provided herein may be synthesized according to the general schemes and/or synthetic procedures described below. In the Schemes below, it should be appreciated that each of the compounds shown therein may have protecting groups as required present at any step. Standard protecting groups are well within the purview of one skilled in the art. Further, unless otherwise defined, the various substituents depicted in the following Schemes (e.g., $X^5$, $X^7$, $R^1$, $R^2$, $R^3$, $R^4$, $R^6$, $R^{10}$, $R^{11}$, etc.) are as defined in the embodiments and compounds disclosed herein.

Scheme A shows an exemplary synthetic route for the synthesis of compounds provided herein (e.g., compounds of Formula I). In Scheme A, $X^5$, $X^7$, $R^1$, $R^2$, $R^3$, $R^4$, $R^6$, $R^{10}$, and $R^{11}$, are as defined herein, $P^1$ is hydrogen or a suitable protecting group, Z may be the moiety —$NR^{10}R^{11}$, or a suitable precursor thereto (e.g., a protected amino moiety, —OH or —O-alkyl, and the like), LG is a leaving group, and X and Y are each, respectively, suitable complimentary functional groups capable of forming a covalent bond therebetween.

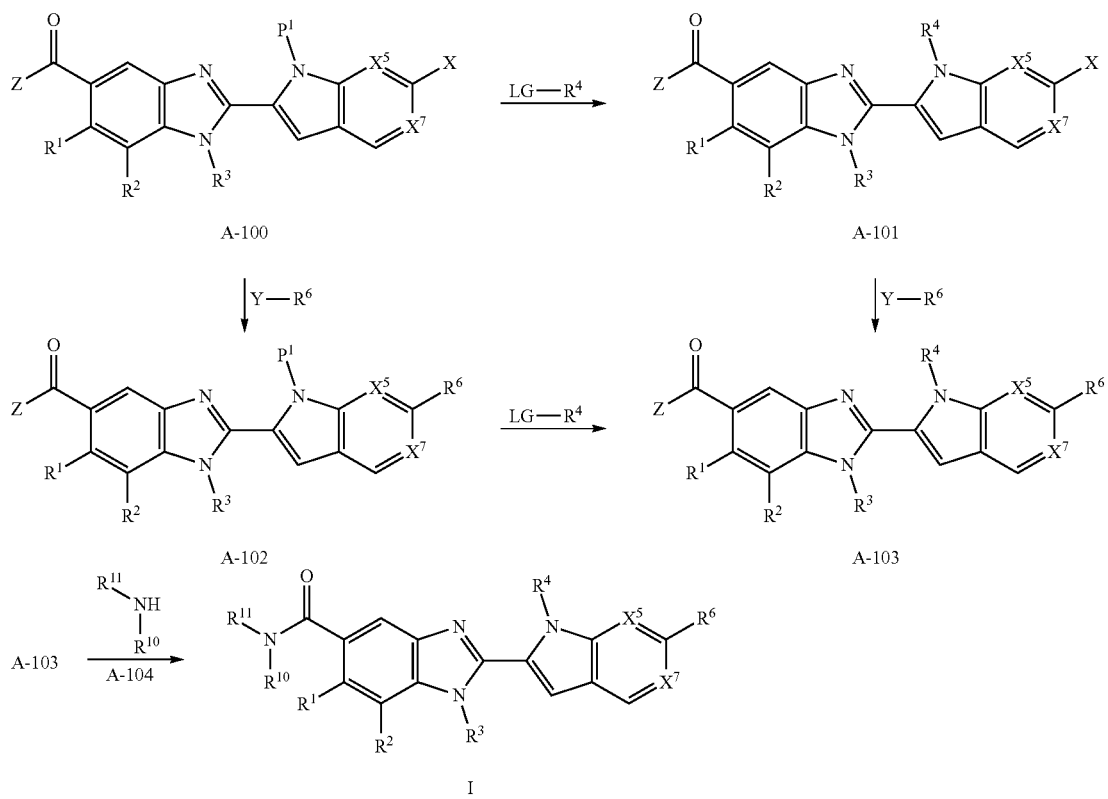

Scheme A

In Scheme A, a compound A-100 can first be deprotected as needed and then reacted with a compound of formula LG-$R^4$, where LG is a leaving group (e.g., halo), under suitable conditions to provide compound A-101. Compound A-101 can then be converted to compound A-103 upon contact with a compound of formula Y—$R^6$ under suitable coupling conditions. Alternatively, compound A-100 can be reacted with a compound of formula Y—$R^6$ under suitable coupling conditions to provide compound A-102. Exemplary functional groups, and well as other functional group modifications, are detailed in the Schemes and Procedures below.

In Scheme A, compound A-103 can be further modified to install the —$NR^{10}R^{11}$ moiety and thus provide compounds of Formula I. In certain embodiments of compound A-100, A-102 or A-103, Z is —$NR^{10}R^{11}$. Thus, it can be understood that at any point in the synthesis prior to the formation of the macrocyclic ring, an intermediate can be modified to convert a Z group, where Z is suitable precursor (e.g., —OH or —O-alkyl, and the like), to Z is —$NR^{10}R^{11}$.

In certain embodiments, $R^{10}$ or $R^{11}$ may contain a protected amine substituent (e.g., —$NHP^1$, —$NP^1P^2$, or —$NR^{12}P^1$, where examples of $P^1$ and $P^2$ include -Boc, -Cbz, -trityl, or any other group known to be useful as an amine protective group). Additionally, $R^{11}$ may be a nitrogen-containing heterocycle wherein the ring nitrogen is protected with $P^1$, as defined above. In these cases, removal of $P^1$ and $P^2$ can be carried out using standard conditions, including TFA or HCl for -Boc or -trityl, and hydrogenolysis over a suitable catalyst (e.g., Pd/C) for -Cbz to afford amine products.

Where the individual steps do not provide a desired isomer (e.g., stereoisomer), resolution of the isomers of Formula I, or any intermediate used in the preparation thereof, can be performed as needed using standard chiral separation/resolution conditions (e.g., chromatography, crystallization, etc.).

Suitably substituted compounds A-100, A-101, A-102, and A-103 for use in the methods provided herein can be purchased from commercial sources or synthesized by known methods, or according to methods described in the Schemes and Procedures detailed herein.

Scheme A-1

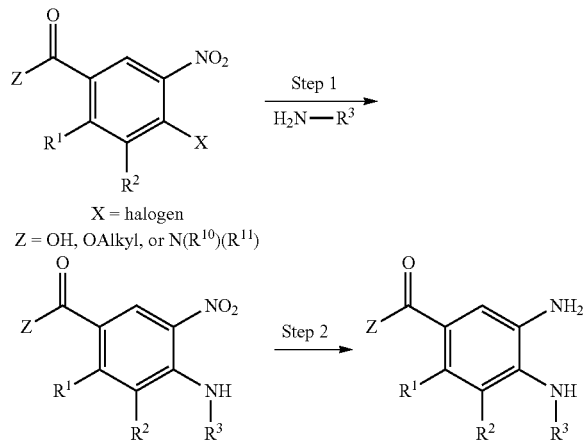

Scheme A-1 describes the synthesis of amino nitroarenes and arylenediamines useful for construction of benzimidazole intermediates.

Step 1 describes the synthesis of 2-amino nitroarene by treatment of a suitable halo nitroarene or (especially when X=F, Cl) with an amine R-$NH_2$ along with base (e.g., triethylamine, Hunig's base). Examples of intermediates prepared by this approach include I-1a and I-3c. Alternatively, NH—$R^3$ can be installed by palladium-mediated cross coupling (especially when X=Cl, Br, I). In certain cases, similar amino nitroarenes may also be prepared by direct nitration of the corresponding aryl or heteroaryl amine. These nitroanilines may be reduced to the corresponding arylenediamine species as described below in Step 2 or may be used directly to construct benzimidazoles as described in Scheme C-1.

Step 2 describes the reduction of nitroanilines to arylenediamines. This may be accomplished using standard conditions known to those versed in the art, including hydrogenation over a suitable catalyst (e.g., Pd/C, Pt/C) or by treatment with other reducing agents (e.g., $SnCl_2$, sodium dithionite, Fe/HOAc, Zn/HOAc). A particularly useful method for nitro reduction is hydrogenation over a mixed catalyst system comprised of Pt and V on carbon (Evonik Noblyst P8078), especially when $R^3$=cyclopropyl. Examples of intermediates prepared by this approach include I-4a and I-5e.

Scheme B-1

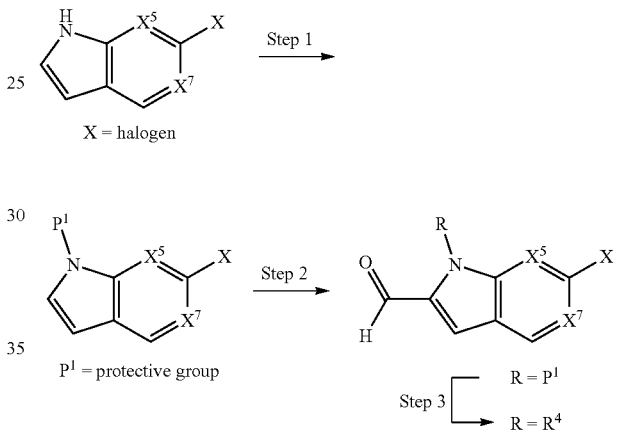

Scheme B-1 depicts the preparation of an indole or azaindole aldehyde intermediate that contains a halogen functional handle.

Step 1 describes the protection of a halogenated indole or aza-indole with $P^1$. Such protective groups can be installed using standard procedures, including treatment with SEM-Cl, $Boc_2O$, or benzenesulfonyl chloride in the presence of a suitable base (e.g., Hunig's base, $Et_3N$, NaH, NaHMDS, etc.) to provide $P^1$=SEM, $P^1$=Boc, and $P^1$=benzenesulfonyl, respectively.

Step 2 describes installation of a carbaldehyde moiety by deprotonation of the protected indole or azaindole derivative with a suitable base (e.g., BuLi, LDA) followed by treatment with a suitable formyl transfer reagent (e.g., N,N-dimethylformamide, N-formylpiperidine, N-formylmorpholine, ethyl formate, etc.). Additives such as TMEDA or HMPA facilitate the deprotonation in certain cases. An example of an intermediate prepared by this approach was described in the synthesis of I-6.

Step 3 describes the removal of protective group $P^1$ using standard conditions known to those versed in the art to provide R=H and the optional installation of $R^4$ by alkylation with $R^4$—X, where X=halogen or pseudohalide (e.g., cyclopropylmethyl bromide) in the presence of base (e.g., $Cs_2CO_3$, NaH, etc.). It is understood that in certain cases $P^1$ can be exchanged for $R^4$ prior to the lithiation/formylation described in Step 2.

Scheme B-2

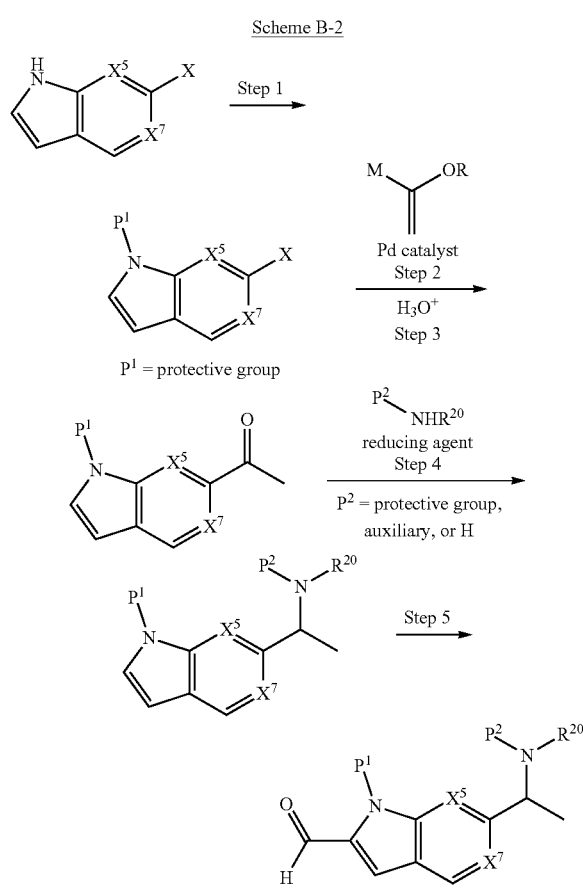

P¹ = protective group

P² = protective group, auxiliary, or H

Scheme B-2 depicts the synthesis of an aminoethyl-containing indole or azaindole aldehyde intermediate.

Step 1 is as described in Scheme B-1.

Steps 2 and 3 describes installation of an acetyl moiety by cross coupling of a vinyl ether nucleophile mediated by a suitable palladium catalyst followed by acidic hydrolysis. In this sequence, M is often trialkylstannane, but can also be boronic ester, acid, or trifluoroborate salt, or magnesium or zinc halide. Alternatively, a Heck coupling can be employed where M=H.

Step 4 describes the installation of an amino moiety $N(R^{20})(P^2)$ by initial condensation with a suitable amine derivative followed by reduction of the formed imine intermediate. It is understood that this transformation can be accomplished in several ways, including but not limited to: a) in situ reductive amination, where the acetyl intermediate is treated with an amine derivative and a suitable reducing agent (e.g., $NaBH(OAc)_3$, $NaBH_3CN$) concurrently, and b) stepwise amine installation, where a suitable amine derivative (especially tert-butyl sulfinamide) is condensed in the presence of a Lewis acid dehydrating reagent (e.g., $Ti(OiPr)_4$, $Ti(OEt)_4$) to provide a imine (or sulfinimine) that is then reduced in a second step with a suitable reducing agent (e.g., $NaBH_4$, L-selectride). This method is useful due to the availability of enantiomeric forms of tert-butyl sulfinamide and the known ability of these to exert control over stereoconfiguration in the reduction step. It is understood that protective group/auxiliary manipulation can take place following this sequence (e.g., $P^2$=S(O)tBu can be removed and/or converted to Boc) using standard conditions.

Step 5 describes installation of a carbaldehyde moiety by deprotonation of the protected indole or azaindole derivative with a suitable base (e.g., BuLi, LDA) followed by treatment with a suitable formyl transfer reagent (e.g., N,N-dimethylformamide, N-formylpiperidine, N-formylmorpholine, ethyl formate, etc.). Additives such as TMEDA or HMPA facilitate the deprotonation in certain cases. An example of an intermediate prepared by this approach is I-12.

Scheme B-3

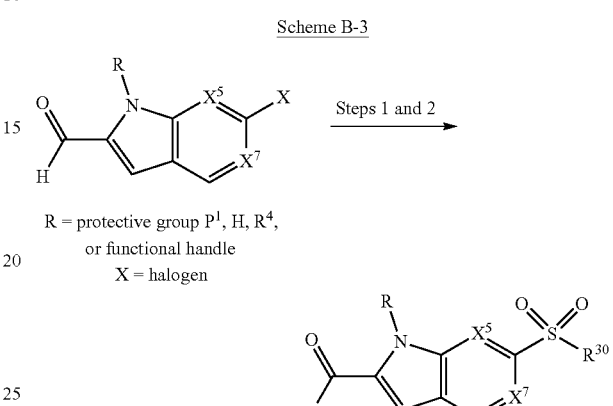

R = protective group $P^1$, H, $R^4$, or functional handle
X = halogen

Scheme B-3 describes the installation of a sulfone substituent on an azaindole ($X^5$=N).

Step 1 depicts the nucleophilic displacement of a halogen by a thiolate, which can be introduced as a salt or generated in situ in the presence of base (e.g., KO′Bu). $R^{30}$ corresponds to examples described herein. In Step 2, the resulting sulfide is oxidized to the corresponding sulfone upon exposure to suitable conditions, such as $RuCl_3$ and $NaIO_4$. An example of an intermediate prepared by this approach was described in the synthesis of I-13.

Scheme C-1

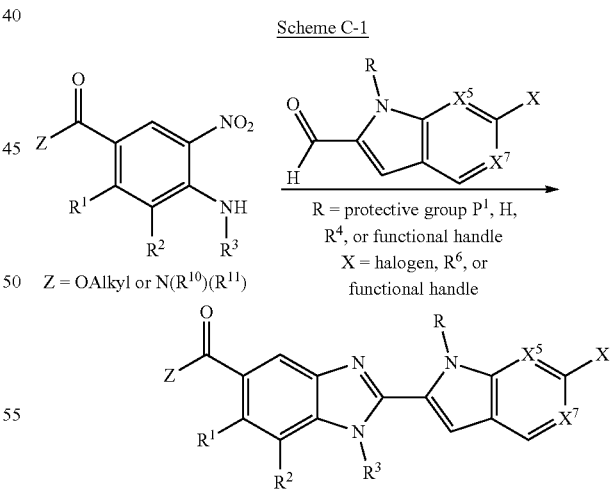

Z = OAlkyl or $N(R^{10})(R^{11})$

R = protective group $P^1$, H, $R^4$, or functional handle
X = halogen, $R^6$, or functional handle Scheme C-1 describes benzimidazole synthesis accomplished by treating 2-amino nitroarene or heteroarenes described in Scheme A-1 with a suitably protected and/or functionalized heteroaryl aldehyde described in Scheme B-1, B-2 or B-3 in the presence of sodium dithionite, generally in aqueous alcohol solvent and at elevated temperature (e.g., 50-100° C.). R may be a protective group $P^1$ (e.g., SEM, benzenesulfonyl), H, $R^4$ (e.g., cyclopropylmethyl) or functional precursor to $R^4$ groups described herein. An example of an intermediate prepared by this approach is I-16m.

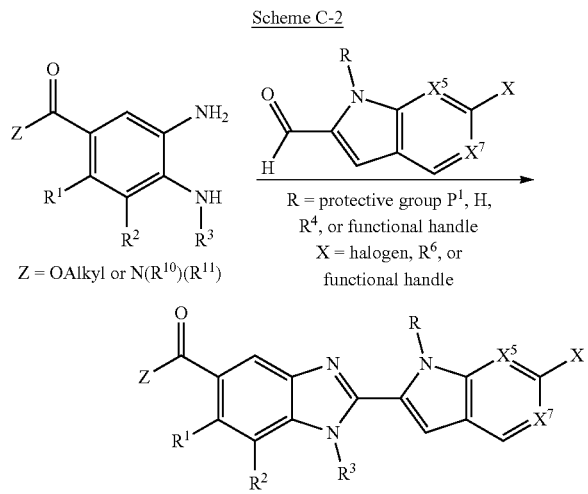

Scheme C-2

Scheme C-2 describes the synthesis of benzimidazole intermediates from arylenediamine species described in Scheme A-1 and heteroaryl aldehydes described in Scheme B-1, B-2 or B-3. This may be accomplished by combining these intermediates under suitable conditions; an especially useful condition utilizes HOAc as solvent and is carried out at elevated temperature (ca. 60-90° C.) under air. In certain cases, protective group $P^1$ may be removed over the course of this process. An example of an intermediate prepared by this approach was described in the synthesis of I-18d.

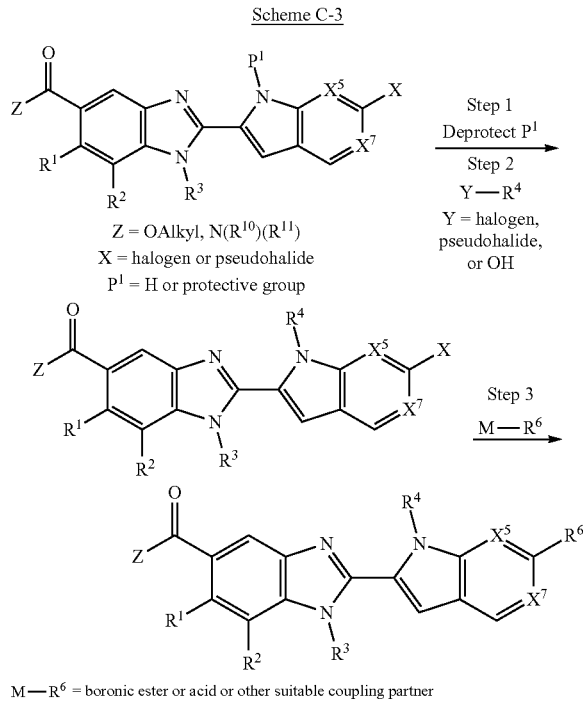

Scheme C-3

Scheme C-3 describes the installation of $R^6$ by cross coupling.

Step 1 describes the removal of $P^1$ (where $P^1$=protective group) to provide the corresponding NH indole or aza-indole. This can be accomplished using standard methods (for example, by treatment with TFA or HCl when $P^1$=Boc or SEM, or by treatment with TBAF when $P^1$=benzenesulfonyl). This step is omitted when $P^1$=H.

Step 2 describes the installation of $R^4$. This may be accomplished by alkylation with Y—$R^4$, where $R^4$ is as described herein and Y=halogen (e.g., Br or I) or pseudohalide (e.g., triflate) in the presence of a suitable base (e.g., $Cs_2CO_3$, NaH, NaHMDS). Alternatively, this may be accomplished using a Mitsunobu protocol when Y=OH (for example, using DIAD and $PPh_3$). It is understood that a functional precursor to the ultimately desired $R^4$ group may be used in this step, and that subsequent elaboration may be accomplished using known methods to provide the desired $R^4$ group.

Step 3 describes the installation of R. This can be accomplished with $MR^6$ in the presence of a suitable palladium catalyst when M is a boronic ester, acid, trifluoroborate salt, trialkylstannane or organozinc or organomagnesium halide. Such organometallic $MR^6$ groups may be commercially available or prepared using standard methods (e.g., hydroboration or metal-catalyzed borylation, lithium/halogen exchange followed by transmetallation to tin, zinc, or magnesium, direct halogen/magnesium exchange, etc.). Functional precursors to $R^6$ groups may also be used in this step, wherein the product of this coupling step may be further elaborated to the $R^6$ groups described herein using methods known to those versed in the art. An example of an intermediate prepared by this approach was described in the synthesis of Example 246.

It is also understood that the order of steps depicted in Scheme C-3 could be changed, for instance Step 3 may precede Steps 1 and 2. Where functional precursors to ultimately desired $R^4$ or $R^6$ are used in Steps 2 or 3, it is understood that other ordering of steps may be suitable to provide the desired groups.

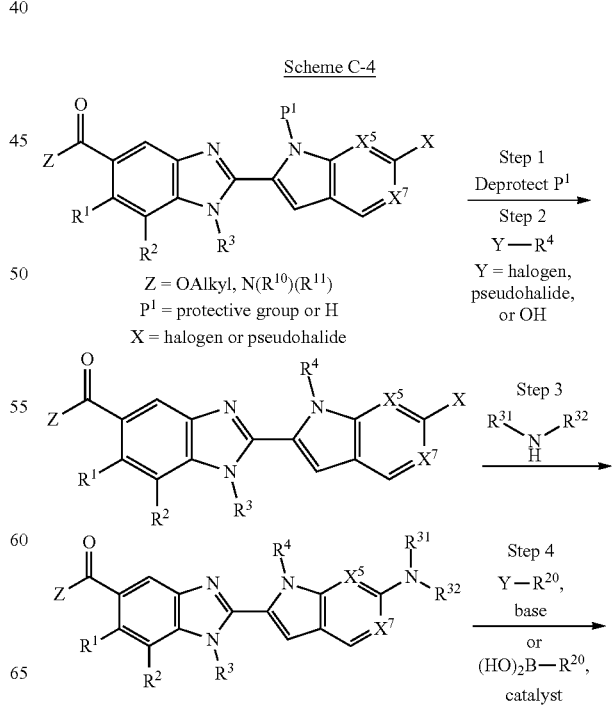

Scheme C-4

-continued

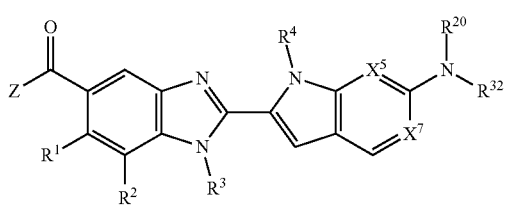

$R^{31}$ = H, $R^{20}$, protective group, etc.
$R^{32}$ = H, $SO_2R^9$, $C(O)R^9$, $CO_2R^9$, etc.

Scheme C-4 describes the synthesis of various N-linked $R^6$ groups.

Steps 1 and 2 are as described in Scheme C-3 above.

Step 3 describes the C-N coupling with $HN(R^{31})(R^{32})$ utilizing a suitable transition metal catalyst system (e.g., allyl palladium dimer+Jackiephos, tBuXPhos Pd G3, copper iodide). This method is useful for synthesis of N-linked sulfonamide or carbamate $R^6$ groups (e.g., $HN(R^{31})(R^{32})$=MeNHSO$_2$Me or EtNHCO$_2$Me, respectively) described herein.

Step 4 describes optional further derivatization of $NR^{31}R^{32}$. For instance, when $R^{31}$=H, alkylation with Y—$R^{20}$ where Y=halogen (e.g., Br or I) in the presence of a suitable base (e.g., $Cs_2CO_3$, NaH, NaHMDS) installs $R^{14}$. An example when $NR^{31}R^{32}$=NHSO$_2$Me is installation of $R^{20}$=CHF$_2$ using chlorodifluoromethane and $K_2CO_3$. Alternatively, $R^{20}$ may be installed using a cross coupling approach, for example a Chan-Lam type coupling in the presence of a suitable copper catalyst where Y—$R^{20}$=$R^{20}$—B(OH)$_2$. Examples of intermediates prepared by this approach are described in the syntheses of Example 32 and Example 63.

It is understood that the order of events depicted in Scheme C-4 could be rearranged; for example, steps 3 and 4 could precede steps 1 and 2.

Scheme C-5 depicts the synthesis of carbonyl-containing intermediates useful for the synthesis of $R^6$ groups described herein.

Step 1 and 2 describe installation of an acetyl moiety by cross coupling of a vinyl ether nucleophile mediated by a suitable palladium catalyst (e.g., Pd(tBu$_3$P)$_2$, PdCl$_2$(dppf)) followed by acidic hydrolysis. In this sequence, M is often trialkylstannane (for example, as in 1-ethoxyvinyltributylstannane), but other suitable organometallic species for cross-coupling may also be used. Alternatively, a Heck coupling mediated by a suitable palladium catalyst may be used where M=H. An example of an intermediate prepared by this approach was described in the synthesis of I-19a.

Steps 3 and 4 describe an alternate method to prepare carbonyl-containing precursors to $R^6$ groups. In this approach, an alkenyl organometallic species (e.g., —potassium isopropenyltrifluoroborate, vinyl tributylstannane) may be coupled in the presences of a suitable palladium catalyst, and the resulting olefin-containing product may be oxidatively cleaved (e.g., OsO$_4$/NaIO$_4$, O$_3$ followed by PPh$_3$) to provide the depicted carbonyl-containing intermediate. An example of an intermediate prepared by this approach was described in the synthesis of I-21a.

Scheme C-6

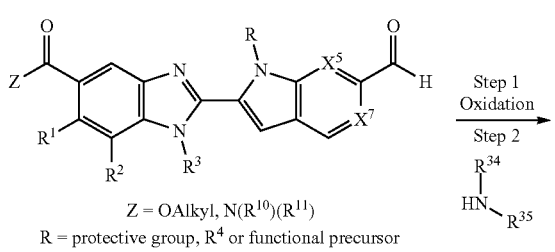

Z = OAlkyl, $N(R^{10})(R^{11})$
R = protective group, $R^4$ or functional precursor Scheme C-5

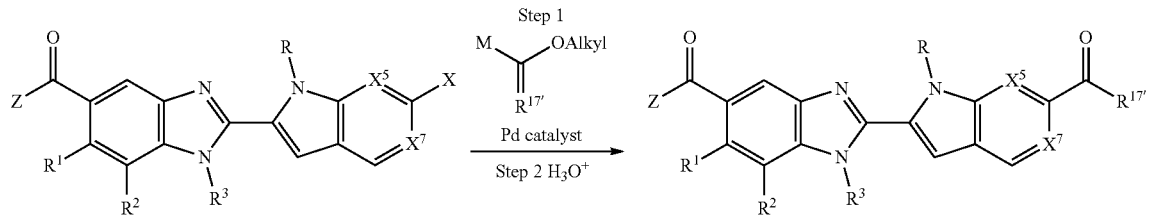

Z = OAlkyl, $N(R^{10})(R^{11})$
X = halogen
R = protective group, $R^4$ or functional precursor $R^{17'}$ = $R^{17}$ or functional precursor

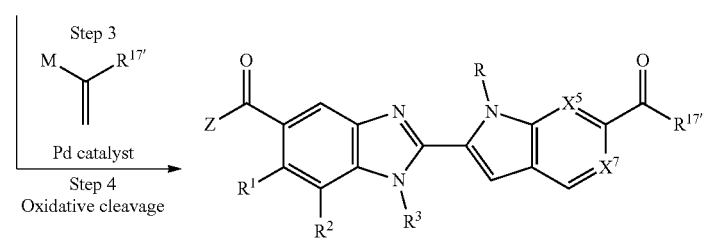

-continued

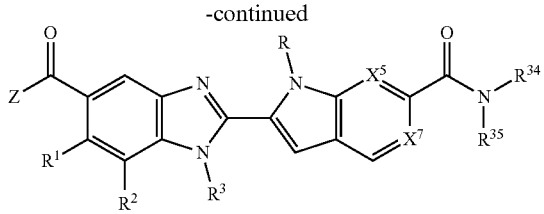

Scheme C-6 describes an example of how aldehyde-containing intermediates described in Scheme C-5 ($R^{17}$=H) can be further elaborated.

Step 1 describes the conversion of the aldehyde to the carboxylic acid using a suitable oxidant (e.g., NaClO$_2$, oxone). Step 2 describes amide coupling with $R^{34}R^{35}$NH using a suitable coupling reagent (e.g., HATU), where $R^{34}$ and $R^{35}$ correspond to examples described herein. An example of an intermediate prepared by this approach was described in the synthesis of Example 250.

Scheme C-7

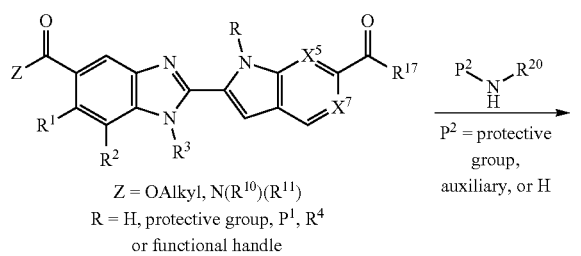

Scheme C-7 depicts the synthesis of amine-containing $R^6$ groups from carbonyl-containing precursors described in Scheme C-5.

This approach entails the initial condensation of a suitable amine-containing fragment $P^2$NHR$^{20}$ followed by treatment with a nucleophilic $R^{17'}$ group. Variations on this approach include reductive amination in a single step (e.g., treatment with $P^2$NHR$^{20}$ along with a reducing agent such as NaBH(OAc)$_3$ or NaBH$_3$CN in situ) or stepwise condensation with $P^2$NHR$^{20}$ followed by treatment with a suitable metal hydride (where $R^{17'}$=H) or organometallic or other nucleophile.

An especially useful embodiment of the stepwise approach is initial condensation with tert-butyl sulfinamide (NHP$^2$R$^{20}$=NH$_2$S(O)tBu) in the presence of a suitable Lewis acid (e.g., Ti(OEt)$_4$ or Ti(OiPr)$_4$) to provide the corresponding N-sulfinyl imine, followed by treatment with a reducing agent (e.g., NaBH$_4$, L-selectride) to provide $R^{17'}$=H, or with an organometallic nucleophile M-R$^{17'}$ (e.g., MeMgBr, cyclopropyl-MgBr) to provide other $R^{17'}$ groups. This method is useful due to the availability of enantiomeric forms of tert-butyl sulfinamide and the known ability of these to exert control over stereoconfiguration in the reduction or nucleophilic addition step. Other nucleophiles such as that generated from TMS-CF$_3$ in the presence of a fluoride activator (e.g., TASF) may be used in this transformation. An example of an intermediate prepared by this approach was described in the synthesis of I-26.

Scheme C-8

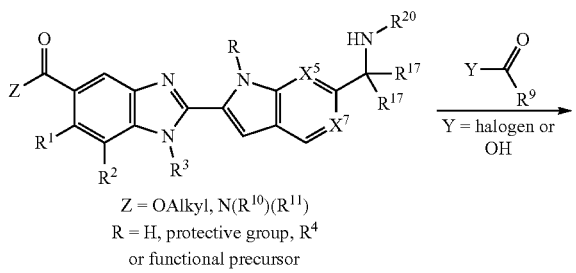

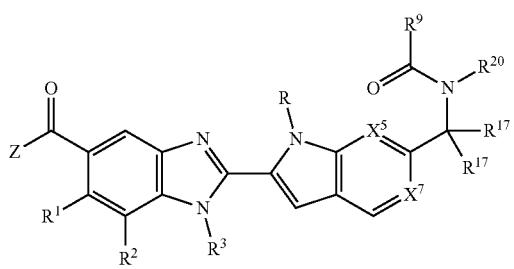

Scheme C-8 describes the preparation of amide-containing $R^6$ groups. This may be accomplished by acylation of an amine precursor using standard conditions, including treatment with a commercially available or prepared acid chloride (e.g., AcCl) in the presence of a suitable base (e.g., Hunig's base, triethylamine, etc.) or treatment with a carboxylic acid (e.g., AcOH, BzOH) in the presence of a suitable amide coupling reagent (e.g., EDC, HATU, DIC, etc.). An example of an intermediate prepared by this approach was described in the synthesis of Example 120.

It is understood that similar well-known chemistries could be used to afford related amine derivatives. For example, treatment with an isocyanate or chloroformate in the presence of base would yield a urea or carbamate derivate, respectively (e.g., providing —C(O)N(R$^9$)(R$^{20}$) or —C(O)OR$^9$ in place of —C(O)R$^9$ as depicted above). Several of these variations are depicted in Schemes C-9 and C-10 below.

Scheme C-9

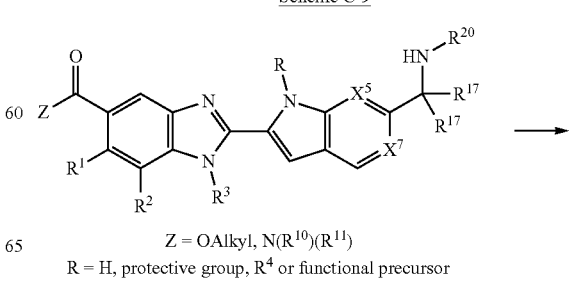

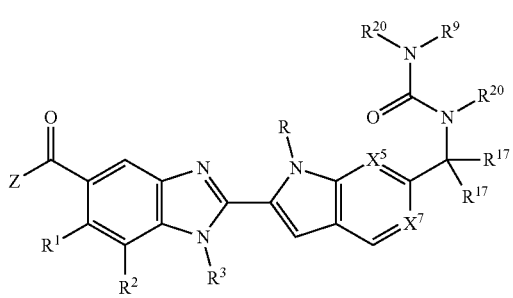

Scheme C-9 describes the preparation of urea-containing R groups. This may be accomplished by treatment of an amine precursor with a commercially available or prepared carbamoyl chloride (e.g., ClC(O)NMe$_2$) in the presence of a suitable base (e.g., Hunig's base, triethylamine, etc.). This may also be accomplished in stepwise fashion, for instance by initial treatment with an activated carbonyl-containing reagent (e.g., phosgene/diphosgene/triphosgene, carbonyldiimidazole, ClC(O)(p-NO$_2$Ph) in the presence of suitable base followed by treatment with HN(R$^{20}$)(R$^9$). This may also be accomplished by treatment with a suitable isocyanate in the presence of base. An example of an intermediate prepared by this approach was described in the synthesis of Example 238.

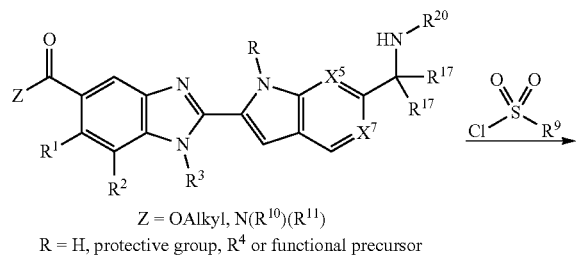

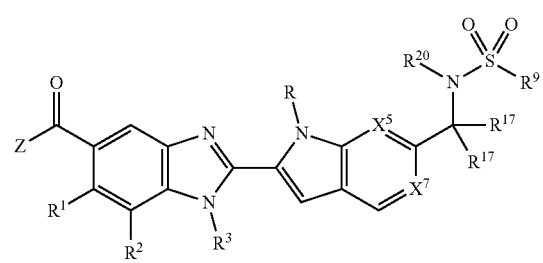

Scheme C-10 describes the synthesis of sulfonamide containing R groups. This can be accomplished by treatment of an amine containing precursor with a sulfonyl chloride (e.g., ClSO$_2$Me) in the presence of a suitable base (e.g., Et$_3$N, Hunig's base). An example of an intermediate prepared by this approach was described in the synthesis of Example 240.

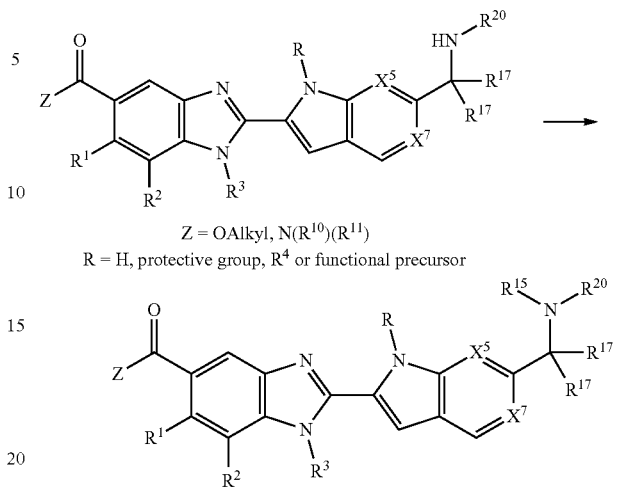

Scheme C-11 describes the synthesis of aminoarene or animoheteroarene containing R6 groups. This may be accomplished by treatment of an amine precursor with an electron deficient fluoro- or chloroarene or -heteroarene (e.g., 2-chloropyrimidine) in the presence of a suitable base at elevated temperature. Alternatively, this may be accomplished by treatment with an aryl or heteroaryl halide (e.g., Br, I, Cl) along with a suitable palladium catalyst (e.g., XPhos Pd G3) and base (e.g., KOtBu).

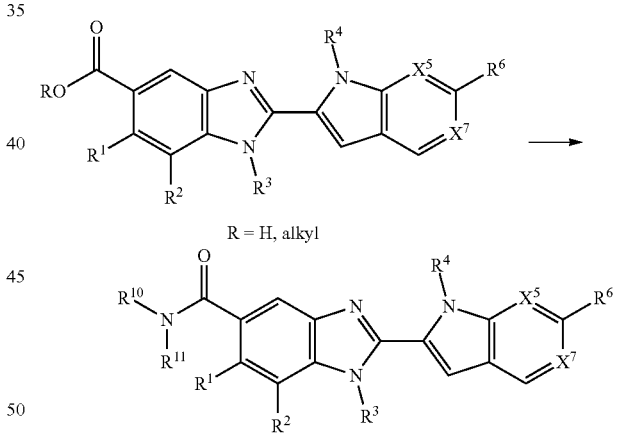

Scheme D-1 depicts the incorporation of a N(R$^{10}$)(R$^{11}$) from the corresponding carboxylic acid or ester. In the case where R=H, treatment with HN(R$^{10}$)(R$^{11}$) along with an amide coupling reagent (e.g., EDC, HATU) and suitable base provides the corresponding product. Alternatively, this acid may be converted to the corresponding acid chloride using standard conditions (e.g., oxalyl chloride and catalytic DMF) which upon treatment with HN(R$^{10}$)(R$^{11}$) along with a suitable base provides the product. In the case where R=alkyl, ester hydrolysis can be accomplished using known conditions (e.g., Alkali hydroxide in aqueous solvent, Me$_3$SnOH) to provide the corresponding acid, which can then be converted to the product as described above. An example of an intermediate prepared by this approach was described in the synthesis of Example 223.

In many cases, N(R$^{10}$)(R$^{11}$) as drawn in this scheme may contain a protected amino substituent (e.g., NHBoc, NHCbz, NHTrityl), which may be deprotected in a subsequent step using standard conditions (e.g., TFA or HCl for NHBoc, H$_2$ over Pd/C for NHCbz) to provide the specific N(R$^{10}$)(R$^{11}$) groups described herein. Additionally, N(R$^{10}$)(R$^{11}$) as drawn in this scheme may include a protected nitrogen-containing heterocycle (e.g., where R$^{11}$=N-Boc piperidine), which may be likewise deprotected to provide the specific N(R$^{10}$)(R$^{11}$) groups described herein.

It is understood that installation of N(R$^{10}$)(R$^{11}$) as described above may take place at an earlier stage in the synthesis, e.g., prior to installation of R$^6$ or R$^4$, or prior to the benzimidazole-forming step described in Schemes C-1 and C-2.

Preparation Examples

Methods for preparing the novel compounds described herein will be apparent to those of skill in the art with suitable procedures being described, for example, in the reaction schemes and examples below.

The chemical names of the Examples in Tables 1-4 were generated using ChemBioDraw Ultra 14.0 or OpenEye, implemented in Dassault Systemes' Biovia Pipeline Pilot (version 19.1.0.1963). ChemBioDraw Ultra 14.0 or the naming function residing within Biovia Notebook 2019 (version 19.1.0.23) was used to generate names for intermediates reported herein. It should be understood that other names may be used to identify Examples or intermediates of the same structure. Other compounds, such as reactants, reagents and solvents, may be named with common names, or systematic or non-systematic names. The compounds may also be named using other nomenclature systems and symbols that are commonly recognized in the art of chemistry including, for example, Chemical Abstract Service (CAS) and International Union of Pure and Applied Chemistry (IUPAC). The naming and numbering of the compounds of the present disclosure is illustrated with representative compounds of Formula I. The compounds of Formula I (or any subformula described herein) or compound provided in Tables 1-4 may be a single enantiomer (e.g., (S)-enantiomer, (R)-enantiomer), or the compounds may be present in a racemic or scalemic composition having one or more diastereomers or enantiomers as a mixture.

Synthesis of Intermediates A1 to A13

The following intermediates were purchased from commercial sources.

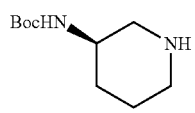

tert-butyl (R)-piperidin-3-ylcarbamate

A1.01

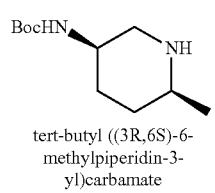

tert-butyl ((3R,6S)-6-methylpiperidin-3-yl)carbamate

A1.02

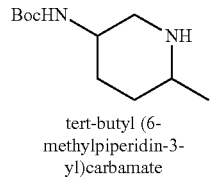

tert-butyl (6-methylpiperidin-3-yl)carbamate

A1.03

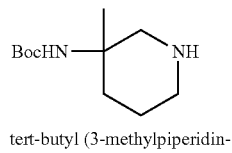

tert-butyl (3-methylpiperidin-3-yl)carbamate

A1.04

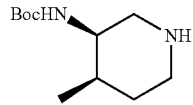

tert-butyl ((3R,4R)-4-methylpiperidin-3-yl)carbamate

A1.05

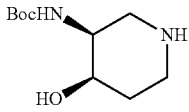

tert-butyl ((3S,4R)-4-hydroxypiperidin-3-yl)carbamate

A1.06

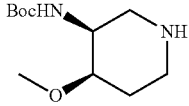

tert-butyl ((3S,4R)-4-methoxypiperidin-3-yl)carbamate

A1.07

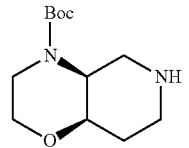

tert-butyl (+/-)-(4aS,8aR)-octahydro-4H-pyrido[4,3-b][1,4]oxazine-4-carboxylate

A1.08

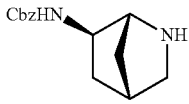

benzyl ((1R,4S,6R)-2-azabicyclo[2.2.1]heptan-6-yl)carbamate

A1.09

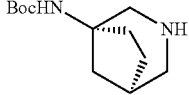

tert-butyl ((1R,5R)-3-azabicyclo[3.2.1]octan-1-yl)carbamate

A1.10

-continued

A1.11

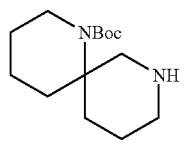

tert-butyl 1,8-diazaspiro[5.5]
undecane-1-carboxylate

A1.12

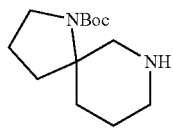

tert-butyl 1,7-diazaspiro[4.5]
decane-1-carboxylate

A1.13

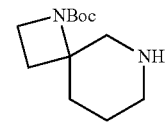

tert-butyl 1,6-diazaspiro[3.5]
nonane-1-carboxylate

A1.14

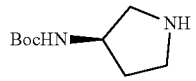

tert-butyl (R)-pyrrolidin-
3-ylcarbamate

A1.15

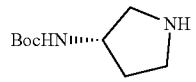

tert-butyl (S)-pyrrolidin-
3-ylcarbamate

A1.16

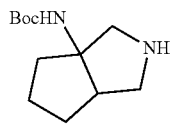

tert-butyl (hexahydrocyclopenta
[c]pyrrol-3a(1H)-yl)carbamate

A1.17

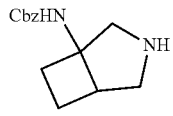

benzyl (3-azabicyclo[3.2.0]
heptan-1-yl)carbamate

A1.18

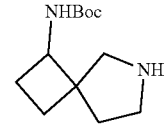

tert-butyl (6-azaspiro[3.4]
octan-1-yl)carbamate

A1.19

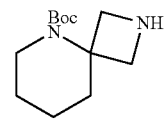

tert-butyl 2,5-diazaspiro[3.5]
nonane-5-carboxylate

A1.20

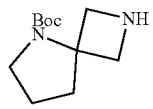

tert-butyl 2,5-diazaspiro[3.4]
octane-5-carboxylate

A1.21

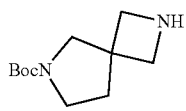

tert-butyl 2,6-diazaspiro[3.4]
octane-6-carboxylate

A1.22

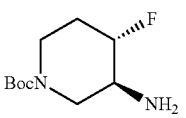

tert-butyl (3S,4S)-3-amino-4-
fluoropiperidine-1-carboxylate

A1.23

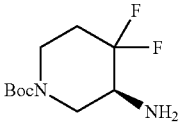

tert-butyl (S)-3-amino-4,4-
difluoropiperidine-1-carboxylate

A1.24

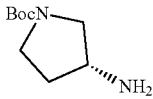

tert-butyl (R)-3-aminopyrrolidine-
1-carboxylate

A1.25

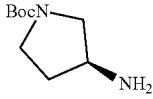

tert-butyl (S)-3-aminopyrrolidine-
1-carboxylate

A1.26

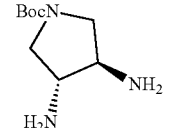

tert-butyl (+/-)-(3R,4R)-3,4-
diaminopyrrolidine-1-carboxylate

A1.27

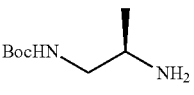

tert-butyl (R)-(2-
aminopropyl)carbamate

Preparation of tert-butyl ((1R,2R,4S)-7-azabicyclo[2.2.1]heptan-2-yl)carbamate (A2)

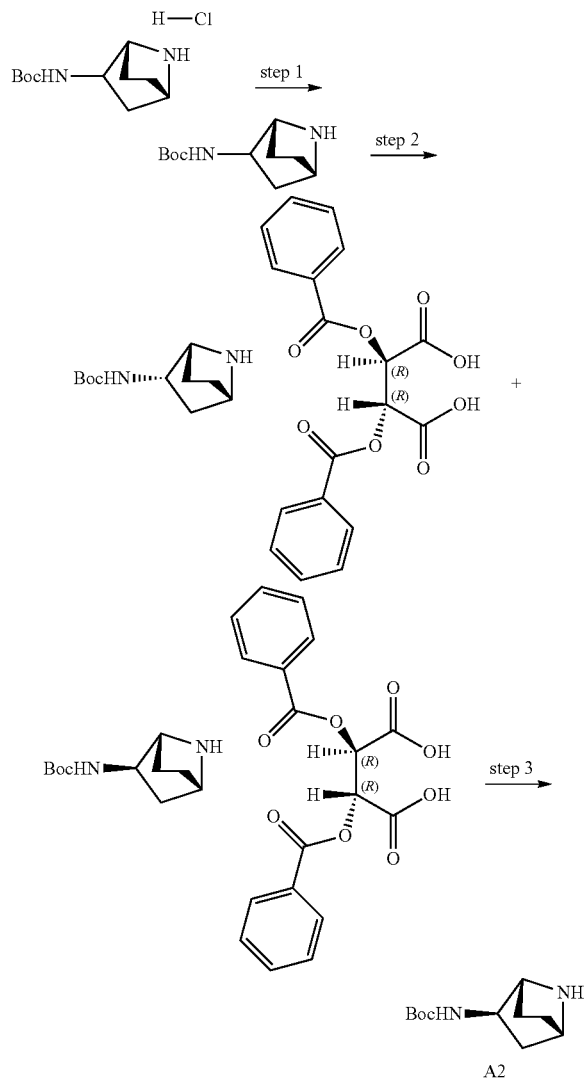

Step 1. The HCl salt of tert-butyl ((1R,4S)-7-azabicyclo[2.2.1]heptan-2-yl)carbamate (60.2 g, 242 mmol, commercially available as [2098589-07-0]) was dissolved in 100 mL water. To this was added a solution of sodium carbonate (38.5 g, 363 mmol) in 200 mL water, producing a voluminous white precipitate. The reaction was extracted into EtOAc (4×200 mL), dried over Na$_2$SO$_4$, filtered, and concentrated to give the free base. This material is commercially available as [2098589-06-9].

Step 2. tert-Butyl ((1R,4S)-7-azabicyclo[2.2.1]heptan-2-yl)carbamate (49.7 g, 234 mmol) was added to 900 mL MeCN to give a cloudy solution. (−)-Dibenzoyl-L-tartaric acid [2743-38-6] (83.9 g, 234 mmol) was added as a solid to give a suspension, which was stirred at ambient temperature. The solids were collected by filtration and washed with cold MeCN, then were re-suspended in MeCN and allowed to stir at ambient temperature. The solids were collected via filtration. The solids were slurried in MeCN and filtered 4 additional times to provide tert-butyl ((1R,2R,4S)-7-azabicyclo[2.2.1]heptanyl)carbamate (2R,3R)-2,3-bis(benzoyloxy)succinate. $^1$H NMR (400 MHz, DMSO-d6) δ 9.28 (br. s, 2H), 7.97-7.90 (m, 4H), 7.68-7.58 (m, 2H), 7.50 (t, J=7.8 Hz, 4H), 7.35 (d, J=5.9 Hz, 1H), 5.64 (s, 2H), 4.04-3.92 (m, 3H), 2.14-2.02 (m, 1H), 1.89-1.68 (m, 2H), 1.67-1.49 (m, 2H), 1.38 (s, 9H), 1.28 (dd, J=13.2, 4.1 Hz, 1H).

Step 3. tert-Butyl ((1R,2R,4S)-7-azabicyclo[2.2.1]heptan-2-yl)carbamate (2R,3R)-2,3-bis(benzoyloxy)succinate (64.3 g, 113 mmol) was added to a solution of sodium carbonate (17.9 g, 169 mmol) in water (500 mL). EtOAc (1000 mL) was added and the mixture stirred until all solids had dissolved. The phases were separated and the aqueous phase was extracted repeatedly with EtOAc, followed by DCM. The combined extracts were dried over Na$_2$SO$_4$, filtered, and concentrated to provide the product as a white foam, 21.72 g (91%). 1H NMR (400 MHz, DMSO-d6) δ 6.93 (d, J=6.8 Hz, 1H), 3.65-3.54 (m, 1H), 3.39 (t, J=4.6 Hz, 1H), 3.33 (t, J=4.7 Hz, 1H), 2.18 (s, 1H), 1.74 (tdd, J=11.8, 5.2, 2.6 Hz, 1H), 1.69-1.58 (m, 1H), 1.38 (s, 9H), 1.44-1.26 (m, 2H), 1.28-1.16 (m, 1H), 0.95 (dd, J=12.0, 4.7 Hz, 1H). Chiral purity 94.5-95.5% ee (see procedure below for determination). Note—chiral purity can be improved to >99% ee by repeating steps 2 (single treatment with MeCN rather than 5 treatments) and 3.

Determination of Chiral Purity of A2:

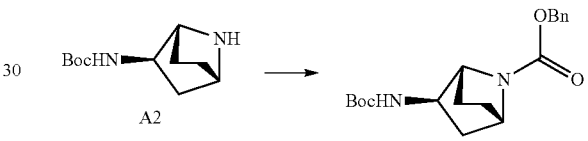

To a solution of tert-butyl ((1R,2R,4S)-7-azabicyclo[2.2.1]heptan-2-yl)carbamate (100 mg, 0.175 mmol) in dioxane and water (1 mL each) was added sodium carbonate (0.84 mL of a 2 M aqueous solution, 1.7 mmol) and carbobenzoxysuccinimide (82 mg, 0.33 mmol). The mixture was allowed to stir at ambient temperature for 5 hours, at which point the thick suspension was diluted further with water. The mixture was extracted into EtOAc, then concentrated and adsorbed to isolute. Purification by silica gel chromatography (eluent: EtOAc in hexane) provided the benzyl (1R,2R,4S)-2-((tert-butoxycarbonyl)amino)-7-azabicyclo[2.2.1]heptane-7-carboxylate. ES/MS: m/z 369.1 [M+Na]$^+$. $^1$H NMR (400 MHz, DMSO-d6) δ 7.42-7.27 (m, 5H), 7.22 (d, J=6.4 Hz, 1H), 5.09-5.00 (m, 2H), 4.17 (t, J=4.4 Hz, 1H), 4.09 (t, J=4.9 Hz, 1H), 3.81-3.70 (m, 1H), 2.08-1.95 (m, 1H), 1.83-1.72 (m, 1H), 1.66-1.54 (m, 1H), 1.53-1.42 (m, 2H), 1.39 (s, 9H), 1.18 (dd, J=12.4, 4.8 Hz, 1H). Chiral purity determined by SFC using AZ-H column (5 mic, 4.6×100 mm) with 10% EtOH as cosolvent, or with IF column (5 mic, 4.6×100 mm) using 10% EtOH-TFA as cosolvent.

Preparation of tert-butyl ((1R,4R,7R)-2-azabicyclo[2.2.1]heptan-7-yl)carbamate (A3)

tert-Butyl ((1R,4R,7R)-2-azabicyclo[2.2.1]heptan-7-yl)carbamate was prepared according to a literature procedure (Advanced Synthesis and Catalysis, 2005, vol. 347, #9, p. 1242-1246).

Preparation of benzyl ((1R,2R,4S)-7-azabicyclo[2.2.1]heptan-2-yl)carbamate (A4)

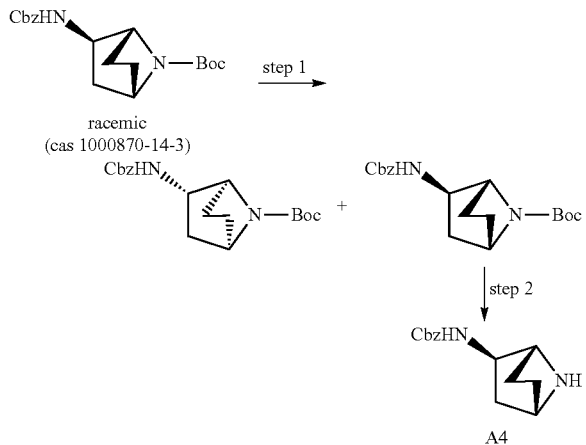

Step 1. A racemic mixture (cas 1000870-14-3) of tert-butyl (1S,2S,4R)(((benzyloxy)carbonyl)amino)-7-azabicyclo[2.2.1]heptane-7-carboxylate and tert-butyl (1R,2R,4S)(((benzyloxy)carbonyl)amino)-7-azabicyclo[2.2.1]heptane-7-carboxylate was separated by chiral SFC (Chiralpak AD-H, 10% MeOH cosolvent). The second eluting isomer was determined to be tert-butyl (1R,2R,4S)-2-(((benzyloxy)carbonyl)amino)-7-azabicyclo[2.2.1]heptane-7-carboxylate.

Step 2. tert-butyl (1R,2R,4S)-2-(((benzyloxy)carbonyl)amino)-7-azabicyclo[2.2.1]heptanecarboxylate (46 mg, 0.13 mmol) was dissolved in dioxane. 4 M hydrochloric acid in dioxane (2 mL) was added, and the resulting mixture was stirred at ambient temperature for 1 h. The reaction mixture was concentrated to provide benzyl ((1R,2R,4S)-7-azabicyclo[2.2.1]heptan-2-yl)carbamate as the HCl salt. ES/MS: m/z 247.0 [M+H]+.

Preparation of tert-butyl ((1S,2S,4R)-7-azabicyclo[2.2.1]heptan-2-1 carbamate (A5)

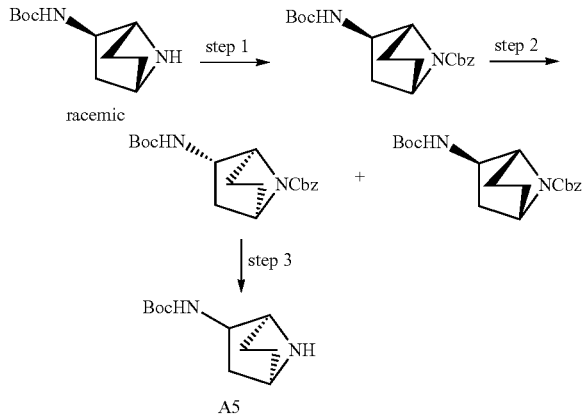

Step 1. To a solution of tert-butyl (+/−)-((1R,2R,4S)-7-azabicyclo[2.2.1]heptan-2-yl)carbamate (0.960 g, 4.52 mmol) and TEA (2.5 mL, 18.1 mmol) in DCM (30 mL) at 0° C. was added benzyl chloroformate (0.71 mL, 4.97 mmol), slowly. The reaction mixture was stirred at 0° C. and progress was monitored by LC-MS. The mixture was diluted with water and the aqueous layer was extracted with EtOAc. The combined organic layers were dried (Na2SO4), filtered, and concentrated. The residue was purified via flash column chromatography to afford benzyl (+/−)-(1R,2R,4S)-2-((tert-butoxycarbonyl)amino)-7-azabicyclo[2.2.1]heptane-7-carboxylate. ES/MS: m/z 369.0 [M+Na]+.

Step 2. benzyl (1R,2R,4S)-2-((tert-butoxycarbonyl)amino)-7-azabicyclo[2.2.1]heptane-7-carboxylate and benzyl (1S,2S,4R)-2-((tert-butoxycarbonyl)amino)-7-methyl-7l4-azabicyclo[2.2.1]heptane-7-carboxylate were separated by chiral SFC (Chiralpak AD-H, 10% EtOH-TFA cosolvent). The first eluting peak was found to be (1S,2S,4R)-2-((tert-butoxycarbonyl)amino)-7-methyl-7l4-azabicyclo[2.2.1]heptane-7-carboxylate.

Step 3. To a solution of benzyl (1S,2S,4R)-2-((tert-butoxycarbonyl)amino)-7-methyl-7l4-azabicyclo[2.2.1]heptane-7-carboxylate (0.447 g, 1.29 mmol) in EtOAc (8 mL) and MeOH (2 mL) was added 20% Pd(OH)2/C (0.058 g). The mixture was stirred under H2 (1 atm). After 30 min, the mixture was diluted with MeOH (6 mL). After 1 h, the mixture was filtered through Celite and the filtrate was concentrated to afford tert-butyl ((1S,2S,4R)-7-azabicyclo[2.2.1]heptan-2-yl)carbamate. ES/MS: m/z 212.8 [M+H]+.

Preparation of benzyl ((1R,2R,5S)-8-azabicyclo[3.2.1]octan-2-yl)carbamate (A6)

Step 1. tert-butyl rac-(1R,2R,5R)-2-amino-8-azabicyclo[3.2.1]octane-8-carboxylate (from Synthonix) (5.08 g, 22.4 mmol) was dissolved in DCM (125 mL). Aqueous NaOH (1 M, 224 mL, 224 mmol) was added followed by benzyl chloroformate (11.1 mL, 79 mmol). The mixture was stirred for 18 h, and the phases were separated and extracted with DCM. The combined organic phase was dried over Na2SO4, filtered, and concentrated. Purification by silica gel chromatography (0-40% EtOAc in hexanes) provided tert-butyl rac-(1R,2R,5R)-2-(((benzyloxy)carbonyl)amino)-8-azabicyclo[3.2.1]octane-8-carboxylate that was used directly in step 2.

Step 2. tert-butyl rac-(1R,2R,5R)-2-(((benzyloxy)carbonyl)amino)-8-azabicyclo[3.2.1]octane-8-carboxylate (7.80 g, 21.6 mmol) was dissolved in dioxane (50 mL). A solution of hydrochloric acid in dioxane (4M, 54 mL, 216 mmol) was added and the resulting mixture was stirred 18 h. The mixture was concentrated to afford a crude product that was used in Step 3.

Step 3. The product from Step 2 was subjected to preparative SFC chromatography using a Chiral Technologies Chiralpak IC SFC column (5 μM, 4.6×100 mm) with a 30% MeOH eluent, using multiple injections. The slower-eluting peak was confirmed to be benzyl ((1R,2R,5S)-8-azabicyclo[3.2.1]octan-2-yl)carbamate. 1H NMR (for HCl salt) (400

MHz, DMSO-d6) δ 9.28 (s, 2H), 7.59 (d, J=7.6 Hz, 1H), 7.42-7.28 (m, 5H), 5.06 (d, J=12.3 Hz, 1H), 5.01 (d, J=12.4 Hz, 1H), 3.96-3.83 (m, 2H), 3.74 (dd, J=6.9, 2.9 Hz, 1H), 2.05-1.89 (m, 2H), 1.89-1.73 (m, 2H), 1.74-1.63 (m, 2H), 1.63-1.54 (m, 1H), 1.47 (qd, J=12.9, 5.6 Hz, 1H).

Preparation of tert-butyl (+/−)-(piperidin-3-yl-3-d)carbamate (A7)

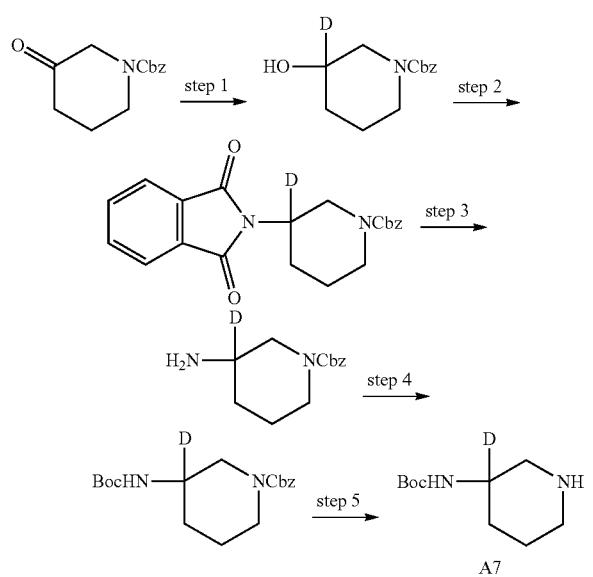

Step 1. To a solution of benzyl 3-oxopiperidine-1-carboxylate (1.60 g, 6.86 mmol) in Me-THF (40 mL) was added (R)-(+)-2-methyl-2-propanesulfinamide (1.08 g, 8.92 mmol) and titanium(IV) ethoxide (3.91 g, 17.2 mmol). The mixture was stirred at 65° C. for 24 h. The mixture was cooled to −5° C. Sodium borodeuteride-d₄ (1.15 g, 27.4 mmol) was added, portionwise, maintaining a temperature below 15° C. After effervescence ceased, the mixture was stirred at rt for 2 h. The mixture was cooled to 0° C. and quenched by addition of MeOH. The solids were removed via filtration through a pad of Celite. The filter pad was rinsed with EtOH. The filtrate was concentrated and the residue was purified via flash column chromatography on silica gel to afford benzyl 3-hydroxypiperidine-1-carboxylate-3-d. ES/MS: m/z 237.0 [M+H]⁺.

Step 2. To a mixture of benzyl 3-hydroxypiperidine-1-carboxylate-3-d (0.200 g, 0.846 mmol) and phthalimide (0.187 g, 1.27 mmol) in Me-THF (4 mL) was added triphenylphosphine (0.42 mL of a 2 M soln in Me-THF, 0.846 mmol) and DIAD (0.28 mL of a 3 M soln in 2-MeTHF, 0.846 mmol). The mixture was stirred at rt for 18 h. The mixture was concentrated and the residue was purified via flash column chromatography on silica gel to yield benzyl 3-(1,3-dioxoisoindolin-2-yl)piperidine-1-carboxylate-3-d. ES/MS: m/z 366.1 [M+H]⁺.

Step 3. A mixture of benzyl 3-(1,3-dioxoisoindolin-2-yl)piperidine-1-carboxylate-3-d (0.106 g, 0.290 mmol) and ethanolamine (0.2 mL) in toluene (4 mL) was stirred at 80° C. for 4 h. The mixture was concentrated to give benzyl 3-aminopiperidine-1-carboxylate-3-d. ES/MS: m/z 236.1 [M+H]⁺.

Step 4. To benzyl 3-aminopiperidine-1-carboxylate-3-d (0.068 g, 0.290 mmol) in EtOAc (10 mL) and sat NaHCO₃ soln (aq, 10 mL) was added di-tert-butyl decarbonate (0.633 g, 2.90 mmol). The mixture was stirred at rt for 18 h. The mixture was concentrated and the residue was purified via flash column chromatography on silica gel to afford benzyl 3-((tert-butoxycarbonyl)amino)piperidinecarboxylate-3-d. ES/MS: m/z 335.9 [M+H]⁺.

Step 5. To a solution of benzyl 3-((tert-butoxycarbonyl)amino)piperidine-1-carboxylate-3-d (0.060 g, 0.179 mmol) in EtOAc (20 mL) was added 10% Pd/C The mixture was flushed with H₂ three times and stirred at rt for 20 h. The catalyst was removed via filtration. The filtrate was concentrated to give tert-butyl (+/−)-(piperidin-3-yl-3-d)carbamate. ES/MS: m/z 202.0 [M+H]⁺.

Preparation of tert-butyl ((2R,3R)-2-methylpiperidin-3-yl)carbamate (A8)

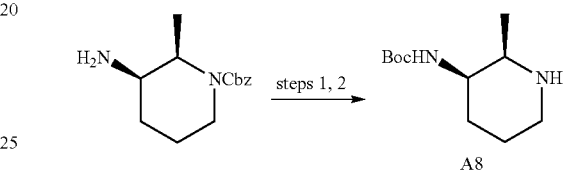

Step 1. Benzyl (2R,3R)-3-amino-2-methyl-piperidine-1-carboxylate (from Synthonix) (7.4 g, 21 mmol) was dissolved in DCM (100 mL). Hunig's base (6.5 mL, 42 mmol) was added followed by tert-butoxycarbonyl tert-butyl carbonate (4.5 g, 21 mmol). The reaction mixture was stirred 24 h and was then partitioned between DCM and aq. HCl. The phases were separated, and the aqueous phase was extracted with DCM. The combined organic phase was dried over Na₂SO₄, filtered, and concentrated to afford crude benzyl (2R,3R)-3-((tert-butoxycarbonyl)amino)-2-methylpiperidine-1-carboxylate material that was used directly in step 2.

Step 2. Benzyl (2R,3R)-3-((tert-butoxycarbonyl)amino)-2-methylpiperidine-1-carboxylate (ca. 21 mmol) was dissolved in THF (200 mL). Palladium on carbon (10% dry basis, 50% total water content) (7.4 g, 3.5 mmol) was added and the vessel was purged with 1 atm H₂. After stirring 18 h, the reaction mixture was filtered through a pad of Celite, and the filtrate was concentrated to afford tert-butyl N-[(2R,3R)-2-methyl-3-piperidyl]carbamate. ¹H NMR (400 MHz, DMSO-d₆) δ 6.30 (d, J=9.1 Hz, 1H), 3.49-3.39 (m, 1H), 2.87-2.77 (m, 1H), 2.76-2.65 (m, 1H), 2.49-2.42 (m, 1H), 1.73-1.58 (m, 1H), 1.56-1.43 (m, 2H), 1.39 (s, 9H), 1.33-1.20 (m, 1H), 0.87 (d, J=6.5 Hz, 3H).

Preparation of tert-butyl rac-(4aR,8aR)-octahydro-1,7-naphthyridine-1(2H)-carboxylate (A9)

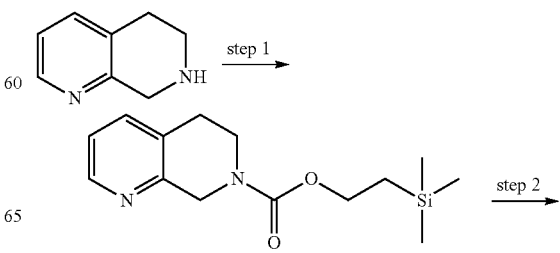

-continued

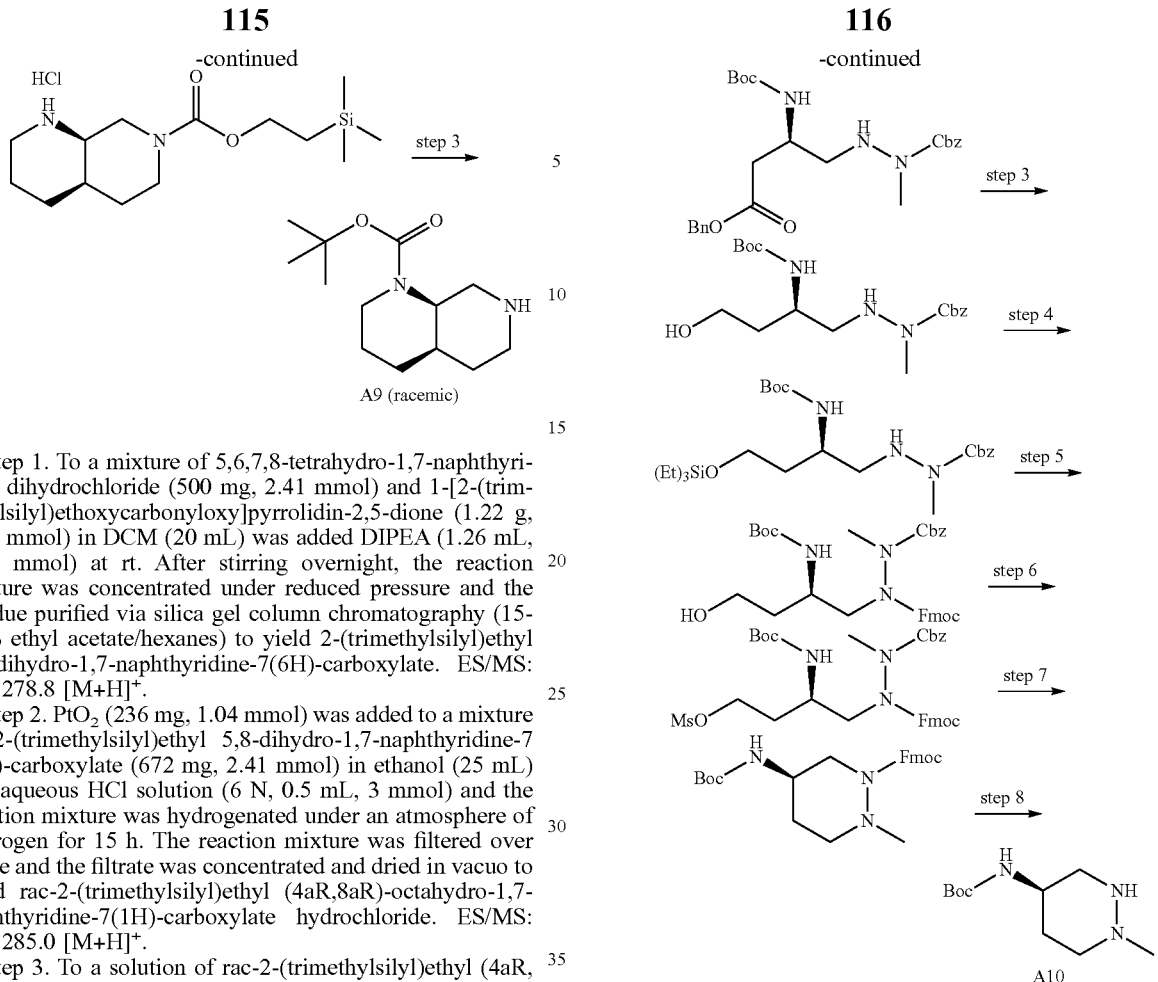

A9 (racemic)

Step 1. To a mixture of 5,6,7,8-tetrahydro-1,7-naphthyridine dihydrochloride (500 mg, 2.41 mmol) and 1-[2-(trimethylsilyl)ethoxycarbonyloxy]pyrrolidin-2,5-dione (1.22 g, 4.70 mmol) in DCM (20 mL) was added DIPEA (1.26 mL, 7.23 mmol) at rt. After stirring overnight, the reaction mixture was concentrated under reduced pressure and the residue purified via silica gel column chromatography (15-60% ethyl acetate/hexanes) to yield 2-(trimethylsilyl)ethyl 5,8-dihydro-1,7-naphthyridine-7(6H)-carboxylate. ES/MS: m/z 278.8 [M+H]$^+$.

Step 2. PtO$_2$ (236 mg, 1.04 mmol) was added to a mixture of 2-(trimethylsilyl)ethyl 5,8-dihydro-1,7-naphthyridine-7(6H)-carboxylate (672 mg, 2.41 mmol) in ethanol (25 mL) and aqueous HCl solution (6 N, 0.5 mL, 3 mmol) and the reaction mixture was hydrogenated under an atmosphere of hydrogen for 15 h. The reaction mixture was filtered over celite and the filtrate was concentrated and dried in vacuo to yield rac-2-(trimethylsilyl)ethyl (4aR,8aR)-octahydro-1,7-naphthyridine-7(1H)-carboxylate hydrochloride. ES/MS: m/z 285.0 [M+H]$^+$.

Step 3. To a solution of rac-2-(trimethylsilyl)ethyl (4aR,8aR)-octahydro-1,7-naphthyridine-7(1H)-carboxylate hydrochloride (350 mg, 1.09 mmol) and triethylamine (0.38 mL, 2.73 mmol) in DCM (8 mL) was added di-tert-butyl dicarbonate (358 mg, 1.64 mmol) and DMAP (21 mg, 0.174 mmol). After 5 h, the reaction mixture was diluted with water and the layers were separated. The aqueous was extracted with DCM and the combined organics washed with 1 N HCl, dried (MgSO$_4$), filtered and concentrated. The resulting residue was dissolved in THF (6 mL) and a solution of TBAF in THF (1M, 1.95 mL, 1.95 mmol) was added. After 10 minutes, the reaction mixture was heated at 55° C. overnight. After cooling to rt, the reaction mixture was diluted with DCM, ethyl acetate, and water. The layers were separated and the organics were dried (MgSO$_4$), filtered, and concentrated under reduced pressure to yield tert-butyl rac-(4aR,8aR)-octahydro-1,7-naphthyridine-1(2H)-carboxylate. ES/MS: m/z 240.9 [M+H]$^+$.

Preparation of tert-butyl (R)-(1-methylhexahydropyridazin-4-yl)carbamate (A10)

Step 1. To a solution of benzyl (3R)-3-(tert-butoxycarbonylamino)-4-hydroxy-butanoate (3.4 g, 10.99 mmol) in dichloromethane (34 mL) was added Dess-Martin periodinane (5.13 g, 12.09 mmol) in several portions over 15 minutes. After stirring for 4 h, the mixture was concentrated, diluted with ethyl acetate (50 mL), and washed with 1 M aqueous NaS$_2$O$_3$ (50 mL), followed by 1 M NaHCO$_3$ (aq, 50 mL). The organic layer was dried with Na$_2$SO$_4$, filtered, and concentrated under vacuum. The crude product was purified by silica chromatography using ethyl acetate in hexanes to afford benzyl (R)-3-((tert-butoxycarbonyl)amino)-4-hydroxybutanoate. $^1$H NMR (400 MHz, Methanol-d4) δ 9.55 (s, 1H), 7.37 (td, J=4.7, 1.7 Hz, 5H), 5.16 (d, J=1.0 Hz, 2H), 4.30 (ddd, J=7.8, 5.2, 2.4 Hz, 1H), 2.95 (dd, J=16.5, 5.4 Hz, 1H), 2.76 (dd, J=16.4, 7.2 Hz, 1H), 1.46 (s, 9H).

Step 2. A solution of benzyl (R)-3-((tert-butoxycarbonyl)amino)-4-hydroxybutanoate (3.4 g, 11.06 mmol), benzyl 1-methylhydrazine-1-carboxylate (1.99 g, 11.06 mmol), and acetic acid (1.99 g, 33.19 mmol) was stirred at ambient temperature for 30 minutes. To the mixture was added sodium cyanoborohydride (2.78 g, 44.25 mmol) over 5 minutes and the mixture was stirred at ambient temperature for 1 hour followed by heating at 40° C. for 30 minutes. The mixture was concentrated, diluted with EtOAc (50 ml), and washed with 1 M aqueous K$_2$HPO$_4$ (50 ml). The organic layer was dried with Na$_2$SO$_4$, filtered, and concentrated. Crude benzyl (R)-3-((tert-butoxycarbonyl)amino)oxobutanoate was taken to next step without further purification. $^1$H NMR (400 MHz, Methanol-d4) δ 7.44-7.27 (m, 10H), 5.18-5.03 (m, 4H), 4.05-3.92 (m, 1H), 3.06 (s, 3H), 3.00-2.92 (m, 1H), 2.92-2.81 (m, 1H), 2.79-2.66 (m, 1H), 2.61-2.43 (m, 1H), 1.43 (s, 9H). ES/MS: m/z 472.2 [M+H]⁺.

Step 3. To a solution of benzyl (R)-3-((tert-butoxycarbonyl)amino)-4-oxobutanoate (5.2 g, 11.03 mmol) in MeTHF (11 mL) was added 2 M LiBH₄ in THF (11 mL). After stirring for 1 h, the mixture was carefully quenched with 4N NH₄Cl (aq, 20 ml) and stirred for 1 h. The organic layer was dried with Na₂SO₄, filtered, and concentrated under vacuum. The crude product was purified by silica chromatography using EtOAc in hexane to afford benzyl (R)-2-(2-((tert-butoxycarbonyl)amino)hydroxybutyl)-1-methylhydrazine-1-carboxylate. ES/MS: m/z 368.2 [M+H]⁺.

Step 4. To a solution of benzyl (R)-2-(2-((tert-butoxycarbonyl)amino)-4-hydroxybutyl)-1-methylhydrazine-1-carboxylate (2.5 g, 6.8 mmol) and EtN(i-Pr)₂ (1.77 ml, 10.21 mmol) in dichloromethane (30 mL) was added triethylsilyl trifluoromethanesulfonate (2.15 ml, 9.53 mmol) at −78° C. The mixture was warmed to ambient over 1 h. The mixture was washed with water (30 mL) and the organic layer was dried with Na₂SO₄, filtered, and concentrated under vacuum. The product was purified by silica chromatography using ethyl acetate in hexane. The partially purified product was refluxed in methanol for 1 h. The mixture was concentrated under vacuum and repurified by silica chromatography using ethyl acetate in hexane to afford benzyl (R)-2-(2-((tert-butoxycarbonyl)amino)((triethylsilyl)oxy)butyl)-1-methylhydrazine-1-carboxylate. ¹H NMR (400 MHz, Chloroform-d) δ 7.43-7.28 (m, 6H), 5.23-5.05 (m, 3H), 4.70 (s, 1H), 3.79-3.53 (m, 2H), 3.09 (s, 3H), 3.02-2.84 (m, 2H), 1.86-1.52 (m, 2H), 1.43 (s, 9H), 0.95 (t, J=7.9 Hz, 9H), 0.59 (q, J=8.0 Hz, 6H). ES/MS: m/z 482.3 [M+H]⁺.

Step 5. To a solution of benzyl (R)-2-(2-((tert-butoxycarbonyl)amino)-4-((triethylsilyl)oxy)butyl)-1-methylhydrazine-1-carboxylate (2.7 g, 5.61 mmol) and EtN(i-Pr)₂ (1.46 ml, 8.41 mmol) in dichloromethane (10 mL) was added FmocCl (1.89 g, 7.29 mmol) at 0° C. The mixture was warmed to ambient temperature and stirred for 2 h. To the reaction was added triethylamine trihydrofluoride (1.8 g, 11.21 mmol). After the stirring for 1 h, the crude product was purified by silica chromatography using EtOAc in hexane to afford 1-((9H-fluoren-9-yl)methyl) 2-benzyl (R)-1-(2-((tert-butoxycarbonyl)amino)-4-hydroxybutyl)-2-methylhydrazine-1,2-dicarboxylate. ES/MS: m/z 590.0 [M+H]⁺.

Step 6. To a solution of 1-((9H-fluoren-9-yl)methyl) 2-benzyl (R)-1-(2-((tert-butoxycarbonyl)amino)-4-hydroxybutyl)-2-methylhydrazine-1,2-dicarboxylate (2.4 g, 4.07 mmol) and EtN(i-Pr)₂ (0.85 ml, 4.88 mmol) in dichloromethane (10 ml) was added methanesulfonyl chloride (0.35 ml, 4.48 mmol) at 0° C. After stirring for 30 minutes, the product was purified by silica chromatography using ethyl acetate in hexane to afford 1-((9H-fluoren-9-yl)methyl) 2-benzyl (R)-1-(2-((tert-butoxycarbonyl)amino)-4-((methylsulfonyl)oxy)butyl)-2-methylhydrazine-1,2-dicarboxylate. ES/MS: m/z 568.2 [M+H]⁺.

Step 7. A mixture of 1-((9H-fluoren-9-yl)methyl) 2-benzyl (R)-1-(2-((tert-butoxycarbonyl)amino)-4-((methylsulfonyl)oxy)butyl)-2-methylhydrazine-1,2-dicarboxylate (2.3 g, 3.44 mmol) and 10% palladium on carbon (0.18 g, 0.17 mmol) in methanol (20 mL) was stirred for 2 h under 1 atm hydrogen. The mixture was filtered through celite and washed with methanol (10 ml). The filtrate was treated with pyridine (0.28 mL, 3.44 mmol) and stirred for 18 h. The mixture was concentrated under vacuum. The crude product was taken to next step without further purification. ES/MS: m/z 438.0 [M+H]⁺.

Step 8. Crude (9H-fluoren-9-yl)methyl (R)-5-((tert-butoxycarbonyl)amino)-2-methyltetrahydropyridazine-1(2H)-carboxylate (0.91 g, 2.1 mmol) in 1:1 dichloromethane:diethylamine (5 mL) was stirred at ambient temperature for 2 h. The mixture was concentrated under vacuum and purified by silica chromatography using methanol in dichloromethane to afford tert-butyl (R)-(1-methylhexahydropyridazin-4-yl)carbamate. ¹H NMR (400 MHz, Methanol-d4) δ 3.48-3.34 (m, 1H), 3.16-3.08 (m, 1H), 3.03-2.89 (m, 1H), 2.79-2.68 (m, 1H), 2.49 (s, 3H), 2.48-2.41 (m, 1H), 2.01-1.90 (m, 1H), 1.75-1.64 (m, 1H), 1.46 (s, 9H). ES/MS: m/z 216.2 [M+H]⁺.

Preparation of tert-butyl (4aS,8aR)-octahydro-4H-pyrido[4,3-b][1,4]oxazine-4-carboxylate (A11)

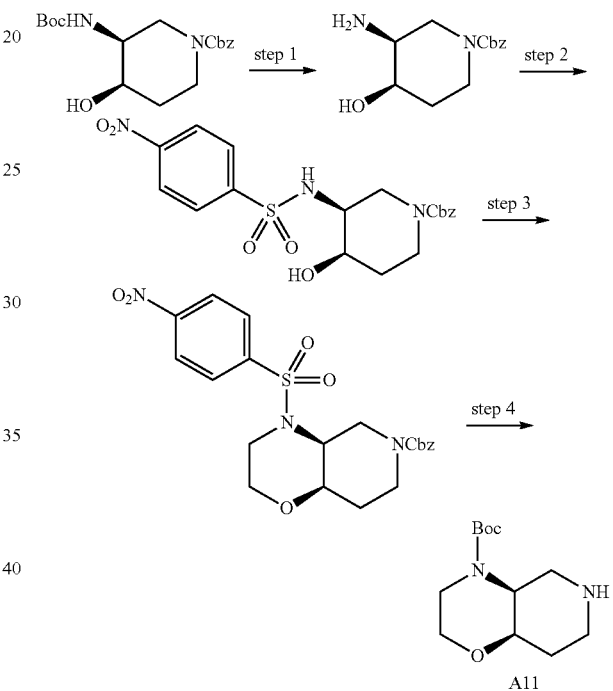

Step 1. To a solution of benzyl (3S,4R)-3-((tert-butoxycarbonyl)amino)-4-hydroxypiperidine-1-carboxylate (1.240 g, 3.54 mmol) in acetonitrile (20 mL) was added HCl (9.00 mL of a 4 M soln in dioxane, 36.0 mmol). The mixture was stirred at rt for 2 h. To the mixture was added hexanes (15 mL) with stirring. After 5 min, EtOAc (5 mL) was added. The resulting solid was isolated via filtration and dried under vacuum to give crude benzyl (3S,4R)-3-amino-4-hydroxypiperidine-1-carboxylate hydrochloride, which was used directly in the next step. ES/MS: m/z 251.0 [M+H]⁺.

Step 2. To a cooled solution of benzyl (3S,4R)-3-amino-4-hydroxypiperidine-1-carboxylate hydrochloride (350 mg, 1.22 mmol) and triethylamine (0.46 mL, 3.30 mmol) in DCM (7 mL) at 0° C. was added 4-nitrobenzenesulfonyl chloride (300 mg, 1.35 mmol). After 5 minutes, the reaction mixture was warmed to rt. After 30 minutes, the reaction mixture was diluted with DCM and water, and layers separated. The aqueous layer was extracted with DCM. The combined organic layers were dried (MgSO₄), filtered, and concentrated under reduced pressure to yield benzyl (3S,4R)-4-hydroxy-3-((4-nitrophenyl)sulfonamido)piperidine- 1-carboxylate, that was used in the next step without purification. ES/MS: m/z 240.9 [M+H]⁺.

Step 3. To a cooled solution of benzyl (3S,4R)-4-hydroxy-3-((4-nitrophenyl)sulfonamido)piperidine-1-carboxylate (345 mg, 0.742 mmol) in DCM (40 mL) at 0° C., was added sodium hydride (60.0% dispersion, 160 mg, 4.00 mmol). After 5 minutes, (2-bromoethyl)diphenylsulfonium trifluoromethanesulfonate (880 mg, 1.99 mmol) was added. The reaction mixture was stirred at 0° C., slowly warming as ice melted. After stirring overnight, triethylamine (0.270 mL, 1.94 mmol) was added. After 8 h, the reaction mixture was diluted with DCM and quenched with sat NH₄Cl. The layers were separated and the aqueous layer was extracted with DCM. The combined organic layers were dried (MgSO₄), filtered, and concentrated under reduced pressure. The resulting residue was purified via silica gel column chromatography (0-65% ethyl acetate/hexanes) to yield the desired benzyl (4aS,8aR)-4-((4-nitrophenyl)sulfonyl)hexahydro-2H-pyrido[4,3-b][1,4]oxazine-6(5H)-carboxylate. ES/MS: m/z 461.7 [M+H]⁺.

Step 4. To a solution of benzyl (4aS,8aR)-4-((4-nitrophenyl)sulfonyl)hexahydro-2H-pyrido[4,3-b][1,4]oxazine-6 (5H)-carboxylate (166 mg, 0.360 mmol) in DMF (3 mL) at rt was added thioglycolic acid (0.060 mL, 0.864 mmol) followed by lithium hydroxide, monohydrate (84.5 mg, 2.01 mmol). After stirring overnight, the reaction mixture was diluted with ethyl acetate and water. The layers were separated and aqueous extracted with ethyl acetate. The combined organics were dried (MgSO₄), filtered, and concentrated under reduced pressure. The resulting residue was dissolved in DCM (4 mL) and triethylamine (0.0800 mL, 0.574 mmol), di-tert-butyl dicarbonate (118 mg, 0.541 mmol), and 4-(dimethylamino)pyridine (7.00 mg, 0.0573 mmol) were added. After 2 h, the aqueous workup above was repeated, extracting with DCM. The combined organics washed with 1 N HCl, dried (MgSO₄), filtered, and concentrated under reduced pressure. The resulting residue was dissolved in EtOAc. Pd/C, (10.0%, 77.0 mg, 0.0724 mmol) was added and the mixture hydrogenated under atmosphere of hydrogen. After 1 h, the reaction mixture was diluted with ethyl acetate and filtered over celite. The filtrate was concentrated under reduced pressure to yield tert-butyl (4aS,8aR)-octahydro-4H-pyrido[4,3-b][1,4]oxazine-4-carboxylate. ES/MS: m/z 242.9 [M+H]⁺.

Preparation of tert-butyl ((1S,4R,5R)-2-azabicyclo[3.2.1]octan-4-yl)carbamate (A12)

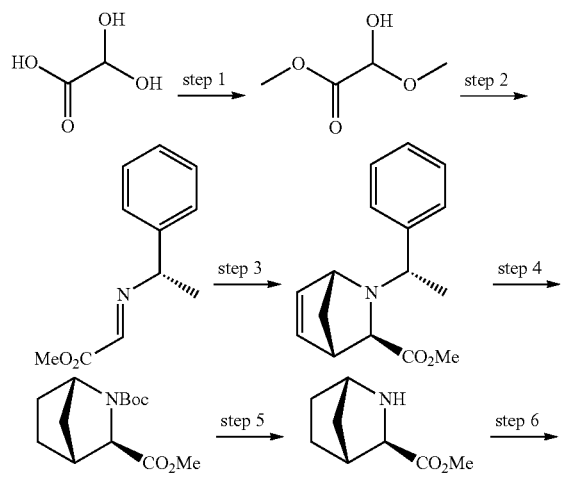

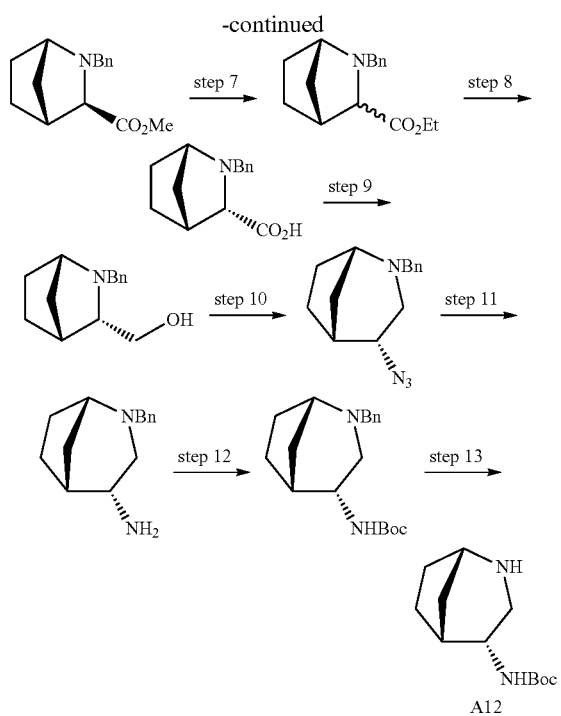

Step 1. A mixture of 2,2-dihydroxyacetic acid (320 g, 3.48 mol) and MeOH (2.24 L) was refluxed for 20 h. The mixture was cooled to rt, concentrated to 1.4 L, and diluted with toluene (1.4 L). The mixture was concentrated to 500 mL, diluted with toluene (1.4 L), and concentrated to 800 mL. The mixture was diluted with toluene to 1.2 L total volume to produce methyl 2-hydroxy-2-methoxyacetate as a 2.3 M solution in toluene (concentration determined by ¹H NMR). ¹H NMR (400 MHz, CDCl₃) δ 4.79 (s, 1H), 3.74 (s, 3H), 3.41 (s, 3H).

Step 2. The solution of methyl 2-hydroxy-2-methoxyacetate (2.40 L of a 2.3 M soln in toluene, 5.54 mol) was sparged with N₂ and then cooled to −10° C. (S)-1-phenylethan-1-amine (714 mL, 5.54 mol) was added while maintaining reaction temperature below 5° C. The mixture was then allowed to warm to rt and was stirred for 2 h. The reaction mixture was diluted with toluene (150 mL) and water (750 mL) and stirred vigorously for 10 min. The mixture was extracted with toluene. The organic layer was washed with brine, dried (Na₂SO₄), filtered, and concentrated to yield methyl (S,E)-2-((1-phenylethyl)imino)acetate.

Step 3. A mixture of methyl (S,E)-2-((1-phenylethyl)imino)acetate (1.04 kg, 5.46 mol) in DMA (728 mL) was sparged with N₂ and cooled to −10° C. TFA (403 mL, 5.46 mol) was added, maintaining reaction temperature below −5° C. Cyclopentadiene (360 g, 5.46 mol) was added, maintaining reaction temperature below −5° C. Water (10 mL) was added, dropwise. The reaction mixture was stirred at −10° C. for 2 h. The mixture was diluted with heptane (400 mL), quenched with K₂CO₃ (360 g in 2 L water), and stirred vigorously for 20 min. The mixture was extracted with heptane. The organic layer was washed with brine, dried (Na₂SO₄), filtered, and concentrated. The resulting residue was purified via flash column chromatography on silica gel to afford methyl (1R,3R,4S)-2-((S)-1-phenylethyl) azabicyclo[2.2.1]hept-5-ene-3-carboxylate. ¹H NMR (400 MHz, CDCl₃): δ 7.29-7.21 (m, 5H), 6.43-6.42 (m, 1H), 6.29-6.27 (m, 1H), 4.31 (s, 1H), 3.36 (s, 3H), 3.04 (q, J=6.8 Hz, 1H), 2.92-2.91 (m, 1H), 2.22 (s, 1H), 2.11 (d, J=8.4 Hz, 1H), 1.44-1.41 (m, 4H).

Step 4. To a mixture of $Pd(OH)_2$ (12.0 g, 85.4 mol) in MeOH (1.1 L) was added methyl (1R,3R,4S)-2-((S)-1-phenylethyl)-2-azabicyclo[2.2.1]hept-5-ene-3-carboxylate (110 g, 427 mol) and DIEA (111 mL, 641 mol). The mixture was stirred under 50 psi $H_2$ at 50° C. for 16 h. The mixture was cooled to rt and $Boc_2O$ (139 g, 641 mol) was added. The mixture was stirred under 15 psi $H_2$ at rt for 16 h. The mixture was filtered to remove $Pd(OH)_2$. The filtrate was concentrated and the resulting residue was purified via flash column chromatography on silica gel. The crude product was slurried with EtOAc at 0° C. The resulting solid was collected via filtration to yield 2-(tert-butyl) 3-methyl (1S,3R,4R)azabicyclo[2.2.1]heptane-2,3-dicarboxylate. $^1$H NMR (400 MHz, $CDCl_3$): δ 4.34-4.21 (m, 1H), 3.83-3.71 (m, 1H), 3.70 (s, 3H), 2.65 (s, 1H), 1.92-1.85 (m, 1H), 1.81-1.59 (m, 3H), 1.55-1.31 (m, 10H), 1.24-1.15 (m, 1H).

Step 5. A mixture of 2-(tert-butyl) 3-methyl (1S,3R,4R)-2-azabicyclo[2.2.1]heptane-2,3-dicarboxylate (150 g, 0.58 mol) in HCl solution (734 mL of a 4 M soln in MeOH) was stirred at rt for 3 h. The mixture was concentrated to afford methyl (1S,3R,4R)-2-azabicyclo[2.2.1]heptane-3-carboxylate.

Step 6. To a mixture of $K_2CO_3$ (240 g, 1.74 mol) in MeCN (1.4 L) was added methyl (1S,3R,4R)-2-azabicyclo[2.2.1]heptane-3-carboxylate (90 g, 0.58 mol). The mixture was sparged with $N_2$ and cooled to 0° C. (Bromomethyl)benzene (69 mL, 0.58 mol) was added, dropwise. The reaction mixture was allowed to warm to rt and was stirred for 16 h. The mixture was filtered to remove solids, and the filtrate was concentrated. The residue was purified via flash column chromatography on silica gel to yield methyl (1S,3R,4R)-2-benzyl-2-azabicyclo[2.2.1]heptane-3-carboxylate.

Step 7. To a solution of diisopropylamine (19 mL, 0.13 mol) in THF (1.38 L) at −78° C. was added n-BuLi (56.2 mL of a 2.5 M soln, 0.14 mol). The reaction mixture was stirred at −78° C. for 30 min and was then warmed to −20° C. A solution of methyl (1S,3R,4R)-2-benzyl-2-azabicyclo[2.2.1]heptane-3-carboxylate (30 g, 0.12 mol) in THF (300 mL) was added and the resulting mixture was stirred at −20° C. for 40 min. The mixture was warmed to −5° C. and sat $NH_4Cl$ soln (1.5 mL) was added. The mixture was stirred at −5° C. for 15 min before it was allowed to warm to rt and stirred for 16 h. Brine was added, and the mixture was extracted with MTBE. The organic layer was concentrated and the resulting residue was purified via flash column chromatography on silica gel to give a mixture of ethyl (1S,3R,4R)-2-benzyl-2-azabicyclo[2.2.1]heptane-3-carboxylate and ethyl (1S,3S,4R)-2-benzylazabicyclo[2.2.1]heptane-3-carboxylate.

Step 8. The epimeric mixture of ethyl (1S,3R,4R)-2-benzyl-2-azabicyclo[2.2.1]heptane-3-carboxylate and ethyl (1S,3S,4R)-2-benzyl-2-azabicyclo[2.2.1]heptane-3-carboxylate (20 g, 0.81 mol) in HCl (204 mL of a 4 M aq soln) was refluxed for 16 h. The mixture was cooled to rt and concentrated. The resulting residue was purified via preparative reverse phase HPLC (Phenomenex Luna C-18, water (0.05% HCl)/MeCN) to isolate (1S,3S,4R)-2-benzyl-2-azabicyclo[2.2.1]heptane-3-carboxylic acid. $^1$H NMR (400 MHz, Methanol-$d_4$) δ 7.58-7.55 (m, 2H), 7.44-7.43 (m, 3H), 4.56 (d, J=12.8 Hz, 1H), 4.10-3.97 (m, 2H), 3.96 (t, J=2.0 Hz, 1H), 2.95 (s, 1H), 2.39-2.36 (m, 1H), 1.97-1.87 (m, 3H), 1.73 (m, 1H), 1.51 (m, 1H).

Step 9. To a slurry of (1S,3S,4R)-2-benzyl-2-azabicyclo[2.2.1]heptane-3-carboxylic acid hydrochloride (7.00 g, 26.1 mmol) in THF (130 mL) at 0° C. was added $BH_3$·DMS (12.4 mL, 131 mmol). The mixture was allowed to warm to rt over 16 h. Reaction progress was monitored by LC-MS. The mixture was cooled to 0° C. and $BH_3$·DMS (3.1 mL, 33 mmol) was added. The mixture was allowed to warm to rt overnight and was then cooled to 0° C. and quenched via slow addition of MeOH. The mixture was partially concentrated and then diluted with EtOAc and washed successively with sat $NaHCO_3$ soln and brine. The organic layer was dried ($Na_2SO_4$), filtered, and concentrated. The residue was purified via flash column chromatography to afford ((1S,3S,4R)-2-benzyl-2-azabicyclo[2.2.1]heptan-3-yl)methanol. $^1$H NMR (400 MHz, $CDCl_3$) δ 7.37-7.28 (m, 4H), 7.25-7.21 (m, 1H), 3.68 (d, J=13.4 Hz, 1H), 3.58 (d, J=13.4 Hz, 1H), 3.48 (dd, J=10.6, 3.9 Hz, 1H), 3.40 (dd, J=10.6, 6.3 Hz, 1H), 3.16-3.08 (m, 1H), 2.84-2.74 (m, 1H), 2.45-2.35 (m, 1H), 1.84-1.69 (m, 2H), 1.60-1.40 (m, 2H), 1.40-1.25 (m, 2H).

Step 10. To a solution of ((1S,3S,4R)-2-benzyl-2-azabicyclo[2.2.1]heptan-3-yl)methanol (0.496 g, 2.28 mmol) and TEA (0.56 mL, 3.99 mmol) in DMF (11 mL) at −40° C. was added $Ms_2O$ (0.497 g, 2.85 mmol). The reaction mixture was stirred at −40° C. and reaction progress was monitored via LC-MS. After 30 min, $Ms_2O$ (0.099 g, 0.568 mmol) was added. The mixture was stirred at −40° C. for 25 min. $NaN_3$ (0.163 g, 2.51 mmol) was added and the mixture was allowed to warm to rt overnight. The mixture was diluted with EtOAc and water. The aq layer was extracted with EtOAc and the combined organic layers were washed successively with water and brine, dried ($Na_2SO_4$), filtered, and concentrated. The residue was purified via flash column chromatography to afford (1S,4R,5R)-4-azido-2-benzyl-2-azabicyclo[3.2.1]octane. $^1$H NMR (400 MHz, $CDCl_3$) δ 7.32-7.21 (m, 5H), 3.67 (ddd, J=10.7, 5.8, 2.9 Hz, 1H), 3.50 (d, J=13.3 Hz, 1H), 3.43 (d, J=13.3 Hz, 1H), 3.14-3.07 (m, 1H), 2.82 (dd, J=11.2, 5.8 Hz, 1H), 2.42-2.35 (m, 1H), 2.00 (t, J=10.9 Hz, 1H), 1.79-1.32 (m, 6H).

Step 11. To LAH (16.8 mL of a 2 M soln in THF, 33.5 mmol) in THF (100 mL) at 0° C. was added a solution of (1S,4R,5R)-4-azido-2-benzyl-2-azabicyclo[3.2.1]octane (4.64 g, 19.1 mmol) in THF (25 mL), slowly. The ice bath was removed and the mixture was stirred at rt for 2 h. The mixture was cooled to 0° C. and quenched via slow addition of water (1.3 mL) followed by NaOH (1.3 mL of a 15 w/v % aq soln) and another portion of water (3.8 mL). The mixture was warmed to rt and was stirred for 15 min before it was dried ($Mg_2SO_4$), filtered, and concentrated to afford (1S,4R,5R)-2-benzylazabicyclo[3.2.1]octan-4-amine. ES/MS: m/z 217.2 [M+H]$^+$.

Step 12. To a solution of (1S,4R,5R)-2-benzyl-2-azabicyclo[3.2.1]octan-4-amine (3.75 g, 17.3 mmol) in DCM (115 mL) was added TEA (3.0 mL, 22 mmol), followed by $Boc_2O$ (4.16 g, 19.1 mmol). The mixture was stirred at rt for 16 h. The mixture was diluted with DCM and water. The aq layer was extracted with DCM and the combined organic layers were washed with brine, dried ($Na_2SO_4$), filtered, and concentrated. The resulting residue was purified via flash column chromatography to afford tert-butyl ((1S,4R,5R)-2-benzyl-2-azabicyclo[3.2.1]octan-4-yl)carbamate. ES/MS: m/z 317.2 [M+H]$^+$.

Step 13. A solution of tert-butyl ((1S,4R,5R)-2-benzyl-2-azabicyclo[3.2.1]octan-4-yl)carbamate (0.578 g, 1.83 mmol) in MeOH (12 mL) was sparged with $N_2$. Pd/C (0.116 g of 10% Pd/C) was added and the mixture was stirred under $H_2$ (1 atm) overnight. The mixture was filtered to remove Pd/C and the filtrate was concentrated to afford tert-butyl ((1S,4R,5R)-2-azabicyclo[3.2.1]octan-4-yl)carbamate. $^1$H NMR (400 MHz, $CDCl_3$) δ 4.46-4.33 (m, 1H), 3.66-3.52 (m, 1H), 3.43-3.35 (m, 1H), 3.06 (dd, J=12.8, 5.7 Hz, 1H), 2.44 (dd, J=12.8, 11.0 Hz, 1H), 2.39-2.31 (m, 1H), 1.85-1.70 (m, 1H), 1.67-1.51 (m, 5H), 1.44 (s, 9H).

Preparation of benzyl (S)-(1,3-oxazinan-5-yl)carbamate (A13)

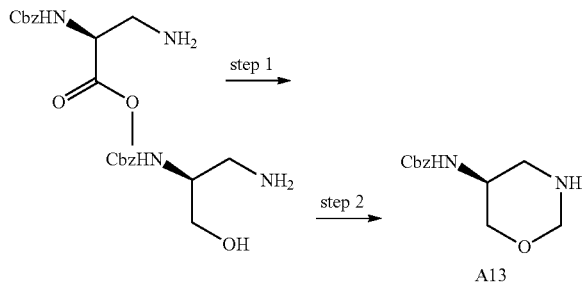

Step 1. To a solution of methyl (S)-3-amino-2-(((benzyloxy)carbonyl)amino)propanoate (3.73 g, 12.9 mmol) in Me-THF (60 mL) and MeOH (40 mL) was added lithium chloride (1.10 g, 25.8 mmol) followed by sodium borohydride (0.977 g, 25.8 mmol), slowly. The reaction mixture was stirred at rt for 20 h and was then quenched via addition of sat NH4Cl soln. The solids were removed via filtration and the filtrate was extracted with chloroform. The organic layer was dried (Na2SO4), filtered, and concentrated to give crude benzyl (S)-(1-amino-3-hydroxypropan-2-yl)carbamate, which was used without purification. ES/MS: m/z 225.1 [M+H]+.

Step 2. To a solution of benzyl (S)-(1-amino-3-hydroxypropan-2-yl)carbamate (0.500 g, 2.23 mmol) in EtOH (20 mL) was added paraformaldehyde (2.0 mL of a 40% aq soln, 8.92 mmol). The reaction mixture was stirred at rt for 18 h. The reaction mixture was concentrated to yield benzyl (S)-(1,3-oxazinan-5-yl)carbamate, which was carried forward without purification. ES/MS: m/z 237.1 [M+H]+.

3. SYNTHESIS OF INTERMEDIATES I-1 to I-27

Preparation of methyl 3-methoxy-4-(methylamino)-5-nitrobenzoate (I-1a)

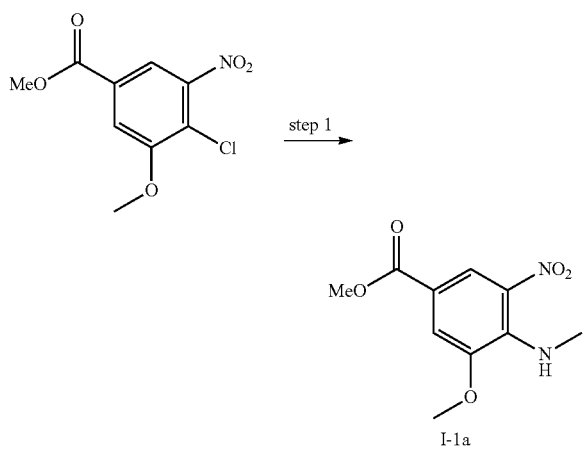

Step 1. A round bottom flask was charged with methyl 4-chloro-3-methoxy-5-nitrobenzoate (14.0 g, 57 mmol) and methylamine hydrochloride salt (4.65 g, 69 mmol). The solids were taken in DMF (100 mL) and triethylamine (14.1 g, 143 mmol) was added. The flask was sealed and the reaction mixture was stirred at 75° C. for 16 h. The reaction was partitioned between water and DCM. The aqueous layer was extracted with DCM and the combined organics were washed with water then brine. The combined organic layer was dried over sodium sulfate, filtered, and evaporated to dryness. The crude product was dissolved in hot EtOAc (80 mL) and hexanes (220 mL) were added. The mixture was allowed to cool to room temperature and the crystallization was aged overnight before collecting solids by filtration to afford methyl 3-methoxy-4-(methylamino)-5-nitrobenzoate. ES/MS: m/z 241.0 [M+H]+.

methyl 4-(cyclopropylamino)-3-methoxy-5-nitrobenzoate (I-1b)

Prepared following a similar procedure to I-1a using cyclopropylamine. ES/MS: m/z 267.0 [M+H]+.

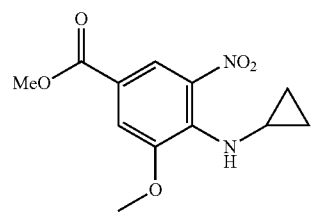

methyl 2-fluoro-4-(methylamino)-5-nitrobenzoate (I-1c)

Prepared following a similar procedure to I-1a using methyl 2,4-difluoro-5-nitrobenzoate. ES/MS: 227.1 [M−H]−.

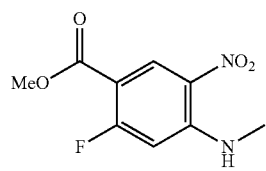

methyl 4-(cyclopropylamino)-2-fluoro-5-nitrobenzoate (I-1d)

Prepared following a similar procedure to I-1a using methyl 2,4-difluoro-5-nitrobenzoate and cyclopropylamine. 1H NMR (400 MHz, DMSO-d6) δ 8.64 (d, J=7.8 Hz, 1H), 8.45 (s, 1H), 7.16 (d, J=14.0 Hz, 1H), 3.84 (s, 3H), 2.76-2.64 (m, 1H), 0.98-0.87 (m, 2H), 0.76-0.64 (m, 2H).

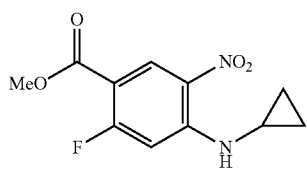

I-1d methyl 2-methyl-4-(methylamino)-5-nitrobenzoate (I-1e)

Prepared following a similar procedure to I-1a using methyl 4-chloro-2-methyl-5-nitrobenzoate. ES/MS: 225.3 [M+H]⁺.

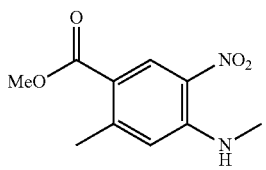

I-1e methyl 4-(cyclopropylamino)-2-methyl-5-nitrobenzoate (I-1f)

Prepared following a similar procedure to I-1a using methyl 4-chloro-2-methyl-5-nitrobenzoate and cyclopropylamine. ES/MS: 251.3 [M+H]⁺.

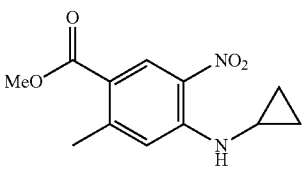

I-1f methyl 4-(cyclopropylamino)-3-nitrobenzoate (I-1g)

Prepared following a similar procedure to I-1a using methyl 4-fluoro-3-nitrobenzoate and cyclopropylamine. ES/MS: m/z 237.8 [M+H]⁺.

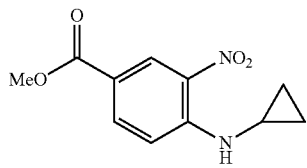

I-1g methyl 3-methoxy-4-(((1-methylcyclopropyl)methyl)amino)-5-nitrobenzoate (I-1h)

Prepared following a similar procedure to I-1a using (1-methylcyclopropyl)methanamine. ES/MS: m/z 294.9 [M+H]⁺.

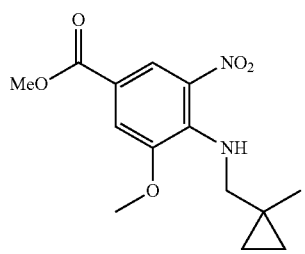

I-1h methyl 3-methoxy-4-((2-methoxyethyl)amino)-5-nitrobenzoate (I-1i)

Prepared following a similar procedure to I-1a using 2-methoxyethan-1-amine. ES/MS: m/z 285.8 [M+H]⁺.

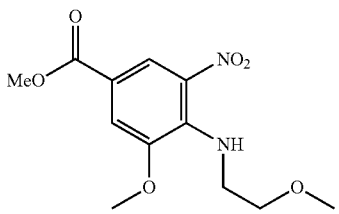

I-1i methyl 4-(bicyclo[1.1.1]pentan-1-ylamino)-3-methoxy-5-nitrobenzoate (I-1j)

Prepared following a similar procedure to I-1a using bicyclo[1.1.1]pentan-1-amine. ES/MS: m/z 293.3 [M+H]⁺.

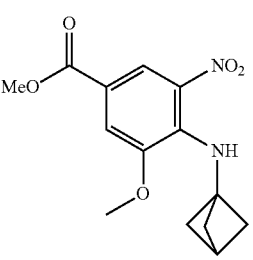

I-1j methyl 4-((cyclopropylmethyl)amino)-3-methoxy-5-nitrobenzoate (I-1k)

Prepared following a similar procedure to I-1a using cyclopropylmethanamine. ES/MS: m/z 281.0 [M+H]⁺.

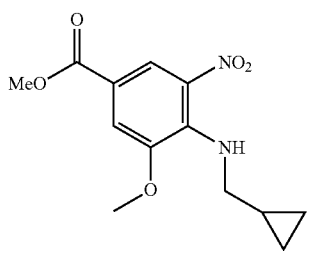

methyl 3-methoxy-5-nitro-4-((oxetan-3-ylmethyl)amino)benzoate (I-1l)

Prepared following a similar procedure to I-1a using oxetan-3-ylmethanamine. ES/MS: m/z 297.1 [M+H]$^+$.

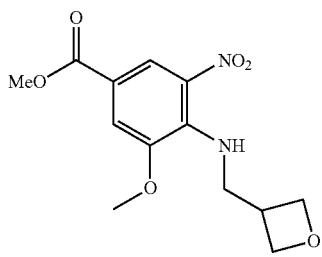

Preparation of tert-butyl ((3R,6S)-1-(3-methoxy-4-(methylamino)-5-nitrobenzoyl)-6-methylpiperidin-3-yl)carbamate (I-2a)

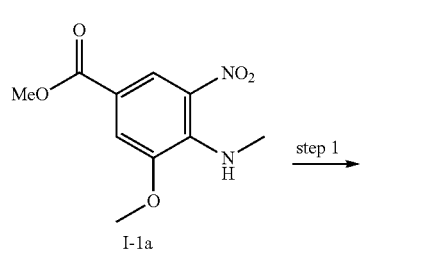

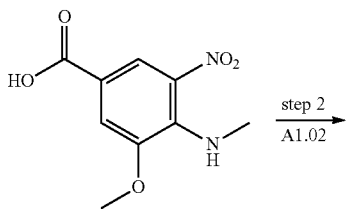

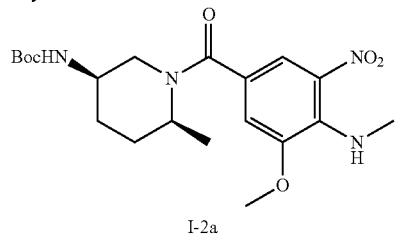

Step 1. To a solution of methyl 3-methoxy-4-(methylamino)-5-nitrobenzoate (I-1a, 4.99 g, 20.8 mmol) in THF (75 mL), MeOH (25 mL) and water (25 mL) was added NaOH (2.53 g, 63.4 mmol). The mixture was stirred at rt for 3 h. HCl (11 mL of a 6 M aq soln, 66.5 mmol) was added. The resulting solids were collected via filtration and dried to yield 3-methoxy-4-(methylamino)-5-nitrobenzoic acid. 1H NMR (400 MHz, DMSO-d6) δ 12.99-12.65 (m, 1H), 8.03 (d, J=1.8 Hz, 1H), 7.68 (q, J=5.3 Hz, 1H), 7.37 (d, J=1.8 Hz, 1H), 3.87 (s, 3H), 2.91 (d, J=5.3 Hz, 3H).

Step 2. To a solution of 3-methoxy-4-(methylamino)-5-nitrobenzoic acid (3.97 g, 17.6 mmol), tert-butyl ((3R,6S)-6-methylpiperidin-3-yl)carbamate (A1.02, 4.07 g, 19.0 mmol) and DIPEA (14.6 mL, 83.8 mmol) in DMF (35 mL) was added HATU (9.08 g, 23.9 mmol). The reaction mixture was stirred at rt for 3 h and was then quenched with sat NaHCO$_3$ soln. The aqueous layer was extracted with EtOAc. The organic portion was washed with 5% LiCl soln (aq), dried (MgSO$_4$), filtered and concentrated to afford tert-butyl ((3R,6S)-1-(3-methoxy-4-(methylamino)-5-nitrobenzoyl)-6-methylpiperidinyl)carbamate. 1H NMR (400 MHz, DMSO-d6) δ 7.46 (d, J=1.8 Hz, 1H), 7.33 (d, J=5.5 Hz, 1H), 7.03 (d, J=1.8 Hz, 1H), 6.85 (d, J=7.9 Hz, 1H), 3.88 (s, 4H), 3.60 (s, 1H), 3.15 (d, J=5.2 Hz, 1H), 2.88 (d, J=5.5 Hz, 4H), 2.67 (s, 2H), 1.58 (d, J=45.4 Hz, 5H), 1.36 (d, J=16.9 Hz, 10H), 1.23 (q, J=7.3, 6.6 Hz, 5H), 1.14 (dd, J=7.0, 2.1 Hz, 3H).

tert-butyl (R)-(1-(3-methoxy-4-(methylamino)-5-nitrobenzoyl)piperidin-3-yl)carbamate (I-2b)

Prepared analogously to I-2a, using A1.01. ES/MS: m/z 409.2 [M+H]$^+$.

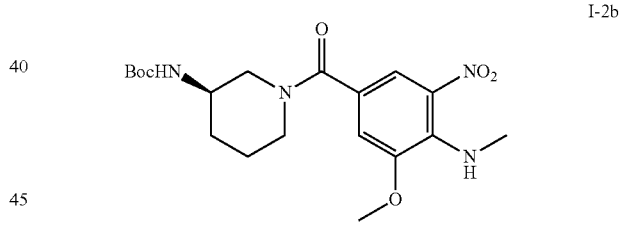

tert-butyl ((2R,3R)-1-(3-methoxy-4-(methylamino)-5-nitrobenzoyl)-2-methylpiperidinyl)-3-carbamate (I-2c)

Prepared analogously to I-2a, using A8. ES/MS: m/z 423.0 [M+H]$^+$.

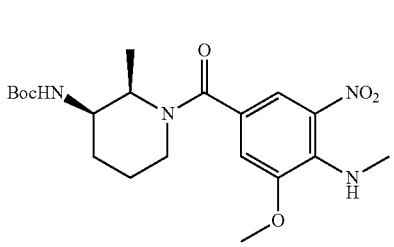

Preparation of methyl 4-(cyclopropylamino)-2,3-difluoro-5-nitrobenzoate (I-3a)

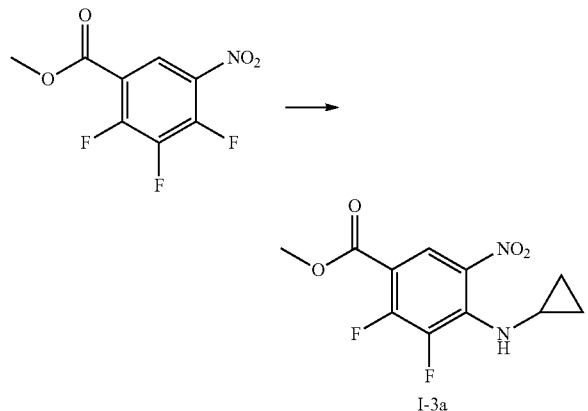

I-3a

A round bottom flask was charged with methyl 2,3,4-trifluoro-5-nitrobenzoate (1.18 g, 5 mmol) a stir bar and THF (20 mL). The solution was cooled to −78° C. and Hunig's base (1.3 mL, 7.5 mmol) was added followed by dropwise addition of cyclopropylamine (346 µL, 5 mmol). The remaining mixture was stirred at −78° C. (acetone dry ice bath) for 30 minutes then at −46° C. (acetonitrile dry ice bath) for 1 h. It was then slowly warmed up to 0° C. over 1 h and quenched with water. After work up (EtOAc and water) the residue was purified by flash chromatography over silica gel (0-10% EtOAc in hexanes) to afford methyl 4-(cyclopropylamino)-2,3-difluoro-5-nitrobenzoate. ES/MS: m/z 270.8 [M+H]$^+$.

methyl 3-fluoro-4-(methylamino)-5-nitrobenzoate (I-3b)

Prepared following a similar procedure to I-3a, using methyl 3,4-difluoro-5-nitrobenzoate and methylamine. ES/MS: m/z 229.0 [M+H]$^+$.

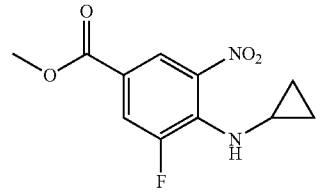

I-3b methyl 4-(cyclopropylamino)-3-fluoro-5-nitrobenzoate (I-3c)

Prepared following a similar procedure to I-3a, using methyl 3,4-difluoro-5-nitrobenzoate. ES/MS: m/z 254.9 [M+H]$^+$.

Preparation of methyl 3-amino-5-methoxy-4-(methylamino)benzoate (I-4a)

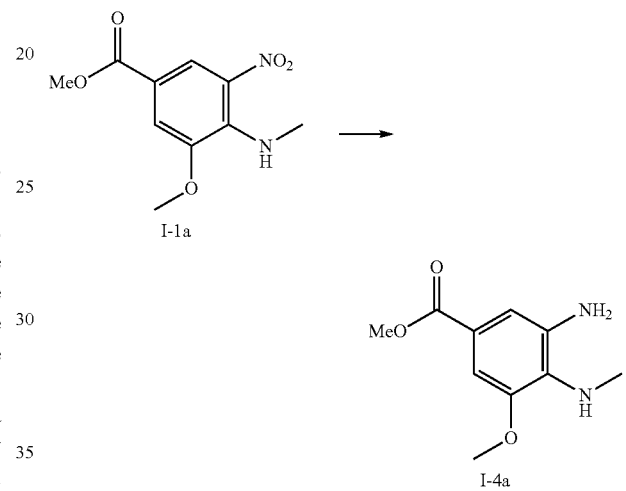

A solution of methyl 3-methoxy-4-(methylamino)-5-nitrobenzoate (I-1a, 1.580 g, 6.58 mmol) in EtOAc (15 mL) and EtOH (30 mL) was sparged with N$_2$. Pd/C (0.700 g of 10% Pd/C) was added and the mixture was stirred at rt under H$_2$ (1 atm) for 16 h. The mixture was filtered through a pad of Celite and the filtrate was concentrated to afford methyl 3-amino-5-methoxy-4-(methylamino)benzoate. ES/MS: m/z 211.1 [M+H]$^+$.

methyl 3-amino-5-methoxy-4-(cyclopropylamino)benzoate (I-4b)

Prepared analogously to I-4a, using I-1b. ES/MS: m/z 237.1 [M+H]$^+$.

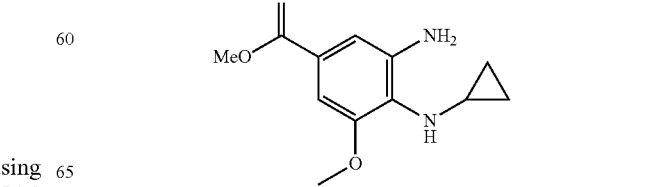

I-4b

Preparation of methyl 5-amino-4-(cyclopropylamino)-2,3-difluorobenzoate (I-5a)

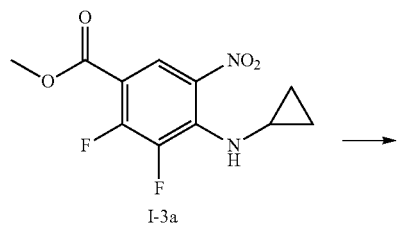

Step 1. Methyl 4-(cyclopropylamino)-2,3-difluoro-5-nitrobenzoate (I-3a, 272 mg, 1 mmol) was charged in a vial and (1% Pt)/(2% V) on carbon (Strem Chemical 78-1536) (55 mg) was added followed by ethyl acetate (3 mL). The mixture was degassed with nitrogen for 5 minutes and then placed under an atmosphere of hydrogen for 12 hours at which point the LCMS analysis showed full conversion of the starting material. Filtration and evaporation yielded the crude methyl 5-amino-4-(cyclopropylamino)-2,3-difluorobenzoate which was used in the next step without further purification. ES/MS: m/z 243.1 [M+H]$^+$.

methyl 5-amino-4-(cyclopropylamino)-2-fluorobenzoate (I-5b)

Prepared following a similar procedure to I-5a using I-1d. ES/MS: m/z 225.1 [M+H]$^+$.

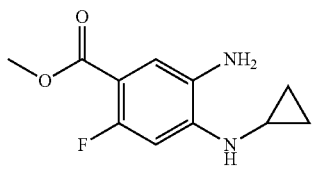

methyl 3-amino-4-(cyclopropylamino)benzoate (I-5c)

Prepared following a similar procedure to I-5a using I-1g. ES/MS: m/z 207.0 [M+H]$^+$.

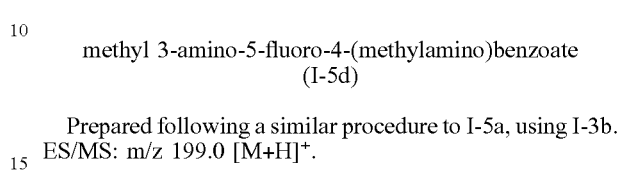

methyl 3-amino-5-fluoro-4-(methylamino)benzoate (I-5d)

Prepared following a similar procedure to I-5a, using I-3b. ES/MS: m/z 199.0 [M+H]$^+$.

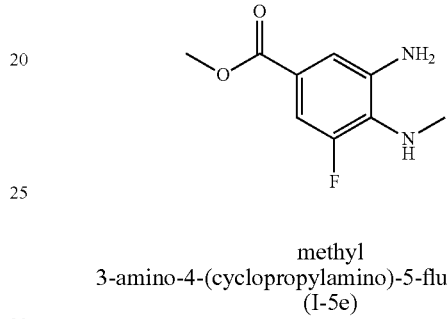

methyl 3-amino-4-(cyclopropylamino)-5-fluorobenzoate (I-5e)

Prepared following a similar procedure to I-5a, using I-3c. ES/MS: m/z 225.0 [M+H]$^+$.

Preparation of 6-bromo-1H-pyrrolo[2,3-b]pyridine-2-carbaldehyde (I-6)

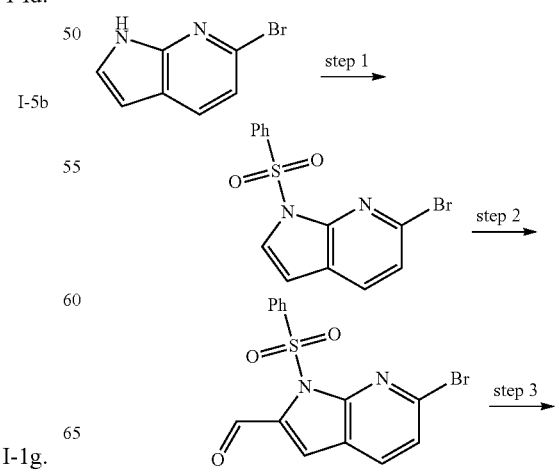

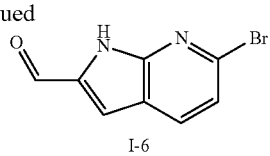

I-6

Step 1. To a stirred solution of 6-bromo-1H-pyrrolo[2,3-b]pyridine (10.0 g, 50.8 mmol) in DMF (100 mL) was added NaH (2.43 g, 101.3 mmol) at 0° C. After stirring for 10 minutes, benzenesulfonyl chloride (7.1 mL, 55.9 mmol) was added and the reaction mixture was held for 2 h at 0° C. The reaction mixture was quenched with ice-water, filtered, washed with cold water and the solid was dried under vacuum to afford 6-bromo-1-(phenylsulfonyl)-1H-pyrrolo[2,3-b]pyridine, which was used directly without any further purification. ¹H NMR (400 MHz, Chloroform-d) δ 8.27-8.20 (m, 2H), 7.72-7.65 (m, 2H), 7.65-7.57 (m, 1H), 7.56-7.48 (m, 2H), 7.32 (dd, J=8.1, 0.6 Hz, 1H), 6.56 (d, J=4.0 Hz, 1H).

Step 2. To a stirred solution of 6-bromo-1-(phenylsulfonyl)-1H-pyrrolo[2,3-b]pyridine (5 g, 14.8 mmol) in THF (50 mL) was added 2 M LDA solution in THF (11.5 mL, 16.3 mmol) under argon at −78° C. The reaction mixture was stirred for 30 min at −78° C., then quenched with DMF (1.62 g) and stirred for 1 h at −78° C. The reaction mixture was quenched with sat. aq. NH₄Cl solution and extracted with ethyl acetate. The organic layer was washed with brine, dried over anhydrous sodium sulfate, and concentrated under reduced pressure. The crude mixture was purified by silica gel column chromatography, eluting with 30% ethyl acetate in petroleum ether to afford 6-bromo-1-(phenylsulfonyl)-1H-pyrrolo[2,3-b]pyridine-2-carbaldehyde. ES/MS: m/z 364.9, 366.9 [M+H]⁺.

Step 3. To a stirred solution of 6-bromo-1-(phenylsulfonyl)-1H-pyrrolo[2,3-b]pyridinecarbaldehyde (13.5 g, 37.1 mmol) in methanol (130 mL) under argon was added 1 M NaOH aqueous solution (270 mL) at 0° C., and the reaction was stirred for 6 h at 0° C. The reaction mixture was filtered through a plug of Celite, washed with methanol and the filtrate was evaporated under reduced pressure. The crude mixture was purified by silica gel column chromatography, eluting with 30% ethyl acetate in petroleum ether to obtain 6-bromo-1H-pyrrolo[2,3-b]pyridine-2-carbaldehyde. ES/MS: m/z 225.1, 227.1 [M+H]⁺.

Preparation of 6-bromo-1-(cyclopropylmethyl)-1H-pyrrolo[2,3-b]pyridine-2-carbaldehyde (I-7)

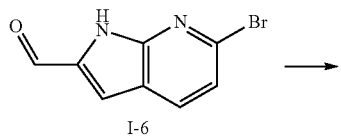

I-6

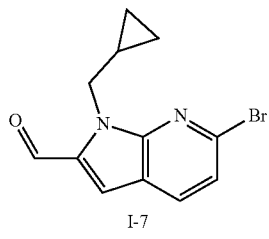

I-7

To a solution of 6-bromo-1H-pyrrolo[2,3-b]pyridine-2-carbaldehyde (I-6, 30.0 g, 111 mmol) in DMF (250 mL) at 0° C. was added Cs₂CO₃ (72.2 g, 222 mmol) followed by (bromomethyl)cyclopropane (18.0 g, 133 mmol) and NaI (cat). The mixture was stirred at 10° C. for 2 h before the reaction was quenched by the addition of ice water. The resulting solid was isolated via filtration, rinsed with cold water, and dried under vacuum to afford 6-bromo-1-(cyclopropylmethyl)-1H-pyrrolo[2,3-b]pyridinecarbaldehyde. ES/MS: m/z 279.6/281.6 [M+H]⁺. H NMR (300 MHz, DMSO-d₆) δ 9.99 (s, 1H), 8.22 (d, J=8.4 Hz, 1H), 7.56 (s, 1H), 7.44 (d, J=8.4 Hz, 1H), 4.42 (d, J=7.2 Hz, 2H), 1.27 (m, 1H), 0.44-0.41 (m, 4H).

Preparation of 6-bromo-1-(cyclopropylmethyl)-1H-indole-2-carbaldehyde (I-8)

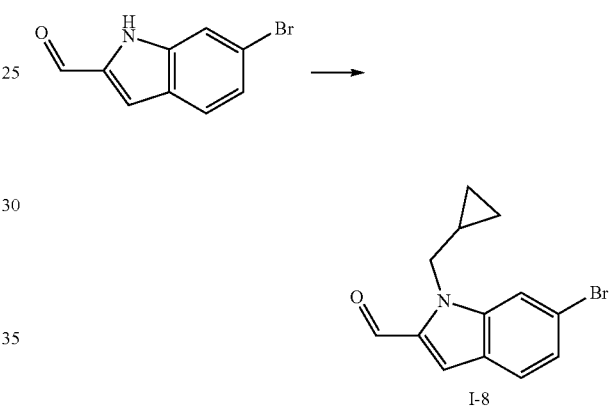

I-8

To a solution of 6-bromo-1H-indole-2-carbaldehyde (1.12 g, 5.00 mmol) and cyclopropylmethyl bromide (0.73 mL, 7.50 mmol) in DMF (10 mL) was added sodium hydride (0.156 g, 6.50 mmol). The mixture was stirred at rt for 17 h and was then quenched via addition of sat NH₄Cl soln. The mixture was diluted with water and DCM and the aqueous layer was extracted with DCM. The combined organic layers were washed with brine, dried (Na₂SO₄), filtered, and concentrated. The residue was purified via flash column chromatography on silica gel to afford 6-bromo-1-(cyclopropylmethyl)-1H-indole-2-carbaldehyde. ¹H NMR (400 MHz, Chloroform-d) δ 9.90 (s, 1H), 7.66-7.58 (m, 2H), 7.33-7.22 (m, 2H), 4.47 (d, J=7.0 Hz, 2H), 1.38-1.24 (m, 1H), 0.56-0.38 (m, 4H).

Preparation of 6-chloro-1-(cyclopropylmethyl)-5-fluoro-1H-indole-2-carbaldehyde (I-9a)

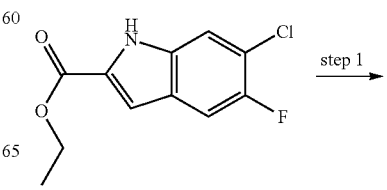

step 1

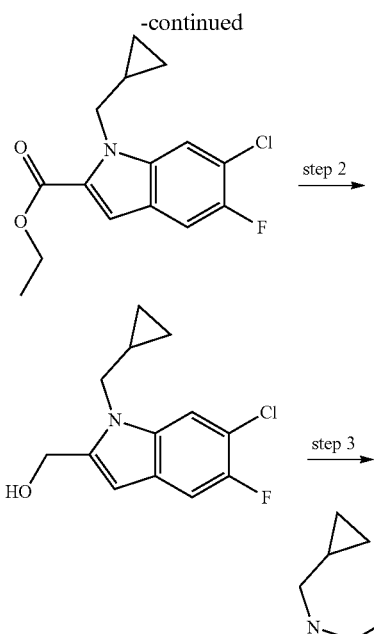

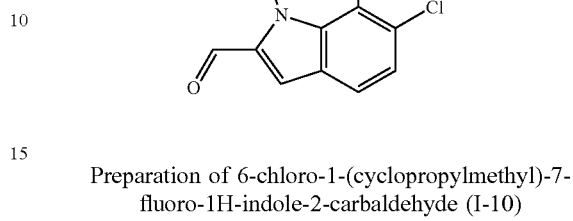

Step 1. The procedure described in the preparation of I-7 was followed, using ethyl 6-chloro-5-fluoro-1H-indole-2-carboxylate, to give ethyl 6-chloro-1-(cyclopropylmethyl)-5-fluoro-1H-indole-2-carboxylate. ES/MS: m/z 296.35 [M+H]⁺.

Step 2. To a solution of ethyl 6-chloro-1-(cyclopropylmethyl)-5-fluoro-1H-indole-2-carboxylate (1.33 g, 4.50 mmol) in THF (22 mL) at 0° C. was added LAH (0.171 g, 4.50 mmol). The mixture was stirred at 0° C. and reaction progress was monitored by LC-MS. The reaction mixture was quenched by addition of saturated Rochelle salt solution and was allowed to warm to rt. The mixture was transferred to a separatory funnel and the aqueous layer was extracted with EtOAc. The organic layer was concentrated and the residue was purified via flash column chromatography on silica gel to afford (6-chloro-1-(cyclopropylmethyl)-5-fluoro-1H-indol-2-yl)methanol. ES/MS: m/z 254.0 [M+H]⁺.

Step 3. To a solution of (6-chloro-1-(cyclopropylmethyl)-5-fluoro-1H-indol-2-yl)methanol (2.34 g, 9.22 mmol) in DCM (40 mL) was added Dess-Martin periodinane (3.91 g, 9.22 mmol). The reaction mixture was stirred at rt and reaction progress was monitored by LC-MS. The mixture was transferred to a separatory funnel and diluted with sat NaHCO₃ soln. The aqueous layer was extracted with DCM. The organic layer was concentrated, and the residue was purified via flash column chromatography on silica gel to yield 6-chloro-1-(cyclopropylmethyl)-5-fluoro-1H-indole-2-carbaldehyde. ES/MS: m/z 252.14 [M+H]⁺.

6-chloro-1-(cyclopropylmethyl)-7-fluoro-1H-indole-2-carbaldehyde (I-9b)

Prepared analogously to I-9a, using 6-chloro-7-fluoro-1H-indole-2-carboxylic acid and 2 equiv (bromomethyl)cyclopropane in Step 1. ¹H NMR (400 MHz, Chloroform-d) δ 9.89 (d, J=0.8 Hz, 1H), 7.45 (d, J=8.6 Hz, 1H), 7.31-7.24 (m, 1H), 7.15 (ddd, J=8.6, 6.2, 0.9 Hz, 1H), 4.67 (d, J=7.1 Hz, 2H), 1.41-1.22 (m, 1H), 0.59-0.32 (m, 4H).

Preparation of 6-chloro-1-(cyclopropylmethyl)-7-fluoro-1H-indole-2-carbaldehyde (I-10)

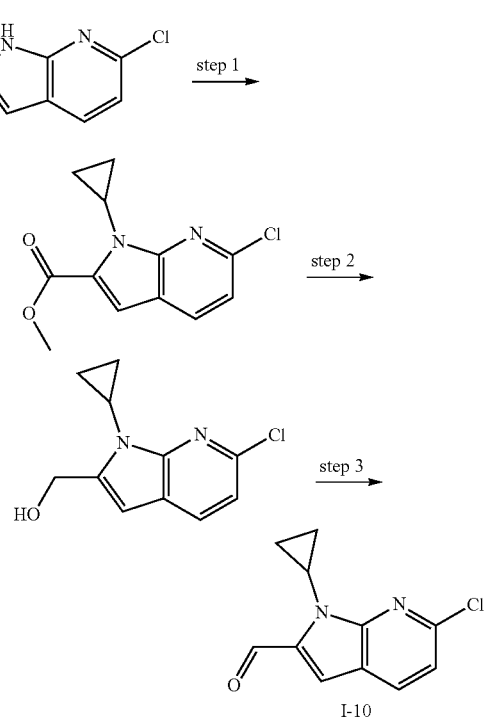

Step 1. To a mixture of methyl 6-chloro-1H-pyrrolo[2,3-b]pyridine-2-carboxylate (0.510 g, 2.42 mmol), 2,2'-bipyridyl (0.408 g, 2.61 mmol, cupric acetate (0.460 g, 2.53 mmol) and sodium carbonate (0.555 g, 5.24 mmol) in DCE (13 mL) was added cyclopropylboronic acid (0.24 mL, 5.06 mmol). The mixture was stirred at 80° C. for 3 h, at which point 0.1 equiv, each, of all reagents were added. The mixture was stirred at 80° C. for 16 h and was then cooled to rt and diluted with water. The mixture was extracted with EtOAc. The organic layer was dried (MgSO₄), filtered, and concentrated. The residue was purified via flash column chromatography on silica gel to yield methyl 6-chloro-1-cyclopropyl-1H-pyrrolo[2,3-b]pyridine-2-carboxylate. ES/MS: m/z 251.0 [M+H]⁺.

Step 2. To a solution of methyl 6-chloro-1-cyclopropyl-1H-pyrrolo[2,3-b]pyridine-2-carboxylate (0.250 g, 0.997 mmol) in THF (8.0 mL) was added lithium borohydride (1.3 mL of a 2 M soln in THF, 2.6 mmol). The mixture was stirred at 70° C. and reaction progress was monitored by LC-MS. The mixture was cooled to rt and quenched via addition of sat NH₄Cl soln (aq). The mixture was stirred until effervescence ceased and was then extracted with EtOAc. The organic layer was dried (MgSO₄), filtered and concentrated to give (6-chloro-1-cyclopropyl-1H-pyrrolo[2,3-b]pyridin-2-yl)methanol. ES/MS: m/z 223.1 [M+H]⁺.

Step 3. To a solution of (6-chloro-1-cyclopropyl-1H-pyrrolo[2,3-b]pyridin-2-yl)methanol (0.220 g, 0.988 mmol) in chloroform (10 mL) was added manganese dioxide (1.136 g, 11.1 mmol). The mixture was stirred at rt for 45 min. The mixture was filtered through Celite, and the filter pad was rinsed with DCM. The filtrate was concentrated to give 6-chloro-1-cyclopropyl-1H-pyrrolo[2,3-b]pyridinecarbaldehyde. ES/MS: m/z 221.0 [M+H]⁺.

Preparation of 6-chloro-1-(cyclopropylmethyl)-1H-pyrrolo[2,3-b]pyridine-2-carbaldehyde (I-11)

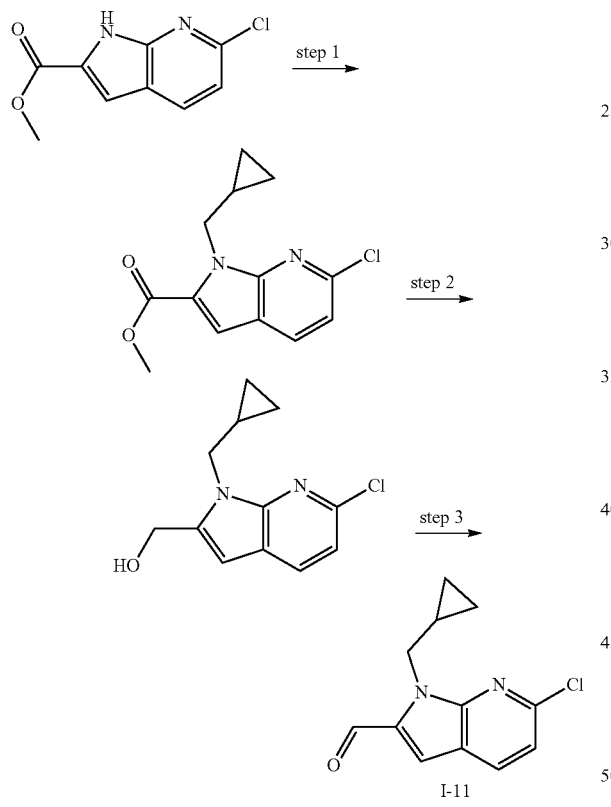

Step 1. To a solution of methyl 6-chloro-1H-pyrrolo[2,3-b]pyridine-2-carboxylate (3.00 g, 14.2 mmol) and cyclopropylmethyl bromide (2.1 mL, 21 mmol) in DMF (50 mL) was added sodium hydride (0.444 g, 18.5 mmol). The mixture was stirred at rt for 16 h and was then quenched by addition of sat NaHCO₃ soln. The mixture was diluted with water and EtOAc and the aqueous layer was extracted with EtOAc. The combined organic layers were washed successively with sat NaHCO₃ soln and brine, dried (Na₂SO₄), filtered, and concentrated to give crude methyl 6-chloro-1-(cyclopropylmethyl)-1H-pyrrolo[2,3-b]pyridine-2-carboxylate, which was taken on without purification. ES/MS: m/z 265.2 [M+H]⁺.

Step 2. A mixture of methyl 6-chloro-1-(cyclopropylmethyl)-1H-pyrrolo[2,3-b]pyridine-2-carboxylate (3.00 g, 11.3 mmol) and lithium borohydride (0.617 g, 28.3 mmol) in THF (60 mL) was stirred at 70° C. for 8 h. The mixture was quenched via dropwise addition of NH₄Cl soln (aq). The aqueous layer was extracted with EtOAc. The combined organic layers were washed with brine, dried (Na₂SO₄), filtered, and concentrated. The residue was purified via flash column chromatography on silica gel to yield (6-chloro-1-(cyclopropylmethyl)-1H-pyrrolo[2,3-b]pyridin-2-yl)methanol. ES/MS: m/z 237.2 [M+H]⁺.

Step 3. To a solution of (6-chloro-1-(cyclopropylmethyl)-1H-pyrrolo[2,3-b]pyridin-2-yl)methanol (2.40 g, 10.2 mmol) in chloroform (40 mL) was added manganese(IV) oxide (11.4 g, 112 mmol). The reaction mixture was stirred at 60° C. for 30 min. The mixture was cooled to rt and the solids were removed via filtration through Celite. The filtrate was concentrated and the residue was purified via flash column chromatography on silica gel to yield 6-chloro-1-(cyclopropylmethyl)-1H-pyrrolo[2,3-b]pyridine-2-carbaldehyde. ES/MS: m/z 235.2 [M+H]⁺.

Preparation of tert-butyl (R)-(1-(2-formyl-1H-pyrrolo[2,3-b]pyridin-6-yl)ethyl)carbamate (I-12)

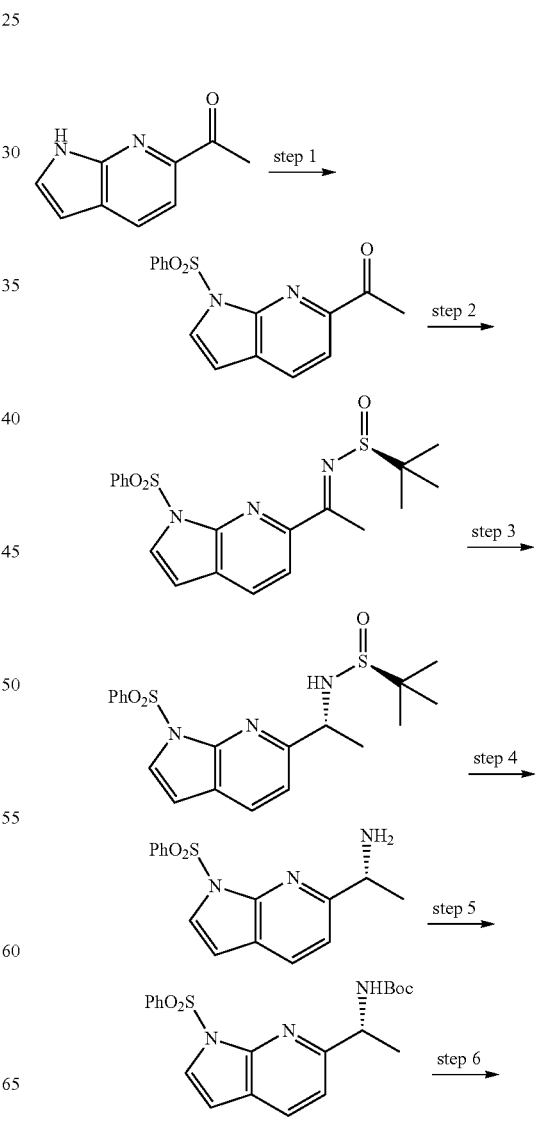

-continued

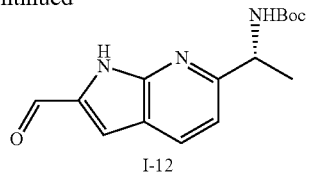

I-12

Step 1. Step 1 in the preparation of I-6 was followed to produce 1-(1-(phenylsulfonyl)-1H-pyrrolo[2,3-b]pyridin-6-yl)ethan-1-one from 1-(1H-pyrrolo[2,3-b]pyridin-6-yl)ethan-1-one. ES/MS: m/z 301.0 [M+H]$^+$.

Step 2. To a mixture of 1-(1-(phenylsulfonyl)-1H-pyrrolo[2,3-b]pyridin-6-yl)ethan-1-one (246 g, 819 mmol) and (S)-2-methylpropane-2-sulfinamide (248 g, 2.04 mol) in THF (4.9 L) was added Ti(OiPr)$_4$ (1860 g, 6.55 mol). The mixture was stirred at 70° C. for 48 h. The mixture was cooled to rt, diluted with EtOAc and brine. Solids were removed via filtration and the filter pad was rinsed with EtOAc. The filtrate was washed with brine, dried (Na$_2$SO$_4$), filtered, and concentrated to give (S,E)methyl-N-(1-(1-(phenylsulfonyl)-1H-pyrrolo[2,3-b]pyridin-6-yl)ethylidene)propane-2-sulfinamide. ES/MS: m/z 404.1 [M+H]$^+$.

Step 3. To a solution of (S,E)-2-methyl-N-(1-(1-(phenylsulfonyl)-1H-pyrrolo[2,3-b]pyridin-6-yl)ethylidene)propane-2-sulfinamide (330 g, 819 mmol) in THF (4 L) at −30° C. was added L-selectride (963 mL of a 1 M soln in THF, 963 mmol), dropwise. The mixture was stirred at −30° C. for 3 h. The mixture was quenched with sat NH$_4$Cl soln (aq) and allowed to warm to rt. The mixture was extracted with EtOAc. The organic layer was washed with brine, dried (Na$_2$SO$_4$), filtered, and concentrated. The residue was purified via flash column chromatography on silica gel to afford (S)-2-methyl-N—((R)-1-(1-(phenylsulfonyl)-1H-pyrrolo[2,3-b]pyridin-6-yl)ethyl)propane-2-sulfinamide. ES/MS: m/z 406.1 [M+H]$^+$.

Step 4. (S)-2-methyl-N—((R)-1-(1-(phenylsulfonyl)-1H-pyrrolo[2,3-b]pyridin-6-yl)ethyl)propane-2-sulfinamide (200 g, 493 mmol) was dissolved in HCl (1 L of a 4 M HCl soln in dioxane). The mixture was stirred vigorously for 1 h and then concentrated. The residue was slurried in MTBE and the resulting solid was collected via filtration to yield (R)-1-(1-(phenylsulfonyl)-1H-pyrrolo[2,3-b]pyridin-6-yl)ethan-1-amine as the HCl salt. ES/MS: m/z 302.1 [M+H]$^+$.

Step 5. To a solution of (R)-1-(1-(phenylsulfonyl)-1H-pyrrolo[2,3-b]pyridin-6-yl)ethan-1-amine (106 g, 283 mmol) and TEA (147 mL, 1.05 mol) in THF (1 L) was added (Boc)$_2$O (92 g, 420 mmol), dropwise. The mixture was allowed to warm to rt and was stirred for 2 h. The mixture was diluted with water and the aqueous layer was extracted with EtOAc. The organic layer was washed successively with sat citric acid (aq) and brine, dried (Na$_2$SO$_4$), filtered, and concentrated. The residue was purified via flash column chromatography on silica gel to afford tert-butyl (R)-(1-(1-(phenylsulfonyl)-1H-pyrrolo[2,3-b]pyridin-6-yl)ethyl)carbamate. ES/MS: m/z 402.1 [M+H]$^+$.

Step 6. A solution of s-BuLi in cyclohexane (1.4 M, 24.9 mL, 34.9 mmol) was added dropwise to cooled solution of tert-butyl N-[(1R)-1-[1-(benzenesulfonyl)pyrrolo[2,3-b]pyridinyl]ethyl]carbamate (4.0 g, 10.0 mmol) in THF (100 mL) at −78° C. After 2 h, N,N-dimethylformamide (5.3 mL, 7.1 mmol) was added dropwise. The reaction mixture was stirred at −78° C. After two hours, the reaction mixture was quenched with aqueous ammonium chloride and extracted with ethyl acetate. The combined organics were washed with water, brine, dried (MgSO$_4$), filtered, and concentrated under reduced pressure. The resulting residue was purified via silica gel column chromatography (0-35% ethyl acetate/hexanes) to yield tert-butyl (R)-(1-(2-formyl-1H-pyrrolo[2,3-b]pyridin-6-yl)ethyl)carbamate. $^1$H NMR (400 MHz, DMSO-d6) δ 12.45 (s, 1H), 9.85 (s, 1H), 8.17 (d, J=8.3 Hz, 1H), 7.40 (d, J=8.3 Hz, 1H), 7.37 (s, 1H), 7.21 (d, J=8.3 Hz, 1H), 4.83-4.61 (m, 1H), 1.38 (d, J=4.8 Hz, 3H), 1.37 (s, 9H).

Preparation of 1-(cyclopropylmethyl)-6-(methylsulfonyl)-1H-pyrrolo[2,3-b]pyridine-2-carbaldehyde (I-13)

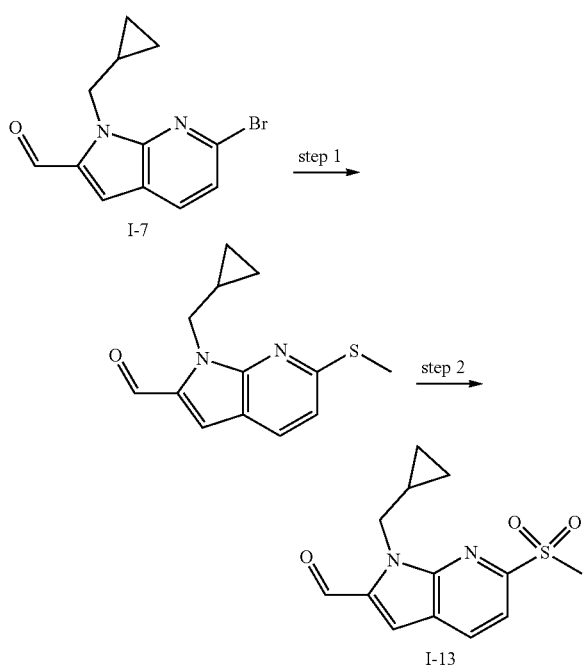

Step 1. To a solution of 6-bromo-1-(cyclopropylmethyl)-1H-pyrrolo[2,3-b]pyridine-2-carbaldehyde (I-7, 0.200 g, 0.716 mmol) in DMF (7 mL) was added sodium thiomethoxide (95 µL, 1.4 mmol). The reaction mixture was stirred at 90° C. for 2 h. The mixture was cooled to rt, diluted with water, and treated with NaOH (2 mL of 1 M NaOH (aq)). The mixture was extracted with EtOAc and the organic layer was dried (Na$_2$SO$_4$), filtered and concentrated. The resulting residue was purified via flash column chromatography on silica gel to afford 1-(cyclopropylmethyl)-6-(methylthio)-1H-pyrrolo[2,3-b]pyridine-2-carbaldehyde. ES/MS: m/z 247.1 [M+H]$^+$.

Step 2. To a solution of 1-(cyclopropylmethyl)-6-(methylthio)-1H-pyrrolo[2,3-b]pyridine-2-carbaldehyde (0.123 g, 0.498 mmol) in DCM (2 mL) and MeCN (2 mL) was added water (4 mL). Sodium periodate (0.266 g, 1.25 mmol) was added, followed by ruthenium(III) chloride (0.005 g, 0.025 mmol). The biphasic mixture was stirred vigorously at rt for 6 h. The mixture was diluted with water and extracted with EtOAc. The organic layer was washed successively with sat. NaHCO$_3$ soln and brine, dried (Na$_2$SO$_4$), filtered and concentrated. The resulting residue was purified via flash column chromatography on silica gel to yield 1-(cyclopropylmethyl)-6-(methylsulfonyl)-1H-pyrrolo[2,3-b]pyridine-2-carbaldehyde. ES/MS: m/z 279.1 [M+H]$^+$.

Preparation of 1-(cyclopropylmethyl)-6-(isopropylsulfonyl)-1H-pyrrolo[2,3-b]pyridine-2-carbaldehyde (I-14)

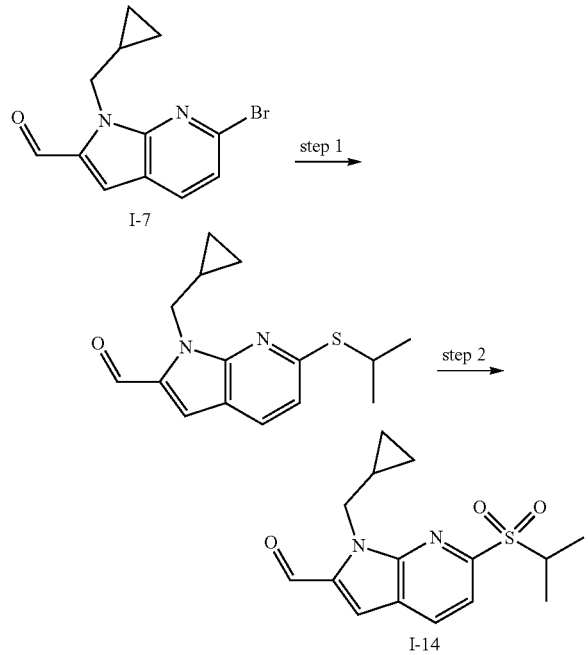

Step 1. To a solution of 6-bromo-1-(cyclopropylmethyl)-1H-pyrrolo[2,3-b]pyridine-2-carbaldehyde (I-7, 0.200 g, 0.716 mmol) and potassium tert-butoxide (0.161 g, 1.43 mmol) in DMF (3 mL) was added 2-propanethiol (133 μL, 1.43 mmol). The reaction mixture was stirred at 90° C. for 40 min. The mixture was cooled to rt, treated with NaOH (2 mL of a 1 M soln (aq)), and extracted with EtOAc. The organic layer was dried ($Na_2SO_4$), filtered and concentrated. The resulting residue was purified via flash column chromatography on silica gel to yield 1-(cyclopropylmethyl)-6-(isopropylthio)-1H-pyrrolo[2,3-b]pyridine-2-carbaldehyde. ES/MS: m/z 275.1 $[M+H]^+$.

Step 2. The procedure described in Step 2 of the preparation of I-13 was followed to give 1-(cyclopropylmethyl)-6-(isopropylsulfonyl)-1H-pyrrolo[2,3-b]pyridine-2-carbaldehyde. ES/MS: m/z 307.1 $[M+H]^+$.

Preparation of 6-(2-((tert-butyldimethylsilyl)oxy)propan-2-yl)-1-(cyclopropylmethyl)-1H-pyrrolo[2,3-b]pyridine-2-carbaldehyde (I-15)

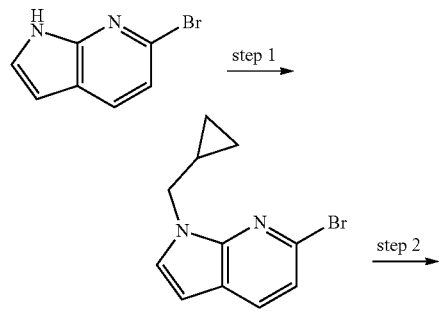

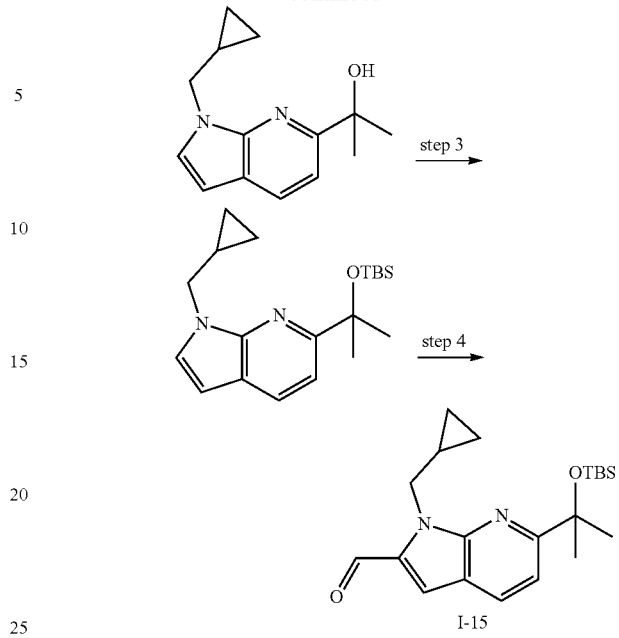

Step 1. To a solution of 6-bromo-1H-pyrrolo[2,3-b]pyridine (9.40 g, 47.7 mmol) in DMA (50 ml) at 0° C. was added NaHMDS (26.3 ml of a 2 M soln in THF, 52.6 mmol), dropwise. After 5 min, bromomethylcyclopropane (9.02 g, 66.8 mmol) was added and the reaction was allowed to warm to rt and was stirred for 16 h. The reaction mixture was quenched by the addition of HCl (52 ml of a 3 M aq soln) and the mixture was stirred for 20 mins. The pH was neutralized with aq $K_2HPO_4$ and the mixture was extracted with EtOAc. The organic layer was washed with 5% LiCl (aq), dried ($Na_2SO_4$), filtered and concentrated to afford 6-bromo-1-(cyclopropylmethyl)-1H-pyrrolo[2,3-b]pyridine. ES/MS: m/z 251.0/253.0 $[M+H]^+$.

Step 2. To a solution of 6-bromo-1-(cyclopropylmethyl)-1H-pyrrolo[2,3-b]pyridine (3.20 g, 12.7 mmol) in MeTHF (32 mL) in a −78° C. bath was added n-butyllithium (6.6 mL of a 2.5 M soln in hexanes, 16.6 mmol), dropwise, maintaining an internal temperature below −60° C. The mixture was stirred for 20 min. To the reaction mixture was added acetone (2.4 mL, 32 mmol). The reaction was allowed to warm to 0° C., quenched with 4 M $NH_4Cl$ (aq). The organic layer was dried ($Na_2SO_4$), filtered, and concentrated. The resulting residue was purified via flash column chromatography on silica gel to give 2-(1-(cyclopropylmethyl)-1H-pyrrolo[2,3-b]pyridin-6-yl)propan-2-ol. ES/MS: m/z 231.0 $[M+H]^+$.

Step 3. To a solution of 2-(1-(cyclopropylmethyl)-1H-pyrrolo[2,3-b]pyridin-6-yl)propan-2-ol (1.4 g, 6.1 mmol) and 2,6-lutidine (1.4 mL, 12 mmol) in DCM (15 mL) at −70° C. was added tert-butyldimethylsilyl trifluoromethanesulfonate (1.7 mL, 7.3 mmol), dropwise. The mixture was allowed to warm to rt and was then concentrated. The residue was diluted with hexanes and washed with water. The organic layer was dried ($Na_2SO_4$), filtered, and concentrated. The resulting residue was purified via flash column chromatography on silica gel to afford 6-(2-((tert-butyldimethylsilyl)oxy)propan-2-yl)-1-(cyclopropylmethyl)-1H-pyrrolo[2,3-b]pyridine. ES/MS: m/z 344.9 $[M+H]^+$.

Step 4. To a solution of 6-(2-((tert-butyldimethylsilyl)oxy)propan-2-yl)-1-(cyclopropylmethyl)-1H-pyrrolo[2,3-b]

pyridine (1.3 g, 3.8 mmol) in 1:1 heptane:MeTHF (13 ml) at −50° C. was added tert-butyllithium (4.4 mL of a 1.7 M soln in heptane, 7.5 mmol). The reaction mixture was stirred for 1 h and was then cooled to −70° C. N,N-dimethylformamide (1.8 mL, 23 mmol) was added in one portion. The reaction mixture was allowed to warm to rt and was then diluted with hexanes and washed with 5% LiCl (aq). The organic layer was dried (Na$_2$SO$_4$), filtered, and concentrated. The resulting residue was purified via flash column chromatography on silica gel to yield 6-(2-((tert-butyldimethylsilyl)oxy)propan-2-yl)-1-(cyclopropylmethyl)-1H-pyrrolo[2,3-b]pyridine-2-carbaldehyde. ES/MS: m/z 372.9 [M+H]$^+$.

Preparation of methyl 2-(6-bromo-1H-pyrrolo[2,3-b]pyridin-2-yl)-7-methoxy-1-methyl-1H-benzo[d]imidazole-5-carboxylate (I-16a)

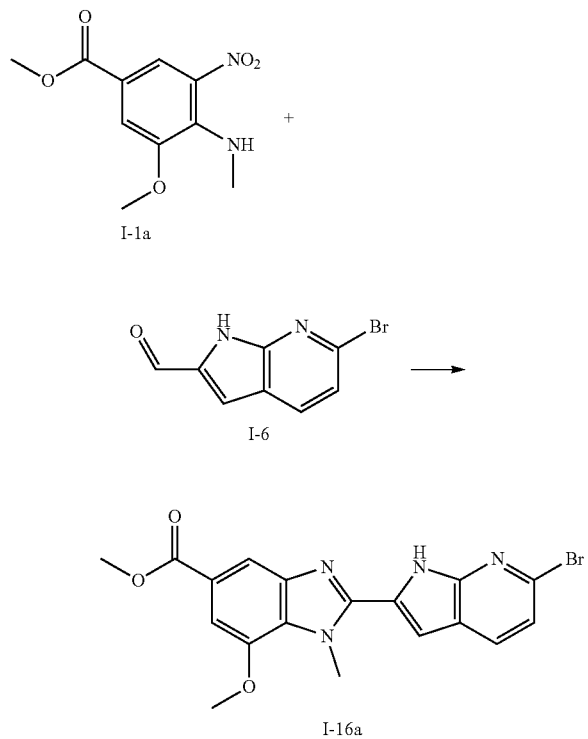

Methyl 3-methoxy-4-(methylamino)-5-nitrobenzoate (I-1a, 4 g, 16.65 mmol) and 6-bromo-1H-pyrrolo[2,3-b]pyridine-2-carbaldehyde (I-6, 3.75 g, 16.65 mmol) were charged in a sealable 500 mL round bottom flask. The mixture was dissolved in 300 mL of EtOH/H$_2$O (2:1) and sodium dithionite (8.70 g, 50 mmol) was added in one portion. The flask was sealed and heated to 90° C. and the reaction mixture was stirred ~2 h. Water (300 mL) was added to the reaction mixture and it was allowed to cool to room temperature. The solids were collected by filtration and washed with water (2×100 mL) followed by diethyl ether (2×75 mL). The solid was dried to afford methyl 2-(6-bromo-1H-pyrrolo[2,3-b]pyridin-2-yl)-7-methoxy-1-methyl-1H-benzo[d]imidazole-5-carboxylate. ES/MS: m/z 415.1, 417.1 [M+H]$^+$.

methyl 2-(6-bromo-1H-indol-2-yl)-7-methoxy-1-methyl-1H-benzo[d]imidazole-5-carboxylate (I-16b)

Prepared following a similar procedure to I-16a using commercially available 6-bromo-1H-indole-2-carbaldehyde instead of I-6. ES/MS: m/z 414.2, 416.2 [M+H]$^+$.

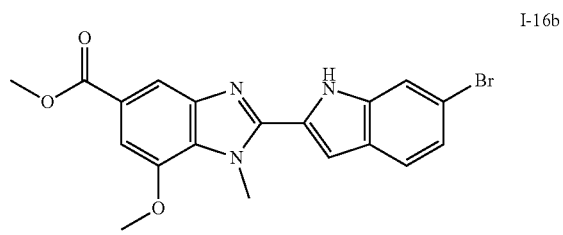 [SMILES: COC(=O)c1cc(OC)c2c(c1)nc(-c1cc3ccc(Br)cc3[nH]1)n2C]

methyl 2-(6-bromo-1H-pyrrolo[2,3-b]pyridin-2-yl)-6-fluoro-1-methyl-1H-benzo[d]imidazole-5-carboxylate (I-16c)

Prepared following a similar procedure to I-16a using I-1c. ES/MS: m/z 403.2, 405.2 [M+H]$^+$.

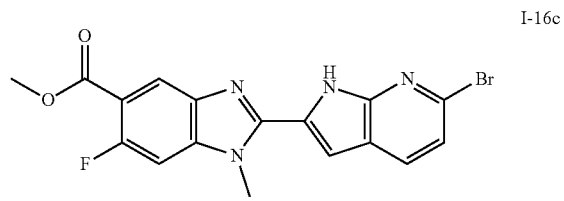 [SMILES: COC(=O)c1cc2nc(-c3cc4ccc(Br)nc4[nH]3)n(C)c2cc1F]

tert-butyl ((2R,3R)-1-(2-(6-chloro-1-cyclopropyl-1H-pyrrolo[2,3-b]pyridin-2-yl)-7-methoxy-1-methyl-1H-benzo[d]imidazole-5-carbonyl)-2-methylpiperidin-3-yl)carbamate (I-16d)

Prepared following a similar procedure to I-16a using I-2c and I-10. ES/MS: m/z 593.6 [M+H]$^+$.

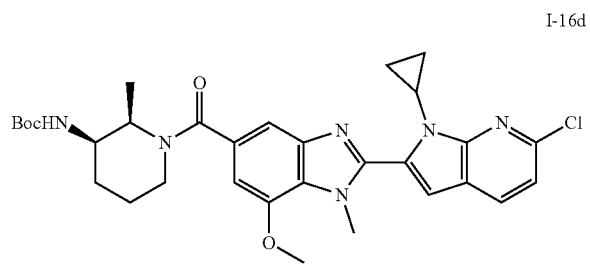 [SMILES: COc1cc(C(=O)N2CCC[C@@H](NC(=O)OC(C)(C)C)[C@H]2C)cc2nc(-c3cc4ccc(Cl)nc4n3C3CC3)n(C)c12]

methyl 2-(6-chloro-1-cyclopropyl-1H-pyrrolo[2,3-b]pyridin-2-yl)-1-(cyclopropylmethyl)-7-methoxy-1H-benzo[d]imidazole-5-carboxylate (I-16e)

Prepared following a similar procedure to I-16a using I-1k and I-10. ES/MS: m/z 451.2 [M+H]$^+$.

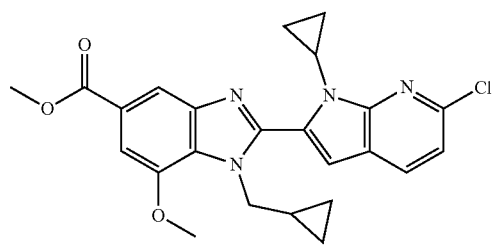

I-16e methyl 2-(6-bromo-1-(cyclopropylmethyl)-1H-pyr-rolo[2,3-b]pyridin-2-yl)-1,6-dimethyl-1H-benzo[d]imidazole-5-carboxylate (I-16f)

Prepared following a similar procedure to I-16a using I-1e and I-7. ES/MS: m/z 454.2 [M+H]⁺.

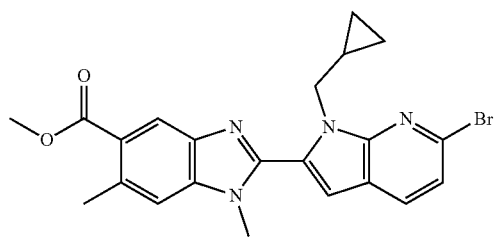

I-16f methyl 2-(6-chloro-1-(cyclopropylmethyl)-1H-pyr-rolo[2,3-b]pyridin-2-yl)-1-(cyclopropylmethyl)-7-methoxy-1H-benzo[d]imidazole-5-carboxylate (I-16g)

Prepared following a similar procedure to I-16a using I-1k and I-11. ES/MS: m/z 465.3 [M+H]⁺.

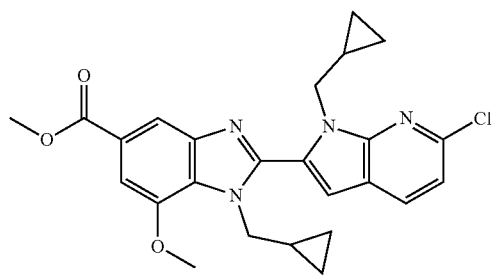

I-16g methyl 2-(6-bromo-1-(cyclopropylmethyl)-1H-pyr-rolo[2,3-b]pyridin-2-yl)-7-methoxy-1-((1-methylcyclopropyl)methyl)-1H-benzo[d]imidazole-5-carboxylate (I-16h)

Prepared following a similar procedure to I-16a using I-1h and I-7. ES/MS: m/z 523.0, 525.0 [M+H]⁺.

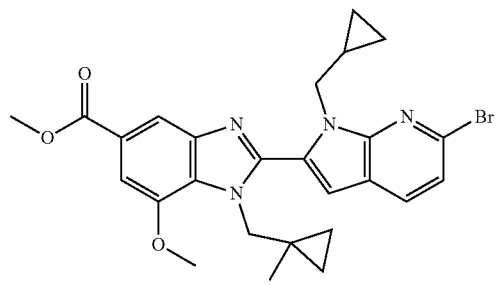

I-16h methyl 1-(bicyclo[1.1.1]pentan-1-yl)-2-(6-bromo-1-(cyclopropylmethyl)-1H-pyrrolo[2,3-b]pyridin-2-yl)-7-methoxy-1H-benzo[d]imidazole-5-carboxylate (I-16i)

Prepared following a similar procedure to I-16a using I-1j and I-7. ES/MS: m/z 521.1, 523.0 [M+H]⁺.

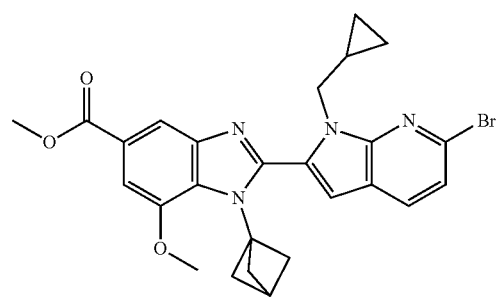

I-16i methyl 2-(6-bromo-1-(cyclopropylmethyl)-1H-pyr-rolo[2,3-b]pyridin-2-yl)-7-methoxy-1-(2-methoxyethyl)-1H-benzo[d]imidazole-5-carboxylate (I-16j)

Prepared following a similar procedure to I-16a using I-1i and I-7. ES/MS: m/z 513.4, 515.3 [M+H]⁺.

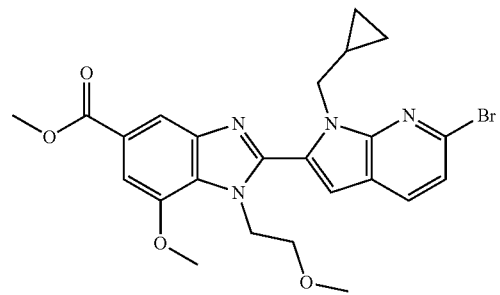

I-16j methyl 2-(6-bromo-1-(cyclopropylmethyl)-1H-pyr-rolo[2,3-b]pyridin-2-yl)-7-methoxy-1-(oxetan-3-ylmethyl)-1H-benzo[d]imidazole-5-carboxylate (I-16k)

Prepared following a similar procedure to I-16a using I-1l and I-7. ES/MS: m/z 525.5, 527.3 [M+H]⁺.

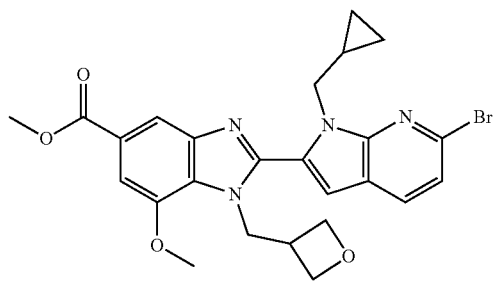

I-16k methyl 2-(6-(2-((tert-butyldimethylsilyl)oxy)propan-2-yl)-1-(cyclopropylmethyl)-1H-pyrrolo[2,3-b]pyridin-2-yl)-7-methoxy-1-methyl-1H-benzo[d]imidazole-5-carboxylate (I-16l)

Prepared following a similar procedure to I-16a using I-15 instead of I-6. ES/MS: m/z 563.4 [M+H]⁺.

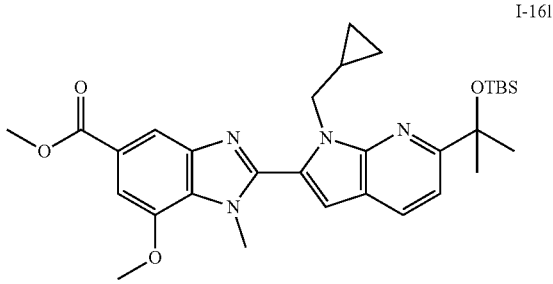 [SMILES: COC(=O)c1cc(OC)c2c(c1)nc(-c1cc3ccc(C(C)(C)O[Si](C)(C)C(C)(C)C)nc3n1CC1CC1)n2C]

I-16l methyl 2-(6-bromo-1-(cyclopropylmethyl)-1H-pyrrolo[2,3-b]pyridin-2-yl)-7-methoxy-1-methyl-1H-benzo[d]imidazole-5-carboxylate (I-16m)

Prepared following a similar procedure to I-16a using I-7 instead of I-6. ES/MS: m/z 469.3/471.3 [M+H]⁺. ¹H NMR (400 MHz, DMSO-d₆) δ 8.11 (d, J=8.0 Hz, 1H), 7.99 (d, J=0.8 Hz, 1H), 7.41-7.39 (m, 2H), 7.17 (s, 1H), 4.43 (d, J=6.8 Hz, 2H), 4.15 (s, 3H), 4.03 (s, 3H), 3.90 (s, 3H), 1.16-1.11 (m, 1H), 0.33-0.29 (m, 2H), 0.15-0.12 (m, 2H).

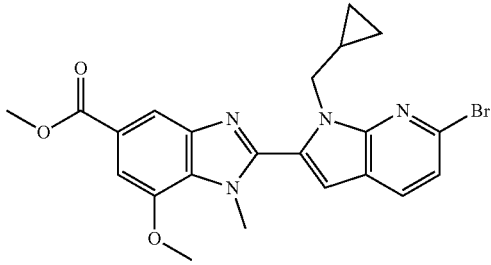

I-16m tert-butyl ((3R,6S)-1-(2-(6-bromo-1-(cyclopropylmethyl)-1H-pyrrolo[2,3-b]pyridin-2-yl)-7-methoxy-1-methyl-1H-benzo[d]imidazole-5-carbonyl)-6-methylpiperidin-3-yl)carbamate (I-16n)

Prepared in a manner similar to I-16a, using I-2a and I-7. ¹H NMR (400 MHz, DMSO-d6) δ 8.07 (d, J=8.2 Hz, 1H), 7.37 (d, J=8.2 Hz, 1H), 7.29 (s, 1H), 7.11 (s, 1H), 6.85 (s, 2H), 4.41 (d, J=7.1 Hz, 2H), 4.10 (s, 3H), 4.06-3.95 (m, 4H), 3.30 (s, 4H), 2.69 (d, J=18.8 Hz, 1H), 1.97 (s, 2H), 1.66 (s, 4H), 1.34 (s, 8H), 1.19-1.05 (m, 6H), 0.32-0.25 (m, 2H), 0.11 (d, J=4.5 Hz, 2H).

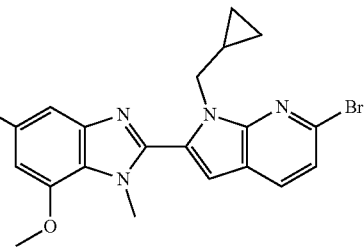

I-16n tert-butyl (R)-(1-(2-(1-(cyclopropylmethyl)-6-(methylsulfonyl)-1H-pyrrolo[2,3-b]pyridin-2-yl)-7-methoxy-1-methyl-1H-benzo[d]imidazole-5-carbonyl)piperidin-3-yl)carbamate (I-16o)

Prepared in a manner similar to I-16a, using I-2b and I-13. ES/MS: m/z 637.3 [M+H]⁺.

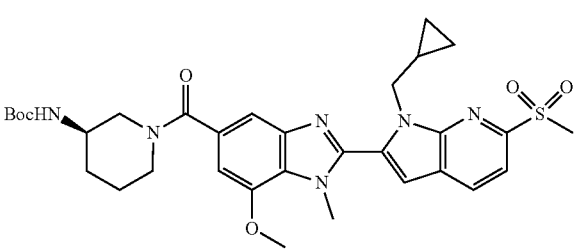

I-16o tert-butyl (R)-(1-(2-(1-(cyclopropylmethyl)-6-(isopropylsulfonyl)-1H-pyrrolo[2,3-b]pyridin-2-yl)-7-methoxy-1-methyl-1H-benzo[d]imidazole-5-carbonyl)piperidin-3-yl)carbamate (I-16p)

Prepared in a similar manner to I-16a, using I-2b and I-14. ES/MS: m/z 665.3 [M+H]⁺.

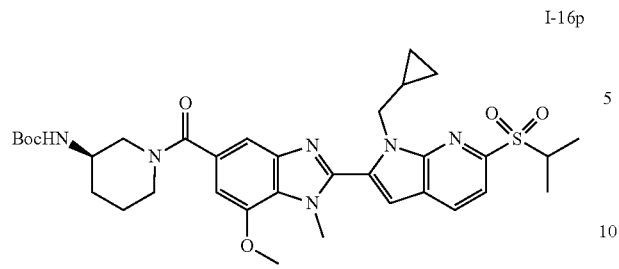

I-16p methyl (R)-2-(6-(1-((tert-butoxycarbonyl)amino)ethyl)-1H-pyrrolo[2,3-b]pyridin-2-yl)-6-fluoro-1-methyl-1H-benzo[d]imidazole-5-carboxylate (I-16q)

Prepared following a similar procedure to I-16a, using I-1c and I-12. $^1$H NMR (400 MHz, DMSO-d6) δ 12.39 (d, J=2.2 Hz, 1H), 8.18 (d, J=6.5 Hz, 1H), 8.07 (d, J=8.1 Hz, 1H), 7.78 (d, J=11.4 Hz, 1H), 7.37 (d, J=7.9 Hz, 1H), 7.20 (s, 1H), 7.19 (d, J=9.6 Hz, 1H), 4.86-4.69 (m, 1H), 4.08 (s, 3H), 3.89 (s, 3H), 1.41 (d, 3H), 1.39 (s, 9H).

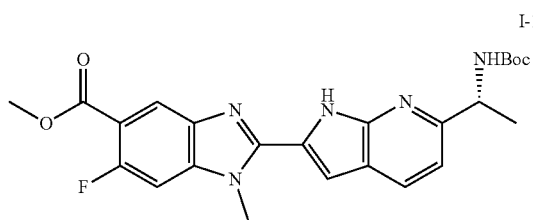

I-16q methyl (R)-2-(6-(1-((tert-butoxycarbonyl)amino)ethyl)-1H-pyrrolo[2,3-b]pyridin-2-yl)-7-methoxy-1-methyl-1H-benzo[d]imidazole-5-carboxylate (I-16r)

Prepared following a similar procedure to I-16a starting with I-12 instead of I-6. ES/MS: m/z 480.26 [M+H]$^+$.

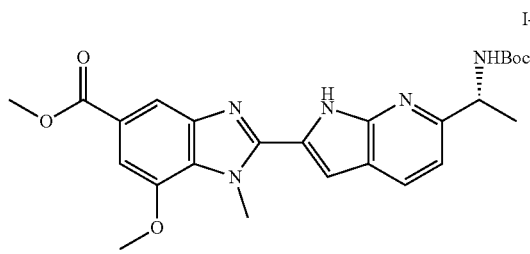

I-16r methyl 2-(6-bromo-1-(cyclopropylmethyl)-1H-indol-2-yl)-7-methoxy-1-methyl-1H-benzo[d]imidazole-5-carboxylate (I-16s)

Prepared following a similar procedure to I-16a starting with I-8 instead of I-6. ES/MS: m/z 468.2, 470.2 [M+H]$^+$.

I-16s tert-butyl (R)-(1-(2-(6-chloro-1-(cyclopropylmethyl)-1H-pyrrolo[2,3-b]pyridin-2-yl)-7-methoxy-1-methyl-1H-benzo[d]imidazole-5-carbonyl)piperidin-3-yl)carbamate (I-16t)

Prepared following a similar procedure to I-16a starting with I-2b and I-11. ES/MS: m/z 593.5 [M+H]$^+$.

I-16t methyl 2-(6-bromo-1H-pyrrolo[2,3-b]pyridin-2-yl)-3,4-dihydro-5-oxa-1,2a-diazaacenaphthylene-7-carboxylate (I-16u)

Prepared following a similar procedure to I-16a starting with methyl 5-nitro-3,4-dihydro-2H-benzo[b][1,4]oxazine-7-carboxylate. ES/MS: m/z 413.1 [M+H]$^+$.

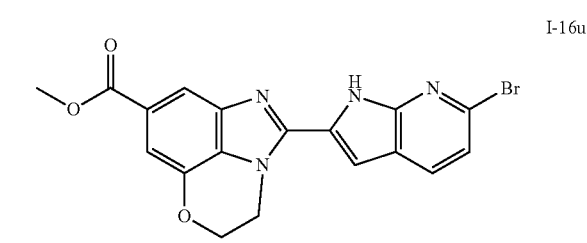 [SMILES: COC(=O)c1cc2c3c(c1)nc(-c1cc4ccc(Br)nc4[nH]1)n3CCO2]

I-16u methyl 2-(6-(2-((tert-butoxycarbonyl)amino)propan-2-yl)-1H-pyrrolo[2,3-b]pyridin-2-yl)-7-methoxy-1-methyl-1H-benzo[d]imidazole-5-carboxylate (I-16v)

Prepared following a similar procedure to I-16a starting with I-29 instead of I-6. ES/MS: m/z 494.2 [M+H]$^+$.

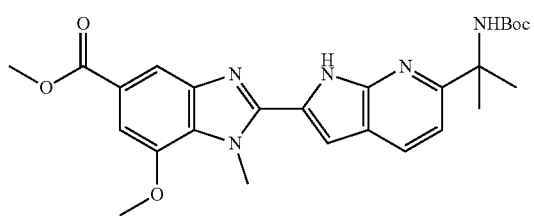

Preparation of methyl 2-(6-bromo-1H-pyrrolo[2,3-b]pyridin-2-yl)-1-cyclopropyl-7-methoxy-1H-benzo[d]imidazole-5-carboxylate (I-17a)

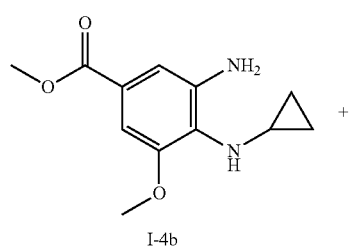

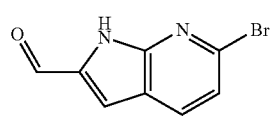

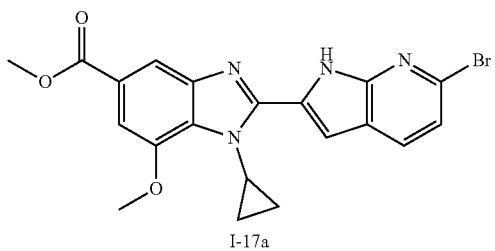

OXONE®, monopersulfate compound (711 mg, 2.31 mmol) was added to a mixture of methyl 3-amino-4-(cyclopropylamino)-5-methoxybenzoate (I-4b, 455 mg, 1.93 mmol) and 6-bromo-1H-pyrrolo[2,3-b]pyridine-2-carbaldehyde (I-6, 477 mg, 2.12 mmol) in DMF (6 mL) and water (2.5 mL). After 2 h, water was added to precipitate solids. The solids were collected by filtration, washed with water, and dried in vacuo to yield methyl 2-(6-bromo-1H-pyrrolo[2,3-b]pyridin-2-yl)-1-cyclopropyl-7-methoxy-1H-benzo[d]imidazole-5-carboxylate. ES/MS: m/z 441.1, 443.1 [M+H]⁺.

methyl 2-(6-bromo-1H-indol-2-yl)-1-cyclopropyl-7-methoxy-1H-benzo[d]imidazole-5-carboxylate (I-17b)

Prepared following a similar procedure to I-17a using 6-bromo-1H-indolecarbaldehyde (CAS 105191-12-6) instead of I-6. ES/MS: m/z 440.1, 442.1 [M+H]⁺.

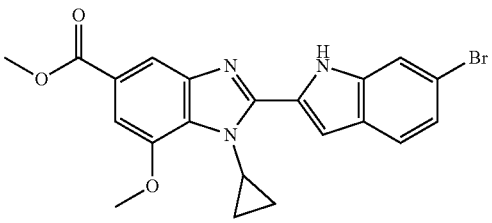

methyl 2-(6-bromo-1H-pyrrolo[2,3-b]pyridin-2-yl)-1-cyclopropyl-6-fluoro-1H-benzo[d]imidazole-5-carboxylate (I-17c)

Prepared following a similar procedure to I-17a using I-5b. ES/MS: m/z 429.2, 431.2 [M+H]⁺.

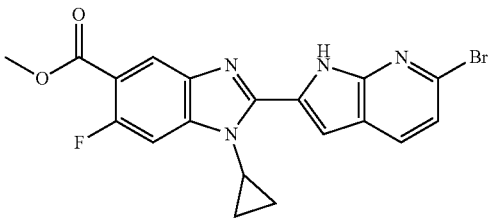

methyl 2-(6-bromo-1H-pyrrolo[2,3-b]pyridin-2-yl)-1-cyclopropyl-1H-benzo[d]imidazole-5-carboxylate (I-17d)

Prepared following a similar procedure to I-17a using I-5c instead of I-14b. ES/MS: m/z 411.2, 413.1 [M+H]⁺.

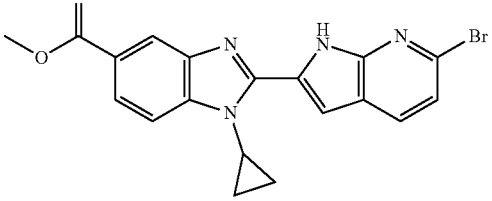

methyl 2-(6-chloro-1-(cyclopropylmethyl)-7-fluoro-1H-indol-2-yl)-7-methoxy-1-methyl-1H-benzo[d]imidazole-5-carboxylate (I-17e)

Prepared following a similar procedure to I-17a using I-4a and I-9b. ES/MS: m/z 442.2 [M+H]⁺.

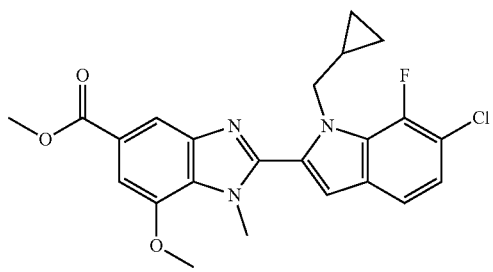

methyl 2-(6-chloro-1-(cyclopropylmethyl)-5-fluoro-1H-indol-2-yl)-7-methoxy-1-methyl-1H-benzo[d]imidazole-5-carboxylate (I-17f)

Prepared following a similar procedure to I-17a using I-4a and I-9a. ES/MS: m/z 442.2 [M+H]⁺.

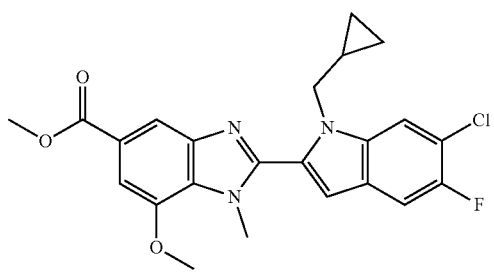

Preparation of methyl (R)-2-(6-(1-((tert-butoxycarbonyl)amino)ethyl)-1H-pyrrolo[2,3-b]pyridin-2-yl)-1-cyclopropyl-6,7-difluoro-1H-benzo[d]imidazole-5-carboxylate (I-18a)

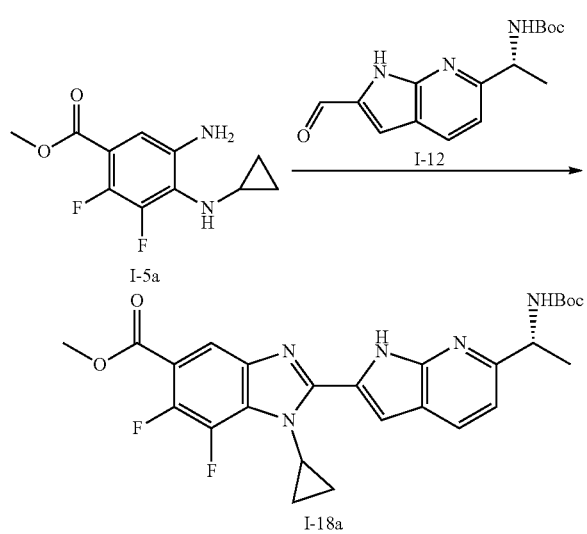

Methyl 5-amino-4-(cyclopropylamino)-2,3-difluorobenzoate (I-5a, 190 mg, 0.78 mmol) and tert-butyl (R)-(1-(2-formyl-1H-pyrrolo[2,3-b]pyridin-6-yl)ethyl)carbamate (I-12, 227 mg, 0.78 mmol) were charged in a vial equipped with a stir bar and acetic acid was added (5 mL). The resulting mixture was stirred at 50° C. for 12 h. The acetic acid was removed under vacuo and the residue was purified by flash chromatography over silica gel (10-100% EtOAc in DCM) to afford methyl (R)-2-(6-(1-((tert-butoxycarbonyl)amino)ethyl)-1H-pyrrolo[2,3-b]pyridin-2-yl)-1-cyclopropyl-6,7-difluoro-1H-benzo[d]imidazole-5-carboxylate. ES/MS: 511.9 (M+H)+. ¹H NMR (400 MHz, DMSO-d6) δ 12.41 (brs, 1H), 8.08 (d, J=8.2 Hz, 1H), 7.98-7.95 (m, 1H), 7.38 (d, J=7.9 Hz, 1H), 7.34 (d, J=2.1 Hz, 1H), 7.19 (d, J=8.2 Hz, 1H), 4.85-4.66 (m, 1H), 4.06-4.00 (m, 1H), 3.91 (s, 3H), 1.42 (s, 3H), 1.40 (s, 9H), 1.31-1.25 (m, 2H), 1.04-0.96 (m, 2H).

methyl (R)-2-(6-(1-((tert-butoxycarbonyl)amino)ethyl)-1H-pyrrolo[2,3-b]pyridin-2-yl)-1-cyclopropyl-6-fluoro-1H-benzo[d]imidazole-5-carboxylate (I-18b)

Prepared following a similar procedure to I-18a using I-5b instead of I-5a. ES/MS: m/z 461.9 [M+H]⁺.

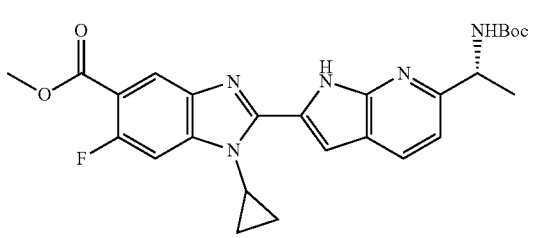

methyl (R)-2-(6-(1-((tert-butoxycarbonyl)amino)ethyl)-1H-pyrrolo[2,3-b]pyridin-2-yl)-7-fluoro-1-methyl-1H-benzo[d]imidazole-5-carboxylate (I-18c)

Prepared following a similar procedure to I-18a starting with I-5d instead of I-5a. ES/MS: m/z 468.0 [M+H]⁺.

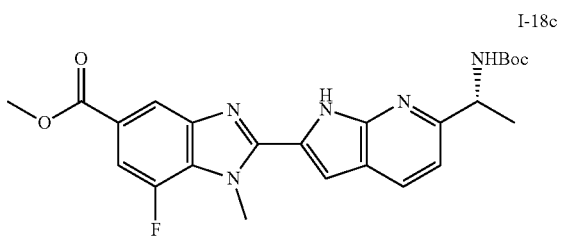 [SMILES: COC(=O)c1cc(F)c2c(c1)nc(-c1cc3ccc([C@@H](C)NC(=O)OC(C)(C)C)nc3[nH]1)n2C]

methyl (R)-2-(6-(1-((tert-butoxycarbonyl)amino)ethyl)-1H-pyrrolo[2,3-b]pyridin-2-yl)-1-cyclopropyl-7-fluoro-1H-benzo[d]imidazole-5-carboxylate (I-18d)

Prepared following a similar procedure to I-18a starting with I-5e instead of I-5a. ES/MS: m/z 493.9 [M+H]⁺.

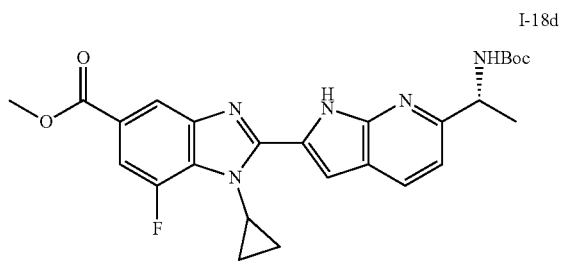 [SMILES: COC(=O)c1cc(F)c2c(c1)nc(-c1cc3ccc([C@@H](C)NC(=O)OC(C)(C)C)nc3[nH]1)n2C1CC1]

Preparation of methyl 2-(6-acetyl-1-((2-(trimethylsilyl)ethoxy)methyl)-1H-pyrrolo[2,3-b]pyridin-2-yl)-7-methoxy-1-methyl-1H-benzo[d]imidazole-5-carboxylate (I-19a)

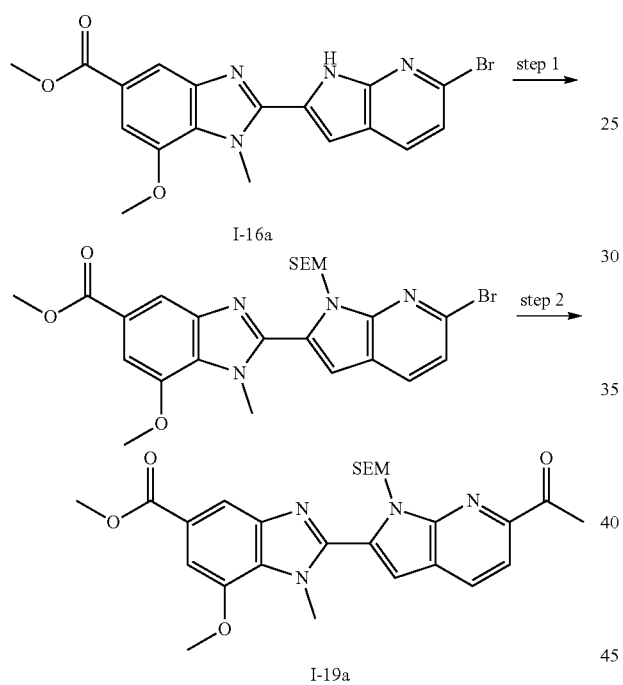

Step 1. A suspension of methyl 2-(6-bromo-1H-pyrrolo[2,3-b]pyridin-2-yl)-7-methoxy-1-methyl-1H-benzo[d]imidazole-5-carboxylate (I-16a, 10.68 g, 25.7 mmol) in DMF (260 mL) was cooled to −15° C. (sodium chloride ice bath) and a solution of NaHMDS (2 M in THF, 14.1 mL, 28.3 mmol) was added dropwise over 10 minutes. The resulting mixture was stirred 1 hour at −15° C. and then 4 hours at 0° C. before 2-(chloromethoxy) ethyl-trimethyl-silane (5.14 g, 30.8 mmol) was added. The resulting mixture was stirred at 0° C. until full conversion. The mixture was then carefully quenched with saturated aqueous ammonium chloride and after usual work up (EtOAc/water) the residual oil was purified by silica gel column chromatography (0-40% EtOAc in hexanes) to afford methyl 2-(6-bromo-1-((2-(trimethylsilyl)ethoxy)methyl)-1H-pyrrolo[2,3-b]pyridin-2-yl)-7-methoxy-1-methyl-1H-benzo[d]imidazole-5-carboxylate. ES/MS: m/z 544.8, 546.8 [M+H]⁺.

Step 2. Methyl 2-(6-bromo-1-((2-(trimethylsilyl)ethoxy)methyl)-1H-pyrrolo[2,3-b]pyridin-2-yl)-7-methoxy-1-methyl-1H-benzo[d]imidazole-5-carboxylate (6.92 g, 12.7 mmol) and PdCl₂(dppf).CH₂Cl₂ (600 mg, 0.735 mmol, 6 mol %) were taken up in dioxane (150 mL), and the headspace was flushed with N₂. 1-Ethoxyvinyltributyltin (7.5 mL, 22.2 mmol, 1.75 equiv.) was added, and the resulting mixture was stirred at 100° C. for 6 h. Upon cooling, the mixture was filtered with EtOAc through Celite and the filtrate was concentrated. The resulting residue was dissolved in DCM and was filtered through a plug of silica gel, eluting with 1:1 DCM/EtOAc. The filtrate was concentrated and was dissolved in THF (200 mL) and water (50 mL). Hydrochloric acid (3 M, 4.2 mL, 12.6 mmol) was added, and the resulting solution was stirred 20 min. Solid NaHCO₃ (2.5 g, 30 mmol) was added, and the mixture was diluted further with brine and DCM (50 mL). The organic phase was washed with brine, dried over Na₂SO₄, filtered, and concentrated. The resulting crude solid was slurried in 10 mL EtOAc and 100 mL hexanes. The product was collected via filtration, and the filter cake was washed with additional 15% EtOAc in hexanes (30 mL) and 100% hexanes to afford methyl 2-(6-acetyl-1-((2-(trimethylsilyl)ethoxy)methyl)-1H-pyrrolo[2,3-b]pyridin-2-yl)-7-methoxy-1-methyl-1H-benzo[d]imidazole-5-carboxylate. ES/MS: m/z 509.3 [M+H]⁺.

methyl 2-(6-acetyl-1-((2-(trimethylsilyl)ethoxy)methyl)-1H-pyrrolo[2,3-b]pyridin-2-yl)-1-cyclopropyl-1H-benzo[d]imidazole-5-carboxylate (I-19b)

Prepared analogously to I-19a, using I-17d. ES/MS: m/z 505.0 [M+H]⁺.

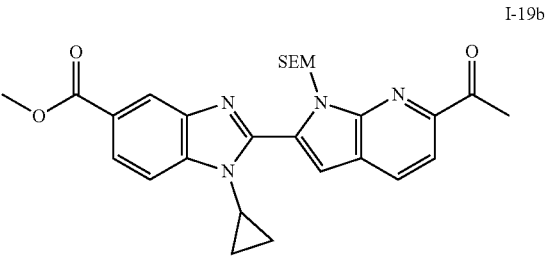 [SMILES: COC(=O)c1ccc2c(c1)nc(-c1cc3ccc(C(C)=O)nc3n1COCC[Si](C)(C)C)n2C1CC1]

Preparation of methyl 2-(6-acetyl-1-(tert-butoxycarbonyl)-1H-indol-2-yl)-1-cyclopropyl-7-methoxy-1H-benzo[d]imidazole-5-carboxylate (I-20a)

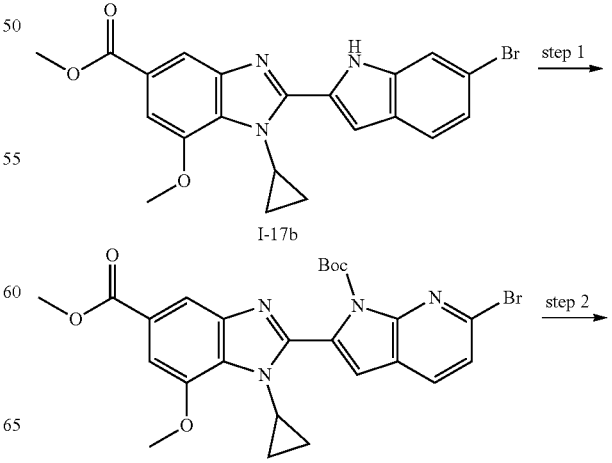

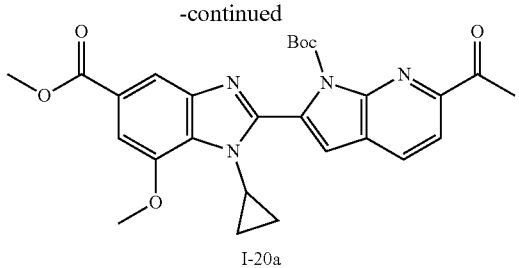

I-20a

Step 1. To a mixture of methyl 2-(6-bromo-1H-indol-2-yl)-1-cyclopropyl-7-methoxy-1H-benzo[d]imidazole-5-carboxylate (I-17b, 3.60 g, 8.18 mmol) and TEA (2.3 mL, 16.4 mmol) in DCM (200 mL) was added Boc₂O (1.96 g, 8.99 mmol) followed by DMAP (0.499 g, 4.09 mmol). The mixture was stirred at rt for 1 h. The solvent was evaporated and the crude residue was purified via flash column chromatography on silica gel to afford methyl 2-(6-bromo-1-(tert-butoxycarbonyl)-1H-indol-2-yl)-1-cyclopropyl-7-methoxy-1H-benzo[d]imidazole-5-carboxylate. ES/MS: m/z 540.75 [M+H]$^+$.

Step 2. The procedure described for Step 2 in the preparation of I-19a was followed, yielding methyl 2-(6-acetyl-1-(tert-butoxycarbonyl)-1H-indol-2-yl)-1-cyclopropyl-7-methoxy-1H-benzo[d]imidazole-5-carboxylate. ES/MS: m/z 504.96 [M+H]$^+$.

methyl 2-(6-acetyl-1-(tert-butoxycarbonyl)-1H-indol-2-yl)-7-methoxy-1-methyl-1H-benzo[d]imidazole-5-carboxylate (I-20b)

Prepared in a manner similar to I-20a, using I-16b. ES/MS: m/z 478.0 [M+H]$^+$.

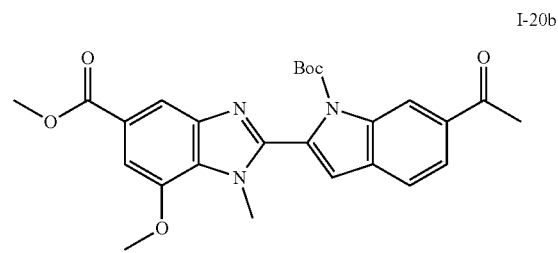 [SMILES: COC(=O)c1cc(OC)c2c(c1)nc(-c1cc3ccc(C(C)=O)cc3n1C(=O)OC(C)(C)C)n2C]

I-20b

Preparation of methyl 2-(6-acetyl-1-(cyclopropylmethyl)-5-fluoro-1H-indol-2-yl)-7-methoxy-1-methyl-1H-benzo[d]imidazole-5-carboxylate (I-21a)

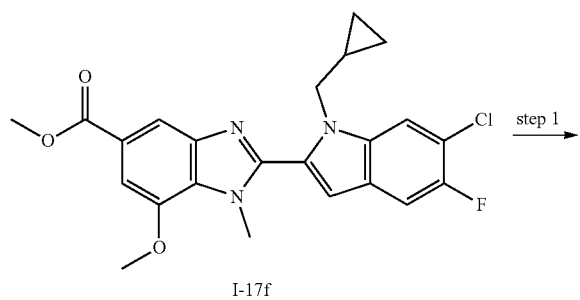

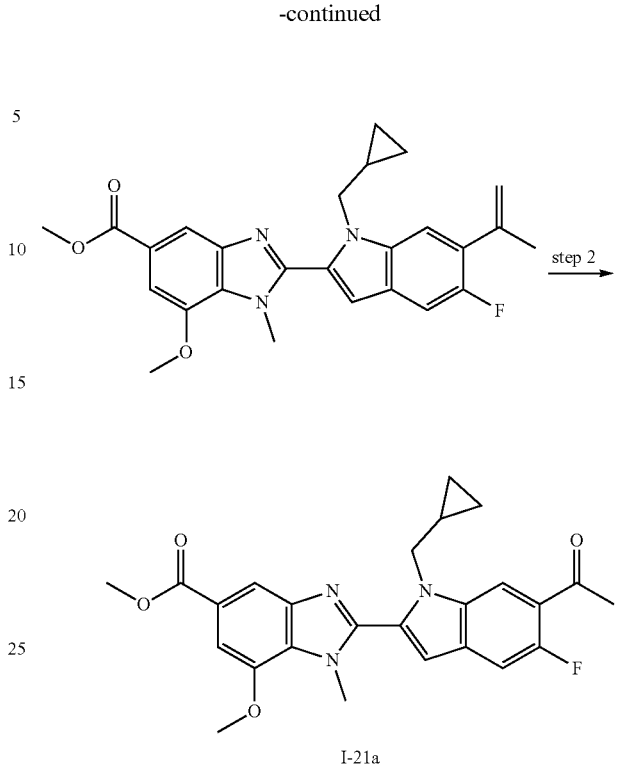

I-21a

Step 1. A mixture of methyl 2-(6-chloro-1-(cyclopropylmethyl)-5-fluoro-1H-indol-2-yl)-7-methoxy-1-methyl-1H-benzo[d]imidazole-5-carboxylate (I-17f, 1.58 g, 3.58 mmol), 2-isopropenyl-4,4,5,5-tetramethyl-1,3,2-dioxaborolane (1.80 g, 10.7 mmol), and potassium phosphate tribasic (2.28 g, 10.7 mmol) in DMF (14.5 mL) and water (2.5 mL) was sparged with N₂ for several minutes. SPhos Pd G4 precatalyst (0.284 g, 0.358 mmol) was added and the mixture was stirred at 100° C. Reaction progress was monitored via LC-MS. The mixture was cooled to rt and diluted with water and EtOAc. The aqueous layer was extracted with EtOAc and the combined organic layers were washed with brine, dried (Na₂SO₄), filtered, and concentrated. The residue was purified via flash column chromatography on silica gel to yield methyl 2-(1-(cyclopropylmethyl)-5-fluoro-6-(prop-1-en-2-yl)-1H-indol-2-yl)-7-methoxy-1-methyl-1H-benzo[d]imidazole-5-carboxylate. ES/MS: m/z 448.3 [M+H]$^+$.

Step 2. To a solution of methyl 2-(1-(cyclopropylmethyl)-5-fluoro-6-(prop-1-en-2-yl)-1H-indol-2-yl)-7-methoxy-1-methyl-1H-benzo[d]imidazole-5-carboxylate (1.50 g, 3.35 mmol) in THF (13 mL) and water (7 mL) was added potassium osmate (0.037 g, 0.101 mmol) and sodium periodate (2.15 g, 10.1 mmol). The mixture was stirred at rt and reaction progress was monitored via LC-MS. The reaction mixture was diluted with sodium thiosulfate soln (aq) and stirred for 3 h. The aqueous layer was extracted with EtOAc. The organic layer was washed successively with water and brine, dried (Na₂SO₄), filtered, and concentrated. The resulting residue was purified via flash column chromatography on silica gel to afford methyl 2-(6-acetyl-1-(cyclopropylmethyl)-5-fluoro-1H-indol-2-yl)-7-methoxy-1-methyl-1H-benzo[d]imidazole-5-carboxylate. ES/MS: m/z 450.3 [M+H]$^+$.

methyl 2-(6-acetyl-1-(cyclopropylmethyl)-7-fluoro-1H-indol-2-yl)-7-methoxy-1-methyl-1H-benzo[d]imidazole-5-carboxylate (I-21b)

Prepared in a similar manner to I-21a using I-17e. ES/MS: m/z 450.2 [M+H]+.

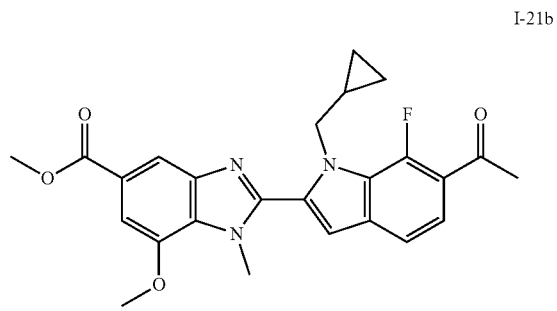 [SMILES: COC(=O)c1cc(OC)c2c(c1)nc(-c1cc3ccc(C(C)=O)c(F)c3n1CC1CC1)n2C]

I-21b

Preparation of methyl 2-(6-acetyl-1-((2-(trimethylsilyl)ethoxy)methyl)-1H-pyrrolo[2,3-b]pyridin-2-yl)-1-cyclopropyl-7-methoxy-1H-benzo[d]imidazole-5-carboxylate (I-22)

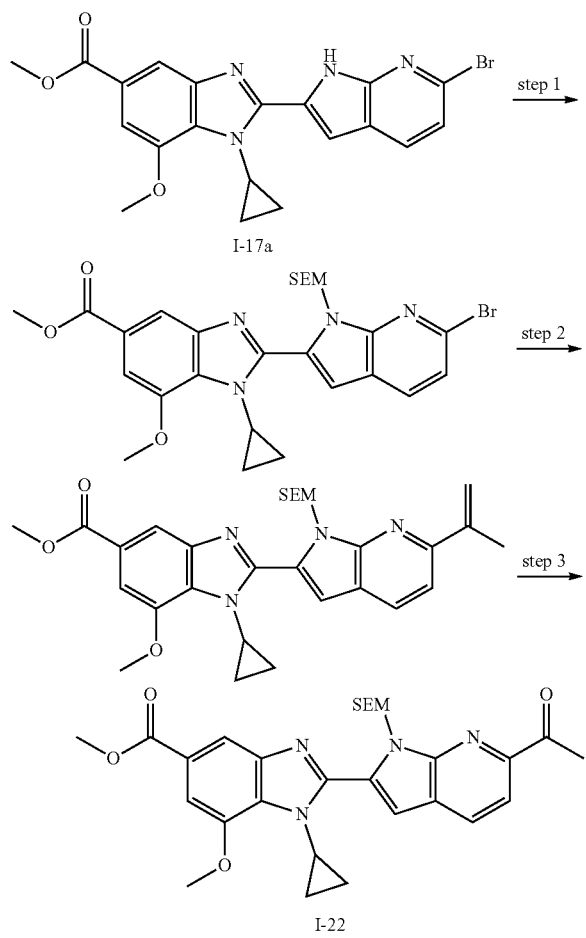

Step 1. To a solution of methyl 2-(6-bromo-1H-pyrrolo[2,3-b]pyridin-2-yl)-1-cyclopropyl-7-methoxy-1H-benzo[d]imidazole-5-carboxylate (I-17a, 1.30 g, 2.95 mmol) in DMF (20 mL) at 0° C. was added NaH (0.137 g of a 60 wt % dispersion in mineral oil, 3.43 mmol). After 20 min, SEMCl (0.58 mL, 3.28 mmol) was added and the mixture was stirred at rt for 5 h. The mixture was diluted with water and EtOAc. The aqueous layer was extracted with EtOAc. The combined organic layers were washed with brine, dried (MgSO4), filtered, and concentrated to afford methyl 2-(6-bromo-1-((2-(trimethylsilyl)ethoxy)methyl)-1H-pyrrolo[2,3-b]pyridin-2-yl)-1-cyclopropyl-7-methoxy-1H-benzo[d]imidazole-5-carboxylate, which was used directly without purification. ES/MS: m/z 573.1 [M+H]+.

Step 2. A mixture of methyl 2-(6-bromo-1-((2-(trimethylsilyl)ethoxy)methyl)-1H-pyrrolo[2,3-b]pyridin-2-yl)-1-cyclopropyl-7-methoxy-1H-benzo[d]imidazole-5-carboxylate (1.71 g, 2.98 mmol), potassium isopropenyltrifluoroborate (1.33 g, 9.00 mmol), PdCl2(dppf).CH2Cl2 (0.244 g, 0.298 mmol) and TEA (2.1 mL, 15.1 mmol) in EtOH (30 mL) was sparged with Argon for 5 min. The mixture was then refluxed for 3 h. The mixture was cooled to rt and filtered through a pad of Celite. The filtrate was concentrated to afford crude methyl 1-cyclopropyl-7-methoxy-2-(6-(prop-1-en-2-yl)-1-((2-(trimethylsilyl)ethoxy)methyl)-1H-pyrrolo[2,3-b]pyridin-2-yl)-1H-benzo[d]imidazole-5-carboxylate, which was used directly without purification. ES/MS: m/z 532.9 [M+H]+.

Step 3. The procedure described for Step 2 in the preparation of I-21a was followed to give methyl 2-(6-acetyl-1-((2-(trimethylsilyl)ethoxy)methyl)-1H-pyrrolo[2,3-b]pyridin-2-yl)-1-cyclopropyl-7-methoxy-1H-benzo[d]imidazole-5-carboxylate. ES/MS: m/z 534.9 [M+H]+.

Preparation of isopropyl (R)-2-(6-(1-((tert-butoxycarbonyl)amino)ethyl)-1H-pyrrolo[2,3-b]pyridin-2-yl)-7-methoxy-1-methyl-1H-benzo[d]imidazole-5-carboxylate (I-23a)

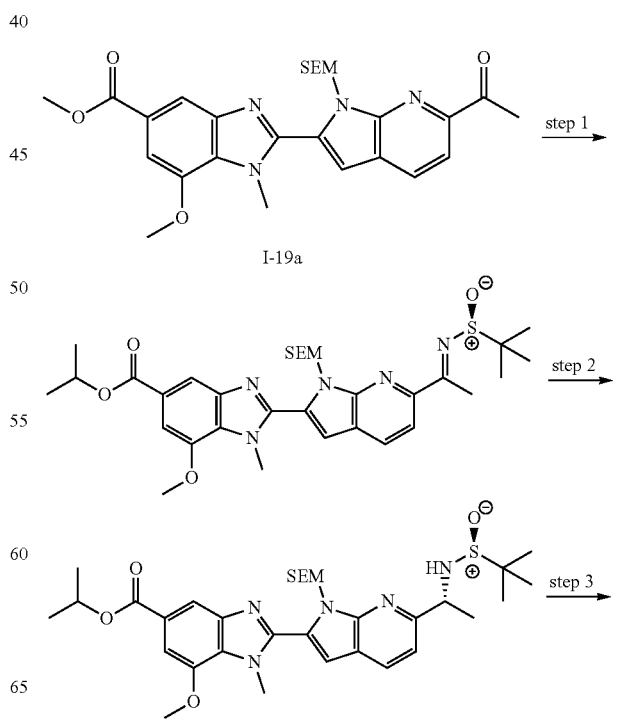

-continued

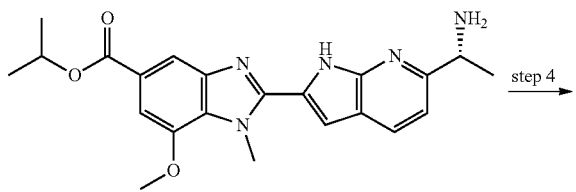

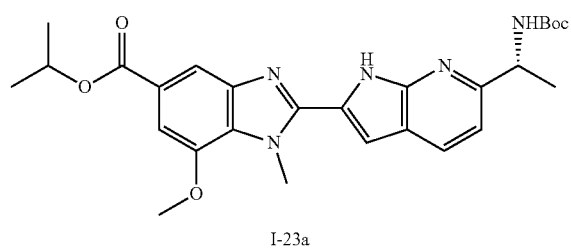

I-23a

Step 1. Methyl 2-(6-acetyl-1-((2-(trimethylsilyl)ethoxy)methyl)-1H-pyrrolo[2,3-b]pyridin-2-yl)-7-methoxy-1-methyl-1H-benzo[d]imidazole-5-carboxylate (I-19a, 5.58 g, 11.0 mmol) and (S)-2-methylpropane-2-sulfinamide (5.3 g, 44 mmol. 4 equiv.) were taken up in THF (100 mL) under nitrogen. Titanium(IV) isopropoxide (26 mL, 88 mmol, 8 equiv.) was added, and the resulting stirred mixture was heated at 60° C. After 16 h, brine (7 mL) and EtOAc (200 mL) were added and the reaction mixture was stirred vigorously. The organic phase was decanted off, and EtOAc (150 mL) was added with stirring followed by some DCM to cut the emulsion. The organic layer was decanted, and this process was repeated once more. The aqueous phase was diluted with EtOAc (150 mL), and Celite (40 g) was added. The mixture was filtered through Celite. The combined organic phase was dried over $Na_2SO_4$, filtered, and concentrated. Purification by silica gel (15-80% EtOAc in hexanes) provided isopropyl (S,E)-2-(6-(1-((tert-butylsulfinyl)imino)ethyl)-1-((2-(trimethylsilyl)ethoxy)methyl)-1H-pyrrolo[2,3-b]pyridin-2-yl)-7-methoxy-1 methyl-1H-benzo[d]imidazole-5-carboxylate. ES/MS: m/z 640.3 $[M+H]^+$.

Step 2. Isopropyl (S,E)-2-(6-(1-((tert-butylsulfinyl)imino)ethyl)-1-((2-(trimethylsilyl)ethoxy)methyl)-1H-pyrrolo[2,3-b]pyridin-2-yl)-7-methoxy-1 methyl-1H-benzo[d]imidazole-5-carboxylate (5.7 g, 4.2 mmol) was dissolved in THF (120 mL) under nitrogen. The resulting mixture was cooled to −78° C. 1 M L-Selectride in THF (5.1 mL, 5.1 mmol, 1.2 equiv.) was then added dropwise over 5 min, and the resulting mixture was stirred for 6 h at −78° C. The reaction was removed from the cold bath and placed in an ice bath once the internal temperature was −5° C. The reaction was stirred an additional 20 min, whereupon LCMS indicated complete conversion. The reaction was quenched with sat. aq. $NH_4Cl$ and diluted with EtOAc and water. The phases were separated, and the organic phase was dried over $MgSO_4$, filtered, and concentrated. The obtained residue was purified by silica gel chromatography (10-60% acetone in hexanes) to afford product isopropyl 2-(6-((R)-1-(((S)-tert-butylsulfinyl)amino)ethyl)-1-((2-(trimethylsilyl)ethoxy)methyl)-1H-pyrrolo[2,3-b]pyridin-2-yl)-7-methoxy-1-methyl-1H-benzo[d]imidazole-5-carboxylate. ES/MS: m/z 642.4 $[M+H]^+$.

Step 3. Isopropyl (S,E)-2-(6-(1-((tert-butylsulfinyl)imino)ethyl)-1-((2-(trimethylsilyl)ethoxy)methyl)-1H-pyrrolo[2,3-b]pyridin-2-yl)-7-methoxy-1 methyl-1H-benzo[d]imidazole-5-carboxylate (3.48 g, 3.86 mmol) was dissolved in MeCN (50 mL). 4M HCl in dioxane (24 mL, 97 mmol) was added, resulting in an immediate precipitation of solids that re-dissolved on further addition of HCl. The resulting solution was heated to 45° C. and stirred for 6 h, over which time solids precipitated out. The reaction mixture was then concentrated in vacuo, suspended in DCM (20 mL), and diluted with diethyl ether (60 mL). Filtration followed by washing with diethyl ether provided isopropyl (R)-2-(6-(1-aminoethyl)-1H-pyrrolo[2,3-b]pyridin-2-yl)-7-methoxy-1-methyl-1H-benzo[d]imidazole-5-carboxylate (putative bis-HCl salt) that was used without further purification. ES/MS: m/z 408.3 $[M+H]^+$. *This procedure was also followed in the case where Boc was used instead of SEM as protecting group (for the synthesis of I-23d and I-23e, where I-20a and I-20b were used, respectively, in place of I-19a).

Step 4. Isopropyl (R)-2-(6-(1-aminoethyl)-1H-pyrrolo[2,3-b]pyridin-2-yl)-7-methoxy-1-methyl-1H-benzo[d]imidazole-5-carboxylate (HCl salt) from above was taken up in DCM (50 mL, suspension), and trimethylamine (5.4 mL, 38 mmol, 10 equiv.) was added. The resulting mixture was cooled in an ice water bath, and $Boc_2O$ (842 mg, 3.85 mmol) was added as a solution in DCM (5 mL). The resulting mixture was removed from the cold bath and stirred an additional 10 min. The mixture was diluted with DCM and washed with a mixture of 5% aq. $Na_2CO_3$ and water. DCM was used to extract, and the combined organic phase was dried ($Na_2SO_4$), filtered, and concentrated. The resulting residue was slurried in 20 mL EtOAc, and 60 mL hexane was added in portions. After stirring an additional 30 min, the mixture was filtered to collect solids. The solids were washed with additional 20% EtOAC in hexanes (20 mL) followed by hexanes. Drying afforded isopropyl (R)-2-(6-(1-((tert-butoxycarbonyl)amino)ethyl)-1H-pyrrolo[2,3-b]pyridin-2-yl)-7-methoxy-1-methyl-1H-benzo[d]imidazole-5-carboxylate. ES/MS: m/z 508.3 $[M+H]^+$. $^1$H NMR (400 MHz, DMSO-d6) δ 12.33 (d, J=2.1 Hz, 1H), 8.06 (d, J=8.2 Hz, 1H), 7.93 (d, J=1.3 Hz, 1H), 7.38 (d, J=8.1 Hz, 1H), 7.36 (d, J=1.3 Hz, 1H), 7.19 (d, J=8.2 Hz, 1H), 7.13 (d, J=2.0 Hz, 1H), 5.16 (hept, J=6.3 Hz, 1H), 4.77 (p, J=7.2 Hz, 1H), 4.29 (s, 3H), 4.03 (s, 3H), 1.43-1.34 (m, 18H).

isopropyl (R)-2-(6-(1-((tert-butoxycarbonyl)amino)ethyl)-1H-pyrrolo[2,3-b]pyridin-2-yl)-1-cyclopropyl-7-methoxy-1H-benzo[d]imidazole-5-carboxylate (I-23b)

Prepared following a similar procedure to I-23a starting with I-22. ES/MS: m/z 534.1 $[M+H]^+$.

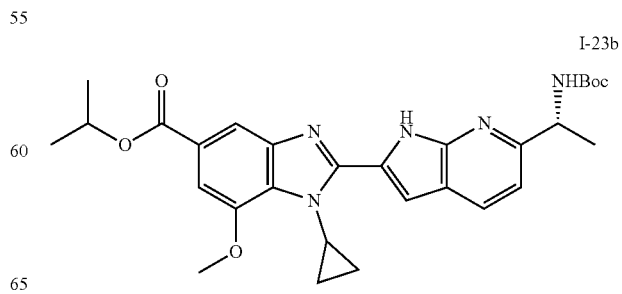

I-23b isopropyl (R)-2-(6-(1-((tert-butoxycarbonyl)amino) ethyl)-1H-pyrrolo[2,3-b]pyridin-2-yl)-1-cyclopropyl-1H-benzo[d]imidazole-5-carboxylate (I-23c)

Prepared following a similar procedure to I-23a starting with I-19b. ES/MS: m/z 504.1 [M+H]$^+$.

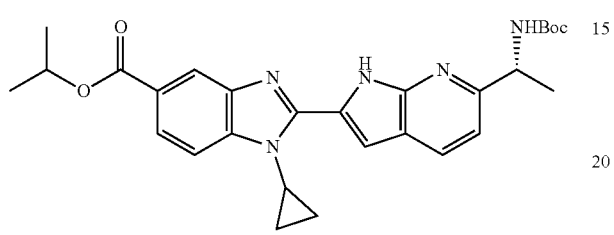

isopropyl (R)-2-(6-(1-((tert-butoxycarbonyl)amino) ethyl)-1H-indol-2-yl)-1-cyclopropyl-7-methoxy-1H-benzo[d]imidazole-5-carboxylate (I-23d)

Prepared following a similar procedure to I-23a starting with I-20a. ES/MS: m/z 533.3 [M+H]$^+$. $^1$H NMR (400 MHz, DMSO-d6) δ 11.86 (brs, 1H), 7.86 (d, J=1.3 Hz, 1H), 7.59 (d, J=8.2 Hz, 1H), 7.46 (d, J=8.2 Hz, 1H), 7.41 (s, 1H), 7.37 (d, J=1.4 Hz, 1H), 7.31-7.28 (m, 1H), 7.05 (dd, J=8.3, 1.5 Hz, 1H), 5.20-5.12 (m, 1H), 4.76-4.63 (m, 1H), 4.02 (s, 3H), 3.95-3.84 (m, 1H), 1.39 (s, 9H), 1.37 (d, J=6.3 Hz, 6H), 1.32-1.23 (m, 2H), 1.25 (brs, 3H), 0.91-0.85 (m, 2H).

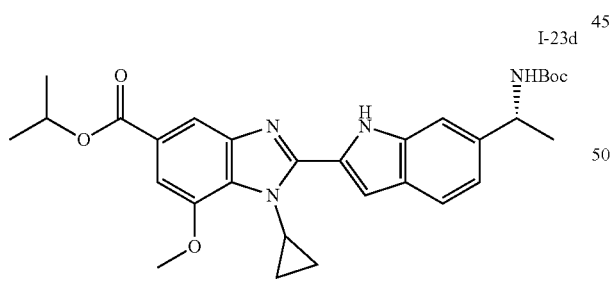

isopropyl (R)-2-(6-(1-((tert-butoxycarbonyl)amino) ethyl)-1H-indol-2-yl)-7-methoxy-1-methyl-1H-benzo[d]imidazole-5-carboxylate (I-23e)

Prepared following a similar procedure to I-23a starting with I-20b. ES/MS: m/z 507.3 [M+H]$^+$. $^1$H NMR (400 MHz, DMSO-d6) δ 11.92 (d, J=2.2 Hz, 1H), 7.91 (d, J=1.3 Hz, 1H), 7.59 (d, J=8.3 Hz, 1H), 7.46 (d, J=8.3 Hz, 1H), 7.42 (s, 1H), 7.34 (d, J=1.3 Hz, 1H), 7.15 (d, J=2.1 Hz, 1H), 7.06 (d, J=8.3, 1H), 5.22-5.16 (m, 1H), 4.77-4.64 (m, 1H), 4.32 (s, 3H), 4.02 (s, 3H), 1.38 (brs, 9H), 1.37 (s, 6H), 1.36 (s, 3H).

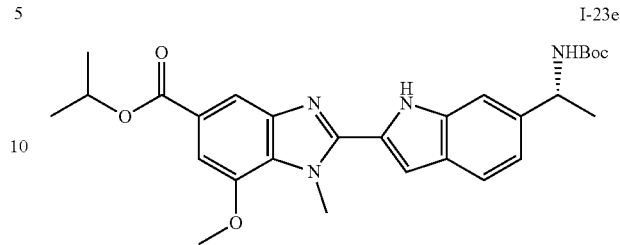

Preparation of isopropyl (R)-2-(6-(1-aminoethyl)-1-(cyclopropylmethyl)-5-fluoro-1H-indol-2-yl)-7-methoxy-1-methyl-1H-benzo[d]imidazole-5-carboxylate (I-24a)

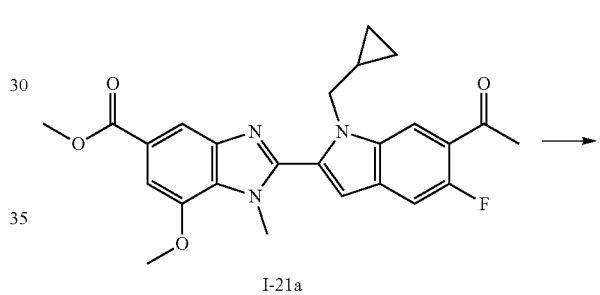

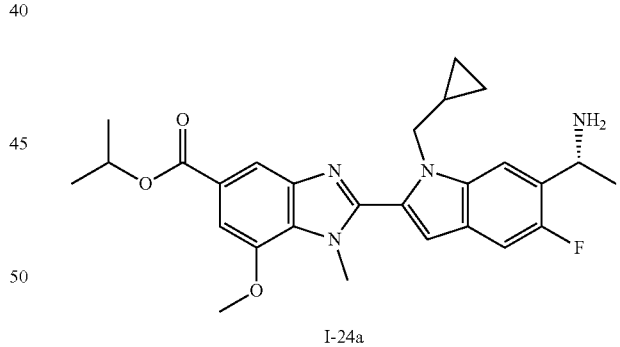

isopropyl (R)-2-(6-(1-aminoethyl)-1-(cyclopropylmethyl)-5-fluoro-1H-indol-2-yl)-7-methoxy-1-methyl-1H-benzo[d]imidazole-5-carboxylate was prepared according to the methods described in steps 1-3 for I-23a, using I-21a. ES/MS: m/z 479.38 [M+H]$^+$.

isopropyl (R)-2-(6-(1-aminoethyl)-1-(cyclopropylmethyl)-7-fluoro-1H-indol-2-yl)-7-methoxy-1-methyl-1H-benzo[d]imidazole-5-carboxylate (I-24b)

Prepared in a similar manner to I-24a using I-21b. ES/MS: m/z 479.34 [M+H]$^+$.

Preparation of isopropyl (R)-2-(6-(1-aminoethyl)-1-(cyclopropylmethyl)-1H-pyrrolo[2,3-b]pyridin-2-yl)-7-methoxy-1-methyl-1H-benzo[d]imidazole-5-carboxylate (I-25a)

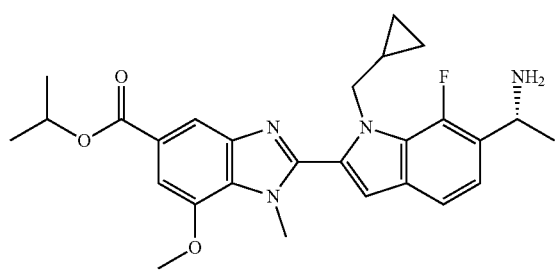

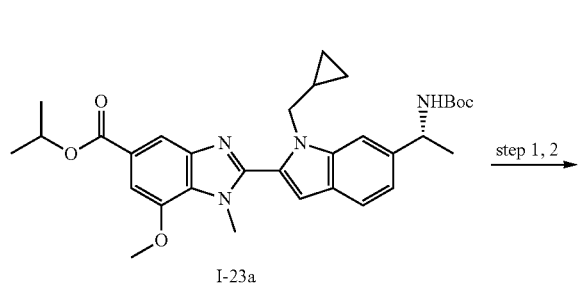

Step 1. To a solution of isopropyl 2-[6-[(1R)-1-(tert-butoxycarbonylamino)ethyl]-1H-pyrrolo[2,3-b]pyridin-2-yl]-7-methoxy-1-methyl-benzimidazole-5-carboxylate (I-23a, 1.0 g, 2.0 mmol) in DMF (15 mL) was added bromomethylcyclopropane (0.35 mL, 3.9 mmol) followed by $Cs_2CO_3$ (1.93 g, 5.91 mmol). The mixture was stirred at 50° C. overnight (ca. 18 h) and was partitioned between EtOAc, water, and brine. The phases were separated, and the organic phase was washed with water and brine, dried over Na2SO4, filtered, and concentrated. Purification by silica gel chromatography (20-80% EtOAc in hexanes) provided isopropyl 2-[6-[(1R)-1-(tert-butoxycarbonylamino)ethyl]-1-(cyclopropylmethyl)pyrrolo[2,3-b]pyridin-2-yl]-7-methoxy-1-methyl-benzimidazole-5-carboxylate. ES/MS: m/z 562.12 [M+H]$^+$.

Step 2. To a solution of isopropyl 2-[6-[(1R)-1-(tert-butoxycarbonylamino)ethyl]-1-(cyclopropylmethyl)pyrrolo[2,3-b]pyridin-2-yl]-7-methoxy-1-methyl-benzimidazole-5-carboxylate (910 mg, 1.6 mmol) in DCM (40 mL) was added TFA (20 mL). The reaction mixture was stirred for 1 h and was concentrated to afford crude isopropyl 2-[6-[(1R)-1-aminoethyl]-1-(cyclopropylmethyl)pyrrolo[2,3-b]pyridin-2-yl]-7-methoxy-1-methyl-benzimidazole-5-carboxylate as a TFA salt that was used without further purification. ES/MS: m/z 461.98 [M+H]$^+$.

methyl 2-(6-(2-aminopropan-2-yl)-1-(cyclopropylmethyl)-1H-pyrrolo[2,3-b]pyridin-2-yl)-7-methoxy-1-methyl-1H-benzo[d]imidazole-5-carboxylate (I-25b)

Prepared in a similar manner to I-25a, using I-16v instead of I-23a. ES/MS: m/z 448.3 [M+H]$^+$.

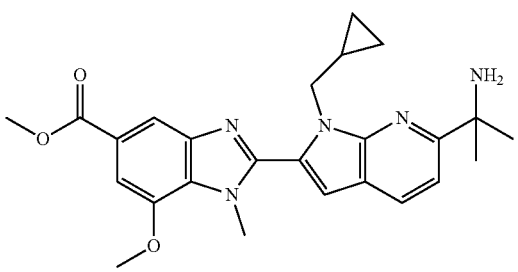

methyl (R)-2-(6-(1-aminoethyl)-1-(2-hydroxy-2-methylpropyl)-1H-pyrrolo[2,3-b]pyridin-2-yl)-7-methoxy-1-methyl-1H-benzo[d]imidazole-5-carboxylate (I-25c)

Prepared in a similar manner to I-25a, using I-16r instead of I-23a, and 2,2-dimethyloxirane instead of bromomethylcyclopropane. ES/MS: m/z 452.1 [M+H]$^+$.

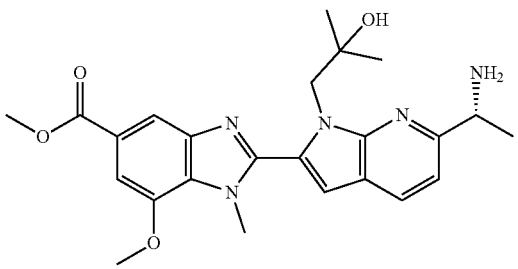

isopropyl (R)-2-(6-(1-aminoethyl)-1-((1-fluorocyclopropyl)methyl)-1H-pyrrolo[2,3-b]pyridin-2-yl)-7-methoxy-1-methyl-1H-benzo[d]imidazole-5-carboxylate (I-25d)

Prepared in a similar manner to I-25a, using 1-(bromomethyl)-1-fluorocyclopropane instead of bromomethylcyclopropane. ES/MS: m/z 480.0 [M+H]$^+$.

I-25d

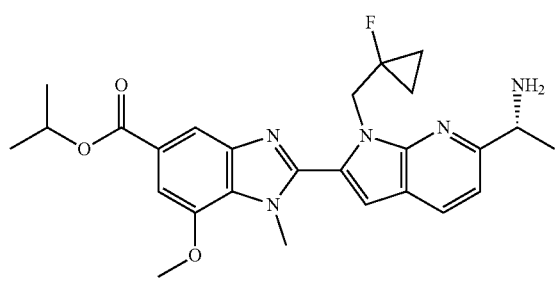

methyl (R)-2-(6-(1-aminoethyl)-1-(cyclopropylmethyl)-1H-pyrrolo[2,3-b]pyridin-2-yl)-1-cyclopropyl-7-fluoro-1H-benzo[d]imidazole-5-carboxylate (I-25e)

Prepared in a similar manner to I-25a, using I-18d instead of I-23a. ES/MS: m/z 447.9 [M+H]$^+$.

I-25e

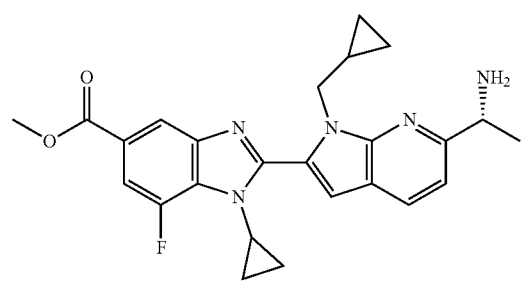

Preparation of ethyl (R)-2-(6-(1-aminoethyl)-1-(cyclopropylmethyl)-1H-pyrrolo[2,3-b]pyridin-2-yl)-7-methoxy-1-methyl-1H-benzo[d]imidazole-5-carboxylate (I-26)

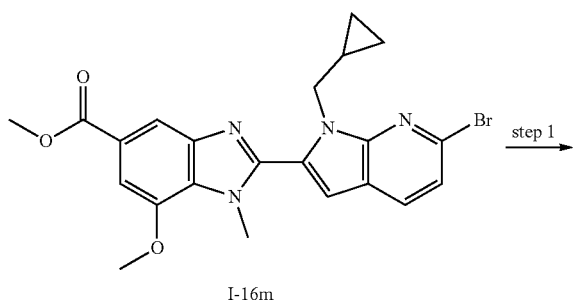

I-16m

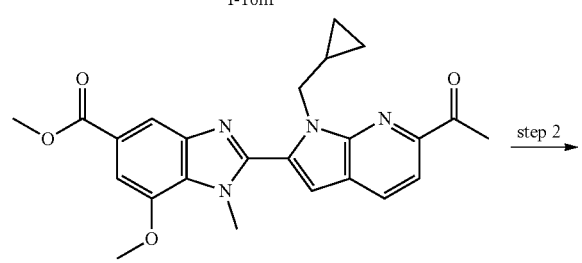

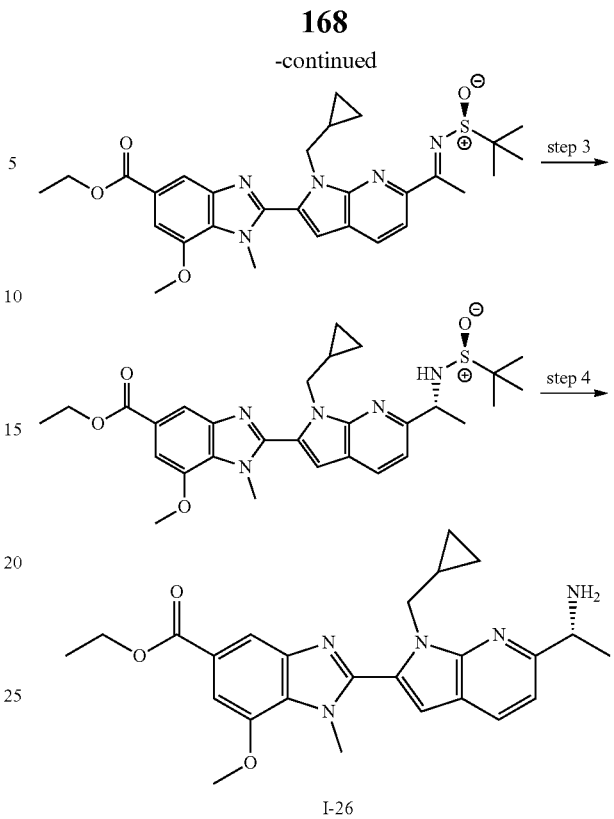

I-26

Step 1. To methyl 2-(6-bromo-1-(cyclopropylmethyl)-1H-pyrrolo[2,3-b]pyridin-2-yl)-7-methoxy-1-methyl-1H-benzo[d]imidazole-5-carboxylate (I-16m, 1.00 g, 2.13 mmol) and Pd(t-Bu$_3$P)$_2$ (0.054 g, 0.107 mmol) in THF (8 mL) was added 1-ethoxyvinyltributyltin (0.83 mL, 2.46 mmol). The mixture was stirred at rt for 5 min and then at 90° C. for 6 h. Additional 1-ethoxyvinyltributyltin (0.83 mL, 2.46 mmol) was added, and after 1 h, another portion of Pd(t-Bu$_3$P)$_2$ (0.108 g, 0.214 mmol) was added. The mixture was stirred at 90° C. for 10 h. The mixture was cooled to rt and poured into rapidly stirring HCl solution (30 mL of a 1 M aq soln). THF (7 mL) was added and the mixture was stirred for 1 h. The mixture was diluted with EtOAc and the pH was adjusted to pH=9 with aq NaOH soln. Solids were removed via filtration through Celite. The filtrate was transferred to a separatory funnel and the aqueous layer was extracted with EtOAc. The combined organic layers were dried (Na$_2$SO$_4$), filtered, and concentrated. The residue was purified via flash column chromatography on silica gel to afford methyl 2-(6-acetyl-1-(cyclopropylmethyl)-1H-pyrrolo[2,3-b]pyridin-2-yl)-7-methoxy-1-methyl-1H-benzo[d]imidazole-5-carboxylate. ES/MS: m/z 433.7 [M+H]$^+$.

Step 2. To a mixture of methyl 2-(6-acetyl-1-(cyclopropylmethyl)-1H-pyrrolo[2,3-b]pyridin-2-yl)-7-methoxy-1-methyl-1H-benzo[d]imidazole-5-carboxylate (1.00 g, 2.31 mmol) and (S)methylpropane-2-sulfinamide (1.17 g, 9.65 mmol) in THF (30 mL) was added titanium(IV) ethoxide (3.88 mL, 18.5 mmol). The mixture was stirred at 70° C. for 5 h. The mixture was cooled to rt, diluted with THF, and poured into brine. The mixture was diluted with EtOAc and water with stirring and was then filtered through a pad of Celite to remove solids. The organic layer was dried (Na$_2$SO$_4$), filtered, and concentrated to afford ethyl (E)-2-(6-(1-((tert-butylsulfinyl)imino)ethyl)-1-(cyclopropylmethyl)-1H-pyrrolo[2,3-b]pyridin-2-yl)-7-methoxy-1-methyl-1H-benzo[d]imidazole-5-carboxylate. ES/MS: m/z 549.9 [M+H]$^+$.

Step 3. To a solution of ethyl (E)-2-(6-(1-((tert-butylsulfinyl)imino)ethyl)-1-(cyclopropylmethyl)-1H-pyrrolo[2,3-b]pyridin-2-yl)-7-methoxy-1-methyl-1H-benzo[d]imidazole-5-carboxylate (0.890 g, 1.62 mmol) in THF (20 mL) at −45° C. was added L-Selectride (1.9 mL of a 1 M soln in THF, 1.9 mmol), dropwise over 1 min. The mixture was stirred at −45° C. for 30 min and was then warmed to 0° C. After 30 min the reaction was quenched via addition of sat NH$_4$Cl soln and then diluted with EtOAc and water. The organic layer was dried (Na$_2$SO$_4$), filtered, and concentrated. The residue was purified via flash column chromatography on silica gel to afford ethyl 2-(6-((1R)-1-((tert-butylsulfinyl)amino)ethyl)-1-(cyclopropylmethyl)-1H-pyrrolo[2,3-b]pyridin-2-yl)-7-methoxy-1-methyl-1H-benzo[d]imidazole-5-carboxylate. ES/MS: m/z 552.1 [M+H]$^+$.

Step 4. To a solution of ethyl 2-(6-((1R)-1-((tert-butylsulfinyl)amino)ethyl)(cyclopropylmethyl)-1H-pyrrolo[2,3-b]pyridin-2-yl)-7-methoxy-1-methyl-1H- benzo[d]imidazole-5-carboxylate (0.830 g, 1.50 mmol) in dioxane (15 mL) was added HCl (1.9 mL of a 4 M soln in dioxane, 7.52 mmol). The mixture was stirred at rt for 15 min and was then concentrated to yield ethyl (R)-2-(6-(1-aminoethyl)-1-(cyclopropylmethyl)-1H-pyrrolo[2,3-b]pyridin-2-yl)-7-methoxy-1-methyl-1H-benzo[d]imidazole-5-carboxylate. ES/MS: m/z 448.0 [M+H]$^+$.

Preparation of tert-butyl ((R)-2-(2-(6-((R)-1-aminoethyl)-1-(cyclopropylmethyl)-1H-pyrrolo[2,3-b]pyridin-2-yl)-7-methoxy-1-methyl-1H-benzo[d]imidazole-5-carbonyl)-1-methylhexahydropyridazin-4-yl)carbamate (I-27a)

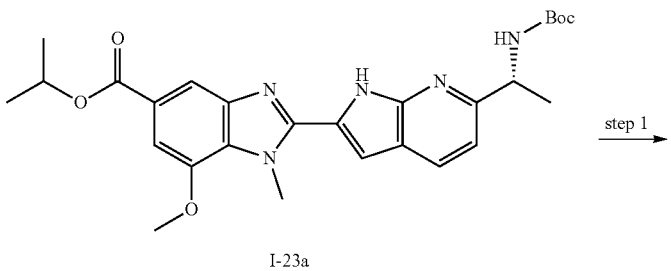

I-23a

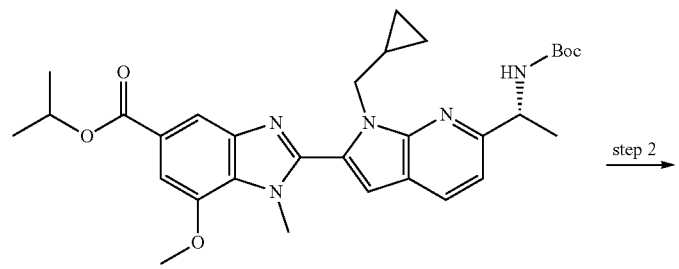

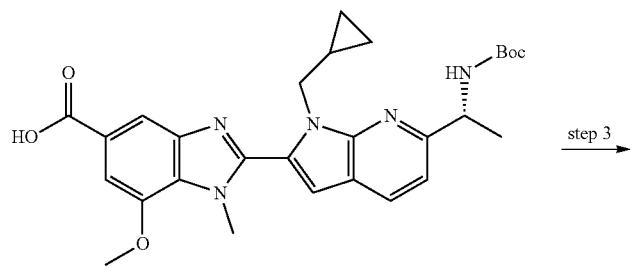

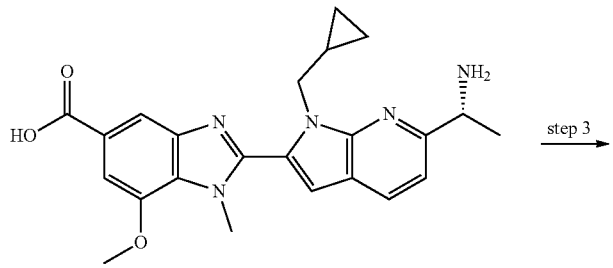

-continued

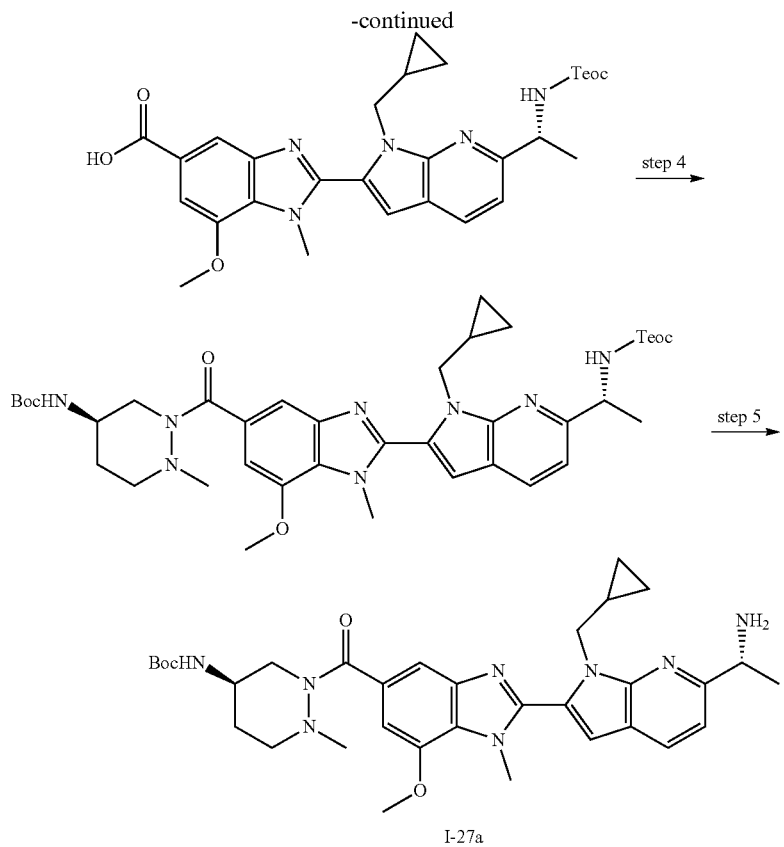

I-27a

Step 1. To a solution of isopropyl (R)-2-(6-(1-((tert-butoxycarbonyl)amino)ethyl)-1H-pyrrolo[2,3-b]pyridin-2-yl)-7-methoxy-1-methyl-1H-benzo[d]imidazole-5-carboxylate (I-23a, 2.80 g, 5.52 mmol) in DMF (11 mL) was added $Cs_2CO_3$ (2.34 g, 7.17 mmol) followed by (bromomethyl)cyclopropane (0.64 mL, 6.62 mmol). The reaction mixture was stirred at rt overnight. The reaction mixture was diluted with EtOAc and washed with brine. The organic layer was dried ($Na_2SO_4$), filtered and concentrated to afford isopropyl (R)-2-(6-(1-((tert-butoxycarbonyl)amino)ethyl)-1-(cyclopropylmethyl)-1H-pyrrolo[2,3-b]pyridin-2-yl)-7-methoxy-1-methyl-1H-benzo[d]imidazolecarboxylate. ES/MS: m/z 562.1 [M+H]⁺.

Step 2. To a solution of isopropyl (R)-2-(6-(1-((tert-butoxycarbonyl)amino)ethyl)-1-(cyclopropylmethyl)-1H-pyrrolo[2,3-b]pyridin-2-yl)-7-methoxy-1-methyl-1H-benzo[d]imidazole-5-carboxylate (2.00 g, 3.56 mmol) in MeOH (10 mL) was added LiOH (8.9 mL of a 2 M aq soln, 17.8 mmol). The reaction mixture was stirred at 100° C. for 15 min. The reaction mixture was cooled to rt, concentrated to a slurry, acidified to pH 3, and extracted with MeTHF. The organic layer was dried ($Na_2SO_4$), filtered and concentrated to afford (R)-2-(6-(1-((tert-butoxycarbonyl)amino)ethyl)-1-(cyclopropylmethyl)-1H-pyrrolo[2,3-b]pyridin-2-yl)-7-methoxy-1-methyl-1H-benzo[d]imidazolecarboxylic acid. ES/MS: m/z 520.1 [M+H]⁺.

Step 3. (R)-2-(6-(1-((tert-butoxycarbonyl)amino)ethyl)-1-(cyclopropylmethyl)-1H-pyrrolo[2,3-b]pyridin-2-yl)-7-methoxy-1-methyl-1H-benzo[d]imidazole-5-carboxylic acid (1.50 g, 2.89 mmol) in MeCN (20 mL) was treated with HCl (8.1 mL of a 4 M soln in dioxane, 32.4 mmol). The reaction mixture was sonicated for 1 h and was then concentrated to afford crude (R)-2-(6-(1-aminoethyl)-1-(cyclopropylmethyl)-1H-pyrrolo[2,3-b]pyridin-2-yl)-7-methoxy-1-methyl-1H-benzo[d]imidazole-5-carboxylic acid. ES/MS: m/z 420.9 [M+H]⁺.

Step 4. To a suspension of (R)-2-(6-(1-aminoethyl)-1-(cyclopropylmethyl)-1H-pyrrolo[2,3-b]pyridin-2-yl)-7-methoxy-1-methyl-1H-benzo[d]imidazole-5-carboxylic acid (1.42 g, 2.88 mmol) in MeCN (40 mL) was added DIPEA (1.5 mL, 8.7 mmol) followed by N-[2-(trimethylsilyl)ethoxycarbonyloxy)succinimide (0.897 g, 3.46 mmol). The reaction mixture was stirred at rt for 1 h and was then concentrated. The residue was taken up in DCM and washed with water. The organic layer was dried ($Na_2SO_4$), filtered and concentrated. The residue was purified via flash column chromatography on a silica gel column to afford (R)-2-(1-(cyclopropylmethyl)-6-(1-(((2-(trimethylsilyl)ethoxy)carbonyl)amino)ethyl)-1H-pyrrolo[2,3-b]pyridin-2-yl)-7-methoxy-1-methyl-1H-benzo[d]imidazole-5-carboxylic acid. ES/MS: m/z 564.3 [M+H]⁺.

Step 5. To a solution of (R)-2-(1-(cyclopropylmethyl)-6-(1-(((2-(trimethylsilyl)ethoxy)carbonyl)amino)ethyl)-1H-pyrrolo[2,3-b]pyridin-2-yl)-7-methoxy-1-methyl-1H-benzo[d]imidazole-5-carboxylic acid (0.450 g, 0.798 mmol), tert-butyl (R)-(1-methylhexahydropyridazin-4-yl)carbamate (A10, 0.241 g, 1.12 mmol) and DIPEA (0.21 mL, 1.20 mmol) in NMP (2 mL) was added HATU (0.334 g, 0.878 mmol). The mixture was stirred at rt for 18 h. The reaction mixture was diluted with EtOAc and washed with 5% LiCl soln. The organic layer was dried ($Na_2SO_4$), filtered and concentrated to afford tert-butyl ((R)-2-(2-(1-(cyclopropylmethyl)-6-((R)-1-(((2-(trimethylsilyl)ethoxy)carbonyl)amino)ethyl)-1H-pyrrolo[2,3-b]pyridin-2-yl)-7-methoxy-1- methyl-1H-benzo[d]imidazole-5-carbonyl)-1-methylhexahydropyridazin-4-yl)carbamate. ES/MS: m/z 761.2 [M+H]+.

Step 6. To a solution of tert-butyl ((R)-2-(2-(1-(cyclopropylmethyl)-6-((R)-1-(((2-(trimethylsilyl)ethoxy)carbonyl)amino)ethyl)-1H-pyrrolo[2,3-b]pyridin-2-yl)-7-methoxy-1-methyl-1H-benzo[d]imidazole-5-carbonyl)-1-methylhexahydropyridazin-4-yl)carbamate (0.550 g, 0.720 mmol) in THF (5 mL) was added TBAF (2.9 mL of a 1 M soln in THF, 2.9 mmol). The reaction mixture was stirred at 50° C. for 4 h. The mixture was partially concentrated, diluted with EtOAc, and washed with water. The aqueous layer was extracted with EtOAc. The combined organic layers were concentrated and the resulting residue was purified via flash column chromatography on a silica gel column to afford tert-butyl ((R)-2-(2-(6-((R)-1-aminoethyl)-1-(cyclopropylmethyl)-1H-pyrrolo[2,3-b]pyridin-2-yl)-7-methoxy-1-methyl-1H-benzo[d]imidazole-5-carbonyl)-1-methylhexahydropyridazin-4-yl)carbamate. ES/MS: m/z 617.6 [M+H]+.

tert-butyl ((1R,2R,4S)-7-(2-(6-((R)-1-aminoethyl)-1-(cyclopropylmethyl)-1H-pyrrolo[2,3-b]pyridin-2-yl)-7-methoxy-1-methyl-1H-benzo[d]imidazole-5-carbonyl)-7-azabicyclo[2.2.1]heptan-2-yl)carbamate (I-27b)

Prepared in a manner similar to I-27a using A2 in place of A10 in Step 5. ES/MS: m/z 614.3 [M+H]+.

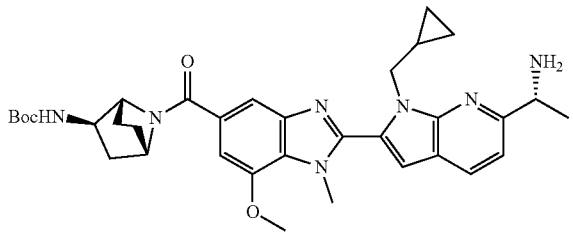

I-27b

Preparation of (S)-3-methyl-1,2-thiazinane 1,1-dioxide (I-28)

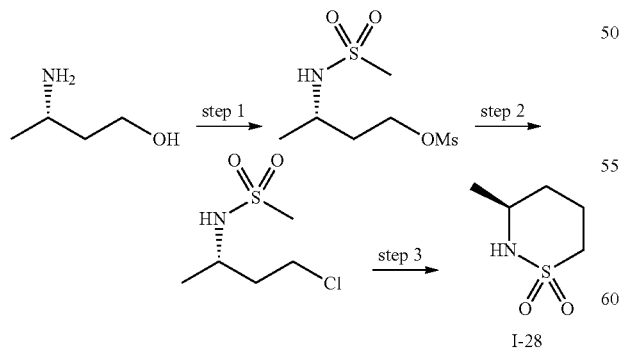

Step 1. Methanesulfonyl chloride (54.3 mL, 701 mmol) was added to a stirred solution of (S)aminobutan-1-ol (25 g, 280 mmol) and triethylamine (97.5 mL, 701 mmol) in THF (500 mL) at −5° C. to 0° C. and the reaction was allowed to room temperature and stirred for 2 h. The mixture was filtered and the solid was washed with THF. The filtrate was concentrated under reduced pressure to yield (S)(methylsulfonamido)butyl methanesulfonate, which was used without purification. ES/MS: m/z 246.1 [M+H]+.

Step 2. To a stirred solution of (S)-3-(methylsulfonamido)butyl methanesulfonate (48 g, 196 mmol) in DMF (833 mL), NaCl (48 g, 822 mmol) was added at room temperature and the mixture was heated at 80° C. for 16 h. The reaction mixture was cooled to room temperature and diluted with ethyl acetate and water. The layers were separated and the aqueous was extracted with EtOAc. The combined organic layers were washed with brine solution, dried (Na2SO4), and concentrated under reduced pressure. The resulting residue was purified by silica gel column chromatography using 40%-50% EtOAc in pet ether to yield (S)—N-(4-chlorobutan-2-yl)methanesulfonamide. ES/MS: m/z 186.1 [M+H]+.

Step 3. To a stirred solution of (S)—N-(4-chlorobutan-2-yl)methanesulfonamide (22 g, 119 mmol) in THF (393 mL), 1,10-Phenanthroline (55 mg, 0.5 mmol), diisopropylamine (4.2 mL, 29.7 mmol) were added and cooled to −78° C. n-BuLi (2.5 M in THF, 167 mL, 417 mmol) was added dropwise at −78° C. and the reaction mixture was warmed to rt and stirred 16 hours. The reaction mixture was quenched with aqueous ammonium chloride solution and the mixture was extracted with EtOAc. Combined organics were dried (Na2SO4), filtered, and concentrated under reduced pressure. The resulting residue was purified by silica gel column chromatography using 40%-50% EtOAc in pet ether to yield (S)-3-methyl-1,2-thiazinane 1,1-dioxide. ES/MS: m/z 150.2 [M+H]+.

Preparation of tert-butyl N-[1-(2-formyl-1H-pyrrolo[2,3-b]pyridin-6-yl)-1-methyl-ethyl]carbamate (I-29)

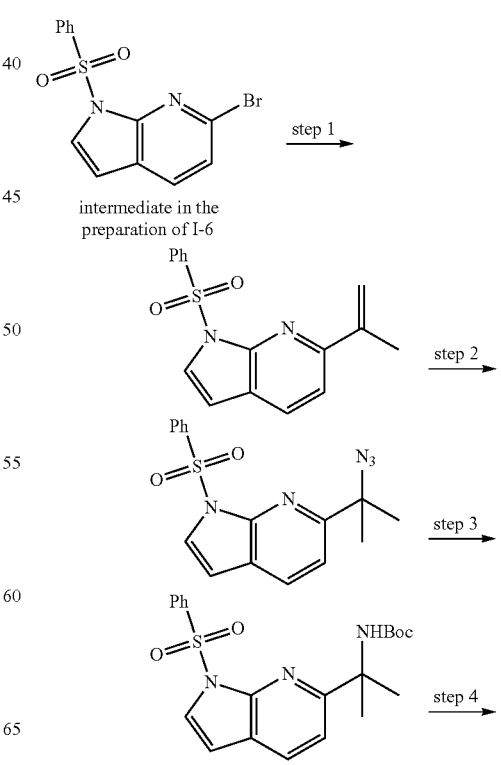

-continued

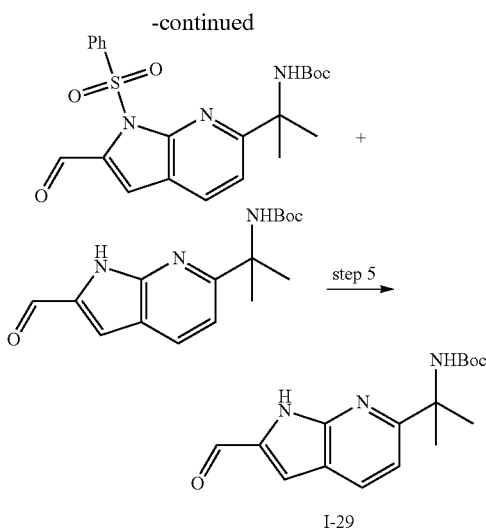

I-29

Step 1. A mixture of 1-(benzenesulfonyl)-6-bromo-pyrrolo[2,3-b]pyridine (intermediate in the preparation of I-6, 3.46 g, 10.3 mmol), potassium isopropenyltrifluoroborate (3.04 g, 20.5 mmol), TEA (7.15 mL, 51.3 mmol), [1,1'-bis(diphenylphosphino)ferrocene]dichloropalladium(II) dichloromethane complex (0.587 g, 0.718 mmol) in EtOH (160 mL) was stirred at 75° C. for 18 h. The mixture was cooled to rt and filtered. The filter pad was rinsed successively with EtOH and EtOAc. The filtrate was concentrated and the resulting residue was purified by flash column chromatography on silica gel to yield 1-(benzenesulfonyl)-6-isopropenyl-pyrrolo[2,3-b]pyridine. ES/MS: m/z 299.0 [M+H]⁺.

Step 2. To a solution of iron(III) oxalate hexahydrate (4.49 g, 9.28 mmol) in water (75 mL) at 0° C. were added sodium azide (0.872 g, 13.4 mmol) and THF (37 mL), followed by a solution of 1-(benzenesulfonyl)-6-isopropenyl-pyrrolo[2,3-b]pyridine (0.554 g, 1.68 mmol) in THF (37 mL). Sodium borohydride (0.450 g, 11.9 mmol) was added slowly. The reaction mixture was stirred for 4 h and then quenched by the addition of NH₄OH (16 mL of 28% aq solution). The resulting mixture was diluted with EtOAc and brine. The aqueous layer was extracted with EtOAc. The combined organic layers were dried (MgSO₄), filtered, and concentrated to give 6-(2-azidopropan-2-yl)-1-(phenylsulfonyl)-1H-pyrrolo[2,3-b]pyridine. ES/MS: m/z 341.9 [M+H]⁺, Step 3. A mixture of 6-(2-azidopropan-2-yl)-1-(phenylsulfonyl)-1H-pyrrolo[2,3-b]pyridine (0.634 g, 1.86 mmol) and Pd/C (0.198 g of 10% Pd/C) in EtOH (15 mL) was stirred under H₂ (1 atm) for 2 h. The mixture was filtered through a pad of Celite, which was rinsed with EtOH and EtOAc. The filtrate was concentrated. The resulting residue was dissolved in DCM (9 mL) and TEA (0.50 mL, 3.6 mmol), and di-tert-butyl decarbonate (0.448 g, 2.05 mmol) was added. The mixture was stirred at rt for 2 h and then concentrated. The resulting residue was purified via flash column chromatography on silica gel to afford tert-butyl N-[1-[1-(benzenesulfonyl)pyrrolo[2,3-b]pyridin-6-yl]-1-methyl-ethyl]carbamate. ES/MS: m/z 415.9 [M+H]⁺.

Step 4. To a solution of tert-butyl N-[1-[1-(benzenesulfonyl)pyrrolo[2,3-b]pyridin-6-yl]-1-methyl-ethyl]carbamate (0.379 g, 0.912 mmol) in THF (8 mL) at −78° C. was added n-BuLi (1.09 mL of a 2.5 M soln in hexanes, 2.75 mmol) dropwise. The mixture was stirred at −78° C. for 30 min. DMF (0.35 mL, 4.6 mmol) was added dropwise. After 30 min, the reaction mixture was quenched via the addition of NH₄Cl solution and then diluted with brine and EtOAc. The aqueous layer was extracted with EtOAc. The combined organic layers were dried (MgSO₄), filtered, and concentrated to yield a mixture of tert-butyl N-[1-[1-(benzenesulfonyl)-2-formyl-pyrrolo[2,3-b]pyridin-6-yl]-1-methyl-ethyl] carbamate and tert-butyl N-[1-(2-formyl-1H-pyrrolo[2,3-b]pyridin-6-yl)-1-methyl-ethyl]carbamate. ES/MS: m/z 443.8 [M+H]⁺ and 303.8 [M+H]⁺, respectively.

Step 5. To a solution of the crude mixture of tert-butyl N-[1-[1-(benzenesulfonyl)-2-formyl-pyrrolo[2,3-b]pyridin-6-yl]-1-methyl-ethyl]carbamate and tert-butyl N-[1-(2-formyl-1H-pyrrolo[2,3-b]pyridin-6-yl)-1-methyl-ethyl]carbamate (0.405 g, 0.912 mmol) in THF (5 mL) was added TBAF (1.37 mL of a 1 M soln in THF, 1.37 mmol). The mixture was stirred at rt for 1.5 h and then concentrated. The resulting residue was purified via flash column chromatography on silica gel to yield tert-butyl N-[1-(2-formyl-1H-pyrrolo[2,3-b]pyridin-6-yl)-1-methyl-ethyl]carbamate. ES/MS: m/z 303.8 [M+H]⁺.

Example Procedures

Procedure 1 (Example 63)

N-(2-(5-(((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide

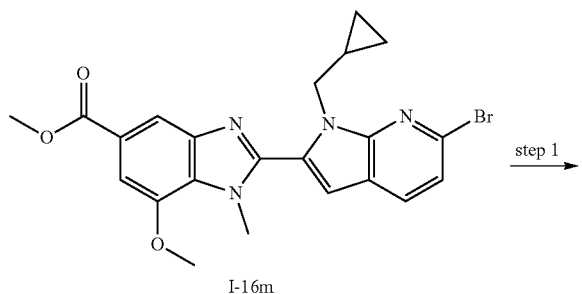

I-16m

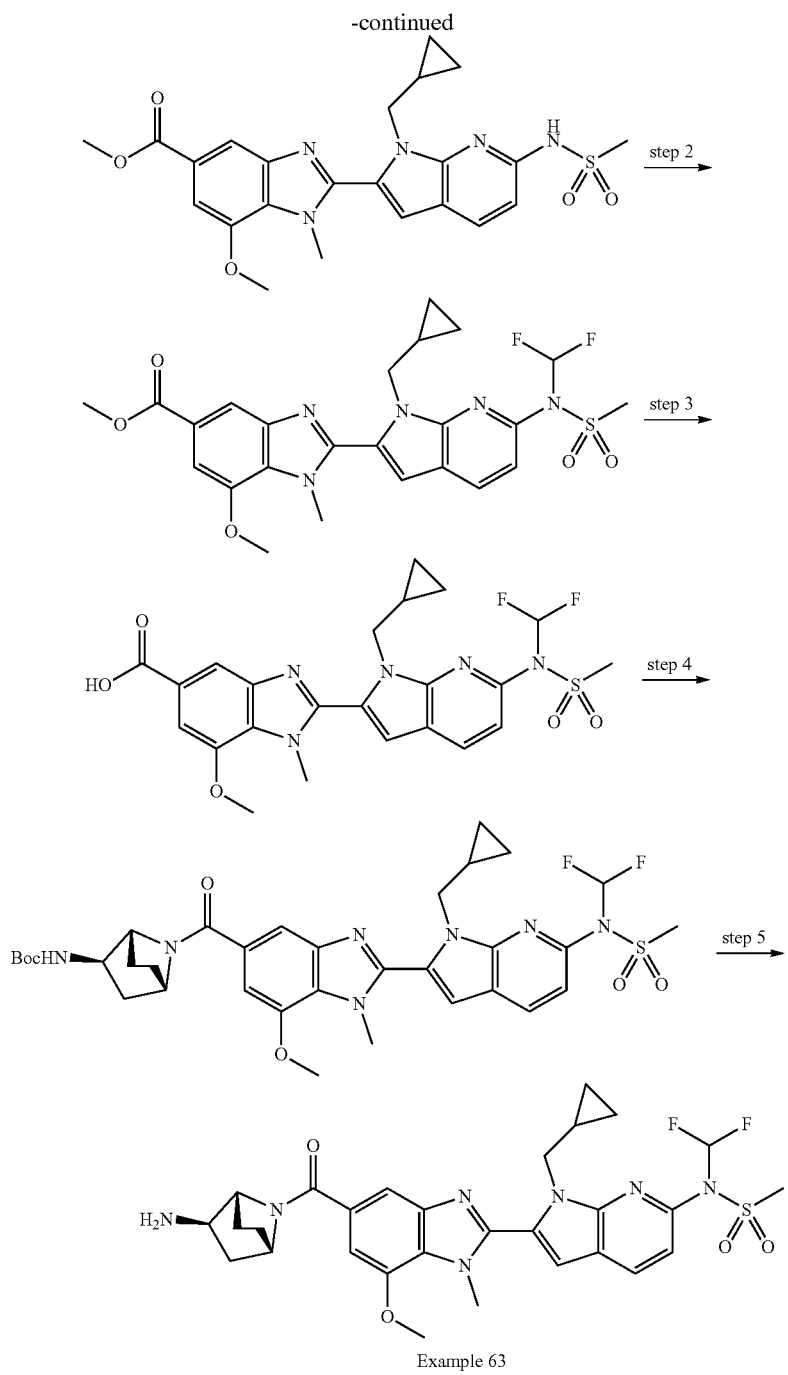

Example 63

Step 1. A mixture of methyl 2-(6-bromo-1-(cyclopropylmethyl)-1H-pyrrolo[2,3-b]pyridin-2-yl)-7-methoxy-1-methyl-1H-benzo[d]imidazole-5-carboxylate (I-16m, 1.00 g, 2.13 mmol), methanesulfonamide (0.405 g, 4.26 mmol), tBuXPhos Pd G1 (0.149 g, 0.217 mmol) and $K_2CO_3$ (0.918 g, 6.64 mmol) was flushed with $N_2$. Dioxane (30 mL) was added, and the mixture was stirred at 100° C. for 4 h. The mixture was cooled to rt and diluted with EtOAc and water. The aqueous layer was extracted with EtOAc. The combined organic layers were dried ($Na_2SO_4$), filtered and concentrated. The resulting residue was purified via flash column chromatography on silica gel to afford methyl 2-(1-(cyclopropylmethyl)-6-(methylsulfonamido)-1H-pyrrolo[2,3-b]pyridin-2-yl)-7-methoxy-1-methyl-1H-benzo[d]imidazole-5-carboxylate. ES/MS: m/z 484.3 $[M+H]^+$.

Step 2. To a solution of methyl 2-(1-(cyclopropylmethyl)-6-(methylsulfonamido)-1H-pyrrolo[2,3-b]pyridin-2-yl)-7-methoxy-1-methyl-1H-benzo[d]imidazole-5-carboxylate (0.650 g, 1.34 mmol) in DMF (20 mL) was added $K_2CO_3$ (1.86 g, 13.4 mmol). The mixture was heated to 90° C. while chlorodifluoromethane was bubbled through the mixture for 20 min. The reaction mixture was cooled to rt and diluted with EtOAc and water. The organic layer was washed with water, dried ($Na_2SO_4$), filtered and concentrated. The resulting residue was purified via flash column chromatography on silica gel to afford methyl 2-(1-(cyclopropylmethyl)-6-

(N-(difluoromethyl)methylsulfonamido)-1H-pyrrolo[2,3-b]pyridin-2-yl)-7-methoxy-1-methyl-1H-benzo[d]imidazole-5-carboxylate. ES/MS: m/z 534.3 [M+H]$^+$.

Step 3. To a solution of methyl 2-(1-(cyclopropylmethyl)-6-(N-(difluoromethyl)methylsulfonamido)-1H-pyrrolo[2,3-b]pyridin-2-yl)-7-methoxy-1-methyl-1H-benzo[d]imidazole-5-carboxylate (0.580 g, 1.09 mmol) in THF (8 mL), MeOH (2 mL), and water (2 mL) was added LiOH-H$_2$O (0.138 g, 3.29 mmol). The reaction mixture was stirred at 40° C. for 30 min. THF (4 mL) was added to solubilize solids. The reaction mixture was stirred at 40° C. for 6 h and was then cooled to rt and quenched by addition of HCl (0.60 mL of a 6 M aq soln, 3.60 mmol). The mixture was concentrated to afford 2-(1-(cyclopropylmethyl)-6-(N-(difluoromethyl)methylsulfonamido)-1H-pyrrolo[2,3-b]pyridin-2-yl)-7-methoxy-1-methyl-1H-benzo[d]imidazole-5-carboxylic acid. ES/MS: m/z 520.21 [M+H]$^+$.

Step 4. To a mixture of 2-(1-(cyclopropylmethyl)-6-(N-(difluoromethyl)methylsulfonamido)-1H-pyrrolo[2,3-b]pyridin-2-yl)-7-methoxy-1-methyl-1H-benzo[d]imidazole-5-carboxylic acid (0.030 g, 0.058 mmol), tert-butyl ((1R,2R,4S)-7-azabicyclo[2.2.1]heptan-2-yl)carbamate (A2, 0.014 g, 0.066 mmol) and HATU (0.036 g, 0.095 mmol) in DMF (1 mL) was added DIPEA (0.04 mL, 0.22 mmol). The reaction mixture was stirred at rt for 30 min and was then diluted with EtOAc. The organic solution was washed successively with sat NH$_4$Cl soln and brine. The combined aqueous portions were extracted with EtOAc. The combined organic layers were dried (MgSO$_4$), filtered and concentrated. The resulting residue was purified via flash column chromatography on silica gel to afford tert-butyl ((1R,2R,4S)-7-(2-(1-(cyclopropylmethyl)-6-(N-(difluoromethyl)methylsulfonamido)-1H-pyrrolo[2,3-b]pyridin-2-yl)-7-methoxy-1-methyl-1H-benzo[d]imidazole-5-carbonyl)-7-azabicyclo[2.2.1]heptan-2-yl)carbamate. ES/MS: m/z 714.3 [M+H]$^+$.

Step 5. tert-butyl ((1R,2R,4S)-7-(2-(1-(cyclopropylmethyl)-6-(N-(difluoromethyl)methylsulfonamido)-1H-pyrrolo[2,3-b]pyridin-2-yl)-7-methoxy-1-methyl-1H-benzo[d]imidazole-5-carbonyl)-7-azabicyclo[2.2.1]heptan-2-yl)carbamate (0.078 g, 0.109 mmol) was dissolved in HCl soln (0.8 mL of a 4 M soln in dioxane) and was stirred at rt for 30 min. The reaction mixture was concentrated and the resulting residue was purified via preparative reverse phase HPLC to afford Example 63.

Procedure 2 (Example 91)

ethyl N-[(1R,2R,4S)-7-[2-[1-(cyclopropylmethyl)[difluoromethyl(methylsulfonyl)amino]pyrrolo[2,3-b]pyridin-2-yl]-7-methoxy-1-methyl-benzimidazole-5-carbonyl]-7-azabicyclo[2.2.1]heptan-2-yl] carbamate

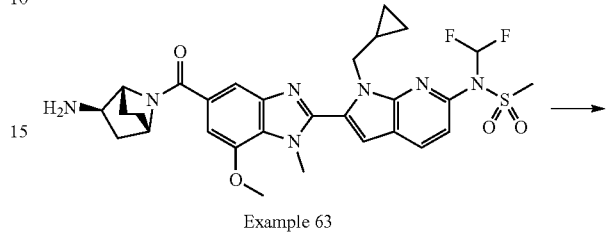

Example 63

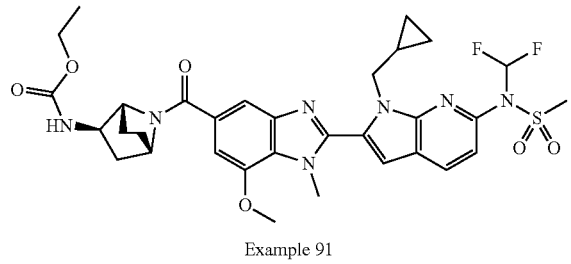

Example 91

To a solution of N-(2-(5-((1R,2R,4S)-2-amino-7-azabicyclo[2.2.1]heptane-7-carbonyl)methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide (Example 63, 0.015 g, 0.025 mmol) in DCM (0.5 mL) at 0° C. was added TEA (10.5 µL, 0.075 mmol) followed by ethyl chloroformate (7.1 µL, 0.075 mmol). The reaction mixture was allowed to warm to rt and was stirred for 30 min. The mixture was concentrated and the residue was purified via preparative reverse phase HPLC to afford Example 91.

Procedure 3 (Examples 45 and 46)

(R)—N-(2-(5-(3-aminopiperidine-1-carbonyl-3-d)-7-methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide and (S)—N-(2-(5-(3-aminopiperidine-1-carbonyl-3-d)-7-methoxy-1-methyl-1H-benzo[d]imidazol-2-yl)-1-(cyclopropylmethyl)-1H-pyrrolo[2,3-b]pyridinyl)-6-yl)-N-(difluoromethyl)methanesulfonamide

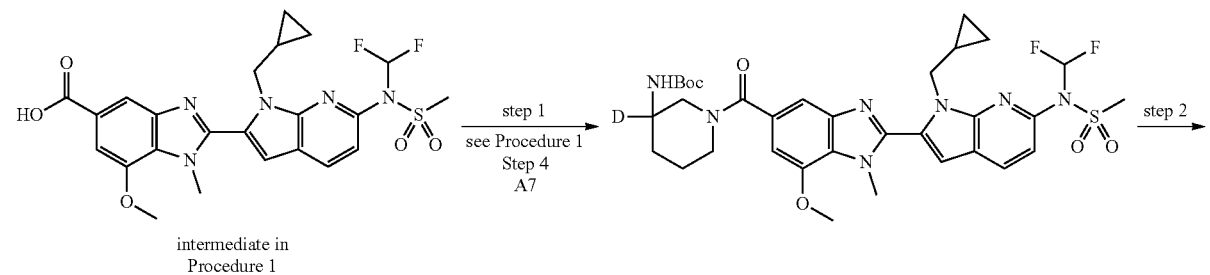

intermediate in
Procedure 1

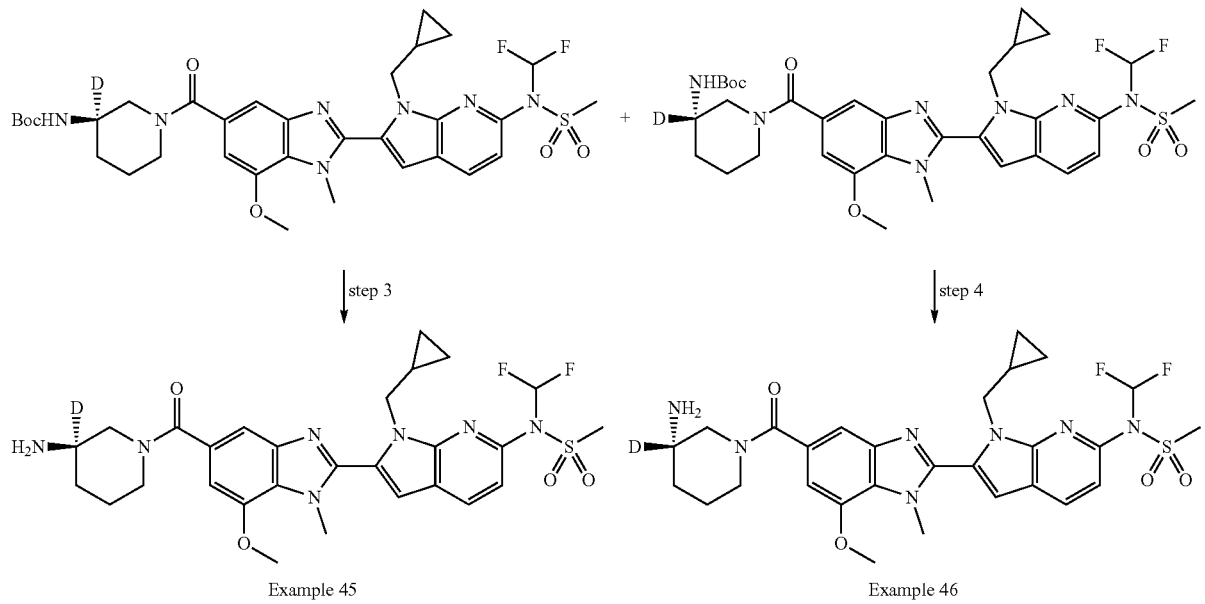

Example 45

Example 46

Step 1. tert-butyl (+/−)-(1-(2-(1-(cyclopropylmethyl)-6-(N-(difluoromethyl)methylsulfonamido)-1H-pyrrolo[2,3-b]pyridin-2-yl)-7-methoxy-1-methyl-1H-benzo[d]imidazole-5-carbonyl)piperidin-3-yl-3-d)carbamate was prepared following the procedure described in Step 4 of Procedure 1, using A7 instead of A2. ES/MS: m/z 703.3 [M+H]$^+$.

Step 2. tert-butyl (R)-(1-(2-(1-(cyclopropylmethyl)-6-(N-(difluoromethyl)methylsulfonamido)-1H-pyrrolo[2,3-b]pyridin-2-yl)-7-methoxy-1-methyl-1H-benzo[d]imidazole-5-carbonyl)piperidin-3-yl-3-d)carbamate and tert-butyl (S)-(1-(2-(1-(cyclopropylmethyl)-6-(N-(difluoromethyl)methylsulfonamido)-1H-pyrrolo[2,3-b]pyridin-2-yl)-7-methoxy-1-methyl-1H-benzo[d]imidazole-5-carbonyl)piperidin-3-yl-3-d)carbamate were separated by chiral SFC (Chiralpak IC, 30% EtOH cosolvent). The faster-eluting peak was identified to be tert-butyl (R)-(1-(2-(1-(cyclopropylmethyl)-6-(N-(difluoromethyl)methylsulfonamido)-1H-pyrrolo[2,3-b]pyridin-2-yl)-7-methoxy-1-methyl-1H-benzo[d]imidazole-5-carbonyl)piperidin-3-yl-3-d)carbamate.

Step 3. A solution of tert-butyl (R)-(1-(2-(1-(cyclopropylmethyl)-6-(N-(difluoromethyl)methylsulfonamido)-1H-pyrrolo[2,3-b]pyridin-2-yl)-7-methoxy-1-methyl-1H-benzo[d]imidazole-5-carbonyl)piperidin-3-yl-3-d)carbamate (0.045 g, 0.064 mmol) in DCM (2.0 mL) and TFA (0.5 mL) was stirred at rt for 1 h. The mixture was concentrated and the resulting residue was purified via preparative reverse phase HPLC to give Example 45.

Step 4. Example 46 was prepared following Step 3 of Procedure 3, using tert-butyl (S)-(1-(2-(1-(cyclopropylmethyl)-6-(N-(difluoromethyl)methylsulfonamido)-1H-pyrrolo[2,3-b]pyridin-2-yl)-7-methoxy-1-methyl-1H-benzo[d]imidazole-5-carbonyl)piperidin-3-yl-3-d)carbamate.

Procedure 4 (Example 71)

2-[1-(cyclopropylmethyl)-6-[difluoromethyl(methylsulfonyl)amino]pyrrolo[2,3-b]pyridin-2-yl]-N-[(3R,4R)-4-[[(E)-4-(dimethylamino)but-2-enoyl]amino]pyrrolidin-3-yl]-7-methoxy-1-methyl-benzimidazole-5-carboxamide

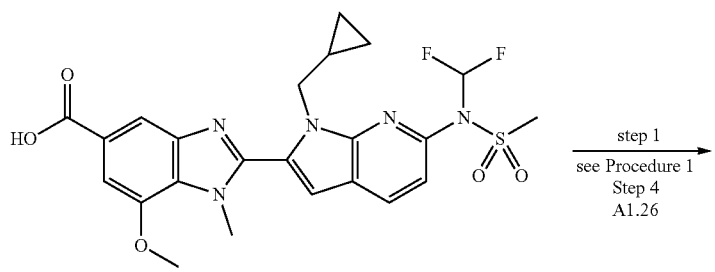

intermediate in
Procedure 1

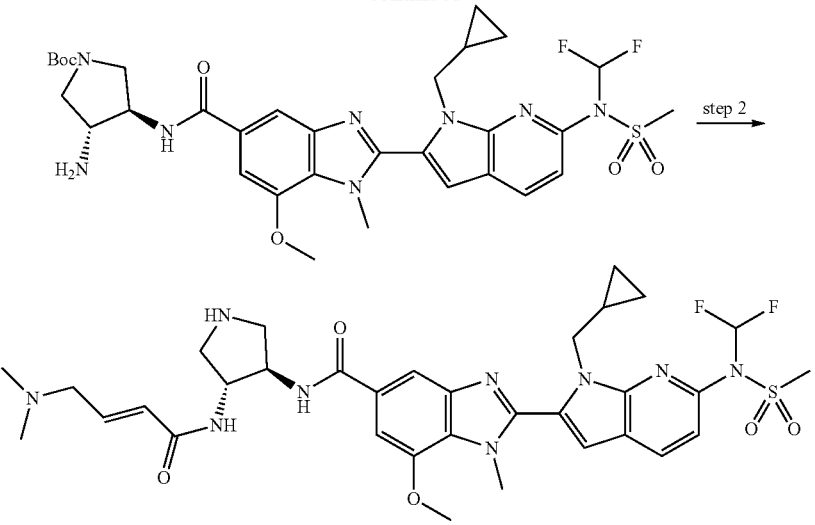

Example 71

Step 1. Tert-butyl (+/−)-(3R,4R)-3-amino-4-(2-(1-(cyclopropylmethyl)-6-(N-(difluoromethyl)methylsulfonamido)-1H-pyrrolo[2,3-b]pyridin-2-yl)-7-methoxy-1-methyl-1H-benzo[d]imidazole-5-carboxamido)pyrrolidine-1-carboxylate was synthesized following the procedure described in Step 4 of Procedure 1, using A1.26 instead of A2. ES/MS: m/z 703.1 [M+H]$^+$.

Step 2. To a solution of tert-butyl (+/−)-(3R,4R)-3-amino-4-(2-(1-(cyclopropylmethyl)-6-(N-(difluoromethyl)methylsulfonamido)-1H-pyrrolo[2,3-b]pyridin-2-yl)-7-methoxy-1-methyl-1H-benzo[d]imidazole-5-carboxamido)pyrrolidine-1-carboxylate (0.050 g, 0.071 mmol) and (E)(dimethylamino)but-2-enoic acid (0.014 g, 0.085 mmol) in DMF (2 mL) was added DIPEA (37 μL, 0.21 mmol) followed by HATU (0.027 g, 0.071 mmol). The mixture was stirred at rt for 1.5 h and then water was added. The resulting solids were collected via filtration. The solids were dissolved in DCM (2.0 mL) and HCl (0.18 mL of a 4 M soln in dioxane, 0.71 mmol) was added. The mixture was stirred at rt for 1 h and was concentrated. The residue was purified via preparative reverse phase HPLC to give Example 71.

Procedure 5 (Example 22)

(R)—N-(cyclopropylmethyl)-N-(1-(cyclopropylmethyl)-2-(5-(3-((cyclopropylmethyl)amino)piperidine-1-carbonyl)-7-methoxy-1-methyl-1H-benzo[d]imidazolyl-2-yl)-1H-pyrrolo[2,3-b]pyridin-6-yl)methanesulfonamide

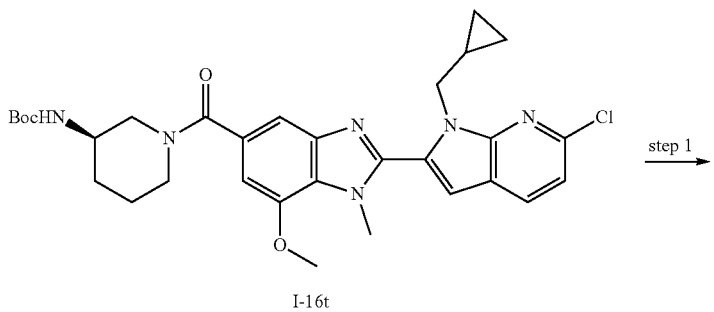

I-16t

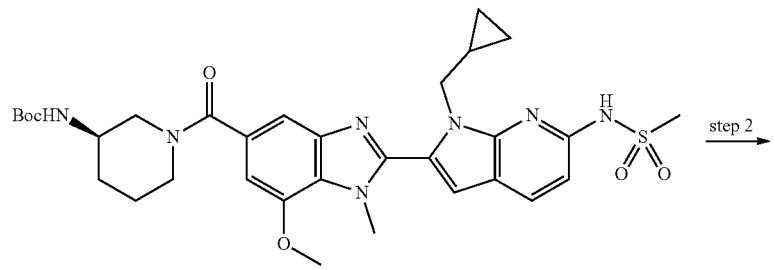

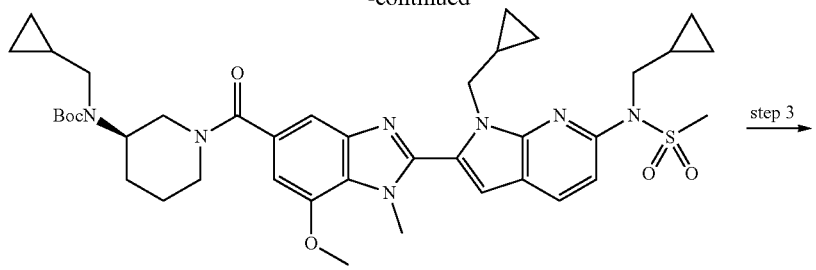

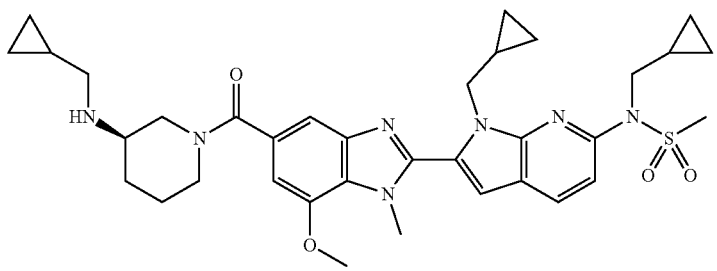

Example 22

Step 1. A vessel containing a mixture of tert-butyl (R)-(1-(2-(6-chloro-1-(cyclopropylmethyl)-1H-pyrrolo[2,3-b]pyridin-2-yl)-7-methoxy-1-methyl-1H-benzo[d]imidazole-5-carbonyl)piperidin-3-yl)carbamate (I-16t, 0.200 g, 0.337 mmol), methanesulfonamide (0.160 g, 1.69 mmol), tBuXPhos Pd G1 (0.023 g, 0.034 mmol) and potassium tert-butoxide (0.189 g, 1.69 mmol) was flushed with Argon. Dioxane (3 mL) was added and the mixture was stirred at 100° C. for 5 h. The reaction mixture was cooled to rt, neutralized with AcOH (0.5 mL) and concentrated. The residue was purified via flash column chromatography on silica gel to give tert-butyl (R)-(1-(2-(1-(cyclopropylmethyl)-6-(methylsulfonamido)-1H-pyrrolo[2,3-b]pyridin-2-yl)-7-methoxy-1-methyl-1H-benzo[d]imidazole-5-carbonyl)piperidin-3-yl)carbamate. ES/MS: m/z 652.5 [M+H]$^+$.

Step 2. To a mixture of tert-butyl (R)-(1-(2-(1-(cyclopropylmethyl)-6-(methylsulfonamido)-1H-pyrrolo[2,3-b]pyridin-2-yl)-7-methoxy-1-methyl-1H-benzo[d]imidazole-5-carbonyl)piperidin-3-yl)carbamate (0.025 g, 0.038 mmol) and NaH (0.006 g, 0.268 mmol) in DMF (1 mL) was added (bromomethyl)cyclopropane (37 µL, 0.38 mmol). The mixture was stirred at rt for 17 h before it was quenched via addition of sat NaHCO$_3$ soln (aq). The aqueous layer was extracted with EtOAc. The combined organic layers were washed with brine, dried (Na$_2$SO$_4$), filtered, and concentrated. The residue was purified via flash column chromatography on silica gel to afford tert-butyl (R)-(cyclopropylmethyl)(1-(2-(1-(cyclopropylmethyl)-6-(N-(cyclopropylmethyl)methylsulfonamido)-1H-pyrrolo[2,3-b]pyridin-2-yl)-7-methoxy-1-methyl-1H-benzo[d]imidazole-5-carbonyl)piperidinyl)carbamate. ES/MS: m/z 760.7 [M+H]$^+$.

Step 3. A solution of tert-butyl (R)-(cyclopropylmethyl)(1-(2-(1-(cyclopropylmethyl)-6-(N-(cyclopropylmethyl)methylsulfonamido)-1H-pyrrolo[2,3-b]pyridin-2-yl)-7-methoxy-1-methyl-1H-benzo[d]imidazole-5-carbonyl)piperidin-3-yl)carbamate (0.024 g, 0.032 mmol) in TFA (1 mL) was stirred at rt for 5 min. The crude product was purified via preparative reverse phase HPLC to yield Example 22.

Procedure 6 (Example 32)

N-(2-(5-((2S,5R)-5-amino-2-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-cyclopropylmethanesulfonamide

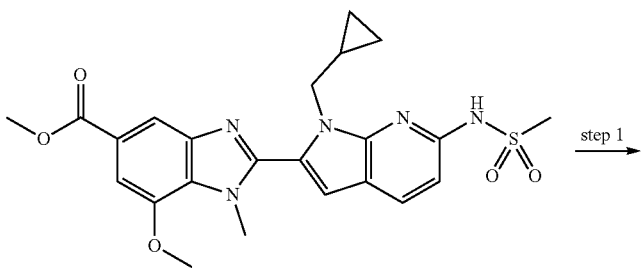

intermediate in
Procedure 1

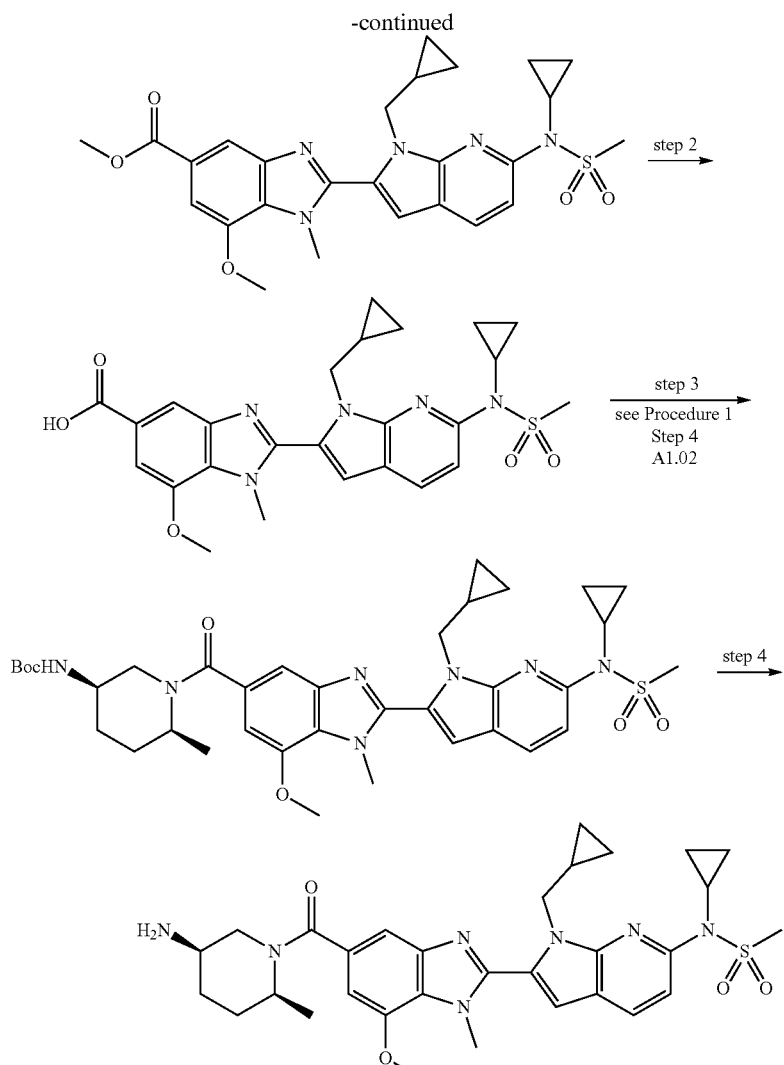

Example 32

Step 1. To methyl 2-(1-(cyclopropylmethyl)-6-(methylsulfonamido)-1H-pyrrolo[2,3-b]pyridin-2-yl)-7-methoxy-1-methyl-1H-benzo[d]imidazole-5-carboxylate (described in Procedure 1) (0.173 g, 0.359 mmol), Cu(OAc)$_2$ (0.195 g, 1.08 mmol), 2,2'-bipyridyl (0.448 g, 2.87 mmol) and Na$_2$CO$_3$ (0.228 g, 2.15 mmol) in DCE (8 mL) was added cyclopropylboronic acid (0.725 g, 7.17 mmol). The reaction mixture was stirred at 75° C. for 18 h. The reaction mixture was cooled to rt and filtered through a pad of Celite. The filtrate was diluted with 4:1 DCM/MeOH and washed successively with sat NaHCO$_3$ soln and sat NH$_4$Cl soln. The combined aqueous layers were extracted with DCM. The combined organic layers were dried (MgSO$_4$), filtered and concentrated. The resulting residue was purified via flash column chromatography on silica gel to afford methyl 2-(1-(cyclopropylmethyl)-6-(N-cyclopropylmethylsulfonamido)-1H-pyrrolo[2,3-b]pyridin-2-yl)-7-methoxy-1-methyl-1H-benzo[d]imidazole-5-carboxylate. ES/MS: m/z 524.4 [M+H]$^+$.

Step 2. To a solution of methyl 2-(1-(cyclopropylmethyl)-6-(N-cyclopropylmethylsulfonamido)-1H-pyrrolo[2,3-b]pyridin-2-yl)-7-methoxy-1-methyl-1H-benzo[d]imidazole-5-carboxylate (0.198 g, 0.378 mmol) in THF (4 mL) and MeOH (1 mL) was added NaOH (0.76 mL of a 1 N aq soln, 0.76 mmol). The reaction mixture was stirred at rt for 4 h. Additional portions of NaOH (2×0.76 mL) were added over 24 h. The reaction mixture was concentrated to give crude 2-(1-(cyclopropylmethyl)-6-(N-cyclopropylmethylsulfonamido)-1H-pyrrolo[2,3-b]pyridin-2-yl)-7-methoxy-1-methyl-1H-benzo[d]imidazole-5-carboxylic acid. ES/MS: m/z 510.3 [M+H]$^+$.

Step 3. tert-butyl ((3R,6S)-1-(2-(1-(cyclopropylmethyl)-6-(N-cyclopropylmethylsulfonamido)-1H-pyrrolo[2,3-b]pyridin-2-yl)-7-methoxy-1-methyl-1H-benzo[d]imidazole-5-carbonyl)-6-methylpiperidin-3-yl)carbamate was prepared following the procedure described in Step 4 of Procedure 1, using A1.02. The crude product was used in the subsequent step. ES/MS: m/z 706.5 [M+H]$^+$.

Step 4. To a solution of tert-butyl ((3R,6S)-1-(2-(1-(cyclopropylmethyl)-6-(N-cyclopropylmethylsulfonamido)-1H-pyrrolo[2,3-b]pyridin-2-yl)-7-methoxy-1-methyl-1H-benzo[d]imidazole-5-carbonyl)-6-methylpiperidin-3-yl)carbamate (0.033 g, 0.046 mmol) in DCM (1 mL) was added TFA (1 mL). The mixture was stirred at rt for 1 h and was then concentrated. The resulting residue was purified via preparative reverse phase HPLC to afford Example 32.

Procedure 7 (Example 90)

N-(2-(7-(((1R,2R,4S)-2-amino-7-azabicyclo[2.2.1]heptane-7-carbonyl)-3,4-dihydro-5-oxa-1,2a-diazaacenaphthylen-2-yl)-1-(cyclopropylmethyl)-1H-pyrrolo[2,3-b]pyridin-6-yl)-N-methylmethanesulfonamide

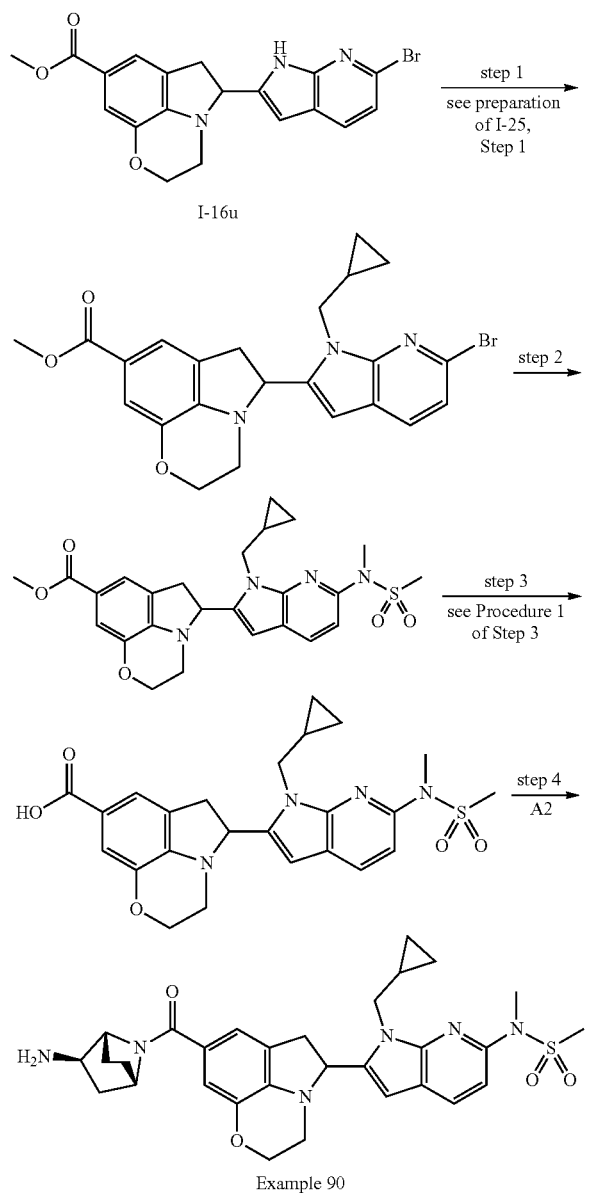

Step 1. Methyl 2-(6-bromo-1H-pyrrolo[2,3-b]pyridin-2-yl)-3,4-dihydro-5-oxa-1,2a-diazaacenaphthylene-7-carboxylate (I-16u) was alkylated following the procedure described in Step 1 for the preparation of I-25a, affording methyl 2-(6-bromo-1-(cyclopropylmethyl)-1H-pyrrolo[2,3-b]pyridin-2-yl)-3,4-dihydro-5-oxa-1,2a-diazaacenaphthylene-7-carboxylate. ES/MS: m/z 467.1, 469.1 [M+H]$^+$.

Step 2. A 5 mL microwave vial was charged with a stir bar, methyl 2-(6-bromo-1-(cyclopropylmethyl)-1H-pyrrolo[2,3-b]pyridin-2-yl)-3,4-dihydro-5-oxa-1,2a-diazaacenaphthylene-7-carboxylate (0.070 g, 0.15 mmol), JackiePhos (0.047 g, 0.06 mmol), cesium carbonate (0.101 g, 0.31 mmol) and N-methyl-methanesulfonamide (0.060 g, 0.55 mmol). The system was placed under and Ar(g) atmosphere and dry toluene (1.5 mL) was added. The solvent was then degassed by bubbling of Ar(g) for 15 minutes. Allylpalladium chloride dimer (0.006 g, 0.015 mmol) was then quickly added and the system was sealed. It was stirred 5 minutes at room temperature then heated to 95° C. overnight. The crude mixture was directly purified by column chromatography over silica gel to afford methyl 2-(1-(cyclopropylmethyl)-6-(N-methylmethylsulfonamido)-1H-pyrrolo[2,3-b]pyridin-2-yl)-3,4-dihydro-5-oxa-1,2a-diazaacenaphthylene-7-carboxylate. ES/MS: m/z 496.2 [M+H]$^+$.

Step 3. 2-(1-(cyclopropylmethyl)-6-(N-methylmethylsulfonamido)-1H-pyrrolo[2,3-b]pyridin-2-yl)-3,4-dihydro-5-oxa-1,2a-diazaacenaphthylene-7-carboxylic acid was synthesized following the procedure described in Step 3 of Procedure 1 using methyl 2-(1-(cyclopropylmethyl)-6-(N-methylmethylsulfonamido)-1H-pyrrolo[2,3-b]pyridin-2-yl)-3,4-dihydro-5-oxa-1,2a-diazaacenaphthylene-7-carboxylate. ES/MS: m/z 482.2 [M+H]$^+$.

Step 4. To a solution of 2-(1-(cyclopropylmethyl)-6-(N-methylmethylsulfonamido)-1H-pyrrolo[2,3-b]pyridin-2-yl)-3,4-dihydro-5-oxa-1,2a-diazaacenaphthylene-7-carboxylic acid (0.052 mmol) and DIPEA (32 μL, 0.18 mmol) in DMF (0.65 mL) was added HATU (0.018 g, 0.077 mmol) followed by tert-butyl ((1R,2R,4S)-7-azabicyclo[2.2.1]heptan-2-yl)carbamate (A2, 0.013 g, 0.062 mmol). The mixture was stirred at rt and reaction progress was monitored by LC-MS. When the coupling was complete, TFA (1 mL) was added and the reaction mixture was heated to 50° C. and reaction progress was monitored by LC-MS. When deprotection was complete, the mixture was cooled to rt and purified via preparative reverse phase HPLC to give Example 90.

Procedure 8 (Example 103)

((1R,2R,4S)-2-amino-7-azabicyclo[2.2.1]heptan-7-yl)(2-(1-(cyclopropylmethyl)-6-((S)-3-methyl-1,1-dioxido-1,2-thiazinan-2-yl)-1H-pyrrolo[2,3-b]pyridin-2-yl)-7-methoxy-1-methyl-1H-benzo[d]imidazol-5-yl)methanone

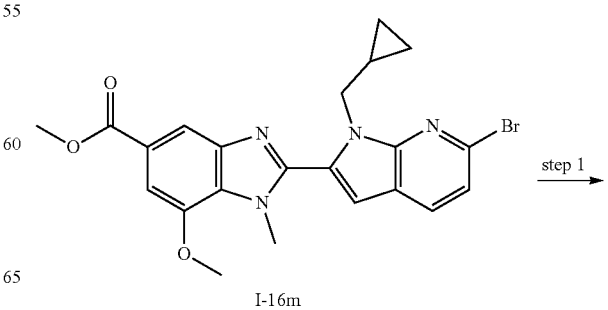

191
-continued

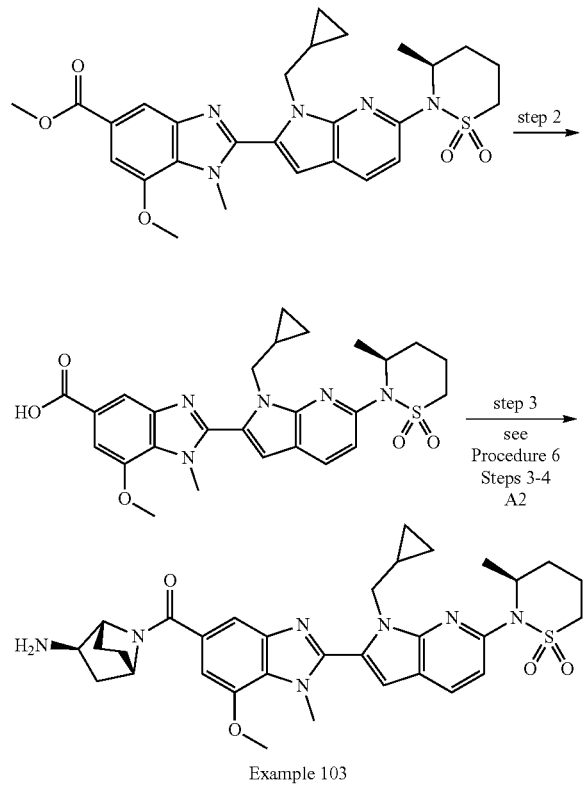

Example 103

Step 1. To a mixture of methyl 2-(6-bromo-1-(cyclopropylmethyl)-1H-pyrrolo[2,3-b]pyridin-2-yl)-7-methoxy-1-methyl-1H-benzo[d]imidazole-5-carboxylate (I-16m, 0.300 g, 0.639 mmol), (S)-3-methylthiazinane 1,1-dioxide (I-28, 0.286 g, 1.92 mmol), JackiePhos Pd G3 precatalyst (0.112 g, 0.096 mmol) and Cs$_2$CO$_3$ (0.417 g, 1.28 mmol) under Argon was added toluene (6 mL). The reaction mixture was stirred at 80° C. for 1.5 h. The mixture was cooled to rt and filtered. The filtrate was concentrated and the resulting residue was purified via flash column chromatography on silica gel to afford methyl (S)-2-(1-(cyclopropylmethyl)-6-(3-methyl-1,1-dioxido-1,2-thiazinan-2-yl)-1H-pyrrolo[2,3-b]pyridin-2-yl)-7-methoxy-1-methyl-1H-benzo[d]imidazole-5-carboxylate. ES/MS: m/z 538.3 [M+H]$^+$.

Step 2. To a solution of methyl (S)-2-(1-(cyclopropylmethyl)-6-(3-methyl-1,1-dioxido-1,2-thiazinan-2-yl)-1H-pyrrolo[2,3-b]pyridin-2-yl)-7-methoxy-1-methyl-1H-benzo[d]imidazole-5-carboxylate (0.340 g, 0.632 mmol) in THF (5 mL), MeOH (2 mL) and water (2 mL) was added LiOH (0.076 g, 3.16 mmol). The mixture was stirred at 45° C. for 2 h. The mixture was cooled to rt, acidified by addition of HCl (0.63 mL of a 6 M aq soln, 3.79 mmol), and concentrated to afford (S)-2-(1-(cyclopropylmethyl)-6-(3-methyl-1,1-dioxido-1,2-thiazinan-2-yl)-1H-pyrrolo[2,3-b]pyridin-2-yl)-7-methoxy-1-methyl-1H-benzo[d]imidazole-5-carboxylic acid. ES/MS: m/z 524.3 [M+H]$^+$.

Step 3. Example 103 was prepared following Steps 3-4 of Procedure 6 were followed, using A2 and (S)-2-(1-(cyclopropylmethyl)-6-(3-methyl-1,1-dioxido-1,2-thiazinan-2-yl)-1H-pyrrolo[2,3-b]pyridin-2-yl)-7-methoxy-1-methyl-1H-benzo[d]imidazole-5-carboxylic acid.

192
Procedure 9 (Example 114)

methyl (2-(5-(((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-indol-6-yl)(methyl)carbamate

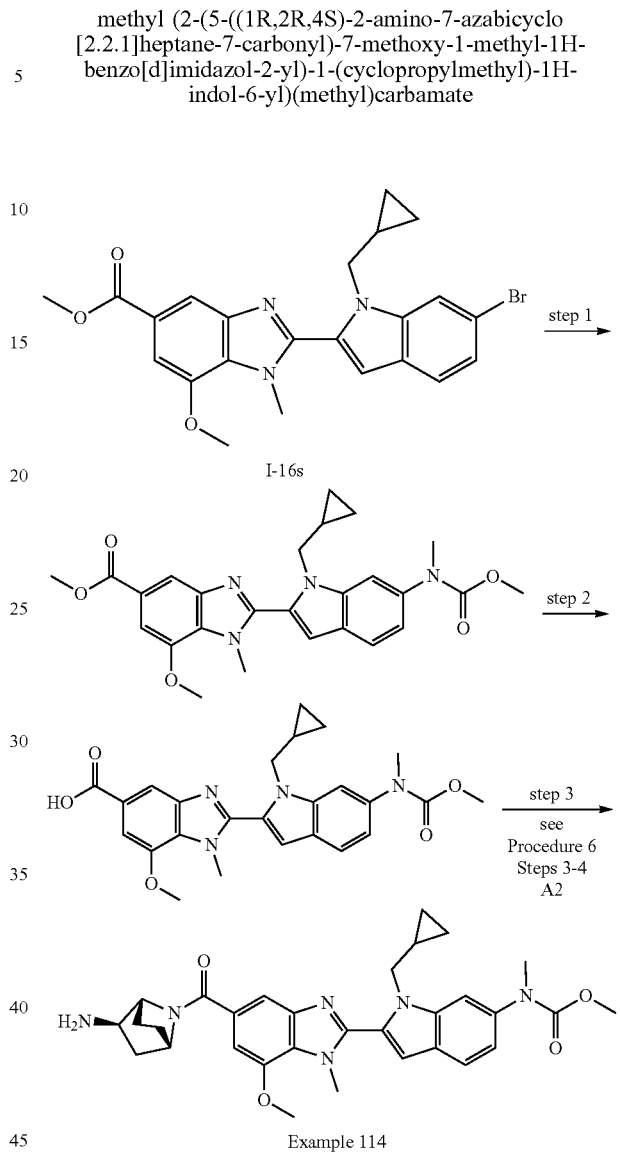

Example 114

Step 1. A vessel containing a mixture of methyl 2-(6-bromo-1-(cyclopropylmethyl)-1H-indo-2-yl)-7-methoxy-1-methyl-1H-benzo[d]imidazole-5-carboxylate (I-16s. 0.100 g, 0.214 mmol), allylpalladium(II) chloride dimer (0.004 g, 0.011 mmol), JackiePhos (0.043 g, 0.053 mmol) and Cs$_2$CO$_3$ (0.139 g, 0.427 mmol) was flushed with Ar. Toluene (2 mL) was added, followed by methyl N-methylcarbamate (0.095 g, 1.07 mmol). The reaction mixture was stirred at 120° C. for 16 h. The reaction mixture was cooled to rt and filtered through a pad of Celite. The filtrate was concentrated to afford methyl 2-(1-(cyclopropylmethyl)-6-((methoxycarbonyl)(methyl)amino)-1H-indol-2-yl)-7-methoxy-1-methyl-1H-benzo[d]imidazole-5-carboxylate. ES/MS: m/z 477.32 [M+H]$^+$.

Step 2. To a solution of methyl 2-(1-(cyclopropylmethyl)-6-((methoxycarbonyl)(methyl)amino)-1H-indol-2-yl)-7-methoxy-1-methyl-1H-benzo[d]imidazole-5-carboxylate (0.047 g, 0.100 mmol) in 1:1 THF/MeOH (1 mL) was added LiOH (0.1 mL of a 2 N aq soln, 0.2 mmol). The reaction mixture was stirred at 50° C. for 5 h. The reaction mixture was cooled to rt, neutralized via an aqueous work-up, and purified via flash column chromatography on silica gel to afford 2-(1-(cyclopropylmethyl)-6-((methoxycarbonyl)(methyl)amino)-1H-indol-2-yl)-7-methoxy-1-methyl-1H-benzo[d]imidazole-5-carboxylic acid. ES/MS: m/z 463.27 [M+H]$^+$.

Step 3. Example 114 was prepared following Steps 3-4 of Procedure 6, using A2 and 2-(1-(cyclopropylmethyl)-6-((methoxycarbonyl)(methyl)amino)-1H-indol-2-yl)-7-methoxy-1-methyl-1H-benzo[d]imidazole-5-carboxylic acid.

TABLE 1a

The compounds below were synthesized according to Procedures 1-9, using intermediates described herein, or intermediates prepared according to General Schemes.

| Ex. | Structure | Name | ES/MS m/z [M + H]$^+$ |
|---|---|---|---|
| 1 | 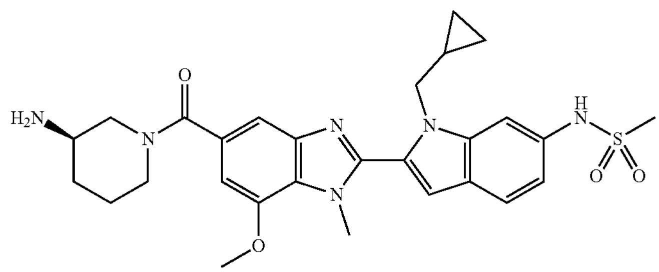 [SMILES: COc1cc(C(=O)N2CCC[C@@H](N)C2)cc2nc(-c3cc4ccc(NS(C)(=O)=O)cc4n3CC3CC3)n(C)c12] | (R)-N-(2-(5-(3-aminopiperidine-1-carbonyl)-7-methoxy-1-methyl-1H-benzo[d]imidazol-2-yl)-1-(cyclopropylmethyl)-1H-indol-6-yl)methanesulfonamide | 551.29 |
| 2 | 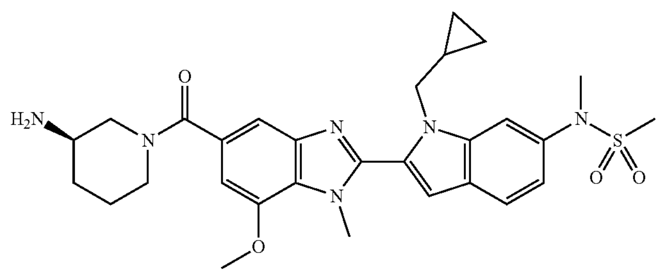 [SMILES: COc1cc(C(=O)N2CCC[C@@H](N)C2)cc2nc(-c3cc4ccc(N(C)S(C)(=O)=O)cc4n3CC3CC3)n(C)c12] | (R)-N-(2-(5-(3-aminopiperidine-1-carbonyl)-7-methoxy-1-methyl-1H-benzo[d]imidazol-2-yl)-1-(cyclopropylmethyl)-1H-indol-6-yl)-N-methylmethanesulfonamide | 565.33 |
| 3 | 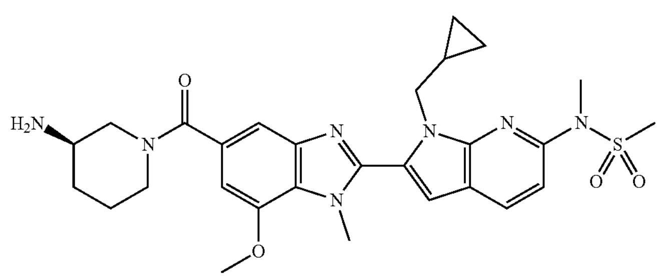 [SMILES: COc1cc(C(=O)N2CCC[C@@H](N)C2)cc2nc(-c3cc4ccc(N(C)S(C)(=O)=O)nc4n3CC3CC3)n(C)c12] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-methylmethanesulfonamide | 566.34 |
| 4 | 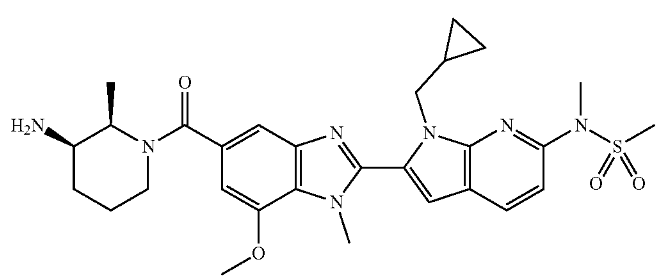 | N-(2-(5-((2R,3R)-3-amino-2-methylpiperidine-1-carbonyl)-7-methoxy-1-methyl-1H-benzo[d]imimidazol-2-yl)-1-(cyclopropylmethyl)-1H-pyrrolo[2,3-b]pyridin-6-yl)-N-methylmethanesulfonamide | 580.33 |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 5 | 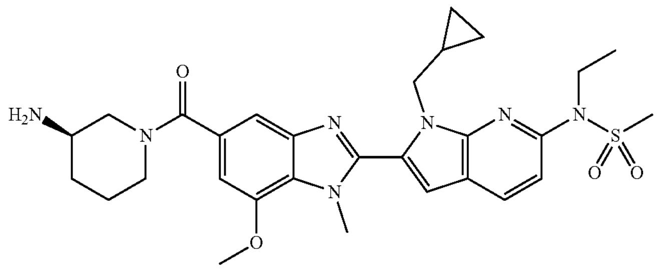 | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-ethylmethanesulfonamide | 580.4 |
| 6 | 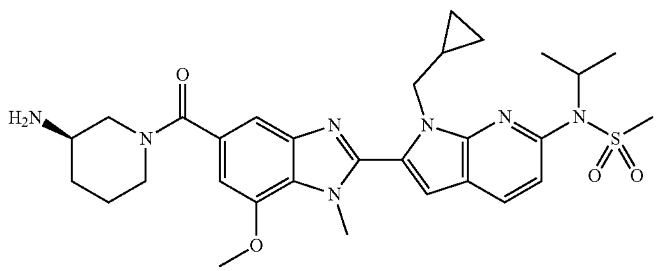 [SMILES: COc1cc(C(=O)N2CCC[C@@H](N)C2)cc2nc(-c3cc4ccc(N(C(C)C)S(C)(=O)=O)nc4n3CC3CC3)n(C)c12] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-isopropylmethanesulfonamide | 594.4 |
| 7 | 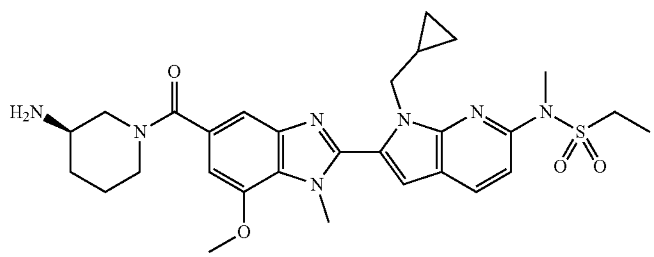 [SMILES: CCS(=O)(=O)N(C)c1ccc2cc(-c3nc4cc(C(=O)N5CCC[C@@H](N)C5)cc(OC)c4n3C)n(CC3CC3)c2n1] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-methylethanesulfonamide | 580.40 |
| 8 | 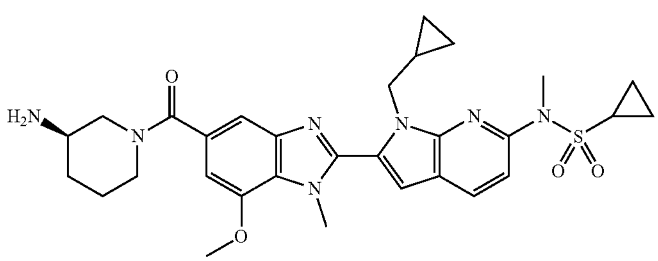 [SMILES: COc1cc(C(=O)N2CCC[C@@H](N)C2)cc2nc(-c3cc4ccc(N(C)S(=O)(=O)C5CC5)nc4n3CC3CC3)n(C)c12] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-methylcyclopropanesulfonamide | 592.42 |
| 9 | 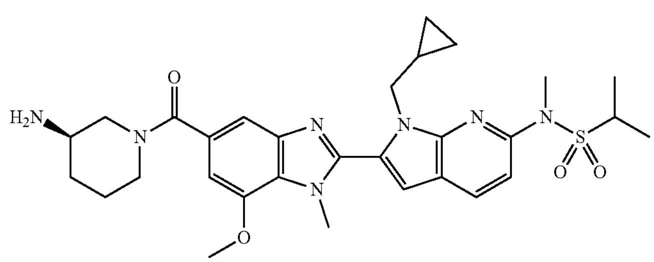 [SMILES: COc1cc(C(=O)N2CCC[C@@H](N)C2)cc2nc(-c3cc4ccc(N(C)S(=O)(=O)C(C)C)nc4n3CC3CC3)n(C)c12] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-methylpropane-2-sulfonamide | 594.45 |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 10 | 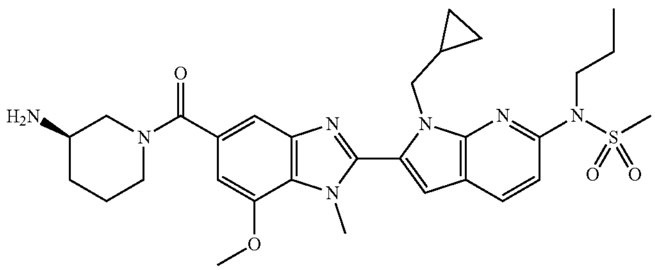 [SMILES: CCCN(c1ccc2cc(-c3nc4cc(C(=O)N5CCC[C@@H](N)C5)cc(OC)c4n3C)n(CC3CC3)c2n1)S(C)(=O)=O] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-propylmethanesulfonamide | 594.46 |
| 11 | 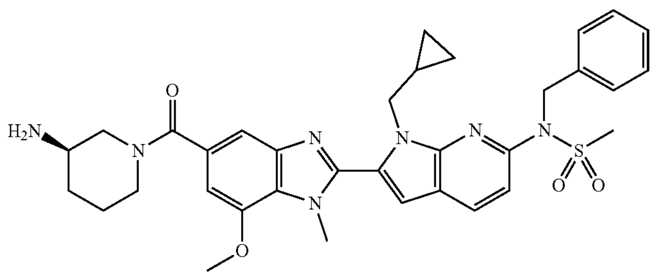 [SMILES: COc1cc(C(=O)N2CCC[C@@H](N)C2)cc2nc(-c3cc4ccc(N(Cc5ccccc5)S(C)(=O)=O)nc4n3CC3CC3)n(C)c12] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-benzylmethanesulfonamide | 642.51 |
| 12 | 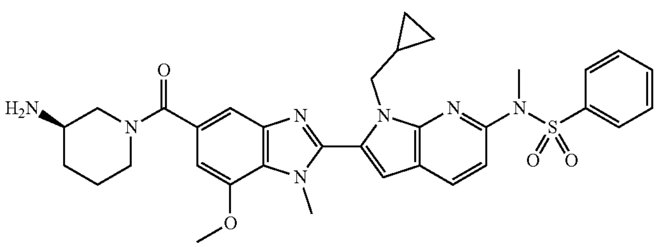 [SMILES: COc1cc(C(=O)N2CCC[C@@H](N)C2)cc2nc(-c3cc4ccc(N(C)S(=O)(=O)c5ccccc5)nc4n3CC3CC3)n(C)c12] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-methylbenzenesulfonamide | 628.47 |
| 13 | 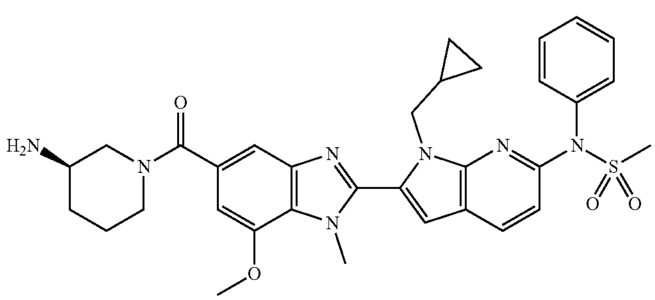 [SMILES: COc1cc(C(=O)N2CCC[C@@H](N)C2)cc2nc(-c3cc4ccc(N(c5ccccc5)S(C)(=O)=O)nc4n3CC3CC3)n(C)c12] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-phenylmethanesulfonamide | 628.42 |
| 14 | 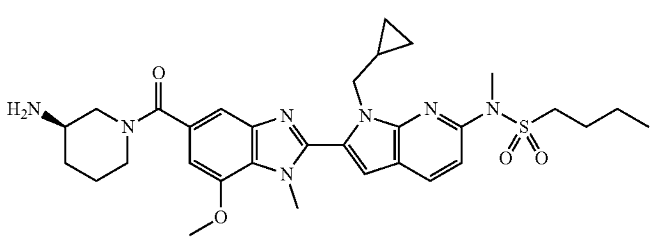 [SMILES: CCCCS(=O)(=O)N(C)c1ccc2cc(-c3nc4cc(C(=O)N5CCC[C@@H](N)C5)cc(OC)c4n3C)n(CC3CC3)c2n1] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-methylbutane-1-sulfonamide | 608.49 |

TABLE 1a-continued

The compounds below were synthesized according to Procedures 1-9, using intermediates described herein, or intermediates prepared according to General Schemes.

| Ex. | Structure | Name | ES/MS m/z [M + H]⁺ |
|---|---|---|---|
| 15 | 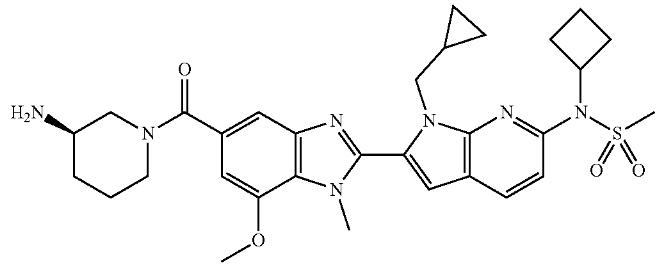 [SMILES: COc1cc(C(=O)N2CCC[C@@H](N)C2)cc2nc(-c3cc4ccc(N(C5CCC5)S(C)(=O)=O)nc4n3CC3CC3)n(C)c12] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-cyclobutylmethanesulfonamide | 606.49 |
| 16 | 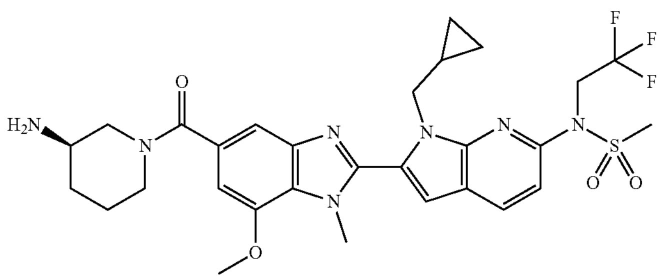 [SMILES: COc1cc(C(=O)N2CCC[C@@H](N)C2)cc2nc(-c3cc4ccc(N(CC(F)(F)F)S(C)(=O)=O)nc4n3CC3CC3)n(C)c12] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-(2,2,2-trifluoroethyl)methanesulfonamide | 634.49 |
| 17 | 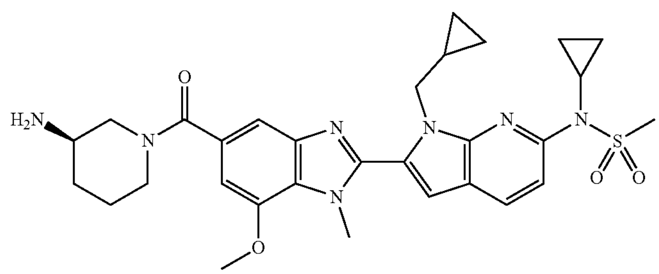 [SMILES: COc1cc(C(=O)N2CCC[C@@H](N)C2)cc2nc(-c3cc4ccc(N(C5CC5)S(C)(=O)=O)nc4n3CC3CC3)n(C)c12] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-cyclopropylmethanesulfonamide | 592.43 |
| 18 | 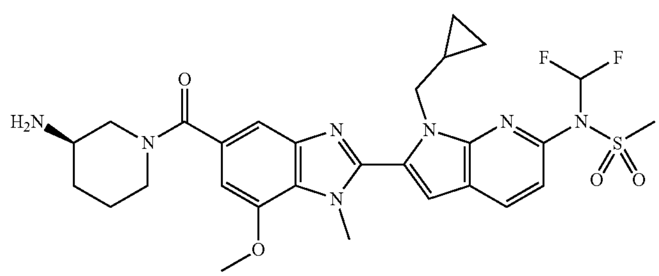 [SMILES: COc1cc(C(=O)N2CCC[C@@H](N)C2)cc2nc(-c3cc4ccc(N(C(F)F)S(C)(=O)=O)nc4n3CC3CC3)n(C)c12] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide | 602.46 |
| 19 | 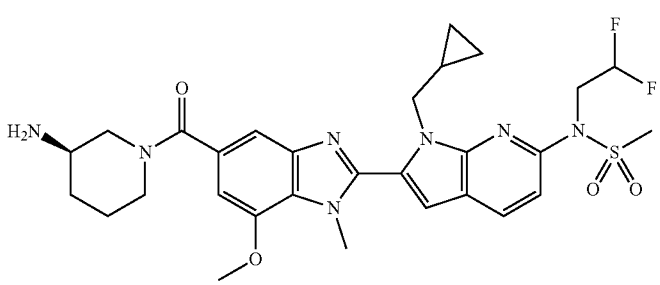 [SMILES: COc1cc(C(=O)N2CCC[C@@H](N)C2)cc2nc(-c3cc4ccc(N(CC(F)F)S(C)(=O)=O)nc4n3CC3CC3)n(C)c12] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-(2,2-difluoroethyl)methanesulfonamide | 616.49 |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 20 | 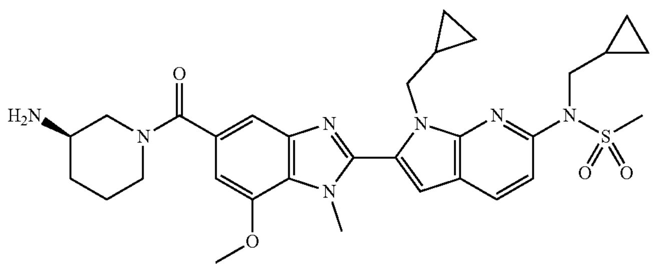 [SMILES: COc1cc(C(=O)N2CCC[C@@H](N)C2)cc2nc(-c3cc4ccc(N(CC5CC5)S(C)(=O)=O)nc4n3CC3CC3)n(C)c12] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-(cyclopropylmethyl)methanesulfonamide | 606.53 |
| 21 | 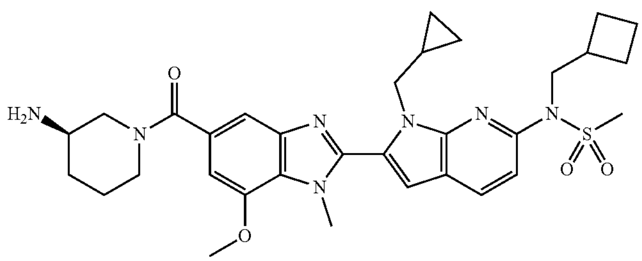 [SMILES: COc1cc(C(=O)N2CCC[C@@H](N)C2)cc2nc(-c3cc4ccc(N(CC5CCC5)S(C)(=O)=O)nc4n3CC3CC3)n(C)c12] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-(cyclobutylmethyl)methanesulfonamide | 620.56 |
| 22 | 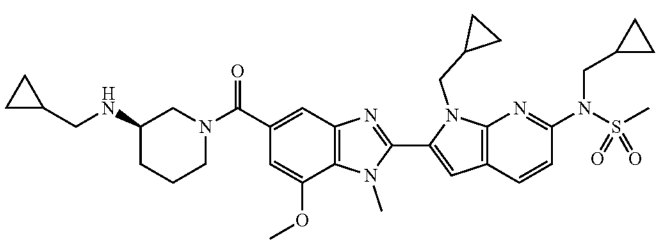 [SMILES: COc1cc(C(=O)N2CCC[C@@H](NCC3CC3)C2)cc2nc(-c3cc4ccc(N(CC5CC5)S(C)(=O)=O)nc4n3CC3CC3)n(C)c12] | (R)-N-(cyclopropylmethyl)-N-(1-(cyclopropylmethyl)-2-(5-(3-((cyclopropylmethyl)amino)piperidine-1-carbonyl)-7-methoxy-1-methyl-1H-benzo[d]imidazol-2-yl)-1H-pyrrolo[2,3-b]pyridin-6-yl)methanesulfonamide | |
| 23 | 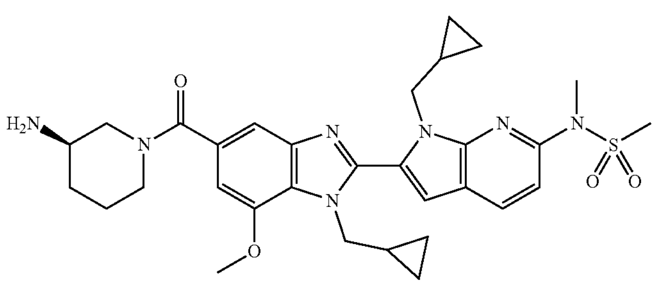 [SMILES: COc1cc(C(=O)N2CCC[C@@H](N)C2)cc2nc(-c3cc4ccc(N(C)S(C)(=O)=O)nc4n3CC3CC3)n(CC3CC3)c12] | (R)-N-(2-(5-(3-aminopiperidine-1-carbonyl)-1-(cyclopropylmethyl)-7-methoxy-1H-benzo[d]imidazol-2-yl)-1-(cyclopropylmethyl)-1H-pyrrolo[2,3-b]pyridin-6-yl)-N-methylmethanesulfonamide | 606.32 |
| 24 | 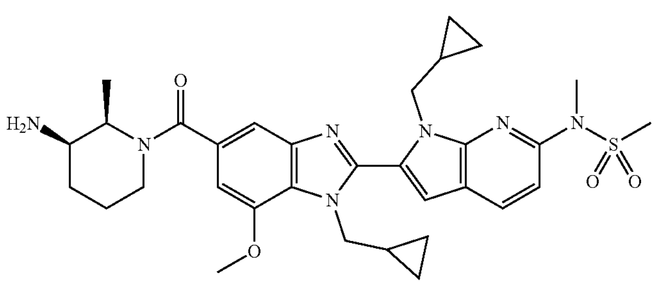 [SMILES: COc1cc(C(=O)N2CCC[C@@H](N)[C@H]2C)cc2nc(-c3cc4ccc(N(C)S(C)(=O)=O)nc4n3CC3CC3)n(CC3CC3)c12] | N-(2-(5-((2R,3R)-3-amino-2-methylpiperidine-1-carbonyl)-1-(cyclopropylmethyl)-7-methoxy-1H-benzo[d]imidazol-2-yl)-1-(cyclopropylmethyl)-1H-pyrrolo[2,3-b]pyridin-6-yl)-N-methylmethanesulfonamide | 620.3 |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 25 | 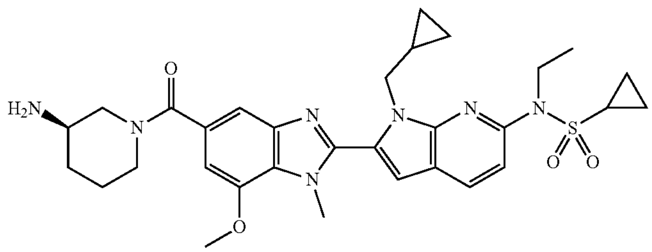 [SMILES: CCN(c1ccc2cc(-c3nc4cc(C(=O)N5CCC[C@@H](N)C5)cc(OC)c4n3C)n(CC3CC3)c2n1)S(=O)(=O)C1CC1] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-ethylcyclopropanesulfonamide | 606.60 |
| 26 | 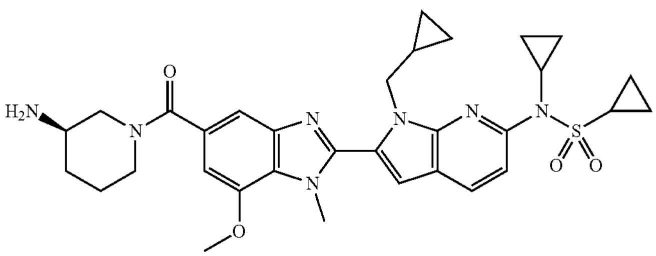 [SMILES: COc1cc(C(=O)N2CCC[C@@H](N)C2)cc2nc(-c3cc4ccc(N(C5CC5)S(=O)(=O)C5CC5)nc4n3CC3CC3)n(C)c12] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-cyclopropylcyclopropanesulfonamide | 618.59 |
| 27 | 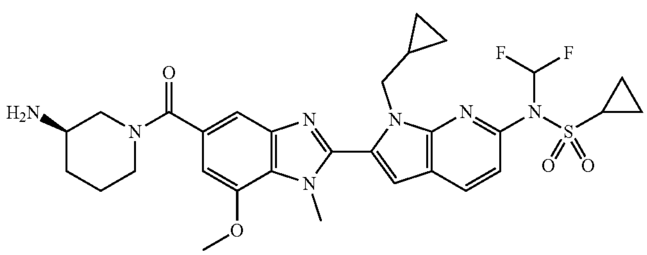 [SMILES: COc1cc(C(=O)N2CCC[C@@H](N)C2)cc2nc(-c3cc4ccc(N(C(F)F)S(=O)(=O)C5CC5)nc4n3CC3CC3)n(C)c12] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl)cyclopropanesulfonamide | 628.59 |
| 28 | 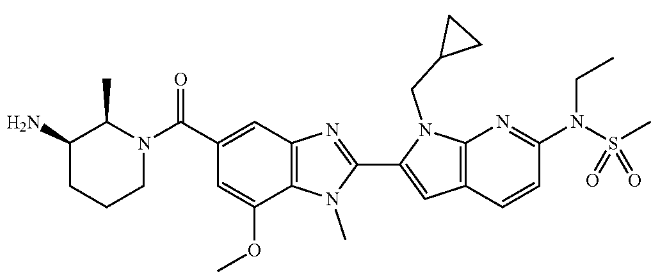 [SMILES: CCN(c1ccc2cc(-c3nc4cc(C(=O)N5CCC[C@@H](N)[C@H]5C)cc(OC)c4n3C)n(CC3CC3)c2n1)S(C)(=O)=O] | N-(2-(5-((2R,3R)-3-amino-2-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-ethylmethanesulfonamide | 594.59 |
| 29 | 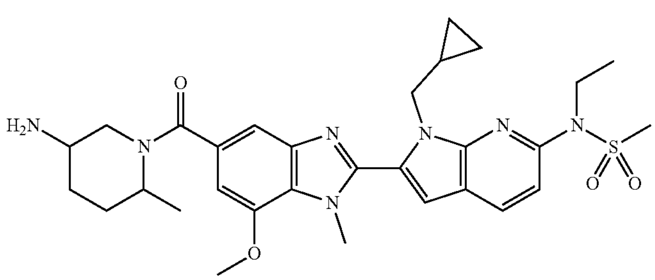 [SMILES: CCN(c1ccc2cc(-c3nc4cc(C(=O)N5CC(N)CCC5C)cc(OC)c4n3C)n(CC3CC3)c2n1)S(C)(=O)=O] | N-(2-(5-(5-amino-2-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-ethylmethanesulfonamide | 594.32 |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 30 | 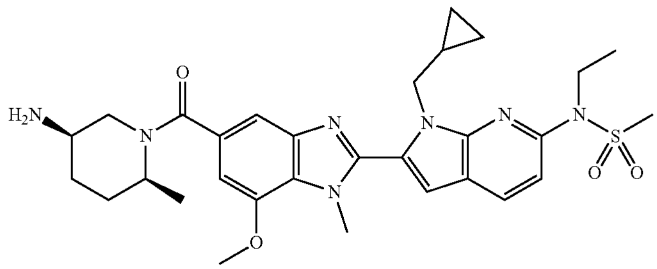 [SMILES: CCN(c1ccc2cc(-c3nc4cc(C(=O)N5C[C@H](N)CC[C@@H]5C)cc(OC)c4n3C)n(CC3CC3)c2n1)S(C)(=O)=O] | N-(2-(5-(((2S,5R)-5-amino-2-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-ethylmethanesulfonamide | 594.32 |
| 31 | 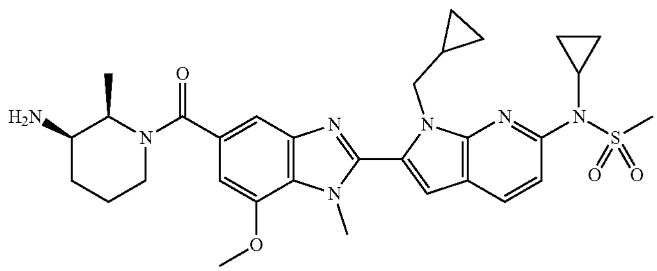 [SMILES: COc1cc(C(=O)N2CCC[C@@H](N)[C@H]2C)cc2nc(-c3cc4ccc(N(C5CC5)S(C)(=O)=O)nc4n3CC3CC3)n(C)c12] | N-(2-(5-(((2R,3R)-3-amino-2-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-cyclopropylmethanesulfonamide | 606.4 |
| 32 | 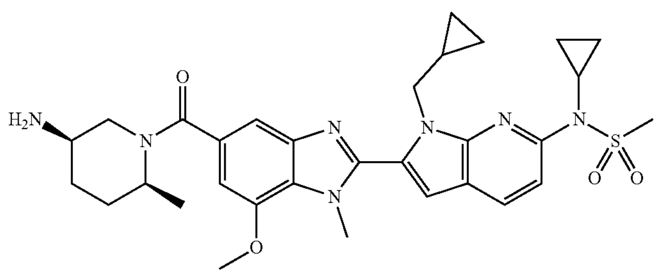 [SMILES: COc1cc(C(=O)N2C[C@H](N)CC[C@@H]2C)cc2nc(-c3cc4ccc(N(C5CC5)S(C)(=O)=O)nc4n3CC3CC3)n(C)c12] | N-(2-(5-(((2S,5R)-5-amino-2-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-cyclopropylmethanesulfonamide | 606.4 |
| 33 | 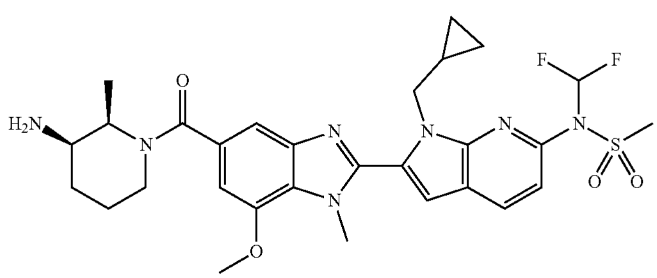 [SMILES: COc1cc(C(=O)N2CCC[C@@H](N)[C@H]2C)cc2nc(-c3cc4ccc(N(C(F)F)S(C)(=O)=O)nc4n3CC3CC3)n(C)c12] | N-(2-(5-(((2R,3R)-3-amino-2-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide | 616.32 |
| 34 | 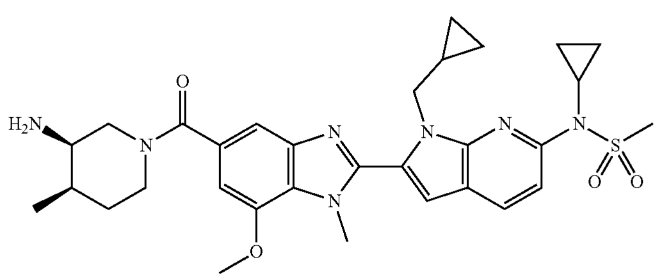 [SMILES: COc1cc(C(=O)N2CC[C@@H](C)[C@@H](N)C2)cc2nc(-c3cc4ccc(N(C5CC5)S(C)(=O)=O)nc4n3CC3CC3)n(C)c12] | N-(2-(5-(((3R,4R)-3-amino-4-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-cyclopropylmethanesulfonamide | 606.5 |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 35 | 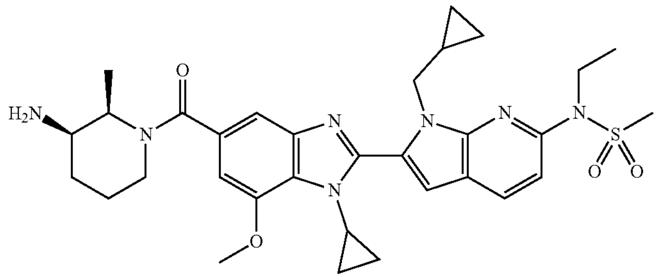 [SMILES: CCN(c1ccc2cc(-c3nc4cc(C(=O)N5CCC[C@@H](N)[C@H]5C)cc(OC)c4n3C3CC3)n(CC3CC3)c2n1)S(C)(=O)=O] | N-(2-(5-((2R,3R)-3-amino-2-methylpiperidine-1-carbonyl)-1-cyclopropyl-7-methoxy-1H-benzo[d]imidazol-2-yl)-1-(cyclopropylmethyl)-1H-pyrrolo[2,3-b]pyridin-6-yl)-N-ethylmethanesulfonamide | 620.33 |
| 36 | 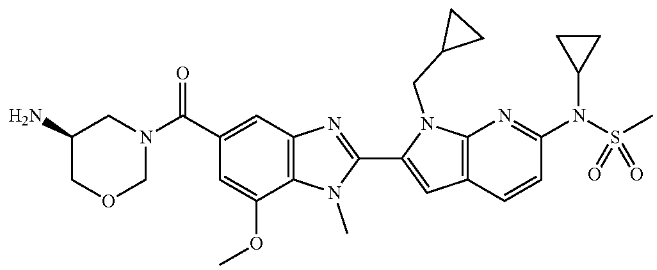 [SMILES: COc1cc(C(=O)N2COC[C@@H](N)C2)cc2nc(-c3cc4ccc(N(C5CC5)S(C)(=O)=O)nc4n3CC3CC3)n(C)c12] | (S)-N-(2-(5-(5-amino-1,3-oxazinane-3-carbonyl)-7-methoxy-1-methyl-1H-benzo[d]imidazol-2-yl)-1-(cyclopropylmethyl)-1H-pyrrolo[2,3-b]pyridin-6-yl)-N-cyclopropylmethanesulfonamide | 594.3 |
| 37 | 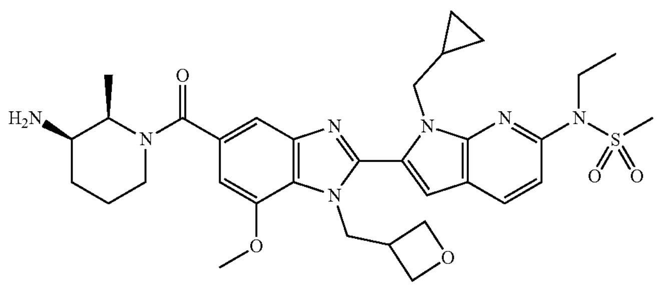 [SMILES: CCN(c1ccc2cc(-c3nc4cc(C(=O)N5CCC[C@@H](N)[C@H]5C)cc(OC)c4n3CC3COC3)n(CC3CC3)c2n1)S(C)(=O)=O] | N-(2-(5-((2R,3R)-3-amino-2-methylpiperidine-1-carbonyl)-7-methoxy-1-(oxetan-3-ylmethyl)-1H-benzo[d]imidazol-2-yl)-1-(cyclopropylmethyl)-1H-pyrrolo[2,3-b]pyridin-6-yl)-N-ethylmethanesulfonamide | 650.35 |
| 38 | 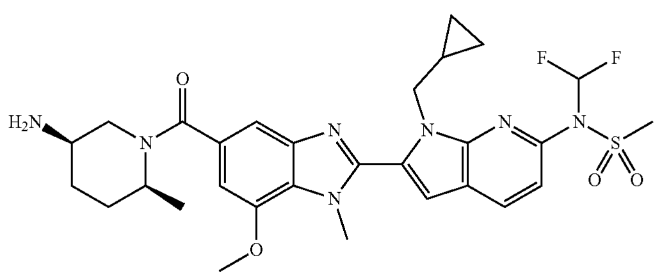 [SMILES: COc1cc(C(=O)N2C[C@H](N)CC[C@@H]2C)cc2nc(-c3cc4ccc(N(C(F)F)S(C)(=O)=O)nc4n3CC3CC3)n(C)c12] | N-(2-(5-((2S,5R)-5-amino-2-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide | 616.24 |
| 39 | 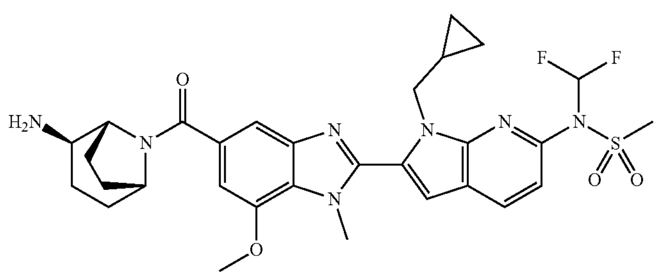 [SMILES: COc1cc(C(=O)N2[C@@H]3CC[C@@H](N)[C@H]2CC3)cc2nc(-c3cc4ccc(N(C(F)F)S(C)(=O)=O)nc4n3CC3CC3)n(C)c12] | N-(2-(5-((1R,2R,5R)-2-amino-8-azabicyclo[3.2.1]octane-8-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide | 628.4 |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 40 | 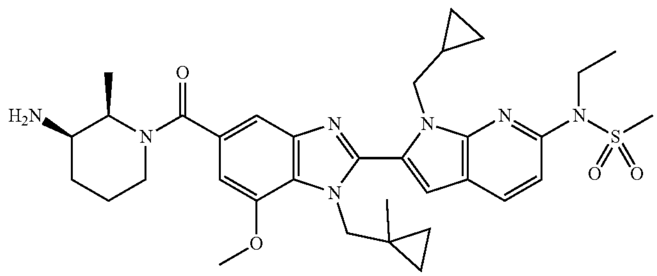 [SMILES: CCN(c1ccc2cc(-c3nc4cc(C(=O)N5CCC[C@@H](N)[C@H]5C)cc(OC)c4n3CC3(C)CC3)n(CC3CC3)c2n1)S(C)(=O)=O] | N-(2-(5-((2R,3R)-3-amino-2-methylpiperidine-1-carbonyl)-7-methoxy-1-((1-methylcyclopropyl)methyl)-1H-benzo[d]imidazol-2-yl)-1-(cyclopropylmethyl)-1H-pyrrolo[2,3-b]pyridin-6-yl)-N-ethylmethanesulfonamide | 648.27 |
| 41 | 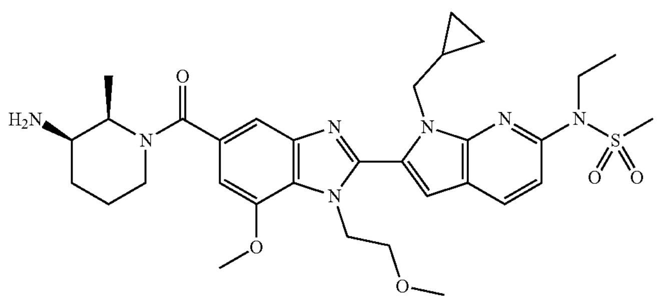 [SMILES: CCN(c1ccc2cc(-c3nc4cc(C(=O)N5CCC[C@@H](N)[C@H]5C)cc(OC)c4n3CCOC)n(CC3CC3)c2n1)S(C)(=O)=O] | N-(2-(5-((2R,3R)-3-amino-2-methylpiperidine-1-carbonyl)-7-methoxy-1-(2-methoxyethyl)-1H-benzo[d]imidazol-2-yl)-1-(cyclopropylmethyl)-1H-pyrrolo[2,3-b]pyridin-6-yl)-N-ethylmethanesulfonamide | 638.34 |
| 42 | 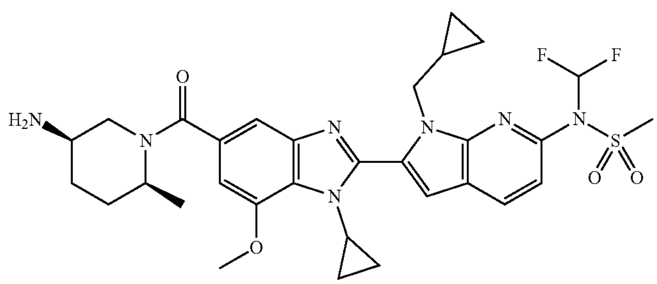 [SMILES: COc1cc(C(=O)N2C[C@H](N)CC[C@@H]2C)cc2nc(-c3cc4ccc(N(C(F)F)S(C)(=O)=O)nc4n3CC3CC3)n(C3CC3)c12] | N-(2-(5-((2S,5R)-5-amino-2-methylpiperidine-1-carbonyl)-1-cyclopropyl-7-methoxy-1H-benzo[d]imidazol-2-yl)-1-(cyclopropylmethyl)-1H-pyrrolo[2,3-b]pyridin-6-yl)-N-(difluoromethyl)methanesulfonamide | 642.36 |
| 43 | 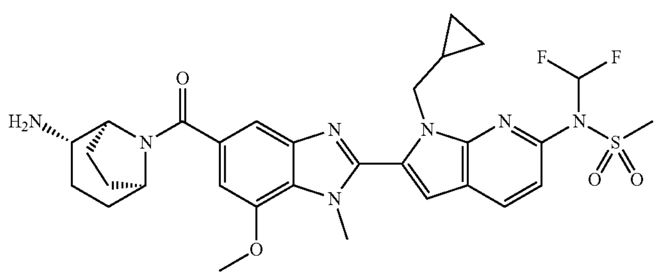 [SMILES: COc1cc(C(=O)N2[C@H]3CC[C@H](N)[C@@H]2CC3)cc2nc(-c3cc4ccc(N(C(F)F)S(C)(=O)=O)nc4n3CC3CC3)n(C)c12] | N-(2-(5-((1S,2S,5S)-2-amino-8-azabicyclo[3.2.1]octane-8-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide | 628.4 |
| 44 | 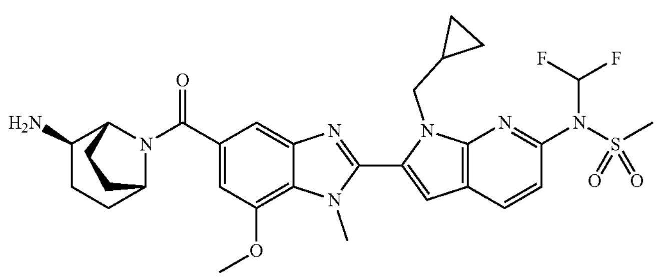 | N-(2-(5-((1R,2R,5R)-2-amino-8-azabicyclo[3.2.1]octane-8-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide | 628.4 |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 45 | 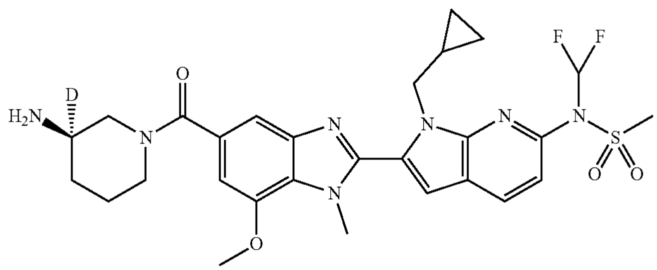 [SMILES: [2H][C@@]1(N)CCCN(C(=O)c2cc(OC)c3c(c2)nc(-c2cc4ccc(N(C(F)F)S(C)(=O)=O)nc4n2CC2CC2)n3C)C1] | (R)-N-(2-(5-(3-aminopiperidine-1-carbonyl-3-d)-7-methoxy-1-methyl-1H-benzo[d]imidazol-2-yl)-1-(cyclopropylmethyl)-1H-pyrrolo[2,3-b]pyridin-6-yl)-N-(difluoromethyl) methanesulfonamide | 603.3 |
| 46 | 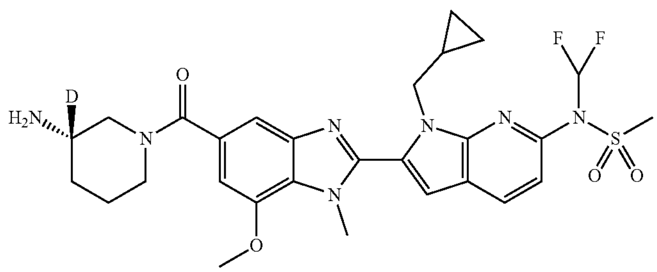 [SMILES: [2H][C@]1(N)CCCN(C(=O)c2cc(OC)c3c(c2)nc(-c2cc4ccc(N(C(F)F)S(C)(=O)=O)nc4n2CC2CC2)n3C)C1] | (S)-N-(2-(5-(3-aminopiperidine-1-carbonyl-3-d)-7-methoxy-1-methyl-1H-benzo[d]imidazol-2-yl)-1-(cyclopropylmethyl)-1H-pyrrolo[2,3-b]pyridin-6-yl)-N-(difluoromethyl) methanesulfonamide | 603.3 |
| 47 | 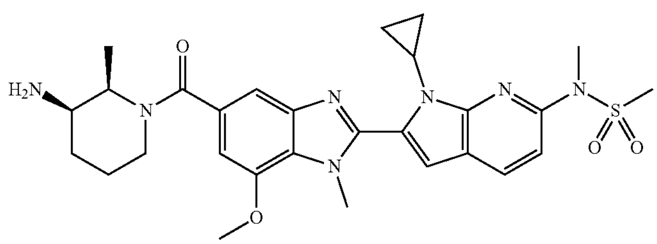 [SMILES: COc1cc(C(=O)N2CCC[C@@H](N)[C@H]2C)cc2nc(-c3cc4ccc(N(C)S(C)(=O)=O)nc4n3C3CC3)n(C)c12] | N-(2-(5-((2R,3R)-3-amino-2-methylpiperidine-1-carbonyl)-7-methoxy-1-methyl-1H-benzo[d]imidazol-2-yl)-1-cyclopropyl-1H-pyrrolo[2,3-b]pyridin-6-yl)-N-methylmethanesulfonamide | 566.32 |
| 48 | 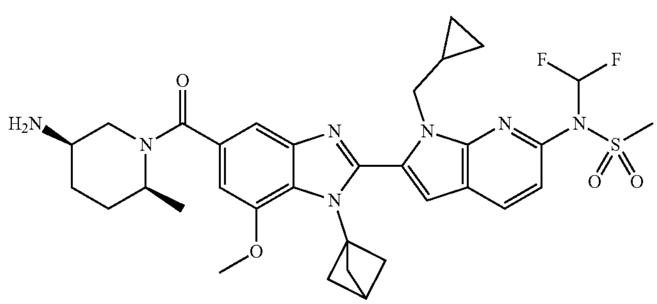 [SMILES: COc1cc(C(=O)N2C[C@H](N)CC[C@@H]2C)cc2nc(-c3cc4ccc(N(C(F)F)S(C)(=O)=O)nc4n3CC3CC3)n(C34CC(C3)C4)c12] | N-(2-(5-((2S,5R)-5-amino-2-methylpiperidine-1-carbonyl)-1-(bicyclo[1.1.1]pentan-1-yl)-7-methoxy-1H-benzo[d]imidazol-2-yl)-1-(cyclopropylmethyl)-1H-pyrrolo[2,3-b]pyridin-6-yl)-N-(difluoromethyl) methane sulfonamide | 668.28 |
| 49 | 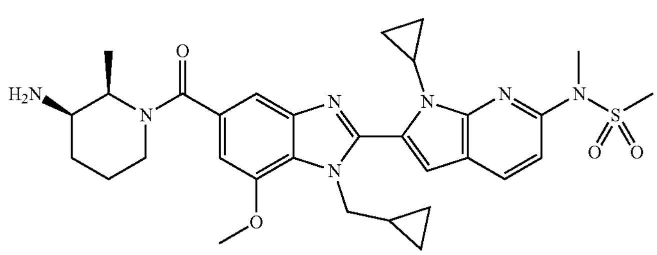 [SMILES: COc1cc(C(=O)N2CCC[C@@H](N)[C@H]2C)cc2nc(-c3cc4ccc(N(C)S(C)(=O)=O)nc4n3C3CC3)n(CC3CC3)c12] | N-(2-(5-((2R,3R)-3-amino-2-methylpiperidine-1-carbonyl)-1-(cyclopropylmethyl)-7-methoxy-1H-benzo[d]imidazol-2-yl)-1-cyclopropyl-1H-pyrrolo[2,3-b]pyridin-6-yl)-N-methylmethanesulfonamide | 606.34 |

TABLE 1a-continued

The compounds below were synthesized according to Procedures 1-9, using intermediates described herein, or intermediates prepared according to General Schemes.

| Ex. | Structure | Name | ES/MS m/z [M + H]⁺ |
|---|---|---|---|
| 50 | 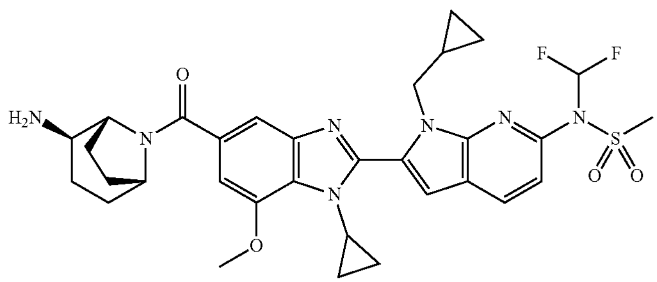 [SMILES: COc1cc(C(=O)N2[C@@H]3CC[C@@H](N)[C@H]2CC3)cc2nc(-c3cc4ccc(N(C(F)F)S(C)(=O)=O)nc4n3CC3CC3)n(C3CC3)c12] | N-(2-(5-((1R,2R,5R)-2-amino-8-azabicyclo[3.2.1]octane-8-carbonyl)-1-cyclopropyl-7-methoxy-1H-benzo[d]imidazol-2-yl)-1-(cyclopropylmethyl)-1H-pyrrolo[2,3-b]pyridin-6-yl)-N-(difluoromethyl)methanesulfonamide | 654.39 |
| 51 | 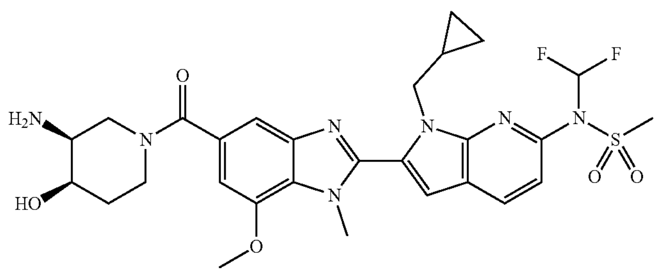 [SMILES: COc1cc(C(=O)N2CC[C@@H](O)[C@@H](N)C2)cc2nc(-c3cc4ccc(N(C(F)F)S(C)(=O)=O)nc4n3CC3CC3)n(C)c12] | N-(2-(5-((3S,4R)-3-amino-4-hydroxypiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide | 618.12 |
| 52 | 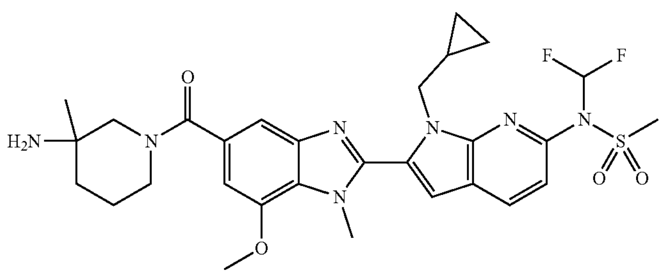 [SMILES: COc1cc(C(=O)N2CCCC(C)(N)C2)cc2nc(-c3cc4ccc(N(C(F)F)S(C)(=O)=O)nc4n3CC3CC3)n(C)c12] | N-(2-(5-(3-amino-3-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide | 616.23 |
| 53 | 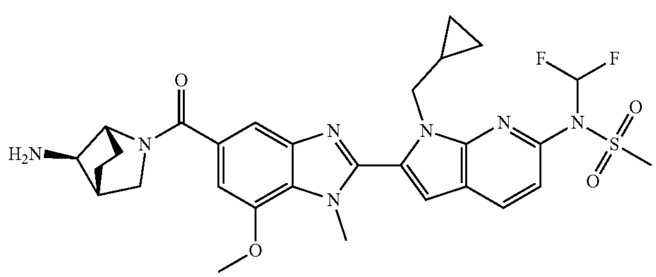 [SMILES: COc1cc(C(=O)N2C[C@H]3CC[C@@H]2[C@@H]3N)cc2nc(-c3cc4ccc(N(C(F)F)S(C)(=O)=O)nc4n3CC3CC3)n(C)c12] | N-(2-(5-((1R,4R,7R)-7-amino-2-azabicyclo[2.2.1]heptane-2-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide | 472 |
| 54 | 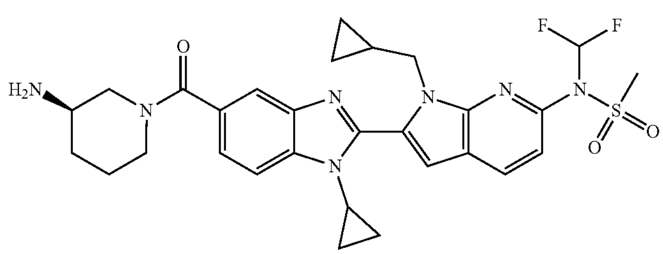 [SMILES: CS(=O)(=O)N(c1ccc2cc(-c3nc4cc(C(=O)N5CCC[C@@H](N)C5)ccc4n3C3CC3)n(CC3CC3)c2n1)C(F)F] | (R)-N-(2-(5-(3-aminopiperidine-1-carbonyl)-1-cyclopropyl-1H-benzo[d]imidazol-2-yl)-1-(cyclopropylmethyl)-1H-pyrrolo[2,3-b]pyridin-6-yl)-N-(difluoromethyl)methanesulfonamide | 598.9 |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 55 | 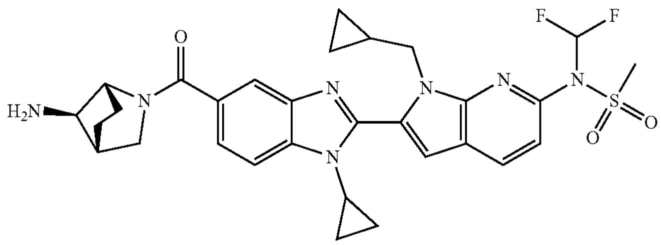 [SMILES: CS(=O)(=O)N(c1ccc2cc(-c3nc4cc(C(=O)N5C[C@H]6CC[C@@H]5[C@@H]6N)ccc4n3C3CC3)n(CC3CC3)c2n1)C(F)F] | N-(2-(5-((1R,4R,7R)-7-amino-2-azabicyclo[2.2.1]heptane-2-carbonyl)-1-cyclopropyl-1H-benzo[d]imidazol-2-yl)-1-(cyclopropylmethyl)-1H-pyrrolo[2,3-b]pyridin-6-yl)-N-(difluoromethyl)methanesulfonamide | 611 |
| 56 | 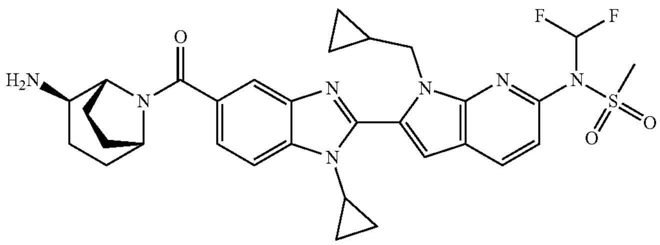 | N-(2-(5-((1R,2R,5R)-2-amino-8-azabicyclo[3.2.1]octane-8-carbonyl)-1-cyclopropyl-1H-benzo[d]imidazol-2-yl)-1-(cyclopropylmethyl)-1H-pyrrolo[2,3-b]pyridin-6-yl)-N-(difluoromethyl)methanesulfonamide | 624.4 |
| 57 | 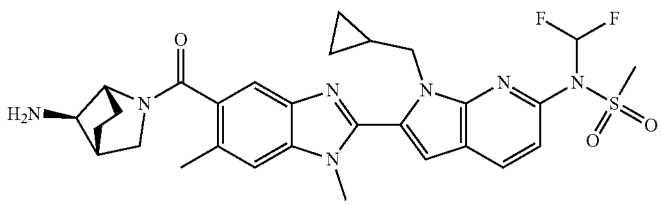 [SMILES: Cc1cc2c(cc1C(=O)N1C[C@H]3CC[C@@H]1[C@@H]3N)nc(-c1cc3ccc(N(C(F)F)S(C)(=O)=O)nc3n1CC1CC1)n2C] | N-(2-(5-((1R,4R,7R)-7-amino-2-azabicyclo[2.2.1]heptane-2-carbonyl)-1,6-dimethyl-1H-benzo[d]imidazol-2-yl)-1-(cyclopropylmethyl)-1H-pyrrolo[2,3-b]pyridin-6-yl)-N-(difluoromethyl)methanesulfonamide | 598.8 |
| 58 | 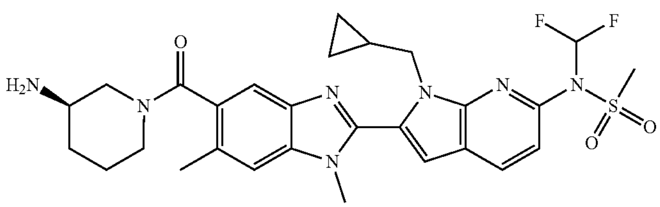 [SMILES: Cc1cc2c(cc1C(=O)N1CCC[C@@H](N)C1)nc(-c1cc3ccc(N(C(F)F)S(C)(=O)=O)nc3n1CC1CC1)n2C] | (R)-N-(2-(5-(3-aminopiperidine-1-carbonyl)-1,6-dimethyl-1H-benzo[d]imidazol-2-yl)-1-(cyclopropylmethyl)-1H-pyrrolo[2,3-b]pyridin-6-yl)-N-(difluoromethyl)methanesulfonamide | 586.7 |
| 59 | 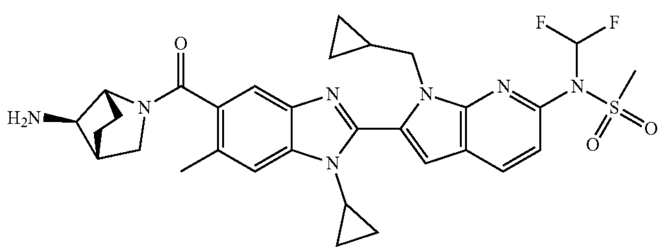 [SMILES: Cc1cc2c(cc1C(=O)N1C[C@H]3CC[C@@H]1[C@@H]3N)nc(-c1cc3ccc(N(C(F)F)S(C)(=O)=O)nc3n1CC1CC1)n2C1CC1] | N-(2-(5-((1R,4R,7R)-7-amino-2-azabicyclo[2.2.1]heptane-2-carbonyl)-1-cyclopropyl-6-methyl-1H-benzo[d]imidazol-2-yl)-1-(cyclopropylmethyl)-1H-pyrrolo[2,3-b]pyridin-6-yl)-N-(difluoromethyl)methanesulfonamide | 625 |
| 60 | 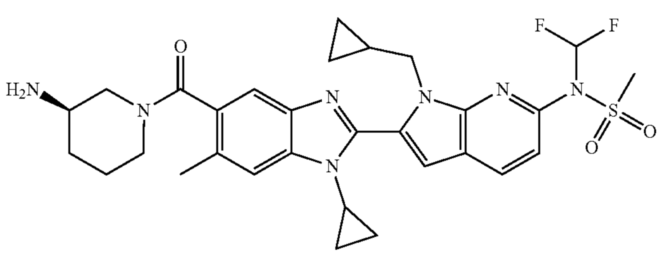 [SMILES: Cc1cc2c(cc1C(=O)N1CCC[C@@H](N)C1)nc(-c1cc3ccc(N(C(F)F)S(C)(=O)=O)nc3n1CC1CC1)n2C1CC1] | (R)-N-(2-(5-(3-aminopiperidine-1-carbonyl)-1-cyclopropyl-6-methyl-1H-benzo[d]imidazol-2-yl)-1-(cyclopropylmethyl)-1H-pyrrolo[2,3-b]pyridin-6-yl)-N-(difluoromethyl)methanesulfonamide | 612.9 |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 61 | 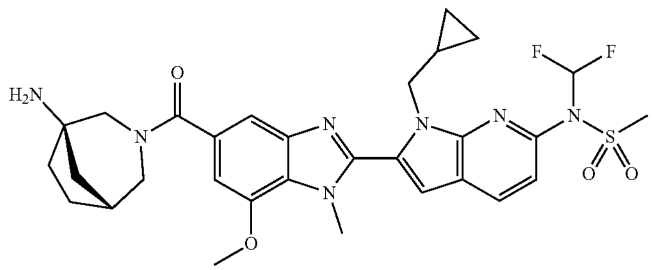 [SMILES: COc1cc(C(=O)N2C[C@@H]3CC[C@@](N)(C3)C2)cc2nc(-c3cc4ccc(N(C(F)F)S(C)(=O)=O)nc4n3CC3CC3)n(C)c12] | N-(2-(5-(((1R,5R)-1-amino-3-azabicyclo[3.2.1]octane-3-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide | 628.3 |
| 62 | 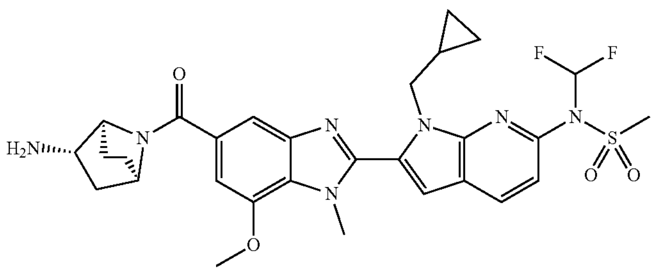 [SMILES: COc1cc(C(=O)N2[C@@H]3CC[C@H]2[C@@H](N)C3)cc2nc(-c3cc4ccc(N(C(F)F)S(C)(=O)=O)nc4n3CC3CC3)n(C)c12] | N-(2-(5-(((1S,2S,4R)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide | 614.3 |
| 63 | 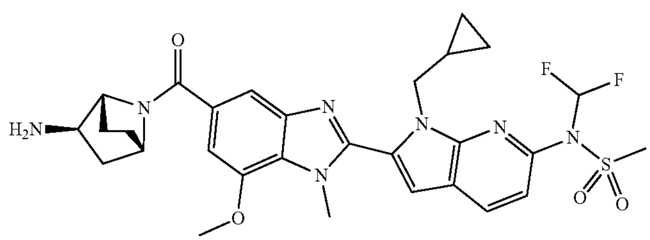 [SMILES: COc1cc(C(=O)N2[C@H]3CC[C@@H]2[C@H](N)C3)cc2nc(-c3cc4ccc(N(C(F)F)S(C)(=O)=O)nc4n3CC3CC3)n(C)c12] | N-(2-(5-(((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide | 614.2 |
| 64 | 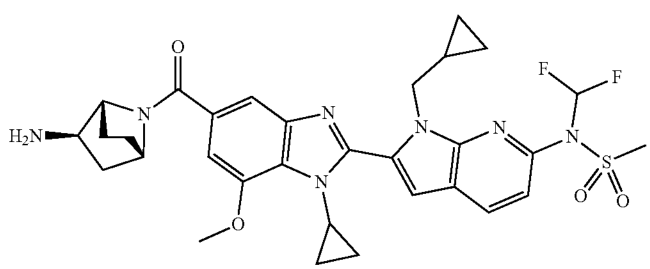 [SMILES: COc1cc(C(=O)N2[C@H]3CC[C@@H]2[C@H](N)C3)cc2nc(-c3cc4ccc(N(C(F)F)S(C)(=O)=O)nc4n3CC3CC3)n(C3CC3)c12] | N-(2-(5-(((1R,2R,4S)-2-amino-7-azabicyclo[2.2.1]heptane-7-carbonyl)-1-cyclopropyl-7-methoxy-1H-benzo[d]imidazol-2-yl)-1-(cyclopropylmethyl)-1H-pyrrolo[2,3-b]pyridin-6-yl)-N-(difluoromethyl)methanesulfonamide | 640.2 |
| 65 | 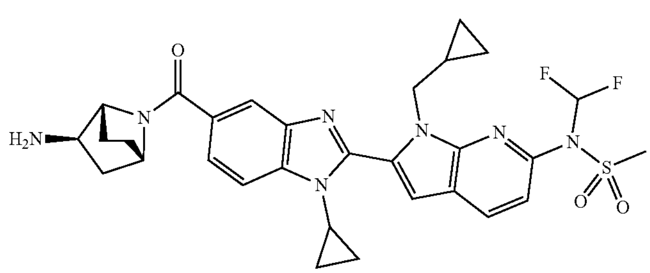 [SMILES: CS(=O)(=O)N(c1ccc2cc(-c3nc4cc(C(=O)N5[C@H]6CC[C@@H]5[C@H](N)C6)ccc4n3C3CC3)n(CC3CC3)c2n1)C(F)F] | N-(2-(5-(((1R,2R,4S)-2-amino-7-azabicyclo[2.2.1]heptane-7-carbonyl)-1-cyclopropyl-1H-benzo[d]imidazol-2-yl)-1-(cyclopropylmethyl)-1H-pyrrolo[2,3-b]pyridin-6-yl)-N-(difluoromethyl)methanesulfonamide | 610.23 |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 66 | 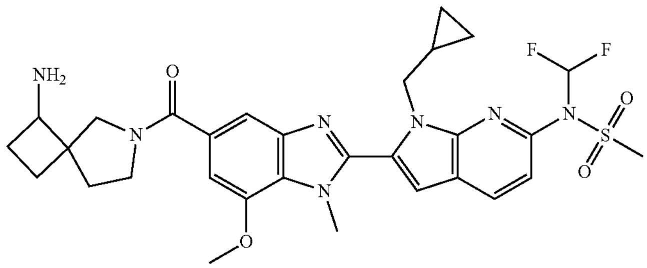 [SMILES: COc1cc(C(=O)N2CCC3(CCC3N)C2)cc2nc(-c3cc4ccc(N(C(F)F)S(C)(=O)=O)nc4n3CC3CC3)n(C)c12] | N-(2-(5-(1-amino-6-azaspiro[3.4]octane-6-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide | 628.24 |
| 67 | 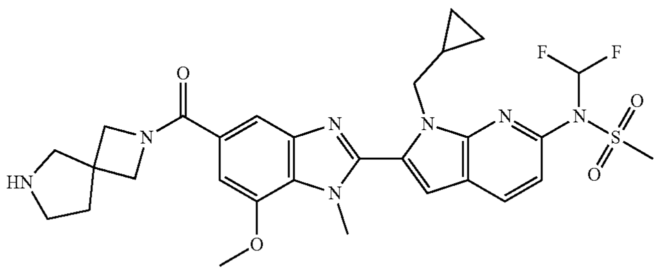 [SMILES: COc1cc(C(=O)N2CC3(CCNC3)C2)cc2nc(-c3cc4ccc(N(C(F)F)S(C)(=O)=O)nc4n3CC3CC3)n(C)c12] | N-(1-(cyclopropylmethyl)-2-(7-methoxy-1-methyl-5-(2,6-diazaspiro[3.4]octane-2-carbonyl)-1H-benzo[d]imidazol-2-yl)-1H-pyrrolo[2,3-b]pyridin-6-yl)-N-(difluoromethyl)methanesulfonamide | 614.26 |
| 68 | 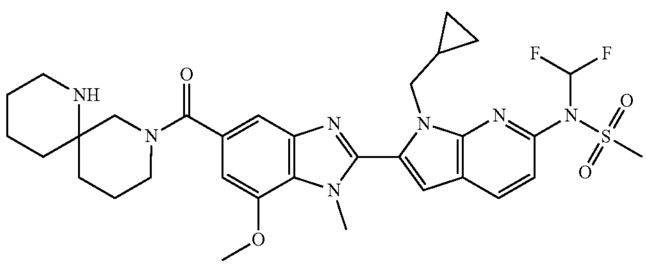 [SMILES: COc1cc(C(=O)N2CCCC3(CCCCN3)C2)cc2nc(-c3cc4ccc(N(C(F)F)S(C)(=O)=O)nc4n3CC3CC3)n(C)c12] | N-(1-(cyclopropylmethyl)-2-(7-methoxy-1-methyl-5-(1,8-diazaspiro[5.5]undecane-8-carbonyl)-1H-benzo[d]imidazol-2-yl)-1H-pyrrolo[2,3-b]pyridin-6-yl)-N-(difluoromethyl)methanesulfonamide | 656.28 |
| 69 | 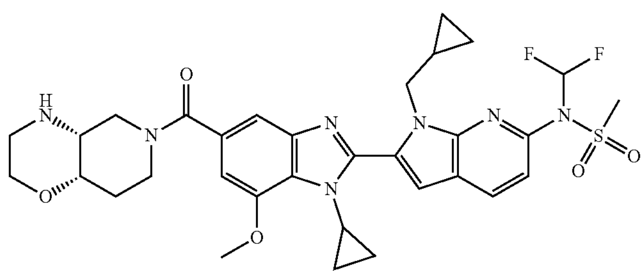 [SMILES: COc1cc(C(=O)N2CC[C@@H]3OCCN[C@@H]3C2)cc2nc(-c3cc4ccc(N(C(F)F)S(C)(=O)=O)nc4n3CC3CC3)n(C3CC3)c12] | N-(2-(1-cyclopropyl-7-methoxy-5-((4aR,8aS)-octahydro-2H-pyrido[4,3-b][1,4]oxazine-6-carbonyl)-1H-benzo[d]imidazol-2-yl)-1-(cyclopropylmethyl)-1H-pyrrolo[2,3-b]pyridin-6-yl)-N-(difluoromethyl)methanesulfonamide | 670.26 |
| 70 | 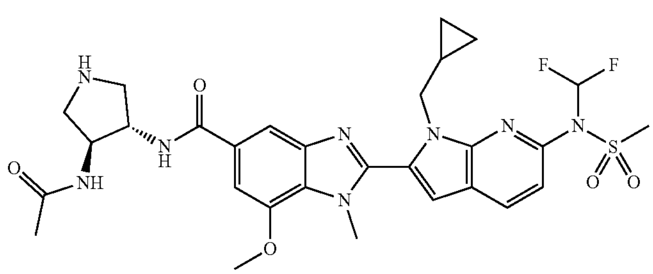 [SMILES: COc1cc(C(=O)N[C@H]2CNC[C@@H]2NC(C)=O)cc2nc(-c3cc4ccc(N(C(F)F)S(C)(=O)=O)nc4n3CC3CC3)n(C)c12] | N-((3S,4S)-4-acetamidopyrrolidin-3-yl)-2-(1-(cyclopropylmethyl)-6-((N-(difluoromethyl)methyl)sulfonamido)-1H-pyrrolo[2,3-b]pyridin-2-yl)-7-methoxy-1-methyl-1H-benzo[d]imidazole-5-carboxamide | 645.1 |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 71 | 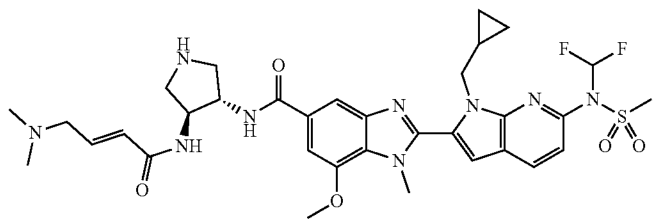 | 2-[1-(cyclopropylmethyl)-6-[difluoromethyl (methylsulfonyl) amino]pyrrolo[2,3-b]pyridin-2-yl]-N-(3R,4R)-4-[[(E)-4-(dimethylamino)but-2-enoyl]amino]pyrrolidin-3-yl]-7-methoxy-1-methyl-benzimidazole-5-carboxamide | 714.2 |
| 72 | 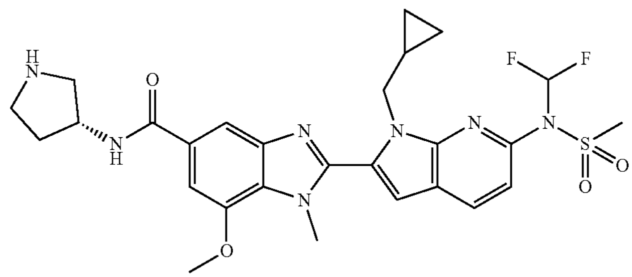 [SMILES: COc1cc(C(=O)N[C@@H]2CCNC2)cc2nc(-c3cc4ccc(N(C(F)F)S(C)(=O)=O)nc4n3CC3CC3)n(C)c12] | (R)-2-(1-(cyclopropylmethyl)-6-((N-(difluoromethyl)methyl) sulfonamido)-1H-pyrrolo[2,3-b]pyridin-2-yl)-7-methoxy-1-methyl-N-(pyrrolidin-3-yl)-1H-benzo[d]imidazole-5-carboxamide | 588.1 |
| 73 | 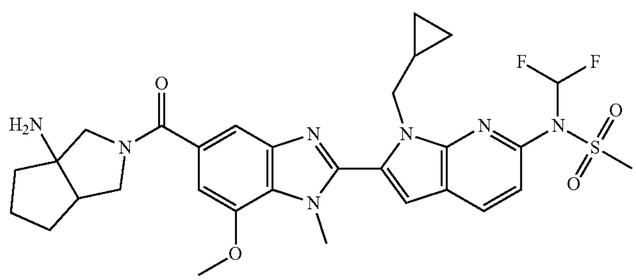 [SMILES: COc1cc(C(=O)N2CC3CCCC3(N)C2)cc2nc(-c3cc4ccc(N(C(F)F)S(C)(=O)=O)nc4n3CC3CC3)n(C)c12] | N-(2-(5-(3a-aminooctahydrocyclopenta[c]pyrrole-2-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl) methanesulfonamide | 628.2 |
| 74 | 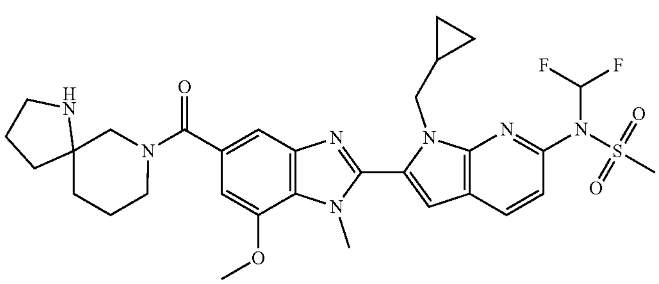 [SMILES: COc1cc(C(=O)N2CCCC3(CCCN3)C2)cc2nc(-c3cc4ccc(N(C(F)F)S(C)(=O)=O)nc4n3CC3CC3)n(C)c12] | N-(1-(cyclopropylmethyl)-2-(7-methoxy-1-methyl-5-(1,7-diazaspiro[4.5]decane-7-carbonyl)-1H-benzo[d]imidazol-2-yl)-1H-pyrrolo[2,3-b]pyridin-6-yl)-N-(difluoromethyl) methanesulfonamide | 642.22 |
| 75 | 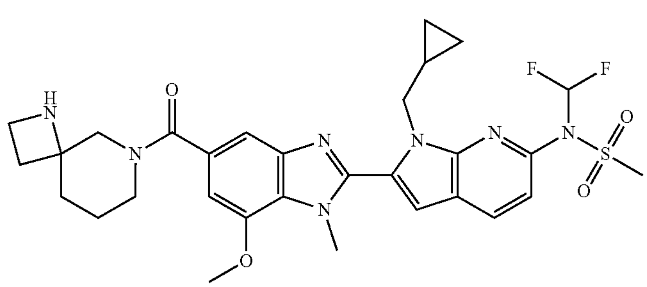 [SMILES: COc1cc(C(=O)N2CCCC3(CCN3)C2)cc2nc(-c3cc4ccc(N(C(F)F)S(C)(=O)=O)nc4n3CC3CC3)n(C)c12] | N-(1-(cyclopropylmethyl)-2-(7-methoxy-1-methyl-5-(1,6-diazaspiro[3.5]nonane-6-carbonyl)-1H-benzo[d]imidazol-2-yl)-1H-pyrrolo[2,3-b]pyridin-6-yl)-N-(difluoromethyl) methanesulfonamide | 628.14 |

TABLE 1a-continued

The compounds below were synthesized according to Procedures 1-9, using
intermediates described herein, or intermediates prepared according to General Schemes.

| Ex. | Structure | Name | ES/MS m/z [M + H]+ |
|---|---|---|---|
| 76 | 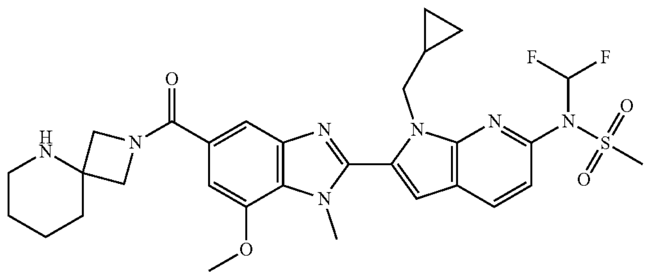 [SMILES: COc1cc(C(=O)N2CC3(CCCCN3)C2)cc2nc(-c3cc4ccc(N(C(F)F)S(C)(=O)=O)nc4n3CC3CC3)n(C)c12] | N-(1-(cyclopropylmethyl)-2-(7-methoxy-1-methyl-5-(2,5-diazaspiro[3.5]nonane-2-carbonyl)-1H-benzo[d]imidazol-2-yl)-1H-pyrrolo[2,3-b]pyridin-6-yl)-N-(difluoromethyl)methanesulfonamide | 628.17 |
| 77 | 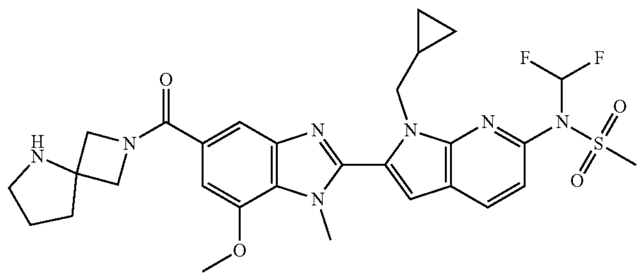 [SMILES: COc1cc(C(=O)N2CC3(CCCN3)C2)cc2nc(-c3cc4ccc(N(C(F)F)S(C)(=O)=O)nc4n3CC3CC3)n(C)c12] | N-(1-(cyclopropylmethyl)-2-(7-methoxy-1-methyl-5-(2,5-diazaspiro[3.4]octane-2-carbonyl)-1H-benzo[d]imidazol-2-yl)-1H-pyrrolo[2,3-b]pyridin-6-yl)-N-(difluoromethyl)methanesulfonamide | 614.09 |
| 78 | 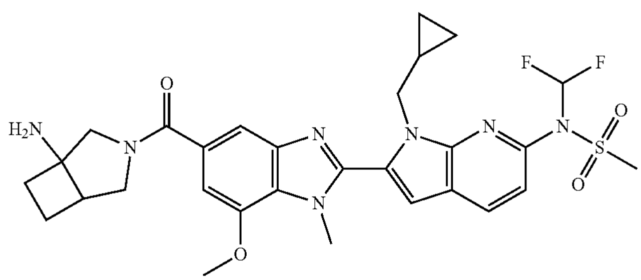 [SMILES: COc1cc(C(=O)N2CC3CCC3(N)C2)cc2nc(-c3cc4ccc(N(C(F)F)S(C)(=O)=O)nc4n3CC3CC3)n(C)c12] | N-(2-(5-(1-amino-3-azabicyclo[3.2.0]heptane-3-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide | 614.16 |
| 79 | 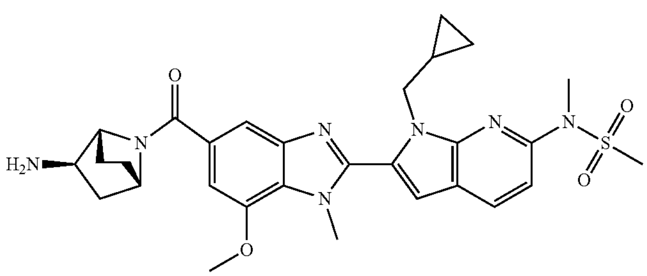 [SMILES: COc1cc(C(=O)N2[C@H]3CC[C@@H]2[C@H](N)C3)cc2nc(-c3cc4ccc(N(C)S(C)(=O)=O)nc4n3CC3CC3)n(C)c12] | N-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)-N-methylmethanesulfonamide | 578.22 |
| 80 | 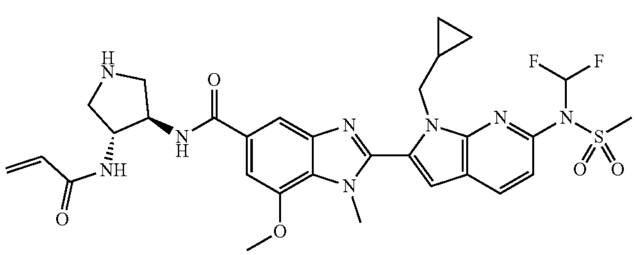 [SMILES: C=CC(=O)N[C@@H]1CNC[C@H]1NC(=O)c1cc(OC)c2c(c1)nc(-c1cc3ccc(N(C(F)F)S(C)(=O)=O)nc3n1CC1CC1)n2C] | N-((3R,4R)-4-acrylamidopyrrolidin-3-yl)-2-(1-(cyclopropylmethyl)-6-((N-(difluoromethyl)methyl)sulfonamido)-1H-pyrrolo[2,3-b]pyridin-2-yl)-7-methoxy-1-methyl-1H-benzo[d]imidazole-5-carboxamide | 657.1 |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 81 | 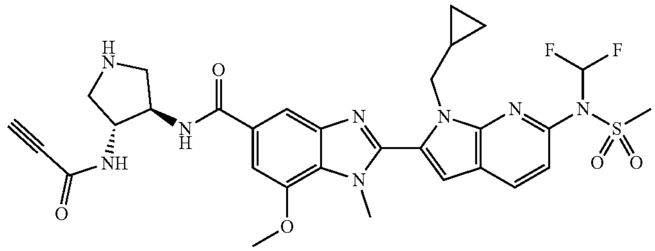 [SMILES: C#CC(=O)N[C@@H]1CNC[C@H]1NC(=O)c1cc(OC)c2c(c1)nc(-c1cc3ccc(N(C(F)F)S(C)(=O)=O)nc3n1CC1CC1)n2C] | 2-(1-(cyclopropylmethyl)-6-((N-(difluoromethyl)methyl)sulfonamido)-1H-pyrrolo[2,3-b]pyridin-2-yl)-7-methoxy-1-methyl-N-((3R,4R)-4-propiolamidopyrrolidin-3-yl)-1H-benzo[d]imidazole-5-carboxamide | 655.1 |
| 82 | 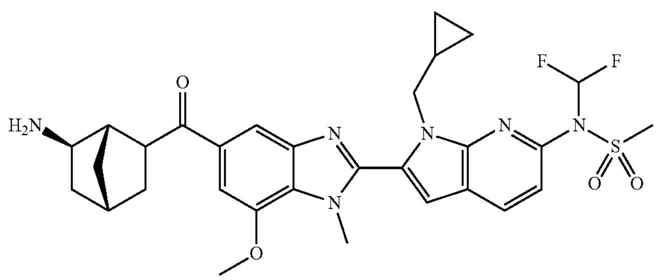 [SMILES: COc1cc(C(=O)C2C[C@@H]3C[C@@H](N)[C@H]2C3)cc2nc(-c3cc4ccc(N(C(F)F)S(C)(=O)=O)nc4n3CC3CC3)n(C)c12] | N-(2-(5-((1R,4R,6R)-6-amino-2-azabicyclo[2.2.1]heptane-2-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide | 614.1 |
| 83 | 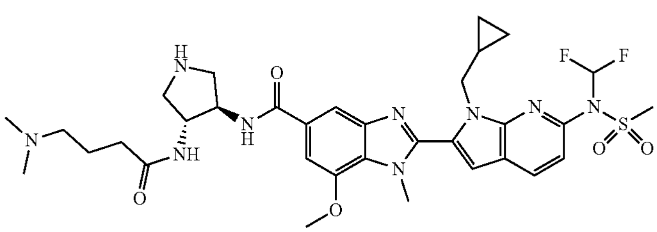 | 2-(1-(cyclopropylmethyl)-6-((N-(difluoromethyl)methyl)sulfonamido)-1H-pyrrolo[2,3-b]pyridin-2-yl)-N-((3R,4R)-4-(4-(dimethylamino)butanamido)pyrrolidin-3-yl)-7-methoxy-1-methyl-1H-benzo[d]imidazole-5-carboxamide | 716.2 |
| 84 | 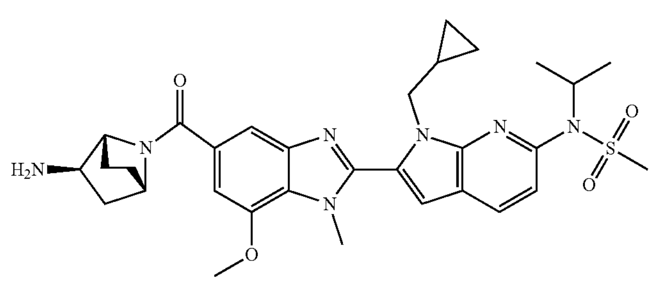 [SMILES: COc1cc(C(=O)N2[C@H]3CC[C@@H]2[C@H](N)C3)cc2nc(-c3cc4ccc(N(C(C)C)S(C)(=O)=O)nc4n3CC3CC3)n(C)c12] | N-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)-N-isopropylmethanesulfonamide | 606.25 |
| 85 | 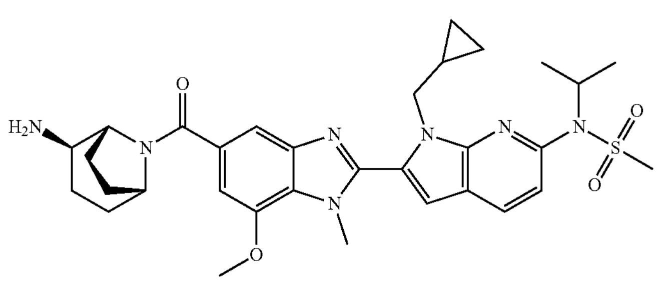 | N-(2-(5-((1R,2R,5R)-2-amino-8-azabicyclo[3.2.1]octane-8-carbonyl)-7-methoxy-1-methyl-1H-benzo[d]imidazol-2-yl)-1-(cyclopropylmethyl)-1H-pyrrolo[2,3-b]pyridin-6-yl)-N-isopropyl-methanesulfonamide | 620.27 |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 86 | 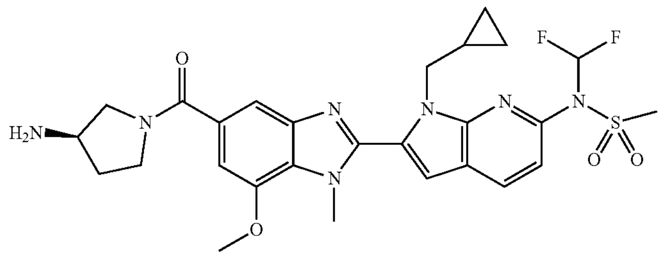 [SMILES: COc1cc(C(=O)N2CC[C@@H](N)C2)cc2nc(-c3cc4ccc(N(C(F)F)S(C)(=O)=O)nc4n3CC3CC3)n(C)c12] | (R)-N-(2-(5-(3-aminopyrrolidine-1-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide | 588.2 |
| 87 | 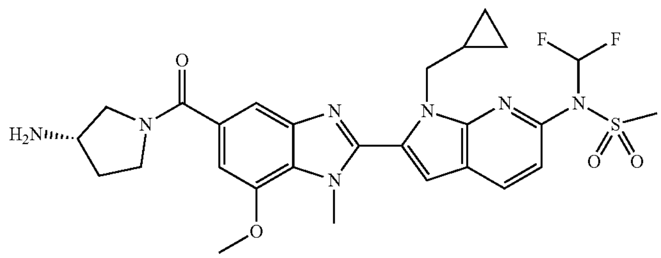 [SMILES: COc1cc(C(=O)N2CC[C@H](N)C2)cc2nc(-c3cc4ccc(N(C(F)F)S(C)(=O)=O)nc4n3CC3CC3)n(C)c12] | (S)-N-(2-(5-(3-aminopyrrolidine-1-carbonyl)-7-methoxy-1-methyl-1H-benzo[d]imidazol-2-yl)-1-(cyclopropylmethyl)-1H-pyrrolo[2,3-b]pyridin-6-yl)-N-(difluoromethyl)methanesulfonamide | 588.2 |
| 88 | 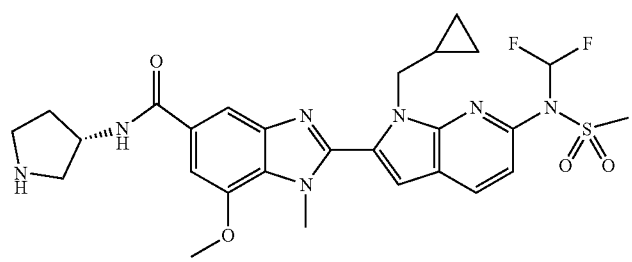 [SMILES: COc1cc(C(=O)N[C@H]2CCNC2)cc2nc(-c3cc4ccc(N(C(F)F)S(C)(=O)=O)nc4n3CC3CC3)n(C)c12] | (S)-2-(1-(cyclopropylmethyl)-6-((N-(difluoromethyl)methyl)sulfonamido)-1H-pyrrolo[2,3-b]pyridin-2-yl)-7-methoxy-1-methyl-N-(pyrrolidin-3-yl)-1H-benzo[d]imidazole-5-carboxamide | 588.1 |
| 89 | 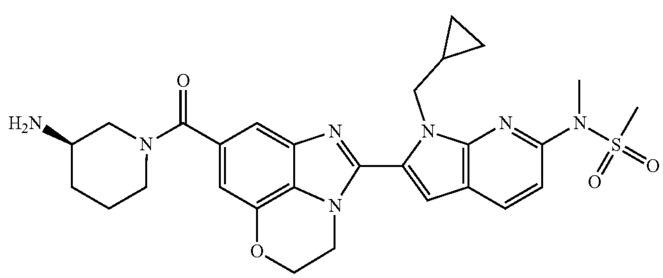 [SMILES: CN(c1ccc2cc(-c3nc4cc(C(=O)N5CCC[C@@H](N)C5)cc5c4n3CCO5)n(CC3CC3)c2n1)S(C)(=O)=O] | (R)-N-(2-(7-(3-aminopiperidine-1-carbonyl)-3,4-dihydro-5-oxa-1,2a-diazaacenaphthylen-2-yl)-1-(cyclopropylmethyl)-1H-pyrrolo[2,3-b]pyridin-6-yl)-N-methylmethanesulfonamide | |
| 90 | 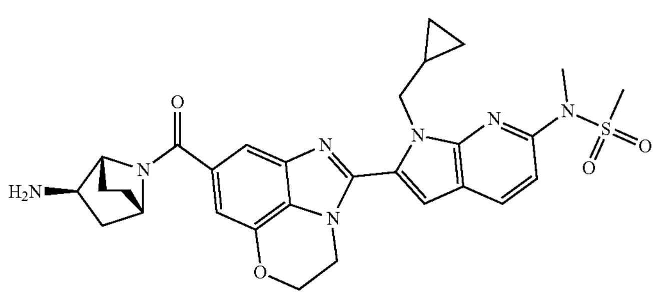 [SMILES: CN(c1ccc2cc(-c3nc4cc(C(=O)N5[C@H]6CC[C@@H]5[C@H](N)C6)cc5c4n3CCO5)n(CC3CC3)c2n1)S(C)(=O)=O] | N-(2-(7-((1R,2R,4S)-2-amino-7-azabicyclo[2.2.1]heptane-7-carbonyl)-3,4-dihydro-5-oxa-1,2a-diazaacenaphthylen-2-yl)-1-(cyclopropylmethyl)-1H-pyrrolo[2,3-b]pyridin-6-yl)-N-methylmethanesulfonamide | |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 91 | 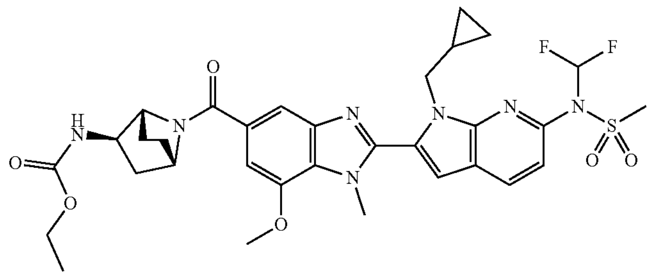 [SMILES: CCOC(=O)N[C@@H]1C[C@@H]2CC[C@H]1N2C(=O)c1cc(OC)c2c(c1)nc(-c1cc3ccc(N(C(F)F)S(C)(=O)=O)nc3n1CC1CC1)n2C] | ethyl N-[(1R,2R,4S)-7-[2-[1-(cyclopropylmethyl)-6-[difluoromethyl(methylsulfonyl)amino]pyrrolo[2,3-b]pyridin-2-yl]-7-methoxy-1-methyl-benzimidazole-5-carbonyl]-7-azabicyclo[2.2.1]heptan-2-yl]carbamate | |
| 92 | 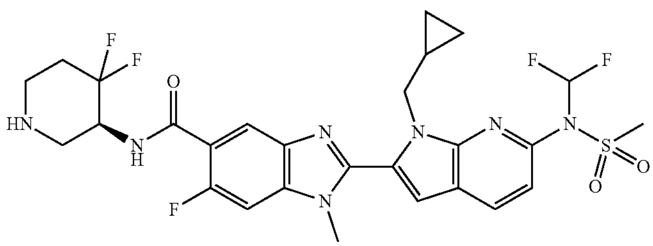 [SMILES: Cn1c(-c2cc3ccc(N(C(F)F)S(C)(=O)=O)nc3n2CC2CC2)nc2cc(C(=O)N[C@H]3CNCCC3(F)F)c(F)cc21] | (S)-2-(1-(cyclopropylmethyl)-6-((N-(difluoromethyl)methyl)sulfonamido)-1H-pyrrolo[2,3-b]pyridin-2-yl)-N-(4,4-difluoropiperidin-3-yl)-6-fluoro-1-methyl-1H-benzo[d]imidazole-5-carboxamide | 608.1 |
| 93 | 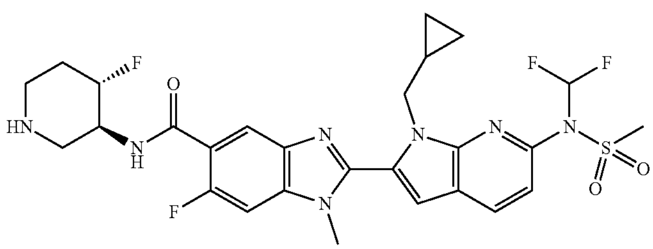 [SMILES: Cn1c(-c2cc3ccc(N(C(F)F)S(C)(=O)=O)nc3n2CC2CC2)nc2cc(C(=O)N[C@H]3CNCC[C@@H]3F)c(F)cc21] | 2-(1-(cyclopropylmethyl)-6-((N-(difluoromethyl)methyl)sulfonamido)-1H-pyrrolo[2,3-b]pyridin-2-yl)-6-fluoro-N-((3S,4S)-4-fluoropiperidin-3-yl)-1-methyl-1H-benzo[d]imidazole-5-carboxamide | 626.1 |
| 94 | 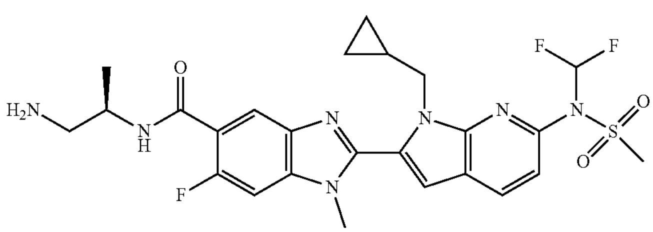 [SMILES: C[C@H](CN)NC(=O)c1cc2nc(-c3cc4ccc(N(C(F)F)S(C)(=O)=O)nc4n3CC3CC3)n(C)c2cc1F] | (R)-N-(1-aminopropan-2-yl)-2-(1-(cyclopropylmethyl)-6-((N-(difluoromethyl)methyl)sulfonamido)-1H-pyrrolo[2,3-b]pyridin-2-yl)-6-fluoro-1-methyl-1H-benzo[d]imidazole-5-carboxamide | 564.1 |
| 95 | 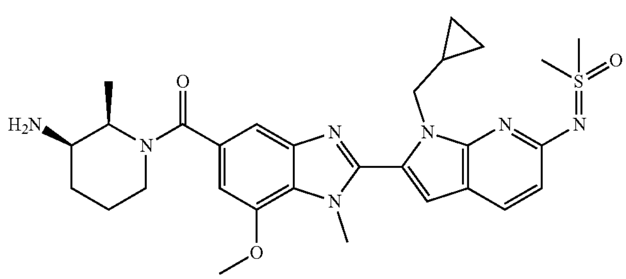 [SMILES: COc1cc(C(=O)N2CCC[C@@H](N)[C@H]2C)cc2nc(-c3cc4ccc(N=S(C)(C)=O)nc4n3CC3CC3)n(C)c12] | ((2-(5-((2R,3R)-3-amino-2-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)imino)dimethyl-16-sulfanone | 564.4 |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 96 | 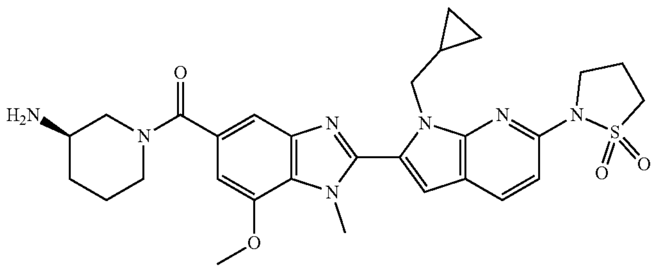 [SMILES: COc1cc(C(=O)N2CCC[C@@H](N)C2)cc2nc(-c3cc4ccc(N5CCCS5(=O)=O)nc4n3CC3CC3)n(C)c12] | (R)-(3-aminopiperidin-1-yl)(2-(1-(cyclopropylmethyl)-6-(1,1-dioxidoisothiazolidin-2-yl)-1H-pyrrolo[2,3-b]pyridin-2-yl)-7-methoxy-1-methyl-1H-benzo[d]imidazol-5-yl)methanone | 578.42 |
| 97 | 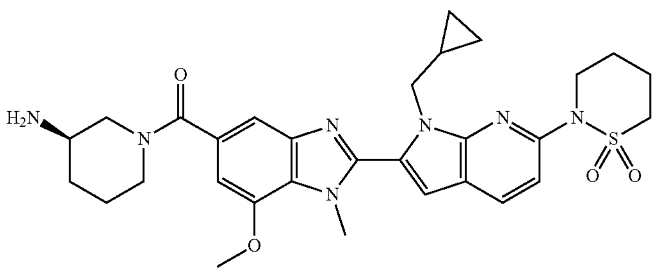 [SMILES: COc1cc(C(=O)N2CCC[C@@H](N)C2)cc2nc(-c3cc4ccc(N5CCCCS5(=O)=O)nc4n3CC3CC3)n(C)c12] | (R)-(3-aminopiperidin-1-yl)(2-(1-(cyclopropylmethyl)-6-(1,1-dioxido-1,2-thiazinan-2-yl)-1H-pyrrolo[2,3-b]pyridin-2-yl)-7-methoxy-1-methyl-1H-benzo[d]imidazol-5-yl)methanone | 592.44 |
| 98 | 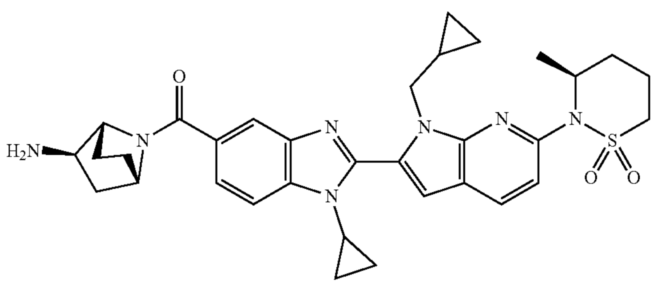 [SMILES: C[C@H]1CCCS(=O)(=O)N1c1ccc2cc(-c3nc4cc(C(=O)N5[C@H]6CC[C@@H]5[C@H](N)C6)ccc4n3C3CC3)n(CC3CC3)c2n1] | ((1R,2R,4S)-2-amino-7-azabicyclo[2.2.1]heptan-7-yl)(1-cyclopropyl-2-(1-(cyclopropylmethyl)-6-((S)-3-methyl-1,1-dioxido-1,2-thiazinan-2-yl)-1H-pyrrolo[2,3-b]pyridin-2-yl)-1H-benzo[d]imidazol-5-yl)methanone | 614.34 |
| 99 | 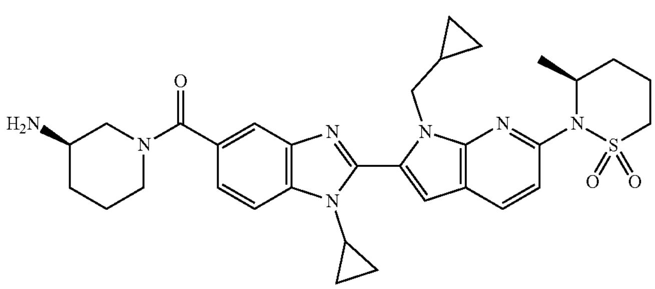 [SMILES: C[C@H]1CCCS(=O)(=O)N1c1ccc2cc(-c3nc4cc(C(=O)N5CCC[C@@H](N)C5)ccc4n3C3CC3)n(CC3CC3)c2n1] | ((R)-3-aminopiperidin-1-yl)(1-cyclopropyl-2-(1-(cyclopropylmethyl)-6-((S)-3-methyl-1,1-dioxido-1,2-thiazinan-2-yl)-1H-pyrrolo[2,3-b]pyridin-2-yl)-1H-benzo[d]imidazol-5-yl)methanone | 602.3 |
| 100 | 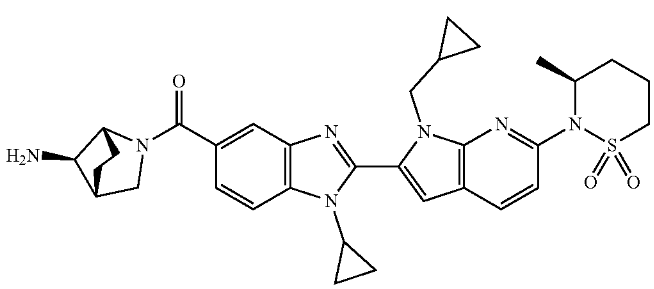 [SMILES: C[C@H]1CCCS(=O)(=O)N1c1ccc2cc(-c3nc4cc(C(=O)N5C[C@H]6CC[C@@H]5[C@@H]6N)ccc4n3C3CC3)n(CC3CC3)c2n1] | ((1R,4R,7R)-7-amino-2-azabicyclo[2.2.1]heptan-2-yl)(1-cyclopropyl-2-(1-(cyclopropylmethyl)-6-((S)-3-methyl-1,1-dioxido-1,2-thiazinan-2-yl)-1H-pyrrolo[2,3-b]pyridin-2-yl)-1H-benzo[d]imidazol-5-yl)methanone | 614.36 |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 101 | 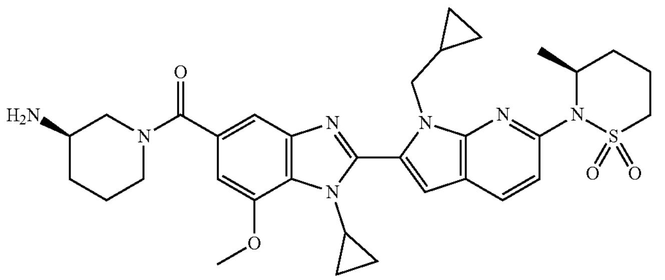 [SMILES: COc1cc(C(=O)N2CCC[C@@H](N)C2)cc2nc(-c3cc4ccc(N5[C@@H](C)CCCS5(=O)=O)nc4n3CC3CC3)n(C3CC3)c12] | ((R)-3-aminopiperidin-1-yl)(1-cyclopropyl-2-(1-(cyclopropylmethyl)-6-((S)-3-methyl-1,1-dioxido-1,2-thiazinan-2-yl)-1H-pyrrolo[2,3-b]pyridin-2-yl)-7-methoxy-1H-benzo[d]imidazol-5-yl)methanone | 632.35 |
| 102 | 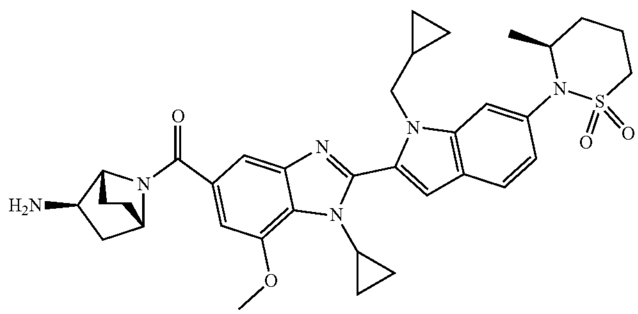 [SMILES: COc1cc(C(=O)N2[C@H]3CC[C@@H]2[C@H](N)C3)cc2nc(-c3cc4ccc(N5[C@@H](C)CCCS5(=O)=O)cc4n3CC3CC3)n(C3CC3)c12] | ((1R,2R,4S)-2-amino-7-azabicyclo[2.2.1]heptan-7-yl)(1-cyclopropyl-2-(1-(cyclopropylmethyl)-6-((S)-3-methyl-1,1-dioxido-1,2-thiazinan-2-yl)-1H-pyrrolo[2,3-b]pyridin-2-yl)-7-methoxy-1H-benzo[d]imidazol-5-yl)methanone | 644.36 |
| 103 | 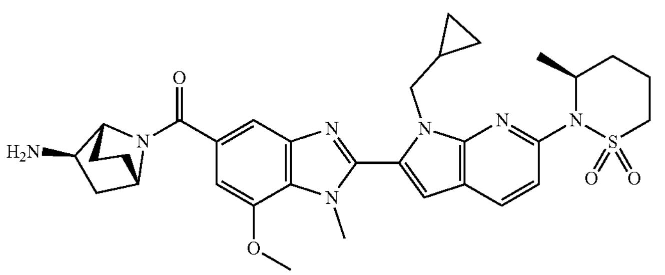 [SMILES: COc1cc(C(=O)N2[C@H]3CC[C@@H]2[C@H](N)C3)cc2nc(-c3cc4ccc(N5[C@@H](C)CCCS5(=O)=O)nc4n3CC3CC3)n(C)c12] | ((1R,2R,4S)-2-amino-7-azabicyclo[2.2.1]heptan-7-yl)(2-(1-(cyclopropylmethyl)-6-((S)-3-methyl-1,1-dioxido-1,2-thiazinan-2-yl)-1H-pyrrolo[2,3-b]pyridin-2-yl)-7-methoxy-1-methyl-1H-benzo[d]imidazol-5-yl) methanone | 618.34 |
| 104 | 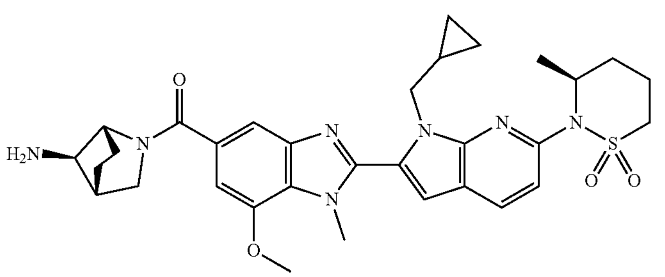 [SMILES: COc1cc(C(=O)N2C[C@H]3CC[C@@H]2[C@@H]3N)cc2nc(-c3cc4ccc(N5[C@@H](C)CCCS5(=O)=O)nc4n3CC3CC3)n(C)c12] | ((1R,4R,7R)-7-amino-2-azabicyclo[2.2.1]heptan-2-yl)(2-(1-(cyclopropylmethyl)-6-((S)-3-methyl-1,1-dioxido-1,2-thiazinan-2-yl)-1H-pyrrolo[2,3-b]pyridin-2-yl)-7-methoxy-1-methyl-1H-benzo[d]imidazol-5-yl) methanone | 618.36 |
| 105 | 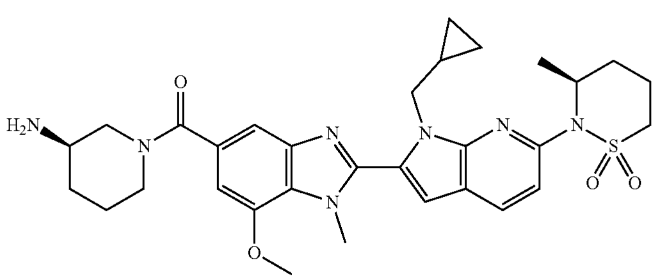 [SMILES: COc1cc(C(=O)N2CCC[C@@H](N)C2)cc2nc(-c3cc4ccc(N5[C@@H](C)CCCS5(=O)=O)nc4n3CC3CC3)n(C)c12] | ((R)-3-aminopiperidin-1-yl)(2-(1-(cyclopropylmethyl)-6-((S)-3-methyl-1,1-dioxido-1,2-thiazinan-2-yl)-1H-pyrrolo[2,3-b]pyridin-2-yl)-7-methoxy-1-methyl-1H-benzo[d]imidazol-5-yl) methanone | 606.36 |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 106 | 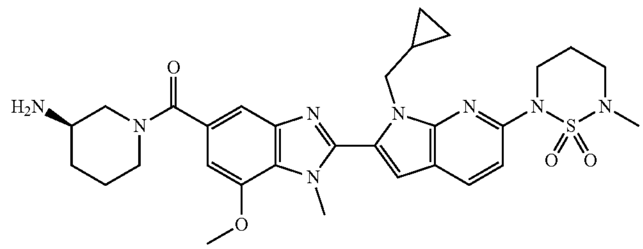 [SMILES: COc1cc(C(=O)N2CCC[C@@H](N)C2)cc2nc(-c3cc4ccc(N5CCCN(C)S5(=O)=O)nc4n3CC3CC3)n(C)c12] | (R)-(3-aminopiperidin-1-yl)(2-(1-(cyclopropylmethyl)-6-(6-methyl-1,1-dioxido-1,2,6-thiadiazinan-2-yl)-1H-pyrrolo[2,3-b]pyridin-2-yl)-7-methoxy-1-methyl-1H-benzo[d]imidazol-5-yl)methanone | 607.50 |
| 107 | 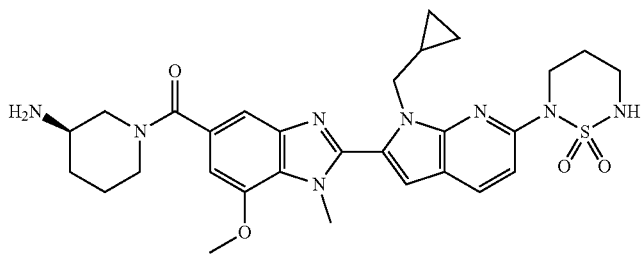 [SMILES: COc1cc(C(=O)N2CCC[C@@H](N)C2)cc2nc(-c3cc4ccc(N5CCCNS5(=O)=O)nc4n3CC3CC3)n(C)c12] | (R)-(3-aminopiperidin-1-yl)(2-(1-(cyclopropylmethyl)-6-(1,1-dioxido-1,2,6-thiadiazinan-2-yl)-1H-pyrrolo[2,3-b]pyridin-2-yl)-7-methoxy-1-methyl-1H-benzo[d]imidazol-5-yl)methanone | 593.47 |
| 108 | 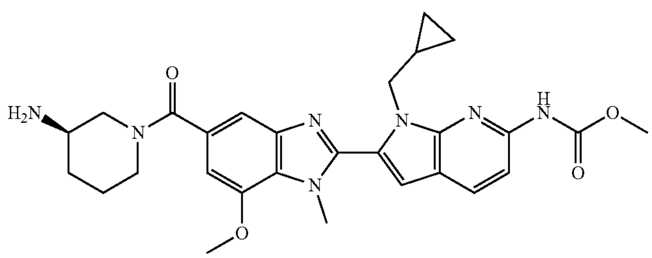 [SMILES: COC(=O)Nc1ccc2cc(-c3nc4cc(C(=O)N5CCC[C@@H](N)C5)cc(OC)c4n3C)n(CC3CC3)c2n1] | (R)-methyl (2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)carbamate | 532.43 |
| 109 | 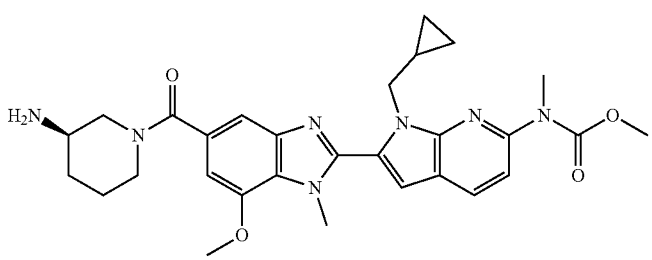 [SMILES: COC(=O)N(C)c1ccc2cc(-c3nc4cc(C(=O)N5CCC[C@@H](N)C5)cc(OC)c4n3C)n(CC3CC3)c2n1] | (R)-methyl (2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)(methyl)carbamate | 546.38 |
| 110 | 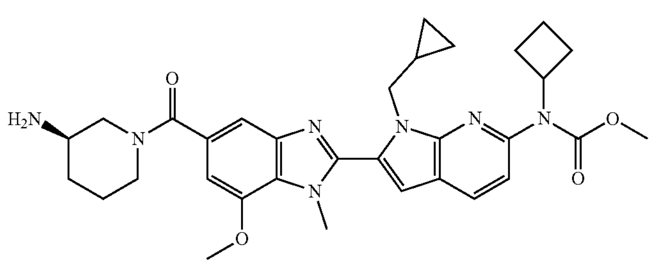 [SMILES: COC(=O)N(c1ccc2cc(-c3nc4cc(C(=O)N5CCC[C@@H](N)C5)cc(OC)c4n3C)n(CC3CC3)c2n1)C1CCC1] | (R)-methyl (2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)(cyclobutyl)carbamate | 586.42 |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 111 | 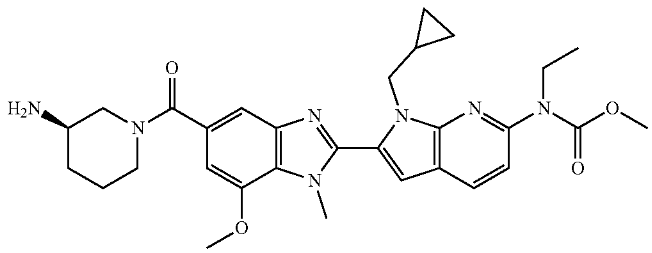 [SMILES: CCN(C(=O)OC)c1ccc2cc(-c3nc4cc(C(=O)N5CCC[C@@H](N)C5)cc(OC)c4n3C)n(CC3CC3)c2n1] | (R)-methyl (2-(5-(3-aminopiperidine-1-carbonyl)-7-methoxy-1-methyl-1H-benzo[b]imidazol-2-yl)-1-(cyclopropylmethyl)-1H-pyrrolo[2,3-b]pyridin-6-yl)(ethyl)carbamate | 560.43 |
| 112 | 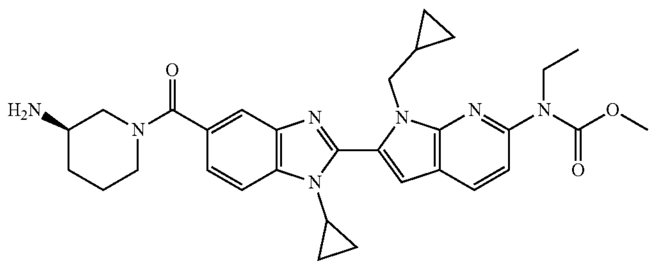 [SMILES: CCN(C(=O)OC)c1ccc2cc(-c3nc4cc(C(=O)N5CCC[C@@H](N)C5)ccc4n3C3CC3)n(CC3CC3)c2n1] | (R)-methyl (2-(5-(3-aminopiperidine-1-carbonyl)-1-cyclopropyl-1H-benzo[d]imidazol-2-yl)-1-(cyclopropylmethyl)-1H-pyrrolo[2,3-b]pyridin-6-yl)(ethyl)carbamate | 556.26 |
| 113 | 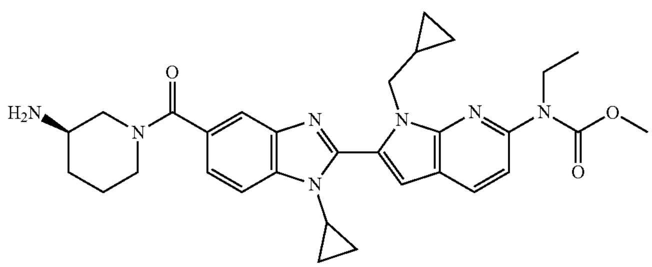 [SMILES: CCN(C(=O)OC)c1ccc2cc(-c3nc4cc(C(=O)N5CCC[C@@H](N)C5)ccc4n3C3CC3)n(CC3CC3)c2n1] | (R)-methyl (2-(5-(3-aminopiperidine-1-carbonyl)-1-cyclopropyl-1H-benzo[d]imidazol-2-yl)-1-(cyclopropylmethyl)-1H-pyrrolo[2,3-b]pyridin-6-yl)(ethyl)carbamate | 556.26 |
| 114 | 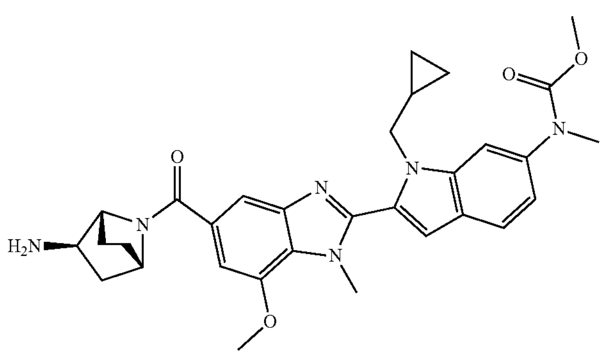 [SMILES: COC(=O)N(C)c1ccc2cc(-c3nc4cc(C(=O)N5[C@H]6CC[C@@H]5[C@H](N)C6)cc(OC)c4n3C)n(CC3CC3)c2c1] | methyl (2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-indol-6-yl)(methyl)carbamate | 557.35 |
| 115 | 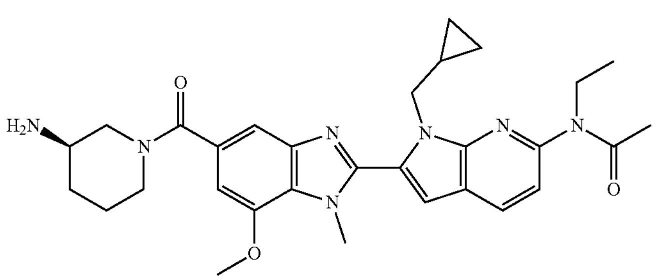 [SMILES: CCN(C(C)=O)c1ccc2cc(-c3nc4cc(C(=O)N5CCC[C@@H](N)C5)cc(OC)c4n3C)n(CC3CC3)c2n1] | (R)-N-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-N-ethylacetamide | 544.42 |

TABLE 1a-continued

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 116 | 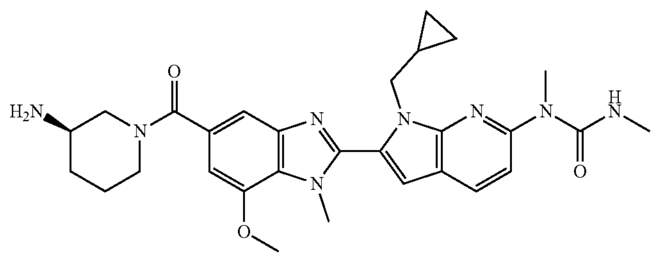 [SMILES: CNC(=O)N(C)c1ccc2cc(-c3nc4cc(C(=O)N5CCC[C@@H](N)C5)cc(OC)c4n3C)n(CC3CC3)c2n1] | (R)-1-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-1,3-dimethylurea | 545.37 |
| 117 | 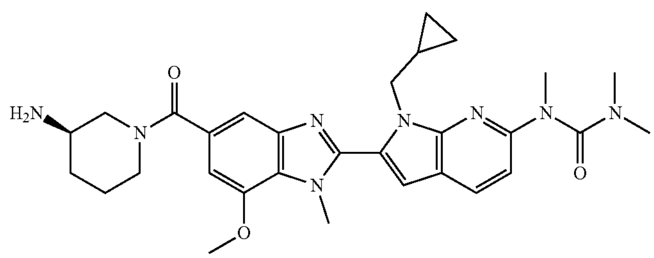 [SMILES: COc1cc(C(=O)N2CCC[C@@H](N)C2)cc2nc(-c3cc4ccc(N(C)C(=O)N(C)C)nc4n3CC3CC3)n(C)c12] | (R)-1-(2-(5-(3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)-1,3,3-trimethylurea | 559.41 |

TABLE 1b

The compounds below were synthesized according to Procedures 1-9, using intermediates described herein, or intermediates prepared according to General Schemes.

| Ex. | Structure | Name | ES/MS m/z [M + H]+ |
|---|---|---|---|
| 287 | 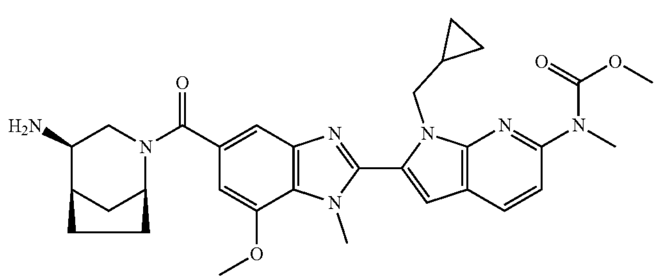 [SMILES: COC(=O)N(C)c1ccc2cc(-c3nc4cc(C(=O)N5C[C@H](N)[C@@H]6CC[C@H]5C6)cc(OC)c4n3C)n(CC3CC3)c2n1] | methyl (2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)(methyl)carbamate | 572.2 |

Procedure 10 (Example 120)

N—((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)pivalamide

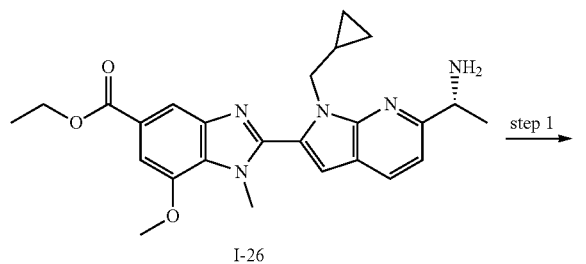

I-26

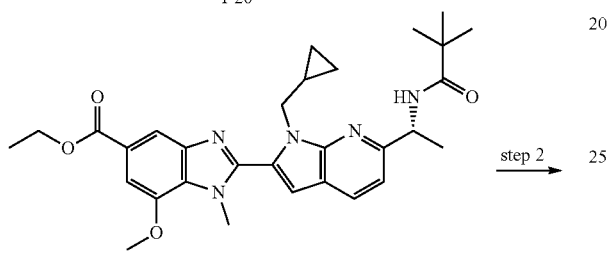

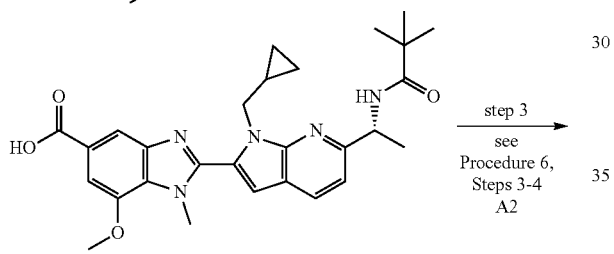

A2

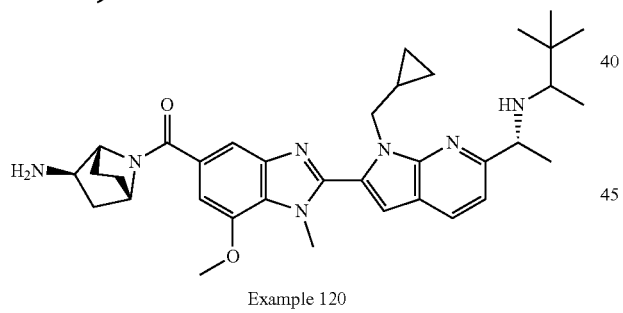

Example 120

Step 1. To a solution of ethyl (R)-2-(6-(1-aminoethyl)-1-(cyclopropylmethyl)-1H-pyrrolo[2,3-b]pyridin-2-yl)-7-methoxy-1-methyl-1H-benzo[d]imidazole-5-carboxylate (I-26, 0.080 g, 0.154 mmol) in DCM (1.5 mL) was added TEA (0.09 mL, 0.62 mmol), followed by 2,2-dimethylpropanoyl chloride (0.037 g, 0.307 mmol). The reaction mixture was stirred at rt for 2 h. The crude reaction mixture was directly purified via flash column chromatography on silica gel to afford ethyl (R)-2-(1-(cyclopropylmethyl)-6-(1-pivalamidoethyl)-1H-pyrrolo[2,3-b]pyridin-2-yl)-7-methoxy-1-methyl-1H-benzo[d]imidazole-5-carboxylate. ES/MS: m/z 532.34 [M+H]⁺.

Step 2. To a solution of ethyl (R)-2-(1-(cyclopropylmethyl)-6-(1-pivalamidoethyl)-1H-pyrrolo[2,3-b]pyridin-2-yl)-7-methoxy-1-methyl-1H-benzo[d]imidazole-5-carboxylate (0.066 g, 0.124 mmol) in THF (1.2 mL) was added LiOH (0.1 mL of a 2 M aq soln, 0.2 mmol). The reaction mixture was stirred at rt for 16 h. The mixture was cooled to 0° C. and acidified with HCl (0.1 mL of a 4 N solution in dioxane, 0.4 mmol). The mixture was concentrated to yield (R)-2-(1-(cyclopropylmethyl)-6-(1-pivalamidoethyl)-1H-pyrrolo[2,3-b]pyridin-2-yl)-7-methoxy-1-methyl-1H-benzo[d]imidazole-5-carboxylic acid. ES/MS: m/z 504.31 [M+H]⁺.

Step 3. Example 120 was prepared following Steps 3-4 of Procedure 6, using A2 and (R)-2-(1-(cyclopropylmethyl)-6-(1-pivalamidoethyl)-1H-pyrrolo[2,3-b]pyridin-2-yl)-7-methoxy-1-methyl-1H-benzo[d]imidazole-5-carboxylic acid.

Procedure 11 (Example 223)

N-[(1R)-1-[2-[5-[(1S,4R,5R)-4-amino-2-azabicyclo[3.2.1]octane-2-carbonyl]-7-methoxy-1-methyl-benzimidazol-2-yl]-1-(cyclopropylmethyl)pyrrolo[2,3-b]pyridin-6-yl]ethyl]-3-fluorobicyclo[1.1.1]pentane-1-carboxamide

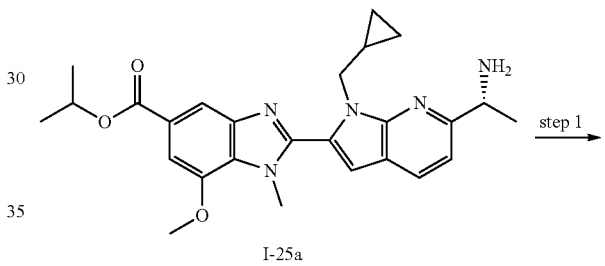

I-25a

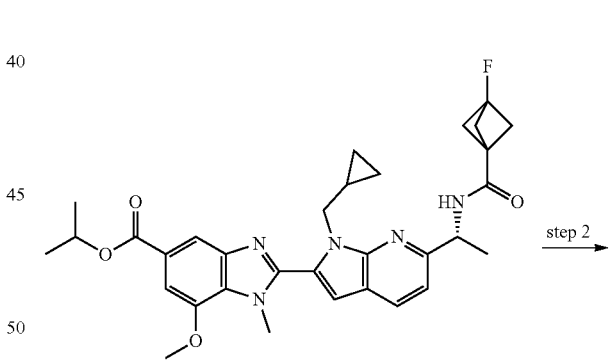


A12

243
-continued


Example 223

Step 1. The crude TFA salt of isopropyl 2-[6-[(1R)-1-aminoethyl]-1-(cyclopropylmethyl)pyrrolo[2,3-b]pyridin-2-yl]-7-methoxy-1-methyl-benzimidazole-5-carboxylate (I-25a, 0.16 mmol) was dissolved in DCM (2.5 mL), and 3-fluorobicyclo[1.1.1]pentane-1-carboxylic acid (42 mg, 0.32 mmol) was added followed by Hunig's base (0.3 mL, 1.7 mmol) and HATU (79 mg, 0.21 mmol). The reaction mixture was stirred until judged complete by LCMS and was then concentrated directly onto silica gel. Purification by silica gel chromatography (EtOAc in hexane gradient) provided isopropyl 2-[1-(cyclopropylmethyl)-6-[(1R)-1-[(3-fluorobicyclo[1.1.1]pentane-1-carbonyl)amino]ethyl]pyrrolo[2,3-b]pyridin-2-yl]-7-methoxy-1-methyl-benzimidazole-5-carboxylate. ES/MS: m/z 574.35 [M+H]+.

Step 2. isopropyl 2-[1-(cyclopropylmethyl)-6-[(1R)-1-[(3-fluorobicyclo[1.1.1]pentane-1-carbonyl)amino]ethyl]pyrrolo[2,3-b]pyridin-2-yl]-7-methoxy-1-methyl-benzimidazole-5-carboxylate (82 mg, 0.14 mmol) was dissolved in THF (2 mL), MeOH (1 mL), and water (1 mL). Lithium hydroxide monohydrate (60 mg, 1.43 mmol) was added and the reaction mixture was heated to 55° C. for 5 h. Hydrochloric acid (6M, 0.31 mL, 1.9 mmol) was added, and the mixture was petitioned between DCM and water. The phases were separated, and the aqueous phase was extracted with DCM. The combined organic phase was dried over Na2SO4, filtered, and concentrated to afford crude 2-[1-(cyclopropylmethyl)-6-[(1R)-1-[(3-fluorobicyclo[1.1.1]pentane-1-carbonyl)amino]ethyl]pyrrolo[2,3-b]pyridin-2-yl]-7-methoxy-1-methyl-benzimidazole-5-carboxylic acid that was used without further purification. ES/MS: m/z 532.21[M+H]+.

Step 3. 2-[1-(cyclopropylmethyl)-6-[(1R)-1-[(3-fluorobicyclo[1.1.1]pentane-1-carbonyl)amino]ethyl]pyrrolo[2,3-b]pyridin-2-yl]-7-methoxy-1-methyl-benzimidazole-5-carboxylic acid (35 mg, 0.066 mmol) was dissolved in DCM (1.5 mL). tert-butyl N-[(1S,4R,5R)-2-azabicyclo[3.2.1]octan-4-yl]carbamate (A12, 15.6 mg, 0.069 mmol) was added followed by Hunig's base (100 uL, 0.57 mmol) and HATU (32.5 mg, 0.086 mmol). The reaction was stirred 20 min, and TFA (2 mL) was added directly to the mixture. After stirring an additional 20 min, the reaction mixture was concentrated and purified directly by preparative HPLC (5-100% MeCN in water, 0.1% TFA) to provide Example 223.

244
Procedure 12 (Example 186)

N—((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-3-chlorobicyclo[1.1.1]pentane-1-carboxamide

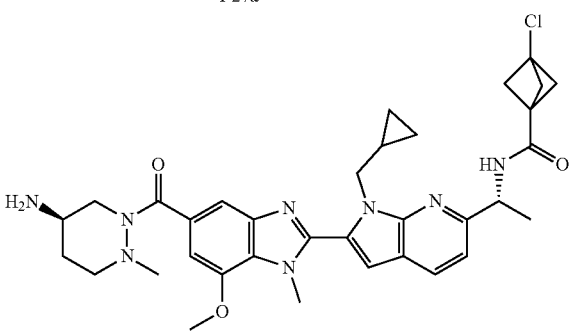

I-27a

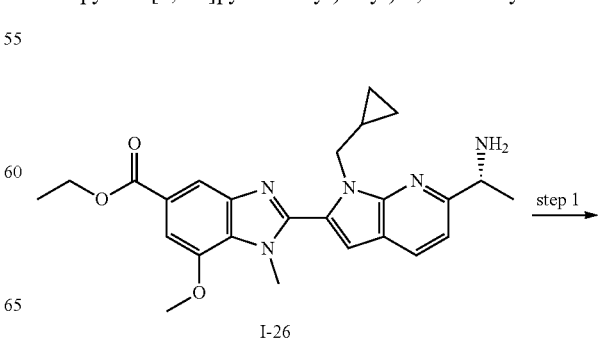

Example 186

To a solution of tert-butyl ((R)-2-(2-(6-((R)-1-aminoethyl)-1-(cyclopropylmethyl)-1H-pyrrolo[2,3-b]pyridin-2-yl)-7-methoxy-1-methyl-1H-benzo[d]imidazole-5-carbonyl)-1-methylhexahydropyridazin-4-yl)carbamate (I-27a, 0.015 g, 0.024 mmol) in DMA (450 μL) was added DIPEA (10 μL, 0.06 mmol) and 3-chlorobicyclo[1.1.1]pentane-1-carboxylic acid (0.004 g, 0.029 mmol), followed by HATU (0.011 g, 0.029 mmol). The mixture was stirred at rt for 15 min and was then concentrated. The resulting residue was taken up in 1:1 DCM/TFA (1 mL) and the solution was stirred at rt for 1 h before being concentrated. The residue was purified via preparative reverse phase HPLC, affording Example 186.

Procedure 13 (Example 235)

3-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)-1,1-dimethylurea

I-26 step 1

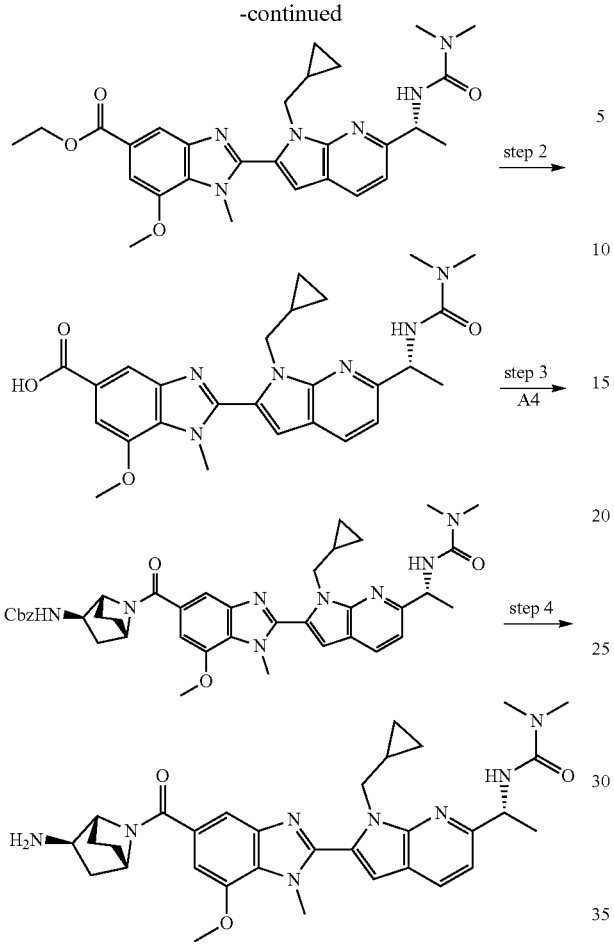

Example 235

Step 1. To a solution of ethyl (R)-2-(6-(1-aminoethyl)-1-(cyclopropylmethyl)-1H-pyrrolo[2,3-b]pyridin-2-yl)-7-methoxy-1-methyl-1H-benzo[d]imidazole-5-carboxylate (I-26, 0.120 g, 0.248 mmol) in DCM (5 mL) was added TEA (0.21 mL, 1.49 mmol), followed by N,N-dimethylcarbamoyl chloride (0.07 mL, 0.77 mmol). The reaction mixture was stirred at rt for 16 h and was then partitioned between EtOAc and water. The organic layer was dried ($Na_2SO_4$), filtered and concentrated. The resulting residue was purified via flash column chromatography on silica gel to afford ethyl (R)-2-(1-(cyclopropylmethyl)-6-(1-(3,3-dimethylureido)ethyl)-1H-pyrrolo[2,3-b]pyridin-2-yl)-7-methoxy-1-methyl-1H-benzo[d]imidazole-5-carboxylate. ES/MS: m/z 519.1 [M+H]+.

Step 2. To a solution of ethyl (R)-2-(1-(cyclopropylmethyl)-6-(1-(3,3-dimethylureido)ethyl)-1H-pyrrolo[2,3-b]pyridin-2-yl)-7-methoxy-1-methyl-1H-benzo[d]imidazole-5-carboxylate (0.103 g, 0.199 mmol) in THF (2 mL), MeOH (1 mL) and water (1 mL) was added $LiOH \cdot H_2O$ (0.045 g, 1.07 mmol). The reaction mixture was stirred at rt for 16 h before being acidified by addition of HCl (0.18 mL of a 6 M aq soln, 1.09 mmol). The resulting mixture was concentrated, yielding (R)-2-(1-(cyclopropylmethyl)-6-(1-(3,3-dimethylureido)ethyl)-1H-pyrrolo[2,3-b]pyridin-2-yl)-7-methoxy-1-methyl-1H-benzo[d]imidazole-5-carboxylic acid. ES/MS: m/z 491.1 [M+H]+.

Step 3. To a solution of (R)-2-(1-(cyclopropylmethyl)-6-(1-(3,3-dimethylureido)ethyl)-1H-pyrrolo[2,3-b]pyridin-2-yl)-7-methoxy-1-methyl-1H-benzo[d]imidazole-5-carboxylic acid (0.098 g, 0.199 mmol) and benzyl ((1R,2R,4S)-7-azabicyclo[2.2.1]heptan-2-yl)carbamate (A4, 0.070 g, 0.284 mmol) in DMF (2.5 mL) was added DIPEA (0.14 mL, 0.80 mmol) followed by HATU (0.091 g, 0.239 mmol). The reaction mixture was stirred at rt for 30 min. The reaction mixture was diluted with water and the resulting solids were collected via filtration, affording benzyl ((1R,2R,4S)-7-(2-(1-(cyclopropylmethyl)-6-((R)-1-(3,3-dimethylureido)ethyl)-1H-pyrrolo[2,3-b]pyridin-2-yl)-7-methoxy-1-methyl-1H-benzo[d]imidazole-5-carbonyl)-7-azabicyclo[2.2.1]heptan-2-yl)carbamate. ES/MS: m/z 719.2 [M+H]+.

Step 4. To a solution of benzyl ((1R,2R,4S)-7-(2-(1-(cyclopropylmethyl)-6-((R)-1-(3,3-dimethylureido)ethyl)-1H-pyrrolo[2,3-b]pyridin-2-yl)-7-methoxy-1-methyl-1H-benzo[d]imidazole-5-carbonyl)-7-azabicyclo[2.2.1]heptan-2-yl)carbamate (0.143 g, 0.199 mmol) in EtOAc (3.5 mL) was added 10 wt % Pd/C (0.110 g). The reaction mixture was stirred at rt under $H_2$ (1 atm). After 2 h, MeOH (1 mL) was added. After an additional 30 min, the reaction mixture was filtered through a pad of Celite. The filtrate was concentrated. The resulting residue was purified via preparative reverse phase HPLC to give Example 235.

Procedure 14 (Example 238)

N—((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)-3,3-difluoroazetidine-1-carboxamide

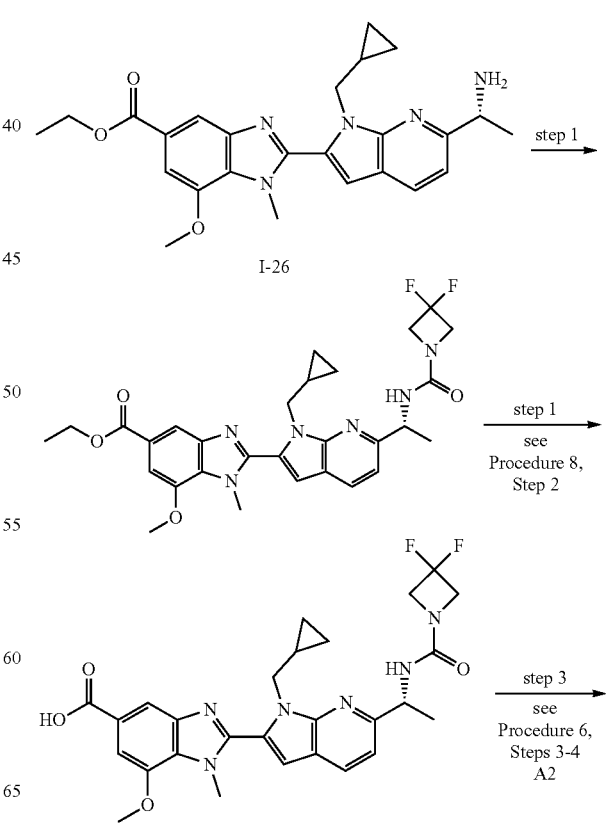

-continued

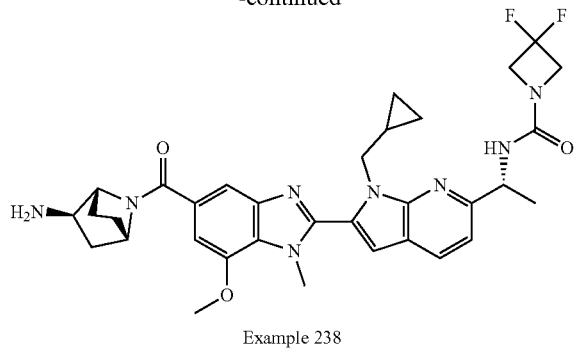

Example 238

Step 1. To a solution of ethyl (R)-2-(6-(1-aminoethyl)-1-(cyclopropylmethyl)-1H-pyrrolo[2,3-b]pyridin-2-yl)-7-methoxy-1-methyl-1H-benzo[d]imidazole-5-carboxylate dihydrochloride (I-26, 0.040 g, 0.277 mmol) in DMF (2.0 mL) was added TEA (0.11 mL, 0.77 mmol), followed by CDI (0.019 g, 0.116 mmol). The reaction mixture was stirred at rt for 16 h, and then at 30° C. for 1.5 h. 3,3-difluoroazetidine hydrochloride (0.040 g, 0.308 mmol) was added and the reaction mixture was stirred at 70° C. Reaction progress was monitored by LC-MS. The reaction mixture was diluted with DCM and water. The aqueous layer was extracted with DCM and the combined organic layers were dried (Na$_2$SO$_4$), filtered and concentrated. The residue was purified via flash column chromatography on silica gel to afford ethyl (R)-2-(1-(cyclopropylmethyl)-6-(1-(3,3-difluoroazetidine-1-carboxamido)ethyl)-1H-pyrrolo[2,3-b]pyridin-2-yl)-7-methoxy-1-methyl-1H-benzo[d]imidazole-5-carboxylate. ES/MS: m/z 566.3 [M+H]$^+$.

Step 2. The procedure described in Step 2 of Procedure 8 was followed, yielding (R)-2-(1-(cyclopropylmethyl)-6-(1-(3,3-difluoroazetidine-1-carboxamido)ethyl)-1H-pyrrolo[2,3-b]pyridin-2-yl)-7-methoxy-1-methyl-1H-benzo[d]imidazole-5-carboxylic acid. ES/MS: m/z 538.3 [M+H]$^+$.

Step 3. Example 238 was prepared following Steps 3-4 of Procedure 6, using A2 and (R)-2-(1-(cyclopropylmethyl)-6-(1-(3,3-difluoroazetidine-1-carboxamido)ethyl)-1H-pyrrolo[2,3-b]pyridin-2-yl)-7-methoxy-1-methyl-1H-benzo[d]imidazole-5-carboxylic acid.

Procedure 15 (Example 240)

N—((R)-1-(2-(5-(((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)propane-1-sulfonamide

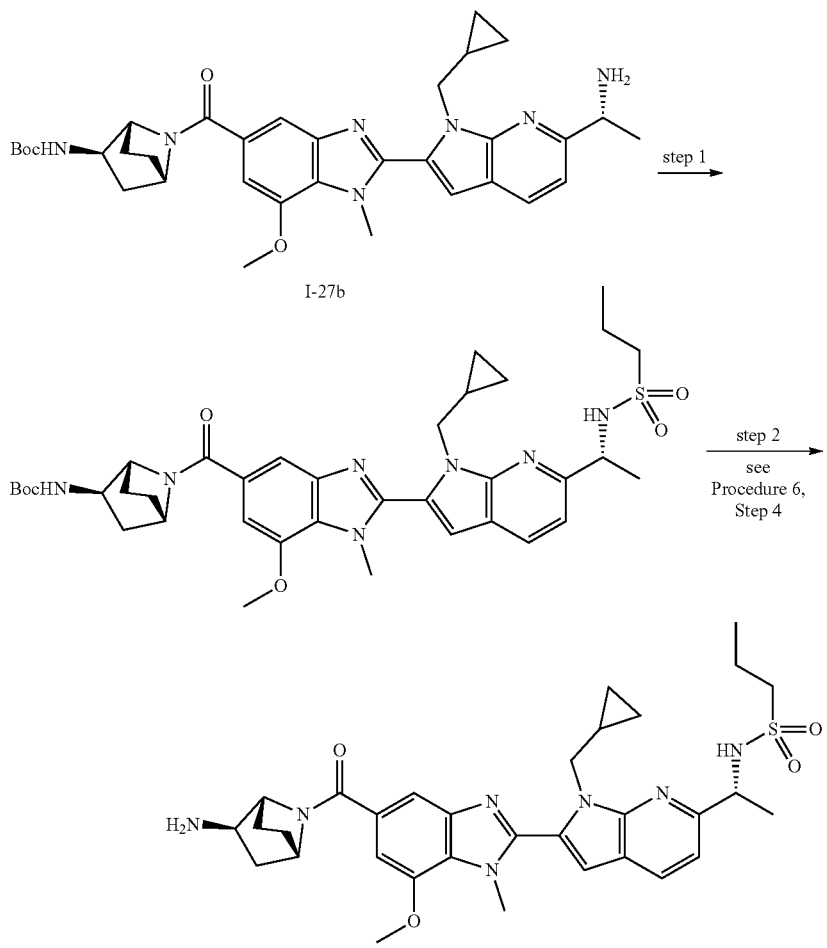

Step 1. tert-butyl N-[(2R)-7-[2-[6-[(1R)-1-aminoethyl]-1-(cyclopropylmethyl)pyrrolo[2,3-b]pyridin-2-yl]-7-methoxy-1-methyl-benzimidazole-5-carbonyl]-7-azabicyclo[2.2.1]heptan-2-yl]carbamate (I-27b, 15 mg, 0.024 mmol) was dissolved in pyridine (1.5 mL). The homogeneous solution was then treated with 1-propanesulfonyl chloride (0.005 mL, 0.049 mmol) and stirred at rt for 3 h. The reaction was diluted with ethyl acetate, washed successively with brine and water, dried (Na$_2$SO$_4$), and concentrated to afford tert-butyl ((1R,2R,4S)-7-(2-(1-(cyclopropylmethyl)-6-((R)-1-(propylsulfonamido)ethyl)-1H-pyrrolo[2,3-b]pyridin-2-yl)-7-methoxy-1-methyl-1H-benzo[d]imidazole-5-carbonyl)-7-azabicyclo[2.2.1]heptan-2-yl)carbamate.

Step 2. Example 240 was prepared following Step 4 of Procedure 6, using tert-butyl ((1R,2R,4S)-7-(2-(1-(cyclopropylmethyl)-6-((R)-1-(propylsulfonamido)ethyl)-1H-pyrrolo[2,3-b]pyridin-2-yl)-7-methoxy-1-methyl-1H-benzo[d]imidazole-5-carbonyl)-7-azabicyclo[2.2.1]heptan-2-yl)carbamate.

Procedure 16 (Example 245)

1-((R)-1-(2-(5-(((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)pyrrolidin-2-one Step 1. To a solution of ethyl (R)-2-(6-(1-aminoethyl)-1-(cyclopropylmethyl)-1H-pyrrolo[2,3-b]pyridin-2-yl)-7-methoxy-1-methyl-1H-benzo[d]imidazole-5-carboxylate (I-26, 0.070 g, 0.130 mmol) and DIPEA (0.09 mL, 0.51 mmol) in DCM (1 mL) was added 4-bromobutanoyl chloride (0.024 g, 0.130 mmol). The reaction mixture was stirred at rt for 1 h and was then quenched via addition of water. The organic layer was dried (Na$_2$SO$_4$), filtered, and concentrated. The residue was taken up in DMF (1 mL) and cooled to 0° C. NaH (0.005 g of a 60% dispersion in mineral oil, 0.130 mmol) was added. After 10 min, the reaction mixture was allowed to warm to rt and was stirred for 4 h. The reaction mixture was diluted with sat NH$_4$Cl soln and EtOAc. The organic layer was washed successively with water and brine, dried (Na$_2$SO$_4$), filtered, and concentrated. The residue was purified via flash column chromatography on silica gel to afford ethyl (R)-2-(1-(cyclopropylmethyl)-6-(1-(2-oxopyrrolidin-1-yl)ethyl)-1H-pyrrolo[2,3-b]pyridin-2-yl)-7-methoxy-1-methyl-1H-benzo[d]imidazole-5-carboxylate. ES/MS: m/z 542.0 [M+H]$^+$.

Step 2. To a solution of ethyl (R)-2-(1-(cyclopropylmethyl)-6-(1-(2-oxopyrrolidin-1-yl)ethyl)-1H-pyrrolo[2,3-b]pyridin-2-yl)-7-methoxy-1-methyl-1H-benzo[d]imidazole-5-carboxylate (0.040 g, 0.074 mmol) in 1:1 THF/water (2 mL) was added MeOH (0.2 mL) and LiOH (0.002 g, 0.074 mmol). The reaction mixture was stirred for 2 h and then concentrated to yield (R)-2-(1-(cyclopropylmethyl)-6-(1-(2-oxopyrrolidin-1-yl)ethyl)-1H-pyrrolo[2,3-b]pyridin-2-yl)-7-methoxy-1-methyl-1H-benzo[d]imidazole-5-carboxylic acid. ES/MS: m/z 514.2 [M+H]$^+$.

Step 3. Example 245 was prepared following Steps 3-4 of Procedure 6, using A2 and (R)-2-(1-(cyclopropylmethyl)-6-(1-(2-oxopyrrolidin-1-yl)ethyl)-1H-pyrrolo[2,3-b]pyridin-2-yl)-7-methoxy-1-methyl-1H-benzo[d]imidazole-5-carboxylic acid.

Procedure 17 (Example 246)

1-((R)-2-(2-(5-(((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)pyrrolidin-1-yl)-2,2-dimethylpropan-1-one

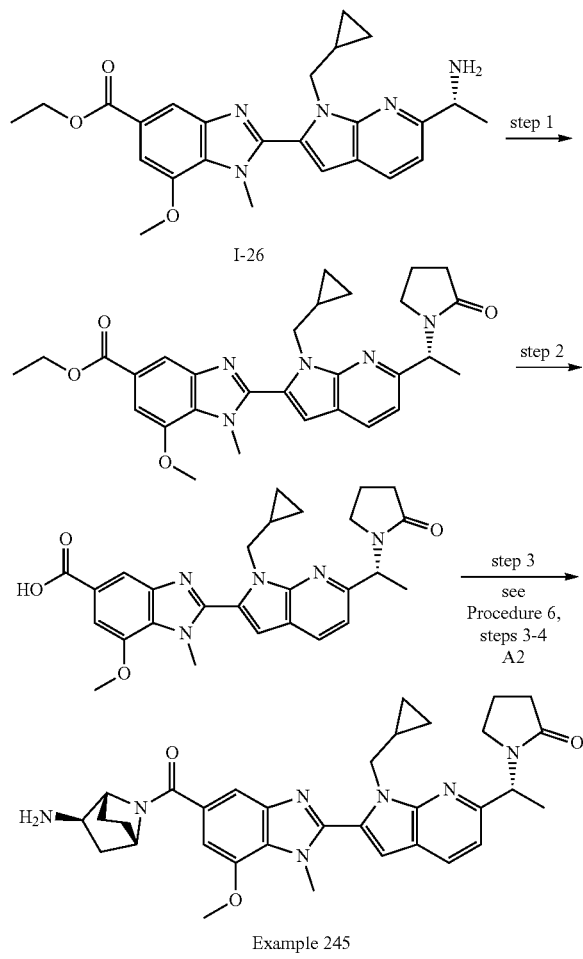

Example 245

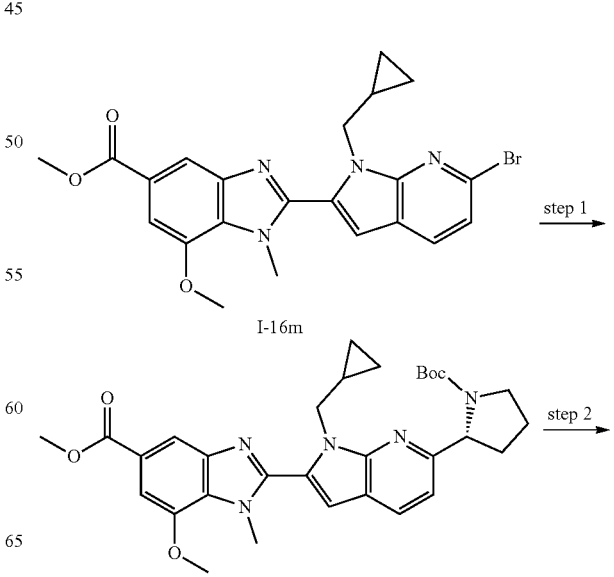

-continued

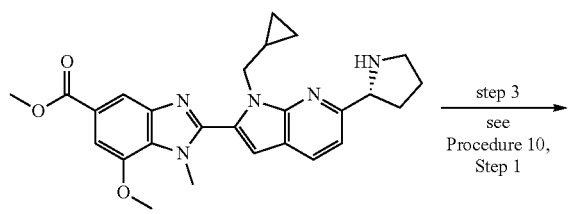

step 3
see
Procedure 10,
Step 1

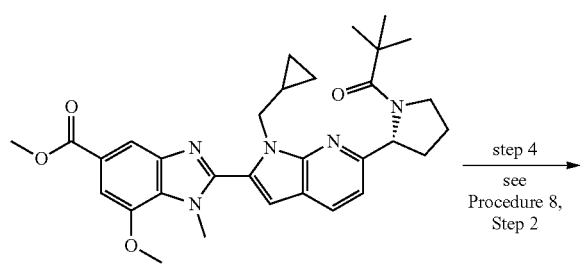

step 4
see
Procedure 8,
Step 2

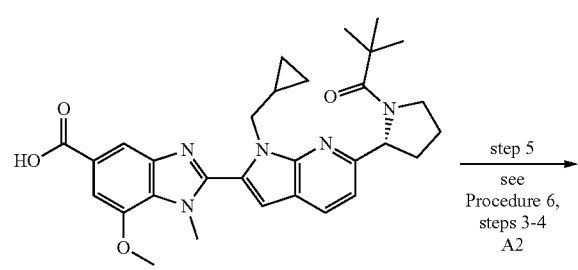

step 5
see
Procedure 6,
steps 3-4
A2

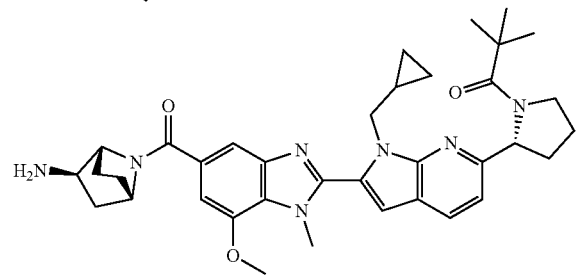

Example 246

Step 1. To a solution of N-Boc-pyrrolidine (0.075 mL, 0.43 mmol) and (−)-sparteine (0.098 mL, 0.43 mmol) in MTBE (1 mL) at −78° C. was added s-BuLi (0.31 mL of a 1.4 M soln in cyclohexane, 0.43 mmol) dropwise. The resulting solution was stirred at −78° C. for 3 h. A solution of ZnCl$_2$ (0.51 mL of a 0.5 M soln in THF, 0.26 mmol) was added to the reaction, dropwise. The reaction mixture was stirred at −78° C. for 30 minutes and was then allowed to warm to rt over 30 min. To this mixture was added methyl 2-[6-bromo-1-(cyclopropylmethyl)pyrrolo[2,3-b]pyridin-2-yl]-7-methoxy-1-methyl-benzimidazole-5-carboxylate (I-16m, 0.090 g, 0.19 mmol), palladium(II) acetate (0.005 g, 0.02 mmol), tri-t-butylphosphonium tetrafluoroborate (0.007 g, 0.02 mmol), and 1,4-dioxane (1 mL). The mixture was stirred overnight at rt. The mixture was filtered through Celite. The filtrate was concentrated onto silica gel and purified via flash column chromatography on silica gel to provide methyl (R)-2-(6-(1-(tert-butoxycarbonyl)pyrrolidin-2-yl)-1-(cyclopropylmethyl)-1H-pyrrolo[2,3-b]pyridin-2-yl)-7-methoxy-1-methyl-1H-benzo[d]imidazole-5-carboxylate. ES/MS: m/z 560.3 [M+H]$^+$.

Step 2. To a solution of methyl (R)-2-(6-(1-(tert-butoxycarbonyl)pyrrolidin-2-yl)-1-(cyclopropylmethyl)-1H-pyrrolo[2,3-b]pyridin-2-yl)-7-methoxy-1-methyl-1H-benzo[d]imidazole-5-carboxylate (0.147 g, 0.263 mmol) in DCM (1.3 mL) was added HCl (1.3 mL of a 4 M soln in dioxane). The mixture was stirred at rt for 3 h and was then concentrated to afford methyl (R)-2-(1-(cyclopropylmethyl)-6-(pyrrolidin-2-yl)-1H-pyrrolo[2,3-b]pyridin-2-yl)-7-methoxy-1-methyl-1H-benzo[d]imidazole-5-carboxylate. ES/MS: m/z 460.3 [M+H]$^+$.

Step 3. methyl (R)-2-(1-(cyclopropylmethyl)-6-(1-pivaloylpyrrolidin-2-yl)-1H-pyrrolo[2,3-b]pyridin-2-yl)-7-methoxy-1-methyl-1H-benzo[d]imidazole-5-carboxylate was prepared following Step 1 of Procedure 10, using methyl (R)-2-(1-(cyclopropylmethyl)-6-(pyrrolidin-2-yl)-1H-pyrrolo[2,3-b]pyridin-2-yl)-7-methoxy-1-methyl-1H-benzo[d]imidazole-5-carboxylate. ES/MS: m/z 544.4 [M+H]$^+$.

Step 4. (R)-2-(1-(cyclopropylmethyl)-6-(1-pivaloylpyrrolidin-2-yl)-1H-pyrrolo[2,3-b]pyridin-2-yl)-7-methoxy-1-methyl-1H-benzo[d]imidazole-5-carboxylic acid was prepared following Step 2 of Procedure 8, using methyl (R)-2-(1-(cyclopropylmethyl)-6-(1-pivaloylpyrrolidin-2-yl)-1H-pyrrolo[2,3-b]pyridin-2-yl)-7-methoxy-1-methyl-1H-benzo[d]imidazole-5-carboxylate. ES/MS: m/z 530.4 [M+H]$^+$.

Step 5. Example 246 was prepared following Steps 3-4 of Procedure 6, using A2 and (R)-2-(1-(cyclopropylmethyl)-6-(1-pivaloylpyrrolidin-2-yl)-1H-pyrrolo[2,3-b]pyridin-2-yl)-7-methoxy-1-methyl-1H-benzo[d]imidazole-5-carboxylic acid.

Procedure 18 (Example 209)

(R)—N-(2-(2-(5-(5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)propanyl)benzamide

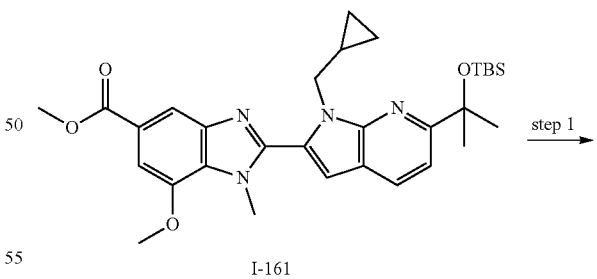

I-161

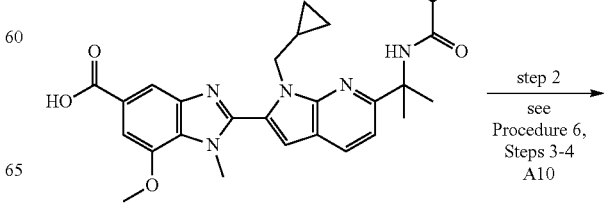

step 1 step 2
see
Procedure 6,
Steps 3-4
A10

-continued

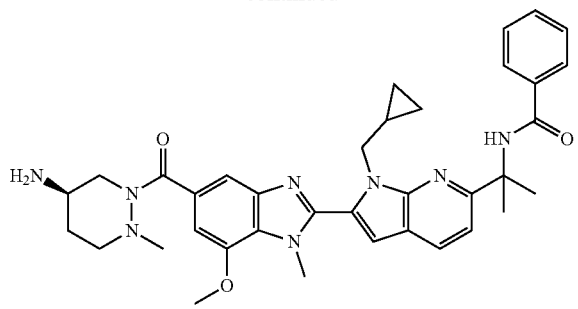

Example 209

Step 1. A solution of methyl 2-(6-(2-((tert-butyldimethylsilyl)oxy)propan-2-yl)-1-(cyclopropylmethyl)-1H-pyrrolo[2,3-b]pyridin-2-yl)-7-methoxy-1-methyl-1H-benzo[d]imidazole-5-carboxylate (I-16l, 0.100 g, 0.178 mmol), benzonitrile (0.092 g, 0.888 mmol) and sulfuric acid (76 μL, 1.42 mmol) was stirred at rt for 18 h. The mixture was then added dropwise to a solution of NaOH (3 mL of 3 M aq soln) in MeOH (3 mL). The resulting mixture was stirred at 50° C. for 1 h. The mixture was partially concentrated, acidified to pH=2 with 2 M HCl, and extracted with EtOAc. The organic layer was dried (Na₂SO₄), filtered, and concentrated. Crude 2-(6-(2-benzamidopropan-2-yl)-1-(cyclopropylmethyl)-1H-pyrrolo[2,3-b]pyridin-2-yl)-7-methoxy-1-methyl-1H-benzo[d]imidazole-5-carboxylic acid was taken on without purification. ES/MS: m/z 538.2 [M+H]⁺.

Step 2. Example 209 was prepared following Steps 3-4 of Procedure 6, using 2-(6-(2-benzamidopropan-2-yl)-1-(cyclopropylmethyl)-1H-pyrrolo[2,3-b]pyridin-2-yl)-7-methoxy-1-methyl-1H-benzo[d]imidazole-5-carboxylic acid and A10.

TABLE 2a

The compounds below were synthesized according to Procedures 10-18, using intermediates described herein, and/or intermediates prepared according to General Schemes.

| Ex. | Structure | Name | ES/MS m/z [M + H]⁺ |
|---|---|---|---|
| 118 | 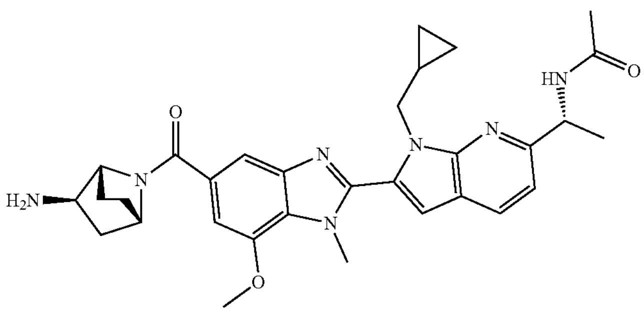 [SMILES: COc1cc(C(=O)N2[C@H]3CC[C@@H]2[C@H](N)C3)cc2nc(-c3cc4ccc([C@@H](C)NC(C)=O)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)acetamide | 556.31 |
| 119 | 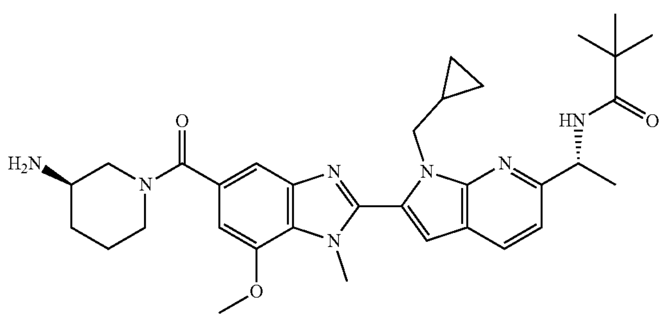 [SMILES: COc1cc(C(=O)N2CCC[C@@H](N)C2)cc2nc(-c3cc4ccc([C@@H](C)NC(=O)C(C)(C)C)nc4n3CC3CC3)n(C)c12] | N-((R)-1-(2-(5-((R)-3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)pivalamide | 586.36 |
| 120 | 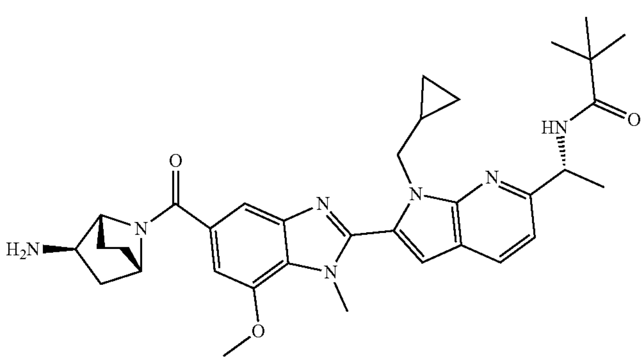 [SMILES: COc1cc(C(=O)N2[C@H]3CC[C@@H]2[C@H](N)C3)cc2nc(-c3cc4ccc([C@@H](C)NC(=O)C(C)(C)C)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)pivalamide | 598.28 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 121 | 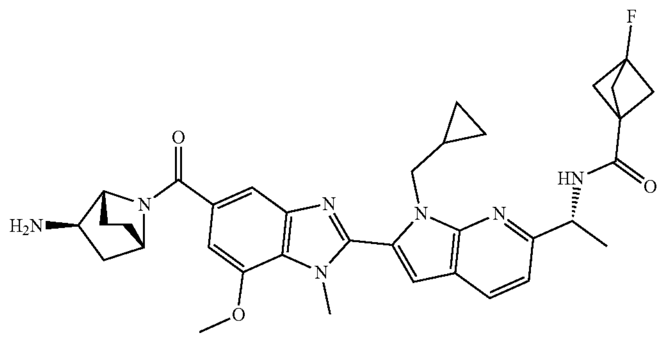 [SMILES: COc1cc(C(=O)N2[C@H]3CC[C@@H]2[C@H](N)C3)cc2nc(-c3cc4ccc([C@@H](C)NC(=O)C56CC(F)(C5)C6)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)-3-fluorobicyclo[1.1.1]pentane-1-carboxamide | 626.36 |
| 122 | 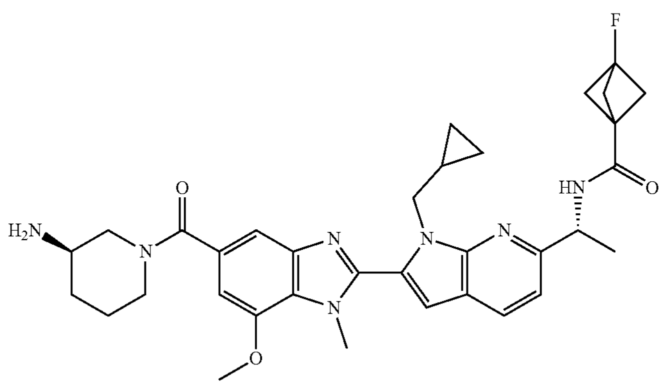 [SMILES: COc1cc(C(=O)N2CCC[C@@H](N)C2)cc2nc(-c3cc4ccc([C@@H](C)NC(=O)C56CC(F)(C5)C6)nc4n3CC3CC3)n(C)c12] | N-((R)-1-(2-(5-((R)-3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-3-fluorobicyclo[1.1.1]pentane-1-carboxamide | 614.32 |
| 123 | 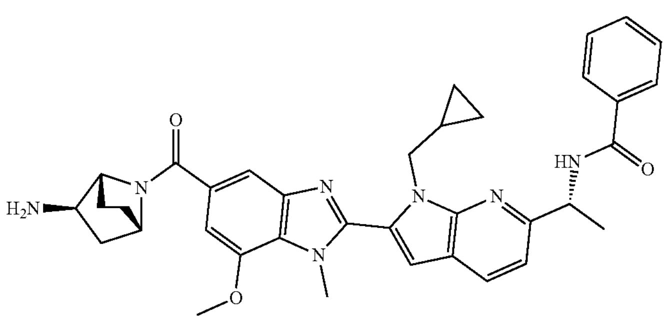 [SMILES: COc1cc(C(=O)N2[C@H]3CC[C@@H]2[C@H](N)C3)cc2nc(-c3cc4ccc([C@@H](C)NC(=O)c5ccccc5)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)benzamide | 618.33 |
| 124 | 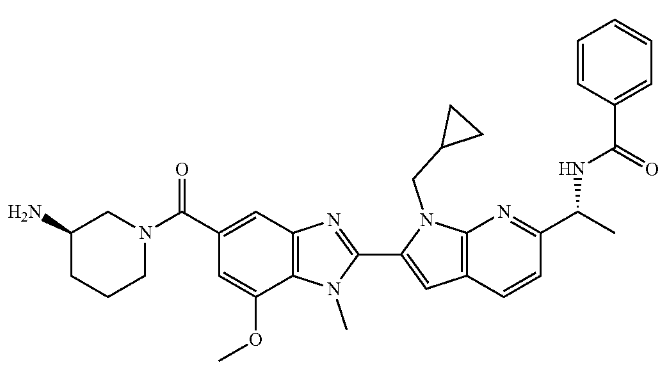 | N-((R)-1-(2-(5-((R)-3-aminopiperidine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)benzamide | 606.33 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 125 | 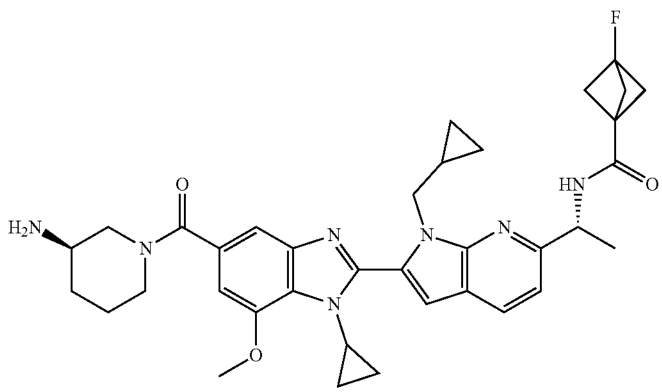 [SMILES: COc1cc(C(=O)N2CCC[C@@H](N)C2)cc2nc(-c3cc4ccc([C@@H](C)NC(=O)C56CC(F)(C5)C6)nc4n3CC3CC3)n(C3CC3)c12] | N-((R)-1-(2-(5-((R)-3-aminopiperidine-1-carbonyl)-1-cyclopropyl-7-methoxy-1H-benzo[d]imidazol-2-yl)-1-(cyclopropylmethyl)-1H-pyrrolo[2,3-b]pyridin-6-yl)ethyl)-3-fluorobicyclo[1.1.1]pentane-1-carboxamide | 640.34 |
| 126 | 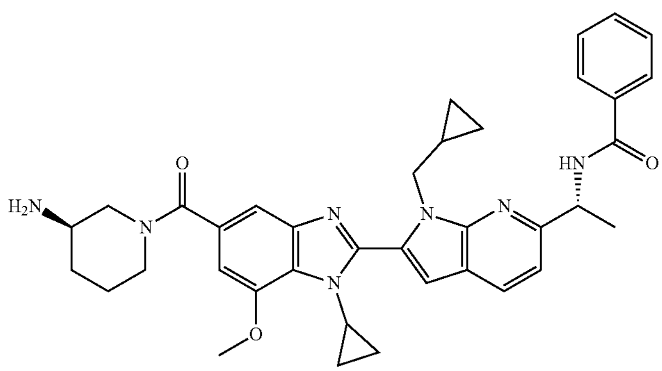 [SMILES: COc1cc(C(=O)N2CCC[C@@H](N)C2)cc2nc(-c3cc4ccc([C@@H](C)NC(=O)c5ccccc5)nc4n3CC3CC3)n(C3CC3)c12] | N-((R)-1-(2-(5-((R)-3-aminopiperidine-1-carbonyl)-1-cyclopropyl-7-methoxy-1H-benzo[d]imidazol-2-yl)-1-(cyclopropylmethyl)-1H-pyrrolo[2,3-b]pyridin-6-yl)ethyl)benzamide | 632.35 |
| 127 | 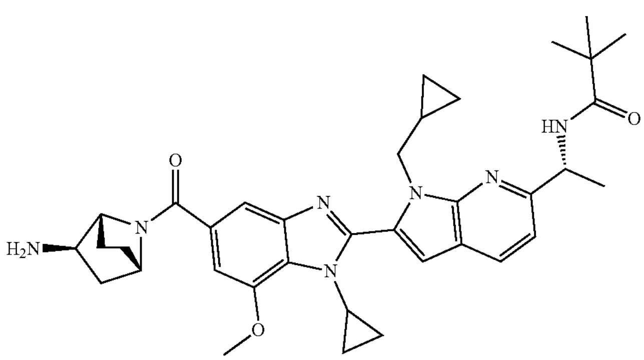 [SMILES: COc1cc(C(=O)N2[C@H]3CC[C@@H]2[C@H](N)C3)cc2nc(-c3cc4ccc([C@@H](C)NC(=O)C(C)(C)C)nc4n3CC3CC3)n(C3CC3)c12] | N-((R)-1-(2-(5-((1R,2R,4S)-2-amino-7-azabicyclo[2.2.1]heptane-7-carbonyl)-1-cyclopropyl-7-methoxy-1H-benzo[d]imidazol-2-yl)-1-(cyclopropylmethyl)-1H-pyrrolo[2,3-b]pyridin-6-yl)ethyl)pivalamide | 624.41 |
| 128 | 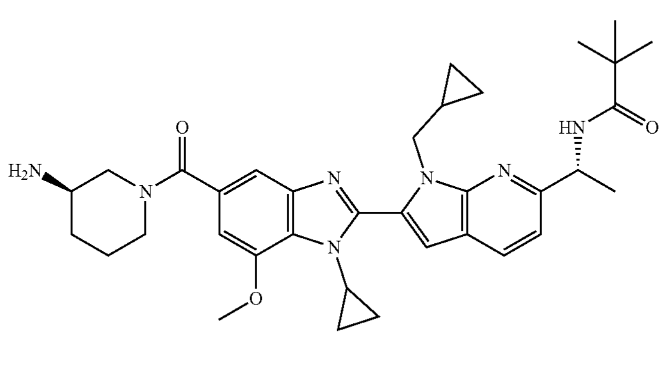 [SMILES: COc1cc(C(=O)N2CCC[C@@H](N)C2)cc2nc(-c3cc4ccc([C@@H](C)NC(=O)C(C)(C)C)nc4n3CC3CC3)n(C3CC3)c12] | N-((R)-1-(2-(5-((R)-3-aminopiperidine-1-carbonyl)-1-cyclopropyl-7-methoxy-1H-benzo[d]imidazol-2-yl)-1-(cyclopropylmethyl)-1H-pyrrolo[2,3-b]pyridin-6-yl)ethyl)pivalamide | 612.35 |

TABLE 2a-continued

The compounds below were synthesized according to Procedures 10-18, using
intermediates described herein, and/or intermediates prepared according to General Schemes.

| Ex. | Structure | Name | ES/MS m/z [M + H]+ |
|---|---|---|---|
| 129 | 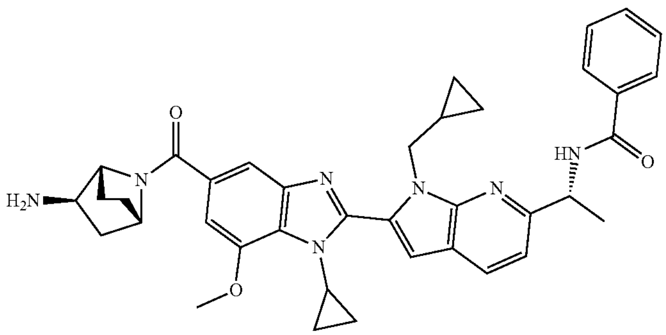 [SMILES: COc1cc(C(=O)N2[C@H]3CC[C@@H]2[C@H](N)C3)cc2nc(-c3cc4ccc([C@@H](C)NC(=O)c5ccccc5)nc4n3CC3CC3)n(C3CC3)c12] | N-((R)-1-(2-(5-((1R,2R,4S)-2-amino-7-azabicyclo[2.2.1]heptane-7-carbonyl)-1-cyclopropyl-7-methoxy-1H-benzo[d]imidazol-2-yl)-1-(cyclopropylmethyl)-1H-pyrrolo[2,3-b]pyridin-6-yl)ethyl)benzamide | 644.35 |
| 130 | 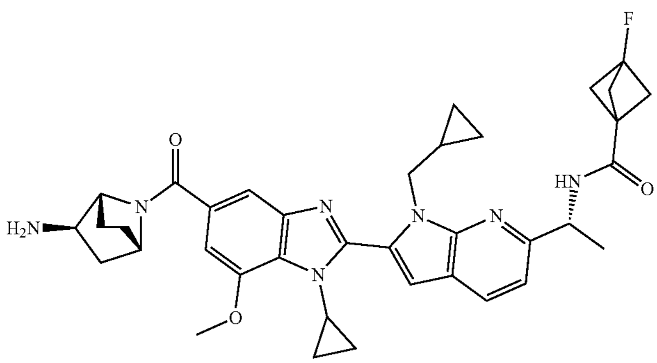 [SMILES: COc1cc(C(=O)N2[C@H]3CC[C@@H]2[C@H](N)C3)cc2nc(-c3cc4ccc([C@@H](C)NC(=O)C56CC(F)(C5)C6)nc4n3CC3CC3)n(C3CC3)c12] | N-((R)-1-(2-(5-((1R,2R,4S)-2-amino-7-azabicyclo[2.2.1]heptane-7-carbonyl)-1-cyclopropyl-7-methoxy-1H-benzo[d]imidazol-2-yl)-1-(cyclopropylmethyl)-1H-pyrrolo[2,3-b]pyridin-6-yl)ethyl)-3-fluorobicyclo[1.1.1]pentane-1-carboxamide | 652.37 |
| 131 | 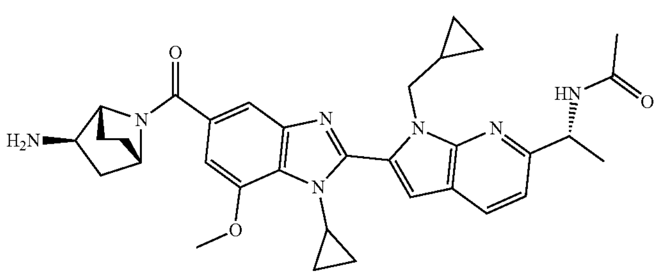 [SMILES: COc1cc(C(=O)N2[C@H]3CC[C@@H]2[C@H](N)C3)cc2nc(-c3cc4ccc([C@@H](C)NC(C)=O)nc4n3CC3CC3)n(C3CC3)c12] | N-((R)-1-(2-(5-((1R,2R,4S)-2-amino-7-azabicyclo[2.2.1]heptane-7-carbonyl)-1-cyclopropyl-7-methoxy-1H-benzo[d]imidazol-2-yl)-1-(cyclopropylmethyl)-1H-pyrrolo[2,3-b]pyridin-6-yl)ethyl)acetamide | 582.36 |
| 132 | 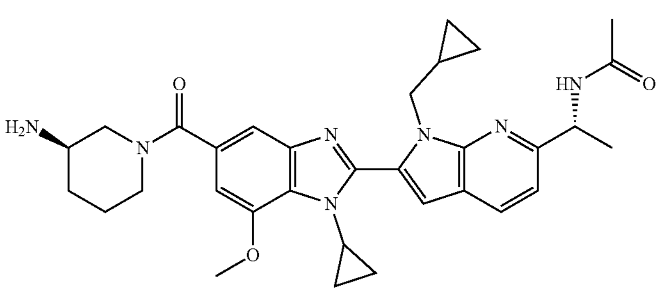 [SMILES: COc1cc(C(=O)N2CCC[C@@H](N)C2)cc2nc(-c3cc4ccc([C@@H](C)NC(C)=O)nc4n3CC3CC3)n(C3CC3)c12] | N-((R)-1-(2-(5-((R)-3-aminopiperidine-1-carbonyl)-1-cyclopropyl-7-methoxy-1H-benzo[d]imidazol-2-yl)-1-(cyclopropylmethyl)-1H-pyrrolo[2,3-b]pyridin-6-yl)ethyl)acetamide | 570.34 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 133 | 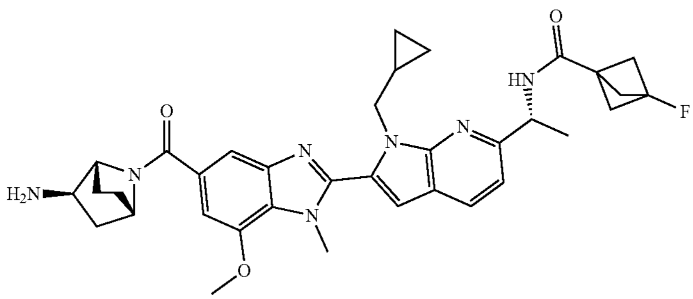 [SMILES: COc1cc(C(=O)N2[C@H]3CC[C@@H]2[C@H](N)C3)cc2nc(-c3cc4ccc([C@@H](C)NC(=O)C56CC(F)(C5)C6)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-indol-6-yl)ethyl)-3-fluorobicyclo[1.1.1]pentane-1-carboxamide | 625.38 |
| 134 | 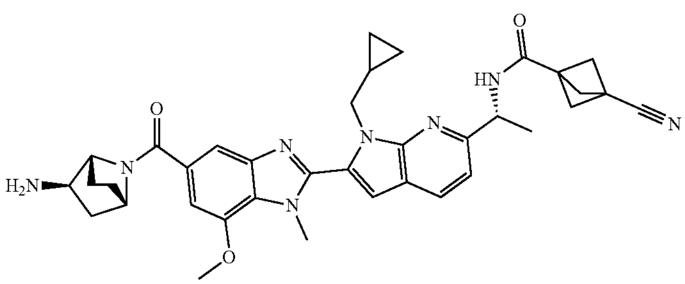 [SMILES: COc1cc(C(=O)N2[C@H]3CC[C@@H]2[C@H](N)C3)cc2nc(-c3cc4ccc([C@@H](C)NC(=O)C56CC(C#N)(C5)C6)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-indol-6-yl)ethyl)-3-cyanobicyclo[1.1.1]pentane-1-carboxamide | 632.4 |
| 135 | 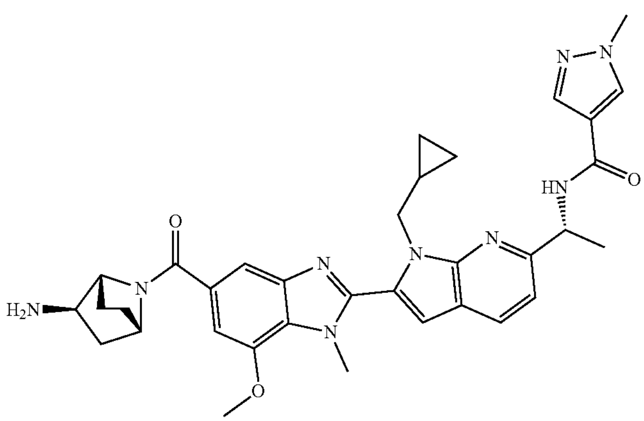 [SMILES: COc1cc(C(=O)N2[C@H]3CC[C@@H]2[C@H](N)C3)cc2nc(-c3cc4ccc([C@@H](C)NC(=O)c5cnn(C)c5)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-indol-6-yl)ethyl)-1-methyl-1H-pyrazole-4-carboxamide | 621.35 |
| 136 | 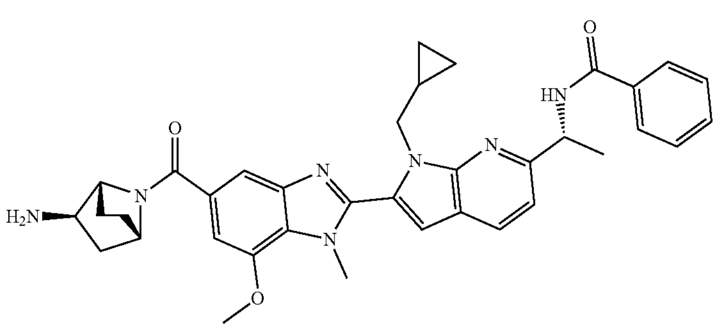 [SMILES: COc1cc(C(=O)N2[C@H]3CC[C@@H]2[C@H](N)C3)cc2nc(-c3cc4ccc([C@@H](C)NC(=O)c5ccccc5)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-indol-6-yl)ethyl)benzamide | 617.36 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 137 | 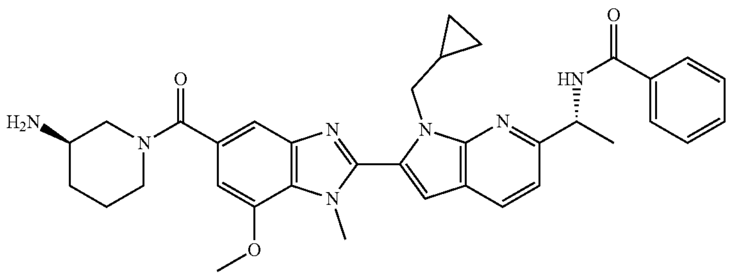 [SMILES: COc1cc(C(=O)N2CCC[C@@H](N)C2)cc2nc(-c3cc4ccc([C@@H](C)NC(=O)c5ccccc5)nc4n3CC3CC3)n(C)c12] | N-((R)-1-(2-(5-((R)-3-aminopiperidine-1-carbonyl)-7-methoxy-1-methyl-1H-benzo[d]imidazol-2-yl)-1-(cyclopropylmethyl)-1H-indol-6-yl)ethyl)benzamide | 605.34 |
| 138 | 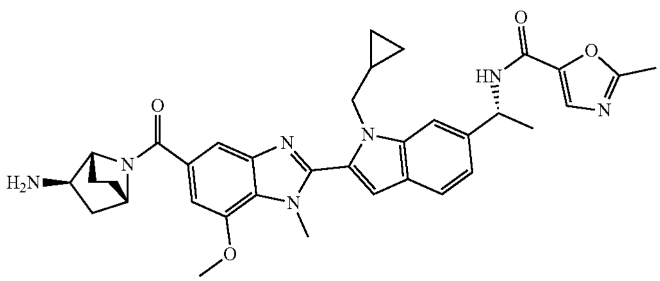 [SMILES: COc1cc(C(=O)N2[C@H]3CC[C@@H]2[C@H](N)C3)cc2nc(-c3cc4ccc([C@@H](C)NC(=O)c5cnc(C)o5)cc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-indol-6-yl)ethyl)-2-methyloxazole-5-carboxamide | 622.33 |
| 139 | 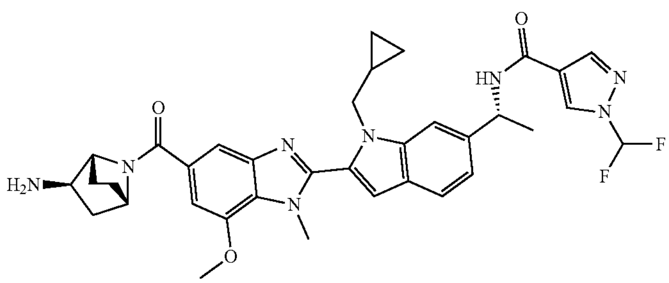 [SMILES: COc1cc(C(=O)N2[C@H]3CC[C@@H]2[C@H](N)C3)cc2nc(-c3cc4ccc([C@@H](C)NC(=O)c5cnn(C(F)F)c5)cc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-indol-6-yl)ethyl)-1-(difluoromethyl)-1H-pyrazole-4-carboxamide | 657.4 |
| 140 | 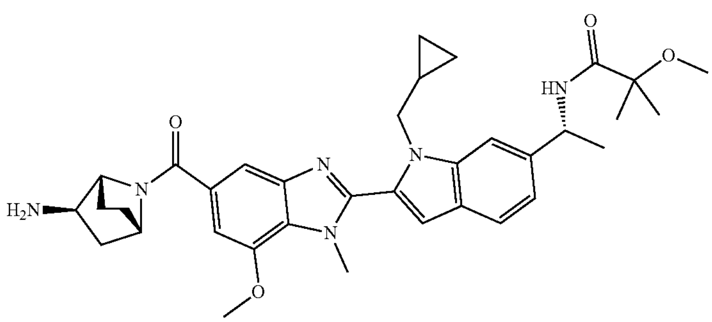 [SMILES: COc1cc(C(=O)N2[C@H]3CC[C@@H]2[C@H](N)C3)cc2nc(-c3cc4ccc([C@@H](C)NC(=O)C(C)(C)OC)cc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-indol-6-yl)ethyl)-2-methoxy-2-methylpropanamide | 613.22 |
| 141 | 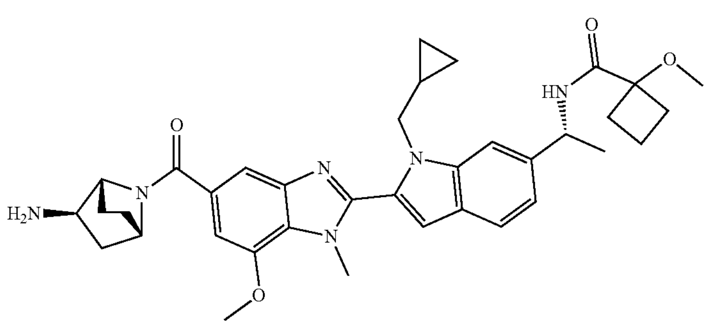 [SMILES: COc1cc(C(=O)N2[C@H]3CC[C@@H]2[C@H](N)C3)cc2nc(-c3cc4ccc([C@@H](C)NC(=O)C5(OC)CCC5)cc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-indol-6-yl)ethyl)-1-methoxycyclobutane-1-carboxamide | 625.42 |

TABLE 2a-continued

The compounds below were synthesized according to Procedures 10-18, using
intermediates described herein, and/or intermediates prepared according to General Schemes.

| Ex. | Structure | Name | ES/MS m/z [M + H]+ |
|---|---|---|---|
| 142 | 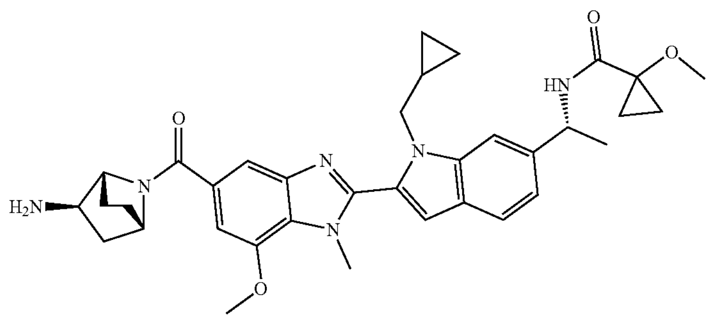 [SMILES: COc1cc(C(=O)N2[C@H]3CC[C@@H]2[C@H](N)C3)cc2nc(-c3cc4ccc([C@@H](C)NC(=O)C5(OC)CC5)cc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-indol-6-yl)ethyl)-1-methoxycyclopropane-1-carboxamide | 611.44 |
| 143 | 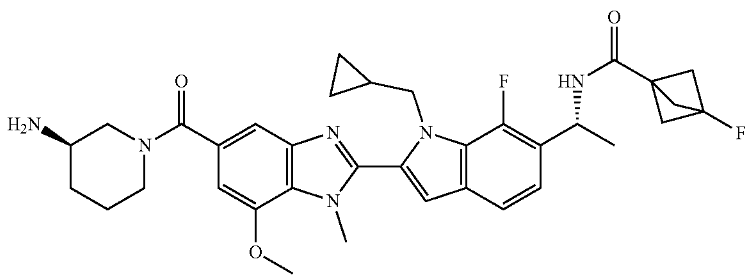 [SMILES: COc1cc(C(=O)N2CCC[C@@H](N)C2)cc2nc(-c3cc4ccc([C@@H](C)NC(=O)C56CC(F)(C5)C6)c(F)c4n3CC3CC3)n(C)c12] | N-((R)-1-(2-(5-((R)-3-aminopiperidine-1-carbonyl)-7-methoxy-1-methyl-1H-benzo[d]imidazol-2-yl)-1-(cyclopropylmethyl)-7-fluoro-1H-indol-6-yl)ethyl)-3-fluorobicyclo[1.1.1]pentane-1-carboxamide | 631.36 |
| 144 | 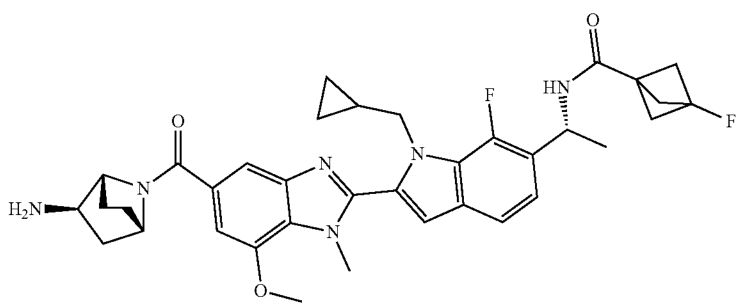 [SMILES: COc1cc(C(=O)N2[C@H]3CC[C@@H]2[C@H](N)C3)cc2nc(-c3cc4ccc([C@@H](C)NC(=O)C56CC(F)(C5)C6)c(F)c4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-7-fluoro-1H-indol-6-yl)ethyl)-3-fluorobicyclo[1.1.1]pentane-1-carboxamide | 634.37 |
| 145 | 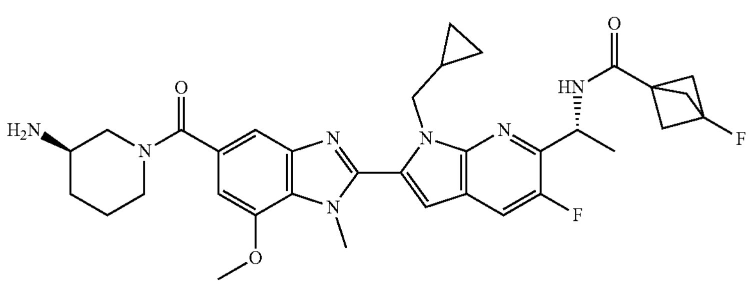 [SMILES: COc1cc(C(=O)N2CCC[C@@H](N)C2)cc2nc(-c3cc4cc(F)c([C@@H](C)NC(=O)C56CC(F)(C5)C6)nc4n3CC3CC3)n(C)c12] | N-((R)-1-(2-(5-((R)-3-aminopiperidine-1-carbonyl)-7-methoxy-1-methyl-1H-benzo[d]imidazol-2-yl)-1-(cyclopropylmethyl)-5-fluoro-1H-indol-6-yl)ethyl)-3-fluorobicyclo[1.1.1]pentane-1-carboxamide | 631.34 |
| 146 | 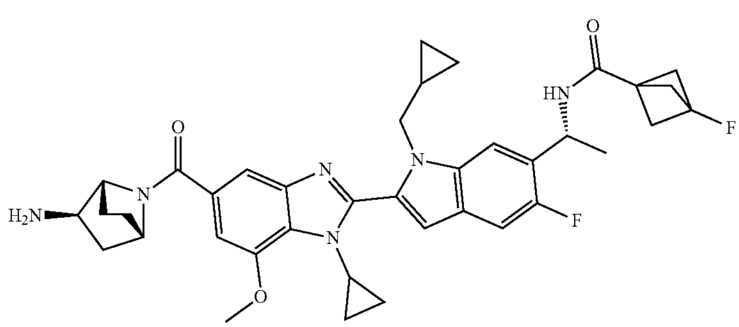 [SMILES: COc1cc(C(=O)N2[C@H]3CC[C@@H]2[C@H](N)C3)cc2nc(-c3cc4cc(F)c([C@@H](C)NC(=O)C56CC(F)(C5)C6)cc4n3CC3CC3)n(C3CC3)c12] | N-((R)-2-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-5-fluoro-1H-indol-6-yl)ethyl)-3-fluorobicyclo[1.1.1]pentane-1-carboxamide | 643.22 |

TABLE 2a-continued

| Ex. | Structure | Name | ES/MS m/z [M + H]+ |
|---|---|---|---|
| 147 | 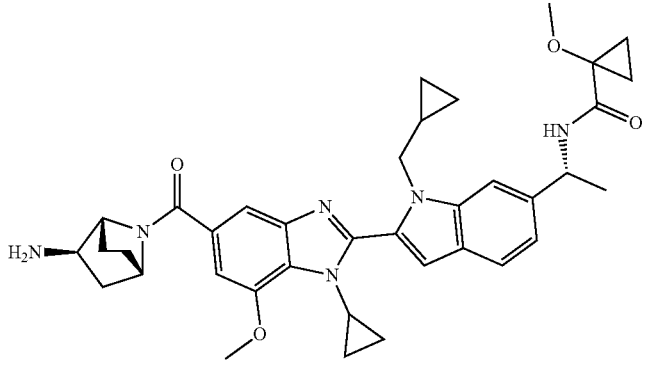 [SMILES: COc1cc(C(=O)N2[C@H]3CC[C@@H]2[C@H](N)C3)cc2nc(-c3cc4ccc([C@@H](C)NC(=O)C5(OC)CC5)cc4n3CC3CC3)n(C3CC3)c12] | N-((R)-1-(2-(5-(((1R,2R,4S)-2-amino-7-azabicyclo[2.2.1]heptane-7-carbonyl)-1-cyclopropyl-7-methoxy-1H-benzo[d]imidazol-2-yl)-1-(cyclopropylmethyl)-1H-indol-6-yl)ethyl)-1-methoxycyclopropane-1-carboxamide | 637.49 |
| 148 | 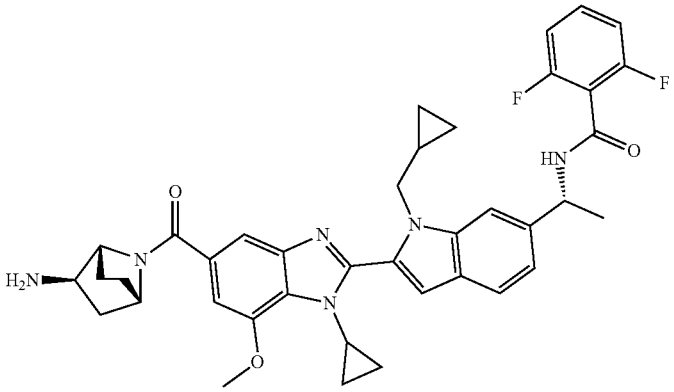 [SMILES: COc1cc(C(=O)N2[C@H]3CC[C@@H]2[C@H](N)C3)cc2nc(-c3cc4ccc([C@@H](C)NC(=O)c5c(F)cccc5F)cc4n3CC3CC3)n(C3CC3)c12] | N-((R)-1-(2-(5-(((1R,2R,4S)-2-amino-7-azabicyclo[2.2.1]heptane-7-carbonyl)-1-cyclopropyl-7-methoxy-1H-benzo[d]imidazol-2-yl)-1-(cyclopropylmethyl)-1H-indol-6-yl)ethyl)-2,6-difluorobenzamide | 679.42 |
| 149 | 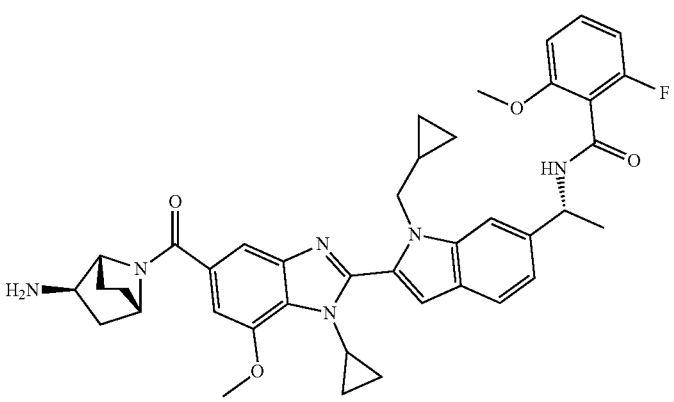 [SMILES: COc1cccc(F)c1C(=O)N[C@H](C)c1ccc2cc(-c3nc4cc(C(=O)N5[C@H]6CC[C@@H]5[C@H](N)C6)cc(OC)c4n3C3CC3)n(CC3CC3)c2c1] | N-((R)-1-(2-(5-(((1R,2R,4S)-2-amino-7-azabicyclo[2.2.1]heptane-7-carbonyl)-1-cyclopropyl-7-methoxy-1H-benzo[d]imidazol-2-yl)-1-(cyclopropylmethyl)-1H-indol-6-yl)ethyl)-2-fluoro-6-methoxybenzamide | 691.48 |
| 150 | 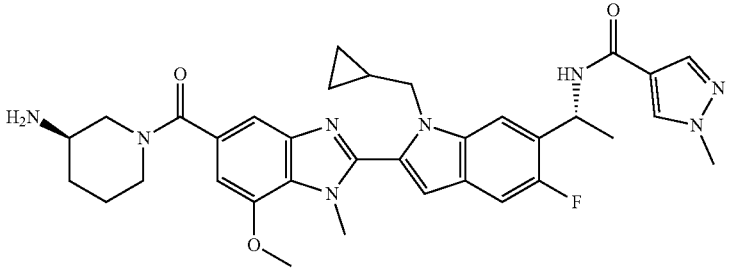 [SMILES: COc1cc(C(=O)N2CCC[C@@H](N)C2)cc2nc(-c3cc4cc(F)c([C@@H](C)NC(=O)c5cnn(C)c5)cc4n3CC3CC3)n(C)c12] | N-((R)-1-(2-(5-((R)-3-aminopiperidine-1-carbonyl)-7-methoxy-1-methyl-1H-benzo[d]imidazol-2-yl)-1-(cyclopropylmethyl)-5-fluoro-1H-indol-6-yl)ethyl)-1-methyl-1H-pyrazole-4-carboxamide | 627.36 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 151 | 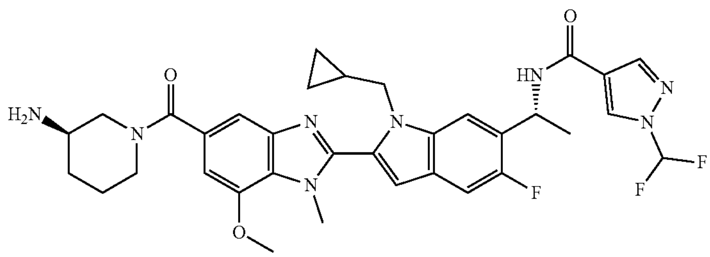 [SMILES: COc1cc(C(=O)N2CCC[C@@H](N)C2)cc2nc(-c3cc4cc(F)c([C@@H](C)NC(=O)c5cnn(C(F)F)c5)cc4n3CC3CC3)n(C)c12] | N-((R)-1-(2-(5-((R)-3-aminopiperidine-1-carbonyl)-7-methoxy-1-methyl-1H-benzo[d]imidazol-2-yl)-1-(cyclopropylmethyl)-5-fluoro-1H-indol-6-yl)ethyl)-1-(difluoromethyl)-1H-pyrazole-4-carboxamide | 663.31 |
| 152 | 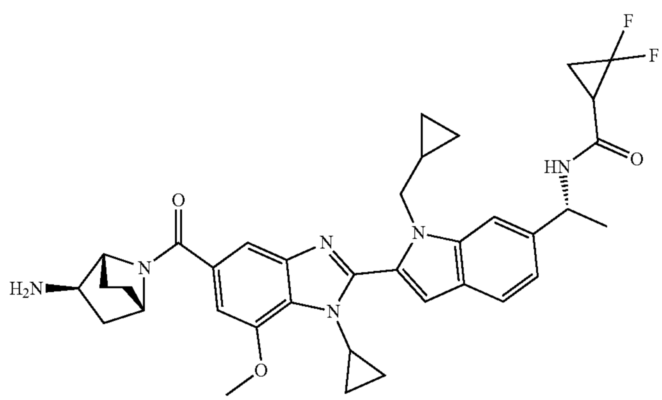 [SMILES: COc1cc(C(=O)N2[C@H]3CC[C@@H]2[C@H](N)C3)cc2nc(-c3cc4ccc([C@@H](C)NC(=O)C5CC5(F)F)cc4n3CC3CC3)n(C3CC3)c12] | N-((R)-1-(2-(5-((1R,2R,4S)-2-amino-7-azabicyclo[2.2.1]heptane-7-carbonyl)-1-cyclopropyl-7-methoxy-1H-benzo[d]imidazol-2-yl)-1-(cyclopropylmethyl)-1H-indol-6-yl)ethyl)-2,2-difluorocyclopropane-1-carboxamide | 643.34 |
| 153 | 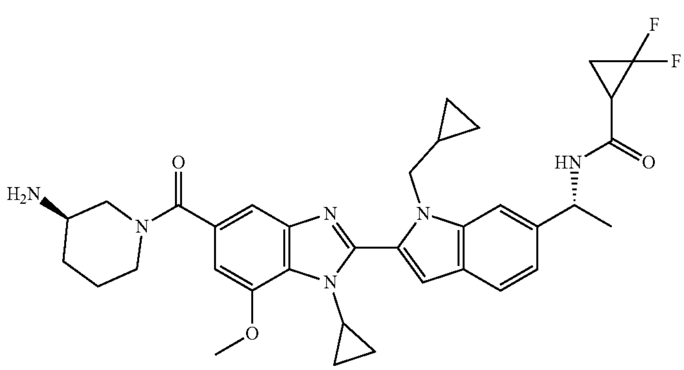 [SMILES: COc1cc(C(=O)N2CCC[C@@H](N)C2)cc2nc(-c3cc4ccc([C@@H](C)NC(=O)C5CC5(F)F)cc4n3CC3CC3)n(C3CC3)c12] | N-((R)-1-(2-(5-((R)-3-aminopiperidine-1-carbonyl)-1-cyclopropyl-7-methoxy-1H-benzo[d]imidazol-2-yl)-1-(cyclopropylmethyl)-1H-indol-6-yl)ethyl)-2,2-difluorocyclopropane-1-carboxamide | 631.34 |
| 154 | 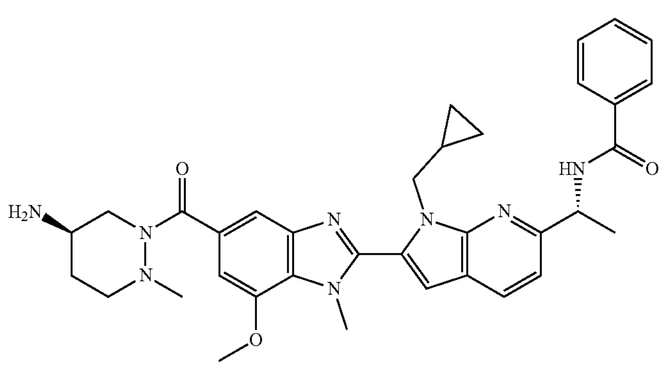 | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)benzamide | 621.3 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 155 | 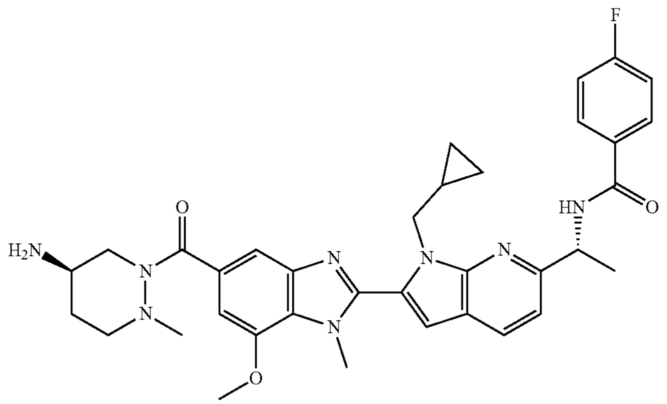 [SMILES: COc1cc(C(=O)N2C[C@H](N)CCN2C)cc2nc(-c3cc4ccc([C@@H](C)NC(=O)c5ccc(F)cc5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-4-fluorobenzamide | 639.3 |
| 156 | 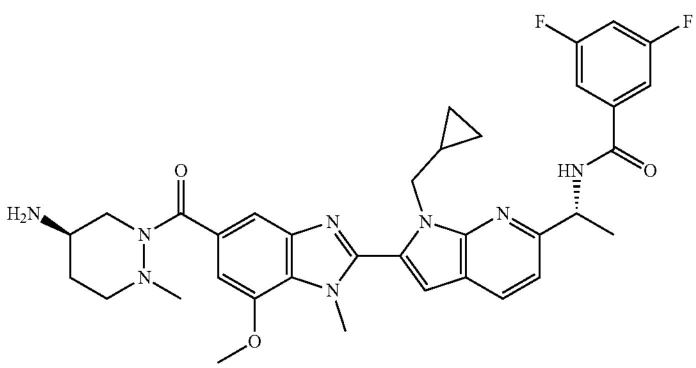 [SMILES: COc1cc(C(=O)N2C[C@H](N)CCN2C)cc2nc(-c3cc4ccc([C@@H](C)NC(=O)c5cc(F)cc(F)c5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-3,5-difluorobenzamide | 657.2 |
| 157 | 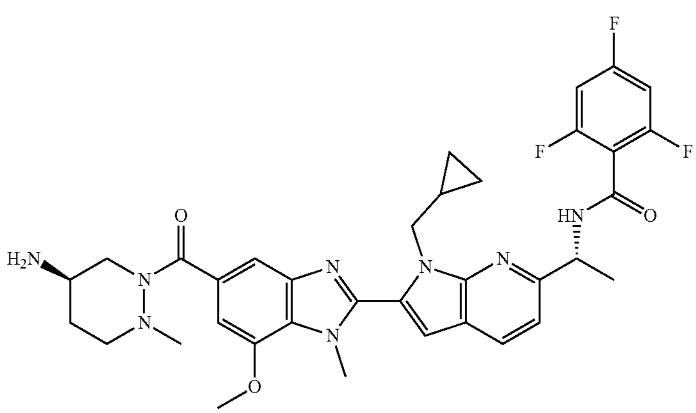 [SMILES: COc1cc(C(=O)N2C[C@H](N)CCN2C)cc2nc(-c3cc4ccc([C@@H](C)NC(=O)c5c(F)cc(F)cc5F)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-2,4,6-trifluorobenzamide | 675.2 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 158 | 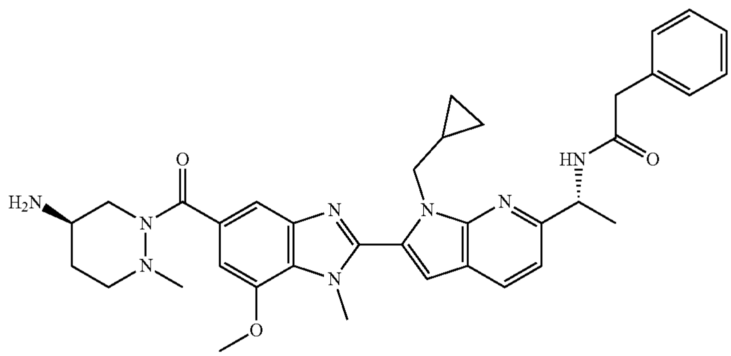 [SMILES: COc1cc(C(=O)N2C[C@H](N)CCN2C)cc2nc(-c3cc4ccc([C@@H](C)NC(=O)Cc5ccccc5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-phenylacetamide | 635.3 |
| 159 | 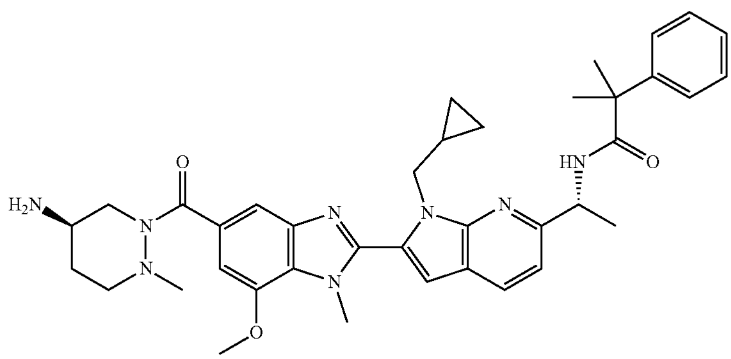 [SMILES: COc1cc(C(=O)N2C[C@H](N)CCN2C)cc2nc(-c3cc4ccc([C@@H](C)NC(=O)C(C)(C)c5ccccc5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-methyl-2-phenylpropanamide | 663.3 |
| 160 | 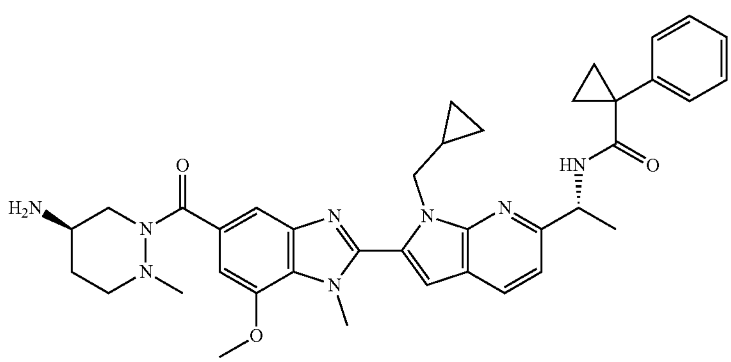 [SMILES: COc1cc(C(=O)N2C[C@H](N)CCN2C)cc2nc(-c3cc4ccc([C@@H](C)NC(=O)C5(c6ccccc6)CC5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-phenylcyclopropane-1-carboxamide | 661.3 |
| 161 | 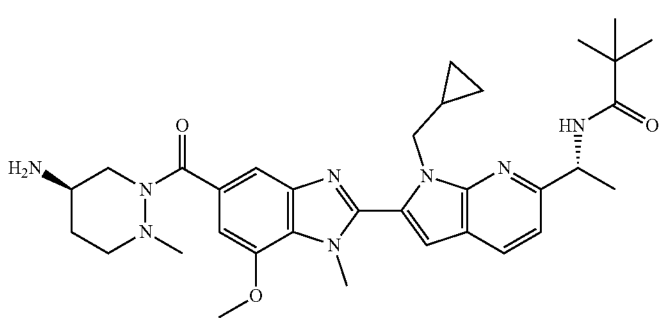 [SMILES: COc1cc(C(=O)N2C[C@H](N)CCN2C)cc2nc(-c3cc4ccc([C@@H](C)NC(=O)C(C)(C)C)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)pivalamide | 601.3 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 162 | 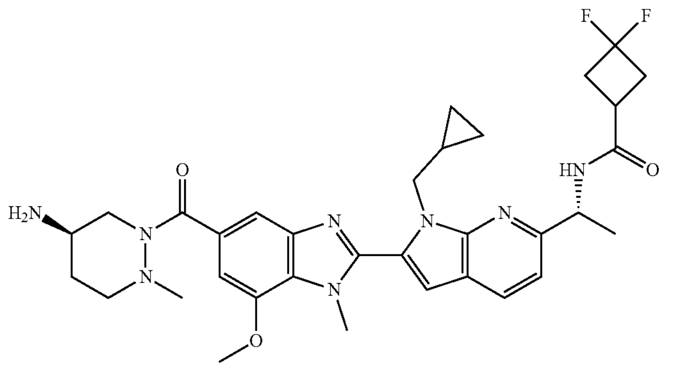 [SMILES: COc1cc(C(=O)N2C[C@H](N)CCN2C)cc2nc(-c3cc4ccc([C@@H](C)NC(=O)C5CC(F)(F)C5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-3,3-difluorocyclobutane-1-carboxamide | 635.2 |
| 163 | 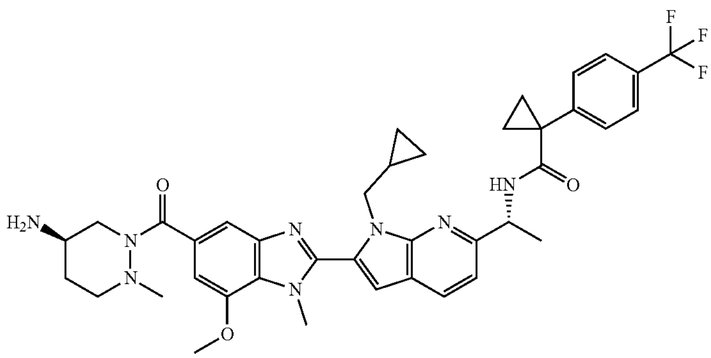 [SMILES: COc1cc(C(=O)N2C[C@H](N)CCN2C)cc2nc(-c3cc4ccc([C@@H](C)NC(=O)C5(c6ccc(C(F)(F)F)cc6)CC5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-(4-(trifluoromethyl)phenyl)cyclopropane-1-carboxamide | 729.29 |
| 164 | 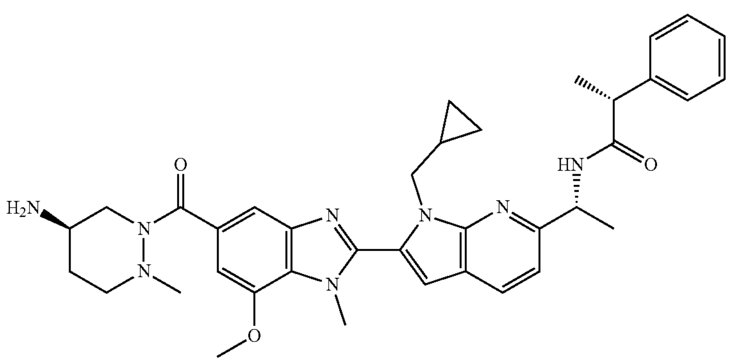 [SMILES: COc1cc(C(=O)N2C[C@H](N)CCN2C)cc2nc(-c3cc4ccc([C@@H](C)NC(=O)[C@H](C)c5ccccc5)nc4n3CC3CC3)n(C)c12] | (R)-N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-phenylpropanamide | 649.34 |
| 165 | 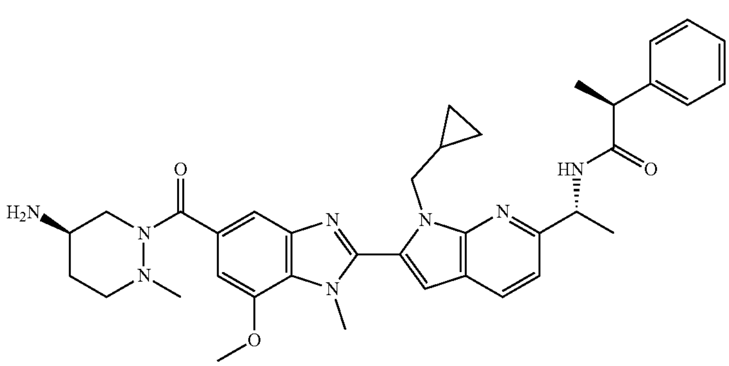 [SMILES: COc1cc(C(=O)N2C[C@H](N)CCN2C)cc2nc(-c3cc4ccc([C@@H](C)NC(=O)[C@@H](C)c5ccccc5)nc4n3CC3CC3)n(C)c12] | (S)-N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-phenylpropanamide | 649.34 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 166 | 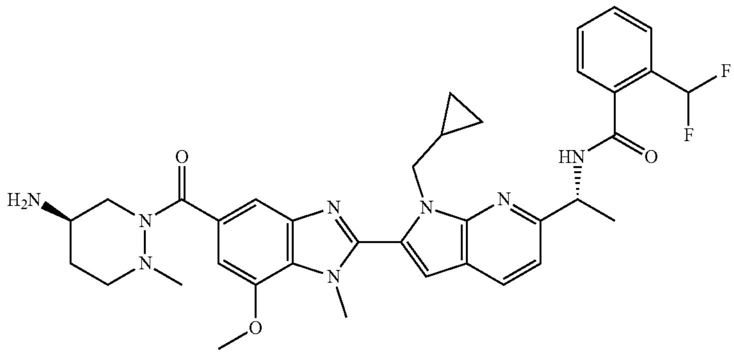 [SMILES: COc1cc(C(=O)N2C[C@H](N)CCN2C)cc2nc(-c3cc4ccc([C@@H](C)NC(=O)c5ccccc5C(F)F)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-(difluoromethyl)benzamide | 671.32 |
| 167 | 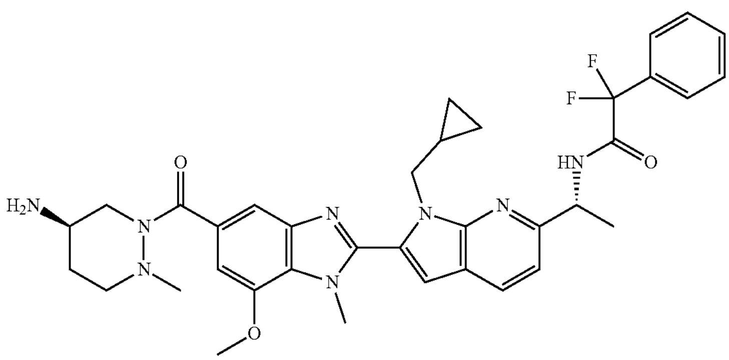 | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-2,2-difluoro-2-phenylacetamide | 671.31 |
| 168 | 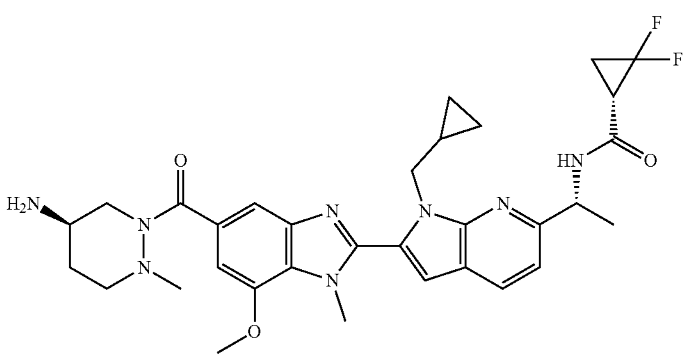 [SMILES: COc1cc(C(=O)N2C[C@H](N)CCN2C)cc2nc(-c3cc4ccc([C@@H](C)NC(=O)[C@@H]5CC5(F)F)nc4n3CC3CC3)n(C)c12] | (S)-N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-2,2-difluorocyclopropane-1-carboxamide | 621.29 |
| 169 | 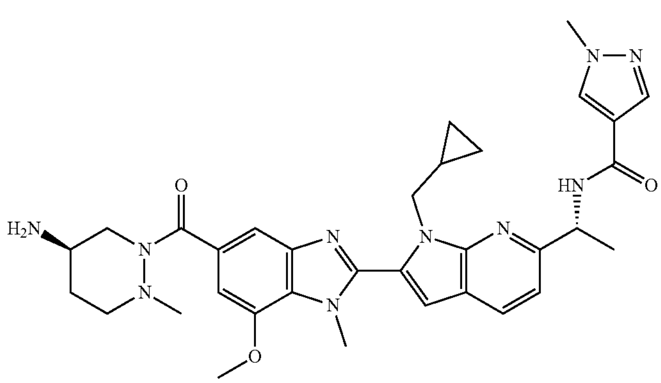 [SMILES: COc1cc(C(=O)N2C[C@H](N)CCN2C)cc2nc(-c3cc4ccc([C@@H](C)NC(=O)c5cnn(C)c5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-methyl-1H-pyrazole-4-carboxamide | 625.35 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 170 | 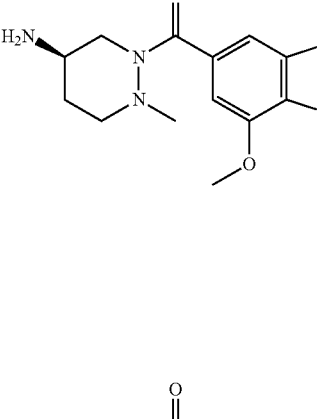 | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-(difluoromethyl)-1H-pyrazole-4-carboxamide | 661.29 |
| 171 | 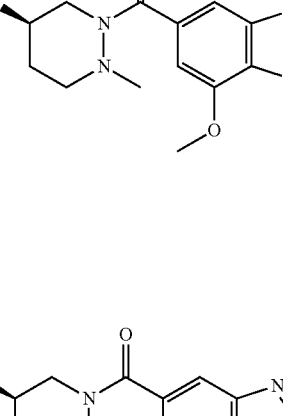 | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-3-fluorobicyclo[1.1.1]pentane-1-carboxamide | 629.32 |
| 172 | 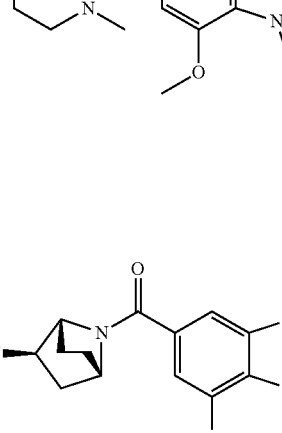 | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-2,6-dimethylbenzamide | 649.42 |
| 173 | 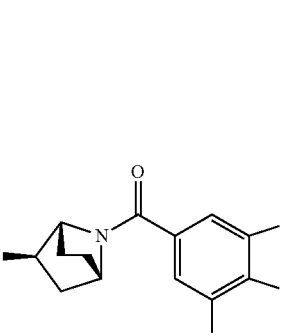 | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-(1H-pyrazol-1-yl)cyclopropane-1-carboxamide | 648.27 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 174 | 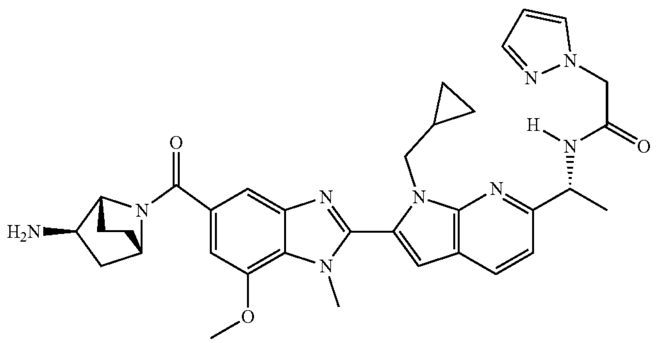 [SMILES: COc1cc(C(=O)N2[C@H]3CC[C@@H]2[C@H](N)C3)cc2nc(-c3cc4ccc([C@@H](C)NC(=O)Cn5cccn5)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-(1H-pyrazol-1-yl)acetamide | 622.25 |
| 175 | 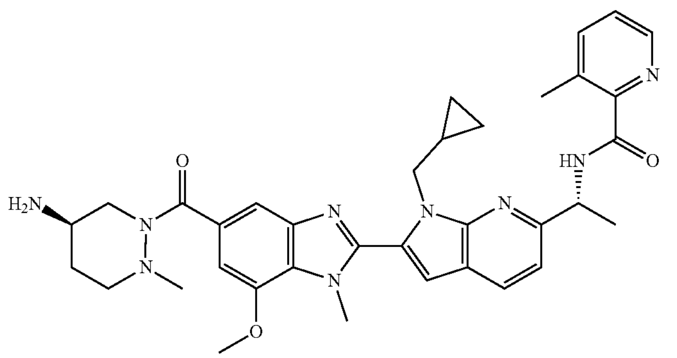 [SMILES: COc1cc(C(=O)N2C[C@H](N)CCN2C)cc2nc(-c3cc4ccc([C@@H](C)NC(=O)c5ncccc5C)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-3-methylpicolinamide | 636.29 |
| 176 | 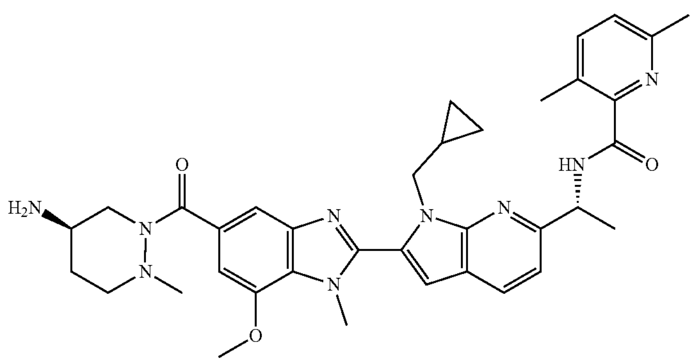 [SMILES: COc1cc(C(=O)N2C[C@H](N)CCN2C)cc2nc(-c3cc4ccc([C@@H](C)NC(=O)c5nc(C)ccc5C)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-3,6-dimethylpicolinamide | 650.33 |
| 177 | 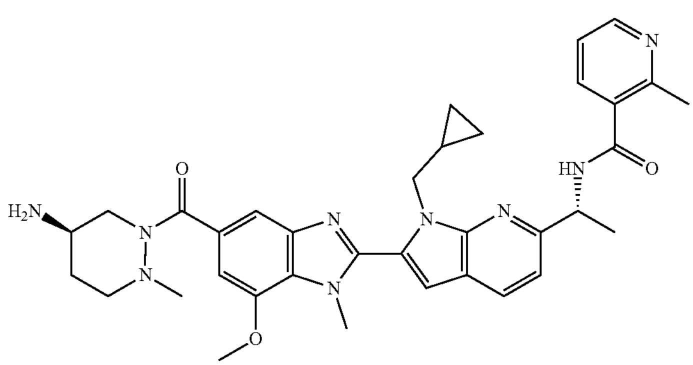 [SMILES: COc1cc(C(=O)N2C[C@H](N)CCN2C)cc2nc(-c3cc4ccc([C@@H](C)NC(=O)c5cccnc5C)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-methylnicotinamide | 636.34 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 178 | 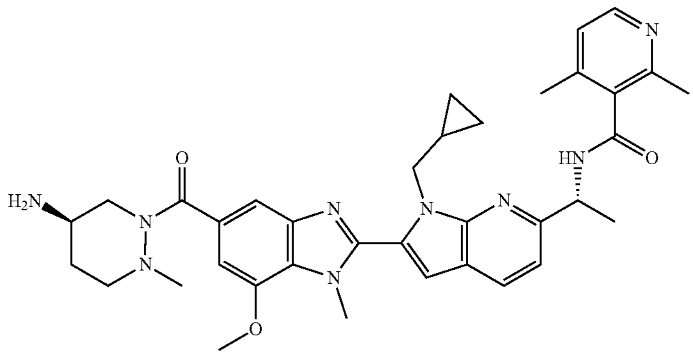 | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-2,4-dimethylnicotinamide | 650.37 |
| 179 | 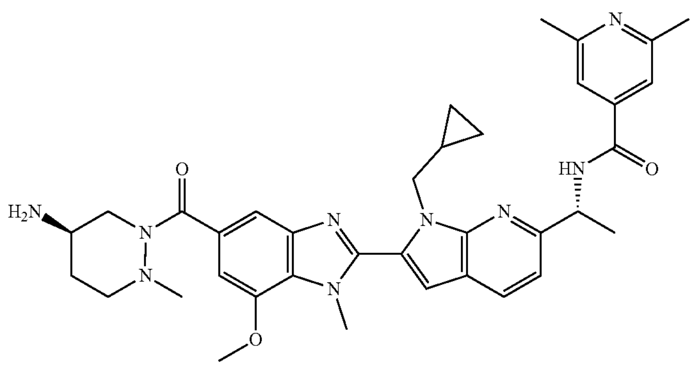 [SMILES: COc1cc(C(=O)N2C[C@H](N)CCN2C)cc2nc(-c3cc4ccc([C@@H](C)NC(=O)c5cc(C)nc(C)c5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-2,6-dimethylisonicotinamide | 650.33 |
| 180 | 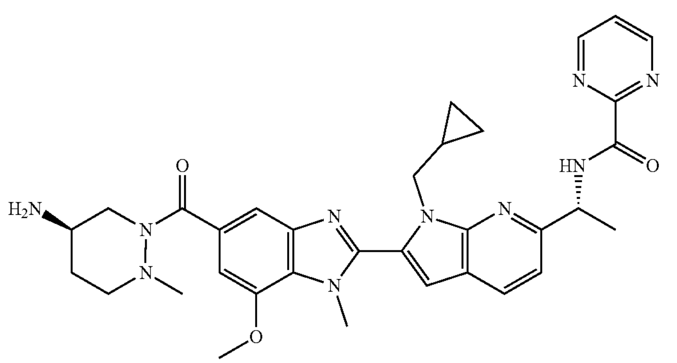 [SMILES: COc1cc(C(=O)N2C[C@H](N)CCN2C)cc2nc(-c3cc4ccc([C@@H](C)NC(=O)c5ncccn5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)pyrimidine-2-carboxamide | 623.41 |
| 181 | 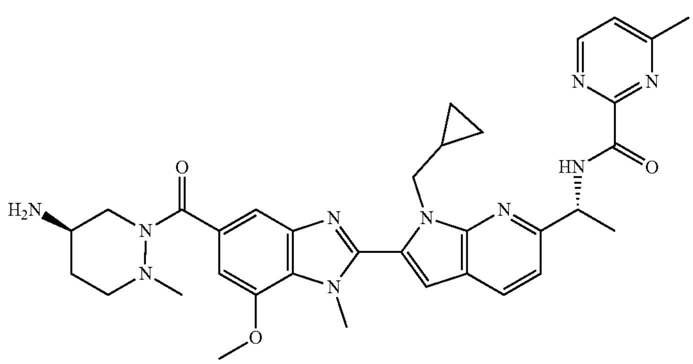 [SMILES: COc1cc(C(=O)N2C[C@H](N)CCN2C)cc2nc(-c3cc4ccc([C@@H](C)NC(=O)c5nccc(C)n5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-4-methylpyrimidine-2-carboxamide | 637.63 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 182 | 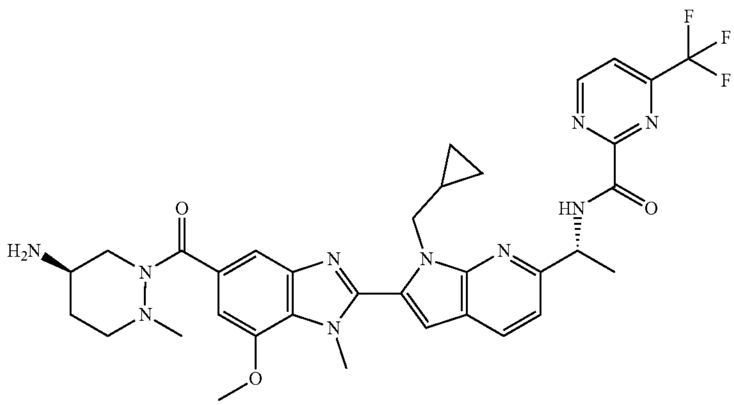 [SMILES: COc1cc(C(=O)N2C[C@H](N)CCN2C)cc2nc(-c3cc4ccc([C@@H](C)NC(=O)c5nccc(C(F)(F)F)n5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-4-(trifluoromethyl)pyrimidine-2-carboxamide | 691.43 |
| 183 | 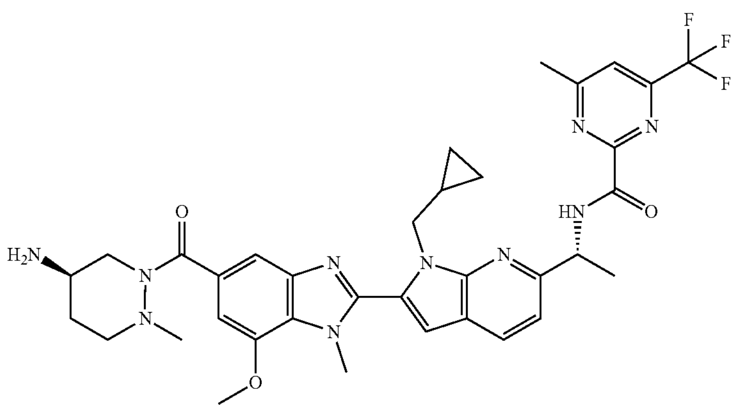 [SMILES: COc1cc(C(=O)N2C[C@H](N)CCN2C)cc2nc(-c3cc4ccc([C@@H](C)NC(=O)c5nc(C)cc(C(F)(F)F)n5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-4-methyl-6-(trifluoromethyl)pyrimidine-2-carboxamide | 705.34 |
| 184 | 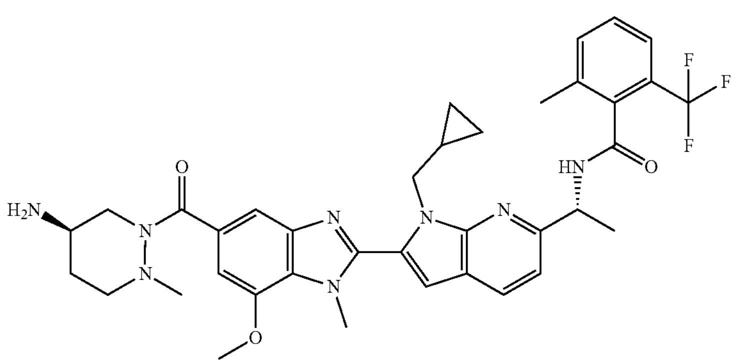 [SMILES: COc1cc(C(=O)N2C[C@H](N)CCN2C)cc2nc(-c3cc4ccc([C@@H](C)NC(=O)c5c(C)cccc5C(F)(F)F)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-methyl-6-(trifluoromethyl)benzamide | 703.32 |
| 185 | 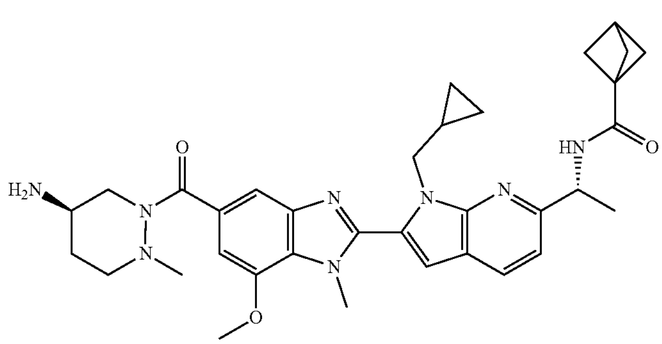 [SMILES: COc1cc(C(=O)N2C[C@H](N)CCN2C)cc2nc(-c3cc4ccc([C@@H](C)NC(=O)C56CC(C5)C6)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)bicyclo[1.1.1]pentane-1-carboxamide | 611.29 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 186 | 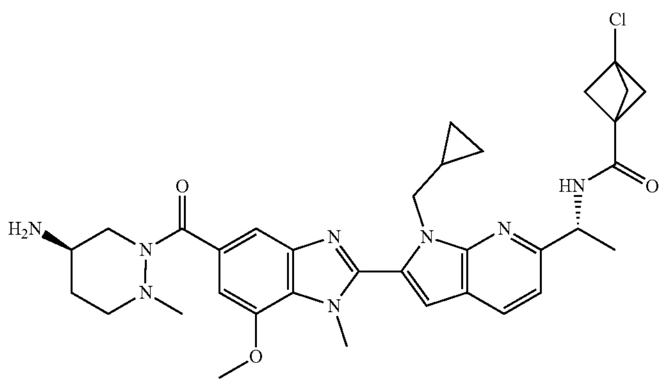 | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-3-chlorobicyclo[1.1.1]pentane-1-carboxamide | 645.35 |
| 187 | 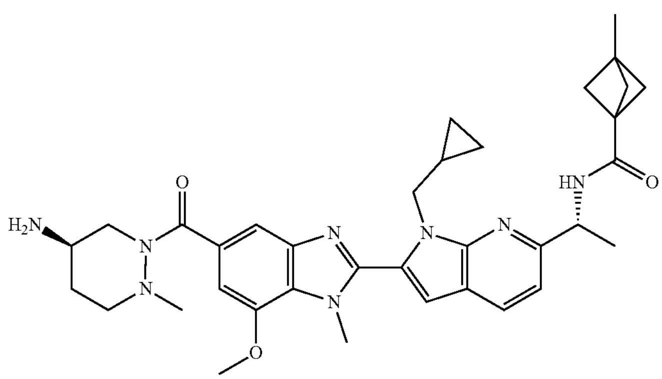 [SMILES: COc1cc(C(=O)N2C[C@H](N)CCN2C)cc2nc(-c3cc4ccc([C@@H](C)NC(=O)C56CC(C)(C5)C6)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-3-methylbicyclo[1.1.1]pentane-1-carboxamide | 625.4 |
| 188 | 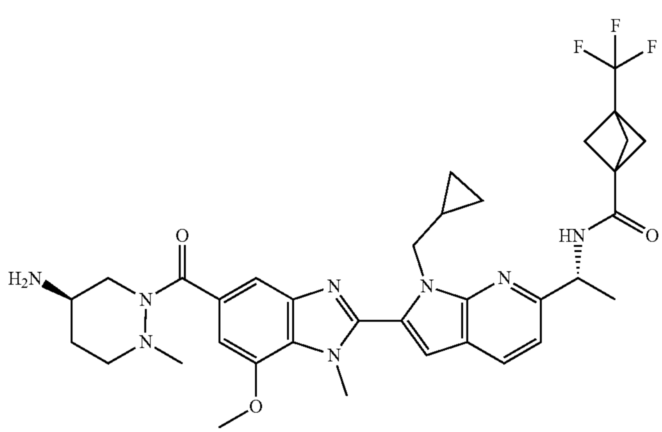 [SMILES: COc1cc(C(=O)N2C[C@H](N)CCN2C)cc2nc(-c3cc4ccc([C@@H](C)NC(=O)C56CC(C(F)(F)F)(C5)C6)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-3-(trifluoromethyl)bicyclo[1.1.1]pentane-1-carboxamide | 679.28 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 189 | 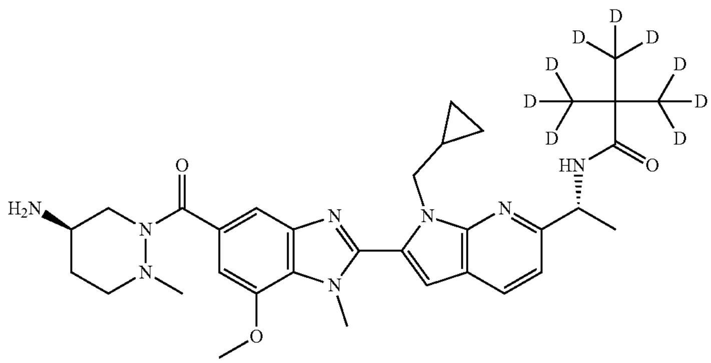 [SMILES: [2H]C([2H])([2H])C(C(=O)N[C@H](C)c1ccc2cc(-c3nc4cc(C(=O)N5C[C@H](N)CCN5C)cc(OC)c4n3C)n(CC3CC3)c2n1)(C([2H])([2H])[2H])C([2H])([2H])[2H]] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-2,2-bis(methyl-d3)propanamide | 610.55 |
| 190 | 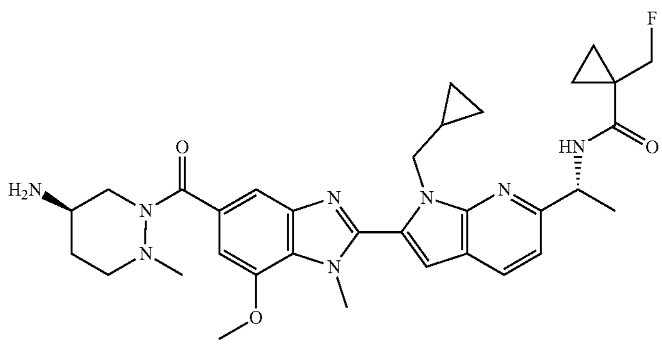 [SMILES: COc1cc(C(=O)N2C[C@H](N)CCN2C)cc2nc(-c3cc4ccc([C@@H](C)NC(=O)C5(CF)CC5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-(fluoromethyl)cyclopropane-1-carboxamide | 617.35 |
| 191 | 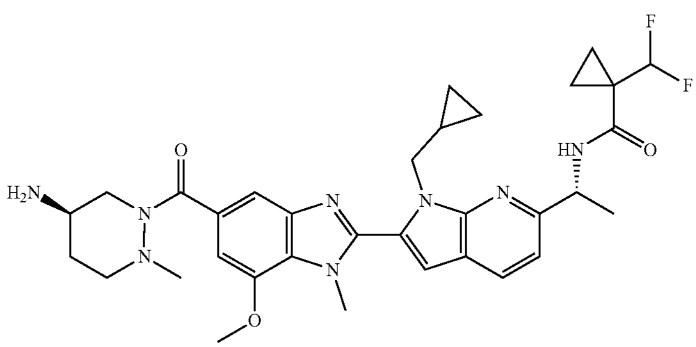 [SMILES: COc1cc(C(=O)N2C[C@H](N)CCN2C)cc2nc(-c3cc4ccc([C@@H](C)NC(=O)C5(C(F)F)CC5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-(difluoromethyl)cyclopropane-1-carboxamide | 635.32 |
| 192 | 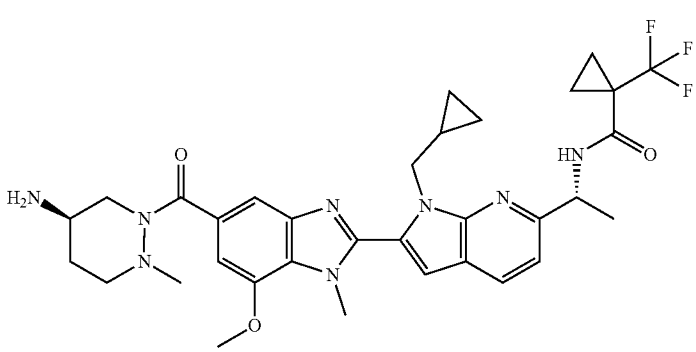 [SMILES: COc1cc(C(=O)N2C[C@H](N)CCN2C)cc2nc(-c3cc4ccc([C@@H](C)NC(=O)C5(C(F)(F)F)CC5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-(trifluoromethyl)cyclopropane-1-carboxamide | 653.31 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 193 | 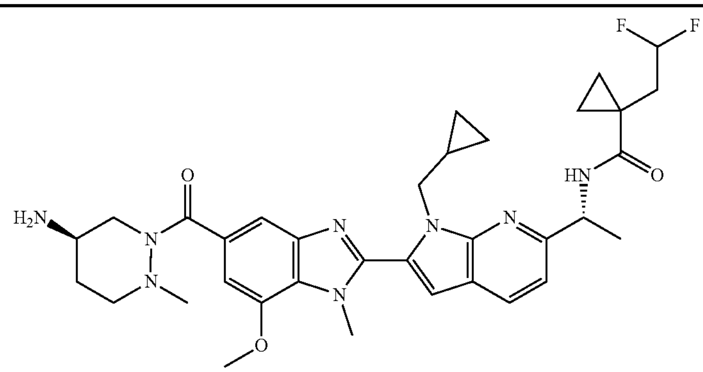 | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-(2,2-difluoroethyl)cyclopropane-1-carboxamide | 649.31 |
| 194 | 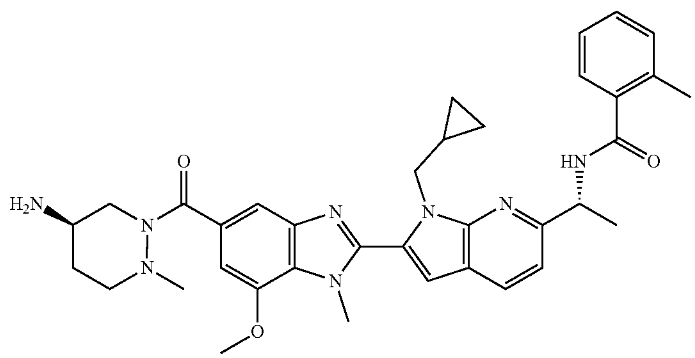 [SMILES: COc1cc(C(=O)N2C[C@H](N)CCN2C)cc2nc(-c3cc4ccc([C@@H](C)NC(=O)c5ccccc5C)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-methylbenzamide | 635.34 |
| 195 | 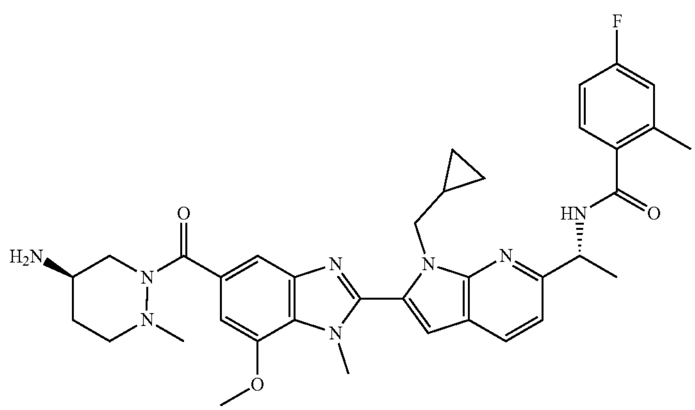 [SMILES: COc1cc(C(=O)N2C[C@H](N)CCN2C)cc2nc(-c3cc4ccc([C@@H](C)NC(=O)c5ccc(F)cc5C)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-4-fluoro-2-methylbenzamide | 653.3 |
| 196 | 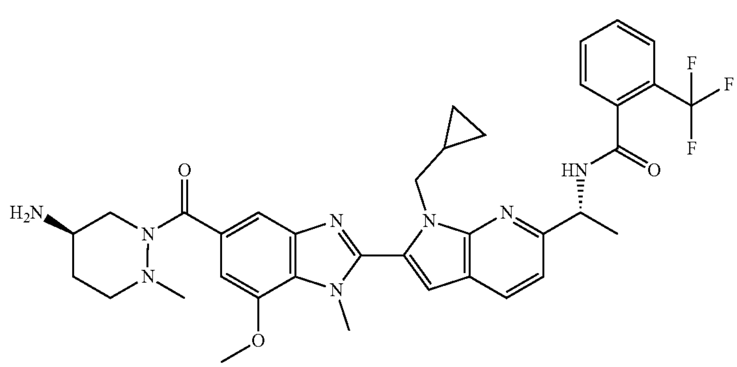 [SMILES: COc1cc(C(=O)N2C[C@H](N)CCN2C)cc2nc(-c3cc4ccc([C@@H](C)NC(=O)c5ccccc5C(F)(F)F)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-(trifluoromethyl)benzamide | 689.32 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 197 | 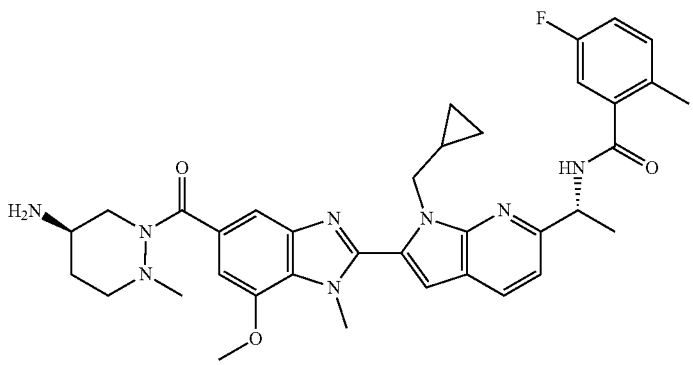 [SMILES: COc1cc(C(=O)N2C[C@H](N)CCN2C)cc2nc(-c3cc4ccc([C@@H](C)NC(=O)c5cc(F)ccc5C)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-5-fluoro-2-methylbenzamide | 653.32 |
| 198 | 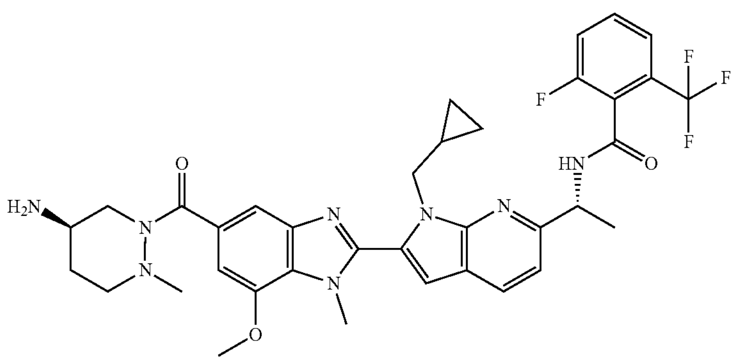 [SMILES: COc1cc(C(=O)N2C[C@H](N)CCN2C)cc2nc(-c3cc4ccc([C@@H](C)NC(=O)c5c(F)cccc5C(F)(F)F)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-fluoro-6-(trifluoromethyl)benzamide | 707.31 |
| 199 | 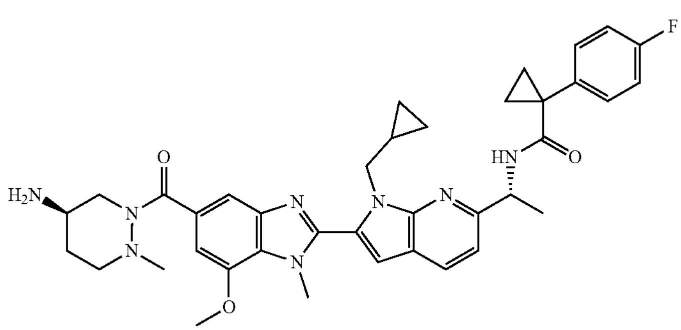 [SMILES: COc1cc(C(=O)N2C[C@H](N)CCN2C)cc2nc(-c3cc4ccc([C@@H](C)NC(=O)C5(c6ccc(F)cc6)CC5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-(4-fluorophenyl)cyclopropane-1-carboxamide | 679.37 |
| 200 | 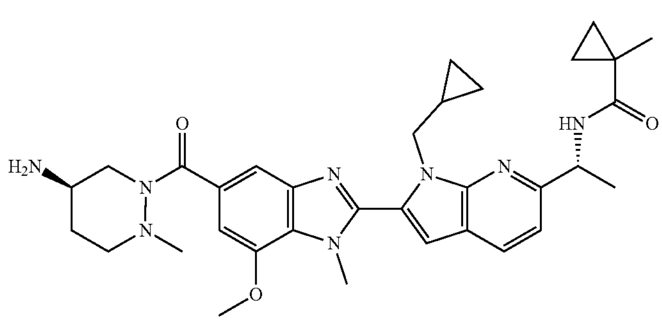 [SMILES: COc1cc(C(=O)N2C[C@H](N)CCN2C)cc2nc(-c3cc4ccc([C@@H](C)NC(=O)C5(C)CC5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-methylcyclopropane-1-carboxamide | 599.32 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 201 | 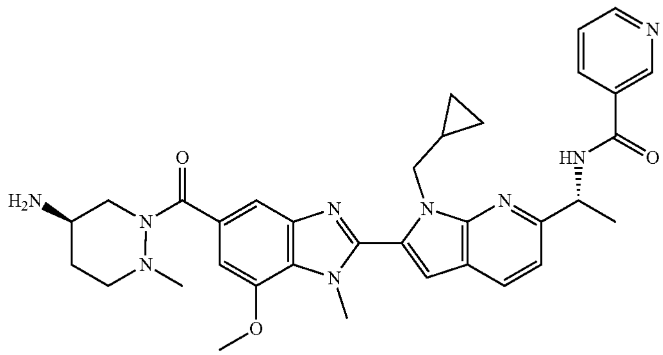 [SMILES: COc1cc(C(=O)N2C[C@H](N)CCN2C)cc2nc(-c3cc4ccc([C@@H](C)NC(=O)c5cccnc5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)nicotinamide | 622.31 |
| 202 | 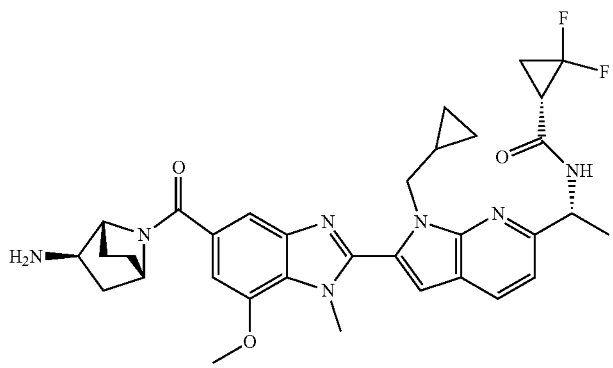 [SMILES: COc1cc(C(=O)N2[C@H]3CC[C@@H]2[C@H](N)C3)cc2nc(-c3cc4ccc([C@@H](C)NC(=O)[C@@H]5CC5(F)F)nc4n3CC3CC3)n(C)c12] | (S)-N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)-2,2-difluorocyclopropane-1-carboxamide | 618.4 |
| 203 | 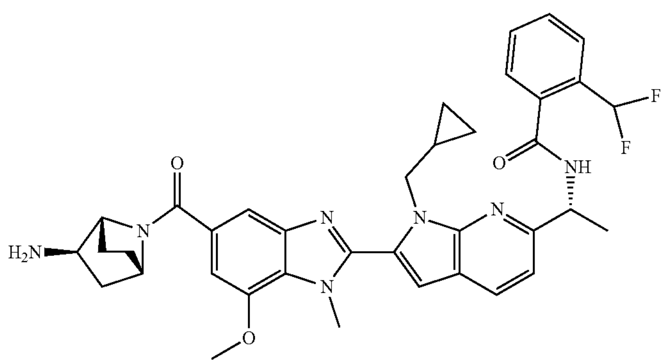 [SMILES: COc1cc(C(=O)N2[C@H]3CC[C@@H]2[C@H](N)C3)cc2nc(-c3cc4ccc([C@@H](C)NC(=O)c5ccccc5C(F)F)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-(difluoromethyl)benzamide | 668.2 |
| 204 | 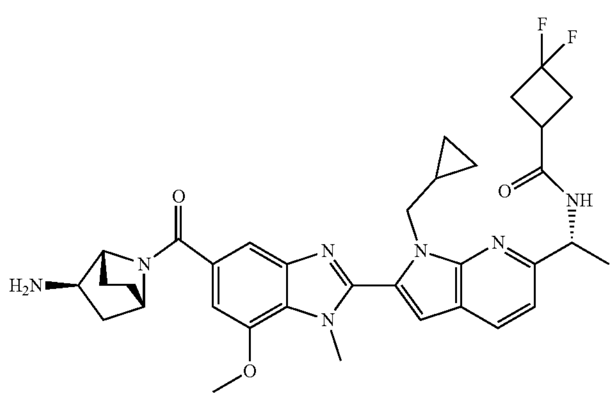 [SMILES: COc1cc(C(=O)N2[C@H]3CC[C@@H]2[C@H](N)C3)cc2nc(-c3cc4ccc([C@@H](C)NC(=O)C5CC(F)(F)C5)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)-3,3-difluorocyclobutane-1-carboxamide | 632.4 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 205 | 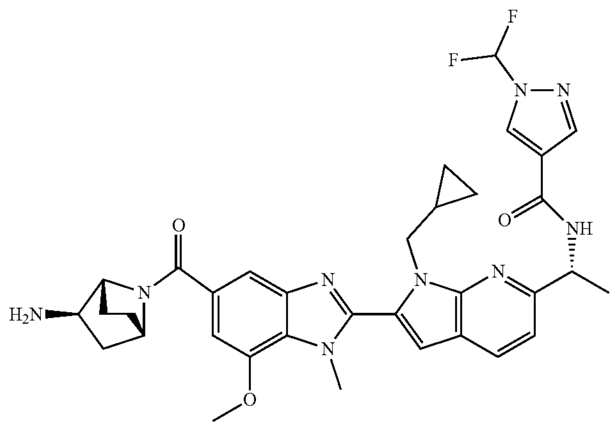 [SMILES: COc1cc(C(=O)N2[C@H]3CC[C@@H]2[C@H](N)C3)cc2nc(-c3cc4ccc([C@@H](C)NC(=O)c5cnn(C(F)F)c5)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-(difluoromethyl)-1H-pyrazole-4-carboxamide | 658.3 |
| 206 | 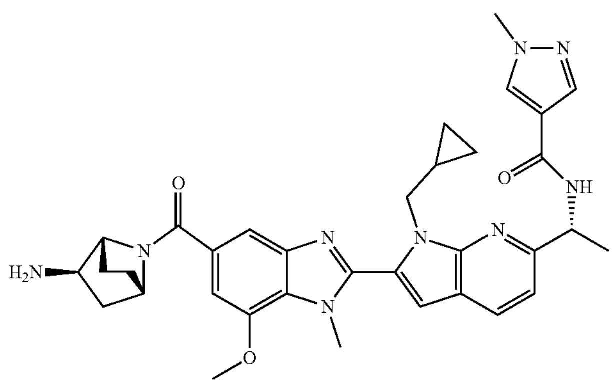 [SMILES: COc1cc(C(=O)N2[C@H]3CC[C@@H]2[C@H](N)C3)cc2nc(-c3cc4ccc([C@@H](C)NC(=O)c5cnn(C)c5)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-methyl-1H-pyrazole-4-carboxamide | 622.3 |
| 207 | 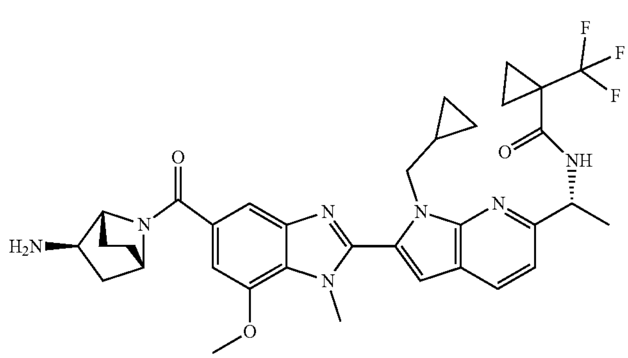 [SMILES: COc1cc(C(=O)N2[C@H]3CC[C@@H]2[C@H](N)C3)cc2nc(-c3cc4ccc([C@@H](C)NC(=O)C5(C(F)(F)F)CC5)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-(trifluoromethyl)cyclopropane-1-carboxamide | 650.1 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 208 | 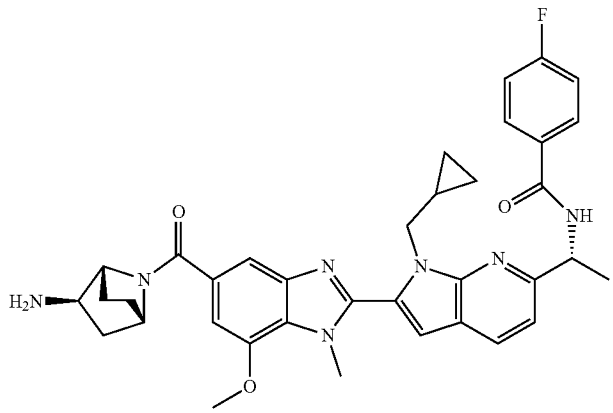 [SMILES: COc1cc(C(=O)N2[C@H]3CC[C@@H]2[C@H](N)C3)cc2nc(-c3cc4ccc([C@@H](C)NC(=O)c5ccc(F)cc5)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)-4-fluorobenzamide | 636.3 |
| 209 | 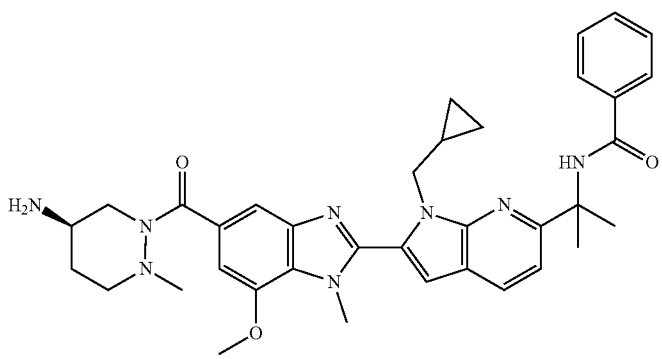 | (R)-N-(2-(2-(5-(5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)propan-2-yl)benzamide | 635.38 |
| 210 | 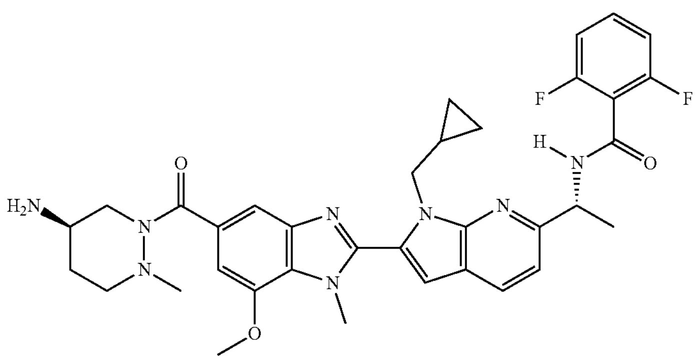 [SMILES: COc1cc(C(=O)N2C[C@H](N)CCN2C)cc2nc(-c3cc4ccc([C@@H](C)NC(=O)c5c(F)cccc5F)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-2,6-difluorobenzamide | 657.23 |
| 211 | 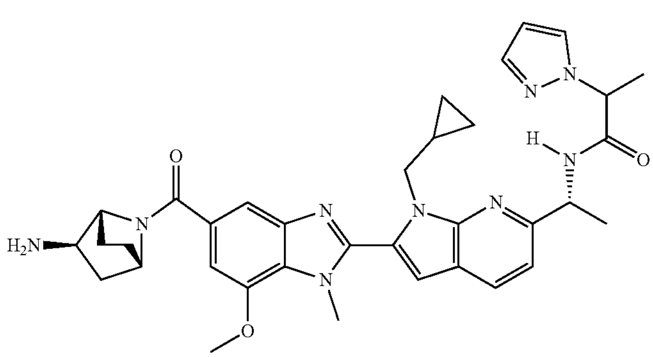 [SMILES: COc1cc(C(=O)N2[C@H]3CC[C@@H]2[C@H](N)C3)cc2nc(-c3cc4ccc([C@@H](C)NC(=O)C(C)n5cccn5)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-(1H-pyrazol-1-yl)propanamide | 636.27 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 212 | 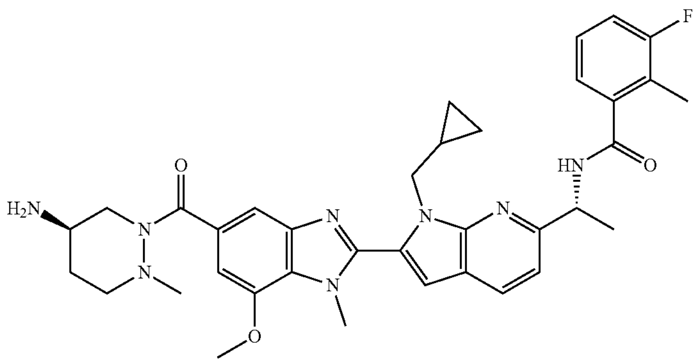 [SMILES: COc1cc(C(=O)N2C[C@H](N)CCN2C)cc2nc(-c3cc4ccc([C@@H](C)NC(=O)c5cccc(F)c5C)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-3-fluoro-2-methylbenzamide | 653.4 |
| 213 | 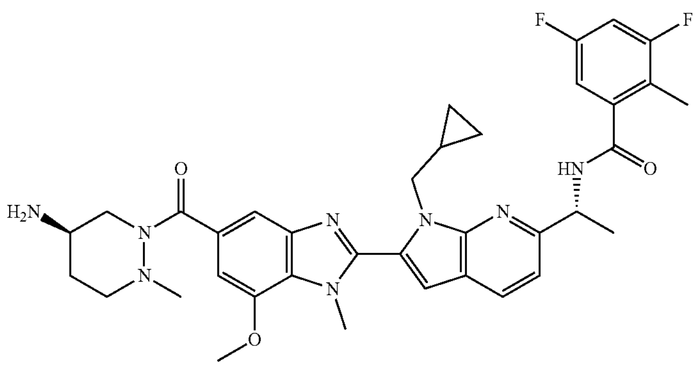 [SMILES: COc1cc(C(=O)N2C[C@H](N)CCN2C)cc2nc(-c3cc4ccc([C@@H](C)NC(=O)c5cc(F)cc(F)c5C)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-3,5-difluoro-2-methylbenzamide | 671.3 |
| 214 | 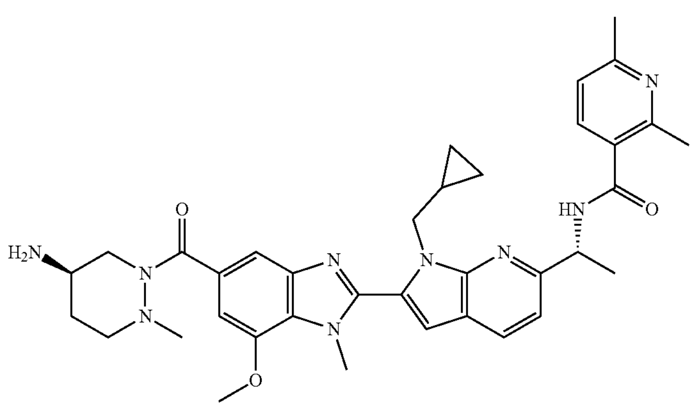 [SMILES: COc1cc(C(=O)N2C[C@H](N)CCN2C)cc2nc(-c3cc4ccc([C@@H](C)NC(=O)c5ccc(C)nc5C)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-2,6-dimethylnicotinamide | 650.4 |
| 215 | 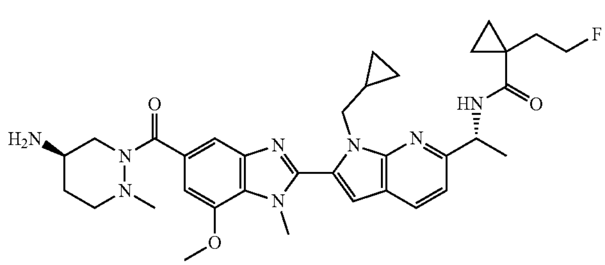 [SMILES: COc1cc(C(=O)N2C[C@H](N)CCN2C)cc2nc(-c3cc4ccc([C@@H](C)NC(=O)C5(CCF)CC5)nc4n3CC3CC3)n(C)c12] | N-((R)-1-(2-(5-((R)-5-amino-2-methylhexahydropyridazine-1-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-(2-fluoroethyl)cyclopropane-1-carboxamide | 631.32 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 216 | 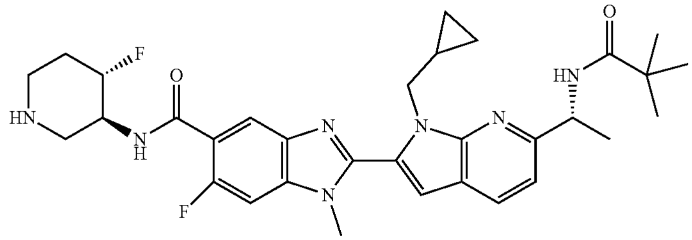 [SMILES: C[C@@H](NC(=O)C(C)(C)C)c1ccc2cc(-c3nc4cc(C(=O)N[C@H]5CNCC[C@@H]5F)c(F)cc4n3C)n(CC3CC3)c2n1] | 2-(1-(cyclopropylmethyl)-6-((R)-1-pivalamidoethyl)-1H-pyrrolo[2,3-b]pyridin-2-yl)-6-fluoro-N-((3S,4S)-4-fluoropiperidin-3-yl)-1-methyl-1H-benzo[d]imidazole-5-carboxamide | 592.6 |
| 217 | 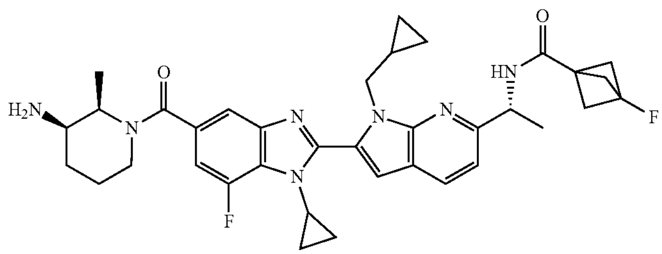 [SMILES: C[C@@H]1[C@H](N)CCCN1C(=O)c1cc(F)c2c(c1)nc(-c1cc3ccc([C@@H](C)NC(=O)C45CC(F)(C4)C5)nc3n1CC1CC1)n2C1CC1] | N-((R)-1-(2-(5-((2R,3R)-3-amino-2-methylpiperidine-1-carbonyl)-1-cyclopropyl-7-fluoro-1H-benzo[d]imidazol-2-yl)-1-(cyclopropylmethyl)-1H-pyrrolo[2,3-b]pyridin-6-yl)ethyl)-3-fluorobicyclo[1.1.1]pentane-1-carboxamide | 642.42 |
| 218 | 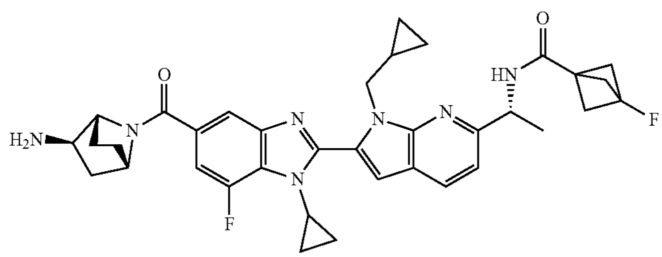 [SMILES: C[C@@H](NC(=O)C12CC(F)(C1)C2)c1ccc2cc(-c3nc4cc(C(=O)N5[C@H]6CC[C@@H]5[C@H](N)C6)cc(F)c4n3C3CC3)n(CC3CC3)c2n1] | N-((R)-1-(2-(5-((1R,2R,4S)-2-amino-7-azabicyclo[2.2.1]heptane-7-carbonyl)-1-cyclopropyl-7-fluoro-1H-benzo[d]imidazol-2-yl)-1-(cyclopropylmethyl)-1H-pyrrolo[2,3-b]pyridin-6-yl)ethyl)-3-fluorobicyclo[1.1.1]pentane-1-carboxamide | 640.22 |
| 219 | 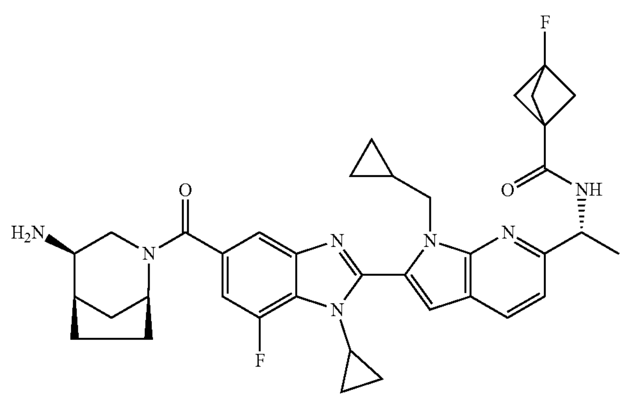 [SMILES: C[C@@H](NC(=O)C12CC(F)(C1)C2)c1ccc2cc(-c3nc4cc(C(=O)N5C[C@H](N)[C@@H]6CC[C@H]5C6)cc(F)c4n3C3CC3)n(CC3CC3)c2n1] | N-((R)-1-(2-(5-((1S,4R,5R)-4-amino-2-azabicyclo[3.2.1]octane-2-carbonyl)-1-cyclopropyl-7-fluoro-1H-benzo[d]imidazol-2-yl)-1-(cyclopropylmethyl)-1H-pyrrolo[2,3-b]pyridin-6-yl)ethyl)-3-fluorobicyclo[1.1.1]pentane-1-carboxamide | 654.3 |
| 220 | 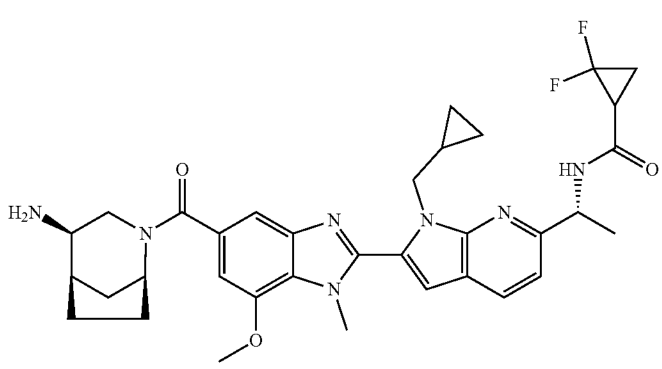 | (R)-N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2,2-difluorocyclopropane-1-carboxamide | 632.30 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 221 | 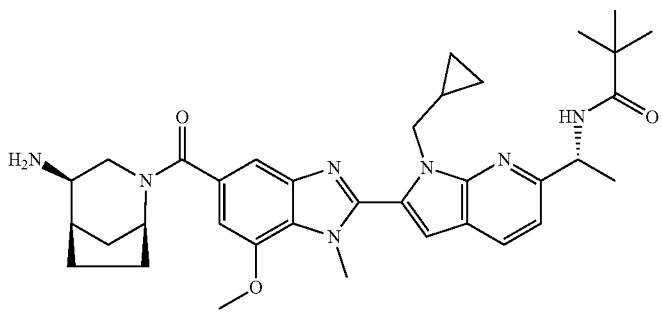 [SMILES: COc1cc(C(=O)N2C[C@H](N)[C@@H]3CC[C@H]2C3)cc2nc(-c3cc4ccc([C@@H](C)NC(=O)C(C)(C)C)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)pivalamide | 612.29 |
| 222 | 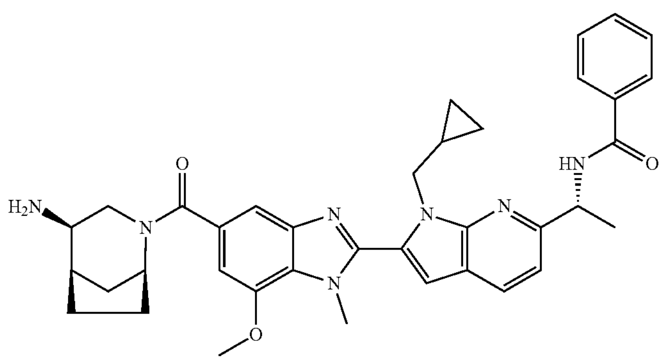 [SMILES: COc1cc(C(=O)N2C[C@H](N)[C@@H]3CC[C@H]2C3)cc2nc(-c3cc4ccc([C@@H](C)NC(=O)c5ccccc5)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)benzamide | 632.28 |
| 223 | 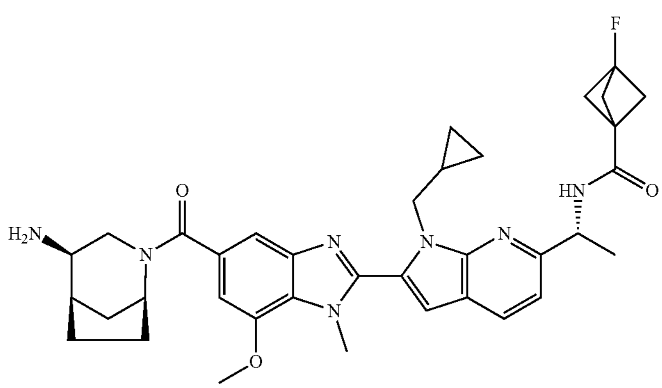 [SMILES: COc1cc(C(=O)N2C[C@H](N)[C@@H]3CC[C@H]2C3)cc2nc(-c3cc4ccc([C@@H](C)NC(=O)C56CC(F)(C5)C6)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-3-fluorobicyclo[1.1.1]pentane-1-carboxamide | 640.26 |
| 224 | 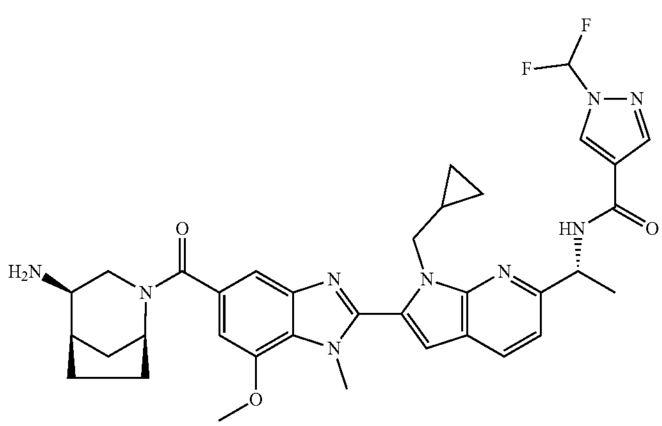 [SMILES: COc1cc(C(=O)N2C[C@H](N)[C@@H]3CC[C@H]2C3)cc2nc(-c3cc4ccc([C@@H](C)NC(=O)c5cnn(C(F)F)c5)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-(difluoromethyl)-1H-pyrazole-4-carboxamide | 672.30 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 225 | 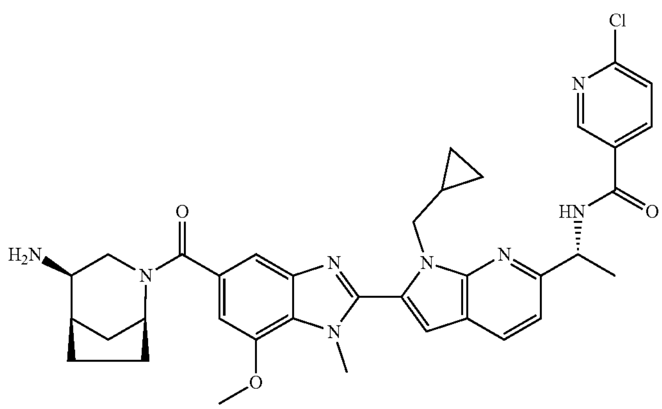 [SMILES: COc1cc(C(=O)N2C[C@H](N)[C@@H]3CC[C@H]2C3)cc2nc(-c3cc4ccc([C@@H](C)NC(=O)c5ccc(Cl)nc5)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-6-chloronicotinamide | 667.32 |
| 226 | 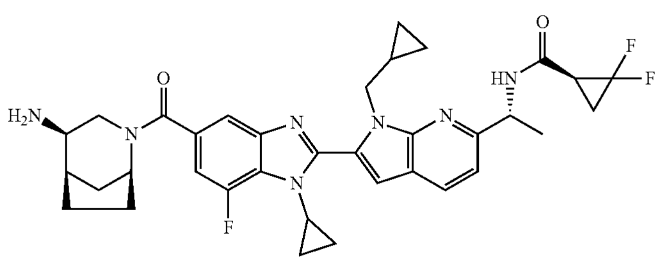 [SMILES: C[C@@H](NC(=O)[C@@H]1CC1(F)F)c1ccc2cc(-c3nc4cc(C(=O)N5C[C@H](N)[C@@H]6CC[C@H]5C6)cc(F)c4n3C3CC3)n(CC3CC3)c2n1] | (S)-N-((R)-1-(2-(5-((1S,4R,5R)-4-amino-2-azabicyclo[3.2.1]octane-2-carbonyl)-1-cyclopropyl-7-fluoro-1H-benzo[d]imidazol-2-yl)-1-(cyclopropylmethyl)-1H-pyrrolo[2,3-b]pyridin-6-yl)ethyl)-2,2-difluorocyclopropane-1-carboxamide | 646.26 |
| 227 | 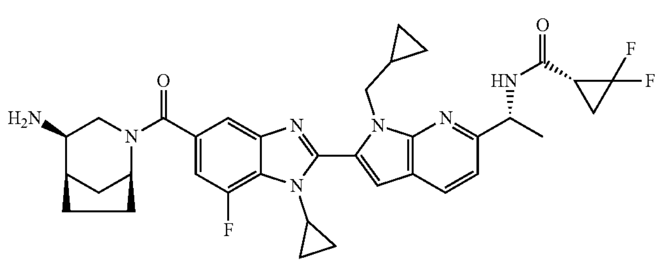 [SMILES: C[C@@H](NC(=O)[C@H]1CC1(F)F)c1ccc2cc(-c3nc4cc(C(=O)N5C[C@H](N)[C@@H]6CC[C@H]5C6)cc(F)c4n3C3CC3)n(CC3CC3)c2n1] | (R)-N-((R)-1-(2-(5-((1S,4R,5R)-4-amino-2-azabicyclo[3.2.1]octane-2-carbonyl)-1-cyclopropyl-7-fluoro-1H-benzo[d]imidazol-2-yl)-1-(cyclopropylmethyl)-1H-pyrrolo[2,3-b]pyridin-6-yl)ethyl)-2,2-difluorocyclopropane-1-carboxamide | 646.26 |
| 228 | 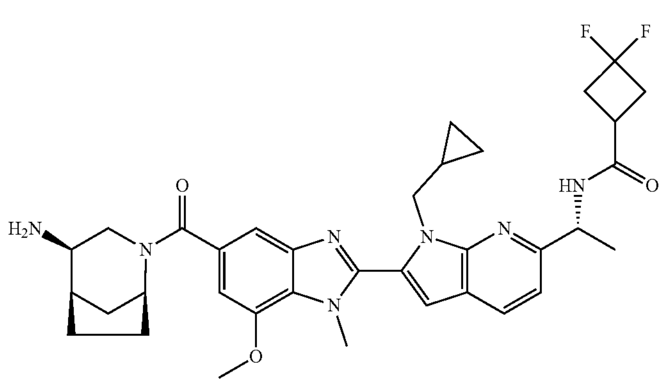 [SMILES: COc1cc(C(=O)N2C[C@H](N)[C@@H]3CC[C@H]2C3)cc2nc(-c3cc4ccc([C@@H](C)NC(=O)C5CC(F)(F)C5)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-3,3-difluorocyclobutane-1-carboxamide | 646.22 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 229 | 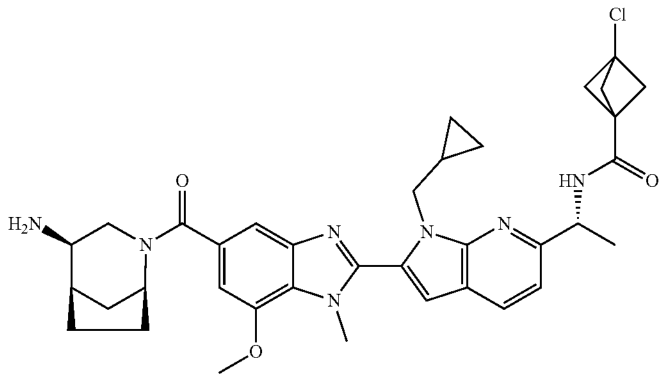 [SMILES: COc1cc(C(=O)N2C[C@H](N)[C@@H]3CC[C@H]2C3)cc2nc(-c3cc4ccc([C@@H](C)NC(=O)C56CC(Cl)(C5)C6)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-3-chlorobicyclo[1.1.1]pentane-1-carboxamide | 656.22 |
| 230 | 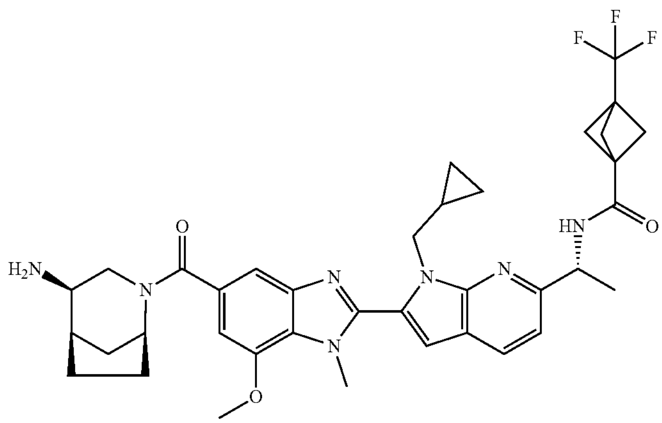 [SMILES: COc1cc(C(=O)N2C[C@H](N)[C@@H]3CC[C@H]2C3)cc2nc(-c3cc4ccc([C@@H](C)NC(=O)C56CC(C(F)(F)F)(C5)C6)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-3-(trifluoromethyl)bicyclo[1.1.1]pentane-1-carboxamide | 690.21 |
| 231 | 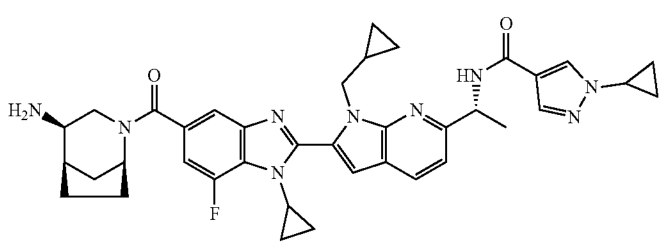 [SMILES: C[C@@H](NC(=O)c1cnn(C2CC2)c1)c1ccc2cc(-c3nc4cc(C(=O)N5C[C@H](N)[C@@H]6CC[C@H]5C6)cc(F)c4n3C3CC3)n(CC3CC3)c2n1] | N-((R)-1-(2-(5-((1S,4R,5R)-4-amino-2-azabicyclo[3.2.1]octane-2-carbonyl)-1-cyclopropyl-7-fluoro-1H-benzo[d]imidazol-2-yl)-1-(cyclopropylmethyl)-1H-pyrrolo[2,3-b]pyridin-6-yl)ethyl)-1-cyclopropyl-1H-pyrazole-4-carboxamide | 676.06 |
| 232 | 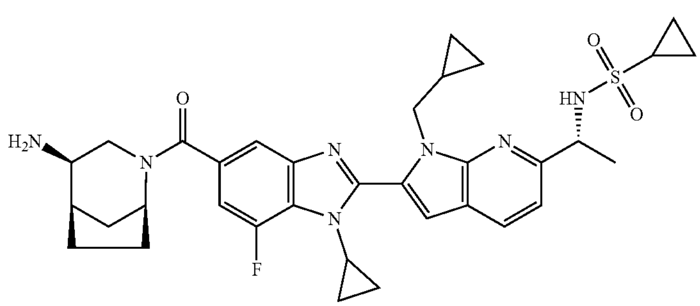 [SMILES: C[C@@H](NS(=O)(=O)C1CC1)c1ccc2cc(-c3nc4cc(C(=O)N5C[C@H](N)[C@@H]6CC[C@H]5C6)cc(F)c4n3C3CC3)n(CC3CC3)c2n1] | N-((R)-1-(2-(5-((1S,4R,5R)-4-amino-2-azabicyclo[3.2.1]octane-2-carbonyl)-1-cyclopropyl-7-fluoro-1H-benzo[d]imidazol-2-yl)-1-(cyclopropylmethyl)-1H-pyrrolo[2,3-b]pyridin-6-yl)ethyl)cyclopropanesulfonamide | 646.05 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 233 | 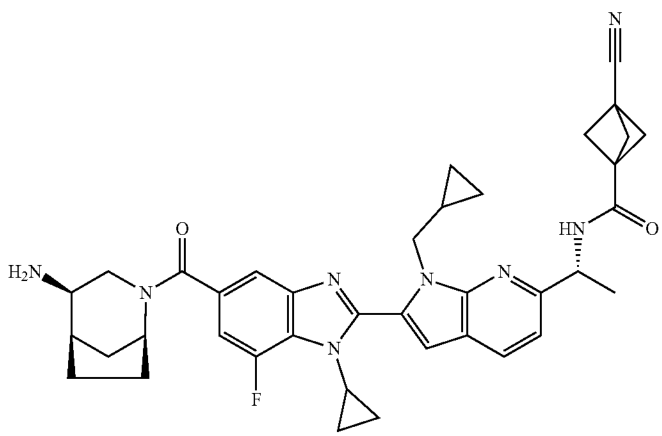 [SMILES: C[C@@H](NC(=O)C12CC(C#N)(C1)C2)c1ccc2cc(-c3nc4cc(C(=O)N5C[C@H](N)[C@@H]6CC[C@H]5C6)cc(F)c4n3C3CC3)n(CC3CC3)c2n1] | N-((R)-1-(2-(5-((1S,4R,5R)-4-amino-2-azabicyclo[3.2.1]octane-2-carbonyl)-1-cyclopropyl-7-fluoro-1H-benzo[d]imidazol-2-yl)-1-(cyclopropylmethyl)-1H-pyrrolo[2,3-b]pyridin-6-yl)ethyl)-3-cyanobicyclo[1.1.1]pentane-1-carboxamide | 661.07 |
| 234 | 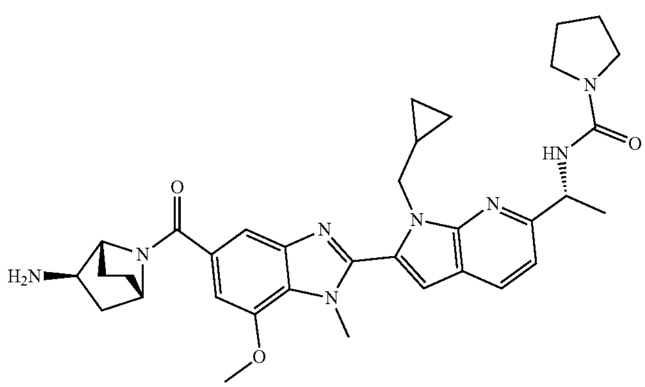 [SMILES: COc1cc(C(=O)N2[C@H]3CC[C@@H]2[C@H](N)C3)cc2nc(-c3cc4ccc([C@@H](C)NC(=O)N5CCCC5)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)pyrrolidine-1-carboxamide | 611.32 |
| 235 | 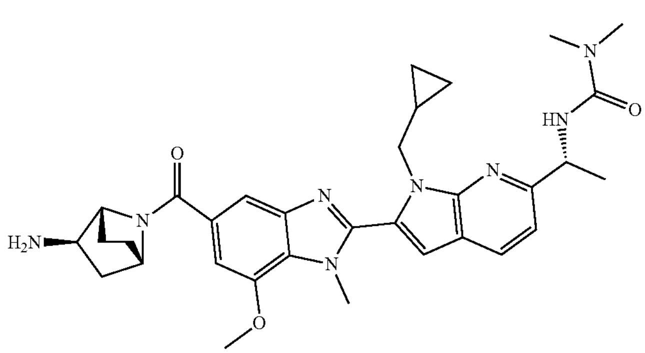 [SMILES: COc1cc(C(=O)N2[C@H]3CC[C@@H]2[C@H](N)C3)cc2nc(-c3cc4ccc([C@@H](C)NC(=O)N(C)C)nc4n3CC3CC3)n(C)c12] | 3-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)-1,1-dimethylurea | 585.22 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 236 | 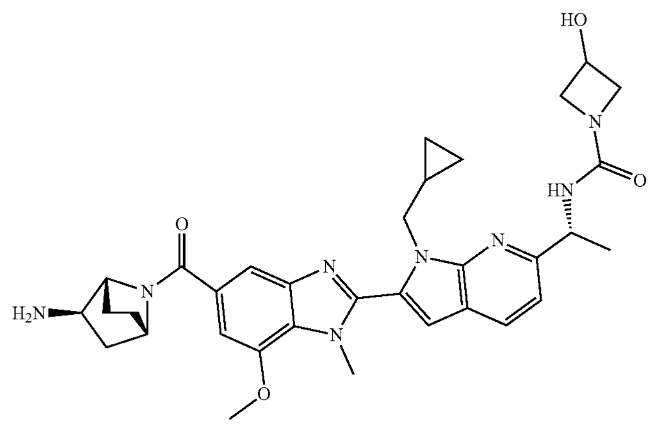 [SMILES: COc1cc(C(=O)N2[C@H]3CC[C@@H]2[C@H](N)C3)cc2nc(-c3cc4ccc([C@@H](C)NC(=O)N5CC(O)C5)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)-3-hydroxyazetidine-1-carboxamide | 613.42 |
| 237 | 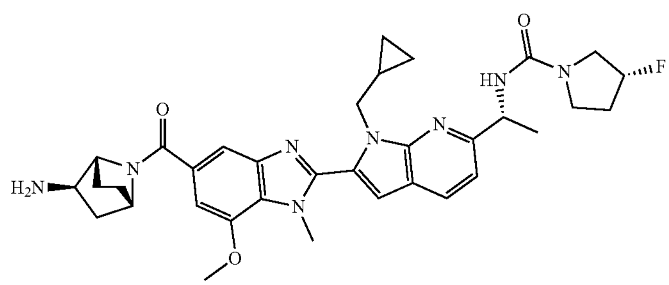 [SMILES: COc1cc(C(=O)N2[C@H]3CC[C@@H]2[C@H](N)C3)cc2nc(-c3cc4ccc([C@@H](C)NC(=O)N5CC[C@@H](F)C5)nc4n3CC3CC3)n(C)c12] | (R)-N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-indol-6-yl)ethyl)-3-fluoropyrrolidine-1-carboxamide | 628.46 |
| 238 | 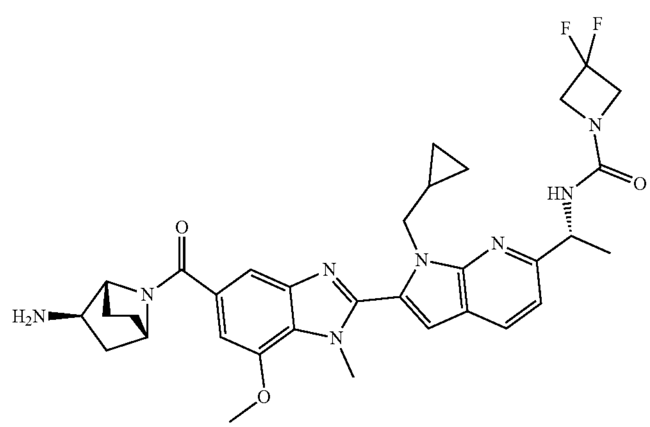 [SMILES: COc1cc(C(=O)N2[C@H]3CC[C@@H]2[C@H](N)C3)cc2nc(-c3cc4ccc([C@@H](C)NC(=O)N5CC(F)(F)C5)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-indol-6-yl)ethyl)-3,3-difluoroazetidine-1-carboxamide | 632.29 |
| 239 | 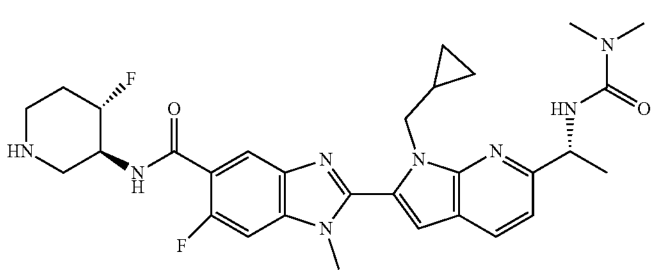 [SMILES: C[C@@H](NC(=O)N(C)C)c1ccc2cc(-c3nc4cc(C(=O)N[C@H]5CNCC[C@@H]5F)c(F)cc4n3C)n(CC3CC3)c2n1] | 2-(1-(cyclopropylmethyl)-6-((R)-1-(3,3-dimethylureido)ethyl)-1H-pyrrolo[2,3-b]pyridin-2-yl)-6-fluoro-N-((3S,4S)-4-fluoropiperidin-3-yl)-1-methyl-1H-benzo[d]imidazole-5-carboxamide | 579.4 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 240 | 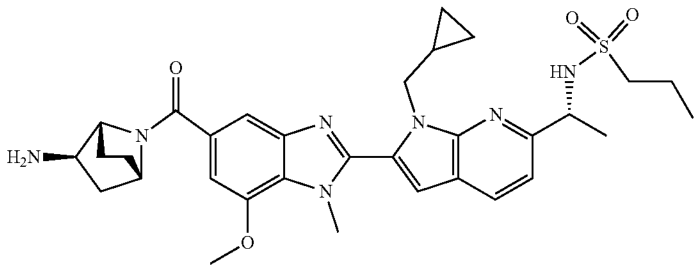 [SMILES: CCCS(=O)(=O)N[C@H](C)c1ccc2cc(-c3nc4cc(C(=O)N5[C@H]6CC[C@@H]5[C@H](N)C6)cc(OC)c4n3C)n(CC3CC3)c2n1] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)propane-1-sulfonamide | 620.4 |
| 241 | 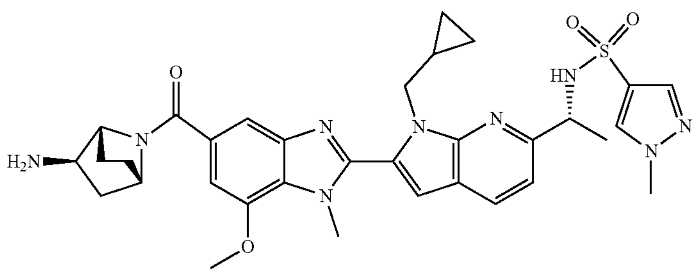 [SMILES: COc1cc(C(=O)N2[C@H]3CC[C@@H]2[C@H](N)C3)cc2nc(-c3cc4ccc([C@@H](C)NS(=O)(=O)c5cnn(C)c5)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-methyl-1H-pyrazole-4-sulfonamide | 658.3 |
| 242 | 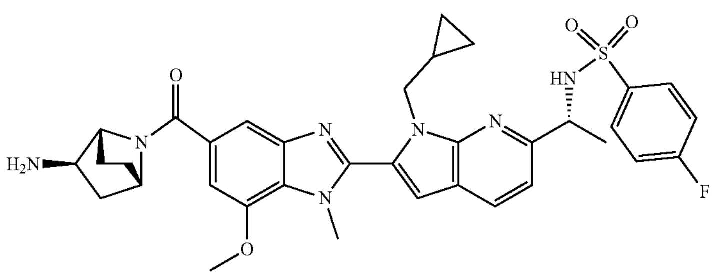 [SMILES: COc1cc(C(=O)N2[C@H]3CC[C@@H]2[C@H](N)C3)cc2nc(-c3cc4ccc([C@@H](C)NS(=O)(=O)c5ccc(F)cc5)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)-4-fluorobenzenesulfonamide | 672.3 |
| 243 | 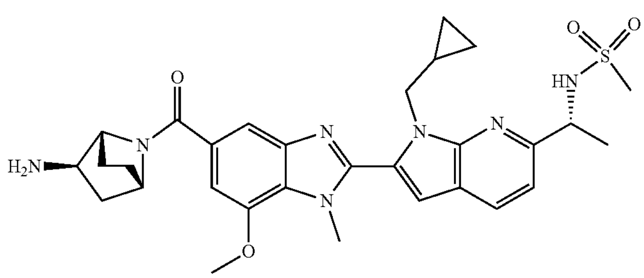 [SMILES: COc1cc(C(=O)N2[C@H]3CC[C@@H]2[C@H](N)C3)cc2nc(-c3cc4ccc([C@@H](C)NS(C)(=O)=O)nc4n3CC3CC3)n(C)c12] | N-((R)-1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)ethyl)methanesulfonamide | 592.3 |
| 244 | 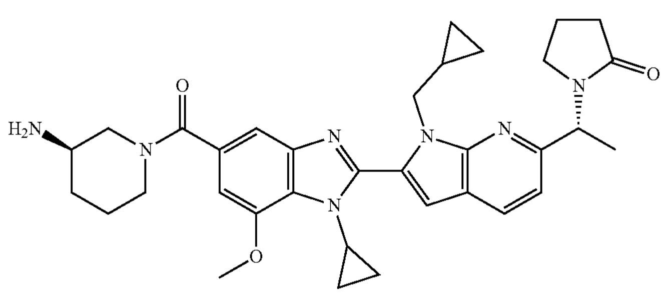 [SMILES: COc1cc(C(=O)N2CCC[C@@H](N)C2)cc2nc(-c3cc4ccc([C@@H](C)N5CCCC5=O)nc4n3CC3CC3)n(C3CC3)c12] | 1-((R)-1-(2-(5-((R)-3-aminopiperidine-1-carbonyl)-1-cyclopropyl-7-methoxy-1H-benzo[d]imidazol-2-yl)-1-(cyclopropylmethyl)-1H-pyrrolo[2,3-b]pyridin-6-yl)ethyl)pyrrolidin-2-one | 596.3 |

TABLE 2a-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 245 | 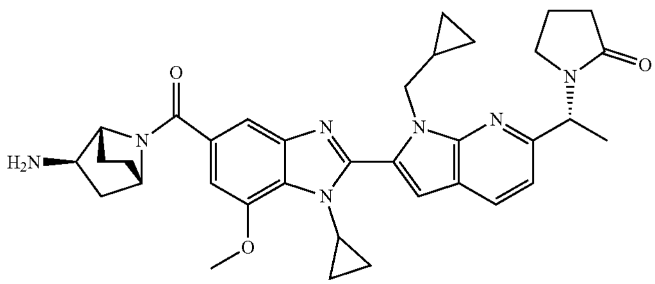 [SMILES: COc1cc(C(=O)N2[C@H]3CC[C@@H]2[C@H](N)C3)cc2nc(-c3cc4ccc([C@@H](C)N5CCCC5=O)nc4n3CC3CC3)n(C3CC3)c12] | 1-((R)-1-(2-(5-((1R,2R,4S)-2-amino-7-azabicyclo[2.2.1]heptane-7-carbonyl)-1-cyclopropyl-7-methoxy-1H-benzo[d]imidazol-2-yl)-1-(cyclopropylmethyl)-1H-pyrrolo[2,3-b]pyridin-6-yl)ethyl)pyrrolidin-2-one | 608.4 |
| 246 | 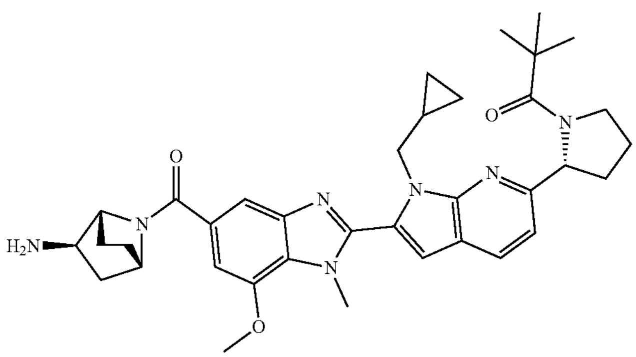 [SMILES: COc1cc(C(=O)N2[C@H]3CC[C@@H]2[C@H](N)C3)cc2nc(-c3cc4ccc([C@H]5CCCN5C(=O)C(C)(C)C)nc4n3CC3CC3)n(C)c12] | 1-((R)-2-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)pyrrolidin-1-yl)-2,2-dimethyl propan-1-one | 624.4 |
| 247 | 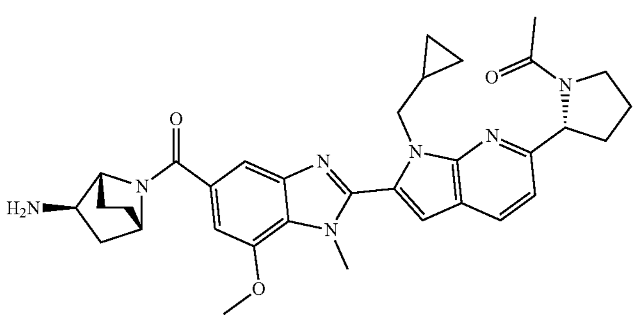 [SMILES: COc1cc(C(=O)N2[C@H]3CC[C@@H]2[C@H](N)C3)cc2nc(-c3cc4ccc([C@H]5CCCN5C(C)=O)nc4n3CC3CC3)n(C)c12] | 1-((R)-2-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)pyrrolidin-1-yl)ethan-1-one | 582.3 |
| 248 | 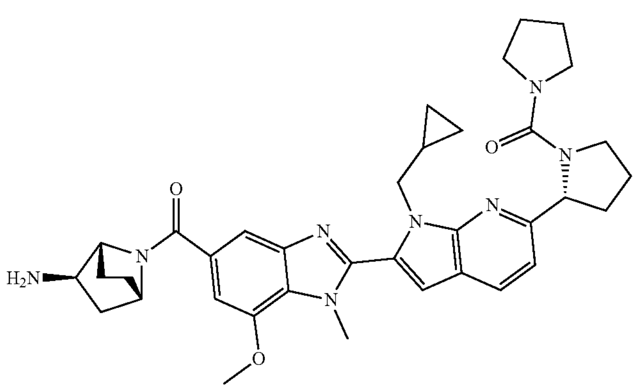 [SMILES: COc1cc(C(=O)N2[C@H]3CC[C@@H]2[C@H](N)C3)cc2nc(-c3cc4ccc([C@H]5CCCN5C(=O)N5CCCC5)nc4n3CC3CC3)n(C)c12] | ((R)-2-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)pyrrolidin-1-yl)(pyrrolidin-1-yl)methanone | 637.4 |

TABLE 2b

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 288 | 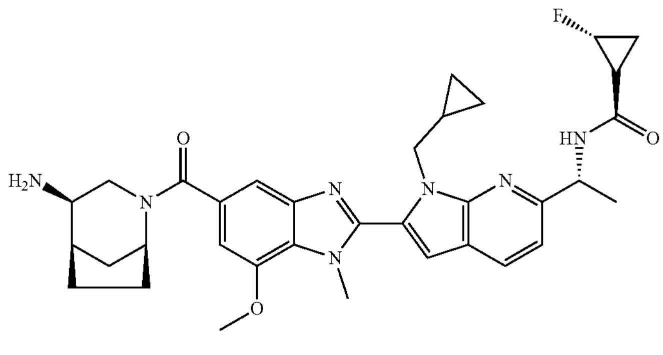 | (1S,2R)-N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-fluorocyclopropane-1-carboxamide | 614.2 |
| 289 | 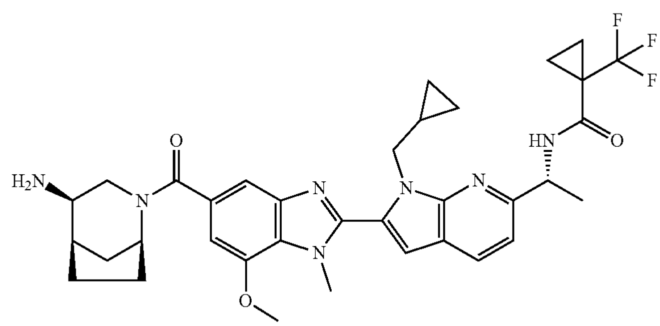 [SMILES: COc1cc(C(=O)N2C[C@H](N)[C@@H]3CC[C@H]2C3)cc2nc(-c3cc4ccc([C@@H](C)NC(=O)C5(C(F)(F)F)CC5)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-(trifluoromethyl)cyclopropane-1-carboxamide | 664.2 |
| 290 | 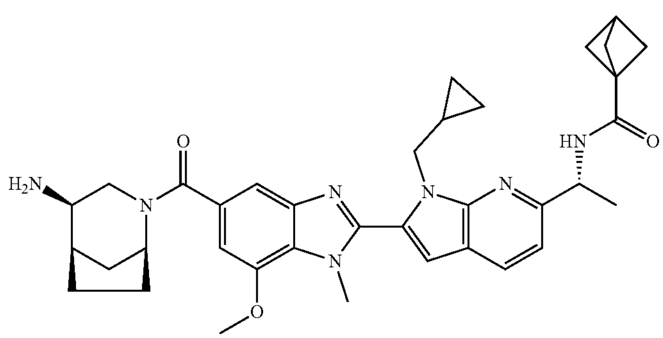 [SMILES: COc1cc(C(=O)N2C[C@H](N)[C@@H]3CC[C@H]2C3)cc2nc(-c3cc4ccc([C@@H](C)NC(=O)C56CC(C5)C6)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)bicyclo[1.1.1]pentane-1-carboxamide | 622.23 |
| 291 | 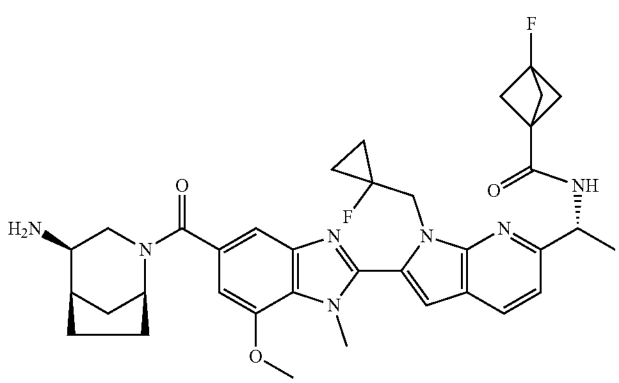 [SMILES: COc1cc(C(=O)N2C[C@H](N)[C@@H]3CC[C@H]2C3)cc2nc(-c3cc4ccc([C@@H](C)NC(=O)C56CC(F)(C5)C6)nc4n3CC3(F)CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-((1-fluorocyclopropyl)methyl)-1H-pyrrolo[2,3-b]pyridin-6-yl)ethyl)-3-fluorobicyclo[1.1.1]pentane-1-carboxamide | 658.2 |

TABLE 2b-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 292 | 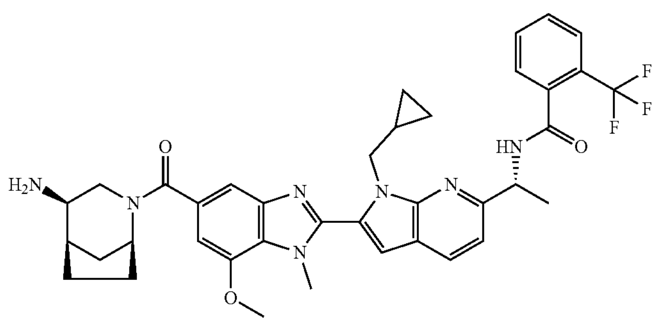 [SMILES: COc1cc(C(=O)N2C[C@H](N)[C@@H]3CC[C@H]2C3)cc2nc(-c3cc4ccc([C@@H](C)NC(=O)c5ccccc5C(F)(F)F)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-(trifluoromethyl)benzamide | 700.2 |
| 293 | 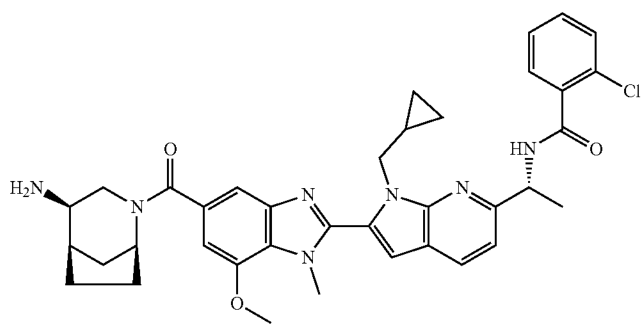 | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-chlorobenzamide | 666.2 |
| 294 | 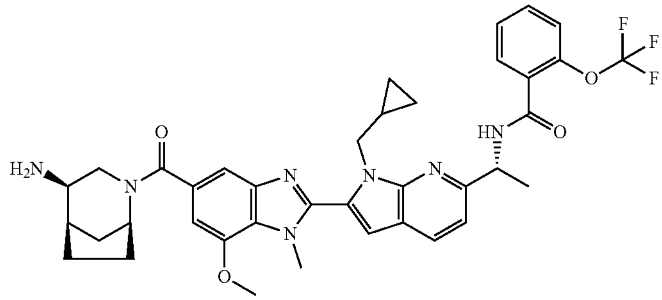 [SMILES: COc1cc(C(=O)N2C[C@H](N)[C@@H]3CC[C@H]2C3)cc2nc(-c3cc4ccc([C@@H](C)NC(=O)c5ccccc5OC(F)(F)F)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-(trifluoromethoxy)benzamide | 716.1 |
| 295 | 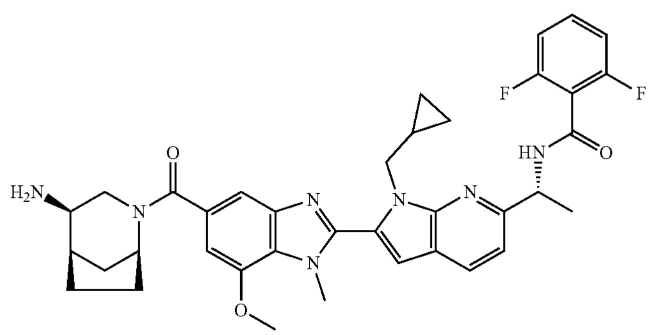 [SMILES: COc1cc(C(=O)N2C[C@H](N)[C@@H]3CC[C@H]2C3)cc2nc(-c3cc4ccc([C@@H](C)NC(=O)c5c(F)cccc5F)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2,6-difluorobenzamide | 668.11 |

TABLE 2b-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 296 | 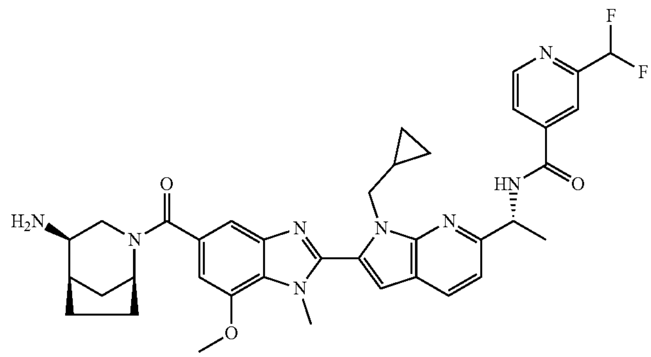 [SMILES: COc1cc(C(=O)N2C[C@H](N)[C@@H]3CC[C@H]2C3)cc2nc(-c3cc4ccc([C@@H](C)NC(=O)c5ccnc(C(F)F)c5)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-(difluoromethyl)isonicotinamide | 683.46 |
| 297 | 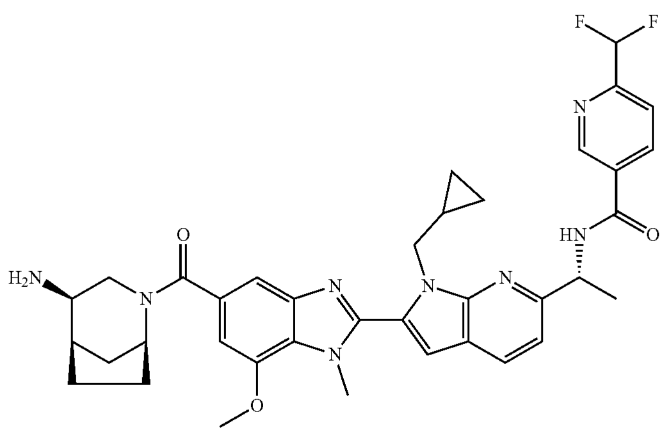 | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-6-(difluoromethyl)nicotinamide | 683.26 |
| 298 | 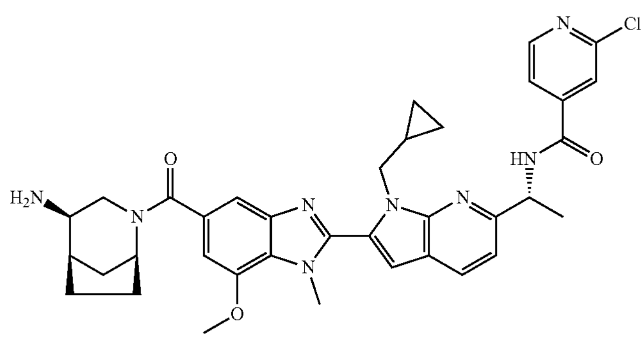 [SMILES: COc1cc(C(=O)N2C[C@H](N)[C@@H]3CC[C@H]2C3)cc2nc(-c3cc4ccc([C@@H](C)NC(=O)c5ccnc(Cl)c5)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-chloroisonicotinamide | 667.32 |
| 299 | 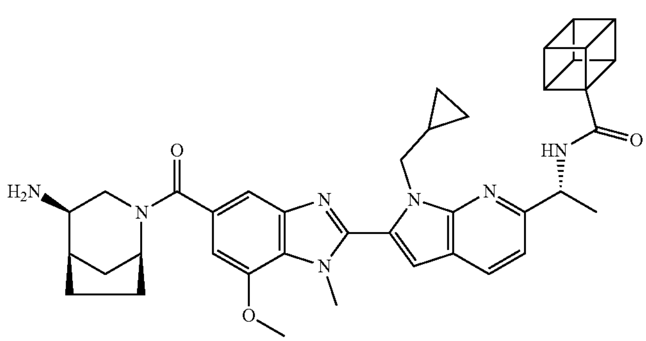 [SMILES: COc1cc(C(=O)N2C[C@H](N)[C@@H]3CC[C@H]2C3)cc2nc(-c3cc4ccc([C@@H](C)NC(=O)C56C7C8C9C7C5C9C86)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)cubane-1-carboxamide | 658.2 |

TABLE 2b-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 300 | 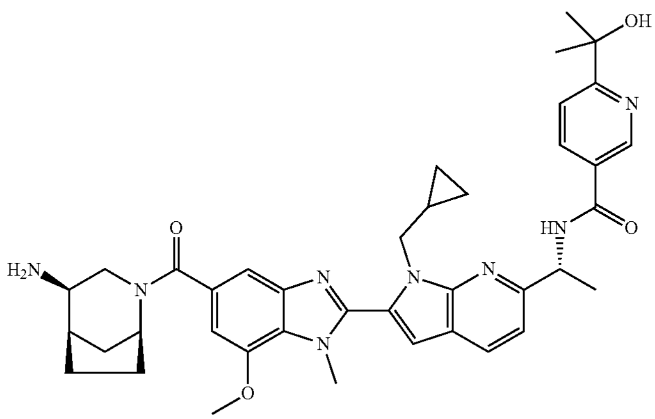 [SMILES: COc1cc(C(=O)N2C[C@H](N)[C@@H]3CC[C@H]2C3)cc2nc(-c3cc4ccc([C@@H](C)NC(=O)c5ccc(C(C)(C)O)nc5)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-6-(2-hydroxypropan-2-yl)nicotinamide | 691.66 |
| 301 | 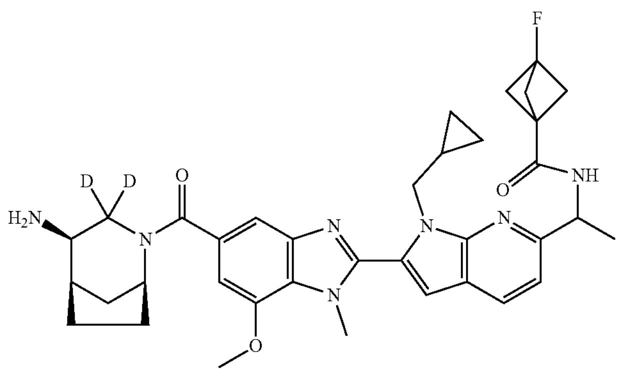 [SMILES: [2H]C1([2H])[C@H](N)[C@@H]2CC[C@@H](C2)N1C(=O)c1cc(OC)c2c(c1)nc(-c1cc3ccc(C(C)NC(=O)C45CC(F)(C4)C5)nc3n1CC1CC1)n2C] | N-((R)-1-(2-(5-((1S,4R,5R)-4-amino-2-azabicyclo[3.2.1]octane-2-carbonyl-3,3-$d_2$)-7-methoxy-1-methyl-1H-benzo[d]imidazol-2-yl)-1-(cyclopropylmethyl)-1H-pyrrolo[2,3-b]pyridin-6-yl)ethyl)-3-fluorobicyclo[1.1.1]pentane-1-carboxamide | 642.1 |
| 302 | 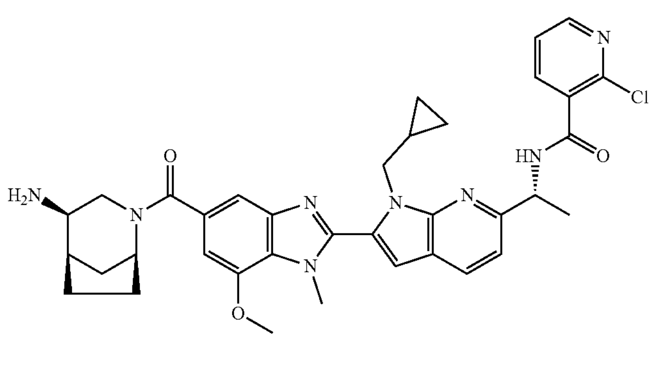 [SMILES: COc1cc(C(=O)N2C[C@H](N)[C@@H]3CC[C@H]2C3)cc2nc(-c3cc4ccc([C@@H](C)NC(=O)c5cccnc5Cl)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-chloronicotinamide | 668.15 |
| 303 | 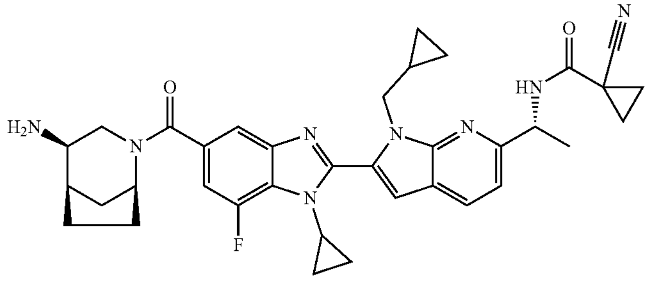 [SMILES: C[C@@H](NC(=O)C1(C#N)CC1)c1ccc2cc(-c3nc4cc(C(=O)N5C[C@H](N)[C@@H]6CC[C@H]5C6)cc(F)c4n3C3CC3)n(CC3CC3)c2n1] | N-((R)-1-(2-(5-((1S,4R,5R)-4-amino-2-azabicyclo[3.2.1]octane-2-carbonyl)-1-cyclopropyl-7-fluoro-1H-benzo[d]imidazol-2-yl)-1-(cyclopropylmethyl)-1H-pyrrolo[2,3-b]pyridin-6-yl)ethyl)-1-cyanocyclopropane-1-carboxamide | 635.3 |

TABLE 2b-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 304 | 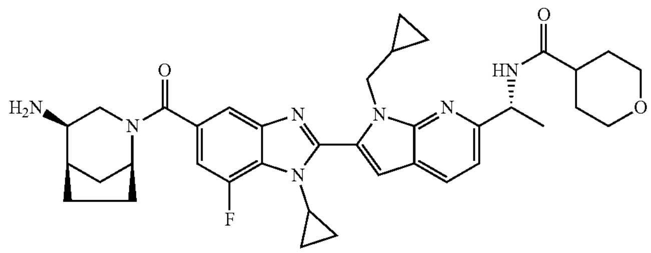 [SMILES: C[C@@H](NC(=O)C1CCOCC1)c1ccc2cc(-c3nc4cc(C(=O)N5C[C@H](N)[C@@H]6CC[C@H]5C6)cc(F)c4n3C3CC3)n(CC3CC3)c2n1] | N-((R)-1-(2-(5-((1S,4R,5R)-4-amino-2-azabicyclo[3.2.1]octane-2-carbonyl)-1-cyclopropyl-7-fluoro-1H-benzo[d]imidazol-2-yl)-1-(cyclopropylmethyl)-1H-pyrrolo[2,3-b]pyridin-6-yl)ethyl)tetrahydro-2H-pyran-4-carboxamide | 654.29 |
| 305 | 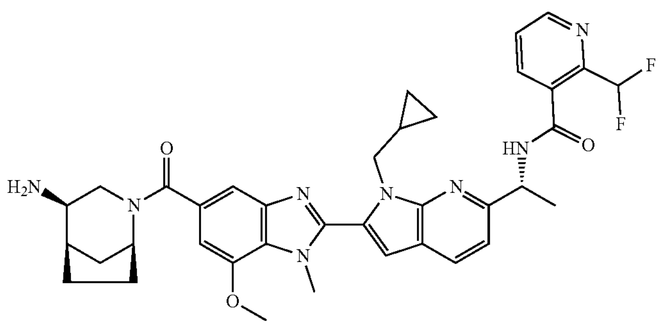 [SMILES: COc1cc(C(=O)N2C[C@H](N)[C@@H]3CC[C@H]2C3)cc2nc(-c3cc4ccc([C@@H](C)NC(=O)c5cccnc5C(F)F)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-(difluoromethyl)nicotinamide | 683.1 |
| 306 | 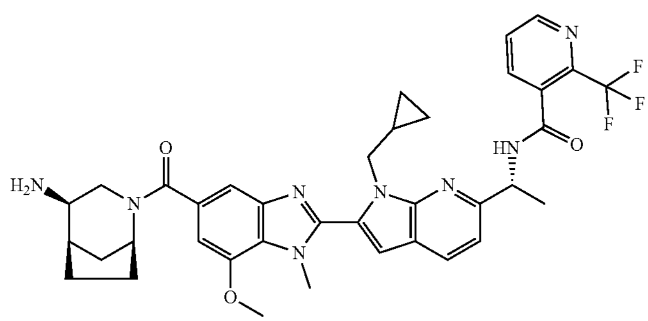 [SMILES: COc1cc(C(=O)N2C[C@H](N)[C@@H]3CC[C@H]2C3)cc2nc(-c3cc4ccc([C@@H](C)NC(=O)c5cccnc5C(F)(F)F)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-(trifluoromethyl)nicotinamide | 701.2 |
| 307 | 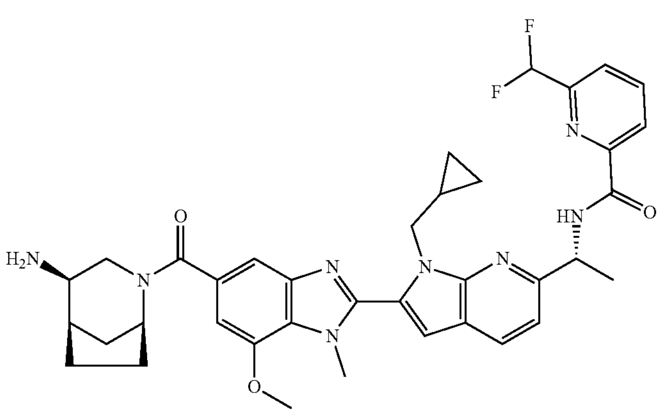 [SMILES: COc1cc(C(=O)N2C[C@H](N)[C@@H]3CC[C@H]2C3)cc2nc(-c3cc4ccc([C@@H](C)NC(=O)c5cccc(C(F)F)n5)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-6-(difluoromethyl)picolinamide | 683.2 |

TABLE 2b-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 308 | 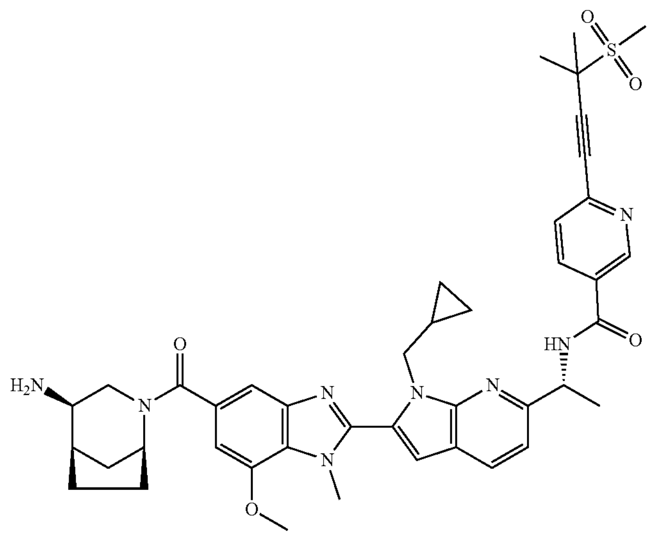 [SMILES: COc1cc(C(=O)N2C[C@H](N)[C@@H]3CC[C@H]2C3)cc2nc(-c3cc4ccc([C@@H](C)NC(=O)c5ccc(C#CC(C)(C)S(C)(=O)=O)nc5)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-6-(3-methyl-3-(methylsulfonyl)but-1-yn-1-yl)nicotinamide | 777.12 |
| 309 | 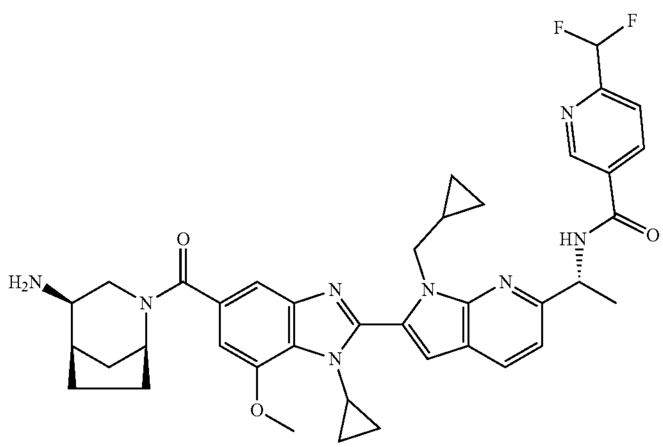 [SMILES: COc1cc(C(=O)N2C[C@H](N)[C@@H]3CC[C@H]2C3)cc2nc(-c3cc4ccc([C@@H](C)NC(=O)c5ccc(C(F)F)nc5)nc4n3CC3CC3)n(C3CC3)c12] | N-((R)-1-(2-(5-((1S,4R,5R)-4-amino-2-azabicyclo[3.2.1]octane-2-carbonyl)-1-cyclopropyl-7-methoxy-1H-benzo[d]imidazol-2-yl)-1-(cyclopropylmethyl)-1H-pyrrolo[2,3-b]pyridin-6-yl)ethyl)-6-(difluoromethyl)nicotinamide | 709.2 |
| 310 | 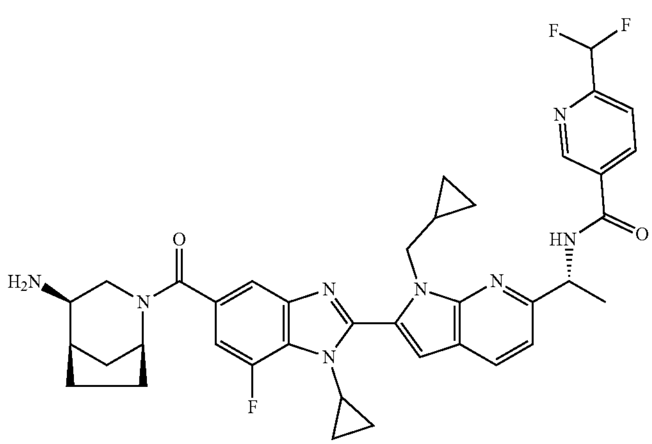 [SMILES: C[C@@H](NC(=O)c1ccc(C(F)F)nc1)c1ccc2cc(-c3nc4cc(C(=O)N5C[C@H](N)[C@@H]6CC[C@H]5C6)cc(F)c4n3C3CC3)n(CC3CC3)c2n1] | N-((R)-1-(2-(5-((1S,4R,5R)-4-amino-2-azabicyclo[3.2.1]octane-2-carbonyl)-1-cyclopropyl-7-fluoro-1H-benzo[d]imidazol-2-yl)-1-(cyclopropylmethyl)-1H-pyrrolo[2,3-b]pyridin-6-yl)ethyl)-6-(difluoromethyl)nicotinamide | 697.2 |

TABLE 2b-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 311 | 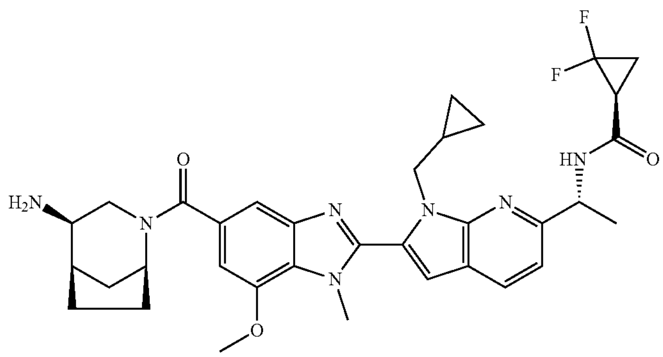 [SMILES: COc1cc(C(=O)N2C[C@H](N)[C@@H]3CC[C@H]2C3)cc2nc(-c3cc4ccc([C@@H](C)NC(=O)[C@@H]5CC5(F)F)nc4n3CC3CC3)n(C)c12] | (S)-N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2,2-difluorocyclopropane-1-carboxamide | 632.214 |
| 312 | 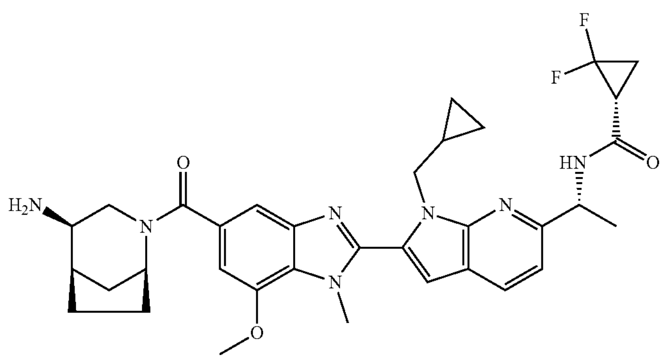 [SMILES: COc1cc(C(=O)N2C[C@H](N)[C@@H]3CC[C@H]2C3)cc2nc(-c3cc4ccc([C@@H](C)NC(=O)[C@H]5CC5(F)F)nc4n3CC3CC3)n(C)c12] | (R)-N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2,2-difluorocyclopropane-1-carboxamide | 632.28 |
| 313 | 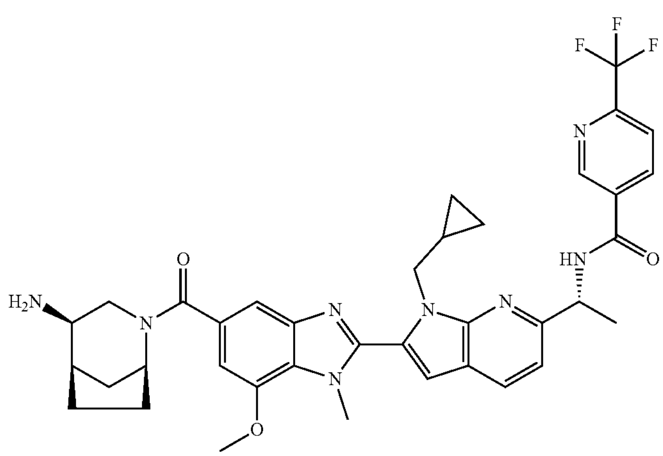 [SMILES: COc1cc(C(=O)N2C[C@H](N)[C@@H]3CC[C@H]2C3)cc2nc(-c3cc4ccc([C@@H](C)NC(=O)c5ccc(C(F)(F)F)nc5)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-6-(trifluoromethyl)nicotinamide | 701.23 |

TABLE 2b-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 314 | 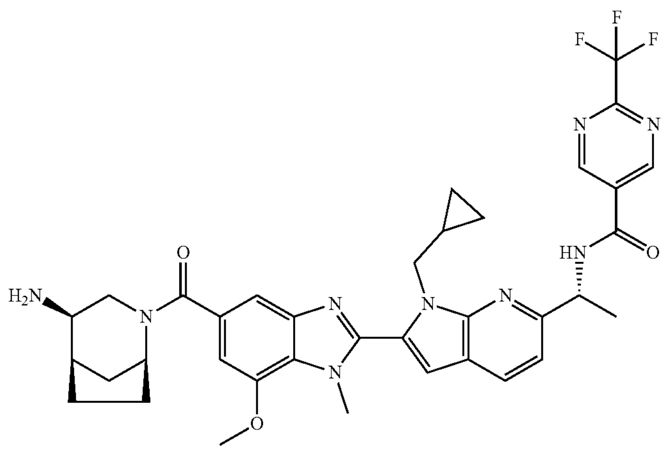 | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-(trifluoromethyl)pyrimidine-5-carboxamide | 702.19 |
| 315 | 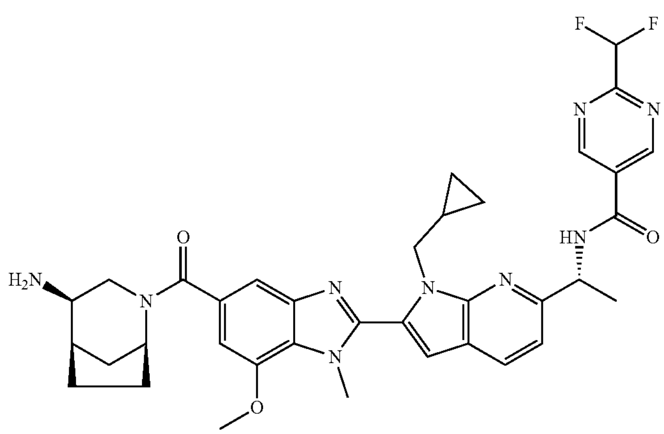 [SMILES: COc1cc(C(=O)N2C[C@H](N)[C@@H]3CC[C@H]2C3)cc2nc(-c3cc4ccc([C@@H](C)NC(=O)c5cnc(C(F)F)nc5)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-(difluoromethyl)pyrimidine-5-carboxamide | 684.17 |
| 316 | 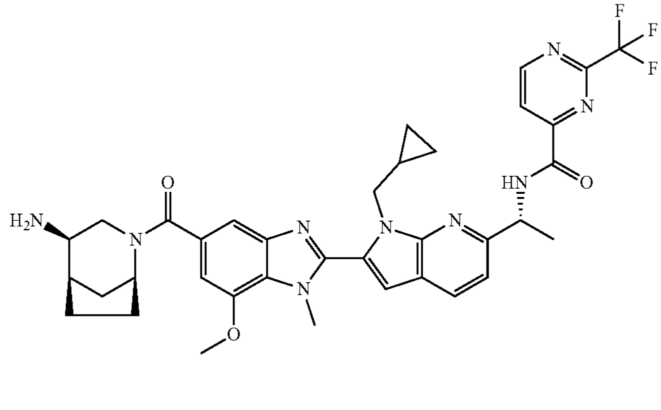 [SMILES: COc1cc(C(=O)N2C[C@H](N)[C@@H]3CC[C@H]2C3)cc2nc(-c3cc4ccc([C@@H](C)NC(=O)c5ccnc(C(F)(F)F)n5)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-(trifluoromethyl)pyrimidine-4-carboxamide | 702.4 |

TABLE 2b-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 317 | 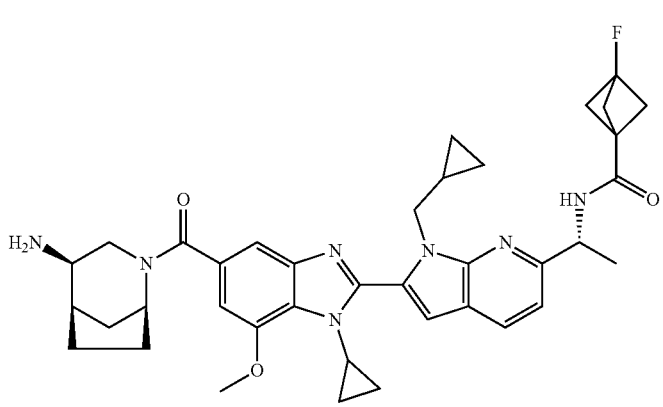 [SMILES: COc1cc(C(=O)N2C[C@H](N)[C@@H]3CC[C@H]2C3)cc2nc(-c3cc4ccc([C@@H](C)NC(=O)C56CC(F)(C5)C6)nc4n3CC3CC3)n(C3CC3)c12] | N-((R)-1-(2-(5-(((1S,4R,5R)-4-amino-2-azabicyclo[3.2.1]octane-2-carbonyl)-1-cyclopropyl-7-methoxy-1H-benzo[d]imidazol-2-yl)-1-(cyclopropylmethyl)-1H-pyrrolo[2,3-b]pyridin-6-yl)ethyl)-3-fluorobicyclo[1.1.1]pentane-1-carboxamide | 666.31 |
| 318 | 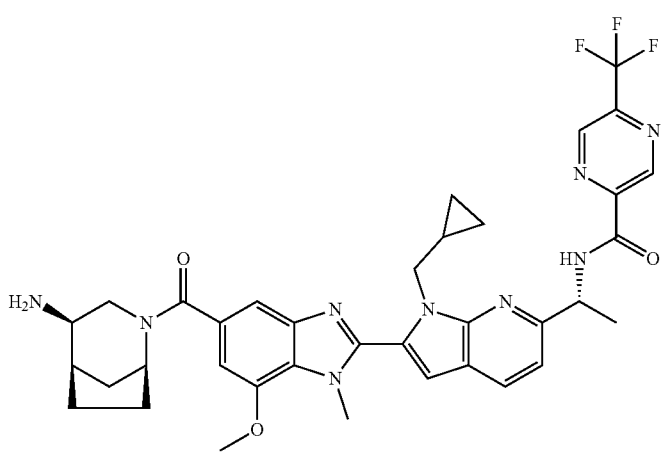 [SMILES: COc1cc(C(=O)N2C[C@H](N)[C@@H]3CC[C@H]2C3)cc2nc(-c3cc4ccc([C@@H](C)NC(=O)c5cnc(C(F)(F)F)cn5)nc4n3CC3CC3)n(C)c12] | N-((R)-1-(2-(5-(((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-5-(trifluoromethyl)pyrazine-2-carboxamide | 702.46 |
| 319 | 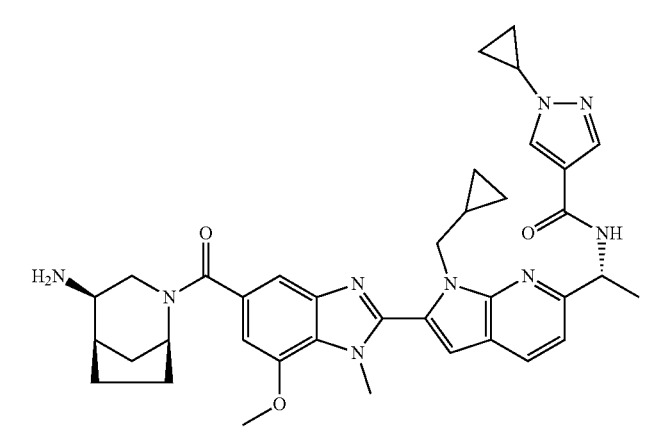 [SMILES: COc1cc(C(=O)N2C[C@H](N)[C@@H]3CC[C@H]2C3)cc2nc(-c3cc4ccc([C@@H](C)NC(=O)c5cnn(C6CC6)c5)nc4n3CC3CC3)n(C)c12] | N-((R)-1-(2-(5-(((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-cyclopropyl-1H-pyrazole-4-carboxamide | 662.3 |

TABLE 2b-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 320 | 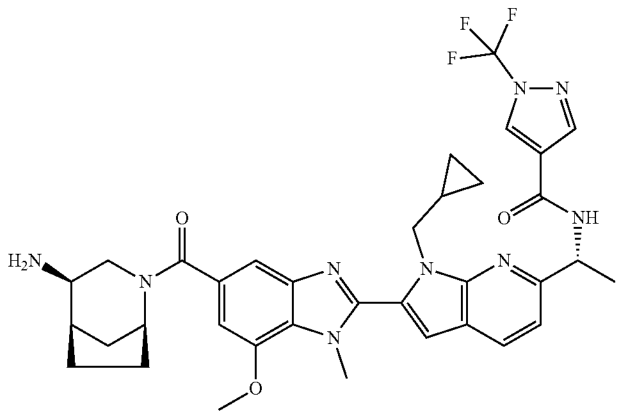 [SMILES: COc1cc(C(=O)N2C[C@H](N)[C@@H]3CC[C@H]2C3)cc2nc(-c3cc4ccc([C@@H](C)NC(=O)c5cnn(C(F)(F)F)c5)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-(trifluoromethyl)-1H-pyrazole-4-carboxamide | 690.2 |
| 321 | 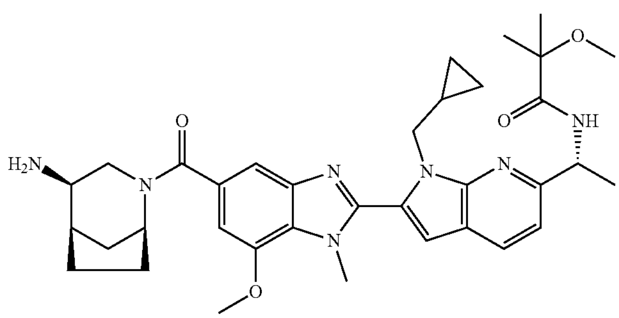 [SMILES: COc1cc(C(=O)N2C[C@H](N)[C@@H]3CC[C@H]2C3)cc2nc(-c3cc4ccc([C@@H](C)NC(=O)C(C)(C)OC)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-methoxy-2-methylpropanamide | 628.3 |
| 322 | 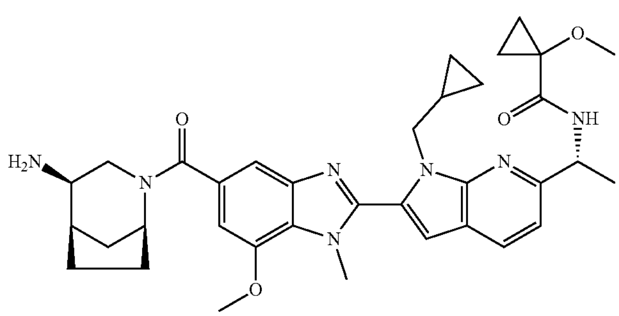 [SMILES: COc1cc(C(=O)N2C[C@H](N)[C@@H]3CC[C@H]2C3)cc2nc(-c3cc4ccc([C@@H](C)NC(=O)C5(OC)CC5)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-methoxycyclopropane-1-carboxamide | 626.3 |
| 323 | 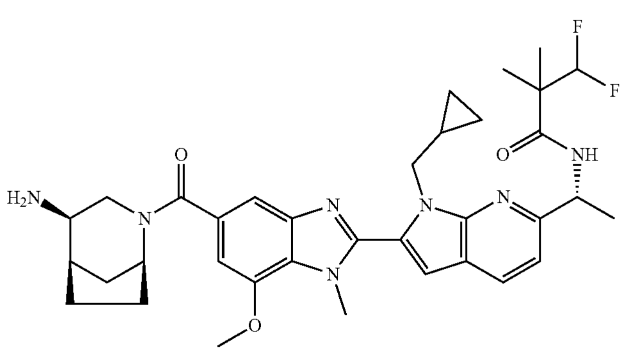 [SMILES: COc1cc(C(=O)N2C[C@H](N)[C@@H]3CC[C@H]2C3)cc2nc(-c3cc4ccc([C@@H](C)NC(=O)C(C)(C)C(F)F)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-3,3-difluoro-2,2-dimethylpropanamide | 648.3 |

TABLE 2b-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 324 | 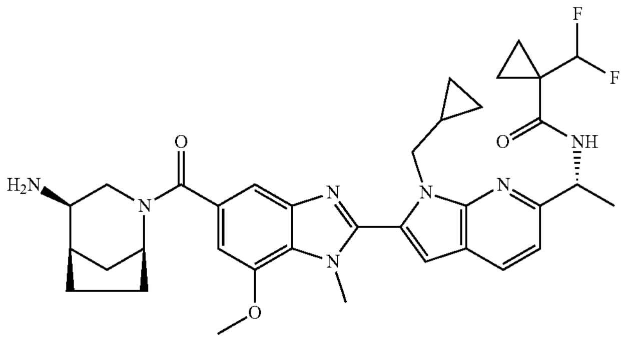 [SMILES: COc1cc(C(=O)N2C[C@H](N)[C@@H]3CC[C@H]2C3)cc2nc(-c3cc4ccc([C@@H](C)NC(=O)C5(C(F)F)CC5)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-(difluoromethyl)cyclopropane-1-carboxamide | 646.3 |
| 325 | 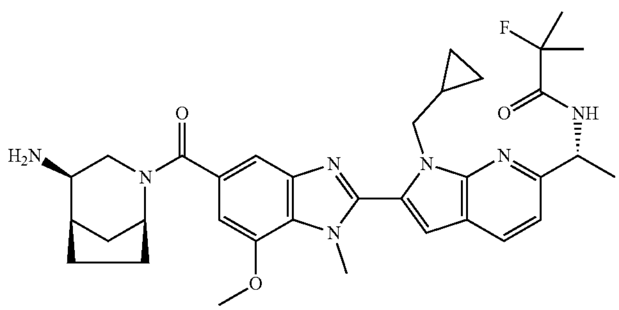 [SMILES: COc1cc(C(=O)N2C[C@H](N)[C@@H]3CC[C@H]2C3)cc2nc(-c3cc4ccc([C@@H](C)NC(=O)C(C)(C)F)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2-fluoro-2-methylpropanamide | 616.2 |
| 326 | 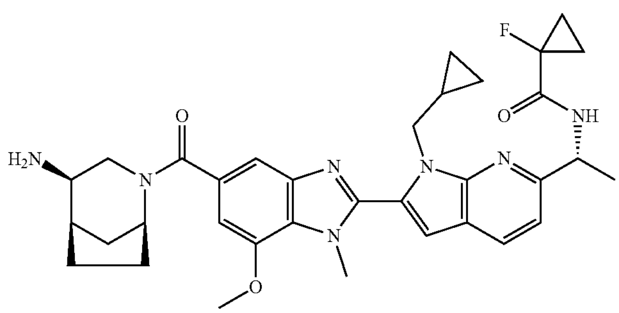 [SMILES: COc1cc(C(=O)N2C[C@H](N)[C@@H]3CC[C@H]2C3)cc2nc(-c3cc4ccc([C@@H](C)NC(=O)C5(F)CC5)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-fluorocyclopropane-1-carboxamide | 614.2 |
| 327 | 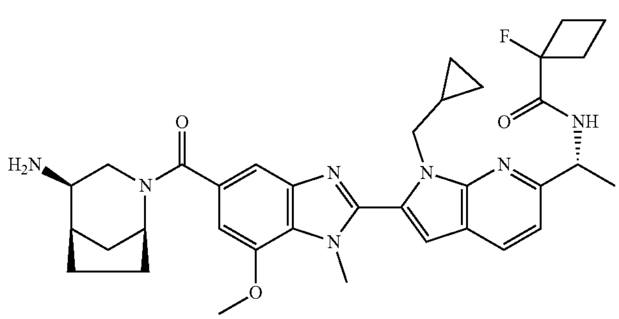 [SMILES: COc1cc(C(=O)N2C[C@H](N)[C@@H]3CC[C@H]2C3)cc2nc(-c3cc4ccc([C@@H](C)NC(=O)C5(F)CCC5)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-1-fluorocyclobutane-1-carboxamide | 628.2 |

TABLE 2b-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 328 | 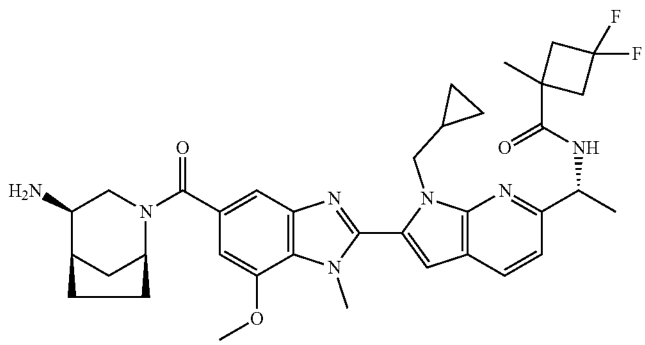 [SMILES: COc1cc(C(=O)N2C[C@H](N)[C@@H]3CC[C@H]2C3)cc2nc(-c3cc4ccc([C@@H](C)NC(=O)C5(C)CC(F)(F)C5)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-3,3-difluoro-1-methylcyclobutane-1-carboxamide | 660.3 |
| 329 | 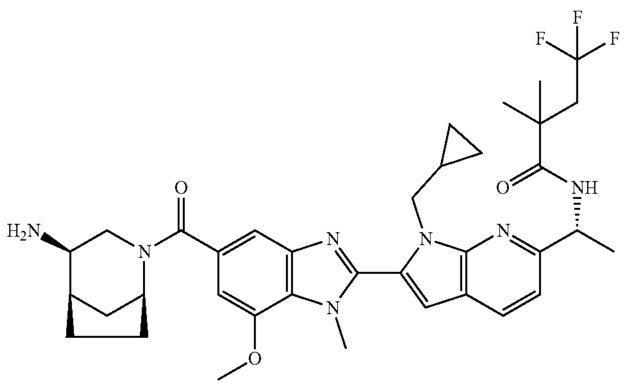 [SMILES: COc1cc(C(=O)N2C[C@H](N)[C@@H]3CC[C@H]2C3)cc2nc(-c3cc4ccc([C@@H](C)NC(=O)C(C)(C)CC(F)(F)F)nc4n3CC3CC3)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-4,4,4-trifluoro-2,2-dimethylbutanamide | 680.2 |
| 330 | 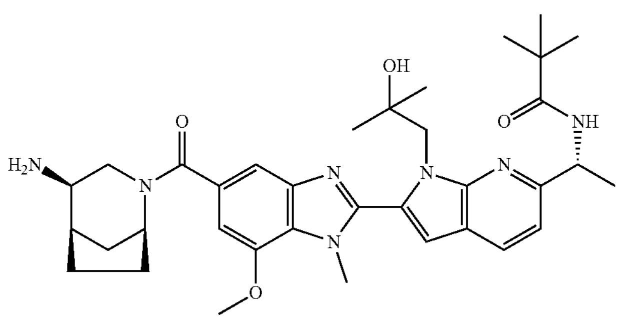 [SMILES: COc1cc(C(=O)N2C[C@H](N)[C@@H]3CC[C@H]2C3)cc2nc(-c3cc4ccc([C@@H](C)NC(=O)C(C)(C)C)nc4n3CC(C)(C)O)n(C)c12] | N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(2-hydroxy-2-methylpropyl)-1H-pyrrolo[2,3-b]pyridin-6-yl)ethyl)pivalamide | 630.3 |
| 331 | 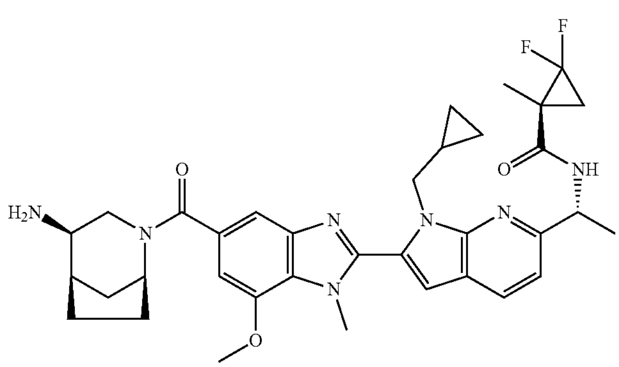 [SMILES: COc1cc(C(=O)N2C[C@H](N)[C@@H]3CC[C@H]2C3)cc2nc(-c3cc4ccc([C@@H](C)NC(=O)[C@]5(C)CC5(F)F)nc4n3CC3CC3)n(C)c12] | (S)-N-((R)-1-(2-(5-((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2,2-difluoro-1-methylcyclopropane-1-carboxamide | 646.4 |

TABLE 2b-continued

The compounds below were synthesized according to Procedures 10-18, using intermediates described herein, and/or intermediates prepared according to General Schemes.

| Ex. | Structure | Name | ES/MS m/z [M + H]+ |
|---|---|---|---|
| 332 | 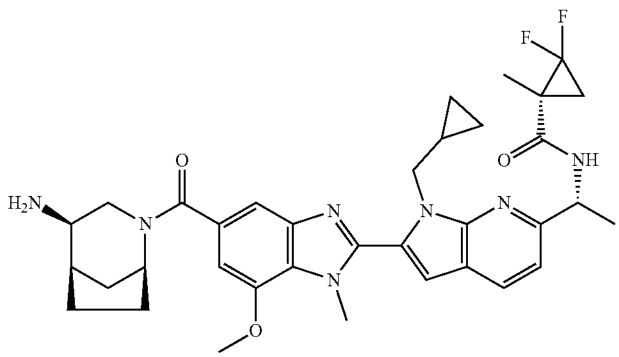 [SMILES: COc1cc(C(=O)N2C[C@H](N)[C@@H]3CC[C@H]2C3)cc2nc(-c3cc4ccc([C@@H](C)NC(=O)[C@@]5(C)CC5(F)F)nc4n3CC3CC3)n(C)c12] | (R)-N-((R)-1-(2-(5-(((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)ethyl)-2,2-difluoro-1-methylcyclopropane-1-carboxamide | 646.4 |
| 333 | 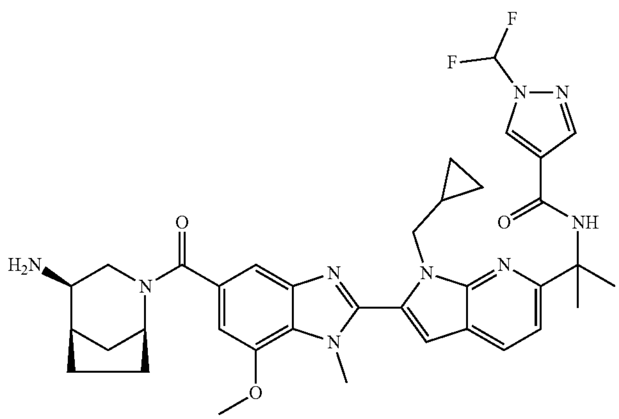 [SMILES: COc1cc(C(=O)N2C[C@H](N)[C@@H]3CC[C@H]2C3)cc2nc(-c3cc4ccc(C(C)(C)NC(=O)c5cnn(C(F)F)c5)nc4n3CC3CC3)n(C)c12] | N-(2-(2-(5-(((1S,4R,5R)-4-amino-2-azabicyclo[3.2.1]octane-2-carbonyl)-7-methoxy-1-methyl-1H-benzo[d]imidazol-2-yl)-1-(cyclopropylmethyl)-1H-pyrrolo[2,3-b]pyridin-6-yl)propan-2-yl)-1-(difluoromethyl)-1H-pyrazole-4-carboxamide | 686.3 |

Procedure 19 (Example 249)

(R)-(5-amino-2-methyltetrahydropyridazin-1(2H)-yl)(2-(1-(cyclopropylmethyl)-6-(2-hydroxypropan-2-yl)-1H-pyrrolo[2,3-b]pyridin-2-yl)-7-methoxy-1-methyl-1H-benzo[d]imidazol-5-yl)methanone

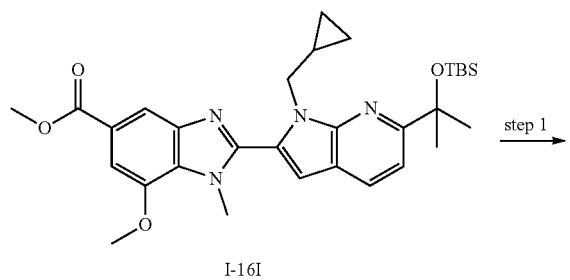

I-16l step 1

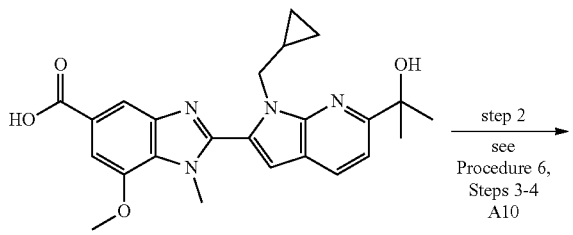

step 2
see Procedure 6, Steps 3-4
A10

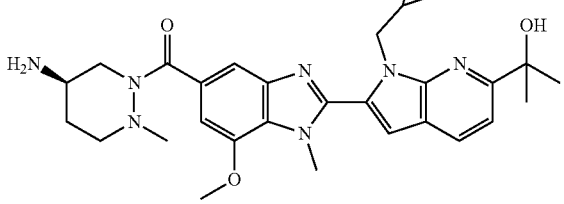

Example 249

Step 1. To a solution of methyl 2-(6-(2-((tert-butyldimethylsilyl)oxy)propan-2-yl)-1-(cyclopropylmethyl)-1H-pyrrolo[2,3-b]pyridin-2-yl)-7-methoxy-1-methyl-1H-benzo[d]imidazole-5-carboxylate (I-16l, 0.150 g, 0.267 mmol) in THF (2.0 mL) was added TBAF (0.40 mL of a 1 M soln in THF, 0.40 mmol). The mixture was stirred at 50° C. for 18 h. The mixture was partially concentrated and extracted with EtOAc. The organic layer was washed with water, dried (Na$_2$SO$_4$), filtered, and concentrated to afford 2-(1-(cyclopropylmethyl)-6-(2-hydroxypropan-2-yl)-1H-pyrrolo[2,3-b]pyridin-2-yl)-7-methoxy-1-methyl-1H-benzo[d]imidazole-5-carboxylic acid. ES/MS: m/z 435.2 [M+H]+.

Step 2. Example 249 was prepared following Steps 3-4 of Procedure 6, using A10 and 2-(1-(cyclopropylmethyl)-6-(2- hydroxypropan-2-yl)-1H-pyrrolo[2,3-b]pyridin-2-yl)-7-methoxy-1-methyl-1H-benzo[d]imidazole-5-carboxylic acid.

Procedure 20 (Example 250)

2-(5-((2S,5R)-5-amino-2-methylpiperidine-1-carbonyl)-7-methoxy-1-methyl-1H-benzo[d]imidazol-2-yl)-1-(cyclopropylmethyl)-N,N-dimethyl-1H-pyrrolo[2,3-b]pyridine-6-carboxamide

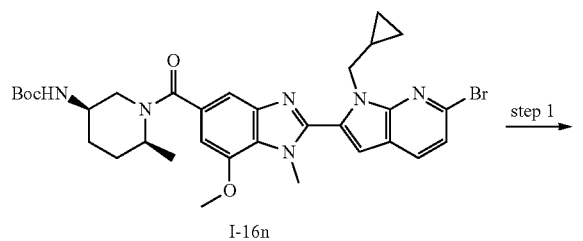

I-16n

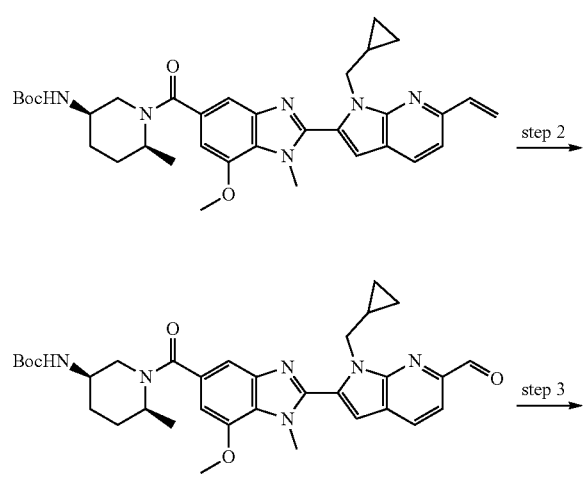

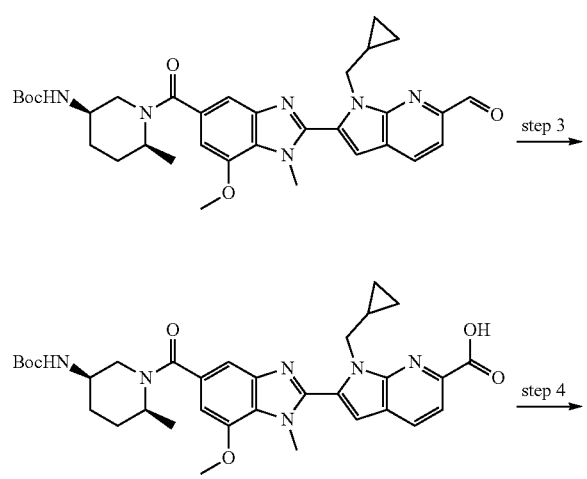

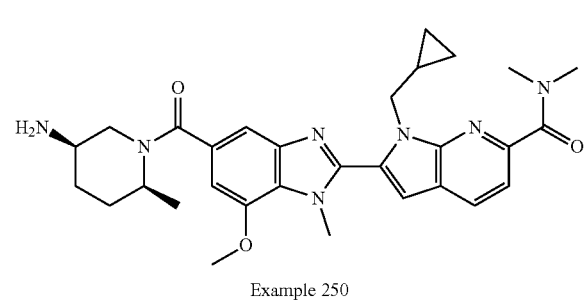

Example 250

Step 1. A mixture of tert-butyl ((3R,6S)-1-(2-(6-bromo-1-(cyclopropylmethyl)-1H-pyrrolo[2,3-b]pyridin-2-yl)-7-methoxy-1-methyl-1H-benzo[d]imidazole-5-carbonyl)-6-methylpiperidin-3-yl)carbamate (I-16n, 1.02 g, 1.57 mmol), potassium trifluorovinylborate (0.294 g, 2.19 mmol), palladium(II) acetate trimer (0.018 g, 0.078 mmol), rac-BINAP (0.102 g, 0.157 mmol) and Cs$_2$CO$_3$ (1.53 g, 4.70 mmol) was placed under Argon atmosphere. DMF (20 mL) was added, and the mixture was stirred at 120° C. for 1 h. The mixture was cooled to rt. TEA (2.1 mL, 1.5 mmol) and di-tert-butyl decarbonate (0.249 g, 1.14 mmol) were added. The reaction mixture was stirred for 1 h and was then diluted with water and EtOAc. The aqueous layer was extracted with EtOAc. The combined organic layers were washed with brine, dried (MgSO$_4$), filtered and concentrated. The resulting residue was purified via flash column chromatography on silica gel to afford tert-butyl ((3R,6S)-1-(2-(1-(cyclopropylmethyl)-6-vinyl-1H-pyrrolo[2,3-b]pyridin-2-yl)-7-methoxy-1-methyl-1H-benzo[d]imidazole-5-carbonyl)-6-methylpiperidin-3-yl)carbamate. ES/MS: m/z 599.6 [M+H]$^+$.

Step 2. To a solution of tert-butyl ((3R,6S)-1-(2-(1-(cyclopropylmethyl)-6-vinyl-1H-pyrrolo[2,3-b]pyridin-2-yl)-7-methoxy-1-methyl-1H-benzo[d]imidazole-5-carbonyl)-6-methylpiperidinyl)carbamate (0.560 g, 0.935 mmol) and sodium periodate (0.600 g, 2.81 mmol) in THF (35 mL) and water (30 mL) was added potassium osmate dihydrate (0.014 g, 0.037 mmol). The reaction mixture was stirred at rt for 1 h and was then diluted with EtOAc and water. The aqueous layer was extracted with EtOAc. The combined organic layers were washed with brine, dried (MgSO$_4$), filtered and concentrated to yield tert-butyl ((3R,6S)-1-(2-(1-(cyclopropylmethyl)-6-formyl-1H-pyrrolo[2,3-b]pyridin-2-yl)-7-methoxy-1-methyl-1H-benzo[d]imidazole-5-carbonyl)-6-methylpiperidin-3-yl)carbamate. ES/MS: m/z 601.6 [M+H]$^+$.

Step 3. To a solution of tert-butyl ((3R,6S)-1-(2-(1-(cyclopropylmethyl)-6-formyl-1H-pyrrolo[2,3-b]pyridin-2-yl)-7-methoxy-1-methyl-1H-benzo[d]imidazole-5-carbonyl)-6-methylpiperidin-3-yl)carbamate (0.334 g, 0.555 mmol) in DMF (5 mL) was added OXONE® (0.386 g, 0.627 mmol). The reaction mixture was stirred at rt for 24 h. The mixture was concentrated and the resulting residue was partitioned between water and EtOAc. The aqueous layer was extracted with EtOAc. The combined organic layers were dried (MgSO$_4$), filtered and concentrated to give 2-(5-((2S,5R)-5-((tert-butoxycarbonyl)amino)-2-methylpiperidine-1-carbonyl)-7-methoxy-1-methyl-1H-benzo[d]imidazol-2-yl)-1-(cyclopropylmethyl)-1H-pyrrolo[2,3-b]pyridine-6-carboxylic acid. ES/MS: m/z 617.5 [M+H]$^+$.

Step 4. To a solution of 2-(5-((2S,5R)-5-((tert-butoxycarbonyl)amino)-2-methylpiperidine-1-carbonyl)-7-methoxy-1-methyl-1H-benzo[d]imidazol-2-yl)-1-(cyclopropylmethyl)-1H-pyrrolo[2,3-b]pyridine-6-carboxylic acid (0.020 g, 0.032 mmol), dimethylamine (17 µL, 0.034 mmol) and HATU (0.012 g, 0.036 mmol) in THF (0.5 mL) was added DIPEA (8.5 µL, 0.049 mmol). The reaction mixture was stirred at rt for 1 h. The mixture was diluted with water and EtOAc. The aqueous layer was extracted with EtOAc. The combined organic layers were dried (MgSO$_4$), filtered and concentrated. The residue was taken up in DCM (5 mL) and TFA (1 mL) was added. The solution was stirred at rt for 1 h before being concentrated. The resulting residue was purified via preparative reverse phase HPLC to afford Example 250.

Procedure 21 (Example 253)

(R)-(3-aminopiperidin-1-yl)(2-(1-(cyclopropylm-ethyl)-6-(methylsulfonyl)-1H-pyrrolo[2,3-b]pyridin-2-yl)-7-methoxy-1-methyl-1H-benzo[d]imidazol-5-yl)methanone

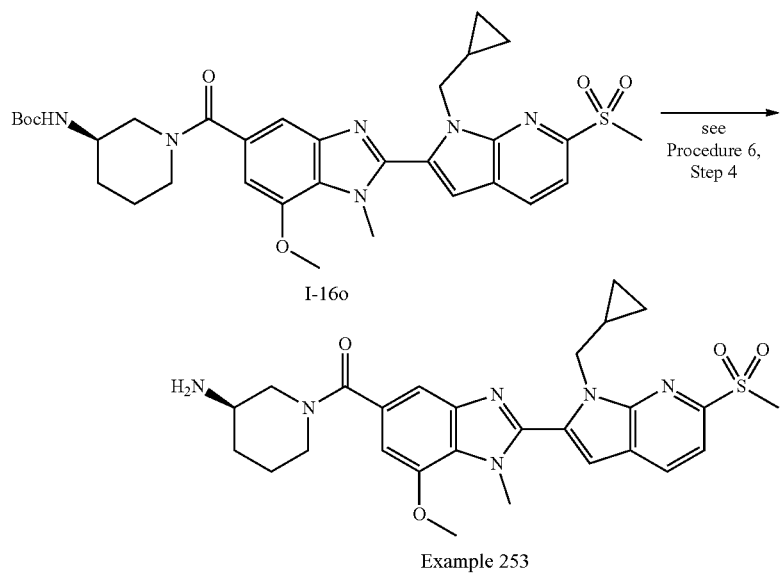

Example 253 was prepared following Step 4 of Procedure 6, using tert-butyl (R)-(1-(2-(1-(cyclopropylmethyl)-6-(methylsulfonyl)-1H-pyrrolo[2,3-b]pyridin-2-yl)-7-methoxy-1-methyl-1H-benzo[d]imidazole-5-carbonyl)piperidin-3-yl)carbamate (I-16o).

TABLE 3

The compounds below were synthesized according to Procedures 19-21, using intermediates described herein, and/or intermediates prepared according to General Schemes.

| Ex. | Structure | Name | ES/MS m/z [M + H]+ |
|---|---|---|---|
| 249 | 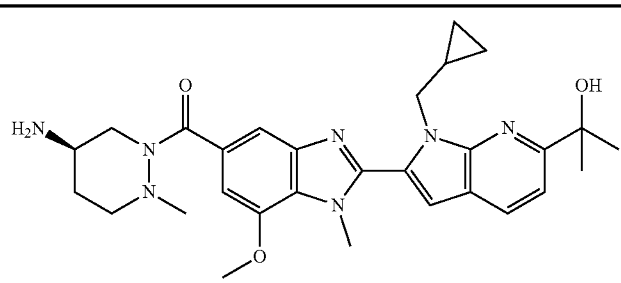 | (R)-(5-amino-2-methyltetrahydropyridazin-1(2H)-yl)(2-(1-(cyclopropylmethyl)-6-(2-hydroxypropan-2-yl)-1H-pyrrolo[2,3-b]pyridin-2-yl)-7-methoxy-2-methyl-1H-benzo[d]imidazol-5-yl)methanone | 532.32 |
| 250 | 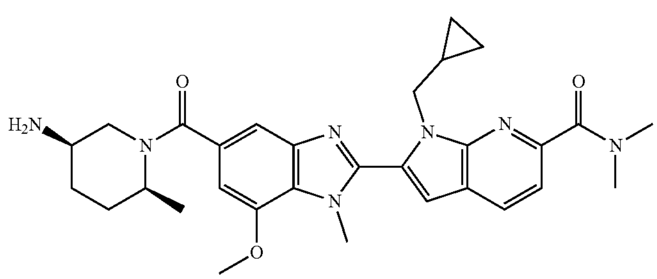 [SMILES: COc1cc(C(=O)N2C[C@H](N)CC[C@@H]2C)cc2nc(-c3cc4ccc(C(=O)N(C)C)nc4n3CC3CC3)n(C)c12] | 2-(5-((2S,5R)-5-amino-2-methylpiperidine-1-carbonyl)-7-methoxy-1-methyl-1H-benzo[d]imidazol-2-yl)-1-(cyclopropylmethyl)-N,N-dimethyl-1H-pyrrolo[2,3-b]pyridine-6-carboxamide | 544.7 |

TABLE 3-continued

The compounds below were synthesized according to Procedures 19-21, using intermediates described herein, and/or intermediates prepared according to General Schemes.

| Ex. | Structure | Name | ES/MS m/z [M + H]⁺ |
|---|---|---|---|
| 251 | 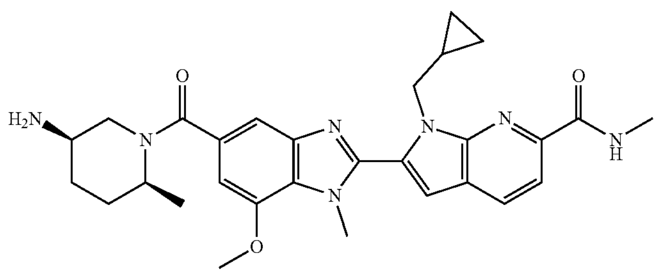 [SMILES: CNC(=O)c1ccc2cc(-c3nc4cc(C(=O)N5C[C@H](N)CC[C@@H]5C)cc(OC)c4n3C)n(CC3CC3)c2n1] | 2-(5-((2S,5R)-5-amino-2-methylpiperidine-1-carbonyl)-7-methoxy-1-methyl-1H-benzo[d]imidazol-2-yl)-1-(cyclopropylmethyl)-N-methyl-1H-pyrrolo[2,3-b]pyridine-6-carboxamide | 530.6 |
| 252 | 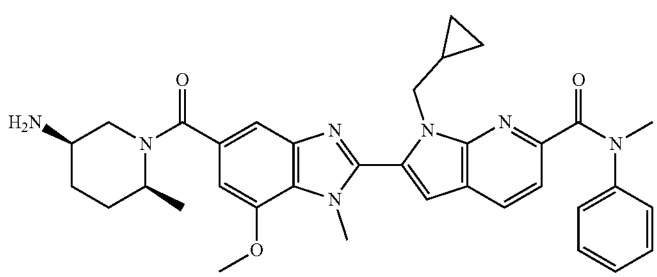 [SMILES: COc1cc(C(=O)N2C[C@H](N)CC[C@@H]2C)cc2nc(-c3cc4ccc(C(=O)N(C)c5ccccc5)nc4n3CC3CC3)n(C)c12] | 2-(5-((2S,5R)-5-amino-2-methylpiperidine-1-carbonyl)-7-methoxy-1-methyl-1H-benzo[d]imidazol-2-yl)-1-(cyclopropylmethyl)-N-methyl-N-phenyl-1H-pyrrolo[2,3-b]pyridine-6-carboxamide | 606.6 |
| 253 | 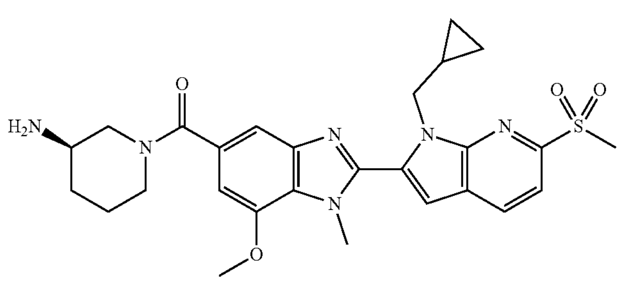 [SMILES: COc1cc(C(=O)N2CCC[C@@H](N)C2)cc2nc(-c3cc4ccc(S(C)(=O)=O)nc4n3CC3CC3)n(C)c12] | (R)-(3-aminopiperidin-1-yl)(2-(1-(cyclopropylmethyl)-6-(methylsulfonyl)-1H-pyrrolo[2,3-b]pyridin-2-yl)-7-methoxy-1-methyl-1H-benzo[d]imidazol-5-yl)methanone | 537.36 |
| 254 | 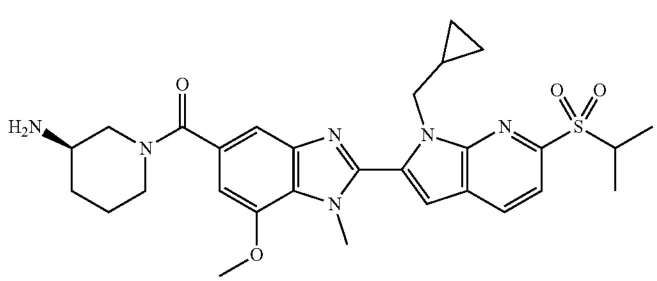 [SMILES: COc1cc(C(=O)N2CCC[C@@H](N)C2)cc2nc(-c3cc4ccc(S(=O)(=O)C(C)C)nc4n3CC3CC3)n(C)c12] | (R)-(3-aminopiperidin-1-yl)(2-(1-(cyclopropylmethyl)-6-(isopropylsulfonyl)-1H-pyrrolo[2,3-b]pyridin-2-yl)-7-methoxy-1-methyl-1H-benzo[d]imidazol-5-yl)methanone | 565.44 |

TABLE 4

The compounds below were synthesized according to the Schemes and Procedures described herein.

| Ex. | Structure | Name | ES/MS m/z [M + H]+ |
|---|---|---|---|
| 255 | 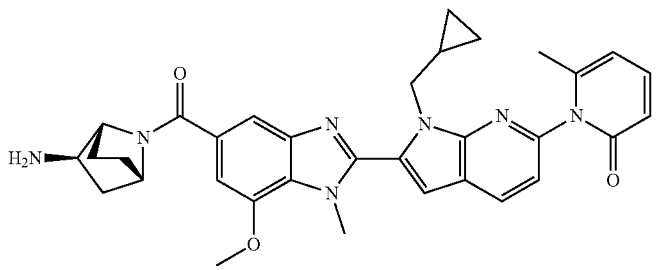 [SMILES: COc1cc(C(=O)N2[C@H]3CC[C@@H]2[C@H](N)C3)cc2nc(-c3cc4ccc(-n5c(C)cccc5=O)nc4n3CC3CC3)n(C)c12] | 1-(2-(5-((1R,2R,4S)-2-amino-7-azabicyclo[2.2.1]heptane-7-carbonyl)-7-methoxy-1-methyl-1H-benzo[d]imidazol-2-yl)-1-(cyclopropylmethyl)-1H-pyrrolo[2,3-b]pyridin-6-yl)-6-methylpyridin-2(1H)-one | 578.4 |
| 256 | 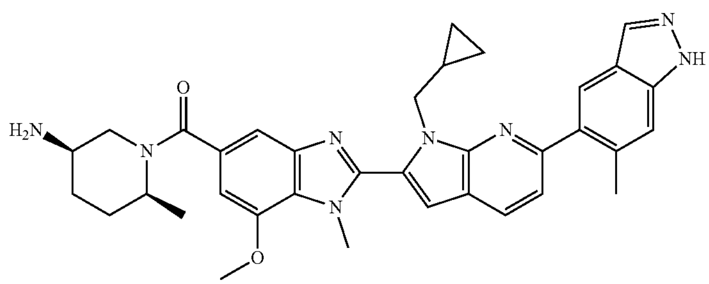 [SMILES: COc1cc(C(=O)N2C[C@H](N)CC[C@@H]2C)cc2nc(-c3cc4ccc(-c5cc6cn[nH]c6cc5C)nc4n3CC3CC3)n(C)c12] | ((2S,5R)-5-amino-2-methylpiperidin-1-yl)(2-(1-(cyclopropylmethyl)-6-(6-methyl-1H-indazol-5-yl)-1H-pyrrolo[2,3-b]pyridin-2-yl)-7-methoxy-1-methyl-1H-benzo[d]imidazol-5-yl)methanone | 603.22 |
| 257 | 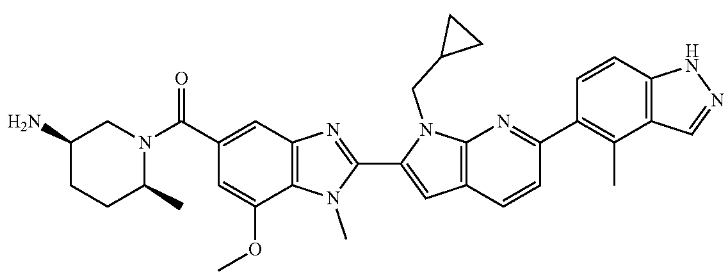 [SMILES: COc1cc(C(=O)N2C[C@H](N)CC[C@@H]2C)cc2nc(-c3cc4ccc(-c5ccc6[nH]ncc6c5C)nc4n3CC3CC3)n(C)c12] | ((2S,5R)-5-amino-2-methylpiperidin-1-yl)(2-(1-(cyclopropylmethyl)-6-(4-methyl-1H-indazol-5-yl)-1H-pyrrolo[2,3-b]pyridin-2-yl)-7-methoxy-1-methyl-1H-benzo[d]imidazol-5-yl)methanone | 603.24 |
| 258 | 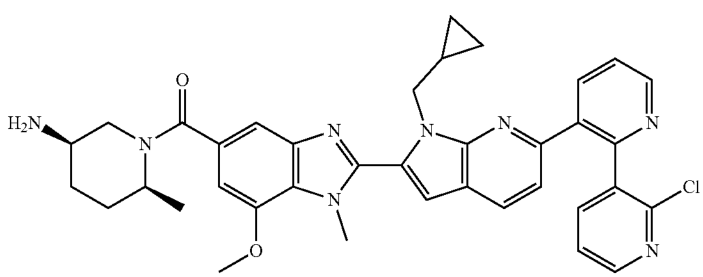 [SMILES: COc1cc(C(=O)N2C[C@H](N)CC[C@@H]2C)cc2nc(-c3cc4ccc(-c5cccnc5-c5cccnc5Cl)nc4n3CC3CC3)n(C)c12] | ((2S,5R)-5-amino-2-methylpiperidin-1-yl)(2-(6-(2'-chloro-[2,3'-bipyridin]-3-yl)-1-(cyclopropylmethyl)-1H-pyrrolo[2,3-b]pyridin-2-yl)-7-methoxy-1-methyl-1H-benzo[d]imidazol-5-yl)methanone | 684.19 |
| 259 | 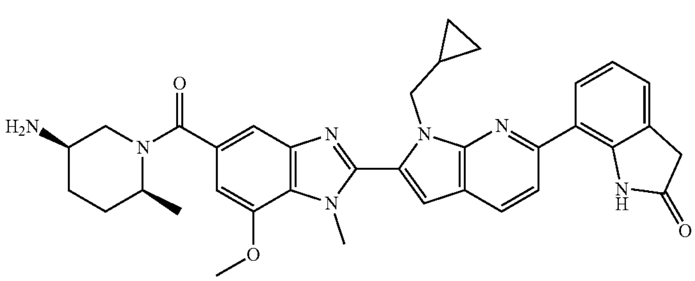 [SMILES: COc1cc(C(=O)N2C[C@H](N)CC[C@@H]2C)cc2nc(-c3cc4ccc(-c5cccc6c5NC(=O)C6)nc4n3CC3CC3)n(C)c12] | 7-(2-(5-((2S,5R)-5-amino-2-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)indolin-2-one | 604.33 |

TABLE 4-continued

The compounds below were synthesized according to the Schemes and Procedures described herein.

| Ex. | Structure | Name | ES/MS m/z [M + H]+ |
|---|---|---|---|
| 260 | 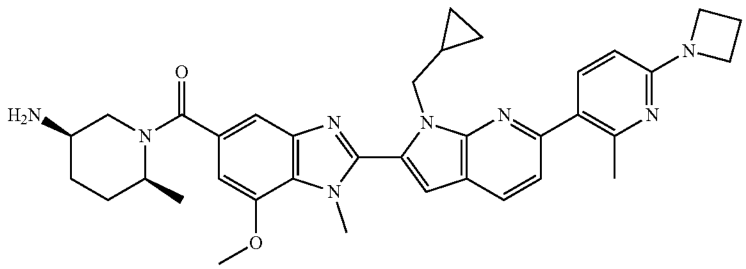 [SMILES: COc1cc(C(=O)N2C[C@H](N)CC[C@@H]2C)cc2nc(-c3cc4ccc(-c5ccc(N6CCC6)nc5C)nc4n3CC3CC3)n(C)c12] | ((2S,5R)-5-amino-2-methylpiperidin-1-yl)(2-(6-(6-(azetidin-1-yl)-2-methylpyridin-3-yl)-1-(cyclopropylmethyl)-1H-pyrrolo[2,3-b]pyridin-2-yl)-7-methoxy-1-methyl-1H-benzo[d]imidazol-5-yl)methanone | 619.48 |
| 261 | 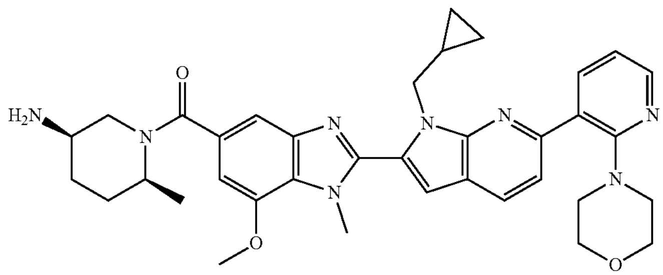 [SMILES: COc1cc(C(=O)N2C[C@H](N)CC[C@@H]2C)cc2nc(-c3cc4ccc(-c5cccnc5N5CCOCC5)nc4n3CC3CC3)n(C)c12] | ((2S,5R)-5-amino-2-methylpiperidin-1-yl)(2-(1-(cyclopropylmethyl)-6-(2-morpholinopyridin-3-yl)-1H-pyrrolo[2,3-b]pyridin-2-yl)-7-methoxy-1-methyl-1H-benzo[d]imidazol-5-yl)methanone | 635.39 |
| 262 | 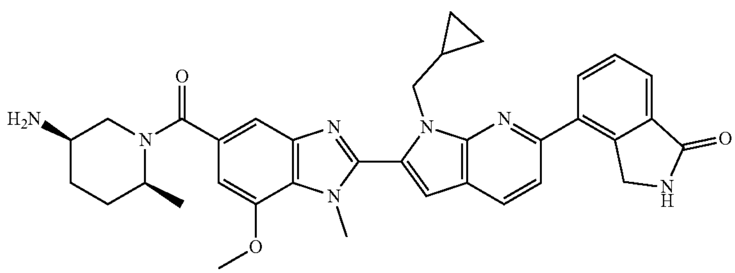 [SMILES: COc1cc(C(=O)N2C[C@H](N)CC[C@@H]2C)cc2nc(-c3cc4ccc(-c5cccc6c5CNC6=O)nc4n3CC3CC3)n(C)c12] | 4-(2-(5-(((2S,5R)-5-amino-2-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)isoindolin-1-one | 604.25 |
| 263 | 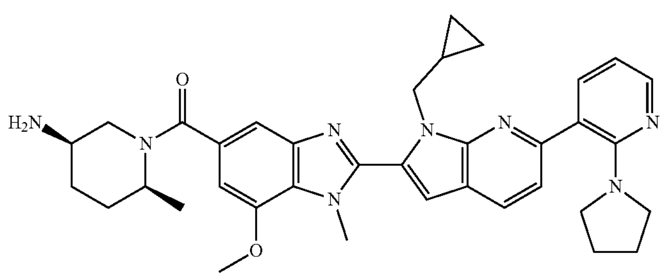 [SMILES: COc1cc(C(=O)N2C[C@H](N)CC[C@@H]2C)cc2nc(-c3cc4ccc(-c5cccnc5N5CCCC5)nc4n3CC3CC3)n(C)c12] | ((2S,5R)-5-amino-2-methylpiperidin-1-yl)(2-(1-(cyclopropylmethyl)-6-(2-(pyrrolidin-1-yl)pyridin-3-yl)-1H-pyrrolo[2,3-b]pyridin-2-yl)-7-methoxy-1-methyl-1-benzo[d]imidazol-5-yl)methanone | 619.36 |
| 264 | 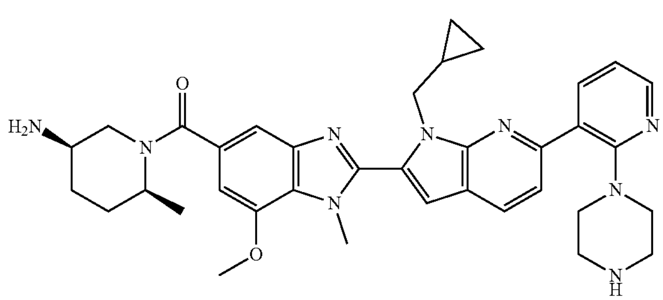 [SMILES: COc1cc(C(=O)N2C[C@H](N)CC[C@@H]2C)cc2nc(-c3cc4ccc(-c5cccnc5N5CCNCC5)nc4n3CC3CC3)n(C)c12] | ((2S,5R)-5-amino-2-methylpiperidin-1-yl)(2-(1-(cyclopropylmethyl)-6-(2-(piperazin-1-yl)pyridin-3-yl)-1H-pyrrolo[2,3-b]pyridin-2-yl)-7-methoxy-1-methyl-1H-benzo[d]imidazol-5-yl)methanone | 634.32 |

TABLE 4-continued

The compounds below were synthesized according to the Schemes and Procedures described herein.

| Ex. | Structure | Name | ES/MS m/z [M + H]+ |
|---|---|---|---|
| 265 | 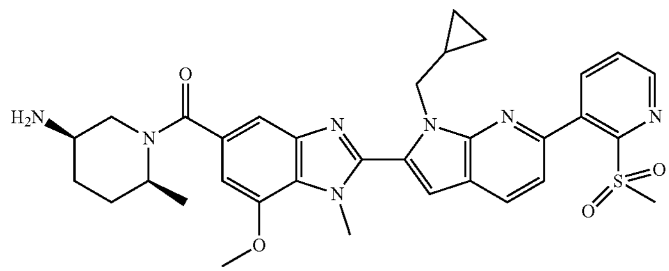 [SMILES: COc1cc(C(=O)N2C[C@H](N)CC[C@@H]2C)cc2nc(-c3cc4ccc(-c5cccnc5S(C)(=O)=O)nc4n3CC3CC3)n(C)c12] | ((2S,5R)-5-amino-2-methylpiperidin-1-yl)(2-(1-(cyclopropylmethyl)-6-(2-(methylsulfonyl)pyridin-3-yl)-1H-pyrrolo[2,3-b]pyridin-2-yl)-7-methoxy-1-methyl-1H-benzo[d]imidazol-5-yl)methanone | 628.2 |
| 266 | 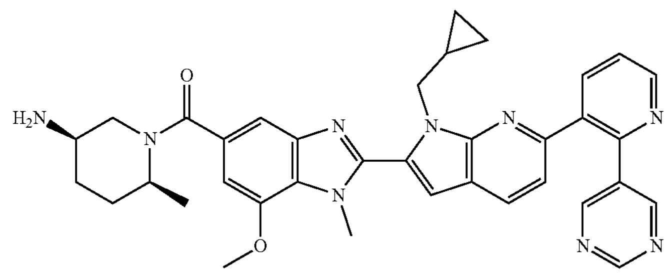 [SMILES: COc1cc(C(=O)N2C[C@H](N)CC[C@@H]2C)cc2nc(-c3cc4ccc(-c5cccnc5-c5cncnc5)nc4n3CC3CC3)n(C)c12] | ((2S,5R)-5-amino-2-methylpiperidin-1-yl)(2-(1-(cyclopropylmethyl)-6-(2-(pyrimidin-5-yl)pyridin-3-yl)-1H-pyrrolo[2,3-b]pyridin-2-yl)-7-methoxy-1-methyl-1H-benzo[d]imidazol-5-yl)methanone | 628.23 |
| 267 | 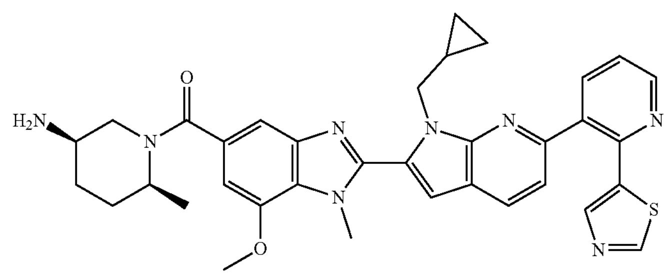 [SMILES: COc1cc(C(=O)N2C[C@H](N)CC[C@@H]2C)cc2nc(-c3cc4ccc(-c5cccnc5-c5cncs5)nc4n3CC3CC3)n(C)c12] | ((2S,5R)-5-amino-2-methylpiperidin-1-yl)(2-(1-(cyclopropylmethyl)-6-(2-(thiazol-5-yl)pyridin-3-yl)-1H-pyrrolo[2,3-b]pyridin-2-yl)-7-methoxy-1-methyl-1H-benzo[d]imidazol-5-yl)methanone | 633.19 |
| 268 | 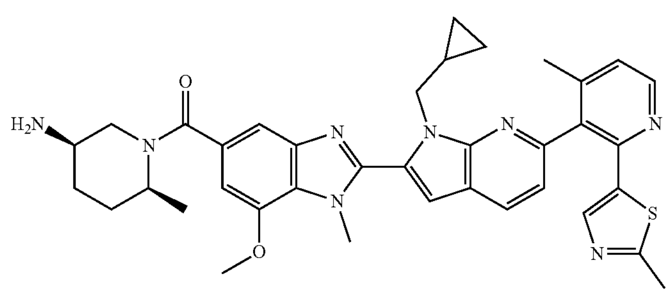 [SMILES: COc1cc(C(=O)N2C[C@H](N)CC[C@@H]2C)cc2nc(-c3cc4ccc(-c5c(C)ccnc5-c5cnc(C)s5)nc4n3CC3CC3)n(C)c12] | ((2S,5R)-5-amino-2-methylpiperidin-1-yl)(2-(1-(cyclopropylmethyl)-6-(4-methyl-2-(2-methylthiazol-5-yl)pyridin-3-yl)-1H-pyrrolo[2,3-b]pyridin-2-yl)-7-methoxy-1-methyl-1H-benzo[d]imidazol-5-yl)methanone | 661.25 |
| 269 | 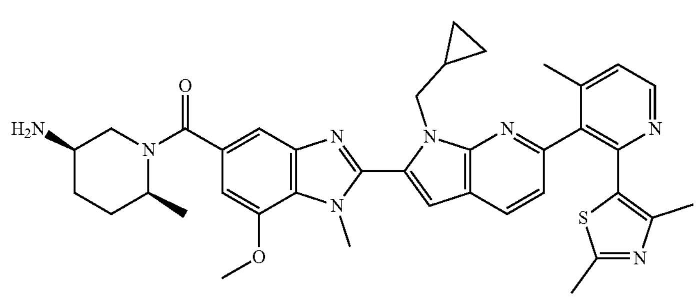 [SMILES: COc1cc(C(=O)N2C[C@H](N)CC[C@@H]2C)cc2nc(-c3cc4ccc(-c5c(C)ccnc5-c5sc(C)nc5C)nc4n3CC3CC3)n(C)c12] | ((2S,5R)-5-amino-2-methylpiperidin-1-yl)(2-(1-(cyclopropylmethyl)-6-(2-(2,4-dimethylthiazol-5-yl)-4-methylpyridin-3-yl)-1H-pyrrolo[2,3-b]pyridin-2-yl)-7-methoxy-1-methyl-1H-benzo[d]imidazol-5-yl)methanone | 675.24 |

TABLE 4-continued

The compounds below were synthesized according to the Schemes and Procedures described herein.

| Ex. | Structure | Name | ES/MS m/z [M + H]+ |
|---|---|---|---|
| 270 | 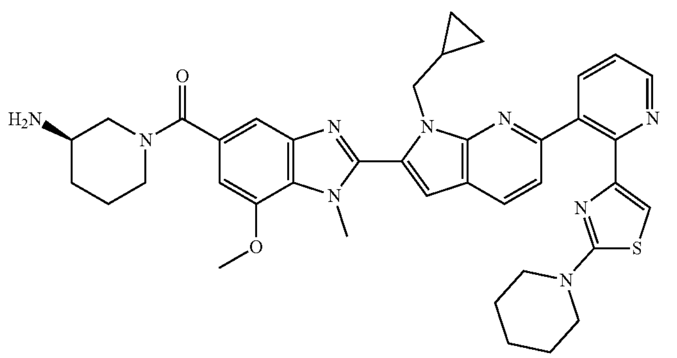 [SMILES: COc1cc(C(=O)N2CCC[C@@H](N)C2)cc2nc(-c3cc4ccc(-c5cccnc5-c5csc(N6CCCCC6)n5)nc4n3CC3CC3)n(C)c12] | (R)-(3-aminopiperidin-1-yl)(2-(1-(cyclopropylmethyl)-6-(2-(2-(piperidin-1-yl)thiazol-4-yl)pyridin-3-yl)-1H-pyrrolo[2,3-b]pyridin-2-yl)-7-methoxy-1-methyl-1H-benzo[d]imidazol-5-yl)methanone | 702.32 |
| 271 | 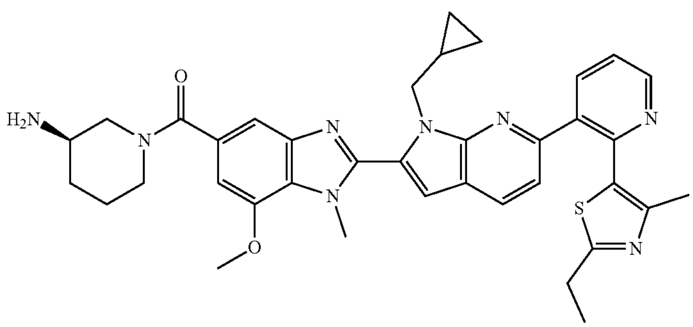 [SMILES: CCc1nc(C)c(-c2ncccc2-c2ccc3cc(-c4nc5cc(C(=O)N6CCC[C@@H](N)C6)cc(OC)c5n4C)n(CC4CC4)c3n2)s1] | (R)-(3-aminopiperidin-1-yl)(2-(1-(cyclopropylmethyl)-6-(2-(2-ethyl-4-methylthiazol-5-yl)pyridin-3-yl)-1H-pyrrolo[2,3-b]pyridin-2-yl)-7-methoxy-1-methyl-1H-benzo[d]imidazol-5-yl)methanone | 661.29 |
| 272 | 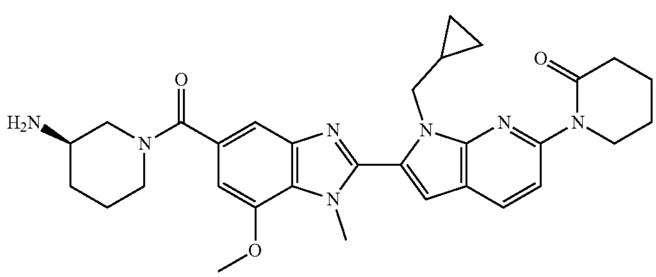 [SMILES: COc1cc(C(=O)N2CCC[C@@H](N)C2)cc2nc(-c3cc4ccc(N5CCCCC5=O)nc4n3CC3CC3)n(C)c12] | 1-(2-(5-((2S,5R)-5-amino-2-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)piperidin-2-one | 570.4 |
| 273 | 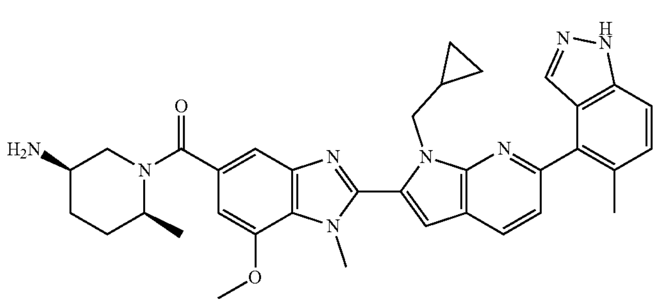 [SMILES: COc1cc(C(=O)N2C[C@H](N)CC[C@@H]2C)cc2nc(-c3cc4ccc(-c5c(C)ccc6[nH]ncc56)nc4n3CC3CC3)n(C)c12] | ((2S,5R)-5-amino-2-methylpiperidin-1-yl)(2-(1-(cyclopropylmethyl)-6-(5-methyl-1H-indazol-4-yl)-1H-pyrrolo[2,3-b]pyridin-2-yl)-7-methoxy-1-methyl-1H-benzo[d]imidazol-5-yl)methanone | 603.19 |

TABLE 4-continued

The compounds below were synthesized according to the Schemes and Procedures described herein.

| Ex. | Structure | Name | ES/MS m/z [M + H]+ |
|---|---|---|---|
| 274 | 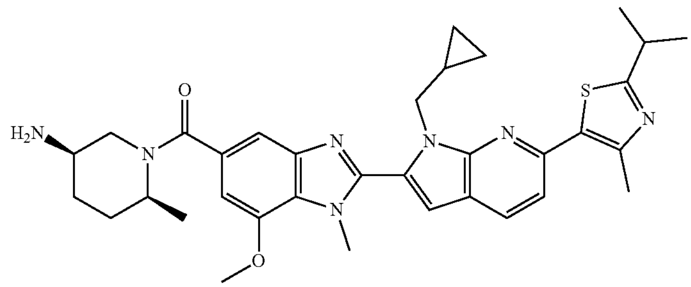 [SMILES: COc1cc(C(=O)N2C[C@H](N)CC[C@@H]2C)cc2nc(-c3cc4ccc(-c5sc(C(C)C)nc5C)nc4n3CC3CC3)n(C)c12] | ((2S,5R)-5-amino-2-methylpiperidin-1-yl)(2-(1-(cyclopropylmethyl)-6-(2-isopropyl-4-methylthiazol-5-yl)-1H-pyrrolo[2,3-b]pyridin-2-yl)-7-methoxy-1-methyl-1H-benzo[d]imidazol-5-yl)methanone | 612.29 |
| 275 | 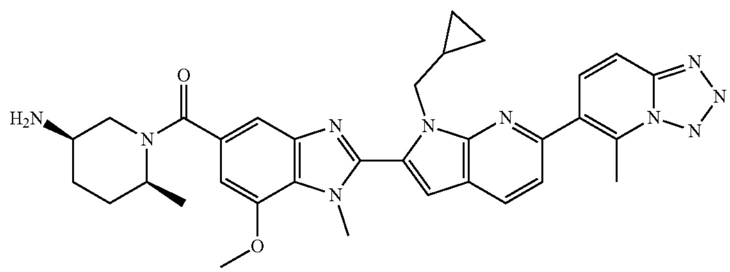 [SMILES: COc1cc(C(=O)N2C[C@H](N)CC[C@@H]2C)cc2nc(-c3cc4ccc(C5=C(C)N6NNN=C6C=C5)nc4n3CC3CC3)n(C)c12] | ((2S,5R)-5-amino-2-methylpiperidin-1-yl)(2-(1-(cyclopropylmethyl)-6-(5-methyltetrazolo[1,5-a]pyridin-6-yl)-1H-pyrrolo[2,3-b]pyridin-2-yl)-7-methoxy-1-methyl-1H-benzo[d]imidazol-5-yl)methanone | 605.11 |
| 276 | 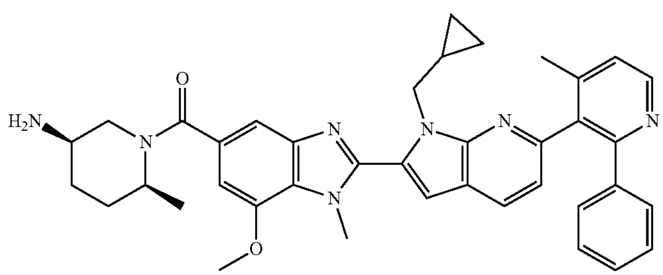 [SMILES: COc1cc(C(=O)N2C[C@H](N)CC[C@@H]2C)cc2nc(-c3cc4ccc(-c5c(C)ccnc5-c5ccccc5)nc4n3CC3CC3)n(C)c12] | ((2S,5R)-5-amino-2-methylpiperidin-1-yl)(2-(1-(cyclopropylmethyl)-6-(4-methyl-2-phenylpyridin-3-yl)-1H-pyrrolo[2,3-b]pyridin-2-yl)-7-methoxy-1-methyl-1H-benzo[d]imidazol-5-yl)methanone | 640.33 |
| 277 | 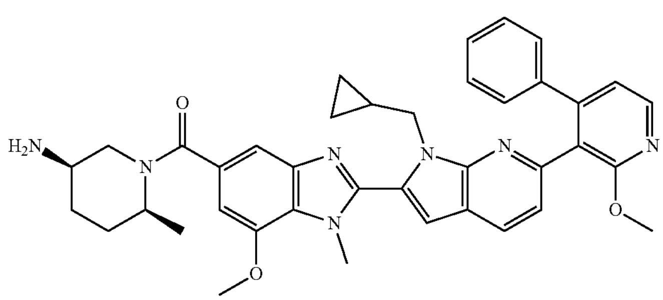 [SMILES: COc1nccc(-c2ccccc2)c1-c1ccc2cc(-c3nc4cc(C(=O)N5C[C@H](N)CC[C@@H]5C)cc(OC)c4n3C)n(CC3CC3)c2n1] | ((2S,5R)-5-amino-2-methylpiperidin-1-yl)(2-(1-(cyclopropylmethyl)-6-(2-methoxy-4-phenylpyridin-3-yl)-1H-pyrrolo[2,3-b]pyridin-2-yl)-7-methoxy-1-methyl-1H-benzo[d]imidazol-5-yl)methanone | 656.29 |
| 278 | 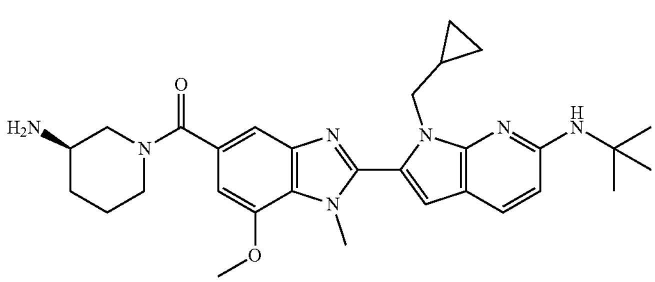 [SMILES: COc1cc(C(=O)N2CCC[C@@H](N)C2)cc2nc(-c3cc4ccc(NC(C)(C)C)nc4n3CC3CC3)n(C)c12] | (R)-(3-aminopiperidin-1-yl)(2-(6-(tert-butylamino)-1-(cyclopropylmethyl)-1H-pyrrolo[2,3-b]pyridin-2-yl)-7-methoxy-1-methyl-1H-benzo[d]imidazol-5-yl)methanone | 530.45 |

TABLE 4-continued

The compounds below were synthesized according to the Schemes and Procedures described herein.

| Ex. | Structure | Name | ES/MS m/z [M + H]+ |
|---|---|---|---|
| 279 | 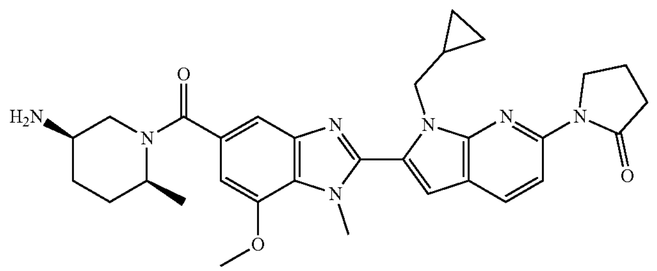 [SMILES: COc1cc(C(=O)N2C[C@H](N)CC[C@@H]2C)cc2nc(-c3cc4ccc(N5CCCC5=O)nc4n3CC3CC3)n(C)c12] | 1-(2-(5-((2S,5R)-5-amino-2-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)pyrrolidin-2-one | 556.6 |
| 280 | 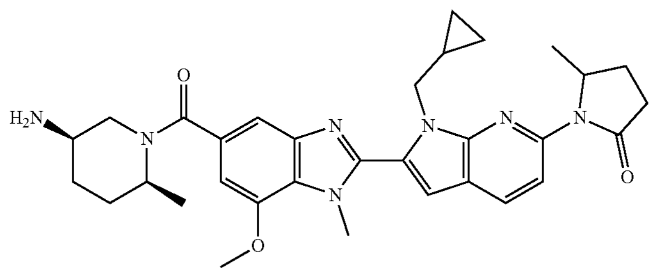 [SMILES: COc1cc(C(=O)N2C[C@H](N)CC[C@@H]2C)cc2nc(-c3cc4ccc(N5C(=O)CCC5C)nc4n3CC3CC3)n(C)c12] | 1-(2-(5-((2S,5R)-5-amino-2-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)-5-methylpyrrolidin-2-one | 570.6 |
| 281 | 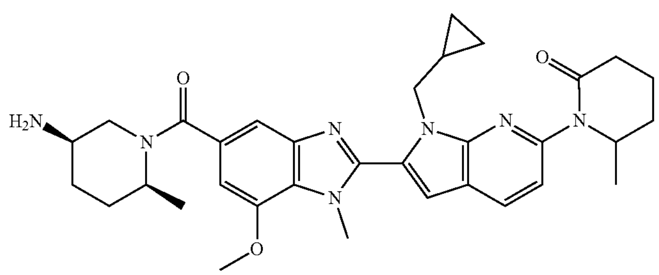 [SMILES: COc1cc(C(=O)N2C[C@H](N)CC[C@@H]2C)cc2nc(-c3cc4ccc(N5C(=O)CCCC5C)nc4n3CC3CC3)n(C)c12] | 1-(2-(5-((2S,5R)-5-amino-2-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)-6-methylpiperidin-2-one | 584.6 |
| 282 | 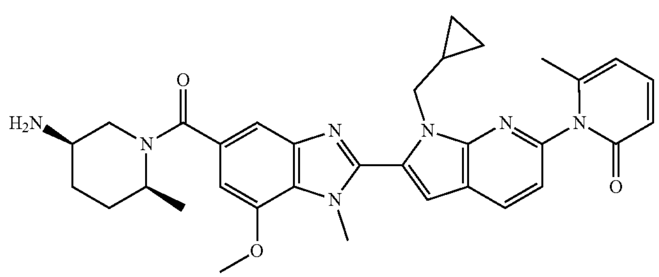 [SMILES: COc1cc(C(=O)N2C[C@H](N)CC[C@@H]2C)cc2nc(-c3cc4ccc(-n5c(C)cccc5=O)nc4n3CC3CC3)n(C)c12] | 1-(2-(5-((2S,5R)-5-amino-2-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)-6-methylpyridin-2(1H)-one | 580.6 |
| 283 | 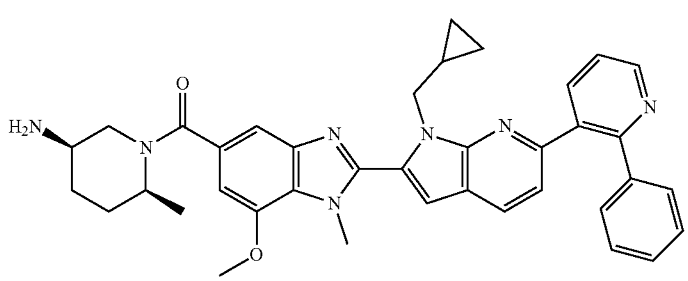 [SMILES: COc1cc(C(=O)N2C[C@H](N)CC[C@@H]2C)cc2nc(-c3cc4ccc(-c5cccnc5-c5ccccc5)nc4n3CC3CC3)n(C)c12] | ((2S,5R)-5-amino-2-methylpiperidin-1-yl)(2-(1-(cyclopropylmethyl)-6-(2-phenylpyridin-3-yl)-1H-pyrrolo[2,3-b]pyridin-2-yl)-7-methoxy-1-methyl-1H-benzo[d]imidazol-5-yl)methanone | 626.8 |

TABLE 4-continued

The compounds below were synthesized according to the Schemes and Procedures described herein.

| Ex. | Structure | Name | ES/MS m/z [M + H]+ |
|---|---|---|---|
| 284 | 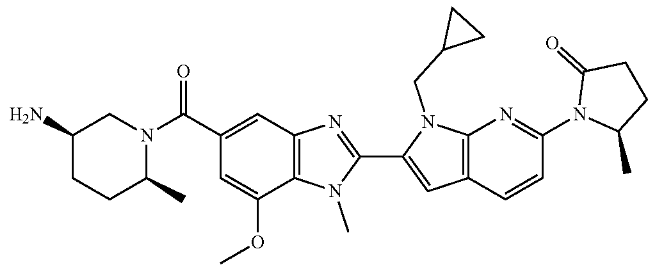 [SMILES: COc1cc(C(=O)N2C[C@H](N)CC[C@@H]2C)cc2nc(-c3cc4ccc(N5C(=O)CC[C@H]5C)nc4n3CC3CC3)n(C)c12] | (R)-1-(2-(5-((2S,5R)-5-amino-2-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)-5-methylpyrrolidin-2-one | 670.6 |
| 285 | 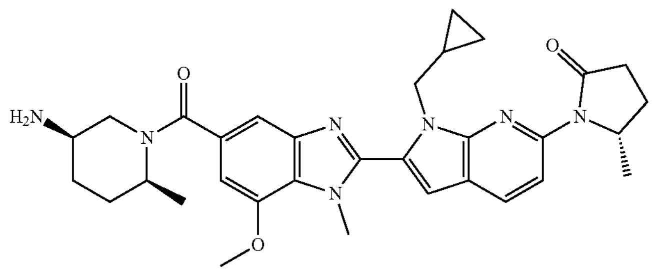 [SMILES: COc1cc(C(=O)N2C[C@H](N)CC[C@@H]2C)cc2nc(-c3cc4ccc(N5C(=O)CC[C@@H]5C)nc4n3CC3CC3)n(C)c12] | (S)-1-(2-(5-((2S,5R)-5-amino-2-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)-5-methylpyrrolidin-2-one | 570.7 |
| 286 | 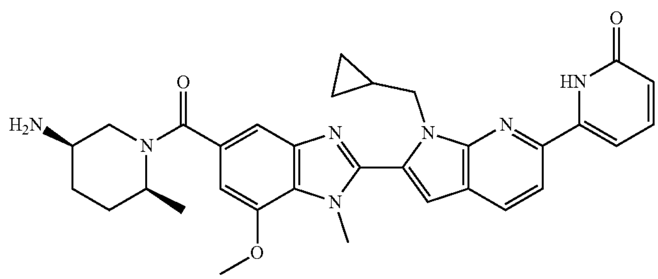 [SMILES: COc1cc(C(=O)N2C[C@H](N)CC[C@@H]2C)cc2nc(-c3cc4ccc(-c5cccc(=O)[nH]5)nc4n3CC3CC3)n(C)c12] | 6-(2-(5-((2S,5R)-5-amino-2-methylpiperidine-1-carbonyl)-7-methoxy-1-methyl-1H-benzo[d]imidazol-2-yl)-1-(cyclopropylmethyl)-1H-pyrrolo[2,3-b]pyridin-6-yl)pyridin-2(1H)-one | 566.5 |

$^1$H NMR data for select compounds disclosed herein is listed in Tables 5a and 5b. It is understood that $^1$H NMR signals and integrations are as observed, and that, due to factors including exchange, line broadening, or obscurement by residual solvent/moisture, integrations may differ from theoretical values.

TABLE 5a

| Ex. | $^1$H NMR |
|---|---|
| 1 | 1H NMR (400 MHz, Methanol-d4) δ 7.67 (d, J = 8.5 Hz, 1H), 7.55 (d, J = 1.8 Hz, 1H), 7.42 (s, 1H), 7.07 (dd, J = 8.5, 1.8 Hz, 1H), 7.02-6.97 (m, 2H), 4.36 (s, 1H), 4.26 (d, J = 6.8 Hz, 2H), 4.15 (s, 3H), 4.06 (s, 3H), 3.82 (s, 1H), 3.45-3.31 (m, 3H), 2.97 (s, 3H), 2.25-2.14 (m, 1H), 1.90-1.62 (m, 3H), 0.97 (td, J = 7.4, 3.9 Hz, 1H), 0.39-0.32 (m, 2H), −0.05 (q, J = 5.1 Hz, 2H). |
| 2 | 1H NMR (400 MHz, Methanol-d4) δ 7.76-7.67 (m, 2H), 7.42 (d, J = 1.2 Hz, 1H), 7.25 (dd, J = 8.5, 1.8 Hz, 1H), 7.04-6.98 (m, 2H), 4.31 (d, J = 6.9 Hz, 3H), 4.15 (s, 3H), 4.06 (s, 3H), 3.75-3.69 (m, 1H), 3.45-3.31 (m, 6H), 2.94 (s, 3H), 2.26-2.14 (m, 1H), 1.91-1.64 (m, 3H), 1.03-0.91 (m, 1H), 0.39-0.29 (m, 2H), −0.06 (q, J = 5.1 Hz, 2H). |
| 3 | 1H NMR (400 MHz, Methanol-d4) δ 8.11 (d, J = 8.4 Hz, 1H), 7.43 (s, 1H), 7.30 (d, J = 8.4 Hz, 1H), 7.00 (d, J = 5.3 Hz, 2H), 4.41 (d, J = 7.1 Hz, 3H), 4.16 (s, 3H), 4.06 (s, 3H), 3.84 (s, 1H), 3.46 (s, 3H), 3.44-3.31 (m, 3H), 3.15 (s, 3H), 2.26-2.12 (m, 1H), 1.91-1.61 (m, 3H), 1.05-0.93 (m, 1H), 0.37-0.27 (m, 2H), 0.07-−0.00 (m, 2H). |
| 4 | 1H NMR (400 MHz, Methanol-d4) δ 8.11 (d, J = 8.4 Hz, 1H), 7.39 (s, 1H), 7.29 (d, J = 8.4 Hz, 1H), 7.00 (s, 1H), 6.94 (s, 1H), 4.41 (d, J = 7.1 Hz, 2H), 4.16 (s, 3H), 4.05 (s, 3H), 3.87 (s, 1H), 3.55-3.44 (m, 4H), 3.33 (dd, J = 3.2, 1.3 Hz, 1H), 3.15 (s, 4H), 1.91 (dtd, J = 30.2, 14.0, 12.3, 5.3 Hz, 3H), 1.78-1.63 (m, 1H), 1.36 (d, J = 7.0 Hz, 3H), 0.99 (dq, J = 7.4, 4.4, 3.9 Hz, 1H), 0.37-0.26 (m, 2H), 0.08-−0.01 (m, 2H). |

TABLE 5a-continued

| Ex. | ¹H NMR |
|---|---|
| 5 | 1H NMR (400 MHz, cd3cn) δ 8.13 (d, J = 8.3 Hz, 1H), 7.50 (d, J = 1.1 Hz, 1H), 7.24 (d, J = 8.3 Hz, 1H), 7.03 (s, 1H), 6.99 (d, J = 1.2 Hz, 1H), 4.38 (d, J = 7.1 Hz, 2H), 4.14 (s, 3H), 4.13-3.22 (m, 6H), 4.03 (s, 3H), 3.97 (q, J = 7.1 Hz, 2H), 3.15 (s, 3H), 2.21-1.49 (m, 3H), 1.19 (t, J = 7.1 Hz, 3H), 1.14-1.00 (m, 1H), 0.38-0.23 (m, 2H), 0.18-0.06 (m, 2H). |
| 6 | 1H NMR (400 MHz, cd3cn) δ 8.13 (d, J = 8.1 Hz, 1H), 7.41 (d, J = 1.2 Hz, 1H), 7.13 (d, J = 8.1 Hz, 1H), 6.99 (s, 1H), 6.92 (d, J = 1.2 Hz, 1H), 4.46 (d, J = 7.2 Hz, 2H), 4.45-4.37 (m, 1H), 4.14 (s, 3H), 4.13-3.28 (m, 6H), 4.01 (s, 3H), 3.27 (s, 3H), 2.18-1.54 (m, 3H), 1.27 (d, J = 6.7 Hz, 6H), 1.23-1.05 (m, 1H), 0.37-0.25 (m, 2H), 0.22-0.11 (m, 2H). |
| 7 | 1H NMR (400 MHz, Methanol-d4) δ 8.10 (d, J = 8.5 Hz, 1H), 7.43 (s, 1H), 7.31 (d, J = 8.4 Hz, 1H), 6.99 (d, J = 1.4 Hz, 2H), 4.40 (d, J = 7.1 Hz, 2H), 4.34 (s, 1H), 4.16 (s, 3H), 4.06 (s, 3H), 3.51 (s, 3H), 3.45 (q, J = 7.4 Hz, 2H), 3.42-3.31 (m, 4H), 2.23-2.15 (m, 1H), 1.91-1.64 (m, 3H), 1.35 (t, J = 7.4 Hz, 3H), 1.04-0.93 (m, 1H), 0.35-0.29 (m, 2H), 0.07-0.02 (m, 2H). |
| 8 | 1H NMR (400 MHz, Methanol-d4) δ 8.08 (d, J = 8.4 Hz, 1H), 7.43 (d, J = 1.2 Hz, 1H), 7.35 (d, J = 8.4 Hz, 1H), 7.00 (s, 1H), 6.99 (d, J = 1.2 Hz, 1H), 4.42 (d, J = 7.0 Hz, 2H), 4.34 (s, 1H), 4.17 (s, 3H), 4.06 (s, 3H), 3.82 (s, 1H), 3.50 (s, 3H), 3.45-3.31 (m, 3H), 2.82 (tt, J = 7.8, 5.0 Hz, 1H), 2.24-2.14 (m, 1H), 1.90-1.63 (m, 3H), 1.06-0.94 (m, 5H), 0.36-0.29 (m, 2H), 0.05 (dt, J = 6.1, 4.5 Hz, 2H). |
| 9 | 1H NMR (400 MHz, Methanol-d4) δ 8.08 (d, J = 8.5 Hz, 1H), 7.43 (d, J = 1.2 Hz, 1H), 7.33 (d, J = 8.5 Hz, 1H), 6.99 (d, J = 2.2 Hz, 2H), 4.39 (d, J = 7.1 Hz, 3H), 4.16 (s, 3H), 4.06 (s, 3H), 3.91 (hept, J = 6.9 Hz, 1H), 3.54 (s, 3H), 3.45-3.31 (m, 4H), 2.26-2.12 (m, 1H), 1.92-1.62 (m, 3H), 1.37 (d, J = 6.9 Hz, 6H), 1.06-0.91 (m, 1H), 0.35-0.29 (m, 2H), 0.08-0.02 (m, 2H). |
| 10 | 1H NMR (400 MHz, Methanol-d4) δ 8.13 (d, J = 8.3 Hz, 1H), 7.44 (s, 1H), 7.26 (d, J = 8.3 Hz, 1H), 7.02 (s, 1H), 6.99 (s, 1H), 4.41 (d, J = 7.0 Hz, 3H), 4.17 (s, 3H), 4.06 (s, 3H), 3.91 (t, J = 7.1 Hz, 2H), 3.46-3.31 (m, 4H), 3.13 (s, 3H), 2.25-2.13 (m, 1H), 1.90-1.65 (m, 3H), 1.56 (h, J = 7.3 Hz, 2H), 1.04-0.92 (m, 4H), 0.36-0.29 (m, 2H), 0.07--0.00 (m, 2H). |
| 11 | 1H NMR (400 MHz, Methanol-d4) δ 8.01 (d, J = 8.4 Hz, 1H), 7.43 (s, 1H), 7.36-7.31 (m, 2H), 7.27-7.12 (m, 4H), 7.00-6.98 (m, 1H), 6.96 (s, 1H), 5.17 (s, 2H), 4.41 (d, J = 7.0 Hz, 3H), 4.14 (s, 3H), 4.05 (s, 3H), 3.83 (s, 1H), 3.45-3.32 (m, 3H), 3.21 (s, 3H), 2.25-2.12 (m, 1H), 1.90-1.64 (m, 3H), 0.99-0.86 (m, 1H), 0.34-0.26 (m, 2H), 0.02--0.05 (m, 2H). |
| 12 | 1H NMR (400 MHz, Methanol-d4) δ 8.10 (d, J = 8.4 Hz, 1H), 7.66-7.56 (m, 3H), 7.50-7.44 (m, 3H), 7.41 (s, 1H), 6.98 (d, J = 1.5 Hz, 2H), 4.34 (s, 1H), 4.16 (d, J = 7.0 Hz, 2H), 4.14 (s, 3H), 4.05 (s, 3H), 3.86 (s, 1H), 3.45-3.31 (m, 6H), 2.23-2.14 (m, 1H), 1.89-1.64 (m, 3H), 0.81-0.64 (m, 1H), 0.21-0.15 (m, 2H), −0.15--0.23 (m, 2H). |
| 13 | 1H NMR (400 MHz, Methanol-d4) δ 8.02 (d, J = 8.4 Hz, 1H), 7.54-7.37 (m, 6H), 7.00 (d, J = 1.7 Hz, 2H), 6.75 (d, J = 8.4 Hz, 1H), 4.46 (d, J = 7.1 Hz, 2H), 4.34 (s, 1H), 4.17 (s, 3H), 4.06 (s, 3H), 3.87 (s, 1H), 3.57 (s, 3H), 3.45-3.31 (m, 3H), 2.24-2.12 (m, 1H), 1.91-1.64 (m, 3H), 1.12-0.99 (m, 1H), 0.39-0.31 (m, 2H), 0.11-0.05 (m, 2H). |
| 14 | 1H NMR (400 MHz, Methanol-d4) δ 8.10 (d, J = 8.4 Hz, 1H), 7.43 (d, J = 0.9 Hz, 1H), 7.29 (d, J = 8.5 Hz, 1H), 6.99 (s, 1H), 6.99 (d, J = 0.9 Hz, 1H), 4.40 (d, J = 7.1 Hz, 2H), 4.34 (s, 1H), 4.16 (s, 3H), 4.06 (s, 3H), 3.87 (s, 1H), 3.50 (s, 3H), 3.48-3.32 (m, 6H), 2.25-2.11 (m, 1H), 1.91-1.64 (m, 5H), 1.46 (h, J = 7.4 Hz, 2H), 1.04-0.96 (m, 1H), 0.93 (t, J = 7.4 Hz, 3H), 0.35-0.29 (m, 2H), 0.06-0.01 (m, 2H). |
| 15 | 1H NMR (400 MHz, Methanol-d4) δ 8.16 (d, J = 8.1 Hz, 1H), 7.44 (s, 1H), 7.16 (d, J = 8.1 Hz, 1H), 7.05 (s, 1H), 6.99 (s, 1H), 4.65 (ddd, J = 16.8, 9.3, 7.2 Hz, 1H), 4.44 (d, J = 7.0 Hz, 2H), 4.35 (s, 1H), 4.17 (s, 3H), 4.06 (s, 3H), 3.87 (s, 1H), 3.43-3.31 (m, 3H), 3.17 (s, 3H), 2.31-2.05 (m, 5H), 1.90-1.55 (m, 5H), 1.04-0.93 (m, 1H), 0.36-0.30 (m, 2H), 0.04--0.02 (m, 2H). |
| 16 | 1H NMR (400 MHz, Methanol-d4) δ 8.18 (d, J = 8.4 Hz, 1H), 7.44 (s, 1H), 7.38 (d, J = 8.3 Hz, 1H), 7.05 (s, 1H), 7.00 (s, 1H), 4.82-4.76 (m, 2H), 4.43 (d, J = 7.0 Hz, 2H), 4.35 (s, 1H), 4.17 (s, 3H), 4.06 (s, 3H), 3.83 (s, 1H), 3.45-3.32 (m, 3H), 3.17 (s, 3H), 2.24-2.12 (m, 1H), 1.91-1.64 (m, 3H), 1.02-0.91 (m, 1H), 0.36-0.29 (m, 2H), 0.05--0.01 (m, 2H). |
| 17 | 1H NMR (400 MHz, Methanol-d4) δ 8.12 (d, J = 8.3 Hz, 1H), 7.44 (s, 1H), 7.14 (d, J = 8.3 Hz, 1H), 7.02 (s, 1H), 6.99 (d, J = 1.2 Hz, 1H), 4.42 (d, J = 7.1 Hz, 2H), 4.34 (s, 1H), 4.16 (s, 3H), 4.06 (s, 3H), 3.35 (d, J = 29.5 Hz, 4H), 3.28 (s, 3H), 3.27-3.22 (m, 1H), 1.04-0.95 (m, 1H), 0.93-0.87 (m, 2H), 0.84-0.79 (m, 2H), 0.36-0.27 (m, 2H), 0.04 (q, J = 5.1 Hz, 2H). |
| 18 | 1H NMR (400 MHz, Methanol-d4) δ 8.24 (d, J = 8.2 Hz, 1H), 7.45 (s, 1H), 7.28 (t, J = 60.0 Hz, 1H), 7.27 (d, J = 8.2 Hz, 1H), 7.10 (s, 1H), 7.00 (d, J = 1.2 Hz, 1H), 4.44 (d, J = 7.1 Hz, 2H), 4.35 (s, 1H), 4.17 (s, 3H), 4.06 (s, 3H), 3.88 (s, 1H), 3.54 (s, 3H), 3.46-3.32 (m, 3H), 2.25-2.12 (m, 1H), 1.91-1.62 (m, 3H), 1.05-0.93 (m, 1H), 0.36-0.28 (m, 2H), 0.08-0.02 (m, 2H). |
| 19 | 1H NMR (400 MHz, Methanol-d4) δ 8.15 (d, J = 8.4 Hz, 1H), 7.44 (d, J = 1.2 Hz, 1H), 7.37 (d, J = 8.4 Hz, 1H), 7.04 (s, 1H), 7.00 (d, J = 1.2 Hz, 1H), 6.08 (tt, J = 56.0, 4.1 Hz, 1H), 4.48-4.27 (m, 5H), 4.17 (s, 3H), 4.06 (s, 3H), 3.82 (s, 1H), 3.45-3.31 (m, 3H), 3.20 (s, 3H), 2.24-2.12 (m, 1H), 1.91-1.63 (m, 3H), 1.05-0.92 (m, 1H), 0.37-0.29 (m, 2H), 0.06--0.02 (m, 2H). |
| 20 | 1H NMR (400 MHz, Methanol-d4) δ 8.02 (d, J = 8.4 Hz, 1H), 7.42 (s, 1H), 6.98 (s, 1H), 6.94 (s, 1H), 6.84 (d, J = 8.4 Hz, 1H), 4.53 (s, 1H), 4.40 (d, J = 7.1 Hz, 2H), 4.16 (s, 3H), 4.05 (s, 3H), 3.45-3.32 (m, 7H), 3.02 (s, 2H), 2.38-2.24 (m, 1H), 1.92-1.59 (m, 3H), 1.17-0.93 (m, 2H), 0.79-0.69 (m, 2H), 0.43 (s, 2H), 0.33-0.26 (m, 2H), 0.04 (q, J = 5.1 Hz, 2H). |
| 21 | 1H NMR (400 MHz, Methanol-d4) δ 8.02 (d, J = 8.5 Hz, 1H), 7.42 (d, J = 1.2 Hz, 1H), 6.98 (d, J = 1.2 Hz, 1H), 6.94 (s, 1H), 6.84 (d, J = 8.4 Hz, 1H), 4.58 (s, 1H), 4.40 (d, J = 7.1 Hz, 2H), 4.16 (s, 3H), 4.05 (s, 3H), 3.87 (s, 1H), 3.41 (s, 3H), 3.39-3.31 (m, 3H), 3.29-3.10 (m, 4H), 2.65 (s, 1H), 2.36-2.12 (m, 3H), 2.07-1.79 (m, 5H), 1.77-1.61 (m, 2H), 1.05-0.93 (m, 1H), 0.33-0.25 (m, 2H), 0.04 (q, J = 5.1 Hz, 2H). |

TABLE 5a-continued

| Ex. | ¹H NMR |
|---|---|
| 22 | 1H NMR (400 MHz, Methanol-d4) δ 8.14 (d, J = 8.3 Hz, 1H), 7.44 (d, J = 1.2 Hz, 1H), 7.31 (d, J = 8.3 Hz, 1H), 7.03 (s, 1H), 6.99 (d, J = 1.2 Hz, 1H), 4.55 (s, 1H), 4.42 (d, J = 7.0 Hz, 2H), 4.17 (s, 3H), 4.06 (s, 3H), 3.82 (d, J = 7.0 Hz, 2H), 3.46-3.31 (m, 4H), 3.19 (s, 3H), 3.02 (s, 2H), 2.29 (d, J = 9.8 Hz, 1H), 1.93-1.61 (m, 3H), 1.16-0.91 (m, 3H), 0.73 (d, J = 5.7 Hz, 2H), 0.48-0.40 (m, 4H), 0.36-0.30 (m, 2H), 0.23-0.16 (m, 2H), 0.07--0.00 (m, 2H). |
| 23 | 1H NMR (400 MHz, DMSO-d6) δ 8.14 (d, J = 8.4 Hz, 1H), 7.94 (s, 3H), 7.44 (s, 1H), 7.23 (d, J = 8.4 Hz, 1H), 7.08 (s, 1H), 6.94 (d, J = 1.2 Hz, 1H), 4.50 (s, 1H), 4.40 (d, J = 7.0 Hz, 2H), 4.39 (d, J = 7.1 Hz, 2H), 4.30-4.01 (m, 2H), 3.99 (s, 3H), 3.36 (s, 3H), 3.33-3.25 (m, 3H), 3.21 (s, 3H), 2.00 (s, 1H), 1.74 (d, J = 9.8 Hz, 1H), 1.57 (s, 2H), 1.08 (s, 2H), 0.31 (t, J = 7.3 Hz, 4H), 0.23 (d, J = 4.7 Hz, 2H), 0.11 (t, J = 4.9 Hz, 2H). |
| 24 | 1H NMR (400 MHz, DMSO-d6) δ 8.14 (d, J = 8.4 Hz, 1H), 7.91 (s, 3H), 7.38 (d, J = 1.1 Hz, 1H), 7.23 (d, J = 8.4 Hz, 1H), 7.07 (s, 1H), 6.90 (s, 1H), 4.94-4.06 (m, 4H), 4.50 (d, J = 7.0 Hz, 2H), 4.39 (d, J = 7.2 Hz, 2H), 4.00 (s, 3H), 3.37 (s, 3H), 3.21 (s, 3H), 1.73 (dd, J = 25.2, 14.1 Hz, 3H), 1.64-1.48 (m, 1H), 1.19 (d, J = 6.9 Hz, 3H), 1.14-1.02 (m, 2H), 0.31 (td, J = 7.5, 2.8 Hz, 4H), 0.24 (t, J = 4.6 Hz, 2H), 0.11 (q, J = 4.9 Hz, 2H). |
| 25 | 1H NMR (400 MHz, Methanol-d4) δ 8.11 (d, J = 8.3 Hz, 1H), 7.44 (d, J = 1.2 Hz, 1H), 7.29 (d, J = 8.3 Hz, 1H), 7.02 (s, 1H), 6.99 (d, J = 1.2 Hz, 1H), 4.42 (d, J = 7.0 Hz, 2H), 4.35 (s, 1H), 4.18 (s, 3H), 4.12-4.03 (m, 5H), 3.87 (s, 1H), 3.46-3.31 (m, 3H), 2.85 (tt, J = 7.6, 5.2 Hz, 1H), 2.24-2.14 (m, 1H), 1.91-1.62 (m, 3H), 1.18 (t, J = 7.1 Hz, 3H), 1.07-0.92 (m, 5H), 0.35-0.29 (m, 2H), 0.07-0.01 (m, 2H). |
| 26 | 1H NMR (400 MHz, Methanol-d4) δ 8.09 (d, J = 8.3 Hz, 1H), 7.44 (d, J = 1.2 Hz, 1H), 7.16 (d, J = 8.3 Hz, 1H), 7.02 (s, 1H), 7.00 (d, J = 1.2 Hz, 1H), 4.42 (d, J = 7.1 Hz, 2H), 4.35 (s, 1H), 4.17 (s, 3H), 4.06 (s, 3H), 3.82 (s, 3H), 3.46-3.31 (m, 4H), 2.94 (tt, J = 7.7, 5.1 Hz, 1H), 2.27-2.13 (m, 1H), 1.91-1.63 (m, 3H), 1.16-1.06 (m, 4H), 0.98 (tt, J = 8.0, 4.8 Hz, 1H), 0.92-0.77 (m, 4H), 0.35-0.28 (m, 2H), 0.09-0.03 (m, 2H). |
| 27 | 1H NMR (400 MHz, Methanol-d4) δ 8.23 (d, J = 8.2 Hz, 1H), 7.45 (d, J = 1.2 Hz, 1H), 7.30 (d, J = 8.2 Hz, 1H), 7.22 (t, J = 59.9 Hz, 1H), 7.09 (s, 1H), 7.00 (d, J = 1.2 Hz, 1H), 4.44 (d, J = 7.1 Hz, 2H), 4.35 (s, 1H), 4.18 (s, 3H), 4.06 (s, 3H), 3.88 (s, 1H), 3.45-3.32 (m, 3H), 3.29-3.19 (m, 1H), 2.27-2.14 (m, 1H), 1.91-1.62 (m, 3H), 1.24-1.19 (m, 4H), 1.05-0.91 (m, 1H), 0.35-0.28 (m, 2H), 0.10-0.04 (m, 2H). |
| 28 | 1H NMR (400 MHz, Methanol-d4) δ 8.13 (d, J = 8.3 Hz, 1H), 7.39 (s, 1H), 7.26 (d, J = 8.3 Hz, 1H), 7.02 (s, 1H), 6.95 (s, 1H), 4.41 (d, J = 7.1 Hz, 2H), 4.17 (s, 3H), 4.06 (s, 3H), 4.00 (q, J = 7.1 Hz, 2H), 3.80 (s, 1H), 3.54-3.46 (m, 1H), 3.41-3.31 (m, 1H), 3.16 (s, 4H), 2.02-1.81 (m, 3H), 1.71 (s, 1H), 1.36 (d, J = 7.0 Hz, 3H), 1.20 (t, J = 7.1 Hz, 3H), 1.05-0.93 (m, 1H), 0.36-0.29 (m, 2H), 0.06--0.00 (m, 2H). |
| 29 | 1H NMR (400 MHz, DMSO-d6) δ 8.16 (d, J = 8.3 Hz, 1H), 7.96 (d, J = 19.5 Hz, 3H), 7.34 (d, J = 1.1 Hz, 1H), 7.19 (d, J = 8.3 Hz, 1H), 7.10 (s, 1H), 6.86 (d, J = 1.2 Hz, 1H), 4.43 (d, J = 7.1 Hz, 2H), 4.29-4.23 (m, 3H), 4.13 (s, 3H), 3.98 (s, 3H), 3.95-3.85 (m, 2H), 3.21 (s, 3H), 3.15 (s, 1H), 3.00 (d, J = 32.7 Hz, 1H), 1.86 (s, 1H), 1.74 (t, J = 9.8 Hz, 2H), 1.56 (s, 1H), 1.19 (d, J = 6.9 Hz, 3H), 1.11 (t, J = 7.1 Hz, 3H), 0.38-0.26 (m, 2H), 0.18 (t, J = 4.6 Hz, 2H). |
| 30 | 1H NMR (400 MHz, DMSO-d6) δ 8.16 (d, J = 8.3 Hz, 1H), 8.10-7.71 (m, 3H), 7.34 (d, J = 1.1 Hz, 1H), 7.19 (d, J = 8.3 Hz, 1H), 7.10 (s, 1H), 6.86 (d, J = 1.2 Hz, 1H), 5.09-4.52 (m, 5H), 4.43 (d, J = 7.1 Hz, 2H), 4.13 (s, 3H), 3.98 (s, 3H), 3.95-3.84 (m, 2H), 3.20-3.09 (m, 2H), 3.00 (d, J = 31.6 Hz, 1H), 1.86 (s, 1H), 1.82-1.69 (m, 2H), 1.56 (s, 1H), 1.19 (d, J = 6.9 Hz, 3H), 1.11 (t, J = 7.1 Hz, 3H), 0.30 (dt, J = 8.0, 2.9 Hz, 2H), 0.18 (t, J = 4.7 Hz, 2H). |
| 31 | 1H NMR (400 MHz, Methanol-d4) δ 8.14 (d, J = 8.3 Hz, 1H), 7.42 (d, J = 1.2 Hz, 1H), 7.17 (d, J = 8.3 Hz, 1H), 7.11 (s, 1H), 7.06 (d, J = 1.2 Hz, 1H), 4.39 (d, J = 7.1 Hz, 2H), 4.19 (s, 3H), 4.07 (s, 3H), 3.26 (dt, J = 6.7, 3.3 Hz, 1H), 3.12 (d, J = 25.6 Hz, 6H), 1.04-0.94 (m, 1H), 0.94-0.87 (m, 2H), 0.81 (q, J = 3.7 Hz, 2H), 0.37-0.28 (m, 2H), 0.11--0.01 (m, 2H).; 1H NMR (400 MHz, Methanol-d4) δ 8.12 (d, J = 8.3 Hz, 1H), 7.40 (d, J = 1.2 Hz, 1H), 7.15 (d, J = 8.3 Hz, 1H), 7.04 (s, 1H), 6.97 (d, J = 1.1 Hz, 1H), 4.41 (d, J = 7.0 Hz, 2H), 4.17 (s, 3H), 4.06 (s, 3H), 3.56-3.40 (m, 1H), 3.28 (s, 3H), 3.25 (dd, J = 6.7, 3.4 Hz, 1H), 2.10-1.57 (m, 3H), 1.36 (d, J = 7.0 Hz, 3H), 0.98 (dq, J = 7.8, 4.7, 4.0 Hz, 1H), 0.89 (td, J = 5.5, 4.6, 2.6 Hz, 2H), 0.83-0.76 (m, 2H), 0.41-0.25 (m, 2H), 0.14--0.02 (m, 2H). |
| 32 | 1H NMR (400 MHz, Methanol-d4) δ 9.07 (dt, J = 8.0, 2.8 Hz, 1H), 8.35 (d, J = 4.3 Hz, 1H), 8.16-8.04 (m, 1H), 8.01-7.94 (m, 1H), 7.90 (t, J = 3.2 Hz, 1H), 5.36 (d, J = 7.7 Hz, 2H), 5.12 (q, J = 3.3, 2.3 Hz, 3H), 5.01 (q, J = 3.4, 2.3 Hz, 3H), 4.10 (d, J = 41.8 Hz, 1H), 2.84 (t, J = 58.5 Hz, 4H), 2.38-2.18 (m, 3H), 1.85 (dd, J = 37.8, 30.9 Hz, 5H), 1.27 (d, J = 8.5 Hz, 2H), 1.00 (s, 2H). |
| 35 | 1H NMR (400 MHz, DMSO-d6) δ 8.14 (d, J = 8.3 Hz, 1H), 7.99 (s, 3H), 7.32 (d, J = 1.1 Hz, 1H), 7.22 (s, 1H), 7.18 (d, J = 8.3 Hz, 1H), 6.88 (s, 1H), 4.56 (d, J = 7.2 Hz, 2H), 4.48-4.07 (m, 5H), 3.98 (s, 3H), 3.89 (q, J = 7.1, 2.9 Hz, 3H), 3.23 (s, 3H), 1.87-1.63 (m, 3H), 1.63-1.42 (m, 1H), 1.18 (d, J = 6.9 Hz, 3H), 1.13 (t, J = 7.0 Hz, 3H), 1.11-0.95 (m, 2H), 0.80-0.54 (m, 2H), 0.40-0.23 (m, 2H), 0.23-0.03 (m, 2H). |
| 38 | 1H NMR (400 MHz, DMSO-d6) δ 8.28 (d, J = 8.2 Hz, 1H), 7.90 (s, 3H), 7.45 (t, J = 59.5 Hz, 1H), 7.36 (d, J = 1.1 Hz, 1H), 7.23 (d, J = 8.1 Hz, 1H), 7.19 (s, 1H), 6.87 (d, J = 1.2 Hz, 1H), 4.45 (d, J = 7.1 Hz, 2H), 4.14 (s, 3H), 3.98 (s, 3H), 3.61 (s, 3H), 3.24-3.08 (m, 1H), 3.05-2.90 (m, 1H), 1.92-1.82 (m, 1H), 1.83-1.67 (m, 2H), 1.65-1.50 (m, 1H), 1.19 (d, J = 6.9 Hz, 3H), 1.17-1.09 (m, 1H), 0.34-0.26 (m, 2H), 0.23-0.15 (m, 2H). (Total 34H, Missing 2) |
| 39 | 1H NMR (400 MHz, cd3cn) δ 8.25 (d, J = 8.2 Hz, 1H), 7.69-7.53 (m, broad, 2H), 7.29 (d, J = 8.2 Hz, 1H), 7.22 (d, JHF = 60.0 Hz, 1H), 7.16-7.00 (m, broad, 2H), 4.80-3.58 (m, 3H), 4.42 (d, J = 7.1 Hz, 2H), 4.14 (s, 3H), 4.03 (s, 3H), 3.53 (s, 3H), 2.21-1.47 (m, 8H), 1.17-0.97 (m, 1H), 0.38-0.24 (m, 2H), 0.23-0.04 (m, 2H). |
| 40 | 1H NMR (400 MHz, DMSO-d6) δ 8.13 (d, J = 8.3 Hz, 1H), 8.01 (d, J = 12.7 Hz, 3H), 7.38 (d, J = 1.1 Hz, 1H), 7.19 (d, J = 8.3 Hz, 1H), 7.06 (s, 1H), 6.91 (d, J = 1.2 Hz, 1H), 5.24-4.76 (m, 3H), 4.69 (s, 2H), 4.40 (d, J = 7.2 Hz, 2H), 4.01 (s, 3H), 3.90 (q, J = 7.1 Hz, 2H), 3.44-3.30 |

TABLE 5a-continued

| Ex. | ¹H NMR |
|---|---|
| | (m, 1H), 3.24-2.76 (m, 3H), 1.90-1.63 (m, 4H), 1.56 (d, J = 13.4 Hz, 1H), 1.19 (d, J = 6.9 Hz, 3H), 1.13 (t, J = 7.1 Hz, 3H), 0.72 (s, 3H), 0.41-0.28 (m, 4H), 0.14-0.07 (m, 2H), 0.07--0.01 (m, 2H). |
| 41 | 1H NMR (400 MHz, DMSO-d6) δ 8.15 (d, J = 8.3 Hz, 1H), 8.00 (d, J = 38.2 Hz, 3H), 7.37 (d, J = 1.1 Hz, 1H), 7.19 (d, J = 8.3 Hz, 1H), 7.13 (s, 1H), 6.90 (s, 1H), 4.75-4.05 (m, 7H), 4.69 (t, J = 5.3 Hz, 2H), 4.35 (d, J = 7.1 Hz, 2H), 3.98 (s, 3H), 3.89 (q, J = 7.1 Hz, 2H), 3.66 (t, J = 5.3 Hz, 2H), 3.45-3.30 (m, 1H), 3.05 (s, 3H), 1.89-1.63 (m, 3H), 1.64-1.48 (m, 1H), 1.19 (d, J = 6.9 Hz, 3H), 1.12 (t, J = 7.1 Hz, 3H), 0.36-0.28 (m, 2H), 0.28-0.20 (m, 2H). |
| 42 | 1H NMR (400 MHz, DMSO-d6) δ 8.27 (d, J = 8.1 Hz, 1H), 7.91 (s, 3H), 7.53 (t, J = 59.5 Hz, 1H), 7.37-7.28 (m, 2H), 7.22 (d, J = 8.2 Hz, 1H), 6.88 (d, J = 1.2 Hz, 1H), 4.58 (d, J = 7.2 Hz, 2H), 4.50-4.02 (m, 2H), 3.99 (s, 3H), 3.92 (dq, J = 7.0, 3.6 Hz, 2H), 3.62 (s, 3H), 3.16 (s, 1H), 2.96 (s, 1H), 1.92-1.82 (m, 1H), 1.82-1.68 (m, 2H), 1.64-1.47 (m, 1H), 1.19 (d, J = 6.9 Hz, 3H), 1.06 (t, J = 7.1 Hz, 3H), 0.78-0.63 (m, 2H), 0.28 (dd, J = 8.1, 1.8 Hz, 2H), 0.17 (dd, J = 4.6 Hz, 2H). |
| 43 | 1H NMR (400 MHz, cd3cn) δ 8.24 (d, J = 8.2 Hz, 1H), 7.60-7.48 (m, broad, 1H), 7.28 (d, J = 8.2 Hz, 1H), 7.22 (t, JHF = 60.0 Hz, 1H), 7.18-6.99 (m, broad, 2H), 4.80-3.56 (m, 3H), 4.46 (d, J = 7.2 Hz, 2H), 4.15 (s, 3H), 4.03 (s, 3H), 3.53 (s, 3H), 2.17-1.55 (m, 8H), 1.18-1.04 (m, 1H), 0.36-0.27 (m, 2H), 0.22-0.12 (m, 2H). |
| 44 | 1H NMR (400 MHz, cd3cn) δ 8.24 (d, J = 8.2 Hz, 1H), 7.58-7.50 (m, broad, 1H), 7.28 (d, J = 8.2 Hz, 1H), 7.22 (t, JHF = 60.0 Hz, 1H), 7.21-6.96 (m, broad, 2H), 4.81-3.59 (m, 3H), 4.45 (d, J = 7.1 Hz, 2H), 4.15 (s, 3H), 4.03 (s, 3H), 3.53 (s, 3H), 2.19-1.53 (m, 8H), 1.19-1.04 (m, 1H), 0.36-0.26 (m, 2H), 0.20-0.12 (m, 2H). |
| 45 | 1H NMR (400 MHz, Methanol-d4) δ 8.23 (d, J = 8.2 Hz, 1H), 7.45 (d, J = 1.2 Hz, 1H), 7.30-7.22 (m, 1H), 7.09 (s, 1H), 7.00 (d, J = 1.2 Hz, 1H), 4.44 (d, J = 7.1 Hz, 2H), 4.17 (s, 3H), 4.06 (s, 3H), 3.55 (s, 3H), 2.18 (t, J = 11.6 Hz, 1H), 1.93-1.62 (m, 2H), 1.28 (s, 1H), 1.00 (d, J = 7.7 Hz, 1H), 0.45-0.22 (m, 2H), 0.15--0.14 (m, 2H). |
| 46 | 1H NMR (400 MHz, Methanol-d4) δ 8.23 (d, J = 8.2 Hz, 1H), 7.45 (d, J = 1.2 Hz, 1H), 7.28 (d, J = 2.4 Hz, 1H), 7.09 (s, 1H), 7.00 (d, J = 1.2 Hz, 1H), 4.44 (d, J = 7.1 Hz, 2H), 4.17 (s, 3H), 4.06 (s, 3H), 3.54 (s, 3H), 2.65 (s, 1H), 2.19 (d, J = 11.6 Hz, 1H), 1.89-1.60 (m, 2H), 1.28 (s, 1H), 1.09-0.81 (m, 1H), 0.38-0.23 (m, 2H), 0.12--0.05 (m, 2H). |
| 47 | 1H NMR (400 MHz, DMSO-d6) δ 8.11 (d, J = 8.4 Hz, 1H), 7.95 (s, 4H), 7.34 (d, J = 1.1 Hz, 1H), 7.22 (d, J = 8.4 Hz, 1H), 6.95 (s, 1H), 6.87 (d, J = 1.2 Hz, 1H), 4.75-4.07 (m, 3H), 4.04 (s, 3H), 3.97 (s, 3H), 3.54 (tt, J = 7.1, 3.9 Hz, 1H), 3.37 (s, 3H), 3.36-3.32 (m, 1H), 3.30 (s, 3H), 1.87-1.63 (m, 3H), 1.63-1.47 (m, 1H), 1.18 (d, J = 6.9 Hz, 3H), 0.92-0.83 (m, 2H), 0.83-0.72 (m, 2H). |
| 48 | 1H NMR (400 MHz, DMSO-d6) δ 8.26 (d, J = 8.2 Hz, 1H), 7.93 (s, 3H), 7.53 (t, J = 59.5 Hz, 1H), 7.36 (d, J = 1.2 Hz, 1H), 7.23 (d, J = 8.2 Hz, 1H), 7.01 (s, 1H), 6.93 (d, J = 1.3 Hz, 1H), 5.08-4.18 (m, 2H), 4.17 (s, 2H), 4.01 (s, 3H), 3.61 (s, 3H), 3.25-3.09 (m, 1H), 3.09-2.89 (m, 1H), 2.44 (s, 1H), 2.18 (s, 6H), 1.93-1.82 (m, 1H), 1.81-1.69 (m, 2H), 1.66-1.49 (m, 1H), 1.19 (d, J = 6.9 Hz, 3H), 1.09-0.86 (m, 1H), 0.38-0.27 (m, 2H), 0.25-0.13 (m, 2H). |
| 49 | 1H NMR (400 MHz, DMSO-d6) δ 8.10 (d, J = 8.4 Hz, 1H), 7.93 (s, 4H), 7.37 (d, J = 1.2 Hz, 1H), 7.22 (d, J = 8.4 Hz, 1H), 6.95 (s, 1H), 6.90 (s, 1H), 4.38 (d, J = 7.0 Hz, 2H), 4.00 (s, 3H), 3.94-3.62 (m, 5H), 3.47 (tt, J = 7.1, 4.1 Hz, 1H), 3.37 (s, 3H), 3.31 (s, 3H), 1.72 (dd, J = 25.5, 14.4 Hz, 2H), 1.56 (d, J = 13.0 Hz, 1H), 1.19 (d, J = 6.9 Hz, 3H), 1.08 (dd, J = 8.5, 3.9 Hz, 1H), 0.92-0.68 (m, 4H), 0.41-0.26 (m, 2H), 0.14--0.06 (m, 2H). |
| 50 | 1H NMR (400 MHz, DMSO-d6) δ 8.27 (d, J = 8.2 Hz, 1H), 7.94 (s, 3H), 7.49 (t, J = 59.4 Hz, 1H), 7.32 (s, 1H), 7.22 (d, J = 8.1 Hz, 1H), 6.98 (d, J = 1.2 Hz, 1H), 4.59 (d, J = 7.2 Hz, 2H), 4.00 (s, 3H), 3.92 (tt, J = 7.2, 3.8 Hz, 1H), 3.62 (s, 3H), 3.61-3.55 (m, 3H), 2.10-1.93 (m, 1H), 1.92-1.83 (m, 1H), 1.79-1.70 (m, 4H), 1.70-1.49 (m, 3H), 1.14-0.99 (m, 3H), 0.79-0.61 (m, 2H), 0.34-0.24 (m, 2H), 0.22-0.11 (m, 2H). |
| 51 | 1H NMR (400 MHz, DMSO-d6) δ 8.28 (d, J = 8.2 Hz, 1H), 7.89 (s, 3H), 7.63-7.29 (m, 2H), 7.23 (d, J = 8.2 Hz, 1H), 7.19 (s, 1H), 6.93 (d, J = 1.2 Hz, 1H), 4.45 (d, J = 7.1 Hz, 2H), 4.14 (s, 3H), 4.04-3.99 (m, 1H), 3.98 (s, 3H), 3.61 (s, 3H), 3.58-3.50 (m, 1H), 3.52-3.27 (m, 2H), 1.86-1.64 (m, 2H), 1.23-1.07 (m, 1H), 0.35-0.24 (m, 2H), 0.24-0.15 (m, 2H). |
| 53 | 1H NMR (400 MHz, DMSO-d6) δ 8.29 (d, J = 8.2 Hz, 1H), 8.14-7.80 (m, 3H), 7.58 (d, J = 15.6 Hz, 1H), 7.44 (d, J = 12.0 Hz, 1H), 7.32-7.21 (m, 1H), 7.20 (s, 1H), 6.98 (d, J = 15.3 Hz, 1H), 4.52-4.41 (m, 3H), 4.20 (s, 4H), 3.98 (d, J = 2.3 Hz, 3H), 3.84-3.69 (m, 1H), 3.61 (s, 5H), 3.17 (t, J = 11.3 Hz, 1H), 2.64 (s, 1H), 1.92 (dt, J = 32.8, 5.8 Hz, 3H), 1.72-1.49 (m, 1H), 1.13 (q, J = 7.3, 6.5 Hz, 1H), 0.30 (h, J = 4.1 Hz, 2H), 0.25-0.09 (m, 2H). |
| 55 | 1H NMR (400 MHz, DMSO-d6) δ 8.29 (d, J = 8.2 Hz, 1H), 8.08 (s, 1H), 7.95 (s, 3H), 7.23 (s, 2H), 7.86-7.71 (m, 2H), 7.54 (d, J = 8.4 Hz, 1H), 7.47 (d, J = 12.8 Hz, 1H), 7.42 (s, 1H), 7.23 (d, J = 8.1 Hz, 1H), 4.63 (d, J = 7.1 Hz, 2H), 4.52 (s, 1H), 4.17 (s, 1H), 3.86 (s, 1H), 3.74 (d, J = 9.0 Hz, 1H), 3.62 (s, 5H), 3.17 (dd, J = 22.0, 10.1 Hz, 2H), 2.65 (s, 1H), 2.55 (s, 1H), 2.03-1.51 (m, 5H), 1.31-0.98 (m, 4H), 0.86-0.64 (m, 2H), 0.33-0.10 (m, 4H). |
| 62 | 1H NMR (400 MHz, Methanol-d4) δ 8.24 (d, J = 8.1 Hz, 1H), 7.61 (d, J = 1.2 Hz, 1H), 7.28 (t, J = 60.0 Hz, 1H), 7.28 (d, J = 8.4 Hz, 1H), 7.14 (d, J = 8.7 Hz, 2H), 4.73 (s, 1H), 4.57 (s, 1H), 4.44 (d, J = 7.1 Hz, 2H), 4.19 (s, 3H), 4.08 (s, 3H), 3.84 (dt, J = 10.1, 4.5 Hz, 1H), 3.55 (s, 3H), 2.50 (td, J = 12.2, 5.1 Hz, 1H), 2.04 (s, 2H), 1.91 (t, J = 8.7 Hz, 1H), 1.74 (t, J = 8.3 Hz, 1H), 1.45 (dd, J = 13.2, 4.5 Hz, 1H), 0.99 (tt, J = 8.0, 4.9 Hz, 1H), 0.39-0.28 (m, 2H), 0.06 (dt, J = 6.1, 4.6 Hz, 2H). |
| 63 | 1H NMR (400 MHz, Methanol-d4) δ 8.24 (d, J = 8.2 Hz, 1H), 7.61 (d, J = 1.2 Hz, 1H), 7.29 (d, J = 1.0 Hz, 1H), 7.27 (t, J = 64.0 Hz, 1H), 7.13 (d, J = 1.2 Hz, 1H), 7.11 (s, 1H), 4.35-5.00 (m, 2H), 4.45 (d, J = 7.1 Hz, 2H), 4.18 (s, 3H), 4.07 (s, 3H), 3.84 (dt, J = 9.9, 4.4 Hz, 1H), 3.55 (s, 3H), 2.50 (td, J = 12.0, 5.1 Hz, 1H), 2.03 (s, 2H), 1.95-1.83 (m, 1H), 1.73 (t, J = 8.3 Hz, 1H), 1.44 (dd, J = 13.2, 4.5 Hz, 1H), 1.07-0.91 (m, 1H), 0.38-0.25 (m, 2H), 0.10--0.02 (m, 2H). |
| 64 | 1H NMR (400 MHz, DMSO-d6) δ 8.30 (d, J = 8.2 Hz, 1H), 7.60 (s, 1H), 7.49 (t, J = 59.4 Hz, 1H), 7.35 (s, 1H), 7.25 (d, J = 8.1 Hz, 1H), 7.08 (d, J = 1.2 Hz, 1H), 4.62 (d, J = 7.2 Hz, 2H), 4.56-4.18 (m, 4H), 4.03 (s, 3H), 4.01-3.91 (m, 1H), 3.88-3.69 (m, 1H), 3.65 (s, 3H), 2.44- |

TABLE 5a-continued

| Ex. | ¹H NMR |
|---|---|
| | 2.17 (m, 1H), 1.96-1.72 (m, 4H), 1.72-1.55 (m, 1H), 1.35 (dd, J = 12.9, 4.4 Hz, 1H), 1.15-0.98 (m, 3H), 0.82-0.62 (m, 2H), 0.37-0.26 (m, 2H), 0.21-0.03 (m, 2H). |
| 65 | 1H NMR (400 MHz, DMSO-d6) δ 8.32 (d, J = 8.2 Hz, 1H), 8.13 (s, 3H), 8.02 (s, 1H), 7.81 (d, J = 8.4 Hz, 1H), 7.68-7.61 (m, 1H), 7.46 (s, 1H), 7.42 (t, J = 59.5 Hz, 1H), 7.26 (d, J = 8.1 Hz, 1H), 4.66 (d, J = 7.2 Hz, 2H), 4.61-4.14 (m, 2H), 3.96-3.86 (m, 1H), 3.84-3.70 (m, 1H), 3.65 (s, 3H), 2.40-2.23 (m, 1H), 1.95-1.74 (m, 3H), 1.71-1.54 (m, 1H), 1.35 (dd, J = 12.9, 4.4 Hz, 1H), 1.27-1.18 (m, 2H), 1.18-1.06 (m, 1H), 0.94-0.61 (m, 2H), 0.39-0.27 (m, 2H), 0.27-0.10 (m, 2H). |
| 66 | 1H NMR (400 MHz, Methanol-d4) δ 8.27 (d, J = 8.2 Hz, 1H), 7.62-7.53 (m, 1H), 7.30 (d, J = 7.9 Hz, 1H), 7.20-7.07 (m, 2H), 4.46 (d, J = 7.1 Hz, 2H), 4.20 (s, 3H), 4.09 (d, J = 3.6 Hz, 3H), 3.75 (dddd, J = 40.2, 28.6, 19.8, 10.1 Hz, 5H), 3.58 (s, 3H), 3.05-2.91 (m, 1H), 2.23-1.82 (m, 5H), 1.44 (s, 1H), 1.08-0.95 (m, 1H), 0.41-0.28 (m, 2H), 0.13-0.00 (m, 2H). |
| 67 | 1H NMR (400 MHz, Methanol-d4) δ 8.26 (d, J = 8.2 Hz, 1H), 7.67 (d, J = 1.3 Hz, 1H), 7.36-7.24 (m, 3H), 7.15 (d, J = 10.7 Hz, 1H), 4.56 (d, J = 15.2 Hz, 2H), 4.47 (d, J = 7.1 Hz, 2H), 4.26 (d, J = 13.5 Hz, 2H), 4.20 (s, 3H), 4.10 (s, 3H), 3.58 (s, 5H), 3.39 (q, J = 7.0 Hz, 2H), 2.39 (t, J = 7.3 Hz, 2H), 1.08-0.97 (m, 1H), 0.43-0.29 (m, 2H), 0.16-0.00 (m, 2H). |
| 68 | 1H NMR (400 MHz, Methanol-d4) δ 8.27 (d, J = 8.2 Hz, 1H), 7.54-7.52 (m, 1H), 7.30 (d, J = 8.0 Hz, 1H), 7.17-7.06 (m, 2H), 4.47 (d, J = 7.1 Hz, 2H), 4.21 (s, 3H), 4.10 (s, 3H), 3.79 (dq, J = 16.2, 6.3, 5.6 Hz, 1H), 3.69 (d, J = 14.1 Hz, 1H), 3.58 (s, 3H), 2.94 (dd, J = 5.2, 4.3 Hz, 4H), 2.13-1.65 (m, 12H), 1.45 (s, 4H), 0.39-0.30 (m, 2H), 0.10--0.03 (m, 2H). |
| 79 | 1H NMR (400 MHz, Methanol-d4) δ 8.14 (dd, J = 8.5, 1.1 Hz, 1H), 7.64 (d, J = 1.2 Hz, 1H), 7.32 (dd, J = 8.4, 1.1 Hz, 1H), 7.20 (t, J = 1.2 Hz, 1H), 7.11 (d, J = 1.6 Hz, 1H), 5.03-4.97 (m, 4H), 4.43 (d, J = 7.1 Hz, 2H), 4.21 (s, 3H), 4.11 (s, 3H), 3.93-3.83 (m, 1H), 3.48 (s, 1.1 Hz, 3H), 3.17 (s, 3H), 2.52 (td, J = 12.3, 5.1 Hz, 1H), 2.08-1.91 (m, 3H), 1.77 (t, J = 7.5 Hz, 1H), 1.50 (dd, J = 13.2, 4.4 Hz, 1H), 1.06-0.95 (m, 1H), 0.34 (dt, J = 10.8, 3.0 Hz, 2H), 0.11-0.03 (m, 2H). |
| 84 | 1H NMR (400 MHz, Methanol-d4) δ 8.20 (d, J = 8.2 Hz, 1H), 7.63 (d, J = 1.1 Hz, 1H), 7.23-7.14 (m, 2H), 7.10 (s, 1H), 4.60 (s, 2H), 4.49 (dd, J = 14.0, 6.9 Hz, 3H), 4.21 (s, 3H), 4.10 (s, 3H), 3.91-3.83 (m, 1H), 2.53 (td, J = 12.1, 5.1 Hz, 1H), 2.07 (s, 2H), 1.92 (t, J = 9.0 Hz, 1H), 1.76 (t, J = 8.2 Hz, 1H), 1.47 (dd, J = 13.2, 4.5 Hz, 1H), 1.34 (d, J = 6.7 Hz, 6H), 1.01 (ddd, J = 12.6, 8.3, 5.0 Hz, 1H), 0.40-0.30 (m, 2H). |
| 86 | ¹H NMR (400 MHz, DMSO-d₆) δ 8.32 (d, J = 8.2 Hz, 1H), 8.18-7.92 (m, 3H), 7.68-7.51 (m, 1H), 7.49 (t, J = 59.4 Hz, 1H), 7.26 (d, J = 8.1 Hz, 1H), 7.23 (s, 1H), 7.03 (d, J = 1.2 Hz, 1H), 4.48 (d, J = 7.1 Hz, 2H), 4.17 (s, 3H), 4.01 (s, 3H), 3.81-3.47 (m, 5H), 3.64 (s, 3H), 2.29-2.16 (m, 1H), 2.09-1.93 (m, 1H), 1.24-1.07 (m, 1H), 0.38-0.27 (m, 2H), 0.27-0.15 (m, 2H). |
| 87 | ¹H NMR (400 MHz, DMSO-d₆) δ 8.32 (d, J = 8.2 Hz, 1H), 8.19-7.90 (m, 3H), 7.68-7.51 (m, 1H), 7.49 (t, J = 59.4 Hz, 1H), 7.26 (d, J = 8.1 Hz, 1H), 7.23 (s, 1H), 7.03 (d, J = 1.2 Hz, 1H), 4.48 (d, J = 7.1 Hz, 2H), 4.17 (s, 3H), 4.01 (s, 3H), 3.71-3.50 (m, 5H), 3.64 (s, 3H), 2.31-2.14 (m, 1H), 2.08-1.92 (m, 1H), 1.24-1.08 (m, 1H), 0.40-0.27 (m, 2H), 0.26-0.14 (m, 2H). |
| 88 | ¹H NMR (400 MHz, DMSO-d₆) δ 8.76 (s, 2H), 8.64 (d, J = 6.1 Hz, 1H), 8.32 (d, J = 8.2 Hz, 1H), 8.03 (d, J = 1.3 Hz, 1H), 7.49 (t, J = 59.5 Hz, 1H), 7.37 (d, J = 1.2 Hz, 1H), 7.27 (s, 1H), 7.26 (d, J = 8.1 Hz, 1H), 4.55 (q, J = 5.8 Hz, 1H), 4.49 (d, J = 7.1 Hz, 2H), 4.19 (s, 3H), 4.03 (s, 3H), 3.64 (s, 3H), 3.54-3.17 (m, 4H), 2.30-2.15 (m, 1H), 2.15-2.03 (m, 1H), 1.28-1.13 (m, 1H), 0.38-0.28 (m, 2H), 0.26-0.18 (m, 2H). |
| 95 | 1H NMR (400 MHz, cd3cn) δ 7.86 (d, J = 8.4 Hz, 1H), 7.41 (d, J = 1.2 Hz, 1H), 6.91 (s, 1H), 6.88 (d, J = 8.4 Hz, 1H), 6.61 (d, J = 1.2 Hz, 1H), 4.44-4.26 (m, 2H), 4.13 (s, 3H), 4.02 (s, 3H), 3.59-2.87 (m, 5H), 3.38 (s, 6H), 2.13-1.51 (m, 4H), 1.27 (d, J = 6.9 Hz, 3H), 1.14-0.96 (m, 1H), 0.35-0.20 (m, 2H), 0.18-0.05 (m, 2H). |
| 96 | 1H NMR (400 MHz, Methanol-d4) δ 8.04 (d, J = 8.6 Hz, 1H), 7.42 (d, J = 1.2 Hz, 1H), 7.19 (d, J = 8.6 Hz, 1H), 6.99 (d, J = 1.2 Hz, 1H), 6.95 (s, 1H), 4.38 (d, J = 7.1 Hz, 2H), 4.34 (s, 1H), 4.16 (s, 3H), 4.12 (t, J = 6.6 Hz, 2H), 4.06 (s, 3H), 3.87 (s, 1H), 3.53 (t, J = 7.4 Hz, 2H), 3.45-3.31 (m, 3H), 2.54 (p, J = 7.0 Hz, 2H), 2.24-2.13 (m, 1H), 1.93-1.64 (m, 3H), 1.03-0.92 (m, 1H), 0.33-0.27 (m, 2H), 0.08-0.03 (m, 2H). |
| 97 | 1H NMR (400 MHz, Methanol-d4) δ 8.06 (d, J = 8.4 Hz, 1H), 7.43 (s, 1H), 7.25 (d, J = 8.4 Hz, 1H), 6.99 (s, 2H), 4.42 (d, J = 7.1 Hz, 2H), 4.33 (s, 1H), 4.16 (s, 3H), 4.12-4.08 (m, 2H), 4.06 (s, 3H), 3.45-3.32 (m, 4H), 3.29-3.26 (m, 2H), 2.42-2.31 (m, 2H), 2.24-2.16 (m, 1H), 2.12-2.03 (m, 2H), 1.91-1.65 (m, 3H), 1.00 (tt, J = 7.9, 4.8 Hz, 1H), 0.36-0.30 (m, 2H), 0.06--0.00 (m, 2H). |
| 98 | 1H NMR (400 MHz, DMSO-d6) δ 8.17 (d, J = 8.1 Hz, 1H), 8.12 (s, 3H), 8.00 (s, 1H), 7.79 (d, J = 8.4 Hz, 1H), 7.62 (dd, J = 8.4, 1.6 Hz, 1H), 7.39 (s, 1H), 7.11 (d, J = 8.1 Hz, 1H), 4.74-4.59 (m, 2H), 4.61-4.33 (m, 2H), 4.30-4.18 (m, 1H), 3.40-3.23 (m, 2H), 2.38-2.10 (m, 4H), 1.93-1.56 (m, 5H), 1.34 (dd, J = 12.9, 4.4 Hz, 1H), 1.26-1.08 (m, 3H), 1.01 (d, J = 6.7 Hz, 3H), 0.87-0.74 (m, 2H), 0.42-0.27 (m, 2H), 0.20-0.05 (m, 2H). |
| 99 | 1H NMR (400 MHz, DMSO-d6) δ 8.17 (d, J = 8.1 Hz, 1H), 7.95 (s, 3H), 7.86 (s, 1H), 7.79 (d, J = 8.3 Hz, 1H), 7.44 (dd, J = 8.4, 1.5 Hz, 1H), 7.39 (s, 1H), 7.11 (d, J = 8.2 Hz, 1H), 4.78-4.58 (m, 2H), 4.30-4.16 (m, 1H), 3.91-3.81 (m, 1H), 3.34-3.18 (m, 2H), 2.40-1.97 (m, 4H), 1.80-1.66 (m, 2H), 1.63-1.51 (m, 3H), 1.27-1.10 (m, 3H), 1.01 (d, J = 6.8 Hz, 3H), 0.84-0.69 (m, 2H), 0.35-0.28 (m, 2H), 0.21-0.13 (m, 2H). |
| 100 | 1H NMR (400 MHz, DMSO-d6) δ 8.17 (d, J = 8.1 Hz, 1H), 8.14-8.08 (m, 1H), 8.00-7.90 (m, 2H), 7.86-7.73 (m, 2H), 7.58-7.46 (m, 1H), 7.39 (s, 1H), 7.11 (d, J = 8.1 Hz, 1H), 4.72-4.52 (m, 2H), 4.30-4.14 (m, 2H), 3.92-3.80 (m, 1H), 3.34-3.07 (m, 1H), 2.39-2.12 (m, 3H), 1.97-1.81 (m, 3H), 1.76-1.57 (m, 2H), 1.28-1.10 (m, 3H), 1.01 (d, J = 6.8 Hz, 3H), 0.86-0.71 (m, 2H), 0.36-0.27 (m, 2H), 0.21-0.10 (m, 2H). |
| 101 | 1H NMR (400 MHz, DMSO-d6) δ 8.13 (d, J = 8.1 Hz, 1H), 7.95 (s, 3H), 7.39 (d, J = 1.2 Hz, 1H), 7.25 (s, 1H), 7.08 (d, J = 8.1 Hz, 1H), 6.92 (d, J = 1.2 Hz, 1H), 4.72-4.50 (m, 2H), 4.29-4.15 (m, 1H), 3.98 (s, 3H), 3.96-3.86 (m, 1H), 3.87-3.52 (m, 7H), 3.44 (td, J = 12.6, 4.2 Hz, |

TABLE 5a-continued

| Ex. | ¹H NMR |
|---|---|
| | 1H), 3.34-3.02 (m, 2H), 2.38-2.06 (m, 2H), 2.06-1.92 (m, 1H), 1.82-1.65 (m, 1H), 1.65-1.47 (m, 1H), 1.15-1.02 (m, 3H), 0.99 (d, J = 6.8 Hz, 3H), 0.81-0.61 (m, 2H), 0.34-0.24 (m, 2H), 0.20-0.02 (m, 2H). |
| 102 | 1H NMR (400 MHz, DMSO-d6) δ 8.15 (d, 1H), 8.12 (s, 3H), 7.56 (d, J = 1.2 Hz, 1H), 7.26 (s, 1H), 7.08 (d, J = 8.1 Hz, 1H), 7.05 (d, J = 1.3 Hz, 1H), 4.70-4.53 (m, 2H), 4.54-4.29 (m, 3H), 4.22 (ddd, J = 9.9, 6.8, 2.9 Hz, 1H), 4.00 (s, 3H), 3.96-3.85 (m, 3H), 3.87-3.50 (m, 3H), 3.49-3.38 (m, 1H), 3.34-3.21 (m, 1H), 2.37-2.23 (m, 1H), 2.23-2.04 (m, 2H), 1.84 (d, J = 19.4 Hz, 3H), 1.73-1.65 (m, 1H), 1.66-1.53 (m, 1H), 1.33 (dd, J = 12.9, 4.4 Hz, 1H), 1.17-1.03 (m, 3H), 0.99 (d, J = 6.8 Hz, 3H), 0.80-0.57 (m, 2H), 0.37-0.24 (m, 2H), 0.17-0.07 (m, 2H). |
| 103 | 1H NMR (400 MHz, DMSO-d6) δ 8.24-8.12 (m, 4H), 7.61 (s, 1H), 7.16 (s, 1H), 7.11 (d, J = 8.1 Hz, 1H), 7.05 (d, J = 1.3 Hz, 1H), 4.50 (d, J = 7.1 Hz, 2H), 4.27-4.21 (m, 1H), 4.16 (s, 3H), 4.02 (s, 3H), 3.81-3.68 (m, 1H), 3.52-3.40 (m, 1H), 3.36-3.25 (m, 1H), 2.40-2.09 (m, 4H), 1.93-1.73 (m, 3H), 1.74-1.55 (m, 2H), 1.36 (dd, J = 12.8, 4.4 Hz, 1H), 1.25-1.09 (m, 1H), 1.00 (d, J = 6.8 Hz, 3H), 0.43-0.29 (m, 2H), 0.21-0.07 (m, 2H). |
| 104 | 1H NMR (400 MHz, DMSO-d6) δ 8.24-7.93 (m, 4H), 7.60-7.38 (m, 1H), 7.15 (s, 1H), 7.11 (d, J = 8.1 Hz, 1H), 7.03-6.91 (m, 1H), 4.59-4.40 (m, 2H), 4.29-4.20 (m, 2H), 4.15 (s, 3H), 4.00 (s, 3H), 3.64-3.52 (m, 2H), 3.52-3.39 (m, 1H), 3.37-3.25 (m, 1H), 3.23-3.13 (m, 1H), 2.72-2.55 (m, 1H), 2.36-2.09 (m, 3H), 2.02-1.85 (m, 3H), 1.73-1.60 (m, 2H), 1.19-1.10 (m, 1H), 1.00 (d, J = 6.8 Hz, 3H), 0.40-0.27 (m, 2H), 0.22-0.09 (m, 2H). |
| 105 | 1H NMR (400 MHz, DMSO-d6) δ 8.17 (d, J = 8.1 Hz, 1H), 7.96 (s, 3H), 7.44 (s, 1H), 7.15 (s, 1H), 7.11 (d, J = 8.1 Hz, 1H), 6.93 (d, J = 1.2 Hz, 1H), 4.64-4.35 (m, 2H), 4.33-4.20 (m, 1H), 4.16 (s, 3H), 4.00 (s, 3H), 3.46-3.42 (m, 2H), 3.37-3.15 (m, 4H), 2.38-1.96 (m, 4H), 1.82-1.51 (m, 4H), 1.21-1.10 (m, 1H), 1.00 (d, J = 6.8 Hz, 3H), 0.38-0.26 (m, 2H), 0.22-0.11 (m, 2H). |
| 106 | 1H NMR (400 MHz, Methanol-d4) δ 8.03 (d, J = 8.5 Hz, 1H), 7.46-7.41 (m, 2H), 7.33 (d, J = 8.5 Hz, 1H), 7.02-6.99 (m, 2H), 6.98 (s, 1H), 4.41 (d, J = 7.0 Hz, 2H), 4.34 (s, 1H), 4.20-4.15 (m, 5H), 4.06 (s, 3H), 3.87 (s, 1H), 3.73-3.67 (m, 2H), 3.45-3.32 (m, 3H), 2.89 (s, 3H), 2.24-2.10 (m, 3H), 1.91-1.64 (m, 3H), 1.03-0.93 (m, 1H), 0.36-0.29 (m, 2H), 0.07-0.01 (m, 2H). |
| 107 | 1H NMR (400 MHz, Methanol-d4) δ 8.02 (d, J = 8.5 Hz, 1H), 7.43 (d, J = 0.9 Hz, 2H), 7.39 (d, J = 8.5 Hz, 1H), 6.99 (s, 1H), 6.97 (s, 1H), 4.41 (d, J = 7.1 Hz, 2H), 4.34 (s, 1H), 4.18-4.13 (m, 5H), 4.06 (s, 3H), 3.86 (s, 1H), 3.56 (t, J = 5.7 Hz, 2H), 3.44-3.32 (m, 3H), 2.24-2.15 (m, 1H), 2.09-2.01 (m, 2H), 1.91-1.65 (m, 3H), 1.04-0.96 (m, 1H), 0.35-0.28 (m, 2H), 0.03 (q, J = 5.1 Hz, 2H). |
| 108 | 1H NMR (400 MHz, Methanol-d4) δ 8.04 (d, J = 8.6 Hz, 1H), 7.82 (d, J = 8.7 Hz, 1H), 7.42 (d, J = 1.2 Hz, 1H), 7.00 (d, J = 1.2 Hz, 1H), 6.95 (s, 1H), 4.38 (d, J = 7.0 Hz, 3H), 4.17 (s, 3H), 4.06 (s, 3H), 3.79 (s, 4H), 3.46-3.32 (m, 3H), 2.26-2.13 (m, 1H), 1.91-1.62 (m, 3H), 0.99-0.85 (m, 1H), 0.32-0.23 (m, 2H), 0.01--0.08 (m, 2H). |
| 109 | 1H NMR (400 MHz, Methanol-d4) δ 8.06 (d, J = 8.5 Hz, 1H), 7.45 (d, J = 8.5 Hz, 1H), 7.43 (d, J = 1.2 Hz, 1H), 6.99 (d, J = 1.2 Hz, 1H), 6.98 (s, 1H), 4.40 (d, J = 7.0 Hz, 3H), 4.16 (s, 3H), 4.06 (s, 3H), 3.80 (s, 4H), 3.49 (s, 3H), 3.46-3.32 (m, 3H), 2.25-2.12 (m, 1H), 1.91-1.63 (m, 3H), 1.04-0.89 (m, 1H), 0.35-0.27 (m, 2H), 0.05--0.02 (m, 2H). |
| 110 | 1H NMR (400 MHz, Methanol-d4) δ 8.15 (d, J = 8.2 Hz, 1H), 7.44 (d, J = 1.1 Hz, 1H), 7.09 (d, J = 8.2 Hz, 1H), 7.04 (s, 1H), 7.00 (d, J = 1.0 Hz, 1H), 4.79-4.68 (m, 1H), 4.42 (d, J = 7.0 Hz, 2H), 4.35 (s, 1H), 4.17 (s, 3H), 4.06 (s, 3H), 3.85 (s, 1H), 3.67 (s, 3H), 3.45-3.31 (m, 3H), 2.29-2.16 (m, 3H), 2.09-1.95 (m, 2H), 1.90-1.79 (m, 1H), 1.78-1.52 (m, 4H), 1.00-0.87 (m, 1H), 0.35-0.27 (m, 2H), 0.05--0.02 (m, 2H). |
| 111 | 1H NMR (400 MHz, Methanol-d4) δ 8.07 (d, J = 8.5 Hz, 1H), 7.43 (d, J = 1.2 Hz, 1H), 7.36 (d, J = 8.5 Hz, 1H), 6.99 (d, J = 1.3 Hz, 1H), 6.99 (s, 1H), 4.40 (d, J = 7.1 Hz, 3H), 4.17 (s, 3H), 4.06 (s, 3H), 4.05-4.00 (m, 2H), 3.78 (s, 3H), 3.45-3.31 (m, 4H), 2.25-2.13 (m, 1H), 1.89-1.62 (m, 3H), 1.27 (t, J = 7.0 Hz, 3H), 0.96 (tt, J = 7.9, 4.9 Hz, 1H), 0.36-0.26 (m, 2H), 0.05--0.01 (m, 2H). |
| 113 | 1H NMR (400 MHz, DMSO-d6) δ 8.15-8.03 (m, 1H), 7.93 (s, 3H), 7.82 (d, J = 1.4 Hz, 1H), 7.75 (d, J = 8.3 Hz, 1H), 7.41 (dd, J = 8.3, 1.5 Hz, 1H), 7.34 (d, J = 8.4 Hz, 1H), 7.29 (s, 1H), 4.57 (d, J = 7.1 Hz, 2H), 4.21-3.98 (m, 2H), 3.93 (q, J = 7.0 Hz, 2H), 3.82 (dq, J = 7.4, 3.7 Hz, 1H), 3.69 (s, 3H), 3.35-3.17 (m, 3H), 2.07-1.92 (m, 1H), 1.73 (s, 1H), 1.66-1.45 (m, 2H), 1.29-1.17 (m, 5H), 1.17-1.07 (m, 1H), 0.77 (d, J = 3.7 Hz, 2H), 0.28 (dt, J = 8.0, 2.8 Hz, 2H), 0.16 (h, J = 3.9 Hz, 2H). |
| 114 | 1H NMR (400 MHz, DMSO-d6) δ 8.11 (brs, 3H), 7.67 (d, J = 7.2 Hz, 1H), 7.65 (s, 1H), 7.59 (s, 1H), 7.09-7.03 (m, 3H), 4.49 (brs, 1H), 4.41 (d, J = 7.0 Hz, 2H), 4.12 (s, 3H), 4.02 (s, 3H), 3.75 (brs, 1H), 3.61 (s, 3H), 3.31 (s, 3H), 2.40-2.27 (m, 1H), 2.00-1.58 (m, 4H), 1.35 (dd, J = 12.8, 4.4 Hz, 1H), 1.11-0.97 (m, 1H), 0.34-0.25 (m, 2H), 0.11-0.00 (m, 2H). |
| 115 | 1H NMR (400 MHz, Methanol-d4) δ 8.21 (d, J = 8.2 Hz, 1H), 7.44 (s, 1H), 7.20 (d, J = 8.2 Hz, 1H), 7.06 (s, 1H), 6.99 (s, 1H), 4.43 (d, J = 7.1 Hz, 2H), 4.35 (s, 1H), 4.17 (s, 3H), 4.06 (s, 3H), 3.93 (q, J = 7.1 Hz, 2H), 3.45-3.31 (m, 4H), 2.26-2.14 (m, 1H), 1.98 (s, 3H), 1.91-1.64 (m, 3H), 1.19 (t, J = 7.1 Hz, 3H), 1.02-0.89 (m, 1H), 0.35-0.29 (m, 2H), 0.05--0.00 (m, 2H). |
| 116 | 1H NMR (400 MHz, Methanol-d4) δ 8.12 (d, J = 8.6 Hz, 1H), 7.43 (d, J = 1.2 Hz, 1H), 7.17 (d, J = 8.6 Hz, 1H), 6.99 (d, J = 1.2 Hz, 1H), 6.98 (s, 1H), 4.39 (d, J = 7.0 Hz, 3H), 4.17 (s, 3H), 4.06 (s, 3H), 3.87 (s, 1H), 3.47 (s, 3H), 3.44-3.32 (m, 3H), 2.88 (s, 3H), 2.24-2.13 (m, 1H), 1.91-1.62 (m, 3H), 1.05-0.93 (m, 1H), 0.38-0.30 (m, 2H), -0.01 (dt, J = 6.1, 4.5 Hz, 2H). |
| 117 | 1H NMR (400 MHz, Methanol-d4) δ 8.02 (d, J = 8.5 Hz, 1H), 7.42 (s, 1H), 6.98 (s, 1H), 6.92 (s, 1H), 6.87 (d, J = 8.5 Hz, 1H), 4.36 (d, J = 7.0 Hz, 2H), 4.16 (s, 3H), 4.05 (s, 3H), 3.77-3.69 (m, 2H), 3.44-3.32 (m, 6H), 2.87 (s, 6H), 2.25-2.14 (m, 1H), 1.89-1.80 (m, 2H), 1.78-1.66 (m, 1H), 1.02-0.91 (m, 1H), 0.35-0.28 (m, 2H), 0.04--0.01 (m, 2H). |

TABLE 5a-continued

| Ex. | ¹H NMR |
|---|---|
| 119 | 1H NMR (400 MHz, DMSO-d6) δ 8.08 (d, J = 8.1 Hz, 1H), 7.96 (brs, 3H), 7.83 (d, J = 7.7 Hz, 1H), 7.44 (s, 1H), 7.20 (d, J = 8.2 Hz, 1H), 7.05 (s, 1H), 6.93 (s, 1H), 5.16-5.04 (m, 1H), 4.60-4.39 (m, 2H), 4.14 (s, 3H), 4.00 (s, 3H), 3.38-3.07 (m, 4H), 2.07-1.87 (m, 1H), 1.82-1.70 (m, 1H), 1.67-1.50 (m, 2H), 1.48 (d, J = 7.0 Hz, 3H), 1.18 (s, 9H), 0.34-0.27 (m, 2H), 0.24-0.14 (m, 2H). |
| 120 | 1H NMR (400 MHz, DMSO-d6) δ 8.10 (brs, 3H), 8.08 (d, J = 8.2 Hz, 1H), 7.83 (d, J = 7.7 Hz, 1H), 7.61 (s, 1H), 7.20 (d, J = 8.2 Hz, 1H), 7.06 (s, 1H), 7.05 (d, J = 1.3 Hz, 1H), 5.14-5.03 (m, 1H), 4.58-4.42 (m, 2H), 4.14 (s, 3H), 4.02 (s, 3H), 3.76 (brs, 1H), 2.40-2.25 (m, 1H), 1.94-1.73 (m, 4H), 1.71-1.58 (m, 1H), 1.48 (d, J = 7.0 Hz, 3H), 1.35 (dd, J = 13.0, 4.3 Hz, 1H), 1.18 (s, 9H), 1.19-1.08 (m, 2H), 0.38-0.26 (m, 2H), 0.24-0.14 (m, 2H). |
| 121 | 1H NMR (400 MHz, DMSO-d6) δ 8.31 (d, J = 7.9 Hz, 1H), 8.06 (s, 3H), 8.04 (d, J = 8.2 Hz, 1H)7.61-7.51 (m, 1H), 7.16 (d, J = 8.2 Hz, 1H), 7.03 (s, 1H), 7.02 (d, J = 1.2 Hz, 1H), 5.08 (p, J = 7.1 Hz, 1H), 4.59-4.30 (m, 2H), 4.11 (s, 3H), 3.99 (s, 3H), 3.80-3.68 (m, 3H), 2.30 (s, 6H), 1.87-1.71 (m, 4H), 1.70-1.56 (m, 1H), 1.47 (d, J = 7.0 Hz, 3H), 1.32 (dd, J = 12.9, 4.5 Hz, 1H), 1.18-1.02 (m, 1H), 0.35-0.25 (m, 2H), 0.23-0.12 (m, 2H). |
| 122 | 1H NMR (400 MHz, DMSO-d6) δ 8.31 (d, J = 7.8 Hz, 1H), 8.06 (d, J = 8.1 Hz, 1H), 7.95 (s, 3H), 7.41 (s, 1H), 7.16 (d, J = 8.1 Hz, 1H), 7.02 (s, 1H), 6.90 (d, J = 1.2 Hz, 1H), 5.08 (p, J = 7.1 Hz, 1H), 4.84-4.68 (m, 3H), 4.54-4.38 (m, 2H), 4.11 (s, 3H), 3.98 (s, 3H), 3.32-3.00 (m, 3H), 2.30 (s, 6H), 2.07-1.92 (m, 1H), 1.85-1.68 (m, 1H), 1.66-1.52 (m, 1H), 1.47 (d, J = 7.0 Hz, 3H), 1.19-1.07 (m, 1H), 0.36-0.25 (m, 2H), 0.25-0.10 (m, 2H). |
| 123 | 1H NMR (400 MHz, DMSO-d6) δ 8.85 (d, J = 7.7 Hz, 1H), 8.15 (s, 3H), 8.06 (d, J = 8.1 Hz, 1H), 7.96-7.84 (m, 2H), 7.58 (d, J = 1.2 Hz, 1H), 7.56-7.49 (m, 1H), 7.49-7.42 (m, 2H), 7.27 (d, J = 8.1 Hz, 1H), 7.04 (s, 1H), 7.03 (d, J = 1.2 Hz, 1H), 5.31 (p, J = 7.1 Hz, 1H), 5.14-4.89 (m, 2H), 4.64-4.29 (m, 2H), 4.11 (s, 3H), 3.99 (s, 3H), 3.83-3.55 (m, 1H), 2.39-2.18 (m, 1H), 1.92-1.72 (m, 3H), 1.65-1.62 (m, 1H), 1.58 (d, 3H), 1.34 (dd, J = 12.8, 4.4 Hz, 1H), 1.17-1.02 (m, 1H), 0.32-0.20 (m, 2H), 0.19-0.07 (m, 2H). |
| 124 | 1H NMR (400 MHz, DMSO-d6) δ 8.85 (d, J = 7.7 Hz, 1H), 8.06 (d, J = 8.1 Hz, 1H), 7.96 (s, 3H), 7.94-7.88 (m, 2H), 7.57-7.44 (m, 3H), 7.41 (d, J = 1.1 Hz, 1H), 7.27 (d, J = 8.2 Hz, 1H), 7.03 (s, 1H), 6.90 (d, J = 1.2 Hz, 1H), 5.31 (p, J = 7.1 Hz, 1H), 5.03-4.41 (m, 5H), 4.53-4.36 (m, 2H), 4.11 (s, 3H), 3.98 (s, 3H), 3.37-2.88 (m, 3H), 2.09-1.96 (m, 1H), 1.82-1.69 (m, 1H), 1.59 (d, J = 7.0 Hz, 3H), 1.20-1.03 (m, 1H), 0.33-0.19 (m, 2H), 0.19-0.09 (m, 2H). |
| 125 | 1H NMR (400 MHz, DMSO-d6) δ 8.33 (d, J = 7.8 Hz, 1H), 8.04 (d, J = 8.1 Hz, 1H), 7.95 (s, 3H), 7.40-7.34 (m, 1H), 7.15 (d, J = 8.3 Hz, 2H), 6.91 (d, J = 1.2 Hz, 1H), 5.08 (p, J = 7.1 Hz, 1H), 4.70-4.46 (m, 2H), 4.40-4.04 (m, 3H), 3.98 (s, 3H), 3.88 (tt, J = 7.2, 3.9 Hz, 1H), 3.33-2.95 (m, 3H), 2.30 (s, 6H), 2.09-1.93 (m, 1H), 1.82-1.67 (m, 1H), 1.66-1.50 (m, 1H), 1.47 (d, J = 7.0 Hz, 3H), 1.13-0.93 (m, 3H), 0.76-0.60 (m, 2H), 0.34-0.20 (m, 2H), 0.20-0.06 (m, 2H). |
| 126 | 1H NMR (400 MHz, DMSO-d6) δ 8.86 (d, J = 7.7 Hz, 1H), 8.04 (d, J = 8.1 Hz, 1H), 7.94 (s, 3H), 7.-7-7.91 (m, 1H), 7.56-7.43 (m, 3H), 7.38 (d, J = 1.1 Hz, 1H), 7.26 (d, J = 8.2 Hz, 1H), 7.14 (s, 1H), 6.91 (d, J = 1.2 Hz, 1H), 5.31 (p, J = 7.1 Hz, 1H), 4.71-4.46 (m, 2H), 3.98 (s, 3H), 3.93-3.85 (m, 5H), 3.33-2.91 (m, 2H), 2.07-1.92 (m, 1H), 1.81-1.69 (m, 1H), 1.59 (d, J = 7.1 Hz, 3H), 1.58-1.49 (m, 2H), 1.12-0.93 (m, 4H), 0.76-0.61 (m, 2H), 0.31-0.21 (m, 2H), 0.21-0.03 (m, 2H). |
| 127 | 1H NMR (400 MHz, DMSO-d6) δ 8.09 (brs, 3H), 8.07 (d, J = 8.1 Hz, 1H), 7.85 (d, J = 7.6 Hz, 1H), 7.58 (s, 1H), 7.19 (d, J = 8.2 Hz, 1H), 7.17 (s, 1H), 7.07 (s, 1H), 5.14-5.03 (m, 1H), 4.70-4.55 (m, 2H), 4.47 (brs, 2H), 4.02 (s, 3H), 3.92 (tt, J = 7.2, 3.8 Hz, 1H), 3.76 (brs, 1H), 2.39-2.25 (m, 1H), 1.94-1.73 (m, 3H), 1.70-1.57 (m, 1H), 1.49 (d, J = 7.0 Hz, 3H), 1.35 (dd, J = 12.9, 4.4 Hz, 1H), 1.19 (s, 9H), 1.13-0.95 (m, 3H), 0.81-0.62 (m, 2H), 0.35-0.22 (m, 2H), 0.23-0.09 (m, 2H). |
| 128 | 1H NMR (400 MHz, DMSO-d6) δ 8.07 (d, J = 8.1 Hz, 1H), 7.95 (brs, 3H), 7.85 (d, J = 7.6 Hz, 1H), 7.41 (s, 1H), 7.19 (d, J = 8.2 Hz, 1H), 7.16 (s, 1H), 6.94 (s, 1H), 5.14-5.04 (m, 1H), 4.72-4.55 (m, 2H), 4.18 (brs, 1H), 4.01 (s, 3H), 3.91 (tt, J = 7.2, 3.8 Hz, 1H), 3.37-3.12 (m, 4H), 2.08-1.97 (m, 1H), 1.87-1.74 (m, 1H), 1.69-1.52 (m, 2H), 1.49 (d, J = 7.0 Hz, 3H), 1.19 (s, 9H), 1.14-1.00 (m, 3H), 0.82-0.62 (m, 2H), 0.35-0.23 (m, 2H), 0.21-0.11 (m, 2H). |
| 129 | 1H NMR (400 MHz, DMSO-d6) δ 8.89 (d, J = 7.7 Hz, 1H), 8.07 (d, J = 8.1 Hz, 1H), 8.00 (s, 3H), 7.96-7.92 (m, 2H), 7.59-7.53 (m, 1H), 7.53-7.45 (m, 2H), 7.41 (s, 1H), 7.28 (d, J = 8.2 Hz, 1H), 7.17 (s, 1H), 6.94 (s, 1H), 5.34 (p, J = 7.1 Hz, 1H), 5.02-4.20 (m, 2H), 4.76-4.45 (m, 2H), 4.00 (s, 3H), 3.97-3.85 (m, 1H), 3.38-2.97 (m, 2H), 2.13-1.91 (m, 1H), 1.86-1.67 (m, 1H), 1.62 (d, J = 7.1 Hz, 3H), 1.60-1.41 (m, 2H), 1.17-0.97 (m, 3H), 0.80-0.58 (m, 2H), 0.35-0.22 (m, 2H), 0.21-0.00 (m, 2H). |
| 130 | 1H NMR (400 MHz, DMSO-d6) δ 8.33 (d, J = 7.8 Hz, 1H), 8.10 (s, 3H), 8.04 (d, J = 8.1 Hz, 1H), 7.58-7.49 (m, 1H), 7.17-7.12 (m, 2H), 7.04 (d, J = 1.2 Hz, 1H), 5.08 (p, J = 7.1 Hz, 1H), 4.70-4.50 (m, 2H), 4.39-4.06 (m, 1H), 4.00 (s, 3H), 3.89 (tt, J = 7.2, 3.8 Hz, 1H), 3.78-3.61 (m, 2H), 2.30 (s, 6H), 1.90-1.73 (m, 4H), 1.68-1.56 (m, 1H), 1.47 (d, J = 7.0 Hz, 3H), 1.33 (dd, J = 12.9, 4.4 Hz, 1H), 1.13-0.91 (m, 3H), 0.77-0.59 (m, 2H), 0.25 (td, J = 9.8, 8.8, 5.5 Hz, 2H), 0.20-0.04 (m, 2H). |
| 131 | 1H NMR (400 MHz, DMSO-d6) δ 8.33 (d, J = 7.8 Hz, 1H), 8.05 (s, 3H), 8.03 (d, J = 8.1 Hz, 2H), 7.55 (s, 1H), 7.16 (d, J = 8.1 Hz, 1H), 7.14 (s, 1H), 7.04 (d, J = 1.2 Hz, 1H), 5.04 (p, J = 7.0 Hz, 1H), 4.71-4.28 (m, 4H), 4.00 (s, 3H), 3.94-3.84 (m, 1H), 2.39-2.13 (m, 1H), 1.88 (s, 3H), 1.86-1.70 (m, 4H), 1.66-1.51 (m, 1H), 1.44 (d, J = 7.0 Hz, 3H), 1.32 (dd, J = 12.9, 4.3 Hz, 1H), 1.03 (d, J = 7.1 Hz, 3H), 0.78-0.60 (m, 2H), 0.33-0.20 (m, 2H), 0.18-0.07 (m, 2H). |
| 132 | 1H NMR (400 MHz, DMSO-d6) δ 8.37 (d, J = 7.8 Hz, 1H), 8.05 (d, J = 8.1 Hz, 1H), 7.98 (s, 3H), 7.41 (s, 1H), 7.19 (d, J = 8.2 Hz, 1H), 7.16 (s, 1H), 6.94 (s, 1H), 5.07 (p, J = 7.1 Hz, 1H), 4.75-4.47 (m, 2H), 4.36-4.05 (m, 1H), 4.01 (s, 3H), 3.97-3.83 (m, 1H), 3.38-3.00 (m, 1H), 2.70 (s, 3H), 2.09-1.99 (m, 1H), 1.90 (s, 3H), 1.87-1.69 (m, 1H), 1.71-1.53 (m, 2H), 1.47 (d, J = 7.0 Hz, 3H), 1.20-0.88 (m, 4H), 0.77-0.57 (m, 2H), 0.36-0.23 (m, 2H), 0.22-0.07 (m, 2H). |

TABLE 5a-continued

| Ex. | ¹H NMR |
|---|---|
| 133 | 1H NMR (400 MHz, DMSO-d6) δ 8.37 (d, J = 8.2 Hz, 1H), 8.11 (brs, 3H), 7.63 (d, J = 8.2 Hz, 1H), 7.57 (d, J = 10.2 Hz, 2H), 7.13 (dd, J = 8.3, 1.3 Hz, 1H), 7.04 (s, 1H), 7.01 (s, 1H), 5.14-5.01 (m, 1H), 4.54 (brs, 2H), 4.44 (dd, J = 14.7, 6.7 Hz, 1H), 4.35 (dd, J = 14.8, 7.1 Hz, 1H), 4.11 (s, 3H), 4.01 (s, 3H), 2.39-2.27 (m, 1H), 2.30 (d, J = 2.6 Hz, 6H), 1.91-1.58 (m, 5H), 1.47 (d, J = 7.0 Hz, 3H), 1.35 (dd, J = 12.9, 4.4 Hz, 1H), 1.15-1.02 (m, 1H), 0.36-0.27 (m, 2H), 0.12-0.02 (m, 2H). |
| 134 | 1H NMR (400 MHz, DMSO-d6) δ 8.40 (d, J = 8.2 Hz, 1H), 8.09 (brs, 3H), 7.63 (d, J = 8.3 Hz, 1H), 7.58 (s, 1H), 7.55 (s, 1H), 7.12 (dd, J = 8.3, 1.3 Hz, 1H), 7.04 (s, 1H), 7.01 (s, 1H), 5.12-5.02 (m, 1H), 4.52 (brs, 2H), 4.44 (dd, J = 14.8, 6.7 Hz, 1H), 4.35 (dd, J = 14.8, 7.1 Hz, 1H), 4.11 (s, 3H), 4.01 (s, 3H), 3.77 (brs, 2H), 2.45 (s, 3H), 2.40-2.27 (m, 1H), 1.91-1.76 (m, 3H), 1.69-1.59 (m, 1H), 1.46 (d, J = 7.0 Hz, 3H), 1.35 (dd, J = 12.8, 4.3 Hz, 1H), 1.27-1.01 (m, 1H), 0.36-0.28 (m, 2H), 0.14-0.03 (m, 2H). |
| 135 | 1H NMR (400 MHz, Methanol-d4) δ 8.10 (s, 1H), 7.97 (d, J = 0.8 Hz, 1H), 7.70 (d, J = 8.4 Hz, 1H), 7.64 (s, 1H), 7.59 (d, J = 1.2 Hz, 1H), 7.27 (dd, J = 8.3, 1.4 Hz, 1H), 7.16 (d, J = 1.2 Hz, 1H), 7.01 (d, J = 0.8 Hz, 1H), 5.39 (q, J = 7.0 Hz, 1H), 4.59 (s, 2H), 4.32 (t, J = 6.5 Hz, 2H), 4.18 (s, 3H), 4.10 (s, 3H), 3.94 (s, 3H), 3.90-3.81 (m, 1H), 2.53 (m, J = 12.2, 5.2 Hz, 1H), 2.05 (d, J = 11.3 Hz, 2H), 1.99-1.86 (m, 1H), 1.76 (t, J = 8.3 Hz, 1H), 1.67 (d, J = 7.0 Hz, 3H), 1.47 (dd, J = 13.2, 4.5 Hz, 1H), 0.98 (dd, J = 7.6, 4.9 Hz, 1H), 0.40-0.26 (m, 2H), −0.08 (p, J = 3.5 Hz, 2H). |
| 136 | 1H NMR (400 MHz, Methanol-d4) δ 7.90-7.86 (m, 2H), 7.73-7.67 (m, 2H), 7.61-7.53 (m, 2H), 7.52-7.46 (m, 2H), 7.30 (dd, J = 8.3, 1.4 Hz, 1H), 7.16 (d, J = 1.2 Hz, 1H), 7.01 (d, J = 0.8 Hz, 1H), 5.44 (q, J = 6.9 Hz, 1H), 4.60 (s, 2H), 4.41-4.26 (m, 2H), 4.18 (s, 3H), 4.10 (s, 3H), 3.87 (m, J = 10.0, 4.5 Hz, 1H), 2.53 (m, J = 12.3, 5.1 Hz, 1H), 2.06 (s, 2H), 1.99-1.88 (m, 1H), 1.81-1.66 (m, 4H), 1.47 (dd, J = 13.2, 4.5 Hz, 1H), 1.08-0.94 (m, 1H), 0.40-0.27 (m, 2H), −0.07 (p, J = 4.3 Hz, 2H). |
| 137 | 1H NMR (400 MHz, Methanol-d4) δ 7.90-7.86 (m, 2H), 7.73-7.67 (m, 2H), 7.59-7.42 (m, 4H), 7.30 (dd, J = 8.3, 1.4 Hz, 1H), 7.05-6.99 (m, 2H), 5.44 (q, J = 6.8 Hz, 1H), 4.31 (t, J = 7.4, 6.8 Hz, 2H), 4.17 (s, 3H), 4.09 (s, 3H), 3.42 (s, 3H), 2.22 (d, J = 12.7 Hz, 1H), 1.94-1.64 (m, 6H), 1.04-0.95 (m, 1H), 0.34 (d, J = 7.9 Hz, 2H), −0.07 (h, J = 4.7, 4.2 Hz, 2H). |
| 138 | 1H NMR (400 MHz, Methanol-d4) δ 7.70 (d, J = 8.3 Hz, 1H), 7.66 (s, 1H), 7.63 (s, 1H), 7.59 (d, J = 1.2 Hz, 1H), 7.28 (dd, J = 8.3, 1.4 Hz, 1H), 7.16 (d, J = 1.2 Hz, 1H), 7.01 (d, J = 0.8 Hz, 1H), 5.40 (q, J = 7.0 Hz, 1H), 4.81-4.50 (m, 2H), 4.41-4.26 (m, 2H), 4.18 (s, 3H), 4.10 (s, 3H), 3.87 (m, J = 10.0, 4.4 Hz, 1H), 2.56 (s, 3H), 2.51 (dd, J = 11.9, 5.0 Hz, 1H), 2.03 (d, J = 12.4 Hz, 2H), 1.99-1.87 (m, 1H), 1.76 (t, J = 8.2 Hz, 1H), 1.69 (d, J = 7.0 Hz, 3H), 1.47 (dd, J = 13.2, 4.5 Hz, 1H), 1.01 (m, J = 21.4, 8.9, 6.4 Hz, 1H), 0.41-0.29 (m, 2H), 0.00−-0.13 (m, 2H). |
| 139 | 1H NMR (400 MHz, Methanol-d4) δ 8.59 (d, J = 0.6 Hz, 1H), 8.17 (s, 1H), 7.74-7.68 (m, 1H), 7.65 (s, 1H), 7.61-7.56 (m, 1H), 7.42 (s, 1H), 7.27 (dd, J = 8.3, 1.4 Hz, 1H), 7.14 (d, J = 1.2 Hz, 1H), 6.99 (d, J = 0.8 Hz, 1H), 5.40 (q, J = 7.0 Hz, 1H), 4.60 (s, 1H), 4.41-4.26 (m, 2H), 4.17 (s, 3H), 4.09 (s, 3H), 3.87 (dt, J = 9.9, 4.4 Hz, 1H), 2.53 (td, J = 12.3, 5.2 Hz, 1H), 2.05 (d, J = 11.2 Hz, 2H), 1.97-1.87 (m, 1H), 1.76 (t, J = 8.3 Hz, 1H), 1.68 (d, J = 7.0 Hz, 3H), 1.47 (dd, J = 13.2, 4.4 Hz, 1H), 1.42-1.22 (m, 1H), 1.06-0.93 (m, 2H), 0.40-0.28 (m, 2H), −0.08 (t, J = 4.7 Hz, 2H). |
| 140 | 1H NMR (400 MHz, DMSO-d6) δ 8.15 (d, J = 8.7 Hz, 1H), 8.12 (brs, 3H), 7.64 (s, 1H), 7.62 (d, J = 8.3 Hz, 1H), 7.58 (s, 1H), 7.22 (d, J = 8.3 Hz, 1H), 7.04 (s, 1H), 7.01 (s, 1H), 5.15-5.04 (m, 1H), 4.40 (d, J = 7.0 Hz, 2H), 4.11 (s, 3H), 4.01 (s, 3H), 3.76 (brs, 2H), 3.18 (s, 3H), 2.37-2.27 (m, 1H), 1.96-1.72 (m, 3H), 1.70-1.57 (m 1H), 1.49 (d, J = 7.0 Hz, 3H), 1.35 (dd, J = 12.9, 4.4 Hz, 1H), 1.30 (s, 3H), 1.25 (s, 3H), 1.15-0.99 (m, 1H), 0.35-0.27 (m, 2H), 0.13−-0.00 (m, 2H). |
| 141 | 1H NMR (400 MHz, Chloroform-d) δ 7.71 (d, J = 8.3 Hz, 1H), 7.65 (s, 1H), 7.50 (s, 1H), 7.22 (d, J = 8.4 Hz, 2H), 7.02 (s, 1H), 6.81 (d, J = 8.0 Hz, 1H), 5.28 (q, J = 7.3 Hz, 1H), 4.56 (s, 2H), 4.21 (s, 3H), 4.07 (s, 3H), 3.79 (s, 2H), 3.23 (s, 3H), 2.48 (tt, J = 8.4, 4.3 Hz, 1H), 2.43-2.29 (m, 2H), 2.29-2.14 (m, 2H), 2.09 (d, J = 16.2 Hz, 1H), 1.99-1.76 (m, 4H), 1.71 (s, 1H), 1.62 (d, J = 6.9 Hz, 3H), 1.53 (d, J = 12.9 Hz, 1H), 0.91 (s, 1H), 0.35 (d, J = 8.0 Hz, 2H), −0.08 (d, J = 7.6 Hz, 2H). |
| 142 | 1H NMR (400 MHz, Chloroform-d) δ 7.72 (d, J = 8.3 Hz, 1H), 7.64 (s, 1H), 7.53 (s, 1H), 7.25 (dd, J = 8.5, 1.3 Hz, 1H), 7.18 (s, 1H), 7.04-6.97 (m, 1H), 5.31 (t, J = 7.3 Hz, 1H), 4.21 (s, 5H), 4.07 (s, 3H), 3.77 (s, 1H), 2.33 (s, 1H), 2.13-1.98 (m, 1H), 1.89 (s, 2H), 1.66 (d, J = 6.9 Hz, 4H), 1.52 (d, J = 13.1 Hz, 1H), 1.37-1.22 (m, 2H), 1.13-1.00 (m, 2H), 0.91 (s, 1H), 0.35 (d, J = 8.2 Hz, 2H), −0.08 (s, 2H). |
| 143 | 1H NMR (400 MHz, DMSO-d6) δ 8.43 (d, J = 7.8 Hz, 1H), 7.96 (brs, 3H), 7.48 (d, J = 8.2 Hz, 1H), 7.42 (s, 1H), 7.14 (dd, J = 8.3, 6.2 Hz, 1H), 7.06 (d, J = 1.9 Hz, 1H), 6.93 (d, J = 1.2 Hz, 1H), 5.42-5.30 (m, 1H), 4.44 (d, J = 7.1 Hz, 2H), 4.21 (brs, 2H), 4.08 (s, 3H), 4.00 (s, 3H), 3.38-3.05 (m, 3H), 2.29 (d, J = 2.6 Hz, 6H), 2.09-1.97 (m, 1H), 1.86-1.68 (m, 1H), 1.68-1.51 (m, 2H), 1.45 (d, J = 7.0 Hz, 3H), 1.16-1.00 (m, 1H), 0.37-0.26 (m, 2H), 0.02−-0.05 (m, 2H). |
| 144 | 1H NMR (400 MHz, DMSO-d6) δ 8.42 (d, J = 7.9 Hz, 1H), 8.09 (brs, 3H), 7.60 (s, 1H), 7.49 (d, J = 8.2 Hz, 1H), 7.14 (dd, J = 8.3, 6.2 Hz, 1H), 7.07 (d, J = 2.0 Hz, 1H), 7.05 (s, 1H), 5.42-5.30 (m, 1H), 4.50 (brs, 2H), 4.45 (d, J = 7.1 Hz, 2H), 4.08 (s, 3H), 4.01 (s, 3H), 3.76 (brs, 1H), 2.40-2.27 (m, 1H), 2.29 (d, J = 2.6 Hz, 6H), 1.92-1.72 (m, 3H), 1.70-1.58 (m, 1H), 1.45 (d, J = 7.0 Hz, 3H), 1.34 (dd, J = 12.8, 4.4 Hz, 1H), 1.12-0.99 (m, 1H), 0.37-0.26 (m, 2H), 0.02−-0.05 (m, 2H). |
| 145 | 1H NMR (400 MHz, DMSO-d6) δ 8.44 (d, J = 8.0 Hz, 1H), 7.95 (brs, 3H), 7.60 (d, J = 6.2 Hz, 1H), 7.43 (d, 1H, J = 8.0 Hz), 7.41 (s, 1H), 7.00 (s, 1H), 6.92 (d, J = 1.2 Hz, 1H), 5.35-5.23 (m, 1H), 4.45 (dd, J = 14.8, 6.5 Hz, 1H), 4.26 (dd, J = 14.9, 7.3 Hz, 1H), 4.10 (s, 3H), 3.99 (s, 3H), 3.92 (brs, 2H), 3.35-3.07 (m, 3H), 2.32 (d, J = 2.6 Hz, 6H), 2.08-1.98 (m, 1H), 1.83-1.71 (m, 1H), 1.67-1.52 (m, 2H), 1.46 (d, J = 7.0 Hz, 3H), 1.18-1.04 (m, 1H), 0.41-0.29 (m, 2H), 0.17-0.06 (m, 2H). |

TABLE 5a-continued

| Ex. | ¹H NMR |
|---|---|
| 146 | 1H NMR (400 MHz, DMSO-d6) δ 8.44 (d, J = 8.0 Hz, 1H), 8.11 (brs, 3H), 7.60 (d, J = 6.5 Hz, 2H), 7.59 (s, 1H), 7.43 (d, J = 10.9 Hz, 1H), 7.04 (s, 1H), 7.00 (s, 1H), 5.35-5.23 (m, 1H), 4.50 (brs, 2H), 4.45 (dd, J = 14.8, 6.5 Hz, 1H), 4.26 (dd, J = 14.8, 7.3 Hz, 1H), 4.10 (s, 3H), 4.01 (s, 3H), 3.75 (s, 1H), 2.32 (d, J = 2.6 Hz, 6H), 1.93-1.75 (m, 3H), 1.70-1.59 (m, 1H), 1.46 (d, J = 6.9 Hz, 3H), 1.35 (dd, J = 12.8, 4.4 Hz, 1H), 1.16-1.01 (m, 1H), 0.42-0.29 (m, 2H), 0.21-0.04 (m, 2H). |
| 147 | 1H NMR (400 MHz, Chloroform-d) δ 7.72 (d, J = 8.3 Hz, 1H), 7.61 (s, 1H), 7.52 (s, 1H), 7.24 (d, J = 1.3 Hz, 1H), 7.19-7.07 (m, 2H), 5.32 (p, J = 7.0 Hz, 2H), 4.33 (s, 2H), 4.07 (s, 3H), 3.80 (s, 2H), 3.38 (s, 3H), 2.33 (s, 1H), 2.06 (s, 1H), 1.88 (s, 3H), 1.66 (d, J = 6.9 Hz, 4H), 1.52 (d, J = 13.0 Hz, 1H), 1.37-1.01 (m, 6H), 0.88 (s, 4H), 0.33 (d, J = 8.0 Hz, 2H), −0.06 (s, 2H). |
| 148 | 1H NMR (400 MHz, DMSO-d6) δ 9.30 (d, J = 8.0 Hz, 1H), 7.68-7.60 (m, 2H), 7.57-7.48 (m, 2H), 7.25-7.13 (m, 3H), 7.05 (d, J = 1.3 Hz, 1H), 5.29 (p, J = 7.0 Hz, 1H), 4.54 (d, J = 7.0 Hz, 3H), 4.02 (s, 3H), 3.90 (m, J = 7.3, 3.8 Hz, 1H), 3.75 (s, 1H), 2.38-2.26 (m, 1H), 1.84 (s, 4H), 1.64 (d, J = 9.3 Hz, 1H), 1.52 (d, J = 7.0 Hz, 3H), 1.35 (dd, J = 12.8, 4.4 Hz, 1H), 1.04 (t, J = 8.7 Hz, 3H), 0.73-0.65 (m, 2H), 0.35-0.26 (m, 2H), 0.10--0.02 (m, 2H). |
| 149 | 1H NMR (400 MHz, DMSO-d6) δ 8.95 (d, J = 8.0 Hz, 1H), 7.67-7.62 (m, 1H), 7.56-7.52 (m, 1H), 7.43-7.37 (m, 1H), 7.20 (dd, J = 8.2, 1.4 Hz, 1H), 7.15 (s, 1H), 7.05 (d, J = 1.3 Hz, 1H), 6.95 (d, J = 8.5 Hz, 1H), 6.86 (t, J = 8.6 Hz, 1H), 5.25 (p, J = 7.0 Hz, 1H), 4.56-4.47 (m, 2H), 4.02 (s, 5H), 3.93-3.87 (m, 2H), 3.82 (s, 3H), 2.38-2.24 (m, 1H), 1.80 (d, J = 30.0 Hz, 4H), 1.64 (d, J = 9.5 Hz, 1H), 1.53-1.45 (m, 3H), 1.35 (dd, J = 12.9, 4.4 Hz, 1H), 1.04 (t, J = 9.1 Hz, 3H), 0.70 (m, J = 7.2, 4.0 Hz, 2H), 0.29 (dd, J = 7.9, 1.5 Hz, 2H), 0.08--0.04 (m, 2H). |
| 150 | 1H NMR (400 MHz, DMSO-d6) δ 8.47 (d, J = 8.0 Hz, 1H), 8.35 (s, 1H), 8.19 (s, 1H), 7.94 (brs, 3H), 7.93 (s, 1H), 7.69 (d, J = 6.2 Hz, 1H), 7.49-7.38 (m, 2H), 6.99 (s, 1H), 6.92 (d, J = 1.2 Hz, 1H), 5.50-5.41 (m, 1H), 4.50-4.23 (m, 2H), 4.09 (s, 3H), 3.99 (s, 3H), 3.86 (s, 3H), 3.34-3.11 (m, 3H), 2.08-1.98 (m, 1H), 1.84-1.71 (m, 1H), 1.66-1.54 (m, 2H), 1.53 (d, J = 7.0 Hz, 3H), 1.10-0.99 (m, 1H), 0.39-0.22 (m, 2H), 0.13--0.04 (m, 2H). |
| 151 | 1H NMR (400 MHz, DMSO-d6) δ 8.77 (d, J = 8.0 Hz, 1H), 8.77 (s, 1H), 8.24 (s, 1H), 7.94 (brs, 3H), 7.88 (t, J = 59.0 Hz, 1H), 7.70 (d, J = 6.2 Hz, 1H), 7.45 (d, J = 10.9 Hz, 1H), 7.41 (s, 1H), 7.00 (s, 1H), 6.92 (d, J = 1.2 Hz, 1H), 5.53-5.42 (m, 1H), 4.44 (dd, J = 14.8, 6.4 Hz, 1H), 4.27 (dd, J = 14.8, 7.4 Hz, 1H), 4.19 (brs, 2H), 4.09 (s, 3H), 3.99 (s, 3H), 3.36-3.11 (m, 2H), 2.08-1.93 (m, 1H), 1.82-1.69 (m, 1H), 1.65-1.54 (m, 1H), 1.55 (d, J = 7.0 Hz, 3H), 1.18-0.97 (m, 1H), 0.45-0.22 (m, 2H), 0.12--0.03 (m, 2H). |
| 152 | 1H NMR (400 MHz, DMSO-d6) δ 8.82 (dd, J = 8.0, 2.1 Hz, 1H), 8.18-8.03 (m, 1H), 7.64 (dd, J = 8.3, 2.8 Hz, 1H), 7.55-7.50 (m, 1H), 7.13 (d, J = 9.8 Hz, 1H), 7.05 (d, J = 1.3 Hz, 1H), 5.11 (m, J = 7.3, 2.9 Hz, 1H), 4.53 (t, J = 6.0 Hz, 2H), 4.02 (s, 3H), 3.89 (m, J = 7.2, 3.8 Hz, 3H), 2.67 (m, J = 14.3, 10.7, 7.9 Hz, 1H), 2.38-2.24 (m, 1H), 1.97-1.73 (m, 6H), 1.64 (d, J = 9.1 Hz, 1H), 1.48 (d, J = 6.9 Hz, 3H), 1.35 (dd, J = 12.9, 4.4 Hz, 1H), 1.02 (d, J = 15.8, 8.6 Hz, 3H), 0.70 (dd, J = 5.9, 3.8 Hz, 2H), 0.34-0.24 (m, 2H), 0.10--0.02 (m, 2H). 19F NMR (376 MHz, DMSO-d6) δ −124.53--125.67 (m), −140.15--141.29 (m). |
| 153 | 1H NMR (400 MHz, DMSO-d6) δ 8.82 (d, J = 7.9, 2.5 Hz, 1H), 7.68-7.53 (m, 2H), 7.37 (s, 1H), 7.16-7.07 (m, 1H), 6.92 (d, J = 1.1 Hz, 1H), 5.11 (m, J = 7.3, 2.9 Hz, 1H), 4.52 (d, J = 6.5 Hz, 2H), 4.00 (s, 3H), 3.88 (m, J = 7.3, 3.8 Hz, 3H), 3.35-3.07 (m, 4H), 2.73-2.59 (m, 2H), 2.05 (d, J = 25.1 Hz, 1H), 1.88 (m, J = 21.5, 11.7, 10.7, 6.3 Hz, 1H), 1.76 (s, 1H), 1.58 (d, J = 8.3 Hz, 2H), 1.48 (d, J = 6.9 Hz, 3H), 1.03 (t, J = 7.5 Hz, 3H), 0.69 (q, J = 7.0, 5.5 Hz, 2H), 0.34-0.23 (m, 2H), 0.05 (m, J = 6.5, 5.6, 3.5 Hz, 2H). |
| 154 | ¹H NMR (400 MHz, Methanol-d₄) δ 8.12 (d, J = 8.2 Hz, 1H), 8.07-8.01 (m, 1H), 7.97-7.89 (m, 2H), 7.66-7.54 (m, 2H), 7.54-7.43 (m, 3H), 7.34 (d, 1H), 7.26-7.17 (m, 1H), 7.08 (s, 1H), 5.46 (q, J = 6.9 Hz, 1H), 4.75-4.61 (m, 1H), 4.49 (dd, J = 14.7, 7.1 Hz, 1H), 4.44 (dd, J = 14.7, 7.0 Hz, 1H), 4.20 (s, 3H), 4.09 (s, 3H), 3.59-3.42 (m, 1H), 3.29-3.08 (m, 2H), 3.08-2.96 (m, 1H), 2.72 (s, 3H), 2.20-1.99 (m, 1H), 1.95-1.80 (m, 1H), 1.71 (d, J = 7.0 Hz, 3H), 1.08-0.88 (m, 1H), 0.38-0.21 (m, 2H), 0.11--0.04 (m, 2H). |
| 155 | ¹H NMR (400 MHz, Methanol-d₄) δ 8.12 (d, J = 8.2 Hz, 1H), 8.05-7.91 (m, 2H), 7.76-7.54 (m, 1H), 7.34 (d, J = 8.2 Hz, 1H), 7.29-7.17 (m, 3H), 7.10 (s, 1H), 5.45 (q, J = 7.0 Hz, 1H), 4.76-4.60 (m, 1H), 4.46 (d, J = 7.1 Hz, 2H), 4.20 (s, 3H), 4.10 (s, 3H), 3.61-3.40 (m, 1H), 3.30-3.13 (m, 2H), 3.10-2.85 (m, 1H), 2.72 (s, 3H), 2.19-2.01 (m, 1H), 1.94-1.78 (m, 1H), 1.71 (d, J = 7.1 Hz, 3H), 1.03-0.90 (m, 1H), 0.37-0.23 (m, 2H), 0.09--0.01 (m, 2H). |
| 156 | ¹H NMR (400 MHz, Methanol-d₄) δ 8.12 (d, J = 8.1 Hz, 1H), 7.79-7.60 (m, 1H), 7.60-7.51 (m, 2H), 7.32 (d, J = 8.2 Hz, 1H), 7.24-7.15 (m, 2H), 7.07 (s, 1H), 5.44 (q, J = 7.0 Hz, 1H), 4.74-4.60 (m, 1H), 4.49 (dd, J = 13.5, 6.1 Hz, 1H), 4.44 (dd, J = 13.4, 5.9 Hz, 1H), 4.20 (s, 3H), 4.09 (s, 3H), 3.59-3.42 (m, 1H), 3.29-3.12 (m, 2H), 3.09-2.94 (m, 1H), 2.72 (s, 3H), 2.17-2.00 (m, 1H), 1.92-1.76 (m, 1H), 1.71 (d, J = 7.0 Hz, 3H), 1.02-0.86 (m, 1H), 0.37-0.21 (m, 2H), 0.10--0.06 (m, 2H). |
| 157 | ¹H NMR (400 MHz, Methanol-d₄) δ 8.13 (d, J = 8.2 Hz, 1H), 7.64 (s, 1H), 7.35 (d, J = 8.2 Hz, 1H), 7.20 (s, 1H), 7.07 (s, 1H), 7.05-6.93 (m, 2H), 5.43 (q, J = 6.9 Hz, 1H), 4.76-4.59 (m, 1H), 4.59-4.39 (m, 2H), 4.20 (s, 3H), 4.10 (s, 3H), 3.61-3.41 (m, 1H), 3.29-3.13 (m, 2H), 3.11-2.95 (m, 1H), 2.72 (s, 3H), 2.20-2.00 (m, 1H), 1.94-1.79 (m, 1H), 1.67 (d, J = 7.0 Hz, 3H), 1.06-0.91 (m, 1H), 0.38-0.27 (m, 2H), 0.10--0.02 (m, 2H). |
| 158 | ¹H NMR (400 MHz, Methanol-d₄) δ 8.06 (d, J = 8.1 Hz, 1H), 7.64 (s, 1H), 7.41-7.17 (m, 8H), 7.05 (s, 1H), 5.22 (q, J = 6.9 Hz, 1H), 4.76-4.53 (m, 1H), 4.45-4.33 (m, 1H), 4.19 (s, 3H), 4.10 (s, 3H), 3.66 (d, J = 14.6 Hz, 1H), 3.62 (d, J = 14.6 Hz, 1H), 3.56-3.43 (m, 1H), 3.29-3.11 (m, 2H), 3.11-2.98 (m, 1H), 2.72 (s, 3H), 2.18-1.98 (m, 1H), 1.93-1.78 (m, 1H), 1.57 (d, J = 6.9 Hz, 3H), 1.00-0.83 (m, 1H), 0.38-0.26 (m, 2H), 0.09--0.05 (m, 2H). |
| 159 | ¹H NMR (400 MHz, Methanol-d₄) δ 8.07 (d, J = 8.1 Hz, 1H), 7.64 (s, 1H), 7.49-7.36 (m, 4H), 7.34-7.27 (m, 1H), 7.20 (s, 1H), 7.15 (d, J = 8.1 Hz, 1H), 7.05 (s, 1H), 5.19 (q, J = 6.8 Hz, 1H), 4.76-4.58 (m, 1H), 4.33 (dd, J = 14.5, 6.8 Hz, 1H), 4.25-4.20 (m, 1H), 4.19 (s, 3H), 4.10 (s, 3H), 3.59-3.41 (m, 1H), 3.30-3.12 (m, 2H), 3.11-2.97 (m, 1H), 2.73 (s, 3H), 2.19-2.00 (m, 1H), 1.93-1.79 (m, 1H), 1.65 (s, 3H), 1.61 (s, 3H), 1.48 (d, J = 6.8 Hz, 3H), 0.92-0.79 (m, 1H), 0.37-0.27 (m, 2H), 0.00--0.10 (m, 2H). |

TABLE 5a-continued

| Ex. | ¹H NMR |
|---|---|
| 160 | ¹H NMR (400 MHz, Methanol-d$_4$) δ 8.07 (d, J = 8.1 Hz, 1H), 7.64 (s, 1H), 7.59-7.41 (m, 5H), 7.19 (s, 1H), 7.15 (d, J = 8.1 Hz, 1H), 7.01 (s, 1H), 5.15 (q, J = 6.6 Hz, 1H), 4.78-4.47 (m, 1H), 4.26-4.19 (m, 1H), 4.18 (s, 3H), 4.09 (s, 3H), 4.04 (dd, J = 14.5, 7.3 Hz, 1H), 3.62-3.46 (m, 1H), 3.30-3.14 (m, 2H), 3.13-2.97 (m, 1H), 2.74 (s, 3H), 2.19-2.00 (m, 1H), 1.94-1.80 (m, 1H), 1.66-1.53 (m, 2H), 1.43 (d, J = 6.7 Hz, 3H), 1.21-1.07 (m, 2H), 0.83-0.72 (m, 1H), 0.37-0.24 (m, 2H), −0.05-−0.21 (m, 2H). |
| 161 | ¹H NMR (400 MHz, Methanol-d$_4$) δ 8.12 (d, J = 8.1 Hz, 1H), 7.64 (s, 1H), 7.26 (d, J = 8.2 Hz, 1H), 7.24-7.16 (m, 1H), 7.09 (s, 1H), 5.22 (q, J = 6.9 Hz, 1H), 4.75-4.60 (m, 1H), 4.56-4.36 (m, 2H), 4.21 (s, 3H), 4.10 (s, 3H), 3.62-3.42 (m, 1H), 3.30-3.14 (m, 2H), 3.10-2.98 (m, 1H), 2.72 (s, 3H), 2.20-1.99 (m, 1H), 1.94-1.79 (m, 1H), 1.58 (d, J = 6.9 Hz, 3H), 1.29 (s, 9H), 1.05-0.93 (m, 1H), 0.42-0.27 (m, 2H), 0.06 (td, J = 3.6, 2.0 Hz, 2H). |
| 162 | ¹H NMR (400 MHz, Methanol-d$_4$) δ 8.09 (d, J = 8.2 Hz, 1H), 7.64 (s, 1H), 7.24 (d, J = 8.2 Hz, 1H), 7.20 (s, 1H), 7.06 (s, 1H), 5.23 (q, J = 7.0 Hz, 1H), 4.78-4.60 (m, 1H), 4.47 (d, J = 7.0 Hz, 2H), 4.20 (s, 3H), 4.09 (s, 3H), 3.58-3.43 (m, 1H), 3.30-3.14 (m, 2H), 3.13-2.92 (m, 3H), 2.89-2.74 (m, 3H), 2.72 (s, 3H), 2.16-2.02 (m, 1H), 1.91-1.81 (m, 1H), 1.58 (d, J = 7.0 Hz, 3H), 1.02-0.91 (m, 1H), 0.39-0.28 (m, 2H), 0.11-−0.01 (m, 2H). |
| 163 | ¹H NMR (400 MHz, Methanol-d$_4$) δ 8.07 (d, J = 8.1 Hz, 1H), 7.80 (d, J = 8.2 Hz, 2H), 7.75 (d, J = 8.2 Hz, 2H), 7.64 (s, 1H), 7.20-7.10 (m, 2H), 6.99 (s, 1H), 5.25-5.16 (m, 1H), 4.77-4.59 (m, 1H), 4.21 (dd, J = 14.5, 6.9 Hz, 1H), 4.16 (s, 3H), 4.08 (s, 3H), 4.07-4.00 (m, 1H), 3.58-3.44 (m, 1H), 3.29-3.13 (m, 2H), 3.11-2.98 (m, 1H), 2.74 (s, 3H), 2.16-2.00 (m, 1H), 1.93-1.78 (m, 1H), 1.72-1.58 (m, 2H), 1.45 (d, J = 6.7 Hz, 3H), 1.26-1.14 (m, 2H), 0.89-0.76 (m, 1H), 0.35-0.24 (m, 2H), −0.09-−0.24 (m, 2H). |
| 164 | ¹H NMR (400 MHz, Methanol-d$_4$) δ 7.93 (d, J = 8.1 Hz, 1H), 7.61 (s, 1H), 7.36-7.31 (m, 2H), 7.31-7.25 (m, 2H), 7.24-7.12 (m, 2H), 7.01-6.96 (m, 2H), 5.18 (q, J = 6.9 Hz, 1H), 4.71-4.54 (m, 1H), 4.35 (dd, J = 14.5, 7.0 Hz, 1H), 4.28 (dd, J = 14.5, 7.1 Hz, 1H), 4.14 (s, 3H), 4.06 (s, 3H), 3.79 (q, J = 7.1 Hz, 1H), 3.55-3.40 (m, 1H), 3.27-3.10 (m, 2H), 3.07-2.93 (m, 1H), 2.70 (s, 3H), 2.12-1.95 (m, 1H), 1.91-1.74 (m, 1H), 1.54 (d, J = 6.9 Hz, 3H), 1.48 (d, J = 7.1 Hz, 3H), 0.93-0.78 (m, 1H), 0.30-0.21 (m, 2H), 0.02-−0.14 (m, 2H). |
| 165 | ¹H NMR (400 MHz, Methanol-d$_4$) δ 8.06 (d, J = 8.1 Hz, 1H), 7.62 (s, 1H), 7.43-7.37 (m, 2H), 7.37-7.30 (m, 2H), 7.29-7.23 (m, 1H), 7.21 (d, J = 8.1 Hz, 1H), 7.17 (s, 1H), 7.02 (s, 1H), 5.15 (q, J = 6.9 Hz, 1H), 4.74-4.53 (m, 1H), 4.42 (dd, J = 15.0, 7.0 Hz, 1H), 4.37 (dd, J = 14.5, 7.1 Hz, 1H), 4.17 (s, 3H), 4.07 (s, 3H), 3.77 (q, J = 7.2 Hz, 1H), 3.58-3.43 (m, 1H), 3.28-3.13 (m, 2H), 3.06-2.95 (m, 1H), 2.70 (s, 3H), 2.16-1.98 (m, 1H), 1.90-1.77 (m, 1H), 1.53-1.44 (m, 6H), 0.97-0.82 (m, 1H), 0.39-0.26 (m, 2H), 0.05-−0.06 (m, 2H). |
| 166 | ¹H NMR (400 MHz, Methanol-d$_4$) δ 8.11 (d, J = 8.1 Hz, 1H), 7.77-7.69 (m, 2H), 7.66-7.56 (m, 3H), 7.33 (d, J = 8.1 Hz, 1H), 7.18 (s, 1H), 7.17 (t, J = 55.7 Hz, 1H), 7.06 (s, 1H), 5.41 (q, J = 7.0 Hz, 1H), 4.71-4.57 (m, 1H), 4.52-4.39 (m, 2H), 4.18 (s, 3H), 4.07 (s, 3H), 3.56-3.40 (m, 1H), 3.28-3.11 (m, 2H), 3.06-2.94 (m, 1H), 2.70 (s, 3H), 2.14-1.99 (m, 1H), 1.88-1.78 (m, 1H), 1.66 (d, J = 7.0 Hz, 3H), 1.01-0.90 (m, 1H), 0.34-0.24 (m, 2H), 0.04-−0.03 (m, 2H). |
| 167 | ¹H NMR (400 MHz, Methanol-d$_4$) δ 8.05 (d, J = 8.1 Hz, 1H), 7.68-7.59 (m, 3H), 7.55-7.42 (m, 3H), 7.21-7.13 (m, 2H), 7.01 (s, 1H), 5.25 (q, J = 7.0, 6.3 Hz, 1H), 4.72-4.56 (m, 1H), 4.41 (d, J = 7.0 Hz, 2H), 4.16 (s, 3H), 4.06 (s, 3H), 3.56-3.40 (m, 1H), 3.26-3.08 (m, 2H), 3.06-2.93 (m, 1H), 2.70 (s, 3H), 2.16-1.98 (m, 1H), 1.92-1.77 (m, 1H), 1.62 (d, J = 7.0 Hz, 3H), 0.99-0.86 (m, 1H), 0.37-0.24 (m, 2H), 0.08-−0.05 (m, 2H). |
| 168 | ¹H NMR (400 MHz, Methanol-d$_4$) δ 8.07 (d, J = 8.1 Hz, 1H), 7.61 (s, 1H), 7.23 (d, J = 8.1 Hz, 1H), 7.18 (s, 1H), 5.23 (q, J = 7.0 Hz, 1H), 4.72-4.57 (m, 1H), 4.46 (d, J = 7.0 Hz, 2H), 4.17 (s, 3H), 4.07 (s, 3H), 3.58-3.42 (m, 1H), 3.26-3.10 (m, 2H), 3.10-2.96 (m, 1H), 2.70 (s, 3H), 2.67-2.60 (m, 1H), 2.15-1.93 (m, 2H), 1.90-1.66 (m, 2H), 1.58 (d, J = 7.0 Hz, 3H), 1.04-0.88 (m, 1H), 0.37-0.22 (m, 2H), 0.09-−0.04 (m, 2H). |
| 169 | ¹H NMR (400 MHz, Methanol-d$_4$) δ 8.10 (s, 1H), 8.07 (d, J = 8.1 Hz, 1H), 7.97 (s, 1H), 7.61 (s, 1H), 7.28 (d, J = 8.2 Hz, 1H), 7.17 (s, 1H), 7.03 (s, 1H), 5.38 (q, J = 7.0 Hz, 1H), 4.72-4.57 (m, 1H), 4.49-4.36 (m, 2H), 4.16 (s, 3H), 4.07 (s, 3H), 3.92 (s, 3H), 3.56-3.40 (m, 1H), 3.27-3.08 (m, 2H), 3.06-2.93 (m, 1H), 2.70 (s, 3H), 2.17-1.99 (m, 1H), 1.91-1.74 (m, 1H), 1.65 (d, J = 7.0 Hz, 3H), 1.01-0.82 (m, 1H), 0.35-0.20 (m, 2H), 0.08-−0.04 (m, 2H). |
| 170 | ¹H NMR (400 MHz, Methanol-d$_4$) δ 8.60 (s, 1H), 8.17 (s, 1H), 8.07 (d, J = 8.2 Hz, 1H), 7.61 (s, 1H), 7.55 (t, J = 59.6 Hz, 1H), 7.28 (d, J = 8.2 Hz, 1H), 7.16 (s, 1H), 7.02 (s, 1H), 5.40 (q, J = 7.0 Hz, 1H), 4.73-4.57 (m, 1H), 4.43 (d, J = 7.1 Hz, 2H), 4.16 (s, 3H), 4.06 (s, 3H), 3.56-3.40 (m, 1H), 3.27-3.08 (m, 2H), 3.06-2.94 (m, 1H), 2.70 (s, 3H), 2.13-1.98 (m, 1H), 1.89-1.78 (m, 1H), 1.67 (d, J = 7.0 Hz, 3H), 0.99-0.85 (m, 1H), 0.33-0.21 (m, 2H), 0.07-−0.06 (m, 2H). |
| 171 | ¹H NMR (400 MHz, Methanol-d$_4$) δ 8.07 (d, J = 8.1 Hz, 1H), 7.62 (s, 1H), 7.21 (d, J = 8.2 Hz, 1H), 7.16 (s, 1H), 7.01 (s, 1H), 5.23 (q, J = 7.0 Hz, 1H), 4.71-4.59 (m, 1H), 4.50-4.38 (m, 2H), 4.16 (s, 3H), 4.06 (s, 3H), 3.48 (d, J = 1.5 Hz, 1H), 3.26-3.11 (m, 2H), 3.07-2.93 (m, 1H), 2.70 (s, 3H), 2.35 (d, J = 2.5 Hz, 6H), 2.15-1.99 (m, 1H), 1.93-1.76 (m, 1H), 1.58 (d, J = 7.0 Hz, 3H), 1.04-0.90 (m, 1H), 0.37-0.25 (m, 2H), 0.08-−0.00 (m, 2H). |
| 172 | ¹H NMR (400 MHz, Methanol-d$_4$) δ 8.10 (d, J = 8.1 Hz, 1H), 7.61 (s, 1H), 7.34 (d, J = 8.1 Hz, 1H), 7.20-7.11 (m, 2H), 7.04 (d, J = 7.6 Hz, 2H), 7.01 (s, 1H), 5.48 (q, J = 6.9 Hz, 1H), 4.73-4.58 (m, 1H), 4.54-4.38 (m, 2H), 4.17 (s, 3H), 4.06 (s, 3H), 3.53-3.39 (m, 1H), 3.27-3.10 (m, 2H), 3.08-2.93 (m, 1H), 2.70 (s, 3H), 2.29 (s, 6H), 2.14-2.00 (m, 1H), 1.91-1.78 (m, 1H), 1.65 (d, J = 7.0 Hz, 3H), 1.00-0.88 (m, 1H), 0.34-0.23 (m, 2H), 0.02-−0.09 (m, 2H). |
| 173 | 1H NMR (400 MHz, DMSO-d6) δ 8.13-8.05 (m, 2H), 8.02 (d, J = 2.4 Hz, 1H), 7.71 (d, J = 1.8 Hz, 1H), 7.61 (s, 1H), 7.19 (dd, J = 13.1, 7.7 Hz, 1H), 7.11-7.02 (m, 1H), 6.43 (t, J = 2.1 Hz, 1H), 5.13 (q, J = 6.8 Hz, 1H), 4.54 (dd, J = 14.1, 6.4 Hz, 2H), 4.28 (dd, J = 14.1, 7.5 Hz, 2H), 4.13 (s, 3H), 4.02 (s, 3H), 1.84 (s, 4H), 1.72-1.58 (m, 3H), 1.55-1.40 (m, 3H), 1.36 (d, J = 6.6 Hz, 3H), 1.01 (s, 1H), 0.38-0.27 (m, 2H), 0.07 (s, 2H). |

TABLE 5a-continued

| Ex. | ¹H NMR |
|---|---|
| 174 | 1H NMR (400 MHz, DMSO-d6) δ 8.49 (d, J = 7.6 Hz, 1H), 8.15-8.05 (m, 1H), 7.75 (d, J = 2.2 Hz, 1H), 7.61 (s, 1H), 7.48 (d, J = 1.8 Hz, 1H), 7.23 (d, J = 8.2 Hz, 1H), 7.10-7.04 (m, 1H), 6.28 (t, J = 2.1 Hz, 1H), 5.11 (p, J = 7.0 Hz, 1H), 4.92 (d, J = 1.3 Hz, 2H), 4.57-4.40 (m, 3H), 4.14 (s, 3H), 4.02 (s, 3H), 3.76 (s, 1H), 3.17 (s, 1H), 1.80 (d, J = 31.6 Hz, 3H), 1.64 (d, J = 9.2 Hz, 1H), 1.48 (d, J = 6.9 Hz, 3H), 1.35 (dd, J = 12.8, 4.4 Hz, 1H), 1.28-1.06 (m, 3H), 0.36-0.25 (m, 2H), 0.18 (q, J = 4.1 Hz, 2H). |
| 175 | ¹H NMR (400 MHz, Methanol-d₄) δ 8.54-8.46 (m, 1H), 8.16 (d, J = 8.1 Hz, 1H), 7.81 (ddd, J = 7.8, 1.7, 0.8 Hz, 1H), 7.64 (s, 1H), 7.49 (dd, J = 7.8, 4.7 Hz, 1H), 7.37 (d, J = 8.2 Hz, 1H), 7.24 (s, 1H), 7.14 (s, 1H), 5.42 (q, J = 6.8 Hz, 1H), 4.78-4.61 (m, 1H), 4.49 (d, J = 7.1 Hz, 2H), 4.22 (s, 3H), 4.11 (s, 3H), 3.59-3.41 (m, 1H), 3.31-3.12 (m, 2H), 3.10-2.95 (m, 1H), 2.72 (s, 3H), 2.65 (s, 3H), 2.21-2.02 (m, 1H), 1.93-1.80 (m, 1H), 1.69 (d, J = 6.9 Hz, 3H), 1.13-0.91 (m, 1H), 0.40-0.26 (m, 2H), 0.23-0.02 (m, 2H). |
| 176 | ¹H NMR (400 MHz, Methanol-d₄) δ 8.16 (d, J = 8.1 Hz, 1H), 7.79 (d, J = 8.0 Hz, 1H), 7.64 (s, 1H), 7.45 (d, J = 7.9 Hz, 1H), 7.36 (d, J = 8.2 Hz, 1H), 7.22 (s, 1H), 7.12 (s, 1H), 5.43 (q, J = 6.8 Hz, 1H), 4.77-4.60 (m, 1H), 4.55 (dd, J = 14.5, 7.0 Hz, 1H), 4.48 (dd, J = 14.5, 7.0 Hz, 1H), 4.22 (s, 3H), 4.10 (s, 3H), 3.60-3.44 (m, 1H), 3.29-3.12 (m, 2H), 3.10-2.97 (m, 1H), 2.72 (s, 3H), 2.64 (s, 3H), 2.60 (s, 3H), 2.22-2.01 (m, 1H), 1.91-1.81 (m, 1H), 1.70 (d, J = 6.8 Hz, 3H), 1.08-0.90 (m, 1H), 0.42-0.28 (m, 2H), 0.10--0.05 (m, 2H). |
| 177 | ¹H NMR (400 MHz, Methanol-d₄) δ 8.78 (dd, J = 5.8, 1.6 Hz, 1H), 8.57 (dd, J = 7.9, 1.6 Hz, 1H), 8.17 (d, J = 8.1 Hz, 1H), 7.93 (dd, J = 7.9, 5.8 Hz, 1H), 7.64 (s, 1H), 7.38 (d, J = 8.2 Hz, 1H), 7.23 (s, 1H), 7.14 (s, 1H), 5.48 (q, J = 7.0 Hz, 1H), 4.72-4.59 (m, 1H), 4.57-4.41 (m, 2H), 4.23 (s, 3H), 4.11 (s, 3H), 3.59-3.43 (m, 1H), 3.30-3.14 (m, 2H), 3.10-2.96 (m, 1H), 2.84 (s, 3H), 2.72 (s, 3H), 2.22-2.04 (m, 1H), 1.95-1.85 (m, 1H), 1.72 (d, J = 7.0 Hz, 3H), 1.05-0.88 (m, 1H), 0.41-0.30 (m, 2H), 0.10--0.03 (m, 2H). |
| 178 | ¹H NMR (400 MHz, Methanol-d₄) δ 8.61 (d, J = 6.1 Hz, 1H), 8.18 (d, J = 8.1 Hz, 1H), 7.83 (d, J = 6.2 Hz, 1H), 7.64 (s, 1H), 7.38 (d, J = 8.1 Hz, 1H), 7.22 (s, 1H), 7.12 (s, 1H), 5.53 (q, J = 6.9 Hz, 1H), 4.73-4.60 (m, 1H), 4.58-4.42 (m, 2H), 4.23 (s, 3H), 4.10 (s, 3H), 3.58-3.44 (m, 1H), 3.29-3.14 (m, 2H), 3.08-2.93 (m, 1H), 2.74 (s, 3H), 2.72 (s, 3H), 2.61 (s, 3H), 2.20-2.06 (m, 1H), 1.93-1.82 (m, 1H), 1.72 (d, J = 7.0 Hz, 3H), 1.02-0.86 (m, 1H), 0.40-0.24 (m, 2H), 0.07--0.11 (m, 2H). |
| 179 | ¹H NMR (400 MHz, Methanol-d₄) δ 8.14 (d, J = 8.2 Hz, 1H), 8.07 (s, 2H), 7.64 (s, 1H), 7.36 (d, J = 8.2 Hz, 1H), 7.21 (s, 1H), 7.10 (s, 1H), 5.48 (q, J = 7.0 Hz, 1H), 4.76-4.62 (m, 1H), 4.54-4.41 (m, 2H), 4.21 (s, 3H), 4.10 (s, 3H), 3.60-3.42 (m, 1H), 3.30-3.13 (m, 2H), 3.10-2.94 (m, 1H), 2.83 (s, 6H), 2.72 (s, 3H), 2.17-2.03 (m, 1H), 1.93-1.80 (m, 1H), 1.74 (d, J = 7.0 Hz, 3H), 1.04-0.89 (m, 1H), 0.40-0.21 (m, 2H), 0.13--0.03 (m, 2H). |
| 180 | ¹H NMR (400 MHz, Methanol-d₄) δ 9.00 (d, J = 4.9 Hz, 2H), 8.15 (d, J = 8.1 Hz, 1H), 7.68 (t, J = 4.9 Hz, 1H), 7.65 (s, 1H), 7.34 (d, J = 8.1 Hz, 1H), 7.19 (s, 1H), 7.08 (s, 1H), 5.47 (q, J = 6.8 Hz, 1H), 4.76-4.62 (m, 1H), 4.58-4.43 (m, 2H), 4.20 (s, 3H), 4.09 (s, 3H), 3.59-3.41 (m, 1H), 3.28-3.11 (m, 2H), 3.10-2.98 (m, 1H), 2.73 (s, 3H), 2.21-2.00 (m, 1H), 1.94-1.81 (m, 1H), 1.72 (d, J = 6.7 Hz, 3H), 1.13-0.96 (m, 1H), 0.44-0.25 (m, 2H), 0.25-0.10 (m, 2H). |
| 181 | ¹H NMR (400 MHz, Methanol-d₄) δ 8.81 (d, J = 5.1 Hz, 1H), 8.15 (d, J = 8.1 Hz, 1H), 7.64 (s, 1H), 7.55 (d, J = 5.1 Hz, 1H), 7.34 (d, J = 8.1 Hz, 1H), 7.21 (s, 1H), 7.11 (s, 1H), 5.46 (q, J = 6.8 Hz, 1H), 4.74-4.62 (m, 1H), 4.61-4.45 (m, 2H), 4.21 (s, 3H), 4.10 (s, 3H), 3.60-3.44 (m, 1H), 3.29-3.13 (m, 2H), 3.09-2.97 (m, 1H), 2.72 (s, 3H), 2.68 (s, 3H), 2.20-2.03 (m, 1H), 1.93-1.79 (m, 1H), 1.71 (d, J = 6.8 Hz, 3H), 1.12-0.96 (m, 1H), 0.43-0.25 (m, 2H), 0.23-0.03 (m, 2H). |
| 182 | ¹H NMR (400 MHz, Methanol-d₄) δ 9.33 (d, J = 5.0 Hz, 1H), 8.17 (d, J = 8.1 Hz, 1H), 8.12 (d, J = 5.1 Hz, 1H), 7.65 (s, 1H), 7.35 (d, J = 8.2 Hz, 1H), 7.23-7.17 (m, 1H), 7.10 (s, 1H), 5.50 (q, J = 6.7 Hz, 1H), 4.76-4.63 (m, 1H), 4.58-4.49 (m, 2H), 4.21 (s, 3H), 4.10 (s, 3H), 3.59-3.46 (m, 1H), 3.30-3.12 (m, 2H), 3.10-2.97 (m, 1H), 2.73 (s, 3H), 2.19-2.02 (m, 1H), 1.93-1.81 (m, 1H), 1.73 (d, J = 6.8 Hz, 3H), 1.09-0.92 (m, 1H), 0.41-0.24 (m, 2H), 0.15--0.03 (m, 2H). |
| 183 | ¹H NMR (400 MHz, Methanol-d₄) δ 8.17 (d, J = 8.2 Hz, 1H), 8.02 (s, 1H), 7.65 (s, 1H), 7.35 (d, J = 8.2 Hz, 1H), 7.20 (s, 1H), 7.10 (s, 1H), 5.49 (q, J = 6.7 Hz, 1H), 4.76-4.64 (m, 1H), 4.62-4.46 (m, 2H), 4.21 (s, 3H), 4.10 (s, 3H), 3.57-3.44 (m, 1H), 3.28-3.16 (m, 2H), 3.10-2.98 (m, 1H), 2.81 (s, 3H), 2.73 (s, 3H), 2.18-2.01 (m, 1H), 1.94-1.82 (m, 1H), 1.72 (d, J = 6.8 Hz, 3H), 1.10-0.93 (m, 1H), 0.41-0.24 (m, 2H), 0.13-0.02 (m, 2H). |
| 184 | ¹H NMR (400 MHz, Methanol-d₄) δ 8.13 (d, J = 8.1 Hz, 1H), 7.68-7.46 (m, 4H), 7.36 (d, J = 8.2 Hz, 1H), 7.18 (s, 1H), 7.05 (s, 1H), 5.50 (q, J = 7.0 Hz, 1H), 4.67 (s, 1H), 4.57-4.41 (m, 2H), 4.20 (s, 3H), 4.09 (s, 3H), 3.60-3.43 (m, 1H), 3.19 (d, J = 29.1 Hz, 2H), 3.04 (d, J = 14.3 Hz, 1H), 2.73 (s, 3H), 2.37 (s, 3H), 2.09 (d, J = 13.1 Hz, 1H), 1.86 (d, J = 12.8 Hz, 1H), 1.67 (d, J = 6.9 Hz, 3H), 0.96 (td, J = 9.6, 8.5, 4.0 Hz, 1H), 0.31 (dd, J = 8.1, 1.9 Hz, 2H), 0.06--0.06 (m, 2H). |
| 185 | ¹H NMR (400 MHz, Methanol-d₄) δ 8.10 (d, J = 8.1 Hz, 1H), 7.64 (s, 1H), 7.24 (d, J = 8.2 Hz, 1H), 7.22 (s, 1H), 7.08 (s, 1H), 5.22 (q, J = 7.0 Hz, 1H), 4.72-4.60 (m, 1H), 4.55-4.37 (m, 2H), 4.20 (s, 3H), 4.10 (s, 3H), 3.60-3.44 (m, 1H), 3.29-3.11 (m, 2H), 3.09-2.97 (m, 1H), 2.72 (s, 3H), 2.48 (s, 1H), 2.19-2.02 (m, 7H), 1.92-1.81 (m, 1H), 1.59 (d, J = 7.0 Hz, 3H), 1.07-0.90 (m, 1H), 0.41-0.31 (m, 2H), 0.17--0.00 (m, 2H). |
| 186 | ¹H NMR (400 MHz, Methanol-d₄) δ 8.10 (d, J = 8.2 Hz, 1H), 7.66-7.60 (m, 1H), 7.24 (d, J = 8.2 Hz, 1H), 7.22 (s, 1H), 7.08 (s, 1H), 5.23 (q, J = 7.0 Hz, 1H), 4.76-4.60 (m, 1H), 4.54-4.38 (m, 2H), 4.20 (s, 3H), 4.10 (s, 3H), 3.59-3.43 (m, 1H), 3.30-3.13 (m, 2H), 3.11-2.98 (m, 1H), 2.72 (s, 3H), 2.45 (s, 6H), 2.20-2.02 (m, 1H), 1.92-1.80 (m, 1H), 1.60 (d, J = 7.1 Hz, 3H), 1.05-0.90 (m, 1H), 0.42-0.31 (m, 2H), 0.16-0.02 (m, 2H). |

TABLE 5a-continued

| Ex. | $^1$H NMR |
|---|---|
| 187 | $^1$H NMR (400 MHz, Methanol-d$_4$) δ 8.10 (d, J = 8.1 Hz, 1H), 7.64 (s, 1H), 7.24 (d, J = 8.2 Hz, 1H), 7.21 (s, 1H), 7.08 (s, 1H), 5.22 (q, J = 6.9 Hz, 1H), 4.75-4.61 (m, 1H), 4.55-4.39 (m, 2H), 4.20 (s, 3H), 4.10 (s, 3H), 3.59-3.43 (m, 1H), 3.29-3.10 (m, 2H), 3.10-2.95 (m, 1H), 2.72 (s, 3H), 2.20-2.02 (m, 1H), 1.96 (s, 6H), 1.91-1.79 (m, 1H), 1.58 (d, J = 7.0 Hz, 3H), 1.22 (s, 3H), 1.08-0.92 (m, 1H), 0.43-0.31 (m, 2H), 0.14-0.02 (m, 2H). |
| 188 | $^1$H NMR (400 MHz, Methanol-d$_4$) δ 8.11 (d, J = 8.2 Hz, 1H), 7.64 (s, 1H), 7.25 (d, J = 8.2 Hz, 1H), 7.22 (s, 1H), 7.08 (s, 1H), 5.25 (q, J = 6.9 Hz, 1H), 4.78-4.60 (m, 1H), 4.56-4.39 (m, 2H), 4.20 (s, 3H), 4.10 (s, 3H), 3.60-3.43 (m, 1H), 3.30-3.14 (m, 2H), 3.10-2.94 (m, 1H), 2.72 (s, 3H), 2.30 (s, 6H), 2.18-2.02 (m, 1H), 1.93-1.77 (m, 1H), 1.61 (d, J = 7.0 Hz, 3H), 1.07-0.88 (m, 1H), 0.41-0.30 (m, 2H), 0.16--0.01 (m, 2H). |
| 189 | $^1$H NMR (400 MHz, Methanol-d$_4$) δ 8.12 (d, J = 8.1 Hz, 1H), 7.64 (s, 1H), 7.25 (d, J = 8.2 Hz, 1H), 7.21 (s, 1H), 7.08 (s, 1H), 5.22 (q, J = 6.9 Hz, 1H), 4.76-4.62 (m, 1H), 4.51 (dd, J = 14.5, 7.1 Hz, 1H), 4.44 (dd, J = 14.5, 7.0 Hz, 1H), 4.21 (s, 3H), 4.10 (s, 3H), 3.58-3.44 (m, 1H), 3.30-3.11 (m, 2H), 3.10-2.96 (m, 1H), 2.72 (s, 3H), 2.22-2.02 (m, 1H), 1.94-1.82 (m, 1H), 1.58 (d, J = 7.0 Hz, 3H), 1.07-0.91 (m, 1H), 0.40-0.27 (m, 2H), 0.13--0.04 (m, 2H). |
| 190 | $^1$H NMR (400 MHz, Methanol-d$_4$) δ 8.14 (d, J = 8.1 Hz, 1H), 7.64 (s, 1H), 7.27 (d, J = 8.2 Hz, 1H), 7.22 (s, 1H), 7.11 (s, 1H), 5.26 (q, J = 6.8 Hz, 1H), 4.85-4.38 (m, 5H), 4.21 (s, 3H), 4.10 (s, 3H), 3.58-3.48 (m, 1H), 3.29-3.13 (m, 2H), 3.12-2.97 (m, 1H), 2.72 (s, 3H), 2.10 (d, J = 13.6 Hz, 1H), 1.86 (d, J = 13.0 Hz, 1H), 1.59 (d, J = 6.8 Hz, 3H), 1.38-1.23 (m, 2H), 1.06-0.88 (m, 3H), 0.41-0.29 (m, 2H), 0.15-0.00 (m, 2H). |
| 191 | $^1$H NMR (400 MHz, Methanol-d$_4$) δ 8.14 (d, J = 8.1 Hz, 1H), 7.64 (s, 1H), 7.26 (d, J = 8.2 Hz, 1H), 7.22 (s, 1H), 7.11 (s, 1H), 6.04 (t, J = 55.8 Hz, 1H), 5.27 (q, J = 6.8 Hz, 1H), 4.75-4.63 (m, 1H), 4.54 (dd, J = 14.6, 7.0 Hz, 1H), 4.44 (dd, J = 14.6, 7.2 Hz, 1H), 4.21 (s, 3H), 4.10 (s, 3H), 3.61-3.44 (m, 1H), 3.30-3.13 (m, 2H), 3.09-2.99 (m, 1H), 2.72 (s, 3H), 2.21-1.99 (m, 1H), 1.93-1.80 (m, 1H), 1.58 (d, J = 6.8 Hz, 3H), 1.42-1.06 (m, 4H), 1.03-0.89 (m, 1H), 0.43-0.27 (m, 2H), 0.14-0.01 (m, 2H). |
| 192 | $^1$H NMR (400 MHz, Methanol-d$_4$) δ 8.15 (d, J = 8.1 Hz, 1H), 7.64 (s, 1H), 7.26 (d, J = 8.1 Hz, 1H), 7.21 (s, 1H), 7.10 (s, 1H), 5.26 (q, J = 6.8 Hz, 1H), 4.76-4.60 (m, 1H), 4.54 (dd, J = 14.6, 6.9 Hz, 1H), 4.43 (dd, J = 14.5, 7.2 Hz, 1H), 4.21 (s, 3H), 4.10 (s, 3H), 3.59-3.43 (m, 1H), 3.29-3.14 (m, 2H), 3.10-2.97 (m, 1H), 2.73 (s, 3H), 2.18-2.00 (m, 1H), 1.92-1.80 (m, 1H), 1.59 (d, J = 6.8 Hz, 3H), 1.50-1.26 (m, 4H), 1.05-0.92 (m, 1H), 0.43-0.30 (m, 2H), 0.10--0.01 (m, 2H). |
| 193 | $^1$H NMR (400 MHz, Methanol-d$_4$) δ 8.11 (d, J = 8.1 Hz, 1H), 7.64 (s, 1H), 7.24 (d, J = 8.2 Hz, 1H), 7.21 (s, 1H), 7.08 (s, 1H), 6.10 (tt, J = 56.8, 4.7 Hz, 1H), 5.22 (q, J = 6.9 Hz, 1H), 4.77-4.62 (m, 1H), 4.51 (dd, J = 14.5, 7.0 Hz, 1H), 4.44 (dd, J = 14.6, 7.1 Hz, 1H), 4.21 (s, 3H), 4.10 (s, 3H), 3.60-3.42 (m, 1H), 3.30-3.13 (m, 2H), 3.14-2.98 (m, 1H), 2.72 (s, 3H), 2.41-2.02 (m, 3H), 1.93-1.79 (m, 1H), 1.57 (d, J = 7.0 Hz, 3H), 1.33-1.18 (m, 2H), 1.07-0.93 (m, 1H), 0.93-0.83 (m, 2H), 0.43-0.29 (m, 2H), 0.11--0.04 (m, 2H). |
| 194 | $^1$H NMR (400 MHz, Methanol-d$_4$) δ 8.15 (d, J = 8.2 Hz, 1H), 7.64 (s, 1H), 7.47 (dd, J = 7.6, 1.6 Hz, 1H), 7.41-7.33 (m, 2H), 7.32-7.20 (m, 3H), 7.12 (s, 1H), 5.44 (q, J = 7.0 Hz, 1H), 4.75-4.62 (m, 1H), 4.51 (dd, J = 14.6, 7.0 Hz, 1H), 4.45 (dd, J = 14.6, 7.0 Hz, 1H), 4.22 (s, 3H), 4.10 (s, 3H), 3.58-3.45 (m, 1H), 3.30-3.13 (m, 2H), 3.10-2.99 (m, 1H), 2.72 (s, 3H), 2.43 (s, 3H), 2.21-2.03 (m, 1H), 1.91-1.79 (m, 1H), 1.68 (d, J = 7.0 Hz, 3H), 1.05-0.92 (m, 1H), 0.38-0.28 (m, 2H), 0.08--0.01 (m, 2H). |
| 195 | $^1$H NMR (400 MHz, Methanol-d$_4$) δ 8.14 (d, J = 8.1 Hz, 1H), 7.64 (s, 1H), 7.52 (dd, J = 8.4, 5.8 Hz, 1H), 7.36 (d, J = 8.2 Hz, 1H), 7.22 (s, 1H), 7.10 (s, 1H), 7.07-6.95 (m, 2H), 5.43 (q, J = 7.0 Hz, 1H), 4.75-4.63 (m, 1H), 4.51 (dd, J = 14.6, 7.0 Hz, 1H), 4.45 (dd, J = 14.5, 7.0 Hz, 1H), 4.21 (s, 3H), 4.10 (s, 3H), 3.59-3.43 (m, 1H), 3.30-3.13 (m, 2H), 3.08-2.96 (m, 1H), 2.72 (s, 3H), 2.44 (s, 3H), 2.20-2.00 (m, 1H), 1.92-1.82 (m, 1H), 1.67 (d, J = 7.0 Hz, 3H), 1.06-0.90 (m, 1H), 0.40-0.24 (m, 2H), 0.08--0.01 (m, 2H). |
| 196 | $^1$H NMR (400 MHz, Methanol-d$_4$) δ 8.15 (d, J = 8.1 Hz, 1H), 7.83-7.77 (m, 1H), 7.76-7.61 (m, 4H), 7.37 (d, J = 8.2 Hz, 1H), 7.22 (s, 1H), 7.10 (s, 1H), 5.44 (q, J = 7.0 Hz, 1H), 4.75-4.61 (m, 1H), 4.57-4.37 (m, 2H), 4.21 (s, 3H), 4.10 (s, 3H), 3.60-3.42 (m, 1H), 3.30-3.14 (m, 2H), 3.11-2.97 (m, 1H), 2.72 (s, 3H), 2.19-2.00 (m, 1H), 1.92-1.81 (m, 1H), 1.68 (d, J = 7.0 Hz, 3H), 1.06-0.89 (m, 1H), 0.39-0.26 (m, 2H), 0.09--0.02 (m, 2H). |
| 197 | $^1$H NMR (400 MHz, Methanol-d$_4$) δ 8.15 (d, J = 8.2 Hz, 1H), 7.64 (s, 1H), 7.36 (d, J = 8.2 Hz, 1H), 7.29 (dd, J = 8.5, 5.4 Hz, 1H), 7.25-7.18 (m, 2H), 7.15-7.06 (m, 2H), 5.43 (q, J = 7.0 Hz, 1H), 4.72-4.63 (m, 1H), 4.53 (dd, J = 14.5, 7.0 Hz, 1H), 4.44 (dd, J = 14.5, 7.1 Hz, 1H), 4.22 (s, 3H), 4.10 (s, 3H), 3.57-3.43 (m, 1H), 3.30-3.12 (m, 2H), 3.10-2.93 (m, 1H), 2.72 (s, 3H), 2.39 (s, 3H), 2.18-1.98 (m, 1H), 1.93-1.79 (m, 1H), 1.67 (d, J = 7.0 Hz, 3H), 1.05-0.89 (m, 1H), 0.42-0.27 (m, 2H), 0.11--0.02 (m, 2H). |
| 198 | $^1$H NMR (400 MHz, Methanol-d$_4$) δ 8.14 (d, J = 8.1 Hz, 1H), 7.72-7.58 (m, 3H), 7.52 (t, J = 8.5 Hz, 1H), 7.38 (d, J = 8.2 Hz, 1H), 7.22 (s, 1H), 7.10 (s, 1H), 5.47 (q, J = 6.9 Hz, 1H), 4.75-4.60 (m, 1H), 4.56-4.41 (m, 2H), 4.22 (s, 3H), 4.10 (s, 3H), 3.60-3.42 (m, 1H), 3.29-3.12 (m, 2H), 3.10-2.96 (m, 1H), 2.72 (s, 3H), 2.20-2.00 (m, 1H), 1.93-1.81 (m, 1H), 1.68 (d, J = 7.0 Hz, 3H), 1.06-0.92 (m, 1H), 0.40-0.22 (m, 2H), 0.11--0.04 (m, 2H). |
| 199 | $^1$H NMR (400 MHz, Methanol-d$_4$) δ 8.08 (d, J = 8.1 Hz, 1H), 7.65 (s, 1H), 7.61-7.53 (m, 2H), 7.29-7.19 (m, 3H), 7.16 (d, J = 8.1 Hz, 1H), 7.04 (s, 1H), 5.16 (q, J = 6.7 Hz, 1H), 4.76-4.64 (m, 1H), 4.29-4.16 (m, 4H), 4.16-4.02 (m, 4H), 3.61-3.43 (m, 1H), 3.29-3.14 (m, 2H), 3.12-2.99 (m, 1H), 2.73 (s, 3H), 2.10 (d, J = 12.8 Hz, 1H), 1.94-1.80 (m, 1H), 1.68-1.51 (m, 2H), 1.44 (d, J = 6.7 Hz, 3H), 1.25-1.06 (m, 2H), 0.86-0.67 (m, 1H), 0.40-0.24 (m, 2H), −0.03--0.14 (m, 1H), −0.14--0.27 (m, 1H). |
| 200 | $^1$H NMR (400 MHz, Methanol-d$_4$) δ 8.12 (d, J = 8.2 Hz, 1H), 7.64 (s, 1H), 7.26 (d, J = 8.2 Hz, 1H), 7.22 (s, 1H), 7.10 (s, 1H), 5.24 (q, J = 6.9 Hz, 1H), 4.77-4.61 (m, 1H), 4.51 (dd, J = 14.6, 7.2 Hz, 1H), 4.45 (dd, J = 14.6, 7.0 Hz, 1H), 4.21 (s, 3H), 4.10 (s, 3H), 3.60-3.44 (m, 1H), 3.30-3.13 (m, 2H), 3.09-2.98 (m, 1H), 2.72 (s, 3H), 2.18-2.02 (m, 1H), 1.91-1.80 (m, 1H), 1.59 (d, J = 6.9 Hz, 3H), 1.47 (s, 3H), 1.23-1.07 (m, 2H), 1.07-0.95 (m, 1H), 0.74-0.59 (m, 2H), 0.40-0.31 (m, 2H), 0.15-0.02 (m, 2H). |

TABLE 5a-continued

| Ex. | ¹H NMR |
|---|---|
| 201 | ¹H NMR (400 MHz, Methanol-d₄) δ 9.20 (d, J = 2.1 Hz, 1H), 8.85 (dd, J = 5.3, 1.6 Hz, 1H), 8.66 (dt, J = 8.1, 1.9 Hz, 1H), 8.14 (d, J = 8.2 Hz, 1H), 7.86 (ddd, J = 8.1, 5.3, 0.9 Hz, 1H), 7.64 (s, 1H), 7.37 (d, J = 8.2 Hz, 1H), 7.24 (s, 1H), 7.13 (s, 1H), 5.49 (q, J = 7.0 Hz, 1H), 4.74-4.61 (m, 1H), 4.45 (d, J = 7.0 Hz, 2H), 4.21 (s, 3H), 4.11 (s, 3H), 3.59-3.42 (m, 1H), 3.29-3.12 (m, 2H), 3.08-2.96 (m, 1H), 2.72 (s, 3H), 2.18-2.02 (m, 1H), 1.93-1.79 (m, 1H), 1.74 (d, J = 7.0 Hz, 3H), 1.05-0.90 (m, 1H), 0.39-0.24 (m, 2H), 0.10--0.09 (m, 2H). |
| 209 | 1H NMR (400 MHz, Methanol-d4) δ 8.13 (d, J = 8.3 Hz, 1H), 7.94-7.85 (m, 2H), 7.64 (s, 1H), 7.61-7.43 (m, 4H), 7.20 (s, 1H), 7.06 (s, 1H), 4.67 (s, 1H), 4.45 (d, J = 7.1 Hz, 2H), 4.20 (s, 3H), 4.10 (s, 3H), 3.58-3.40 (m, 1H), 3.29-3.13 (m, 2H), 3.11-2.97 (m, 1H), 2.73 (s, 3H), 2.20-2.02 (m, 1H), 1.98-1.80 (m, 7H), 1.12-0.90 (m, 1H), 0.39-0.24 (m, 2H), 0.13--0.03 (m, 2H). |
| 210 | 1H NMR (400 MHz, DMSO-d6) δ 9.31 (d, J = 7.7 Hz, 1H), 8.13 (d, J = 8.1 Hz, 1H), 8.03 (s, 1H), 7.60-7.49 (m, 1H), 7.31 (d, J = 8.1 Hz, 1H), 7.23-7.17 (m, 1H), 7.05 (s, 1H), 7.02 (s, 1H), 5.28 (p, J = 7.1 Hz, 1H), 4.57-4.44 (m, 3H), 4.14 (s, 3H), 3.99 (s, 3H), 3.35 (s, 1H), 3.09 (q, J = 11.8 Hz, 2H), 2.88 (d, J = 13.6 Hz, 1H), 2.58 (s, 1H), 1.94 (t, J = 11.8 Hz, 1H), 1.70 (s, 1H), 1.55 (d, J = 7.0 Hz, 3H), 1.16 (s, 1H), 0.31 (d, J = 7.9 Hz, 2H), 0.26-0.17 (m, 2H). |
| 211 | ¹H NMR (400 MHz, DMSO-d₆) δ 8.48 (dd, J = 7.6, 3.2 Hz, 1H), 8.20-8.01 (m, 4H), 7.84 (d, J = 2.4 Hz, 1H), 7.61 (s, 1H), 7.50 (dd, J = 9.4, 1.8 Hz, 1H), 7.18 (dd, J = 18.3, 8.1 Hz, 1H), 7.06 (d, J = 6.7 Hz, 2H), 6.30 (dt, J = 5.7, 2.1 Hz, 1H), 5.24-5.13 (m, 1H), 5.13-5.00 (m, 1H), 4.58-4.41 (m, 4H), 4.16-4.11 (m, 3H), 4.02 (s, 1H), 3.85-3.65 (m, 2H), 2.40-2.25 (m, 1H), 1.94-1.73 (m, 3H), 1.70-1.57 (m, 3H), 1.45 (d, J = 6.9 Hz, 3H), 1.41-1.28 (m, 1H), 1.20-0.99 (m, 1H), 0.37-0.24 (m, 2H), 0.24-0.08 (m, 2H). |
| 212 | ¹H NMR (400 MHz, Methanol-d₄) δ 8.14 (d, J = 8.1 Hz, 1H), 7.64 (s, 1H), 7.36 (d, J = 8.2 Hz, 1H), 7.33-7.27 (m, 2H), 7.21 (s, 1H), 7.20-7.13 (m, 1H), 7.09 (s, 1H), 5.44 (q, J = 7.0 Hz, 1H), 4.74-4.60 (m, 1H), 4.52 (dd, J = 14.5, 7.0 Hz, 1H), 4.45 (dd, J = 14.5, 7.1 Hz, 1H), 4.21 (s, 3H), 4.10 (s, 3H), 3.59-3.44 (m, 1H), 3.29-3.13 (m, 2H), 3.10-2.97 (m, 1H), 2.72 (s, 3H), 2.32 (d, J = 2.2 Hz, 3H), 2.19-2.04 (m, 1H), 1.92-1.82 (m, 1H), 1.68 (d, J = 7.0 Hz, 3H), 1.05-0.90 (m, 1H), 0.38-0.27 (m, 2H), 0.11--0.03 (m, 2H). |
| 213 | ¹H NMR (400 MHz, Methanol-d₄) δ 8.15 (d, J = 8.1 Hz, 1H), 7.64 (s, 1H), 7.35 (d, J = 8.2 Hz, 1H), 7.21 (s, 1H), 7.15-7.00 (m, 3H), 5.42 (q, J = 7.0 Hz, 1H), 4.77-4.62 (m, 1H), 4.53 (dd, J = 14.5, 6.9 Hz, 1H), 4.45 (dd, J = 14.5, 7.1 Hz, 1H), 4.21 (s, 3H), 4.10 (s, 3H), 3.59-3.46 (m, 1H), 3.30-3.12 (m, 2H), 3.10-2.97 (m, 1H), 2.72 (s, 3H), 2.28 (dd, J = 2.4, 1.1 Hz, 3H), 2.18-2.02 (m, 1H), 1.92-1.78 (m, 1H), 1.67 (d, J = 7.0 Hz, 3H), 1.05-0.88 (m, 1H), 0.41-0.25 (m, 2H), 0.11--0.08 (m, 2H). |
| 214 | ¹H NMR (400 MHz, Methanol-d₄) δ 8.44 (d, J = 8.1 Hz, 1H), 8.13 (d, J = 8.1 Hz, 1H), 7.76 (d, J = 8.1 Hz, 1H), 7.63 (s, 1H), 7.34 (d, J = 8.1 Hz, 1H), 7.16 (s, 1H), 7.03 (s, 1H), 5.46 (q, J = 6.9 Hz, 1H), 4.74-4.61 (m, 1H), 4.57-4.43 (m, 2H), 4.19 (s, 3H), 4.08 (s, 3H), 3.57-3.43 (m, 1H), 3.28-3.12 (m, 2H), 3.10-2.98 (m, 1H), 2.81 (s, 3H), 2.79 (s, 3H), 2.73 (s, 3H), 2.17-2.00 (m, 1H), 1.93-1.82 (m, 1H), 1.71 (d, J = 7.0 Hz, 3H), 1.04-0.88 (m, 1H), 0.39-0.21 (m, 2H), 0.07--0.07 (m, 2H). |
| 215 | ¹H NMR (400 MHz, Methanol-d₄) δ 8.09 (d, J = 8.1 Hz, 1H), 7.64 (s, 1H), 7.23 (d, J = 8.1 Hz, 1H), 7.17 (s, 1H), 7.03 (s, 1H), 5.22 (q, J = 6.8 Hz, 1H), 4.69-4.61 (m, 1H), 4.63 (dt, J = 47.5, 6.2 Hz, 2H), 4.52 (dd, J = 14.5, 7.0 Hz, 1H), 4.45 (dd, J = 14.5, 7.1 Hz, 1H), 4.19 (s, 3H), 4.09 (s, 3H), 3.59-3.44 (m, 1H), 3.29-3.14 (m, 2H), 3.11-2.99 (m, 1H), 2.73 (s, 3H), 2.28-2.00 (m, 3H), 1.92-1.75 (m, 1H), 1.57 (d, J = 6.9 Hz, 3H), 1.24-1.08 (m, 2H), 1.07-0.91 (m, 1H), 0.88-0.70 (m, 2H), 0.43-0.26 (m, 2H), 0.10--0.04 (m, 2H). |
| 218 | 1H NMR (400 MHz, DMSO-d6) δ 8.37 (d, J = 7.8 Hz, 1H), 8.11 (d, 1H), 8.20-7.99 (m, 3H), 7.84 (s, 1H), 7.40 (d, J = 11.5 Hz, 1H), 7.27 (s, 1H), 7.19 (d, J = 8.2 Hz, 1H), 5.10 (p, J = 7.0 Hz, 1H), 4.72-4.64 (m, 1H), 4.64-4.52 (m, 1H), 4.55-4.26 (m, 3H), 4.07-3.96 (m, 1H), 3.88-3.66 (m, 1H), 2.33 (s, 6H), 1.89-1.72 (m, 4H), 1.71-1.56 (m, 1H), 1.50 (d, J = 7.0 Hz, 3H), 1.34 (dd, J = 12.9, 4.3 Hz, 1H), 1.18-1.02 (m, 3H), 0.92-0.72 (m, 2H), 0.36-0.27 (m, 2H), 0.26-0.17 (m, 2H). |
| 219 | 1H NMR (400 MHz, DMSO-d6) δ 8.36 (d, J = 7.8 Hz, 1H), 8.09 (d, J = 8.1 Hz, 1H), 7.95 (s, 2H), 7.84-7.55 (m, 2H), 7.33-7.14 (m, 3H), 5.09 (p, J = 7.1 Hz, 1H), 5.04-4.88 (m, 0.4H), 4.65 (dd, J = 14.1, 6.9 Hz, 1H), 4.57 (dd, J = 14.1, 7.4 Hz, 1H), 4.60-4.45 (m, 1H), 4.24-4.13 (m, 1H), 4.05-3.97 (m, 1H), 3.43-3.04 (m, 2H), 2.86-2.70 (m, 0.6H), 2.32 (d, J = 2.6 Hz, 6H), 2.04-1.41 (m, 9H), 1.20-1.04 (m, 3H), 0.91-0.71 (m, 2H), 0.39-0.17 (m, 4H). |
| 221 | 1H NMR (400 MHz, DMSO-d6) δ 8.08 (d, J = 8.2 Hz, 1H), 7.99 (s, 2H), 7.83 (d, J = 7.6 Hz, 1H), 7.77 (s, 1H), 7.39 (s, 1H), 7.20 (d, J = 8.2 Hz, 1H), 7.05 (s, 1H), 6.91 (s, 1H), 5.09 (p, J = 7.1 Hz, 1H), 5.03-4.95 (m, 0.25H), 4.54-4.43 (m, 2H), 4.29-4.19 (m, 0.35H), 4.14 (s, 3H), 4.00 (s, 3H), 3.89-3.74 (m, 0.33H), 3.48-3.20 (m, 0.2H), 3.18-3.06 (m, 0.2H), 2.87-2.71 (m, 0.5H), 2.04-1.92 (m, 1H), 1.92-1.52 (m, 6H), 1.48 (d, J = 7.0 Hz, 3H), 1.18 (s, 9H), 1.-8-1.11 (m, 1H), 0.36-0.25 (m, 2H), 0.26-0.13 (m, 2H). |
| 222 | 1H NMR (400 MHz, DMSO-d6) δ 8.88 (d, J = 7.7 Hz, 1H), 8.09 (d, J = 8.1 Hz, 1H), 8.00 (br-s, 2H), 7.97-7.92 (m, 2H), 7.77 (br-s, 1H), 7.59-7.53 (m, 1H), 7.53-7.46 (m, 2H), 7.39 (s, 1H), 7.30 (d, J = 8.2 Hz, 1H), 7.05 (s, 1H), 6.91 (s, 1H), 5.33 (p, J = 7.1 Hz, 1H), 5.04-4.95 (m, 0.54H), 4.52 (dd, J = 14.1, 6.9 Hz, 1H), 4.46 (dd, J = 14.1, 7.3 Hz, 1H), 4.24 (m, 0.32H), 4.14 (s, 3H), 4.00 (s, 3H), 3.82 (m, 0.5H), 3.-7-3.21 (m, 1H), 3.14 (m, 0.2H), 2.76 (m, 0.46H), 2.-3-1.94 (m, 1H), 1.90-1.55 (m, 6H), 1.61 (d, J = 7.1 Hz, 3H), 1.21-1.07 (m, 1H), 0.35-0.23 (m, 2H), 0.23-0.15 (m, 2H). |
| 223 | 1H NMR (400 MHz, DMSO-d6) δ 8.34 (d, J = 7.8 Hz, 1H), 8.08 (d, J = 8.1 Hz, 1H), 8.01 (s, 2H), 7.78 (s, 1H), 7.39 (s, 1H), 7.19 (d, J = 8.1 Hz, 1H), 7.05 (s, 1H), 6.91 (s, 1H), 5.10 (p, J = 7.1 Hz, 1H), 5.03-4.96 (m, 0.2H), 4.51 (dd, J = 14.3, 7.0 Hz, 1H), 4.50-4.40 (m, 1H), 4.27-4.19 (m, 0.3H), 4.14 (s, 3H), 4.00 (s, 3H), 3.88-3.76 (m, 0.3H), 3.46-3.22 (m, 1H), 3.18-3.09 (m, 0.2H), 2.86-2.73 (m, 0.5H), 2.32 (d, J = 2.6 Hz, 6H), 2.05-1.92 (m, 1H), 1.90-1.72 (m, 1H), 1.62 (s, 5H), 1.49 (d, J = 7.0 Hz, 3H), 1.22-1.08 (m, 1H), 0.37-0.27 (m, 2H), 0.26-0.17 (m, 2H). |

TABLE 5a-continued

| Ex. | ¹H NMR |
|---|---|
| 224 | 1H NMR (400 MHz, DMSO-d6) δ 8.78 (s, 1H), 8.75 (d, J = 7.8 Hz, 1H), 8.24 (s, 1H), 8.08 (d, J = 8.1 Hz, 1H), 7.96 (br-s, 2H), 7.88 (t, J = 59.0 Hz, 3H), 7.74 (br-s, 1H), 7.39 (s, 1H), 7.26 (d, J = 8.1 Hz, 1H), 7.05 (s, 1H), 6.91 (s, 1H), 5.29 (p, J = 7.0 Hz, 1H), 5.-4–4.95 (m, 0.3H), 4.52 (dd, J = 14.1, 6.8 Hz, 1H), 4.44 (dd, J = 14.1, 7.2 Hz, 1H), 4.28-4.21 (m, 0.38H), 4.13 (s, 3H), 4.00 (s, 3H), 2.83-2.70 (m, 0.34H), 2.04-1.91 (m, 1H), 1.91-1.55 (m, 6H), 1.59 (d, J = 7.0 Hz, 3H), 1.19-1.06 (m, 1H), 0.32-0.08 (m, 4H). (Rotamers, expect 40H, observe 36H, partial signals observed for some missing peaks). |
| 225 | 1H NMR (400 MHz, DMSO-d6) δ 9.17 (d, J = 7.6 Hz, 1H), 8.93 (d, J = 2.4 Hz, 1H), 8.33 (dd, J = 8.3, 2.5 Hz, 1H), 8.09 (d, J = 8.1 Hz, 1H), 7.98 (s, 2H), 7.76 (s, 1H), 7.68 (d, J = 8.3 Hz, 1H), 7.39 (s, 1H), 7.30 (d, J = 8.2 Hz, 1H), 7.06 (s, 1H), 6.91 (s, 1H), 5.33 (p, J = 7.1 Hz, 1H), 5.05-4.95 (m, 0.46H), 4.51 (dd, J = 14.1, 6.8 Hz, 1H), 4.44 (dd, J = 14.1, 7.3 Hz, 1H), 4.28-4.21 (m, 0.59jjH), 4.13 (s, 3H), 4.00 (s, 3H), 3.-8–3.01 (m, 0.56H), 2.85-2.68 (m, 0.46H), 2.04-1.92 (m, 1H), 1.88-1.55 (m, 6H), 1.62 (d, J = 7.0 Hz, 3H), 1.22-1.04 (m, 1H), 0.35-0.11 (m, 4H). |
| 226 | 1H NMR (400 MHz, DMSO-d6) δ 8.85 (d, J = 7.7 Hz, 1H), 8.11 (d, J = 8.1 Hz, 1H), 7.97 (s, 2H), 7.73 (s, 3H), 7.62 (s, 1H), 7.27 (s, 1H), 7.20 (d, J = 8.1 Hz, 1H), 5.13 (p, J = 7.0 Hz, 1H), 5.05-4.88 (m, 0.5H), 4.73-4.57 (m, 0.5H), 4.57-4.40 (m, 1H), 4.29-4.13 (m, 1H), 4.09-3.94 (m, 1H), 2.87-2.65 (m, 3H), 2.06-1.75 (m, 4H), 1.74-1.55 (m, 2H), 1.51 (d, J = 7.0 Hz, 3H), 1.21-1.01 (m, 4H), 0.97-0.62 (m, 2H), 0.36-0.27 (m, 2H), 0.25-0.16 (m, 2H). |
| 227 | 1H NMR (400 MHz, Chloroform-d) δ 8.85 (d, J = 7.7 Hz, 1H), 8.08 (dd, J = 9.4, 5.8 Hz, 3H), 7.92-7.75 (m, 2H), 7.64 (d, J = 23.2 Hz, 1H), 7.26 (s, 1H), 7.20 (d, J = 8.1 Hz, 1H), 5.12 (p, J = 7.0 Hz, 1H), 5.06-4.92 (m, 0.5H), 4.63 (qd, J = 14.2, 7.2 Hz, 2H), 4.56-4.48 (m, 1H), 4.27-4.10 (m, 0.6H), 4.05-3.95 (m, 1H), 3.88-3.70 (m, 0.4H), 3.47-3.25 (m, 1H), 3.22-3.03 (m, 0.4H), 2.85-2.63 (m, 2H), 2.05-1.94 (m, 1H), 1.90-1.74 (m, 3H), 1.72-1.55 (m, 2H), 1.50 (d, J = 7.0 Hz, 3H), 1.19-0.99 (m, 3H), 0.91-0.68 (m, 2H), 0.35-0.27 (m, 2H), 0.24-0.12 (m, 2H). |
| 228 | 1H NMR (400 MHz, DMSO-d6) δ 8.54 (d, J = 7.7 Hz, 1H), 8.08 (d, J = 8.1 Hz, 1H), 8.04-7.90 (m, 2H), 7.76 (s, 1H), 7.39 (s, 1H), 7.18 (d, J = 8.1 Hz, 1H), 7.05 (s, 1H), 6.91 (s, 1H), 5.10 (p, J = 7.1 Hz, 1H), 5.03-4.92 (m, 0.46H), 4.56-4.42 (m, 2H), 4.24 (s, 0.42H), 4.14 (s, 3H), 4.00 (s, 3H), 3.48-3.23 (m, 1H), 3.10-2.96 (m, 1H), 2.81-2.65 (m, 4H), 2.04-1.91 (m, 1H), 1.89-1.70 (m, 2H), 1.72-1.51 (m, 5H), 1.47 (d, J = 7.0 Hz, 3H), 1.21-1.06 (m, 1H), 0.36-0.25 (m, 2H), 0.25-0.10 (m, 2H). |
| 229 | 1H NMR (400 MHz, DMSO-d6) δ 8.33 (d, J = 7.8 Hz, 1H), 8.08 (d, J = 8.1 Hz, 1H), 7.99 (s, 2H), 7.77 (s, 1H), 7.39 (s, 1H), 7.18 (d, J = 8.1 Hz, 1H), 7.05 (s, 1H), 6.91 (s, 1H), 5.08 (p, J = 7.2 Hz, 1H), 5.02-4.96 (m, 0.43H), 4.51 (dd, J = 14.2, 6.9 Hz, 1H), 4.45 (dd, J = 14.2, 7.4 Hz, 1H), 4.28-4.20 (m, 0.37H), 4.14 (s, 3H), 4.00 (s, 3H), 3.48-3.22 (m, 1H), 2.84-2.73 (m, 0.57H), 2.41 (s, 6H), 2.04-1.89 (m, 1H), 1.90-1.72 (m, 2H), 1.73-1.52 (m, 5H), 1.49 (d, J = 7.0 Hz, 3H), 1.23-1.08 (m, 1H), 0.36-0.27 (m, 2H), 0.27-0.13 (m, 2H). |
| 230 | 1H NMR (400 MHz, DMSO-d6) δ 8.39 (d, J = 7.8 Hz, 1H), 8.08 (d, J = 8.1 Hz, 1H), 7.98 (s, 2H), 7.76 (s, 1H), 7.39 (s, 1H), 7.19 (d, J = 8.2 Hz, 1H), 7.05 (s, 1H), 6.91 (s, 1H), 5.10 (p, J = 7.0 Hz, 1H), 5.04-4.94 (m, 0.33H), 4.51 (dd, J = 14.7, 7.5 Hz, 1H), 4.45 (dd, J = 14.2, 7.4 Hz, 1H), 4.29-4.20 (m, 0.38H), 4.14 (s, 3H), 4.00 (s, 3H), 3.46-3.22 (m, 1H), 2.85-2.71 (m, 0.6H), 2.23 (s, 6H), 2.05-1.89 (m, 1H), 1.91-1.73 (m, 2H), 1.73-1.53 (m, 5H), 1.50 (d, J = 7.0 Hz, 3H), 1.23-1.08 (m, 1H), 0.36-0.26 (m, 2H), 0.26-0.17 (m, 2H). |
| 231 | 1H NMR (400 MHz, DMSO-d6) δ 8.42 (d, J = 7.9 Hz, 1H), 8.32 (s, 1H), 8.08 (d, J = 8.1 Hz, 1H), 7.98 (brs, 2H), 7.90 (s, 1H), 7.84-7.56 (m, 2H), 7.34-7.17 (m, 3H), 5.32-5.19 (m, 1H), 4.98 (brs, 0.35H), 4.71-4.4 (m, 2H), 4.18 (brs, 0.65H), 4.04-3.96 (m, 1H), 3.85-3.76 (m, 2H), 3.44-3.09 (m, 1H), 2.73 (brs, 1H), 2.03-1.49 (m, 7H), 1.57 (d, J = 7.0 Hz, 3H), 1.19-0.94 (m, 7H), 0.90-0.72 (m, 2H), 0.35-0.07 (m, 4H). |
| 232 | 1H NMR (400 MHz, DMSO-d6) δ 8.13 (d, J = 8.2 Hz, 1H), 8.00 (s, 1H), 7.80 (d, J = 8.5 Hz, 1H), 7.77 (brs, 1H), 7.72-7.57 (m, 1H), 7.39 (d, J = 8.2 Hz, 1H), 7.27 (s, 1H), 7.25 (brs, 1H), 4.98 (brs, 0.35H), 4.75-4.65 (m, 1H), 4.63 (d, J = 7.1 Hz, 2H), 4.52 (brs, 0.65H), 4.18 (brs, 1H), 4.09-3.97 (m, 2H), 3.47-3.08 (m, 2H), 2.77 (brs, 1H), 2.42-2.31 (m, 1H), 2.08-1.49 (m, 6H), 1.55 (d, J = 7.0 Hz, 3H), 1.22-1.05 (m, 3H), 0.96-0.87 (m, 1H), 0.86-0.76 (m, 4H), 0.74-0.63 (m, 1H), 0.34-0.25 (m, 2H), 0.24-0.16 (m, 2H). |
| 233 | 1H NMR (400 MHz, DMSO-d6) δ 8.42 (d, J = 7.8 Hz, 0.2H), 8.30 (d, J = 7.8 Hz, 0.2H), 8.09 (d, J = 8.1 Hz, 0.2H), 8.09 (d, J = 8.1 Hz, 0.8H), 7.99 (brs, 2H), 7.83-7.53 (m, 3H), 7.26 (s, 1H), 7.25 (brs, 2H), 7.18 (d, J = 8.1 Hz, 0.2H), 7.17 (d, J = 8.1 Hz, 0.8H), 5.12-5.02 (m, 1H), 4.98 (brs, 0.2H), 4.69-4.47 (m, 2H), 4.18 (brs, 0.8H), 4.06-3.96 (m, 1H), 3.49-3.08 (m, 3H), 2.78 (brs, 1H), 2.06-1.35 (m, 8H), 1.49 (d, J = 7.1 Hz, 3H), 1.20-1.03 (m, 4H), 0.89-0.74 (m, 2H), 0.36-0.20 (m, 4H). |
| 236 | 1H NMR (400 MHz, DMSO-d6) δ 8.11 (brs, 3H), 8.07 (d, J = 8.2 Hz, 1H), 7.61 (s, 1H), 7.24 (d, J = 8.2 Hz, 1H), 7.05 (s, 2H), 6.67 (d, J = 8.1 Hz, 1H), 5.51 (brs, 2H), 4.99-4.87 (m, 1H), 4.58-4.35 (m, 3H), 4.14 (s, 3H), 4.06-3.99 (m, 1H), 4.02 (s, 3H), 3.76 (brs, 1H), 3.62 (dt, J = 9.3, 5.0 Hz, 2H), 2.37-2.24 (m, 1H), 1.95-1.68 (m, 3H), 1.68-1.58 (m, 1H), 1.46 (d, J = 7.0 Hz, 3H), 1.35 (dd, J = 12.8, 4.4 Hz, 1H), 1.20-1.05 (m, 1H), 0.36-0.25 (m, 2H), 0.24-0.15 (m 2H). |
| 237 | 1H NMR (400 MHz, DMSO-d6) δ 8.09 (brs, 3H), 7.61 (d, J = 8.0 Hz, 1H), 7.60 (d, J = 7.2 Hz, 1H), 7.18 (d, J = 8.5 Hz, 1H), 7.03 (s, 1H), 6.99 (s, 1H), 6.57 (d, J = 8.2 Hz, 1H), 5.38 (brs, 1H), 5.25 (brs, 1H), 5.05-4.94 (m, 1H), 4.44 (dd, J = 14.7, 6.7 Hz, 1H), 4.35 (dd, J = 14.7, 7.2 Hz, 1H), 4.11 (s, 3H), 4.01 (s, 3H), 3.76 (brs, 1H), 3.68-3.58 (m, 1H), 3.57-3.45 (m, 2H), 3.38 (dd, J = 13.0, 3.5 Hz, 1H), 3.34-3.26 (m, 1H), 2.42-2.28 (m, 1H), 2.21-1.91 (m, 1H), 1.89-1.70 (m, 3H), 1.69-1.56 (m, 1H), 1.47 (d, J = 7.0 Hz, 3H), 1.35 (dd, J = 12.8, 4.3 Hz, 1H), 1.09-1.00 (m, 1H), 0.31 (d, J = 8.0 Hz, 3H), 0.19-0.02 (m, 2H). |
| 238 | 1H NMR (400 MHz, Methanol-d4) δ 7.69 (d, J = 8.3 Hz, 1H), 7.59 (dd, J = 3.3, 1.2 Hz, 2H), 7.22 (dd, J = 8.3, 1.4 Hz, 1H), 7.15 (d, J = 1.3 Hz, 1H), 7.00 (d, J = 0.8 Hz, 1H), 5.06 (q, J = 7.0 Hz, 1H), 4.31 (m, J = 12.3, 1.6 Hz, 6H), 4.18 (s, 3H), 4.10 (s, 3H), 3.91-3.82 (m, 1H), 2.58- |

TABLE 5a-continued

| Ex. | ¹H NMR |
|---|---|
| | 2.47 (m, 1H), 2.05 (d, J = 13.5 Hz, 2H), 1.98-1.87 (m, 1H), 1.76 (t, J = 8.3 Hz, 1H), 1.58 (d, J = 7.0 Hz, 3H), 1.47 (dd, J = 13.2, 4.5 Hz, 1H), 1.01 (s, 1H), 0.36 (dd, J = 7.9, 1.7 Hz, 2H), −0.06 (s, 2H). |
| 246 | 1H NMR (400 MHz, DMSO-d6) δ 8.13-7.96 (m, 4H), 7.60 (s, 1H), 7.07-7.00 (m, 3H), 5.29-5.15 (m, 1H), 4.53-4.34 (m, 3H), 4.14 (s, 3H), 4.01 (s, 3H), 3.98-3.65 (m, 4H), 2.38-2.17 (m, 2H), 2.10-1.53 (m, 6H), 1.34 (dd, J = 12.8, 4.4 Hz, 1H), 1.30-0.92 (m, 11H), 0.35-0.23 (m, 2H), 0.19-0.11 (m, 2H). |
| 247 | 1H NMR (400 MHz, DMSO-d6) δ 8.15-7.99 (m, 4H), 7.61 (s, 1H), 7.13-7.06 (m, 2H), 7.06-6.99 (m, 2H), 5.23-5.11 (m, 1H), 4.57-4.34 (m, 4H), 4.14 (d, J = 5.5 Hz, 3H), 4.01 (s, 3H), 3.85-3.50 (m, 3H), 2.37-2.23 (m, 1H), 2.05 (s, 1.5H), 2.03-1.74 (m, 6H), 1.73 (s, 1.5H), 1.69-1.55 (m, 1H), 1.34 (dd, J = 12.9, 4.4 Hz, 1H), 1.19-1.07 (m, 1H), 0.36-0.25 (m, 2H), 0.25-0.13 (m, 2H). |
| 248 | 1H NMR (400 MHz, DMSO-d6) δ 8.13-8.05 (m, 3H), 8.03 (d, J = 8.1 Hz, 1H), 7.60 (s, 1H), 7.14 (d, J = 8.1 Hz, 1H), 7.07-7.00 (m, 2H), 5.12 (t, J = 7.0 Hz, 1H), 4.56-4.34 (m, 4H), 4.14 (s, 3H), 4.01 (s, 3H), 3.79-3.61 (m, 2H), 3.56 (ddd, J = 10.0, 7.0, 3.9 Hz, 1H), 3.39-3.15 (m, 4H), 2.38-2.26 (m, 2H), 2.02-1.54 (m, 11H), 1.34 (dd, J = 12.9, 4.4 Hz, 1H), 1.18-1.05 (m, 1H), 0.35-0.13 (m, 4H). |
| 249 | 1H NMR (400 MHz, Methanol-d4) δ 8.12 (d, J = 8.3 Hz, 1H), 7.64 (s, 1H), 7.55 (d, J = 8.3 Hz, 1H), 7.24-7.15 (m, 1H), 7.05 (s, 1H), 4.77-4.56 (m, 1H), 4.46 (d, J = 7.0 Hz, 2H), 4.20 (s, 3H), 4.10 (s, 3H), 3.51 (s, 1H), 3.21 (d, J = 16.9 Hz, 2H), 3.04 (d, J = 14.2 Hz, 1H), 2.73 (s, 3H), 2.22-1.97 (m, 1H), 1.93-1.81 (m, 1H), 1.66 (s, 6H), 0.97 (tt, J = 10.9, 3.7 Hz, 1H), 0.42-0.26 (m, 2H), 0.17-0.01 (m, 2H). |
| 250 | 1H NMR (400 MHz, DMSO-d6) δ 8.21 (d, J = 8.1 Hz, 1H), 7.89 (s, 3H), 7.38 (d, J = 8.1 Hz, 1H), 7.35 (d, J = 1.1 Hz, 1H), 7.14 (s, 1H), 6.87 (d, J = 1.2 Hz, 1H), 4.48 (d, J = 7.0 Hz, 2H), 4.13 (s, 3H), 3.98 (s, 3H), 3.26-3.09 (m, 1H), 3.04 (s, 3H), 3.04 (s, 3H), 3.01-2.80 (m, 1H), 1.94-1.65 (m, 3H), 1.65-1.46 (m, 1H), 1.19 (d, J = 6.9 Hz, 3H), 1.15-1.01 (m, 1H), 0.38-0.20 (m, 2H), 0.17--0.00 (m, 2H). |
| 251 | 1H NMR (400 MHz, DMSO-d6) δ 8.77 (q, J = 4.9 Hz, 1H), 8.23 (d, J = 8.1 Hz, 1H), 7.92 (s, 3H), 7.89 (d, J = 8.2 Hz, 1H), 7.35 (d, J = 1.1 Hz, 1H), 7.15 (s, 1H), 6.87 (d, J = 1.2 Hz, 1H), 4.62 (d, J = 7.1 Hz, 2H), 4.13 (s, 3H), 3.98 (s, 3H), 3.16 (s, 1H), 3.05-2.91 (m, 1H), 2.88 (d, J = 4.8 Hz, 3H), 1.93-1.65 (m, 3H), 1.65-1.47 (m, 1H), 1.19 (d, J = 6.8 Hz, 3H), 1.13-0.98 (m, 1H), 0.31-0.19 (m, 2H), 0.18-0.06 (m, 2H). |
| 252 | 1H NMR (400 MHz, DMSO-d6) δ 8.09 (d, J = 8.1 Hz, 1H), 7.91 (s, 3H), 7.50 (d, J = 8.1 Hz, 1H), 7.30 (d, J = 1.1 Hz, 1H), 7.24-7.12 (m, 4H), 7.07 (t, J = 7.2 Hz, 1H), 7.02 (s, 1H), 6.84 (d, J = 1.2 Hz, 1H), 4.15-4.04 (m, 5H), 3.96 (s, 3H), 3.43 (s, 3H), 3.23-3.05 (m, 1H), 3.03-2.86 (m, 1H), 1.93-1.63 (m, 3H), 1.63-1.42 (m, 1H), 1.18 (d, J = 6.8 Hz, 3H), 0.74-0.57 (m, 1H), 0.23-0.06 (m, 2H), −0.06--0.21 (m, 2H). (Missing 2H) |
| 253 | 1H NMR (400 MHz, Methanol-d4) δ 8.39 (d, J = 8.2 Hz, 1H), 7.93 (d, J = 8.2 Hz, 1H), 7.46 (s, 1H), 7.18 (s, 1H), 7.01 (d, J = 1.2 Hz, 1H), 4.52 (d, J = 7.1 Hz, 2H), 4.36 (s, 1H), 4.18 (s, 3H), 4.06 (s, 3H), 3.81 (s, 1H), 3.46-3.33 (m, 3H), 3.32 (s, 3H), 2.25-2.13 (m, 1H), 1.90-1.63 (m, 3H), 1.11-0.97 (m, 1H), 0.41-0.31 (m, 2H), 0.13-0.07 (m, 2H). |
| 272 | 1H NMR (400 MHz, DMSO-d6) δ 8.13-8.01 (m, 1H), 7.88 (s, 4H), 7.45 (d, J = 8.5 Hz, 1H), 7.34 (d, J = 1.1 Hz, 1H), 7.05 (s, 1H), 6.86 (d, J = 1.2 Hz, 1H), 4.42 (d, J = 7.0 Hz, 2H), 4.12 (s, 3H), 3.98 (s, 3H), 3.91 (t, J = 5.9 Hz, 2H), 3.85-3.41 (m, 3H), 3.25-3.10 (m, 1H), 3.04-2.91 (m, 2H), 1.99-1.80 (m, 4H), 1.82-1.66 (m, 2H), 1.67-1.51 (m, 2H), 1.19 (d, J = 7.0 Hz, 3H), 1.17-1.02 (m, 1H), 0.33-0.24 (m, 2H), 0.23-0.09 (m, 2H). |
| 278 | 1H NMR (400 MHz, Methanol-d4) δ 7.94 (d, J = 8.5 Hz, 1H), 7.42 (s, 1H), 7.05 (d, J = 6.1 Hz, 2H), 6.78 (d, J = 8.4 Hz, 1H), 4.40 (d, J = 7.1 Hz, 3H), 4.21 (s, 3H), 4.07 (s, 3H), 3.78 (s, 1H), 3.45-3.31 (m, 3H), 2.26-2.13 (m, 1H), 1.89-1.63 (m, 3H), 1.52 (s, 9H), 1.01-0.88 (m, 1H), 0.36-0.26 (m, 2H), 0.03--0.06 (m, 2H). |
| 279 | 1H NMR (400 MHz, DMSO-d6) δ 8.21 (d, J = 8.7 Hz, 1H), 8.10 (d, J = 8.7 Hz, 1H), 7.97 (s, 3H), 7.33 (d, J = 1.1 Hz, 1H), 7.03 (s, 1H), 6.85 (d, J = 1.2 Hz, 1H), 4.41 (d, J = 7.1 Hz, 3H), 4.11 (d, J = 4.6 Hz, 6H), 3.97 (s, 3H), 3.15 (s, 1H), 2.96 (s, 1H), 2.61 (t, J = 8.0 Hz, 2H), 2.09 (q, J = 7.5 Hz, 2H), 1.93-1.44 (m, 4H), 1.19 (d, J = 6.9 Hz, 4H), 0.30 (dt, J = 7.8, 2.8 Hz, 2H), 0.26-0.12 (m, 2H). |
| 280 | 1H NMR (400 MHz, DMSO-d6) δ 8.10 (d, J = 8.6 Hz, 1H), 8.06 (d, J = 8.7 Hz, 1H), 7.95 (s, 2H), 7.33 (d, J = 1.1 Hz, 1H), 7.04 (s, 1H), 6.85 (d, J = 1.2 Hz, 1H), 4.86 (ddd, J = 8.8, 6.3, 2.7 Hz, 1H), 4.42 (t, J = 8.0 Hz, 5H), 4.13 (s, 3H), 3.98 (s, 3H), 3.16 (s, 1H), 2.96 (s, 1H), 2.77 (dt, J = 17.0, 9.4 Hz, 1H), 2.29 (dq, J = 12.2, 9.4 Hz, 2H), 1.94-1.65 (m, 4H), 1.56 (d, J = 8.7 Hz, 1H), 1.36 (d, J = 6.2 Hz, 3H), 1.19 (d, J = 6.9 Hz, 3H), 0.31 (dd, J = 7.9, 2.0 Hz, 2H), 0.15 (s, 2H). |
| 281 | 1H NMR (400 MHz, DMSO-d6) δ 8.08 (d, J = 8.3 Hz, 1H), 7.91 (s, 3H), 7.34 (d, J = 1.1 Hz, 1H), 7.19 (d, J = 8.3 Hz, 1H), 7.07 (s, 1H), 6.86 (d, J = 1.1 Hz, 1H), 4.50 (dt, J = 14.5, 6.8 Hz, 3H), 4.34 (dd, J = 14.3, 7.6 Hz, 2H), 4.13 (d, J = 1.1 Hz, 3H), 3.98 (s, 5H), 3.16 (s, 1H), 2.95 (s, 1H), 2.39 (dt, J = 17.7, 6.7 Hz, 1H), 1.99-1.64 (m, 6H), 1.19 (d, J = 6.9 Hz, 3H), 1.05 (d, J = 6.4 Hz, 4H), 0.29 (t, J = 6.8 Hz, 2H), 0.22-0.01 (m, 2H). |
| 282 | 1H NMR (400 MHz, DMSO-d6) δ 8.18 (d, J = 8.3 Hz, 1H), 7.90 (s, 4H), 7.77 (t, J = 7.7 Hz, 1H), 7.32 (d, J = 1.2 Hz, 1H), 7.10-7.05 (m, 2H), 6.92 (s, 1H), 6.90 (s, 1H), 6.85 (d, J = 1.2 Hz, 1H), 4.25 (d, J = 7.1 Hz, 3H), 4.13 (s, 4H), 3.97 (s, 5H), 3.05 (d, J = 80.3 Hz, 3H), 2.33 (s, 3H), 1.91-1.47 (m, 6H), 1.18 (d, J = 6.9 Hz, 5H), 1.12-0.96 (m, 1H), 0.33-0.12 (m, 4H). |
| 283 | 1H NMR (400 MHz, DMSO-d6) δ 8.74 (dd, J = 4.8, 1.7 Hz, 1H), 8.12 (dd, J = 7.8, 1.7 Hz, 1H), 8.02 (d, J = 8.1 Hz, 1H), 7.91 (s, 3H), 7.58 (dd, J = 7.8, 4.8 Hz, 1H), 7.35-7.19 (m, 6H), 7.08 (d, J = 8.1 Hz, 1H), 7.05 (s, 1H), 6.86 (d, J = 1.2 Hz, 1H), 4.32 (d, J = 7.1 Hz, 3H), 4.13 (s, 4H), 3.97 (s, 3H), 3.15 (s, 1H), 2.95 (s, 1H), 1.92-1.64 (m, 3H), 1.19 (d, J = 6.9 Hz, 3H), 0.95-0.77 (m, 1H), 0.17 (dd, J = 8.0, 1.9 Hz, 2H). |

TABLE 5a-continued

| Ex. | ¹H NMR |
|---|---|
| 284 | 1H NMR (400 MHz, DMSO-d6) δ 8.10 (d, J = 8.6 Hz, 1H), 8.06 (d, J = 8.7 Hz, 1H), 7.87 (s, 3H), 7.33 (d, J = 1.2 Hz, 1H), 7.04 (s, 1H), 6.85 (d, J = 1.2 Hz, 1H), 4.87 (d, J = 6.2 Hz, 1H), 4.42 (s, 3H), 4.13 (s, 3H), 3.98 (s, 4H), 3.16 (s, 2H), 2.95 (s, 1H), 2.77 (dt, J = 17.0, 9.4 Hz, 1H), 2.29 (dd, J = 11.2, 6.8 Hz, 1H), 1.91-1.44 (m, 5H), 1.36 (d, J = 6.2 Hz, 3H), 1.19 (d, J = 6.9 Hz, 4H), 0.31 (d, J = 7.7 Hz, 2H), 0.15 (d, J = 4.2 Hz, 2H). |
| 285 | 1H NMR (400 MHz, DMSO-d6) δ 8.14-8.03 (m, 2H), 7.88 (s, 3H), 7.33 (d, J = 1.2 Hz, 1H), 7.04 (s, 1H), 6.85 (d, J = 1.2 Hz, 1H), 4.86 (s, 1H), 4.51-4.34 (m, 2H), 3.98 (s, 3H), 3.60-3.55 (m, 1H), 3.15 (s, 1H), 2.95 (s, 2H), 2.77 (dt, J = 17.1, 9.4 Hz, 1H), 2.39-2.21 (m, 1H), 1.86 (s, 1H), 1.74 (tq, J = 6.7, 3.2, 2.8 Hz, 3H), 1.56 (s, 1H), 1.36 (d, J = 6.2 Hz, 3H), 1.22-1.11 (m, 4H), 0.31 (dd, J = 8.0, 2.0 Hz, 2H), 0.15 (s, 2H). |

TABLE 5b

| Ex. | ¹H NMR |
|---|---|
| 287 | 1H NMR (400 MHz, DMSO-d6) δ 8.49 (d, J = 8.3 Hz, 0.2H), 8.31 (d, J = 8.3 Hz, 0.2H), 8.11 (d, J = 8.6 Hz, 0.8H), 7.97 (brs, 2H), 7.76 (brs, 1H), 7.47 (d, J = 8.4 Hz, 0.8H), 7.39 (brs, 1H), 7.18 (s, 0.2H), 7.08 (s, 0.8H), 6.91 (brs, 1H), 5.00 (brs, 0.2H), 4.66 (d, J = 7.0 Hz, 0.4H), 4.56 (brs, 0.8H), 4.44 (d, J = 7.0 Hz, 1.6H), 4.24 (brs, 1H), 4.20 (s, 0.6H), 4.15 (s, 2.4H), 4.02 (s, 0.6H), 4.00 (s, 2.4H), 3.73 (s, 3H), 3.43 (s, 3H), 3.25-2.70 (m, 1H), 2.13-1.50 (m, 7H), 1.36-1.08 (m, 1H), 0.42-0.37 (m, 0.4H), 0.36-0.29 (m, 1.6H), 0.23-0.15 (m, 2H). |
| 288 | 1H NMR (400 MHz, DMSO-d6) δ 8.77 (d, J = 7.9 Hz, 1H), 8.09 (d, J = 8.1 Hz, 1H), 8.00 (brs, 2H), 7.78 (brs, 1H), 7.39 (brs, 1H), 7.22 (d, J = 8.1 Hz, 1H), 7.06 (s, 1H), 6.91 (s, 1H), 5.13-5.03 (m, 1H), 5.01 (brs, 1H), 4.79 (ddd, J = 6.2, 3.1, 1.6 Hz, 1H), 4.63 (ddd, J = 6.1, 3.1, 1.6 Hz, 1H), 4.59-4.42 (m, 2H), 4.23 (brs, 1H), 4.14 (s, 3H), 4.00 (s, 3H), 3.50-3.03 (m, 1H), 2.77 (brs, 1H), 2.36-2.21 (m, 1H), 2.04-1.53 (m, 7H), 1.48 (d, J = 7.0 Hz, 3H), 1.45-1.31 (m, 1H), 1.20-1.06 (m, 1H), 0.37-0.28 (m, 2H), 0.26-0.17 (m, 2H). |
| 289 | 1H NMR (400 MHz, DMSO-d6) δ 8.24 (d, J = 7.3 Hz, 1H), 8.11 (d, J = 8.1 Hz, 1H), 7.97 (brs, 2H), 7.75 (brs, 1H), 7.39 (brs, 1H), 7.22 (d, J = 8.1 Hz, 1H), 7.06 (s, 1H), 6.91 (s, 1H), 5.19-5.08 (m, 1H), 5.00 (brs, 0.6H), 4.60-4.42 (m, 3H), 4.28 (brs, 0.4H), 4.14 (s, 3H), 4.00 (s, 3H), 3.46-3.07 (m, 1H), 2.77 (brs, 1H), 2.01-1.53 (m, 7H), 1.49 (d, J = 6.9 Hz, 3H), 1.44-1.35 (m, 2H), 1.34-1.23 (m, 2H), 1.22-1.08 (m, 1H), 0.38-0.26 (m, 2H), 0.26-0.13 (m, 2H). |
| 290 | 1H NMR (400 MHz, DMSO-d6) δ 8.08 (d, J = 8.0 Hz, 2H), 8.00 (s, 2H), 7.78 (s, 1H), 7.39 (s, 1H), 7.19 (d, J = 8.2 Hz, 1H), 7.05 (s, 1H), 6.91 (s, 1H), 5.07 (p, J = 7.2 Hz, 1H), 5.03-4.93 (m, 0.41H), 4.52 (dd, J = 14.1, 6.8 Hz, 1H), 4.45 (dd, J = 14.2, 7.3 Hz, 1H), 4.29-4.19 (m, 0.38H), 4.14 (s, 3H), 4.00 (s, 3H), 3.87-3.77 (m, 0.32H), 3.49-3.21 (m, 1H), 3.22-3.06 (m, 0.5H), 2.84-2.71 (m, 0.5H), 2.44 (s, 1H), 2.01 (s, 6H), 1.99-1.93 (m, 1H), 1.90-1.74 (m, 2H), 1.73-1.51 (m, 5H), 1.48 (d, J = 6.9 Hz, 3H), 1.16 (s, 1H), 0.37-0.28 (m, 2H), 0.27-0.17 (m, 2H). |
| 291 | ¹H NMR (400 MHz, DMSO-d₆) δ 8.35 (d, J = 7.8 Hz, 1H), 8.11 (d, J = 8.1 Hz, 1H), 8.00 (brs, 2H), 7.77 (brs, 1H), 7.38 (brs, 1H), 7.21 (d, J = 8.1 Hz, 1H), 7.05 (s, 1H), 6.90 (brs, 1H), 5.31-4.95 (m, 3H), 4.54 (brs, 1H), 4.22 (brs, 1H), 4.11 (s, 3H), 3.99 (s, 3H), 2.77 (brs, 1H), 2.31 (d, J = 2.6 Hz, 6H), 2.09-1.52 (m, 8H), 1.48 (d, J = 7.0 Hz, 3H), 0.93-0.74 (m, 4H). |
| 292 | 1H NMR (400 MHz, DMSO-d6) δ 9.05 (d, J = 7.9 Hz, 1H), 8.12 (d, J = 8.1 Hz, 1H), 8.02 (brs, 2H), 7.83-7.79 (m, 1H), 7.78-7.72 (m, 1H), 7.77 (brs, 1H), 7.67 (t, J = 7.6 Hz, 1H), 7.62 (d, J = 7.6 Hz, 1H), 5.00 (brs, 1H), 4.51 (d, J = 7.1 Hz, 2H), 4.24 (brs, 1H), 4.15 (s, 3H), 4.00 (s, 3H), 3.83 (brs, 1H), 3.57-3.06 (m, 3H), 2.78 (brs, 1H), 2.15-1.58 (m, 8H), 1.55 (d, J = 7.0 Hz, 3H), 1.23-1.07 (m, 1H), 0.39-0.26 (m, 2H), 0.24-0.13 (m, 2H). |
| 293 | 1H NMR (400 MHz, DMSO-d6) δ 9.00 (d, J = 7.8 Hz, 1H), 8.12 (d, J = 8.1 Hz, 1H), 8.02 (brs, 2H), 7.79 (brs, 1H), 7.55-7.50 (m, 2H), 7.49-7.40 (m, 2H), 7.39 (brs, 1H), 7.35 (d, J = 8.2 Hz, 1H), 7.06 (s, 1H), 6.91 (s, 1H), 5.33-5.22 (m, 1H), 5.00 (brs, 1H), 4.59-4.46 (m, 2H), 4.24 (brs, 1H), 4.15 (s, 3H), 4.00 (s, 3H), 3.55-3.00 (m, 2H), 2.78 (brs, 1H), 2.05-1.60 (m, 6H), 1.56 (d, J = 7.0 Hz, 3H), 1.22-1.08 (m, 1H), 0.36-0.26 (m, 2H), 0.24-0.15 (m, 2H). |
| 294 | 1H NMR (400 MHz, DMSO-d6) δ 8.97 (d, J = 7.8 Hz, 1H), 8.10 (d, J = 8.1 Hz, 1H), 8.03 (brs, 2H), 7.80 (brs, 1H), 7.67 (dd, J = 7.5, 1.8 Hz, 1H), 7.62 (td, J = 7.8, 1.8 Hz, 1H), 7.54-7.43 (m, 2H), 7.39 (brs, 1H), 7.32 (d, J = 8.2 Hz, 1H), 7.06 (s, 1H), 6.91 (s, 1H), 5.36-5.22 (m, 1H), 5.00 (brs, 1H), 4.57-4.42 (m, 2H), 4.24 (brs, 0.6H), 4.14 (s, 3H), 4.00 (s, 3H), 3.84 (brs, 0.4H), 3.45-3.05 (m, 2H), 2.74 (brs, 1H), 2.09-1.58 (m, 6H), 1.56 (d, J = 7.0 Hz, 3H), 1.22-1.06 (m, 1H), 0.37-0.25 (m, 2H), 0.24-0.13 (m, 2H). |
| 295 | 1H NMR (400 MHz, DMSO-d6) δ 9.30 (d, J = 7.8 Hz, 1H), 8.13 (d, J = 8.2 Hz, 1H), 8.01 (brs, 2H), 7.79 (brs, 1H), 7.59-7.48 (m, 1H), 7.39 (brs, 1H), 7.31 (d, J = 8.1 Hz, 1H), 7.25-7.15 (m, 2H), 7.07 (s, 1H), 6.91 (brs, 1H), 5.33-5.23 (m, 1H), 4.61-4.42 (m, 2H), 4.15 (s, 3H), 4.00 (s, 3H), 3.50-2.97 (m, 2H), 2.08-1.58 (m, 8H), 1.55 (d, J = 7.0 Hz, 3H), 1.26-1.10 (m, 1H), 0.34-0.27 (m, 2H), 0.24-0.14 (m, 2H). |
| 296 | 1H NMR (400 MHz, DMSO-d6) δ 9.38 (d, J = 7.6 Hz, 1H), 8.87 (d, J = 5.0 Hz, 1H), 8.18 (s, 1H), 8.10 (d, J = 8.1 Hz, 1H), 8.03 (dd, J = 5.0, 1.5 Hz, 1H), 7.99 (s, 2H), 7.77 (s, 1H), 7.38 (s, 1H), 7.30 (d, J = 8.1 Hz, 1H), 7.07 (t, J = 54.8 Hz, 1H), 7.06 (s, 1H), 6.91 (s, 1H), 5.35 (p, J = 7.1 Hz, 1H), 5.06-4.93 (m, 0.6H), 4.51 (dd, J = 14.2, 6.9 Hz, 1H), 4.44 (dd, J = 14.1, 7.3 Hz, 1H), 4.29-4.20 (m, 0.34H), 4.13 (s, 3H), 4.00 (s, 3H), 3.85-3.77 (m, 0.46H), 3.46-3.21 (m, 1H), 3.20-3.06 (m, 0.23H), 2.85-2.72 (m, 0.58H), 2.04-1.92 (m, 1H), 1.88-1.77 (m, 2H), 1.63 (d, J = 7.1 Hz, 3H), 1.74-1.50 (m, 5H), 1.19-1.06 (m, 1H), 0.33-0.20 (m, 2H), 0.20-0.11 (m, 2H). |
| 297 | 1H NMR (400 MHz, DMSO-d6) δ 9.25 (d, J = 7.6 Hz, 1H), 9.17 (d, J = 2.1 Hz, 1H), 8.47 (dd, J = 8.1, 2.2 Hz, 1H), 8.10 (d, J = 8.2 Hz, 1H), 8.01 (s, 2H), 7.85 (d, J = 8.1 Hz, 1H), 7.78 (s, 1H), 7.39 (s, 1H), 7.31 (d, J = 8.2 Hz, 1H), 7.06 (s, 1H), 7.06 (t, J = 54.8 Hz, 1H), 6.91 (s, 1H), 5.35 |

TABLE 5b-continued

| Ex. | ¹H NMR |
|---|---|
| | (p, J = 7.1 Hz, 1H), 5.07-4.92 (m, 0.43H), 4.51 (dd, J = 14.1, 6.8 Hz, 1H), 4.44 (dd, J = 14.1, 7.3 Hz, 1H), 4.30-4.19 (m, 0.48H), 4.14 (s, 3H), 4.00 (s, 3H), 3.46-3.22 (m, 1H), 3.20-3.06 (m, 0.25H), 2.84-2.73 (m, 0.6H), 2.07-1.92 (m, 1H), 1.89-1.73 (m, 2H), 1.74-1.50 (m, 8H), 1.21-1.07 (m, 1H), 0.34-0.22 (m, 2H), 0.18 (d, J = 4.2 Hz, 2H). |
| 298 | 1H NMR (400 MHz, DMSO-d6) δ 9.29 (d, J = 7.6 Hz, 1H), 8.59 (d, J = 5.0 Hz, 1H), 8.09 (d, J = 8.1 Hz, 1H), 8.05-7.90 (br-s, 2H), 7.99 (d, J = 1.3 Hz, 1H), 7.84 (dd, J = 5.1, 1.4 Hz, 1H), 7.76 (s, 1H), 7.39 (s, 1H), 7.29 (d, J = 8.2 Hz, 1H), 7.06 (s, 1H), 6.91 (s, 1H), 5.31 (p, J = 7.1 Hz, 1H), 4.99 (s, 0.5H), 4.51 (dd, J = 14.2, 6.9 Hz, 1H), 4.44 (dd, J = 14.1, 7.2 Hz, 1H), 4.28-4.20 (m, 0.5H), 4.13 (s, 3H), 4.00 (s, 3H), 3.86-3.79 (m, 0.42H), 3.45-3.20 (m, 1H), 2.84-2.71 (m, 0.38H), 2.04-1.92 (m, 1H), 1.91-1.73 (m, 2H), 1.72-1.51 (m, 3H), 1.61 (d, J = 7.0 Hz, 3H), 1.21-1.07 (m, 2H), 0.21-0.13 (m, 2H). |
| 299 | ¹H NMR (400 MHz, DMSO-d₆) δ 8.09 (d, J = 8.0 Hz, 1H), 8.08 (d, J = 8.0 Hz, 1H), 7.98 (brs, 2H), 7.75 (brs, 1H), 7.39 (brs, 1H), 7.21 (d, J = 8.1 Hz, 1H), 7.05 (s, 1H), 6.91 (brs, 1H), 5.23-4.90 (m, 2H), 4.61-4.35 (m, 2H), 4.26-4.19 (m, 3H), 4.14 (s, 3H), 4.00 (s, 3H), 4.00-3.90 (m, 3H), 3.52-3.01 (m, 3H), 2.10-1.52 (m, 7H), 1.50 (d, J = 7.0 Hz, 3H), 1.21-1.06 (m, 1H), 0.47-0.12 (m, 4H). |
| 300 | 1H NMR (400 MHz, DMSO-d6) δ 9.04 (d, J = 7.7 Hz, 1H), 9.00 (d, J = 2.2 Hz, 1H), 8.28 (dd, J = 8.3, 2.3 Hz, 1H), 8.09 (d, J = 8.2 Hz, 1H), 7.99 (s, 2H), 7.79 (d, J = 8.3 Hz, 1H), 7.79-7.72 (s, 1H), 7.39 (s, 1H), 7.30 (d, J = 8.2 Hz, 1H), 7.05 (s, 1H), 6.91 (s, 1H), 5.34 (p, J = 6.9 Hz, 1H), 4.51 (dd, J = 14.2, 6.9 Hz, 1H), 4.45 (dd, J = 14.1, 7.3 Hz, 1H), 4.24 (m, 0.35H), 4.14 (s, 3H), 4.00 (s, 4H), 3.82 (s, 0.5H), 3.48-3.22 (m, 1H), 3.19-3.08 (s, 0.2H), 2.83-2.74 (m, 0.5H), 2.04-1.93 (m 1H), 1.89-1.74 (m, 2H), 1.70-1.54 (m, 8H), 1.47 (s, 6H), 1.18-1.07 (m, 1H), 0.34-0.22 (m, 2H), 0.22-0.13 (m, 2H). |
| 301 | 1H NMR (400 MHz, DMSO-d6) δ 8.34 (d, J = 7.9 Hz, 1H), 8.08 (d, J = 8.1 Hz, 1H), 8.00 (brs, 2H), 7.78 (brs, 1H), 7.39 (brs, 1H), 7.18 (d, J = 8.2 Hz, 1H), 7.05 (s, 1H), 6.91 (brs, 1H), 5.16-5.04 (m, 1H), 4.99 (brs, 0.6H), 4.61-4.42 (m, 2.4H), 4.14 (s, 3H), 4.00 (s, 3H), 3.47-3.19 (m, 2H), 2.32 (s, 3H), 2.32 (s, 3H), 2.07-1.55 (m, 6H), 1.49 (d, J = 7.0 Hz, 3H), 1.15 (brs, 1H), 0.38-0.29 (m, 2H), 0.26-0.12 (m, 2H). |
| 302 | 1H NMR (400 MHz, DMSO-d6) δ 9.16 (d, J = 7.8 Hz, 1H), 8.50 (dd, J = 4.8, 1.9 Hz, 1H), 8.12 (d, J = 8.1 Hz, 1H), 8.00 (brs, 2H), 7.97 (dd, J = 7.5, 2.0 Hz, 1H), 7.77 (brs, 1H), 7.53 (dd, J = 7.5, 4.8 Hz, 1H), 7.39 (brs, 1H), 7.35 (d, J = 8.1 Hz, 1H), 7.07 (s, 1H), 6.91 (brs, 1H), 5.34-5.23 (m, 1H), 5.00 (brs, 1H), 4.51 (d, J = 7.1 Hz, 2H), 4.24 (m, 1H), 4.15 (s, 3H), 4.00 (s, 3H), 3.45-3.02 (m, 2H), 2.78 (brs, 1H), 2.04-1.60 (m, 7H), 1.57 (d, J = 7.0 Hz, 3H), 1.15 (brs, 1H), 0.38-0.25 (m, 2H), 0.24-0.15 (m, 2H). |
| 303 | 1H NMR (400 MHz, DMSO-d6) δ 8.60 (d, J = 7.2 Hz, 1H), 8.14 (d, J = 8.1 Hz, 1H), 7.98 (s, 2H), 7.85-7.48 (m, 2H), 7.29 (s, 1H), 7.26 (d, J = 8.2 Hz, 1H), 5.14 (p, J = 7.0 Hz, 1H), 5.06-4.89 (m, 0.37H), 4.64 (d, J = 7.2 Hz, 2H), 4.59-4.47 (m, 0.41H), 4.31-4.10 (m, 0.60H), 4.09-3.95 (m, 1H), 3.95-3.44 (m, 5H), 3.44-3.23 (m, 1H), 3.25-2.99 (m, 0.53H), 2.85-2.70 (m, 0.43H), 2.04-1.91 (m, 1H), 1.92-1.71 (m, 3H), 1.71-1.55 (m, 4H), 1.53 (d, J = 6.9 Hz, 3H), 1.22-1.01 (m, 3H), 0.94-0.69 (m, 2H), 0.39-0.18 (m, 4H). |
| 304 | 1H NMR (400 MHz, DMSO-d6) δ 8.32 (d, J = 7.7 Hz, 1H), 8.08 (d, J = 8.1 Hz, 1H), 8.02 (s, 2H), 7.79 (s, 1H), 7.65 (s, 1H), 7.26 (s, 1H), 7.19 (d, J = 8.1 Hz, 1H), 5.07 (p, J = 7.1 Hz, 1H), 5.02-4.85 (m, 0.48H), 4.63 (h, J = 7.0 Hz, 2H), 4.57-4.42 (m, 0.76H), 4.32-4.12 (m, 0.79H), 4.06-3.97 (m, 1H), 3.92-3.85 (m, 3H), 3.46-3.24 (m, 3H), 3.23-3.10 (m, 0.58H), 2.85-2.69 (m, 0.66H), 2.04-1.91 (m, 1H), 1.89-1.72 (m, 3H), 1.73-1.51 (m, 6H), 1.47 (d, 3H), 1.19-1.03 (m, 4H), 0.94-0.69 (m, 3H), 0.34-0.27 (m, 2H), 0.24-0.10 (m, 2H). |
| 305 | NMR (400 MHz, DMSO-d6) δ 8.44 (d, J = 7.6 Hz, 1H), 7.95 (dd, J = 4.8, 1.6 Hz, 1H), 7.36-7.29 (m, 2H), 6.87 (dd, J = 7.8, 4.9 Hz, 1H), 6.62 (d, J = 1.2 Hz, 1H), 6.53 (d, J = 8.1 Hz, 1H), 6.28 (t, J = 54.4 Hz, 1H), 6.21 (s, 1H), 6.19 (s, 1H), 4.73-4.60 (m, 1H), 4.38 (brs, 1H) 3.95 (brs, 1H), 3.75-3.59 (m, 3H), 3.38 (s, 3H), 3.27 (s, 3H), 2.74 (brs, 1H), 2.16 (brs, 1H), 1.83 (brs, 1H), 1.28-0.92 (m, 9H), 0.89 (d, J = 7.0 Hz, 3H), 0.28-0.09 (m, 1H), −0.46--0.55 (m, 2H), −0.77--0.82 (m, 2H). |
| 306 | 1H NMR (400 MHz, DMSO-d6) δ 8.44 (d, J = 7.8 Hz, 1H), 7.97 (d, J = 4.7 Hz, 1H), 7.31 (d, J = 8.1 Hz, 1H), 7.25 (d, J = 8.1 Hz, 1H), 6.93 (dd, J = 7.9, 4.8 Hz, 1H), 6.62 (s, 1H), 6.53 (d, J = 8.1 Hz, 1H), 6.21 (s, 1H), 6.19 (s, 1H), 4.70-4.59 (m, 1H), 4.38 (brs, 1H), 3.93 (brs, 1H), 3.74-3.62 (m, 2H), 3.38 (s, 3H), 3.28 (s, 3H), 2.74 (s, 1H), 2.17 (s, 1H), 1.84 (brs, 1H), 1.37-0.87 (s, 9H), 0.88 (d, J = 6.9 Hz, 3H), 0.24-0.13 (m, 1H), −0.45--0.53 (m, 2H), −0.78--0.84 (m, 2H). |
| 307 | 1H NMR (400 MHz, DMSO-d6) δ 9.36 (d, J = 7.7 Hz, 1H), 8.26 (d, J = 4.5 Hz, 2H), 8.15 (d, J = 8.0 Hz, 1H), 8.01 (brs, 2H), 7.98-7.93 (m, 1H), 7.78 (brs, 1H), 7.40 (brs, 1H), 7.35 (d, J = 8.0 Hz, 1H), 7.10 (s, 1H), 7.08 (t, J = 54.9 Hz, 1H), 6.92 (brs, 1H), 5.45-5.33 (m, 1H), 5.00 (brs, 0.4H), 4.55 (d, J = 7.1 Hz, 2H), 4.24 (brs, 0.6H), 4.15 (s, 3H), 4.00 (s, 3H), 3.49-3.03 (m, 4H), 2.78 (brs, 1H), 2.05-1.48 (m, 5H), 1.61 (d, J = 6.7 Hz, 3H), 1.22-1.10 (m, 1H), 0.38-0.15 (m, 4H). |
| 308 | 1H NMR (400 MHz, DMSO-d6) δ 9.20 (d, J = 7.6 Hz, 1H), 9.09 (d, J = 2.2 Hz, 1H), 8.33 (dd, J = 8.1, 2.3 Hz, 1H), 8.09 (d, J = 8.1 Hz, 1H), 7.98 (brs, 2H), 7.78 (brs, 1H), 7.73 (d, J = 8.1 Hz, 1H), 7.39 (s, 1H), 7.30 (d, J = 8.2 Hz, 1H), 7.06 (s, 1H), 6.91 (s, 1H), 5.39-5.28 (m, 1H), 5.00 (brs, 0.4H), 4.57-4.39 (m, 2H), 4.24 (brs, 0.6H), 4.13 (s, 3H), 4.00 (s, 3H), 3.85 (brs, 2H), 3.38 (brs, 2H), 3.21 (s, 3H), 2.77 (brs, 1H), 2.09-1.54 (m, 4H), 1.69 (s, 6H), 1.62 (d, J = 7.0 Hz, 3H), 1.31-1.06 (m, 1H), 0.38-0.11 (m, 4H). |
| 309 | 1H NMR (400 MHz, DMSO-d6) δ 9.26 (d, J = 7.6 Hz, 1H), 9.18 (d, J = 2.0 Hz, 1H), 8.47 (dd, J = 8.1, 2.2 Hz, 1H), 8.08 (d, J = 8.1 Hz, 1H), 8.00 (brs, 2H), 7.85 (d, J = 8.2 Hz, 1H), 7.77 (brs, 1H), 7.35 (brs, 1H), 7.17 (s, 1H), 7.05 (t, J = 54.7 Hz, 1H), 6.92 (s, 1H), 5.41-5.29 (m, 1H), 5.00 (brs, 1H), 4.71-4.51 (m, 2H), 4.25 (brs, 1H), 4.00 (s, 3H), 3.96-3.85 (m, 1H), 3.45-2.67 (m, 2H), 2.05-1.46 (m, 6H), 1.64 (d, J = 7.1 Hz, 3H), 1.31-1.18 (m, 1H), 1.15-1.00 (m, 3H), 0.81-0.63 (m, 2H), 0.36-0.11 (m, 4H). |

TABLE 5b-continued

| Ex. | ¹H NMR |
|---|---|
| 310 | ¹H NMR (400 MHz, DMSO-d₆) δ 9.26 (d, J = 7.6 Hz, 1H), 9.18 (d, J = 2.1 Hz, 1H), 8.47 (dd, J = 8.1, 2.2 Hz, 1H), 8.11 (d, J = 8.1 Hz, 1H), 7.99 (brs, 2H), 7.85 (d, J = 8.1 Hz, 1H), 7.76 (brs, 1H), 7.61 (brs, 1H), 7.32 (d, J = 8.2 Hz, 1H), 7.27 (s, 1H), 7.26 (brs, 1H), 7.06 (t, J = 54.8 Hz, 1H), 5.46-5.26 (m, 1H), 4.98 (brs, 1H), 4.75-4.46 (m, 2H), 4.18 (brs, 1H), 4.07-3.97 (m, 1H), 3.76 (brs, 1H), 3.45-3.04 (m, 2H), 2.76 (brs, 1H), 2.03-1.46 (m, 4H), 1.64 (d, J = 7.1 Hz, 3H), 1.20-1.02 (m, 3H), 0.90-0.72 (m, 2H), 0.34-0.12 (m, 4H). |
| 311 | 1H NMR (400 MHz, DMSO-d6) δ 8.84 (d, J = 7.8 Hz, 1H), 8.10 (d, J = 8.2 Hz, 1H), 8.00 (s, 2H), 7.78 (s, 1H), 7.39 (s, 1H), 7.20 (d, J = 8.2 Hz, 1H), 7.06 (s, 1H), 6.91 (s, 1H), 5.13 (p, J = 7.0 Hz, 1H), 5.00 (s, 0.5H), 4.57-4.42 (m, 2H), 4.24 (s, 0.5H), 4.14 (s, 3H), 4.00 (s, 3H), 3.45-3.21 (m, 1H), 3.13 (s, 0.5H), 2.81-2.68 (m, 1H), 2.01-1.79 (m, 2H), 1.65-1.60 (m, 5H), 1.50 (d, J = 7.0 Hz, 3H), 1.15 (s, 1H), 0.36-0.26 (m, 2H), 0.25-0.18 (m, 2H). |
| 312 | 1H NMR (400 MHz, DMSO-d6) δ 8.84 (d, J = 7.8 Hz, 1H), 8.09 (d, J = 8.1 Hz, 1H), 8.02 (s, 2H), 7.79 (s, 1H), 7.39 (s, 1H), 7.21 (d, J = 8.1 Hz, 1H), 7.06 (s, 1H), 6.91 (s, 1H), 5.12 (p, J = 7.1 Hz, 1H), 5.00 (s, 0.5H), 4.58-4.41 (m, 2H), 4.24 (s, 0.5H), 4.14 (s, 3H), 4.00 (s, 3H), 3.47-3.21 (m, 1H), 3.13 (s, 0.5H), 2.79-2.65 (m, 1H), 2.01-1.96 (m, 1H), 1.95-1.77 (m, 2H), 1.63 (s, 5H), 1.50 (d, J = 7.0 Hz, 3H), 1.19-1.10 (m, 1H), 0.36-0.23 (m, 2H), 0.25-0.18 (m, 2H). |
| 313 | 1H NMR (400 MHz, DMSO-d6) δ 9.33 (d, J = 7.6 Hz, 1H), 9.24 (d, J = 2.0 Hz, 1H), 8.55 (dd, J = 8.2, 2.0 Hz, 1H), 8.13-8.05 (m, 2H), 7.98 (s, 2H), 7.76 (s, 1H), 7.39 (s, 1H), 7.32 (d, J = 8.2 Hz, 1H), 7.06 (s, 1H), 6.91 (s, 1H), 5.36 (p, J = 7.2 Hz, 1H), 5.00 (s, 0.5H), 4.56-4.39 (m, 2H), 4.24 (s, 0.5H), 4.14 (s, 3H), 4.00 (s, 3H), 3.46-3.22 (m, 1H), 3.16-3.11 (m, 0.5H), 2.80-2.75 (m, 0.5H), 2.01-1.93 (m, 1H), 1.84-1.79 (m, 3H), 1.64 (d, J = 7.1 Hz, 3H), 1.72-1.57 (m, 3H), 1.16-1.11 (m, 1H), 0.34-0.20 (m, 2H), 0.17 (d, J = 4.2 Hz, 2H). |
| 314 | 1H NMR (400 MHz, DMSO-d6) δ 9.50-9.43 (m, 3H), 8.11 (d, J = 8.1 Hz, 1H), 8.00 (s, 2H), 7.78 (s, 1H), 7.39 (s, 1H), 7.34 (d, J = 8.2 Hz, 1H), 7.07 (s, 1H), 6.91 (s, 1H), 5.37 (p, J = 7.1 Hz, 1H), 5.00 (s, 0.5H), 4.57-4.39 (m, 2H), 4.24 (s, 0.5H), 4.14 (s, 3H), 4.00 (s, 3H), 3.82 (s, 0.5H), 3.45-3.22 (m, 1H), 3.15-3.10 (m, 0.5H), 2.80-2.75 (m, 0.5H), 1.97 (d, J = 11.3 Hz, 1H), 1.84-1.79 (m, 2H), 1.72-1.50 (m, 3H), 1.65 (d, J = 7.0 Hz, 3H), 1.17-1.08 (m, 1H), 0.34-0.20 (m, 2H), 0.20-0.14 (m, 2H). |
| 315 | 1H NMR (400 MHz, DMSO-d6) δ 9.43-9.36 (m, 3H), 8.10 (d, J = 8.1 Hz, 1H), 8.00 (s, 2H), 7.78 (s, 1H), 7.39 (s, 1H), 7.34 (d, J = 8.1 Hz, 1H), 7.08 (t, J = 53.8 Hz, 1H), 7.06 (s, 1H), 6.91 (s, 1H), 5.36 (p, J = 7.1 Hz, 1H), 5.00 (s, 0.5H), 4.57-4.39 (m, 2H), 4.24 (s, 0.5H), 4.14 (s, 3H), 4.00 (s, 3H), 3.48-3.19 (m, 1H), 3.13 (s, 0.5H), 2.77 (s, 0.5H), 2.01-1.93 (m, 1H), 1.84-1.79 (m, 2H), 1.71-1.49 (m, 3H), 1.64 (d, J = 7.1 Hz, 3H), 1.14 (s, 1H), 0.32-0.22 (m, 2H), 0.20-0.15 (m, 2H). |
| 316 | 1H NMR (400 MHz, DMSO-d6) δ 9.55 (d, J = 7.5 Hz, 1H), 9.36 (d, J = 5.0 Hz, 1H), 8.36 (d, J = 5.0 Hz, 1H), 8.17 (d, J = 8.1 Hz, 1H), 8.02 (s, 2H), 7.80 (s, 1H), 7.40 (s, 1H), 7.37 (d, J = 8.1 Hz, 1H), 7.11 (s, 1H), 6.92 (s, 1H), 5.41 (p, J = 6.9 Hz, 1H), 5.01 (s, 0.5H), 4.63-4.47 (m, 2H), 4.27-4.22 (m, 0.5H), 4.15 (s, 3H), 4.00 (s, 3H), 3.46-3.23 (m, 1H), 3.16-3.11 (m, 0.5H), 2.80-2.75 (m, 0.5H), 2.01-1.94 (m, 1H), 1.85-1.80 (m, 2H), 1.69-1.50 (m, 3H), 1.63 (d, J = 6.8 Hz, 3H), 1.20-1.13 (m, 1H), 0.32-0.25 (m, 2H), 0.19-0.08 (m, 2H). |
| 317 | 1H NMR (400 MHz, DMSO-d6) δ 8.36 (d, J = 7.9 Hz, 1H), 8.06 (d, J = 8.1 Hz, 1H), 8.01 (s, 2H), 7.79 (s, 1H), 7.36 (s, 1H), 7.21-7.14 (m, 2H), 6.92 (s, 1H), 5.10 (p, J = 7.2 Hz, 1H), 4.99 (s, 0.5H), 4.69-4.52 (m, 2H), 4.28-4.23 (m, 0.5H), 4.00 (s, 3H), 3.96-3.86 (m, 0.5H), 3.46-3.21 (m, 1H), 3.17-3.12 (m, 0.5H), 2.80-2.75 (m, 0.5H), 2.35-2.30 (m, 6H), 2.01-1.93 (m, 1H), 1.84-1.79 (m, 2H), 1.65-1.60 (m, 4H), 1.50 (d, J = 7.0 Hz, 3H), 1.11-1.02 (m, 3H), 0.74-0.63 (m, 2H), 0.34-0.25 (m, 2H), 0.21-0.15 (m, 2H). |
| 318 | N/A |
| 319 | 1H NMR (400 MHz, DMSO-d6) δ 8.40 (d, J = 7.9 Hz, 1H), 8.31 (s, 1H), 8.06 (d, J = 8.1 Hz, 1H), 7.90 (s, 1H), 7.99-7.65 (m, 3H), 7.38 (s, 1H), 7.24 (d, J = 8.2 Hz, 1H), 7.04 (s, 1H), 6.90 (s, 1H), 5.26 (p, J = 7.2 Hz, 1H), 5.06-4.90 (m, 0.5H), 4.52 (dd, J = 14.1, 6.8 Hz, 1H), 4.44 (dd, J = 14.1, 7.3 Hz, 1H), 4.13 (s, 3H), 3.99 (s, 3H), 3.88-3.69 (m, 1.5H), 3.44-3.04 (m, 1.5H), 2.85-2.70 (m, 0.5H), 2.04-1.46 (m, 9H), 1.19-1.08 (m, 1H), 1.08-0.92 (m, 4H), 0.36-0.12 (m, 4H). |
| 320 | 1H NMR (400 MHz, DMSO-d6) δ 9.05 (s, 1H), 8.80 (d, J = 7.8 Hz, 1H), 8.37 (s, 1H), 8.08 (d, J = 8.1 Hz, 1H), 8.05-7.66 (m, 3H), 7.38 (s, 1H), 7.27 (d, J = 8.1 Hz, 1H), 7.05 (s, 1H), 6.90 (s, 1H), 5.29 (p, J = 7.1 Hz, 1H), 5.07-4.90 (m, 0.5H), 4.62-4.48 (m, 1.5H), 4.43 (dd, J = 14.1, 7.3 Hz, 1H), 4.31-4.18 (m, 0.5H), 4.13 (s, 3H), 3.99 (s, 3H), 3.92-3.71 (m, 0.5H), 3.46-3.01 (m, 1.5H), 2.87-2.69 (m, 0.5H), 2.05-1.42 (m, 9H), 1.21-1.01 (m, 1H), 0.36-0.09 (m, 4H). |
| 321 | 1H NMR (400 MHz, DMSO-d6) δ 8.20 (d, J = 7.8 Hz, 1H), 8.10 (d, J = 8.1 Hz, 1H), 8.06-7.66 (m, 3H), 7.39 (s, 1H), 7.25 (d, J = 8.1 Hz, 1H), 7.06 (s, 1H), 6.91 (s, 1H), 5.10 (p, J = 7.0 Hz, 1H), 5.03-4.94 (m, 0.5H), 4.55-4.42 (m, 2.5H), 4.28-4.20 (m, 0.5H), 4.14 (s, 3H), 3.99 (s, 3H), 3.89-3.76 (m, 0.5H), 3.45-3.03 (m, 1.5H), 3.25 (s, 3H), 2.85-2.66 (m, 0.5H), 2.05-1.41 (m, 9H), 1.33 (s, 3H), 1.28 (s, 3H), 1.23-1.09 (m, 1H), 0.41-0.28 (m, 2H), 0.28-0.14 (m, 2H). |
| 322 | 1H NMR (400 MHz, DMSO-d6) δ 8.44 (d, J = 7.8 Hz, 1H), 8.11 (d, J = 8.1 Hz, 1H), 8.07-7.67 (m, 3H), 7.38 (s, 1H), 7.28 (d, J = 8.1 Hz, 1H), 7.07 (s, 1H), 6.91 (s, 1H), 5.17 (p, J = 7.0 Hz, 1H), 5.08-4.93 (m, 1H), 4.60-4.43 (m, 0.5H), 4.26-4.20 (m, 2.5H), 4.14 (s, 3H), 3.99 (s, 3H), 3.88-3.75 (m, 0.5H), 3.37 (s, 3H), 3.45-3.03 (m, 1.5H), 2.91-2.69 (m, 0.5H), 2.06-1.43 (m, 9H), 1.22-1.12 (m, 1H), 1.12-0.97 (m, 4H), 0.39-0.24 (m, 2H), 0.24-0.12 (m, 2H). |
| 323 | 1H NMR (400 MHz, DMSO-d6) δ 8.15 (d, J = 7.6 Hz, 1H), 8.08 (d, J = 8.1 Hz, 1H), 8.06-7.66 (m, 3H), 7.38 (s, 1H), 7.19 (d, J = 8.1 Hz, 1H), 7.05 (s, 1H), 6.90 (s, 1H), 6.21 (t, J = 56.5 Hz, 1H), 5.12 (p, J = 7.1 Hz, 1H), 5.07-4.93 (m, 0.5H), 4.60-4.41 (m, 2.5H), 4.29-4.18 (m, 0.5H), 4.13 (s, 3H), 3.99 (s, 3H), 3.89-3.72 (m, 0.5H), 3.47-3.03 (m, 1.5H), 2.86-2.67 (m, 0.5H), 2.06-1.44 (m, 10H), 1.26 (s, 3H), 1.25 (s, 3H), 1.20-1.07 (m, 1H), 0.37-0.24 (m, 2H), 0.24-0.10 (m, 2H). |

TABLE 5b-continued

| Ex. | ¹H NMR |
|---|---|
| 324 | 1H NMR (400 MHz, DMSO-d6) δ 8.15-8.06 (m, 2H), 8.06-7.60 (m, 3H), 7.39 (s, 1H), 7.21 (d, J = 8.1 Hz, 1H), 7.06 (s, 1H), 6.90 (s, 1H), 6.37 (t, J = 56.4 Hz, 1H), 5.15 (p, J = 6.9 Hz, 1H), 5.07-4.93 (m, 0.5H), 4.59-4.42 (m, 2.5H), 4.28-4.17 (m, 0.5H), 4.13 (s, 3H), 3.99 (s, 3H), 3.90-3.73 (m, 0.5H), 3.46-3.02 (m, 1.5H), 2.83-2.68 (m, 0.5H), 2.05-1.40 (m, 9H), 1.30-1.20 (m, 2H), 1.20-1.10 (m, 1H), 1.10-0.95 (m, 2H), 0.31 (d, J = 8.0 Hz, 2H), 0.20 (s, 2H). |
| 325 | 1H NMR (400 MHz, DMSO-d6) δ 8.41 (dd, J = 7.9, 3.3 Hz, 1H), 8.10 (d, J = 8.1 Hz, 1H), 8.05-7.89 (m, 2H), 7.84-7.68 (m, 1H), 7.39 (s, 1H), 7.24 (d, J = 8.1 Hz, 1H), 7.06 (s, 1H), 6.90 (s, 1H), 5.12 (p, J = 7.1 Hz, 1H), 5.06-4.93 (m, 0.5H), 4.59-4.38 (m, 3H), 4.28-4.18 (m, 0.5H), 4.13 (s, 3H), 3.99 (s, 3H), 3.88-3.75 (m, 0.5H), 3.45-3.04 (m, 1H), 2.87-2.65 (m, 0.5H), 2.06-1.43 (m, 16H), 1.22-1.10 (m, 1H), 0.37-0.27 (m, 2H), 0.24-0.16 (m, 2H). |
| 326 | 1H NMR (400 MHz, DMSO-d6) δ 8.72 (d, J = 7.9 Hz, 1H), 8.11 (d, J = 8.1 Hz, 1H), 8.06-7.91 (m, 2H), 7.84-7.68 (m, 1H), 7.39 (s, 1H), 7.27 (d, J = 8.1 Hz, 1H), 7.06 (s, 1H), 6.90 (s, 1H), 5.21 (p, J = 7.1 Hz, 1H), 5.05-4.94 (m, 0.5H), 4.60-4.39 (m, 3H), 4.28-4.19 (m, 0.5H), 4.13 (s, 3H), 3.99 (s, 3H), 3.90-3.77 (m, 0.5H), 3.46-3.04 (m, 1H), 2.84-2.69 (m, 0.5H), 2.04-1.48 (m, 10H), 1.41-1.07 (m, 5H), 0.37-0.16 (m, 4H). |
| 327 | 1H NMR (400 MHz, DMSO-d6) δ 8.42 (dd, J = 7.8, 2.5 Hz, 1H), 8.10 (d, J = 8.1 Hz, 1H), 8.03-7.92 (m, 2H), 7.82-7.65 (m, 1H), 7.39 (s, 1H), 7.23 (d, J = 8.1 Hz, 1H), 7.06 (s, 1H), 6.90 (s, 1H), 5.16 (p, J = 7.1 Hz, 1H), 5.05-4.92 (m, 0.5H), 4.58-4.36 (m, 3H), 4.27-4.18 (m, 0.5H), 4.13 (s, 3H), 3.99 (s, 3H), 3.89-3.77 (m, 0.5H), 3.46-3.04 (m, 1H), 2.80-2.63 (m, 0.5H), 2.53-2.26 (m, 4H), 2.02-1.42 (m, 12H), 1.22-1.06 (m, 1H), 0.34-0.28 (m, 2H), 0.26-0.16 (m, 2H). |
| 328 | 1H NMR (400 MHz, DMSO-d6) δ 8.31 (d, J = 7.7 Hz, 1H), 8.08 (d, J = 8.1 Hz, 1H), 8.04-7.88 (m, 2H), 7.82-7.68 (m, 1H), 7.38 (s, 1H), 7.19 (d, J = 8.1 Hz, 1H), 7.04 (s, 1H), 6.90 (s, 1H), 5.09 (p, J = 7.2 Hz, 1H), 5.03-4.95 (m, 0.5H), 4.58-4.41 (m, 4H), 4.28-4.19 (m, 0.5H), 4.13 (s, 3H), 3.99 (s, 3H), 3.87-3.76 (m, 0.5H), 3.45-3.10 (m, 1H), 3.07-2.90 (m, 2H), 2.80-2.70 (m, 0.5H), 2.50-2.38 (m, 2H), 2.03-1.42 (m, 13H), 1.18-1.07 (m, 1H), 0.34-0.26 (m, 2H), 0.23-0.12 (m, 2H). |
| 329 | 1H NMR (400 MHz, DMSO-d6) δ 8.08 (d, J = 8.1 Hz, 1H), 8.01 (d, J = 7.6 Hz, 1H), 7.99-7.90 (m, 2H), 7.80-7.66 (m, 1H), 7.38 (s, 1H), 7.20 (d, J = 8.1 Hz, 1H), 7.04 (s, 1H), 6.90 (s, 1H), 5.12 (p, J = 7.1 Hz, 1H), 5.06-4.94 (m, 0.5H), 4.60-4.41 (m, 3H), 4.28-4.18 (m, 0.5H), 4.13 (s, 3H), 3.99 (s, 3H), 3.86-3.76 (m, 0.5H), 3.42-3.09 (m, 1H), 2.82-2.57 (m, 2.5H), 2.04-1.52 (m, 7H), 1.48 (d, J = 7.0 Hz, 3H), 1.30 (s, 3H), 1.26 (s, 3H), 1.20-1.08 (m, 1H), 0.34-0.28 (m, 2H), 0.22-0.16 (m, 2H)." |
| 330 | 1H NMR (400 MHz, DMSO-d6) δ 8.07 (d, J = 8.1 Hz, 1H), 8.02-7.89 (m, 2H), 7.80 (d, J = 7.7 Hz, 1H), 7.78-7.67 (m, 1H), 7.36 (s, 1H), 7.18 (d, J = 8.2 Hz, 1H), 7.01 (s, 1H), 6.89 (s, 1H), 5.09 (p, J = 7.1 Hz, 1H), 5.03-4.95 (m, 0.5H), 4.71-4.60 (m, 2H), 4.59-4.47 (m, 1H), 4.32-4.17 (m, 0.5H), 4.10 (s, 3H), 3.99 (s, 3H), 3.85-3.75 (m, 0.5H), 3.46-3.02 (m, 1H), 2.81-2.69 (m, 0.5H), 2.05-1.51 (m, 7H), 1.46 (d, J = 7.0 Hz, 3H), 1.17 (s, 9H), 0.94 (s, 3H), 0.87 (s, 3H). |
| 331 | 1H NMR (400 MHz, DMSO-d6) δ 8.54 (d, J = 7.7 Hz, 1H), 8.07 (d, J = 8.1 Hz, 1H), 8.04-7.88 (m, 2H), 7.82-7.65 (m, 1H), 7.38 (s, 1H), 7.19 (d, J = 8.2 Hz, 1H), 7.04 (s, 1H), 6.90 (s, 1H), 5.09 (p, J = 7.1 Hz, 1H), 5.04-4.93 (m, 0.5H), 4.59-4.38 (m, 3H), 4.21-4.11 (m, 0.5H), 4.13 (s, 3H), 3.99 (s, 3H), 3.80-3.60 (m, 0.5H), 3.44-3.02 (m, 1H), 2.86-2.71 (m, 0.5H), 2.09-1.41 (m, 15H), 1.21-1.04 (m, 1H), 0.34-0.24 (m, 2H), 0.24-0.13 (m, 2H)." |
| 332 | 1H NMR (400 MHz, DMSO-d6) δ 8.51 (d, J = 7.7 Hz, 1H), 8.08 (d, J = 8.1 Hz, 1H), 8.04-7.87 (m, 2H), 7.79-7.67 (m, 1H), 7.38 (s, 1H), 7.20 (d, J = 8.1 Hz, 1H), 7.05 (s, 1H), 6.90 (s, 1H), 5.13 (p, J = 7.0 Hz, 1H), 5.03-4.94 (m, 0.5H), 4.58-4.40 (m, 3H), 4.29-4.20 (m, 0.5H), 4.13 (s, 3H), 3.99 (s, 3H), 3.80-3.60 (m, 0.5H), 3.44-3.05 (m, 1H), 2.82-2.70 (m, 0.5H), 2.14-1.41 (m, 15H), 1.19-1.08 (m, 1H), 0.36-0.25 (m, 2H), 0.25-0.15 (m, 2H)." |
| 333 | 1H NMR (400 MHz, DMSO-d6) δ 8.77 (s, 1H), 8.50 (s, 1H), 8.18 (s, 1H), 8.06 (s, 2H), 8.06-7.99 (m, 2H), 7.84 (s, 1H), 7.81 (t, J = 58.9 Hz, 1H), 7.39 (s, 1H), 7.30 (d, J = 8.3 Hz, 1H), 7.03 (s, 1H), 6.91 (s, 1H), 5.10-4.88 (m, 0.40H), 4.67-4.49 (m, 0.49H), 4.44 (d, J = 7.1 Hz, 2H), 4.29-4.19 (m, 0.33H), 4.14 (s, 3H), 4.00 (s, 3H), 3.91-3.69 (m, 0.45H), 3.52-3.01 (m, 2H), 2.96-2.70 (m, 0.47H), 2.06-1.93 (m, 1H), 1.76 (s, 6H), 1.71-1.38 (m, 3H), 1.15 (d, J = 9.8 Hz, 1H), 0.28 (d, J = 7.7 Hz, 2H), 0.25-0.18 (m, 2H). |

Biological Example

Protein Expression and Purification

The open reading frame of human PAD4 (NM_012387), A2-P663, was PCR amplified from a DNA template purchased from OriGene (catalog number RC206501) using Taq polymerase with the following pair of 5' (GCCCAGGGGACATTGATCCGT) (SEQ ID NO: 1) and 3' (TCAGGGCACCATGTTCCACCA) (SEQ ID NO: 2) primer that contains a stop codon. The PCR product was ligated into linearized pET-SUMO vector (Invitrogen, Carlsbad, CA), which is part of the Champion™ pET SUMO Protein Expression System. After sequence verification for the correct orientation, the pET-SUMO-hPAD4 expression plasmid was transformed into BL21(DE3) cells.

E. Coli BL21(DE3) cells were inoculated in LB medium with kanamycin at 37° C. until A600 nm reached about 0.5. Protein expression was induced by addition of 0.5 mM IPTG (final) and continued overnight at 16° C. at 220 rpm.

Cells were harvested by centrifugation at 5000 rpm for 10 minutes at 4° C. The pellet was resuspended in 300 ml lysis buffer (20 mM Tris-HCl, pH 8.0, 1 mM EDTA, 500 mM NaCl, 1 mM (tris(2-carboxyethyl)phosphine) (TCEP), 10% glycerol, and 1% Triton X100 and EDTA free protease inhibitor) and lysed by 3× passage through a microfluidizer (Microfluidics, Newton, MA) at 18,000 psi. The cell lysate was clarified by centrifugation at 30,000 rpm for 60 minutes at 4° C. The supernatant was applied to a 5 ml Ni-HP (GE HealthCare Cat #17524701) column preequilibrated in Ni-A buffer (20 mM Tris-HCl, pH 8.0, 20 mM Imidazole, 1 mM TCEP, 10% glycerol, and 400 mM NaCl). Bound protein was eluted with a 0-100% linear gradient of 100 mL Ni-B buffer (Ni A buffer+0.5 M Imidazole).

The His-Sumo tag was cleaved using sumo protease (Thermo Fisher Cat #: 12588018) while dialyzing in buffer (20 mM Tris-HCl, pH 8.0, 1 mM EDTA, 500 mM NaCl, 1 mM TCEP, 10% glycerol). The protein was then reloaded onto a Ni-HP column for a reverse purification step and recovered in flow through fraction. The protein with His-Sumo tag removed was then polished using a 16/60 Superdex-200 gel filtration column with gel filtration buffer (20 mM Tris pH 8.0, NaCl 400 mM and 1 mM TCEP). The fractions containing the protein were pulled and frozen at −80° C.

In Vitro PAD4 BAEE Biochemical Assay

The enzymatic activity of human PAD4 was monitored in a biochemical assay in the presence or absence of compounds using the small peptidyl arginine mimic BAEE (Nα-Benzoyl-L-arginine ethyl ester hydrochloride) as substrate. PAD4 activity led to deimination of BAEE and release of ammonia. Levels of ammonia were monitored by using an amine coupling reaction and were indicative of PAD4 enzymatic activity.

One hundred nanoliters of test compounds dissolved in DMSO at various concentrations were dispensed into a 384-well black OptiPlate using a Labcyte Echo instrument. Ten microliters of a solution of recombinant PAD4 and calcium chloride diluted in PAD4 assay buffer (50 mM MOPS [3-(N-morpholino) propanesulfonic acid], pH 7.6; 50 mM sodium chloride; 0.05% Tween-20; 2 mM dithiothreitol) was added to the compound-containing plate and was incubated for 30 minutes at 25° C. Ten microliters of a solution of BAEE (Sigma-Aldrich #B4500) diluted in PAD4 assay buffer was then added to start the reaction. Final concentrations were 5 nM PAD4, 2 mM calcium chloride, and 3 mM BAEE. The reaction mixture was incubated at 25° C. for 2 hours and was stopped with the addition of 10 microliters of a solution of 75 mM EDTA (Ethylenediaminetetraacetic acid) in PAD4 assay buffer. Thirty microliters of detection solution (5 mM o-phthalaldehyde, 50 mM MOPS [3-(N-morpholino) propanesulfonic acid], pH 7.6; 50 mM sodium chloride; 0.05% Tween-20; 5 mM dithiothreitol) was then added and the reaction was incubated for 1 hour at 25° C. The level of fluorescent thiol-substituted isoindole resulting from the reaction of ammonia, o-phthalaldehyde, and dithiothreitol was measured on an Envision plate reader (PerkinElmer) with 405 nm excitation and 535 nm emission.

Data were normalized based on maximum inhibition (50 micromolar of the covalent PAD inhibitor BB-Cl-Amidine (Bicker, K. L.; Anguish, L.; Chumanevich, A. A.; Cameron, M. D.; Cui, X.; Witalison, E.; Subramanian, V.; Zhang, X.; Chumanevich, A. P.; Hofseth, L. J.; Coonrod, S. A.; Thompson, P. R. ACS Med. Chem. Lett. 2012, 3, 1081-1085). and no inhibition (DMSO) controls. Least squares curve fittings were performed using a four-parameter variable slope non-linear regression model. $IC_{50}$ is defined as the concentration of compound required to inhibit 50% of maximum activity. $IC_{50}$ values from multiple experiments were averaged by geometric mean and the standard deviation was calculated. Data is shown in Tables 6a and 6b.

TABLE 6a

| Ex. | PAD4 $IC_{50}$ (nM) |
|---|---|
| 1 | 1580 |
| 2 | 210 |
| 3 | 122 |
| 4 | 149 |
| 5 | 78.6 |
| 6 | 59.5 |
| 7 | 164 |
| 8 | 190 |
| 9 | 238 |
| 10 | 330 |
| 11 | 192 |
| 12 | 225 |
| 13 | 3570 |
| 14 | 249 |
| 15 | 136 |
| 16 | 316 |
| 17 | 88.5 |
| 18 | 83.0 |
| 19 | 181 |
| 20 | 50000 |
| 21 | 50000 |
| 23 | 125 |
| 24 | 124 |
| 25 | 82.0 |
| 26 | 106 |
| 27 | 92.7 |
| 28 | 98.6 |
| 29 | 173 |
| 30 | 88.2 |
| 31 | 110 |
| 32 | 92.6 |
| 33 | 77.3 |
| 34 | 300 |
| 35 | 141 |
| 36 | 11300 |
| 37 | 235 |
| 38 | 93.4 |
| 39 | 184 |
| 40 | 329 |
| 41 | 229 |
| 42 | 221 |
| 43 | 4180 |
| 44 | 81.3 |
| 45 | 110 |
| 46 | 1160 |
| 47 | 1730 |
| 48 | 2130 |
| 49 | 487 |
| 50 | 145 |
| 51 | 141 |
| 52 | 12700 |
| 53 | 214 |
| 54 | 37.4 |
| 55 | 89.6 |
| 56 | 36.2 |
| 57 | 11200 |
| 58 | 4340 |
| 59 | 9410 |
| 60 | 2210 |
| 61 | 36800 |
| 62 | 1540 |
| 63 | 45.1 |
| 64 | 128 |
| 65 | 47.0 |
| 66 | 21700 |
| 67 | 5080 |
| 68 | 50000 |
| 69 | 50000 |
| 70 | 39400 |
| 71 | 490 |
| 72 | 20900 |
| 73 | 7200 |
| 74 | 50000 |
| 75 | 50000 |
| 76 | 50000 |
| 77 | 50000 |
| 78 | 655 |
| 79 | 33.6 |
| 80 | 240 |
| 81 | 4630 |
| 82 | 47600 |
| 83 | 50000 |

TABLE 6a-continued

| Ex. | PAD4 IC$_{50}$ (nM) |
|---|---|
| 84 | 58.3 |
| 85 | 69.8 |
| 86 | 10200 |
| 87 | 1160 |
| 88 | 50000 |
| 89 | 812 |
| 90 | 214 |
| 91 | 50000 |
| 92 | 617 |
| 93 | 146 |
| 94 | 26400 |
| 95 | 1570 |
| 96 | 1050 |
| 97 | 159 |
| 98 | 18.9 |
| 99 | 28.4 |
| 100 | 55.5 |
| 101 | 43.4 |
| 102 | 42.0 |
| 103 | 22.3 |
| 104 | 79.3 |
| 105 | 29.6 |
| 106 | 434 |
| 107 | 538 |
| 108 | 5760 |
| 109 | 401 |
| 110 | 509 |
| 111 | 234 |
| 112 | 5150 |
| 113 | 196 |
| 114 | 34.5 |
| 115 | 379 |
| 116 | 496 |
| 117 | 1120 |
| 118 | 45.6 |
| 119 | 78.4 |
| 120 | 60.6 |
| 121 | 46.3 |
| 122 | 93.9 |
| 123 | 29.2 |
| 124 | 54.6 |
| 125 | 71.3 |
| 126 | 90.8 |
| 127 | 63.7 |
| 128 | 61.5 |
| 129 | 86.0 |
| 130 | 45.1 |
| 131 | 25.9 |
| 132 | 70.7 |
| 133 | 32.2 |
| 134 | 18.2 |
| 135 | 13.0 |
| 136 | 27.6 |
| 137 | 37.2 |
| 138 | 27.6 |
| 139 | 28.9 |
| 140 | 26.1 |
| 141 | 63.3 |
| 142 | 44.5 |
| 143 | 502 |
| 144 | 229 |
| 145 | 62.8 |
| 146 | 45.8 |
| 147 | 78.9 |
| 148 | 123 |
| 149 | 95.4 |
| 150 | 116 |
| 151 | 102 |
| 152 | 63.0 |
| 153 | 102 |
| 154 | 89.7 |
| 155 | 165 |
| 156 | 166 |
| 157 | 87.4 |
| 158 | 76.2 |
| 159 | 229 |
| 160 | 481 |
| 161 | 72.3 |
| 162 | 92.1 |
| 163 | 4050 |
| 164 | 148 |
| 165 | 91.4 |
| 166 | 180 |
| 167 | 388 |
| 168 | 102 |
| 169 | 47.8 |
| 170 | 67.1 |
| 171 | 90.2 |
| 172 | 147 |
| 173 | 96.7 |
| 174 | 45.1 |
| 175 | 139 |
| 176 | 231 |
| 177 | 90.8 |
| 178 | 80.4 |
| 179 | 77.5 |
| 180 | 28.8 |
| 181 | 74.9 |
| 182 | 104 |
| 183 | 198 |
| 184 | 204 |
| 185 | 82.1 |
| 186 | 105 |
| 187 | 96.9 |
| 188 | 149 |
| 189 | 92.2 |
| 190 | 89.7 |
| 191 | 82.4 |
| 192 | 174 |
| 193 | 142 |
| 194 | 123 |
| 195 | 102 |
| 196 | 129 |
| 197 | 116 |
| 198 | 166 |
| 199 | 340 |
| 200 | 64.2 |
| 201 | 67.7 |
| 202 | 58.7 |
| 203 | 155 |
| 204 | 47.4 |
| 205 | 79.7 |
| 206 | 45.5 |
| 207 | 240 |
| 208 | 138 |
| 209 | 199 |
| 210 | 129 |
| 211 | 92.0 |
| 212 | 170 |
| 213 | 134 |
| 214 | 100 |
| 215 | 111 |
| 216 | 158 |
| 220 | 54.9 |
| 221 | 61 |
| 222 | 53.5 |
| 223 | 57.2 |
| 224 | 48.1 |
| 225 | 48.1 |
| 226 | 53.2 |
| 227 | 46.8 |
| 228 | 82.3 |
| 229 | 83.3 |
| 230 | 127 |
| 234 | 34.3 |
| 235 | 40.2 |
| 236 | 51.3 |
| 237 | 18.5 |
| 238 | 28.7 |
| 239 | 166 |
| 240 | 65.6 |
| 241 | 76.7 |
| 242 | 107 |
| 243 | 52.8 |
| 244 | 49.3 |
| 245 | 31.7 |

TABLE 6a-continued

| Ex. | PAD4 IC$_{50}$ (nM) |
|---|---|
| 246 | 48.4 |
| 247 | 36.7 |
| 248 | 40.5 |
| 249 | 227 |
| 250 | 874 |
| 251 | 1720 |
| 252 | 1820 |
| 253 | 797 |
| 254 | 550 |
| 255 | 40.2 |
| 256 | 1330 |
| 257 | 1360 |
| 258 | 245 |
| 259 | 1830 |
| 260 | 364 |
| 261 | 457 |
| 262 | 584 |
| 263 | 687 |
| 264 | 1870 |
| 265 | 269 |
| 266 | 346 |
| 267 | 138 |
| 268 | 386 |
| 269 | 324 |
| 270 | 351 |
| 271 | 134 |
| 272 | 785 |
| 273 | 2330 |
| 274 | 4910 |
| 275 | 658 |
| 276 | 423 |
| 277 | 3430 |
| 278 | 9340 |
| 279 | 1180 |
| 280 | 531 |
| 281 | 643 |
| 282 | 146 |
| 283 | 320 |
| 284 | 1240 |
| 285 | 322 |

TABLE 6b

| Ex. | PAD4 IC$_{50}$ (nM) |
|---|---|
| 219 | 78.6 |
| 231 | 55.9 |
| 232 | 89.8 |

TABLE 6b-continued

| Ex. | PAD4 IC$_{50}$ (nM) |
|---|---|
| 233 | 78.2 |
| 287 | 106 |
| 288 | 70.8 |
| 289 | 174 |
| 290 | 79.2 |
| 291 | 91.9 |
| 292 | 128 |
| 293 | 80.7 |
| 294 | 277 |
| 295 | 65.5 |
| 296 | 74.1 |
| 297 | 65.9 |
| 298 | 86.4 |
| 299 | 74.3 |
| 300 | 72 |
| 301 | 65.8 |
| 302 | 68.4 |
| 303 | 84.1 |
| 304 | 48.6 |
| 305 | 72.7 |
| 306 | 92.8 |
| 307 | 382 |
| 308 | 66.2 |
| 309 | 111 |
| 310 | 89.7 |
| 311 | 67.6 |
| 312 | 55.9 |
| 313 | 113 |
| 314 | 140 |
| 315 | 81.3 |
| 316 | 570 |
| 317 | 124 |
| 318 | 252 |
| 319 | 58 |
| 320 | 82.6 |
| 321 | 72 |
| 322 | 62 |
| 323 | 84.6 |
| 324 | 81.1 |
| 325 | 91.8 |
| 326 | 103 |
| 327 | 88.4 |
| 328 | 101 |
| 329 | 129 |
| 330 | 253 |
| 331 | 71 |
| 332 | 84.2 |
| 333 | |

What is claimed is:

1. A compound of Formula I:

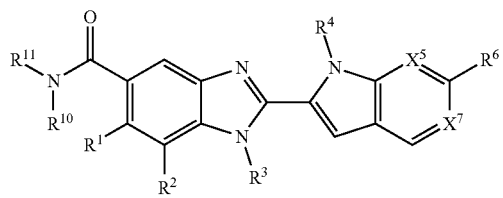

I or a pharmaceutically acceptable salt thereof, wherein:

$X^5$ is N or C-$R^5$;

$X^7$ is N or C-$R^7$;

$R^1$ is hydrogen, halo, —CN, —O$R^{12}$, —N($R^{12}$)$_2$, —S$R^{12}$, —C$_{1-8}$ alkyl optionally substituted with 1 to 3 $Z^1$, C$_{3-6}$ cycloalkyl optionally substituted with 1 to 3 $Z^1$, or 4-6 membered heterocyclyl optionally substituted with 1 to 3 $Z^1$;

$R^2$ is hydrogen, halo, —CN, —O$R^{12}$, —N($R^{12}$)$_2$, —S$R^{12}$, —C$_{1-8}$ alkyl optionally substituted with 1 to 3 $Z^1$, C$_{3-6}$ cycloalkyl optionally substituted with 1 to 3 $Z^1$, or 4-6 membered heterocyclyl optionally substituted with 1 to 3 $Z^1$;

$R^3$ is hydrogen, C$_{1-8}$ alkyl optionally substituted with 1 to 3 $Z^1$, C$_{3-10}$ alkenyl optionally substituted with 1 to 3 $Z^1$, C$_{3-10}$ alkynyl optionally substituted with 1 to 3 $Z^1$, C$_{3-10}$ cycloalkyl optionally substituted with 1 to 3 $Z^1$, or 4-10 membered heterocyclyl optionally substituted with 1 to 3 $Z^1$; or $R^2$ and $R^3$ are taken together with the atoms to which they are attached to form an optionally substituted 6 to 8 membered heterocyclyl ring;

R4 is hydrogen, C$_{1-8}$ alkyl optionally substituted with 1 to 3 $Z^1$, C$_{3-10}$ alkenyl optionally substituted with 1 to 3 $Z^1$, C$_{3-10}$ alkynyl optionally substituted with 1 to 3 $Z^1$, C$_{3-10}$ cycloalkyl optionally substituted with 1 to 3 Z', or 4-10 membered heterocyclyl optionally substituted with 1 to 3 $Z^1$;

$R^5$ is hydrogen, halo, —CN, or —O$R^{12}$;

$R^6$ is

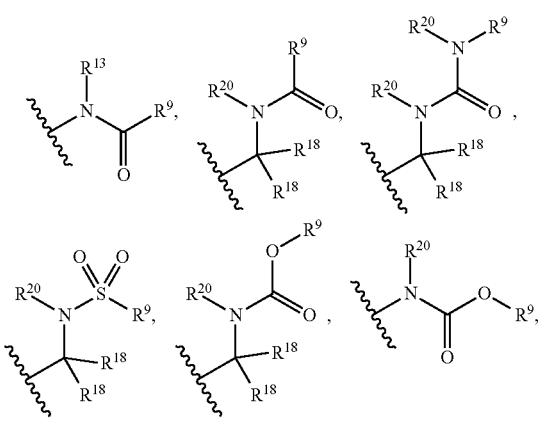

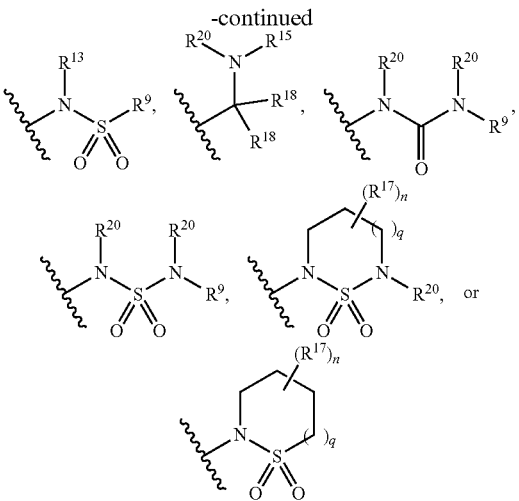

where q is 0, 1 or 2, and n is 0, 1, 2, 3, 4, 5, or 6;

$R^7$ is hydrogen, halo, —CN, or —O$R^{12}$;

$R^9$ is C$_{1-8}$ alkyl optionally substituted with 1 to 3 $Z^1$, C2-8 alkenyl optionally substituted with 1 to 3 $Z^1$, C2-8 alkynyl optionally substituted with 1 to 3 $Z^1$, C$_{3-10}$ cycloalkyl optionally substituted with 1 to 3 $Z^1$, 4-10 membered heterocyclyl optionally substituted with 1 to 3 $Z^1$, C$_{6-10}$ aryl optionally substituted with 1 to 3 $Z^1$, or 5-10 membered heteroaryl optionally substituted with 1 to 3 $Z^1$;

$R^{10}$ is hydrogen, C$_{1-8}$ alkyl optionally substituted with 1 to 3 $Z^{10}$, or C$_{3-6}$ cycloalkyl optionally substituted with 1 to 3 $Z^{10}$;

$R^{11}$ is hydrogen, C$_{1-8}$ alkyl optionally substituted with 1 to 4 $Z^{10}$, C$_{3-8}$ cycloalkyl optionally substituted with 1 to 4 $Z^{10}$, or 4-12-membered heterocyclyl optionally substituted with 1 to 4 $Z^{10}$; or $R^{10}$ and $R^{11}$ are taken together with the nitrogen to which they are attached to form a 4-12-membered heterocyclyl optionally substituted with 1 to 4 $Z^{10}$;

each $R^{12}$ is independently hydrogen, C$_{1-8}$ alkyl optionally substituted with 1 to 3 $Z^{1b}$, C$_{3-8}$ alkenyl optionally substituted with 1 to 3 $Z^{1b}$, C$_{3-8}$ alkynyl optionally substituted with 1 to 3 $Z^{1b}$, C$_{3-10}$ cycloalkyl optionally substituted with 1 to 3 $Z^{1b}$, 4-10 membered heterocyclyl optionally substituted with 1 to 3 $Z^{1b}$, C6-10 aryl optionally substituted with 1 to 3 $Z^{1b}$, or 5-10 membered heteroaryl optionally substituted with 1 to 3 $Z^{1b}$;

$R^{13}$ is C$_{1-8}$ alkyl optionally substituted with 1 to 3 $Z^{1b}$, C$_{3-8}$ alkenyl optionally substituted with 1 to 3 $Z^{1b}$, C$_{3-8}$ alkynyl optionally substituted with 1 to 3 $Z^{1b}$, C$_{3-10}$ cycloalkyl optionally substituted with 1 to 3 $Z^{1b}$, 4-10 membered heterocyclyl optionally substituted with 1 to 3 $Z^{1b}$, C$_{6-10}$ aryl optionally substituted with 1 to 3 $Z^{1b}$, or 5-10 membered heteroaryl optionally substituted with 1 to 3 $Z^{1b}$;

$R^{15}$ is $C_{6-10}$ aryl optionally substituted with 1 to 3 $Z^1$ or 5-10 membered heteroaryl optionally substituted with 1 to 3 $Z^1$;

each $R^{17}$ is independently hydrogen, halo, —$NO_2$, —$N_3$, —CN, $C_{1-8}$ alkyl optionally substituted by 1 to 3 $Z^{1a}$, $C_{2-8}$ alkenyl optionally substituted by 1 to 3 $Z^{1a}$, $C_{2-8}$ alkynyl optionally substituted by 1 to 3 $Z^{1a}$, $C_{3-8}$ cycloalkyl optionally substituted by 1 to 3 $Z^{1a}$, 6-10 membered aryl optionally substituted by 1 to 3 $Z^{1a}$, 4-10 membered heterocyclyl optionally substituted by 1 to 3 $Z^{1a}$, 5-10 membered heteroaryl optionally substituted with 1 to 3 $Z^{1a}$, —$OR^{20}$, —$C(O)R^{20}$, —$C(O)OR^{20}$, —$C(O)N(R^{20})_2$, —$N(R^{20})_2$, —$N(R^{20})_3^+$, —$N(R^{20})C(O)R^{20}$, —$N(R^{20})C(O)OR^{20}$, —$N(R^{20})C(O)N(R^{20})_2$, —$N(R^{20})S(O)_2(R^{20})$, —$NR^{20}S(O)_2N(R^{20})_2$, —$NR^{20}S(O)_2O(R^{20})$, —$NS(O)(R^{20})_2$, —$OC(O)R^{20}$, —$OC(O)OR^{20}$, —$OC(O)N(R^{20})_2$, —$Si(R^{20})_3$, —$SR^{20}$, —$S(O)R^{20}$, —$SF_5$, —$S(O)(NR^{20})R^{20}$, —$S(NR^{20})(NR^{20})R^{20}$, —$S(O)(NR^{20})N(R^{20})_2$, —$S(O)(NCN)R^{20}$, —$S(O)_2R^{20}$, —$S(O)_2N(R^{20})_2$, —$C(O)N(R^{20})S(O)_2R^{20}$, or —$S(O)_2N(R^{20})C(O)R^{20}$; or two $R^{17}$ on the same or different carbon atoms are taken together to form a 3-8-membered ring optionally substituted with 1 to 4 $Z^1$;

each $R^{18}$ independently hydrogen, halo, —$NO_2$, —$N_3$, —CN, $C_{1-8}$ alkyl optionally substituted by 1 to 3 $Z^{1a}$, $C_{2-8}$ alkenyl optionally substituted by 1 to 3 $Z^{1a}$, $C_{2-8}$ alkynyl optionally substituted by 1 to 3 $Z^{1a}$, $C_{3-8}$ cycloalkyl optionally substituted by 1 to 3 $Z^{1a}$, 6-10 membered aryl optionally substituted by 1 to 3 $Z^{1a}$, 4-10 membered heterocyclyl optionally substituted by 1 to 3 $Z^{1a}$, 5-10 membered heteroaryl optionally substituted with 1 to 3 $Z^{1a}$, —$OR^{20}$, —$C(O)R^{20}$, —$C(O)OR^{20}$, —$C(O)N(R^{20})_2$, —$N(R^{20})_2$, —$N(R^{20})_3^+$, —$N(R^{20})C(O)R^{20}$, —$N(R^{20})C(O)OR^{20}$, —$N(R^{20})C(O)N(R^{20})_2$, —$N(R^{20})S(O)_2(R^{20})$, —$NR^{20}S(O)_2N(R^{20})_2$, —$NR^{20}S(O)_2O(R^{20})$, —$NS(O)(R^{20})_2$, —$OC(O)R^{20}$, —$OC(O)OR^{20}$, —$OC(O)N(R^{20})_2$, —$Si(R^{20})_3$, —$SR^{20}$, —$S(O)R^{20}$, —$SF_5$, —$S(O)(NR^{20})R^{20}$, —$S(NR^{20})(NR^{20})R^{20}$, —$S(O)(NR^{20})N(R^{20})_2$, —$S(O)(NCN)R^{20}$, —$S(O)_2R^{20}$, —$S(O)_2N(R^{20})_2$, —$C(O)N(R^{20})S(O)_2R^{20}$, or —$S(O)_2N(R^{20})C(O)R^{20}$;

each $Z^1$ is independently halo, —$NO_2$, —$N_3$, —CN, $C_{1-8}$ alkyl optionally substituted by 1 to 3 $Z^{1a}$, $C_{2-8}$ alkenyl optionally substituted by 1 to 3 $Z^{1a}$, $C_{2-8}$ alkynyl optionally substituted by 1 to 3 $Z^{1a}$, $C_{3-8}$ cycloalkyl optionally substituted by 1 to 3 $Z^{1a}$, 6-10 membered aryl optionally substituted by 1 to 3 $Z^{1a}$, 4-10 membered heterocyclyl optionally substituted by 1 to 3 $Z^{1a}$, 5-10 membered heteroaryl optionally substituted with 1 to 3 $Z^{1a}$, —$OR^{20}$, —$C(O)R^{20}$, —$C(O)OR^{20}$, —$C(O)N(R^{20})_2$, —$N(R^{20})_2$, —$N(R^{20})_3^+$, —$N(R^{20})C(O)R^{20}$, —$N(R^{20})C(O)OR^{20}$, —$N(R^{20})C(O)N(R^{20})_2$, —$N(R^{20})S(O)_2(R^{20})$, —$NR^{20}S(O)_2N(R^{20})_2$, —$NR^{20}S(O)_2O(R^{20})$, —$NS(O)(R^{20})_2$, —$OC(O)R^{20}$, —$OC(O)OR^{20}$, —$OC(O)N(R^{20})_2$, —$Si(R^{20})_3$, —$S(O)R^{20}$, —$SF_5$, —$S(O)(NR^{20})R^{20}$, —$S(NR^{20})(NR^{20})R^{20}$, —$S(O)(NR^{20})N(R^{20})_2$, —$S(O)(NCN)R^{20}$, —$S(O)_2R^{20}$, —$S(O)_2N(R^{20})_2$, —$C(O)N(R^{20})S(O)_2R^{20}$, or —$S(O)_2N(R^{20})C(O)R^{20}$;

each $Z^{1a}$ is independently oxo, halo, —$NO_2$, —$N_3$, —CN, $C_{1-8}$ alkyl optionally substituted by 1 to 3 $Z^{1b}$, $C_{2-8}$ alkenyl optionally substituted by 1 to 3 $Z^{1b}$, $C_{2-8}$ alkynyl optionally substituted by 1 to 3 $Z^{1b}$, $C_{3-8}$ cycloalkyl optionally substituted by 1 to 3 $Z^{1b}$, 6-10 membered aryl optionally substituted by 1 to 3 $Z^{1b}$, 4-10 membered heterocyclyl optionally substituted by 1 to 3 $Z^{1b}$, 5-10 membered heteroaryl optionally substituted with 1 to 3 $Z^{1b}$, —$OR^{21}$, —$C(O)R^{21}$, —$C(O)OR^{21}$, —$C(O)N(R^{21})_2$, —$N(R^{21})_2$, —$N(R^{21})_3^+$, —$N(R^{21})C(O)R^{21}$, —$N(R^{21})C(O)OR^{21}$, —$N(R^{21})C(O)N(R^{21})_2$, —$N(R^{21})S(O)_2(R^{21})$, —$NR^{21}S(O)_2N(R^{21})_2$, —$NR^{21}S(O)_2O(R^{21})$, —$NS(O)(R^{21})_2$, —$OC(O)R^{21}$, —$OC(O)OR^{21}$, —$OC(O)N(R^{21})_2$, —$Si(R^{21})_3$, —$SR^{21}$, —$S(O)R^{21}$, —$SF_5$, —$S(O)(NR^{21})R^{21}$, —$S(NR^{21})(NR^{21})R^{21}$, —$S(O)(NR^{21})N(R^{21})_2$, —$S(O)(NCN)R^{21}$, —$S(O)_2R^{21}$, —$S(O)_2N(R^{21})_2$, —$C(O)N(R^{21})S(O)_2R^{21}$, or —$S(O)_2N(R^{21})C(O)R^{21}$;

each $Z^{1b}$ is independently selected from oxo, halo, —CN, $C_{1-8}$ alkyl optionally substituted by 1 to 3 $Z^{1b}$, $C_{3-8}$ cycloalkyl optionally substituted by 1 to 3 $Z^{1b}$, aryl optionally substituted by 1 to 3 $Z^{1b}$, 4-10 membered heterocyclyl optionally substituted by 1 to 3 $Z^{1b}$, 5-10 membered heteroaryl optionally substituted with 1 to 3 $Z^{1b}$, —$OR^{22}$, —$C(O)R^{22}$, —$C(O)OR^{22}$, —$C(O)N(R^{22})_2$, —$N(R^{22})_2$, —$N(R^{22})_3^+$, —$N(R^{22})C(O)R^{22}$, —$N(R^{22})C(O)OR^{22}$, —$N(R^{22})C(O)N(R^{22})_2$, —$N(R^{22})S(O)_2R^{22}$, —$OC(O)R^{22}$, —$OC(O)OR^{22}$, —$OC(O)$—$N(R^{22})_2$, and —S—$R^{22}$; and each $R^{20}$, $R^{21}$ and $R^{22}$ is independently hydrogen, $C_{1-8}$ alkyl optionally substituted with 1 to 3 $Z^{1b}$, $C_{2-8}$ alkenyl optionally substituted with 1 to 3 $Z^{1b}$, $C_{2-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$;

each $Z^{1b}$ is independently oxo, hydroxy, halo, —$NO_2$, —$N_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, $C_{6-10}$ aryl, 5-10 membered heteroaryl heteroaryl, 4-10 membered heterocyclyl, —$O(C_{1-9}$ alkyl), —$O(C_{2-6}$ alkenyl), —$O(C_{2-6}$ alkynyl), —$O(C_{3-15}$ cycloalkyl), —$O(C_{1-8}$ haloalkyl), —O(aryl), —O(heteroaryl), —O(heterocyclyl), —OC(O) ($C_{1-9}$ alkyl), —$OC(O)(C_{2-6}$ alkenyl), —$OC(O)(C_{2-6}$ alkenyl), —$OC(O)(C_{2-6}$ alkynyl), —$OC(O)(C_{3-15}$ cycloalkyl), —$OC(O)(C_{1-8}$ haloalkyl), —OC(O)(aryl), —OC(O)(heteroaryl), —OC(O)(heterocyclyl), —$NH_2$, —$NH(C_{1-9}$ alkyl), —$NH(C_{2-6}$ alkenyl), —$NH(C_{2-6}$ alkynyl), —$NH(C_{3-15}$ cycloalkyl), —$NH(C_{1-8}$ haloalkyl), —NH(aryl), —NH(heteroaryl), —NH(heterocyclyl), —$N(C_{1-9}$ alkyl)$_2$, —$N(C_{3-15}$ cycloalkyl)$_2$, —$N(C_{2-6}$ alkenyl)$_2$, —$N(C_{2-6}$ alkynyl)$_2$, —$N(C_{3-15}$ cycloalkyl)$_2$, —$N(C_{1-8}$ haloalkyl)$_2$, —$N(aryl)_2$, —$N(heteroaryl)_2$, —$N(heterocyclyl)_2$, —$N(C_{1-9}$ alkyl)($C_{3-15}$ cycloalkyl), —$N(C_{1-9}$ alkyl)($C_{2-6}$ alkenyl), —$N(C_{1-9}$ alkyl)($C_{2-6}$ alkynyl), —$N(C_{1-9}$ alkyl)($C_{3-15}$ cycloalkyl), —$N(C_{1-9}$ alkyl)($C_{1-8}$ haloalkyl), —$N(C_{1-9}$ alkyl)(aryl), —$N(C_{1-9}$ alkyl)(heteroaryl), —$N(C_{1-9}$ alkyl)(heterocyclyl), —$C(O)(C_{1-9}$ alkyl), —$C(O)(C_{2-6}$ alkenyl), —$C(O)(C_{2-6}$ alkynyl), —$C(O)(C_{3-15}$ cycloalkyl), —$C(O)(C_{1-8}$ haloalkyl), —C(O)(aryl), —C(O)(heteroaryl), —C(O)(heterocyclyl), —$C(O)O(C_{1-9}$ alkyl), —$C(O)O(C_{2-6}$ alkenyl), —$C(O)O(C_{2-6}$ alkynyl), —$C(O)O(C_{3-15}$ cycloalkyl), —$C(O)O(C_{1-8}$ haloalkyl), —C(O)O(aryl), —C(O)O(heteroaryl), —C(O)O(heterocyclyl), —$C(O)NH_2$, —$C(O)NH(C_{1-9}$ alkyl), —$C(O)NH(C_{2-6}$ alkenyl), —$C(O)NH(C_{2-6}$ alkynyl), —$C(O)NH(C_{3-15}$ cycloalkyl), —$C(O)NH(C_{1-8}$ haloalkyl), —C(O)NH(aryl), —C(O)NH(heteroaryl), —C(O)NH(heterocyclyl), —$C(O)N(C_{1-9}$ alkyl)$_2$, —$C(O)N(C_{3-15}$ cycloalkyl)$_2$, —$C(O)N(C_{2-6}$ alkenyl)$_2$, —$C(O)N(C_{2-6}$ alkynyl)$_2$, —$C(O)N(C_{1-8}$ haloalkyl)$_2$, —C(O)N(aryl)₂, —C(O)N(heteroaryl)₂, —C(O)N(heterocyclyl)₂, —NHC(O)(C₁₋₉ alkyl), —NHC(O)(C₂₋₆ alkenyl), —NHC(O)(C₂₋₆ alkynyl), —NHC(O)(C₃₋₁₅ cycloalkyl), —NHC(O)(C₁₋₈ haloalkyl), —NHC(O)(aryl), —NHC(O)(heteroaryl), —NHC(O)(heterocyclyl), —NHC(O)O(C₁₋₉ alkyl), —NHC(O)O(C₂₋₆ alkenyl), —NHC(O)O(C₂₋₆ alkynyl), —NHC(O)O(C₃₋₁₅ cycloalkyl), —NHC(O)O(C₁₋₈ haloalkyl), —NHC(O)O(aryl), —NHC(O)O(heteroaryl), —NHC(O)O(heterocyclyl), —NHC(O)NH(C₁₋₉ alkyl), —NHC(O)NH(C2.6 alkenyl), —NHC(O)NH(C₂₋₆ alkynyl), —NHC(O)NH(C₃₋₁₅ cycloalkyl), —NHC(O)NH(C₁₋₈ haloalkyl), —NHC(O)NH(aryl), —NHC(O)NH(heteroaryl), —NHC(O)NH(heterocyclyl), —SH, —S(C₁₋₉ alkyl), —S(C₂₋₆ alkenyl), —S(C₂₋₆ alkynyl), —S(C₃₋₁₅ cycloalkyl), —S(C₁₋₈ haloalkyl), —S(aryl), —S(heteroaryl), —S(heterocyclyl), —NHS(O)(C₁₋₉ alkyl), —N(C₁₋₉ alkyl)(S(O)(C₁₋₉ alkyl), —S(O)N(C₁₋₉ alkyl)₂, —S(O)(C₁₋₉ alkyl), —S(O)(NH)(C₁₋₉ alkyl), —S(O)(C₂₋₆ alkenyl), —S(O)(C₂₋₆ alkynyl), —S(O)(C₃₋₁₅ cycloalkyl), —S(O)(C₁₋₈ haloalkyl), —S(O)(aryl), —S(O)(heteroaryl), —S(O)(heterocyclyl), —S(O)₂(C₁₋₉ alkyl), —S(O)₂(C₂₋₆ alkenyl), —S(O)₂(C₂₋₆ alkynyl), —S(O)₂(C₃₋₁₅ cycloalkyl), —S(O)₂(C₁₋₈ haloalkyl), —S(O)₂(aryl), —S(O)₂(heteroaryl), —S(O)₂(heterocyclyl), —S(O)₂NH(C₁₋₉ alkyl), or —S(O)₂N(C₁₋₉ alkyl)₂;

wherein any alkyl, cycloalkyl, aryl, heteroaryl, or heterocyclyl of $Z^{1b}$ is optionally substituted with one or more halo, C₁₋₉ alkyl, C₁₋₈ haloalkyl, —OH, —NH₂, —NH(C₁₋₉ alkyl), —NH(C₃₋₁₅ cycloalkyl), —NH(C₁₋₈ haloalkyl), —NH(aryl), —NH(heteroaryl), —NH(heterocyclyl), —N(C₁₋₉ alkyl)₂, —N(C₃₋₁₅ cycloalkyl)₂, —NHC(O)(C₃₋₁₅ cycloalkyl), —NHC(O)(C₁₋₈ haloalkyl), —NHC(O)(aryl), —NHC(O)(heteroaryl), —NHC(O)(heterocyclyl), —NHC(O)O(C₁₋₉ alkyl), —NHC(O)O(C₂₋₆ alkynyl), —NHC(O)O(C₃₋₁₅ cycloalkyl), —NHC(O)O(C₁₋₈ haloalkyl), —NHC(O)O(aryl), —NHC(O)O(heteroaryl), —NHC(O)O(heterocyclyl), —NHC(O)NH(C₁₋₉ alkyl), —S(O)(NH)(C₁₋₉ alkyl), —S(O)₂(C₁₋₉ alkyl), —S(O)₂(C₃₋₁₅ cycloalkyl), —S(O)₂(C₁₋₈ haloalkyl), —S(O)₂(aryl), —S(O)₂(heteroaryl), —S(O)₂(heterocyclyl), —S(O)₂NH(C₁₋₉ alkyl), —S(O)₂N(C₁₋₉ alkyl)₂, —O(C₃₋₁₅ cycloalkyl), —O(C₁₋₈ haloalkyl), —O(aryl), —O(heteroaryl), —O(heterocyclyl), or —O(C₁₋₉ alkyl).

2. The compound of claim 1, or a pharmaceutically acceptable salt thereof, wherein $X^5$ is N.

3. The compound of claim 1, or a pharmaceutically acceptable salt thereof, wherein $X^7$ is C—H or C-F.

4. The compound of claim 1, or a pharmaceutically acceptable salt thereof, wherein $R^1$ is hydrogen, halo or —C₁₋₈ alkyl.

5. The compound of claim 1, or a pharmaceutically acceptable salt thereof, wherein $R^2$ is hydrogen, halo, or —O-C₁₋₈ alkyl.

6. The compound of claim 1, or a pharmaceutically acceptable salt thereof, wherein $R^3$ is C₁₋₈ alkyl optionally substituted with 1 to 3 $Z^1$ or C₃₋₁₀ cycloalkyl optionally substituted with 1 to 3 $Z^1$.

7. The compound of claim 1, or a pharmaceutically acceptable salt thereof, wherein $R^3$ is methyl,

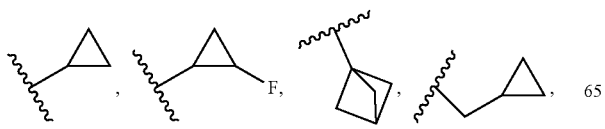

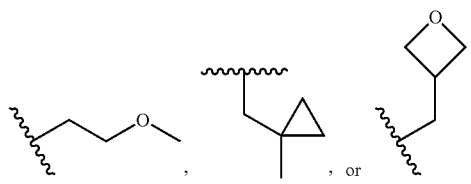

8. The compound of claim 1, or a pharmaceutically acceptable salt thereof, wherein $R^4$ is C₁₋₈ alkyl optionally substituted with 1 to 3 $Z^1$ or C₃₋₁₀ cycloalkyl optionally substituted with 1 to 3 $Z^1$.

9. The compound of claim 1, or a pharmaceutically acceptable salt thereof, wherein $R^{10}$ is hydrogen or —CH₃, and $R^{11}$ is C₁₋₆ alkyl optionally substituted with 1 to 3 $Z^{10}$, C₃₋₆ cycloalkyl optionally substituted with 1 to 3 $Z^{10}$, or 4-12-membered heterocyclyl optionally substituted with 1 to 3 $Z^{10}$; or $R^{10}$ and $R^{11}$ taken together with the nitrogen to which they are attached form a 4-10-membered heterocyclyl optionally substituted with 1 to 3 $Z^{10}$.

10. The compound of claim 1, or a pharmaceutically acceptable salt thereof, wherein $R^{10}$ and $R^{11}$ taken together with the nitrogen to which they are attached form a 4-10 membered heterocyclyl optionally substituted with 1 to 3 $Z^{10}$.

11. The compound of claim 1, or a pharmaceutically acceptable salt thereof, wherein $R^6$ is

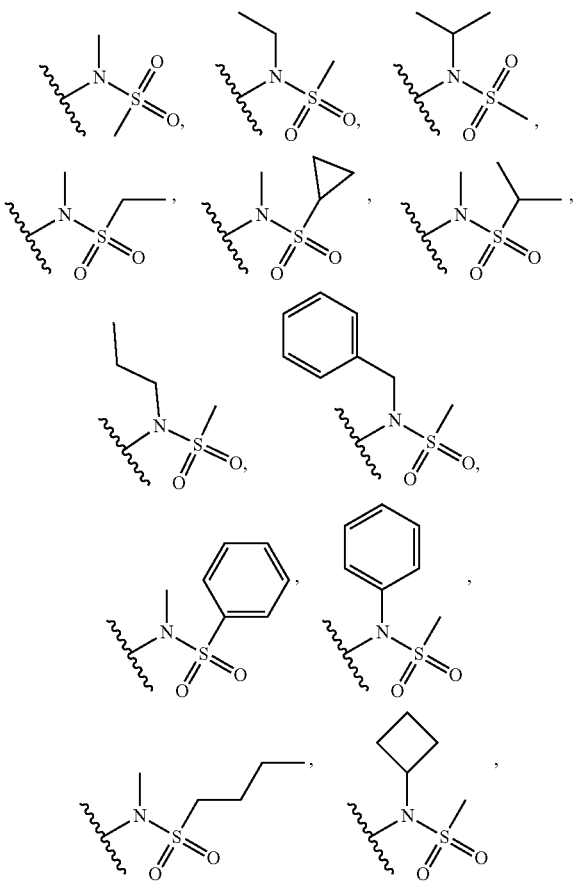

415
-continued
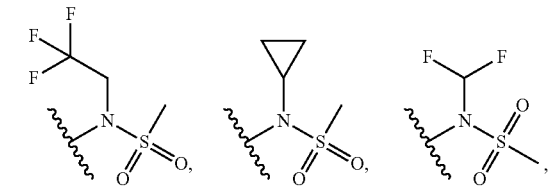
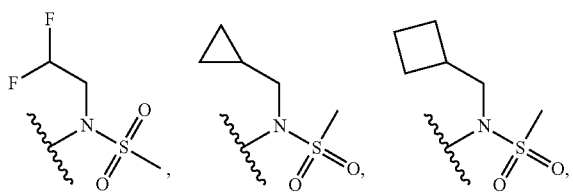
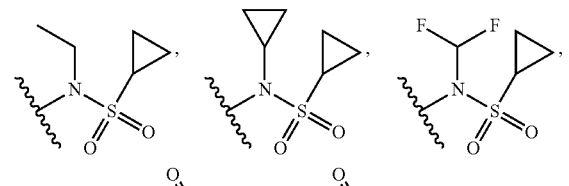
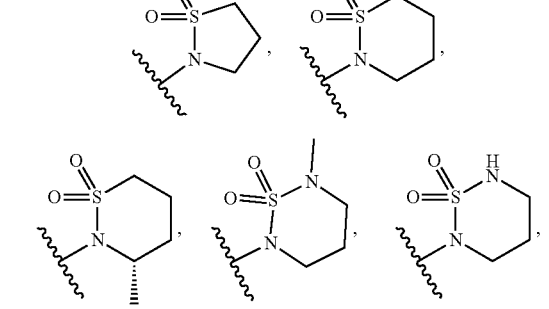
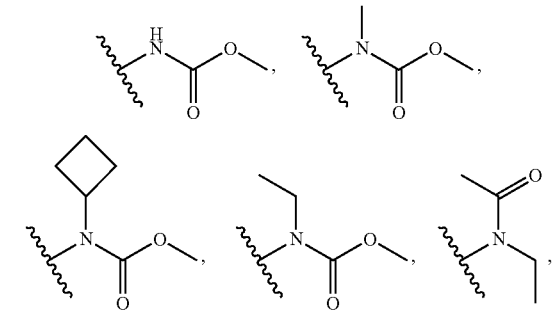
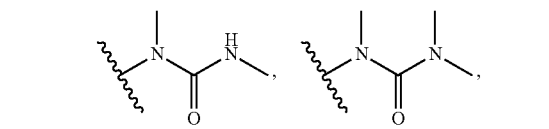
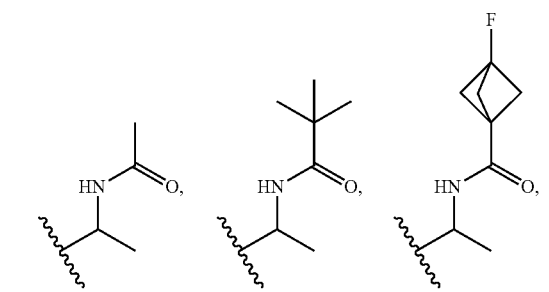
416
-continued
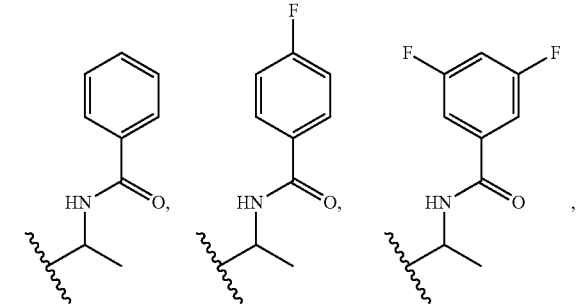
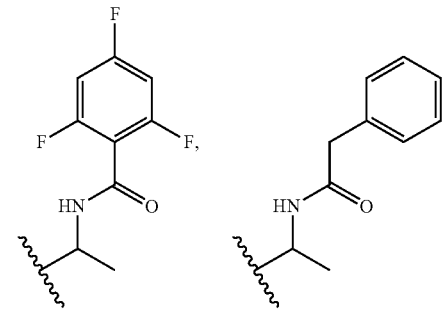
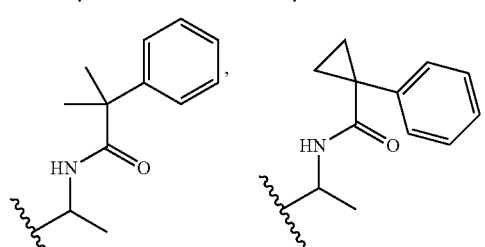
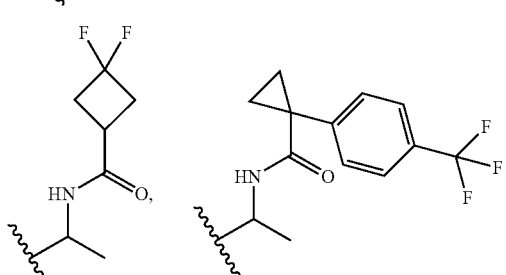
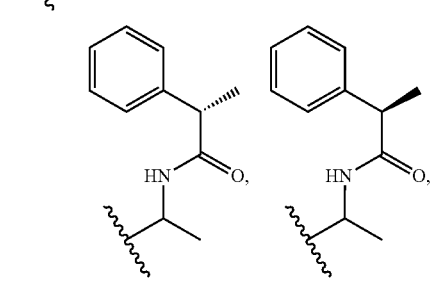
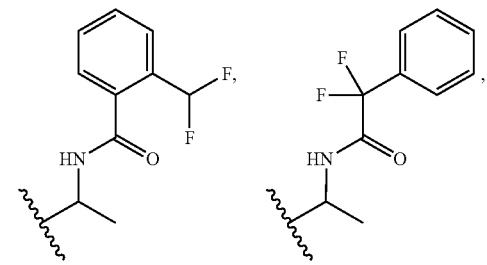

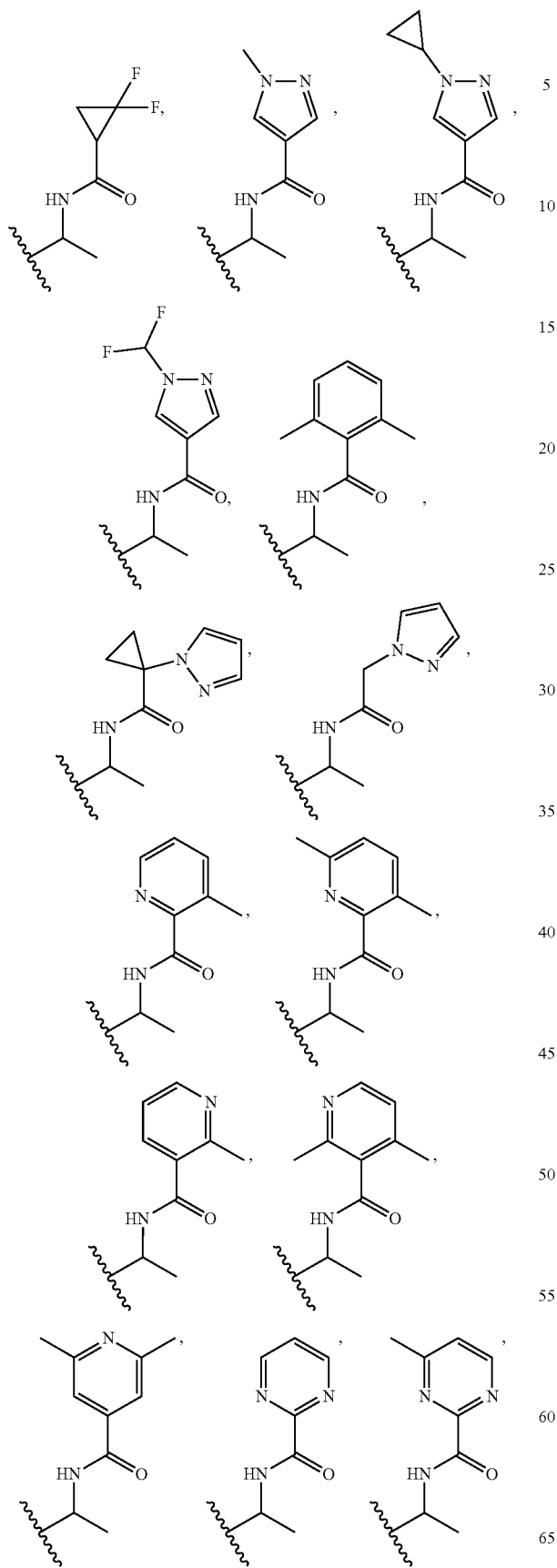
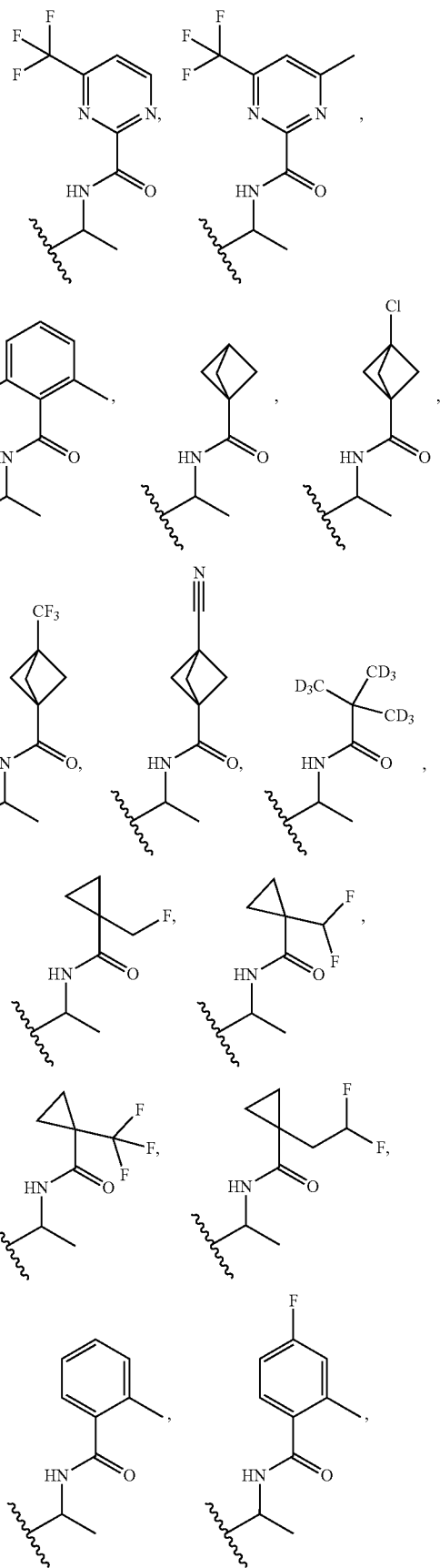

419
-continued
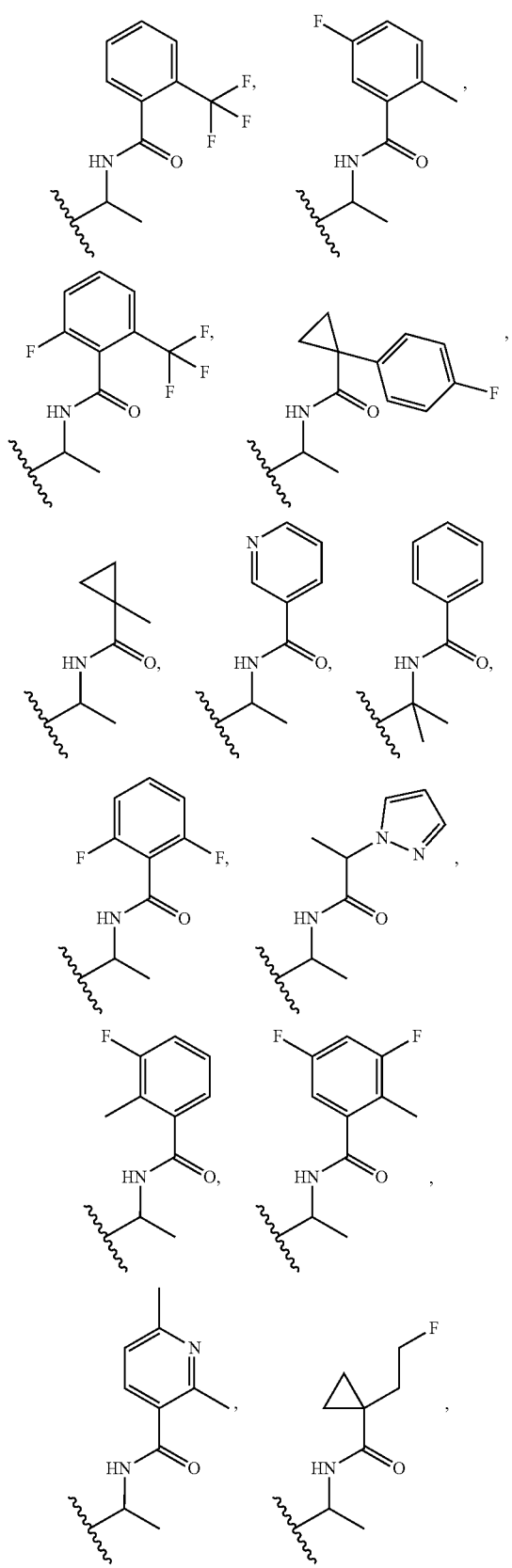
420
-continued
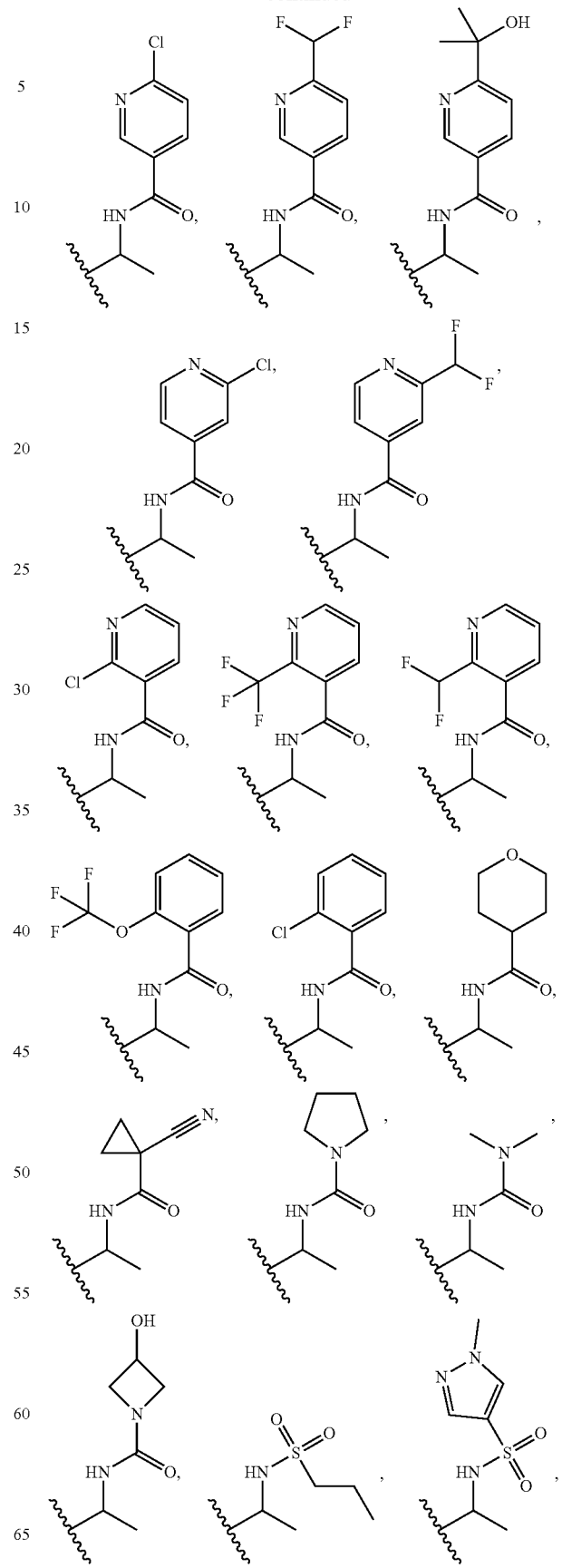

421
-continued
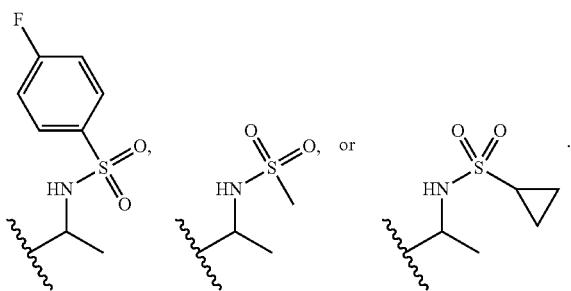
12. The compound of claim 1, or a pharmaceutically acceptable salt thereof, wherein the moiety is:
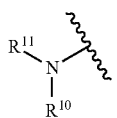
is:
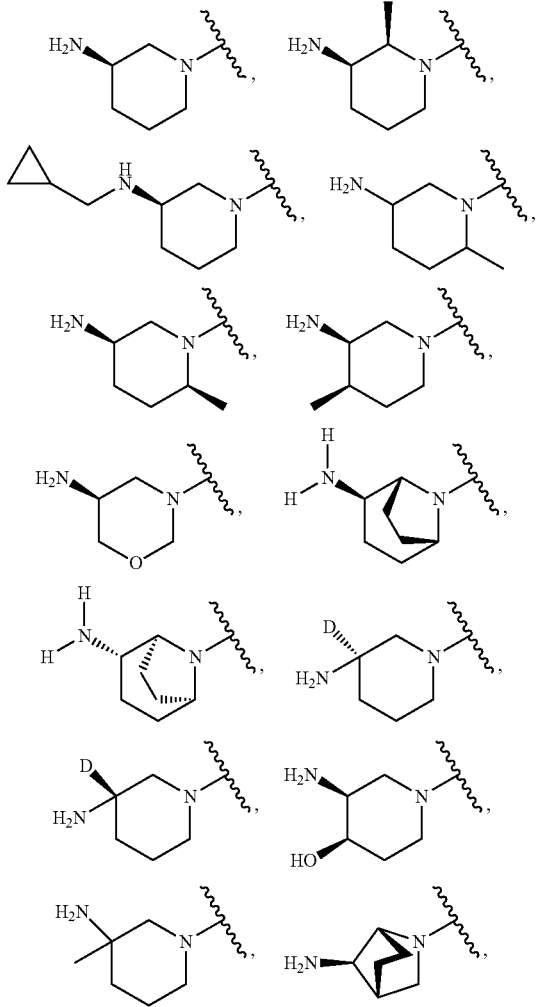
422
-continued
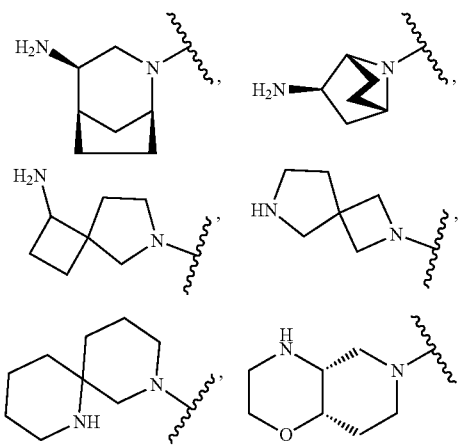
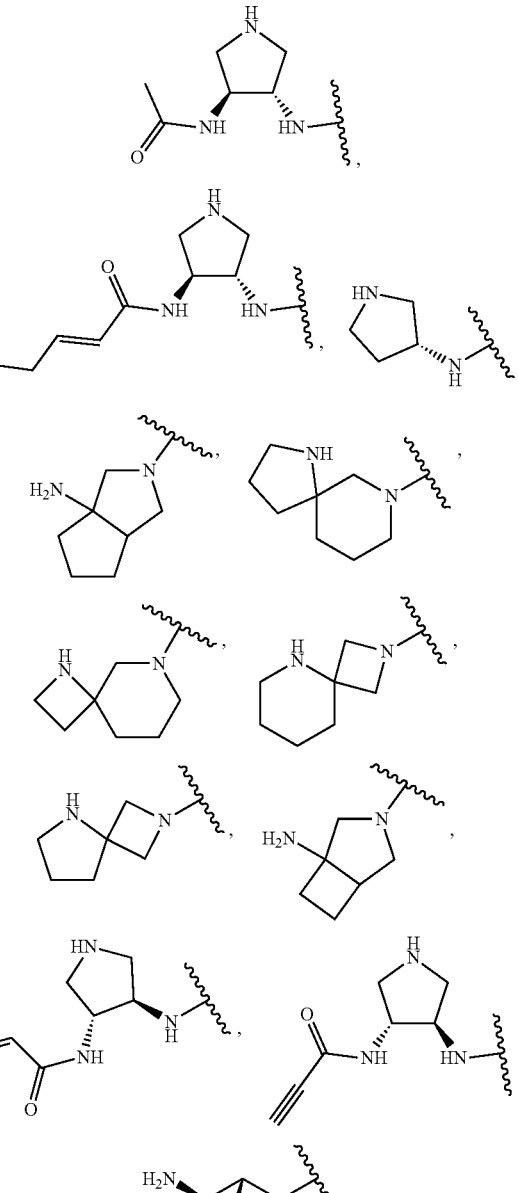

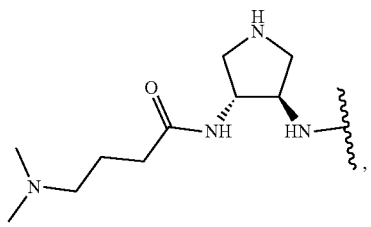
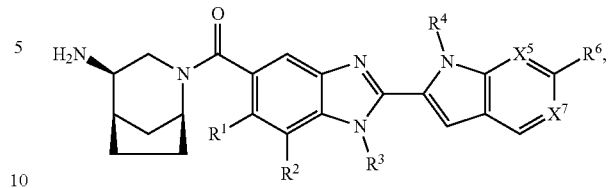
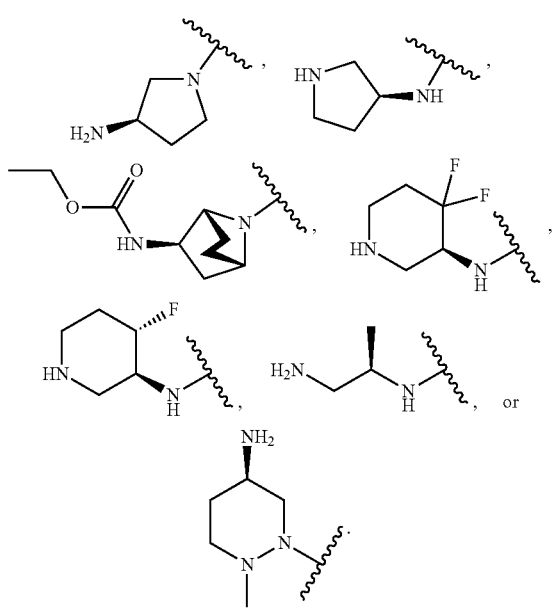
13. The compound of claim 1, or a pharmaceutically acceptable salt thereof, wherein the moiety
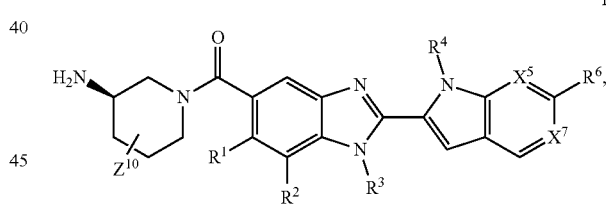
is:
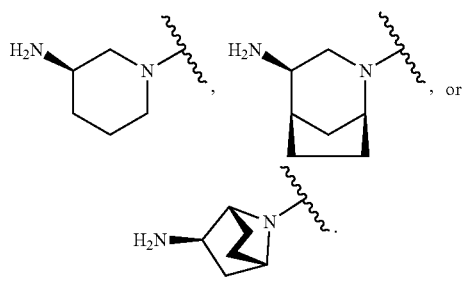
14. The compound of claim 1, or a pharmaceutically acceptable salt thereof, wherein the compound is represented by:
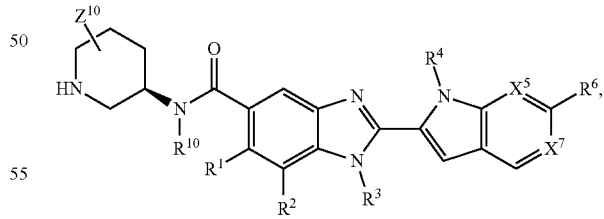
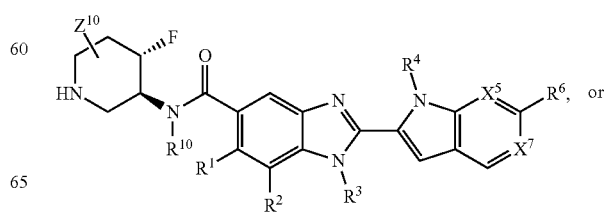

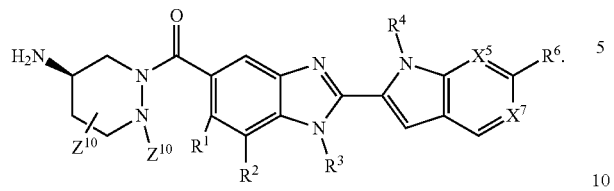
15. A compound selected from the group consisting of
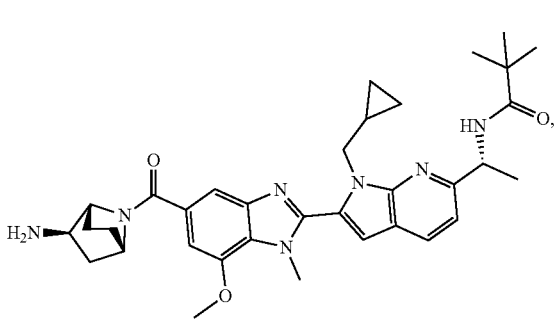
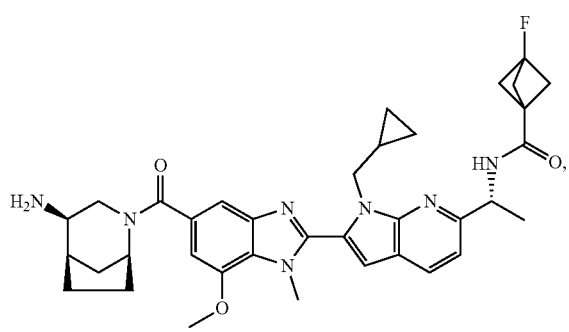
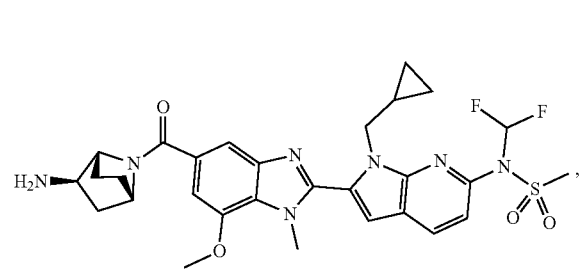
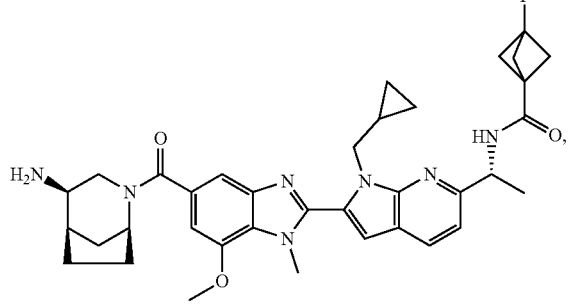
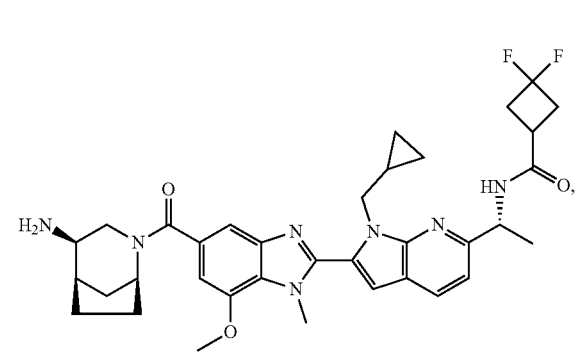
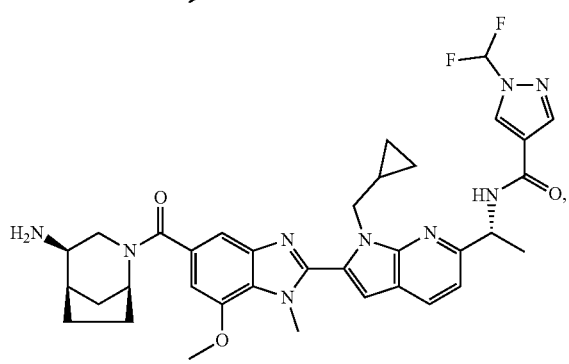
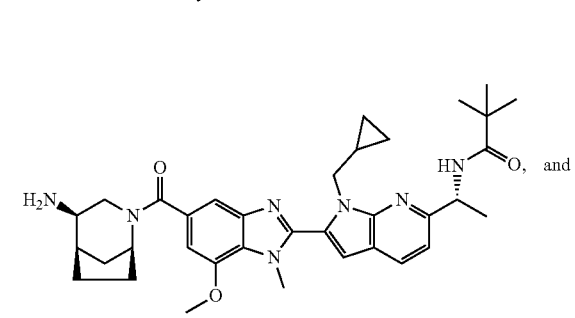
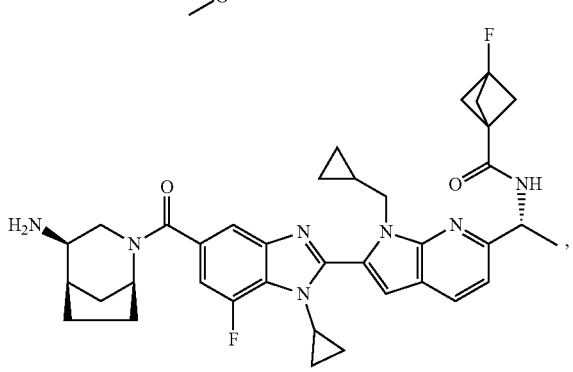
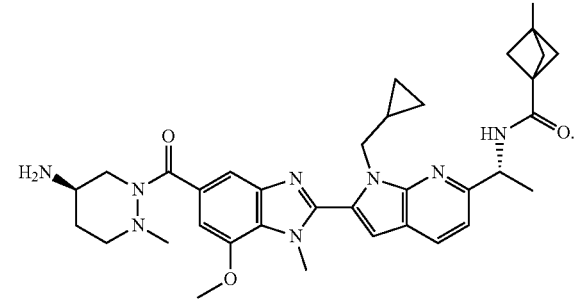
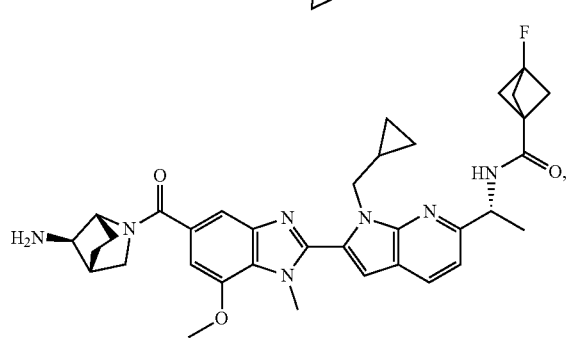
or a pharmaceutically acceptable salt thereof.

16. A compound have a structure:
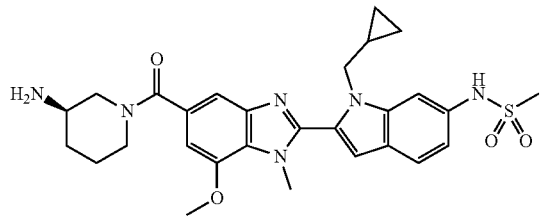
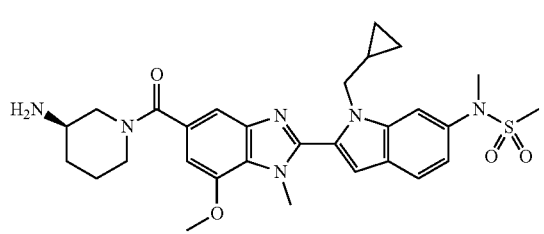
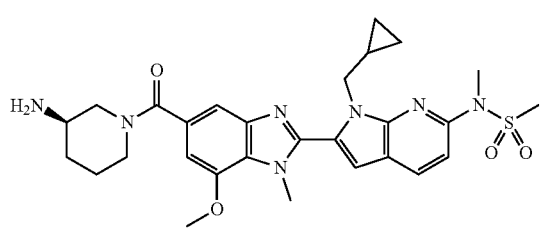
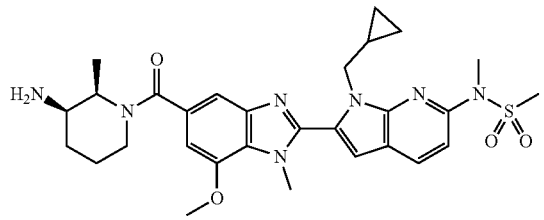
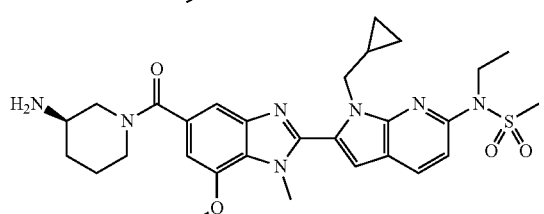
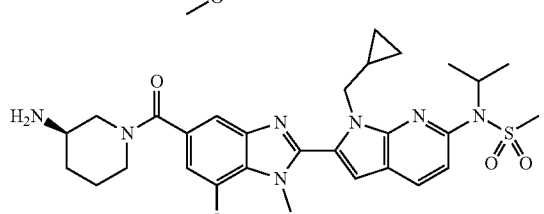
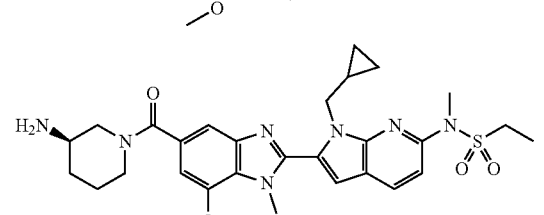
-continued
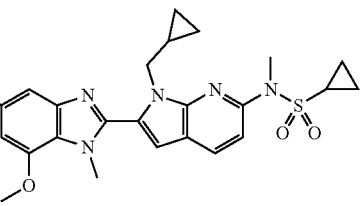
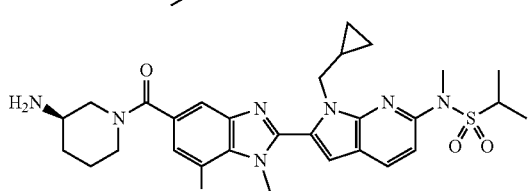
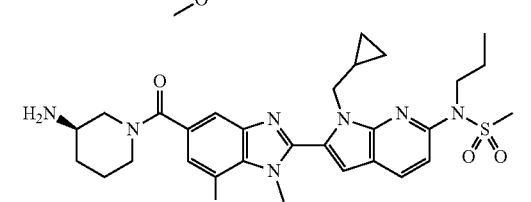
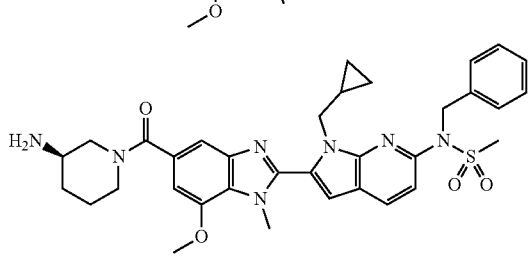
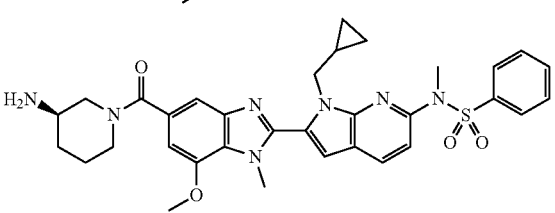
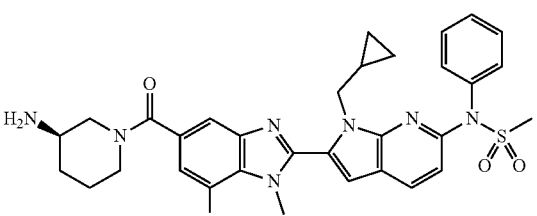
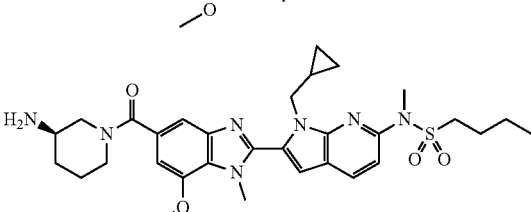
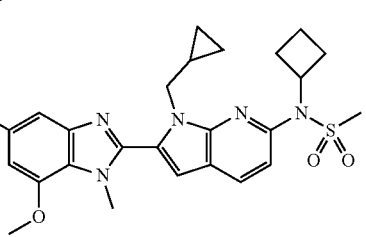

429
-continued
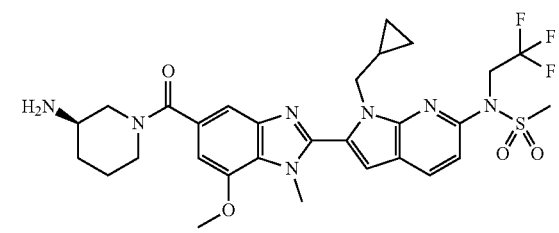
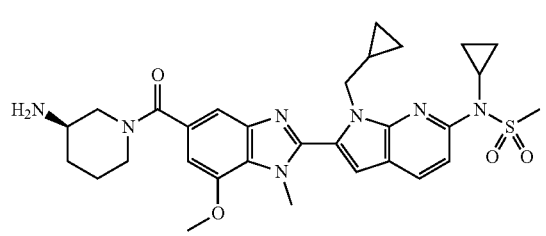
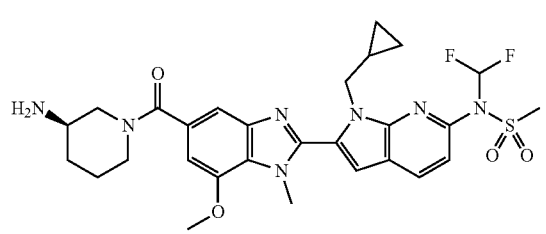
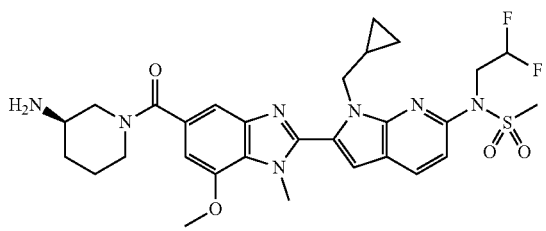
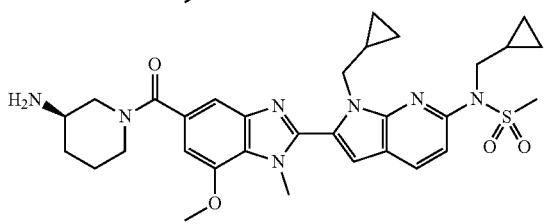
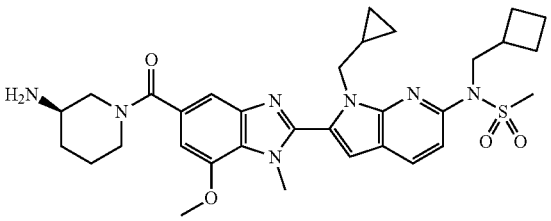
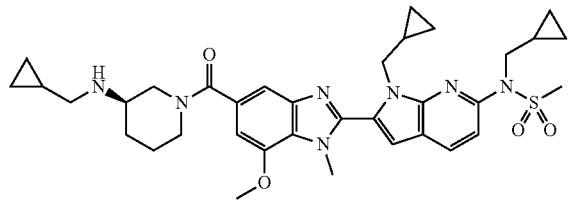
430
-continued
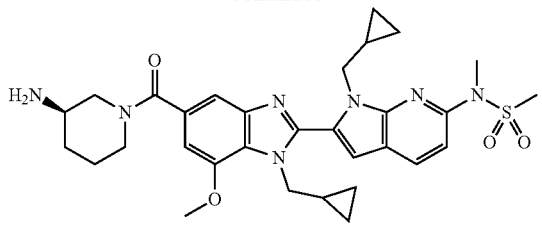
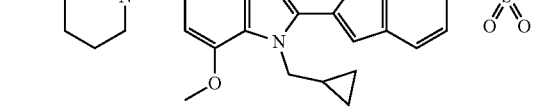
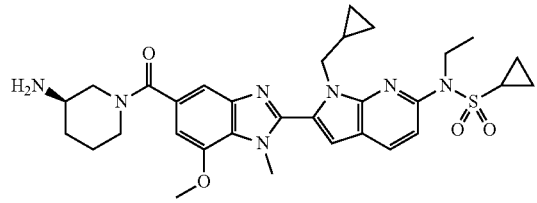
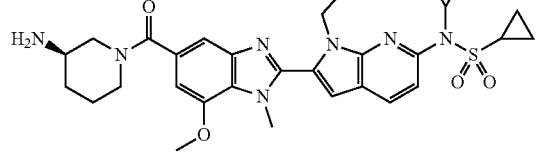
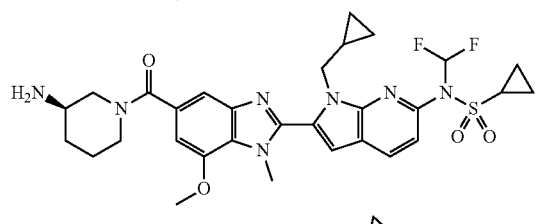
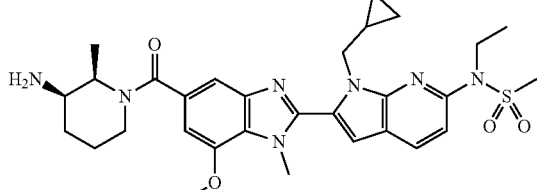
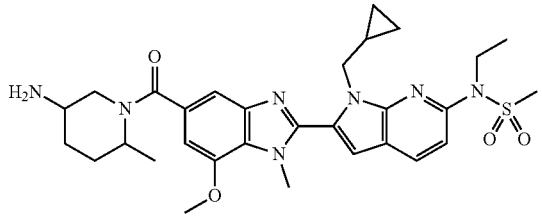
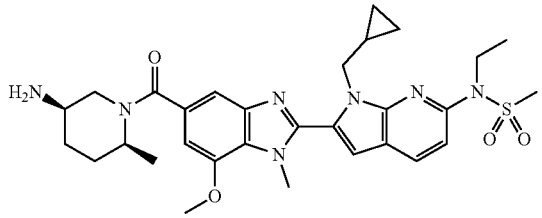

431
-continued
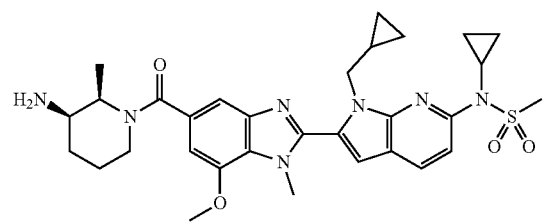
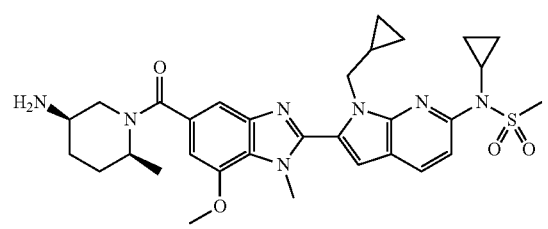
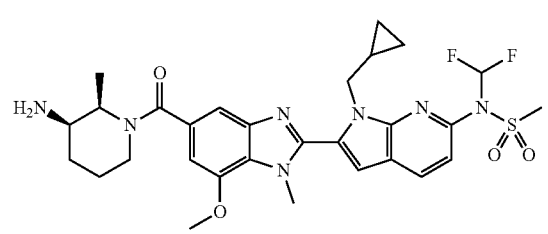
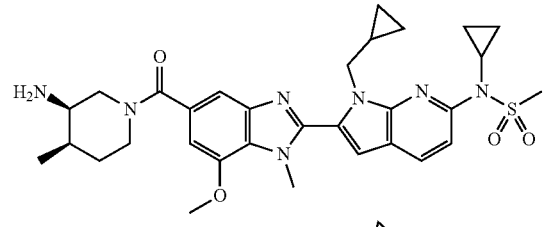
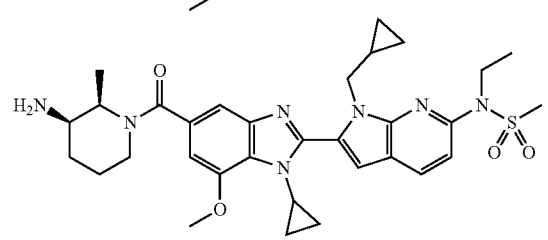
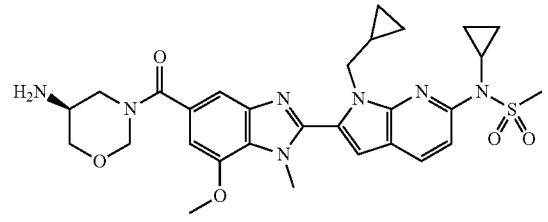
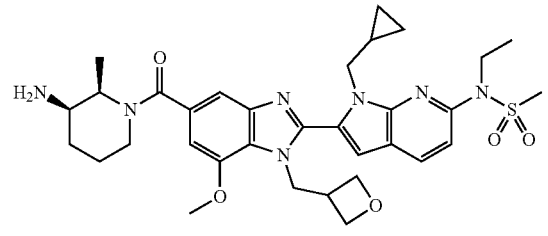
432
-continued
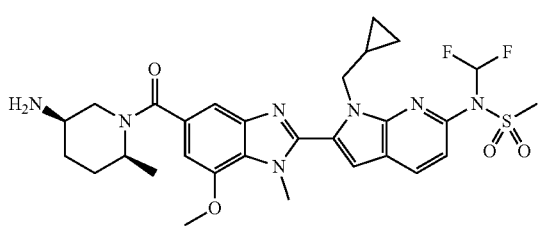
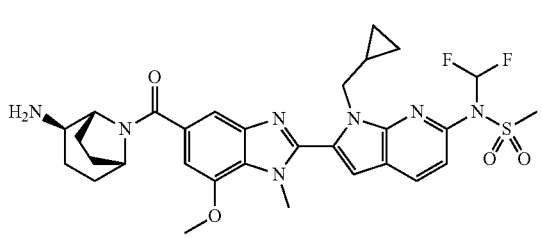
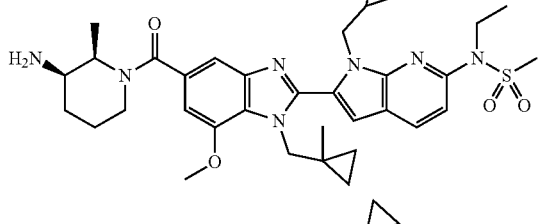
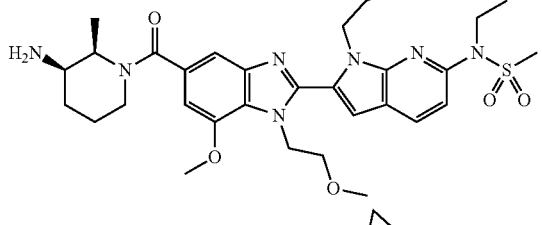
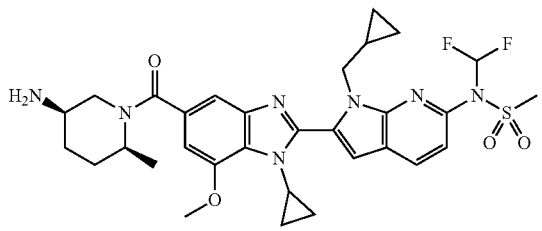
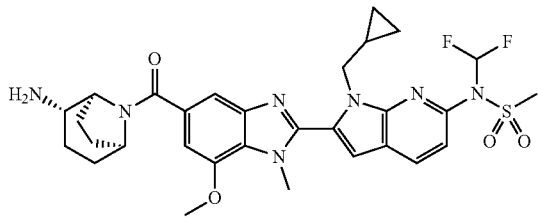
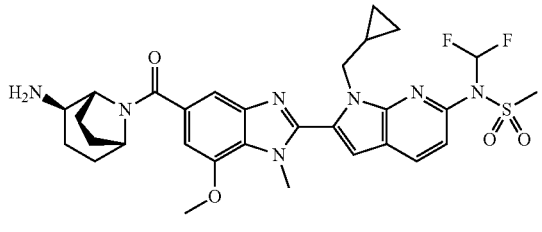

433
-continued
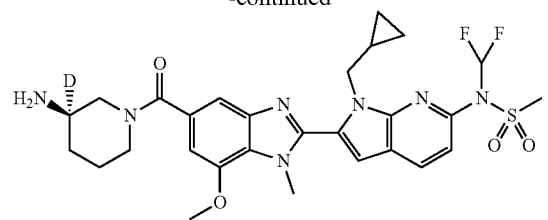
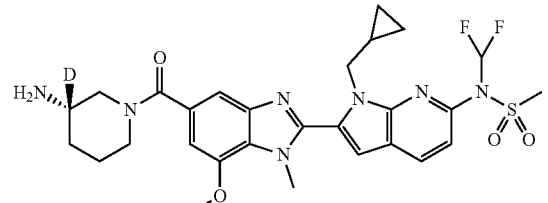
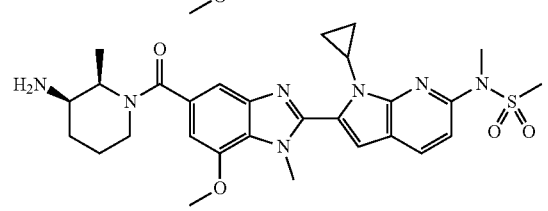
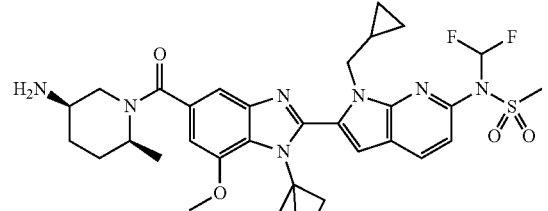
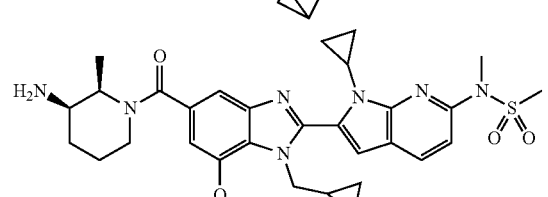
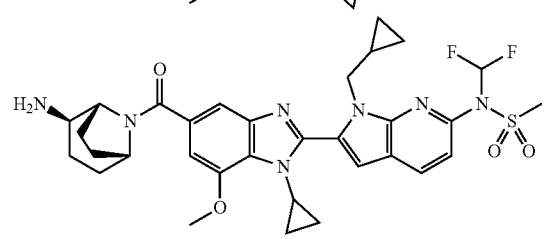
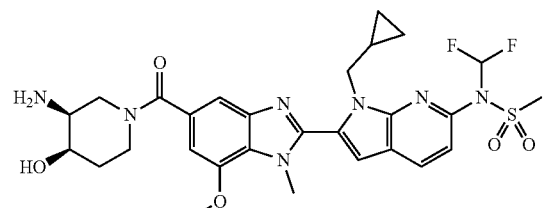
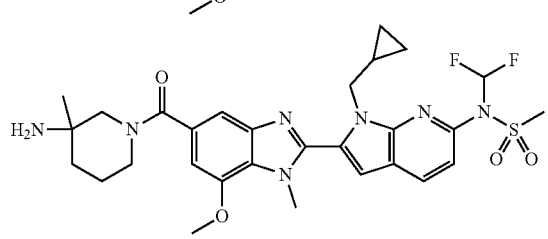
434
-continued
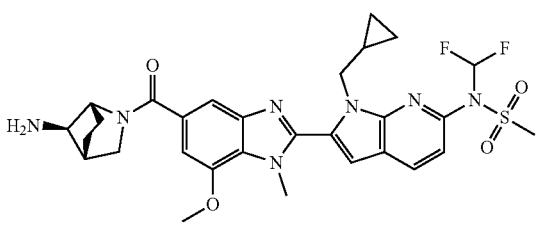
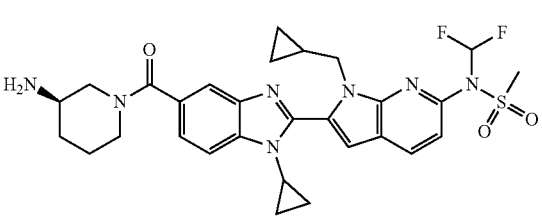
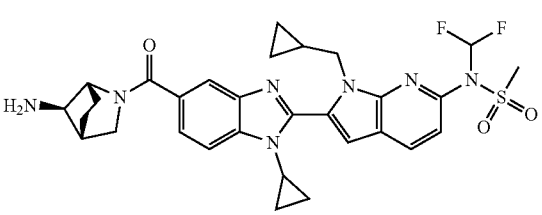
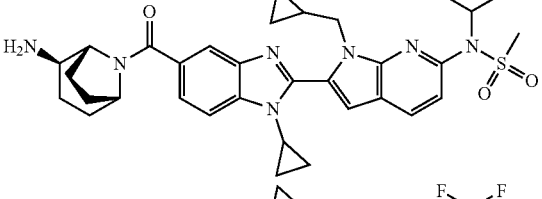
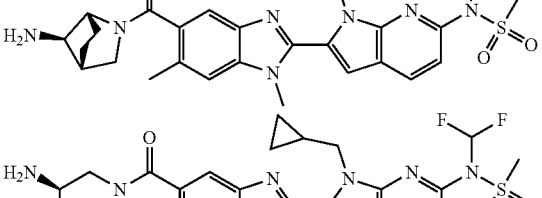
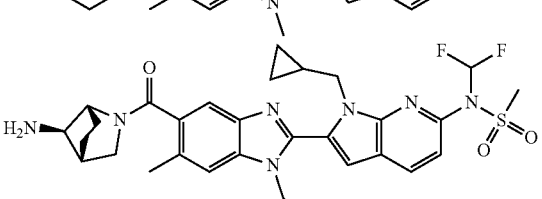
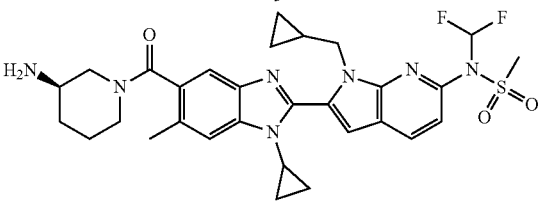

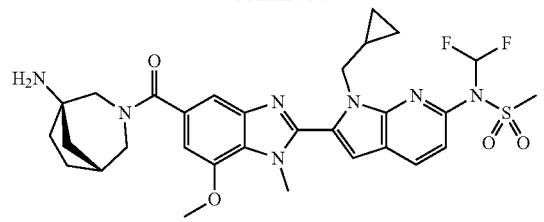
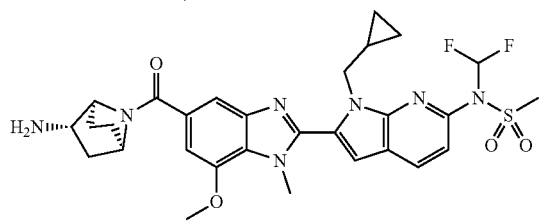
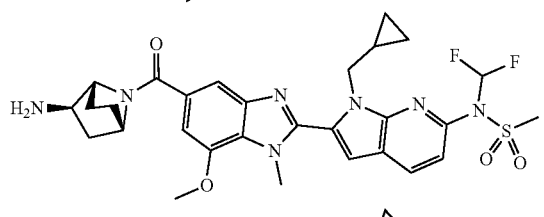
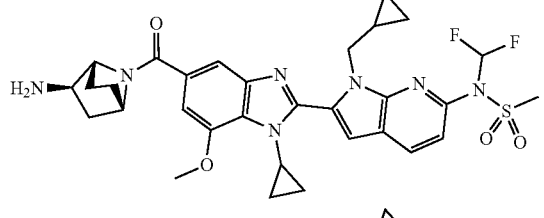
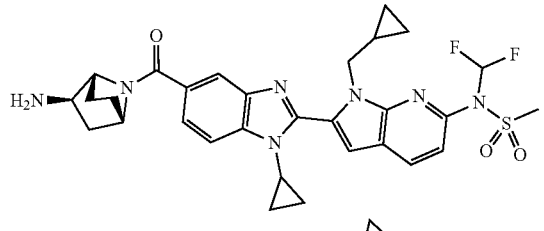
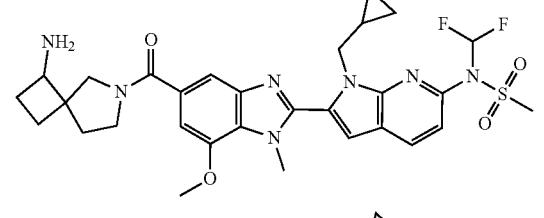
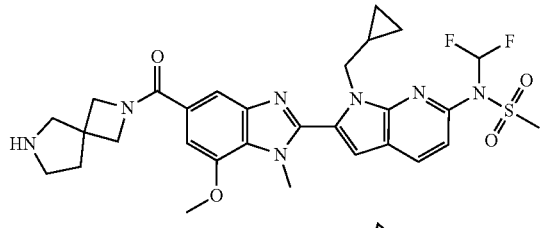
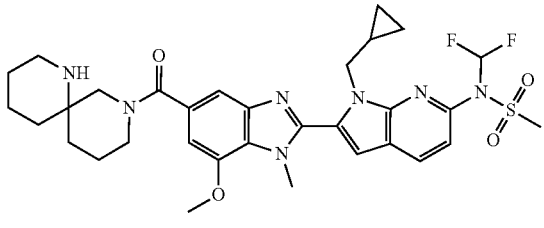
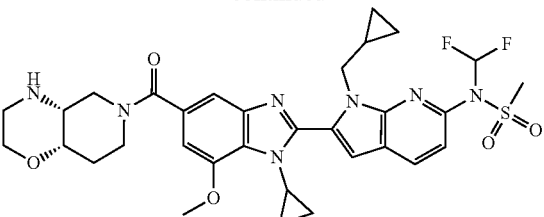
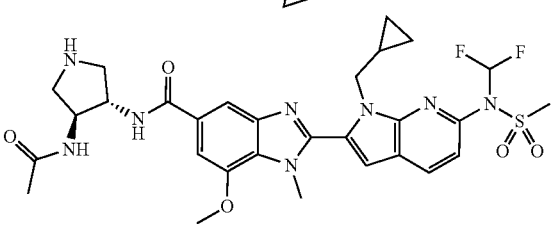
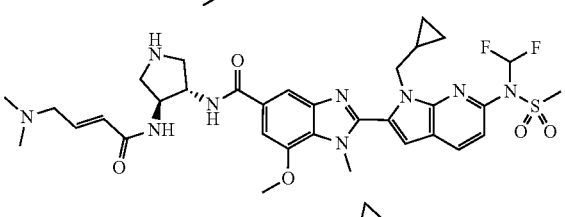
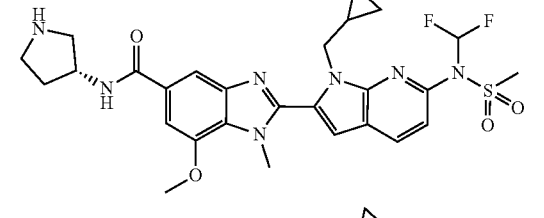
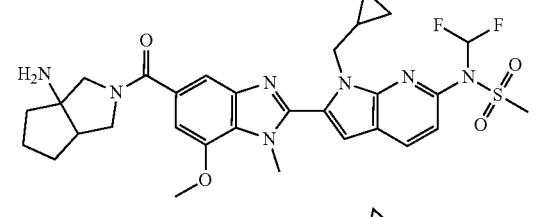
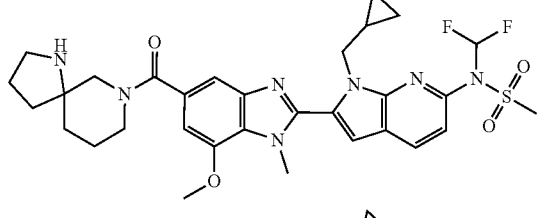
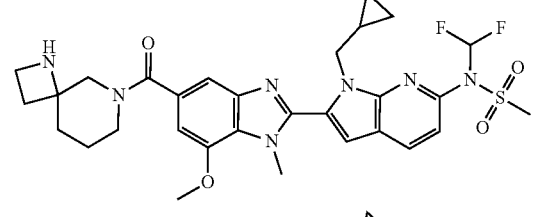
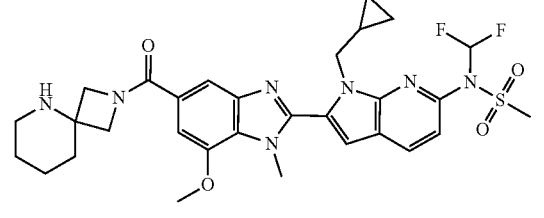

437
-continued
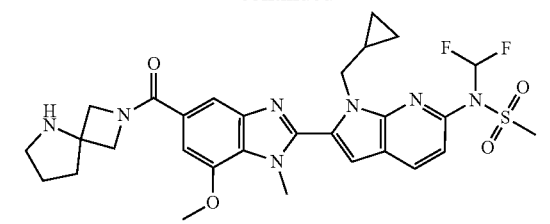
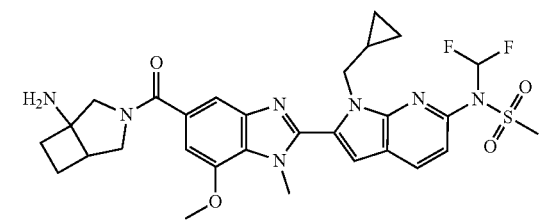
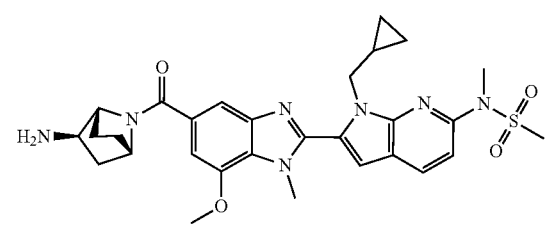
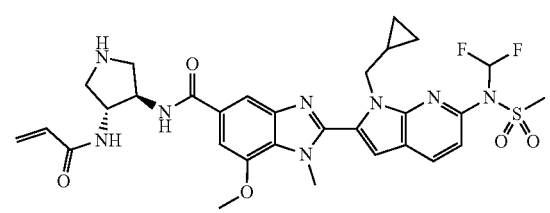
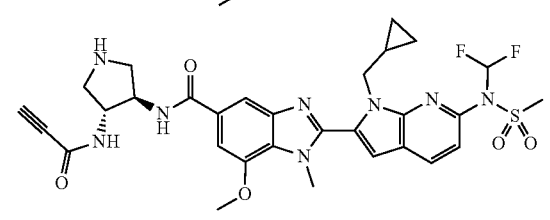
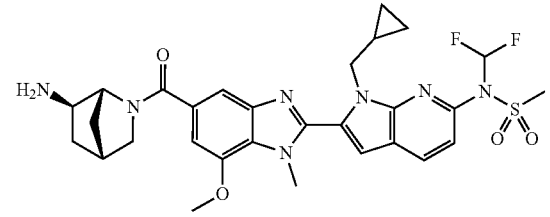
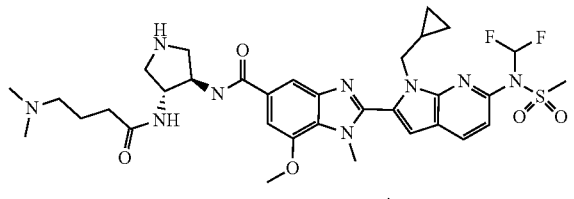
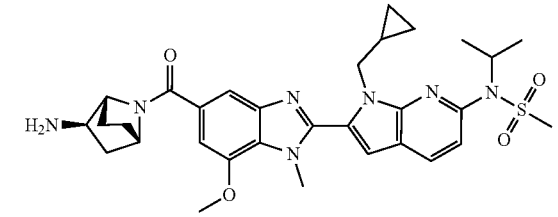
438
-continued
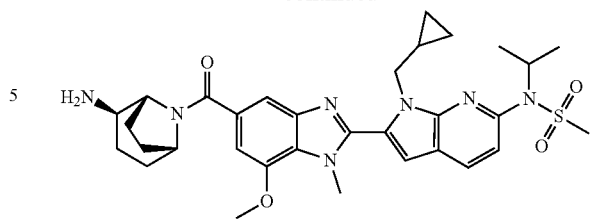
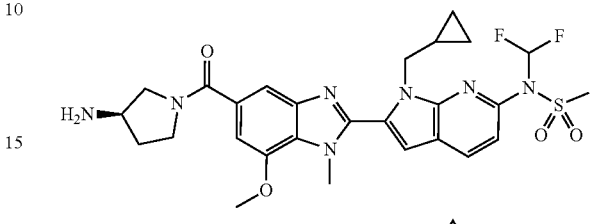
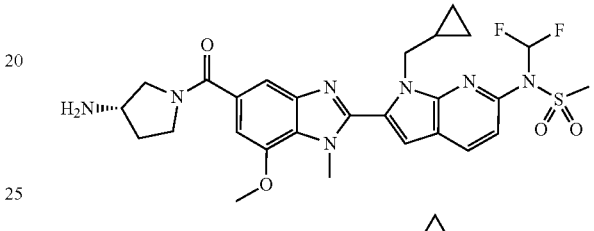
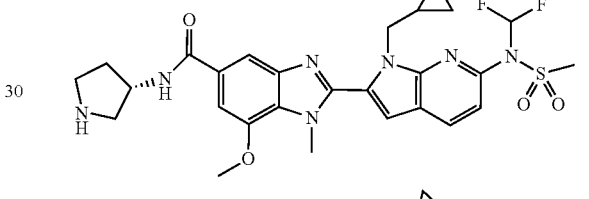
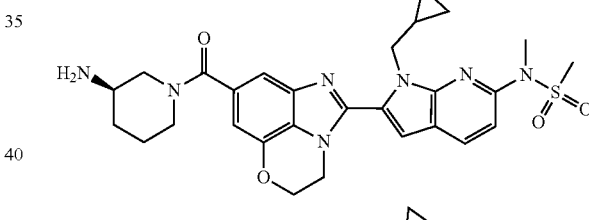
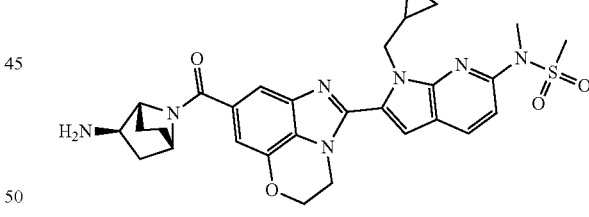
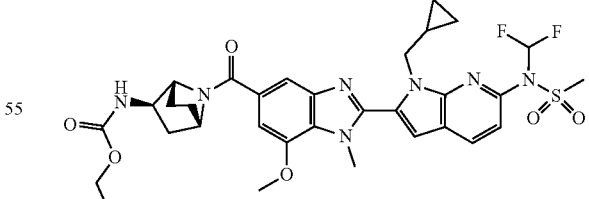
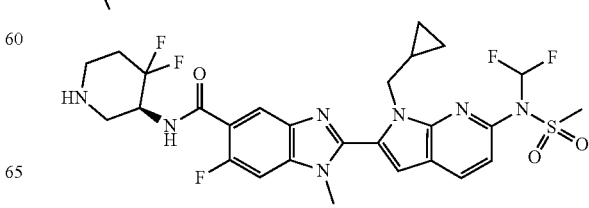

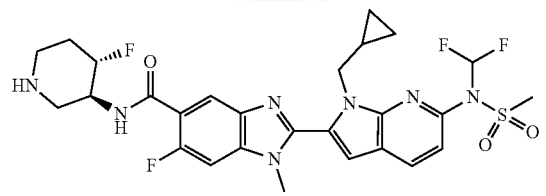
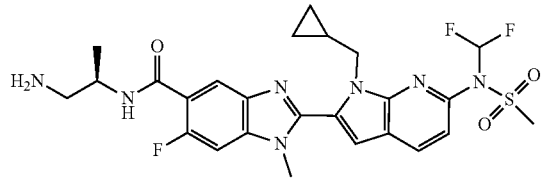
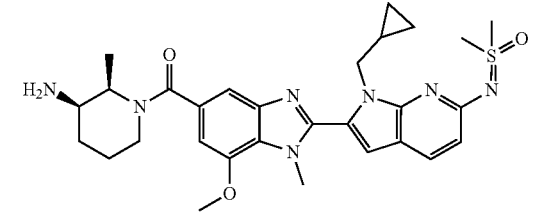
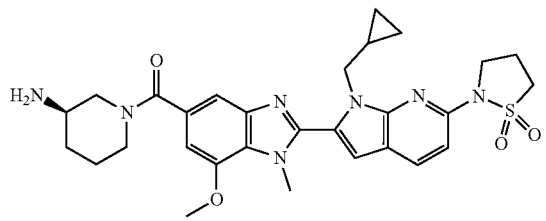
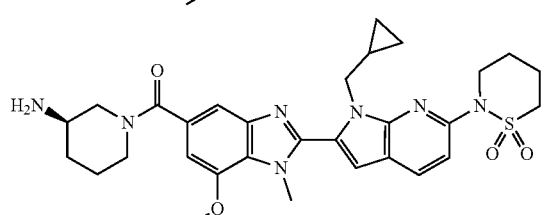
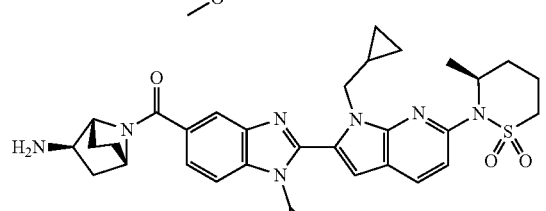
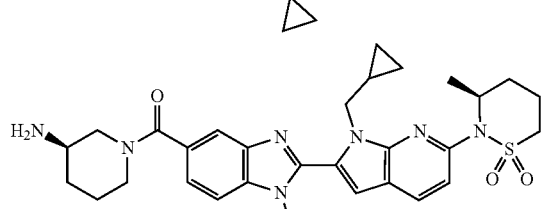
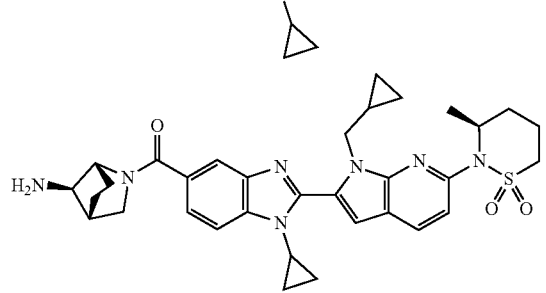
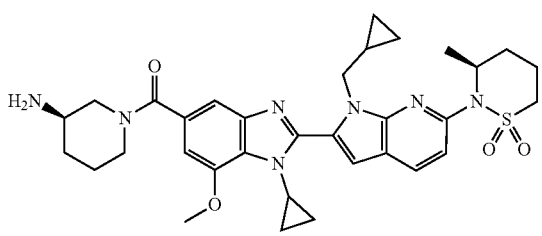
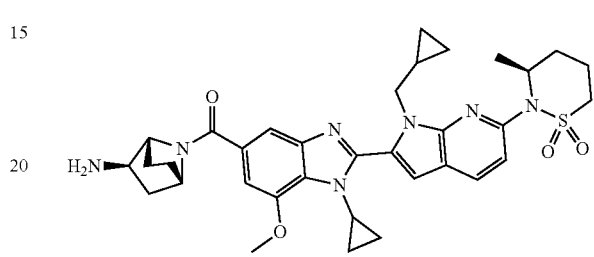
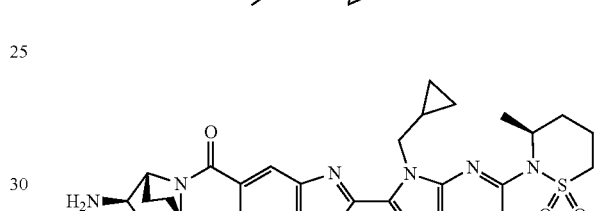
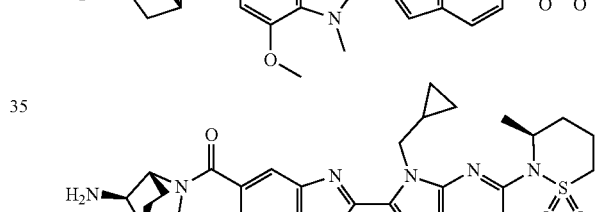
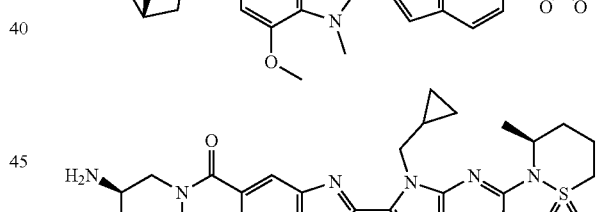
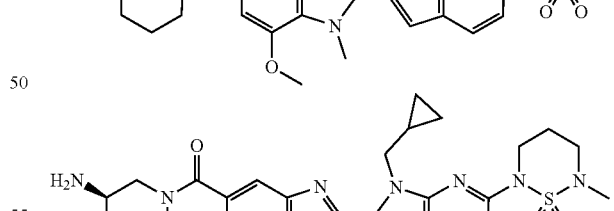
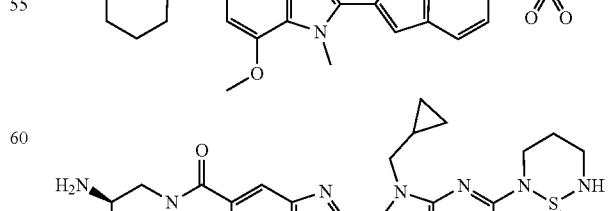
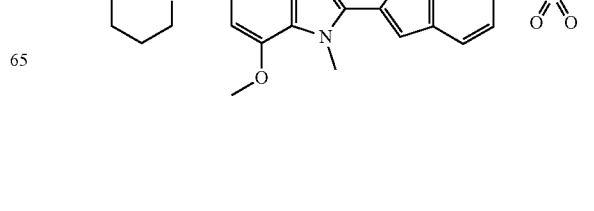

441
-continued
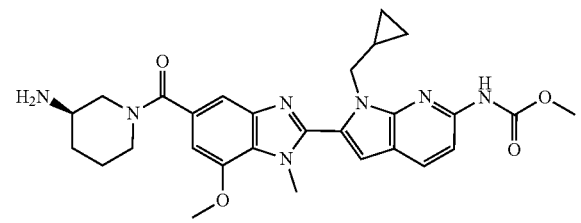
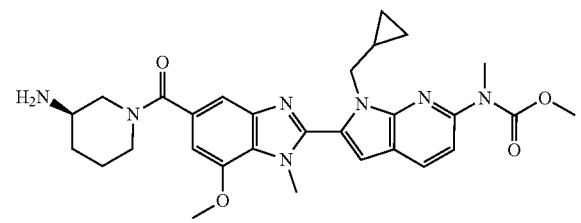
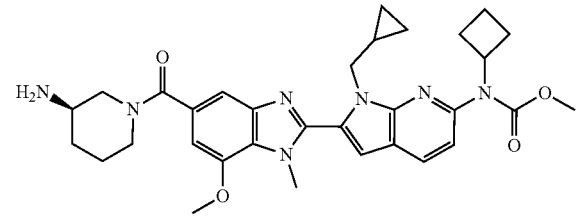
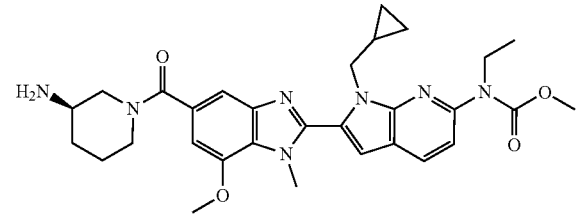
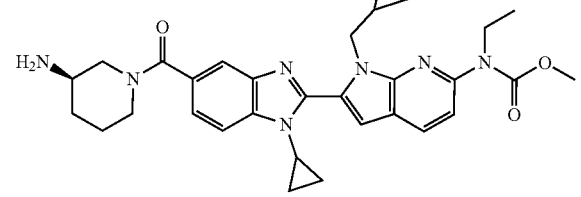
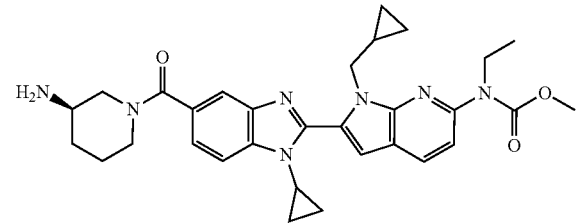
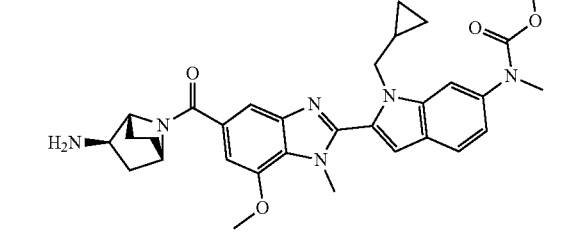
442
-continued
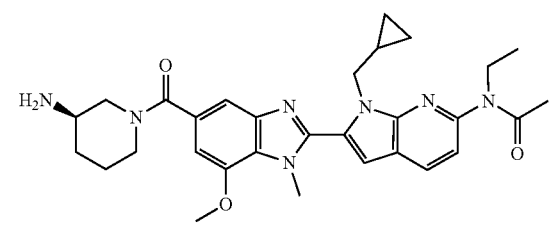
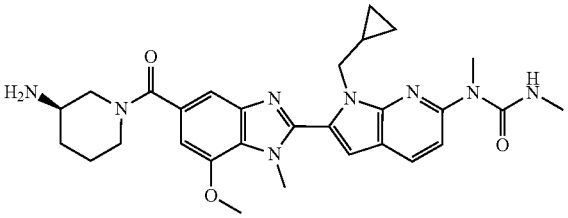
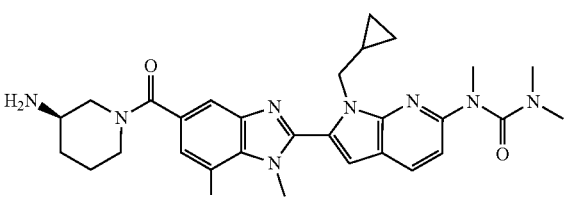
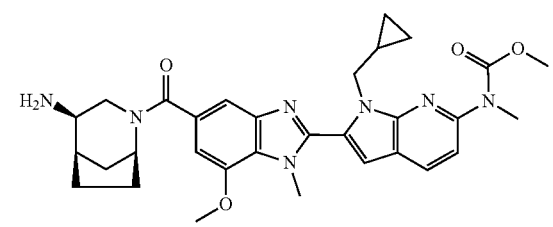
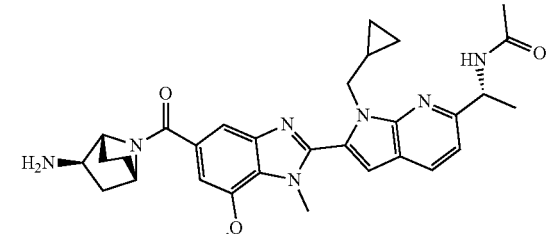
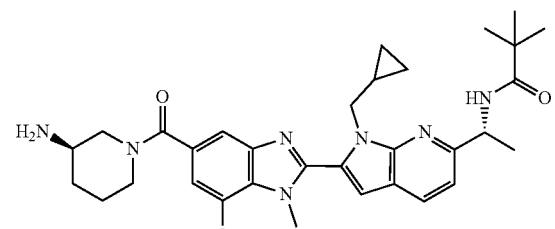
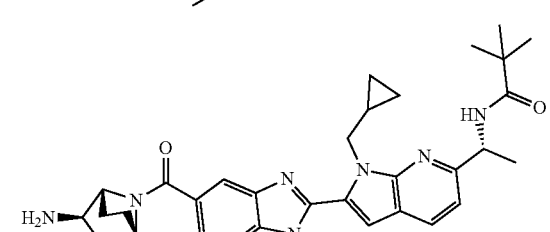

443
-continued
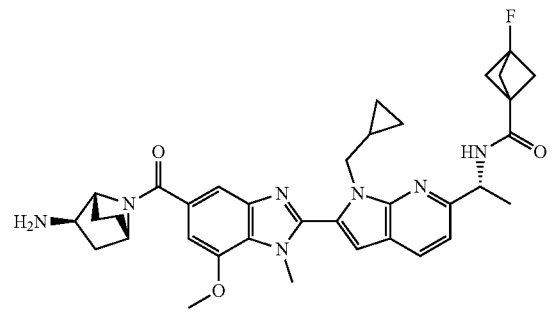
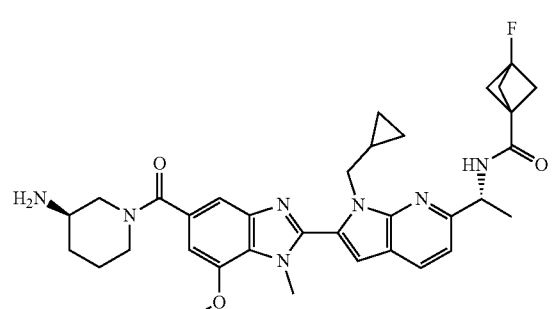
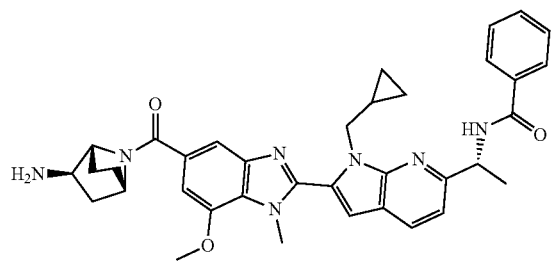
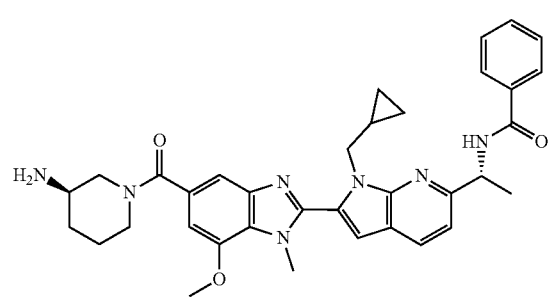
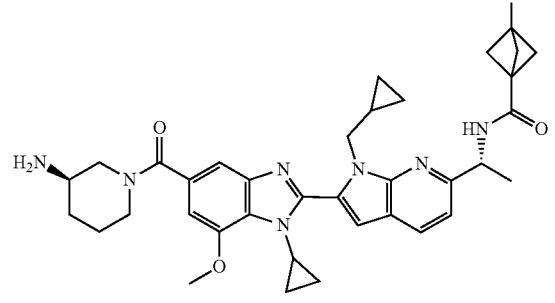
444
-continued
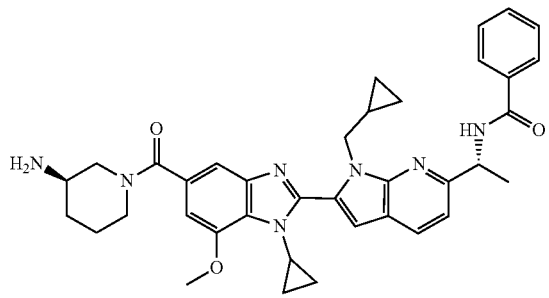
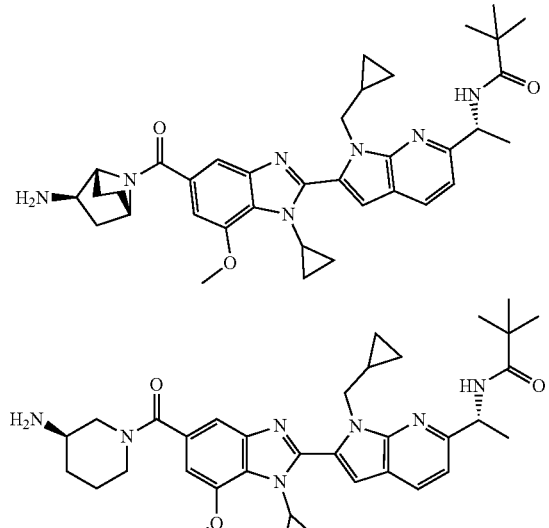
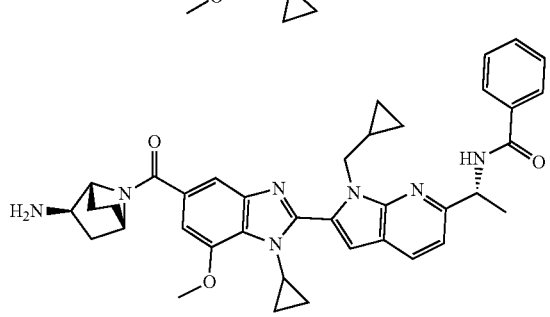
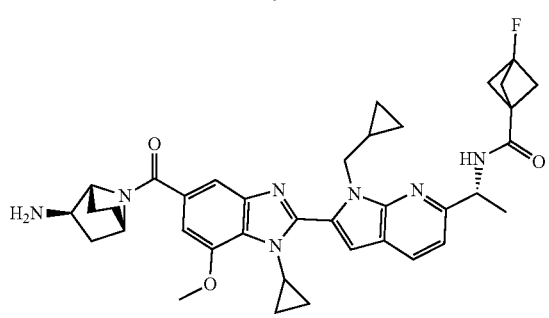
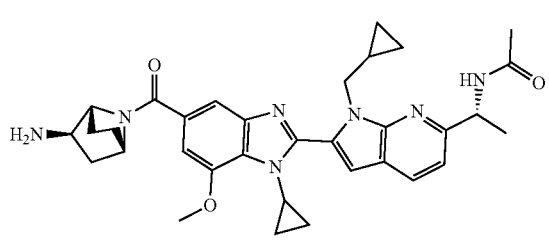

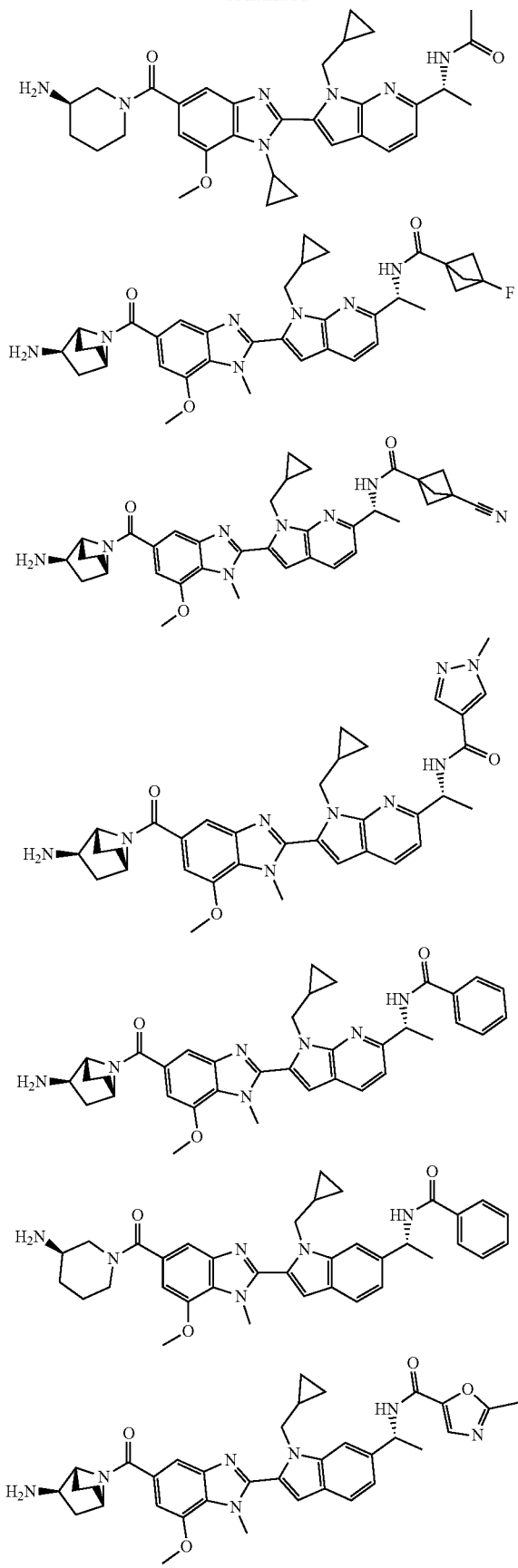
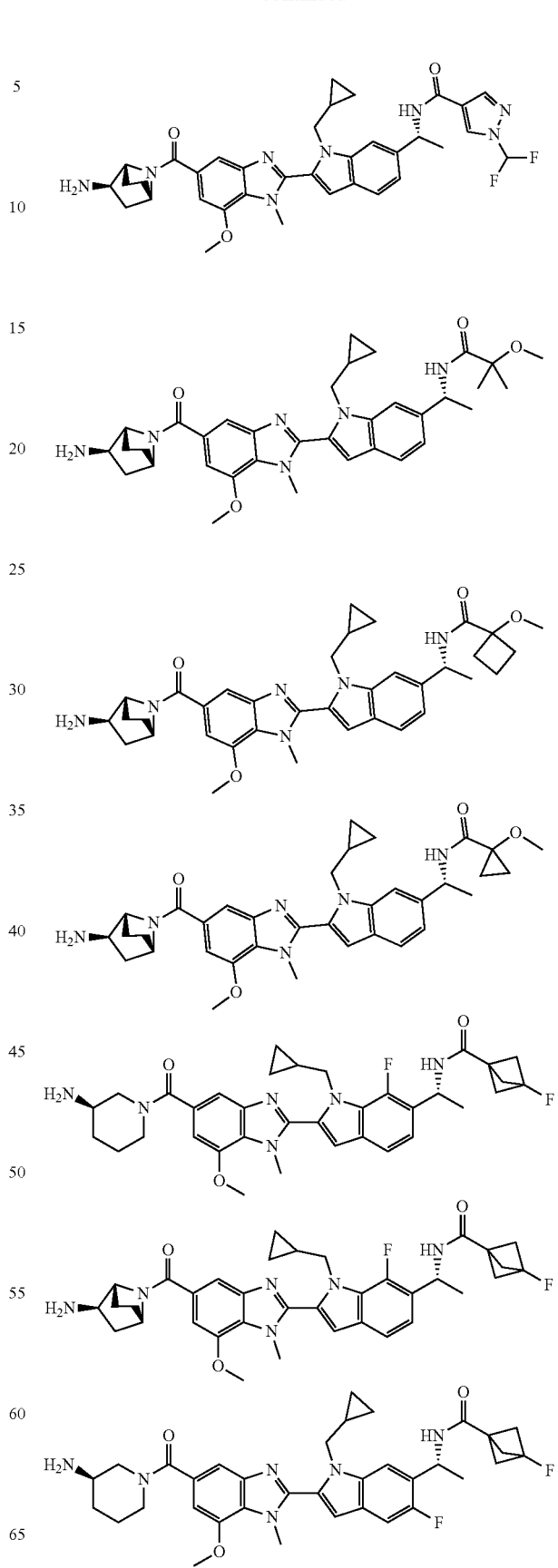

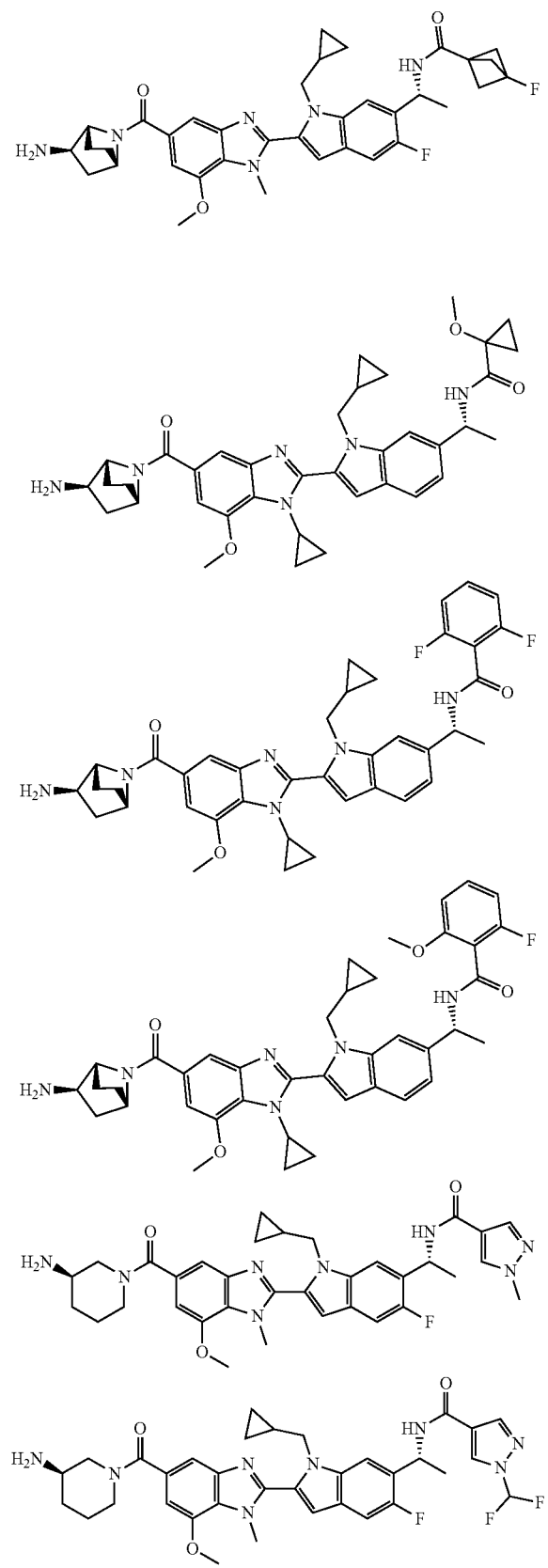
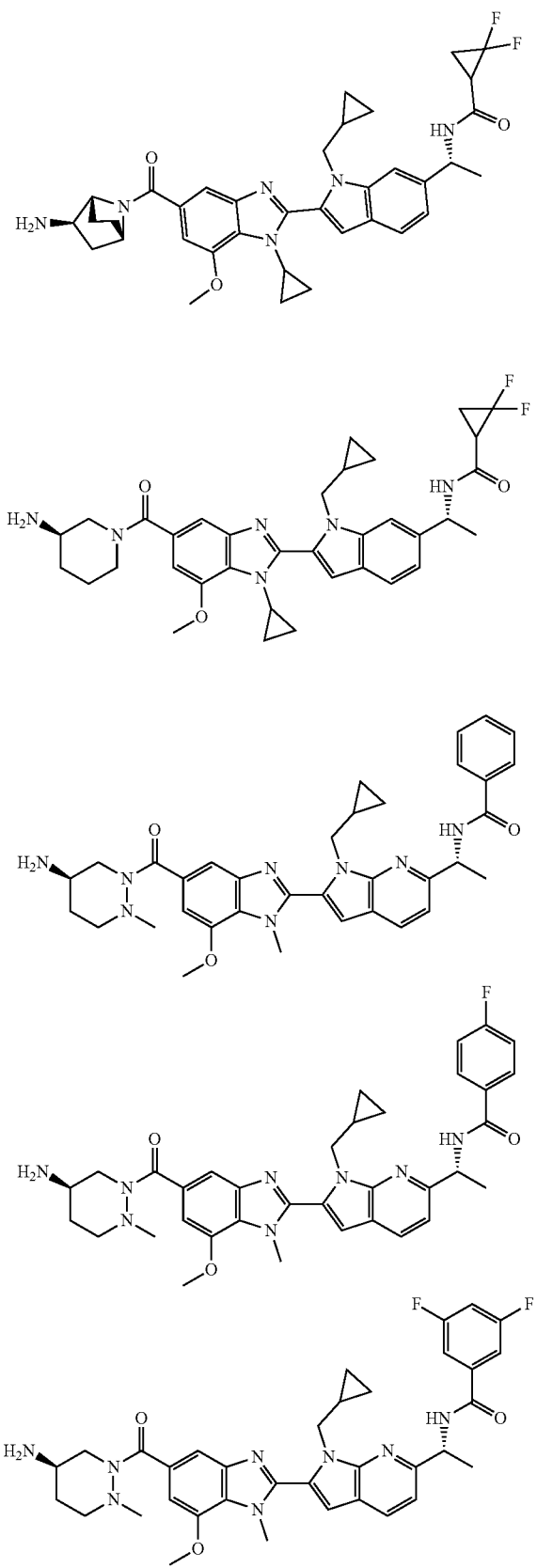

449
-continued
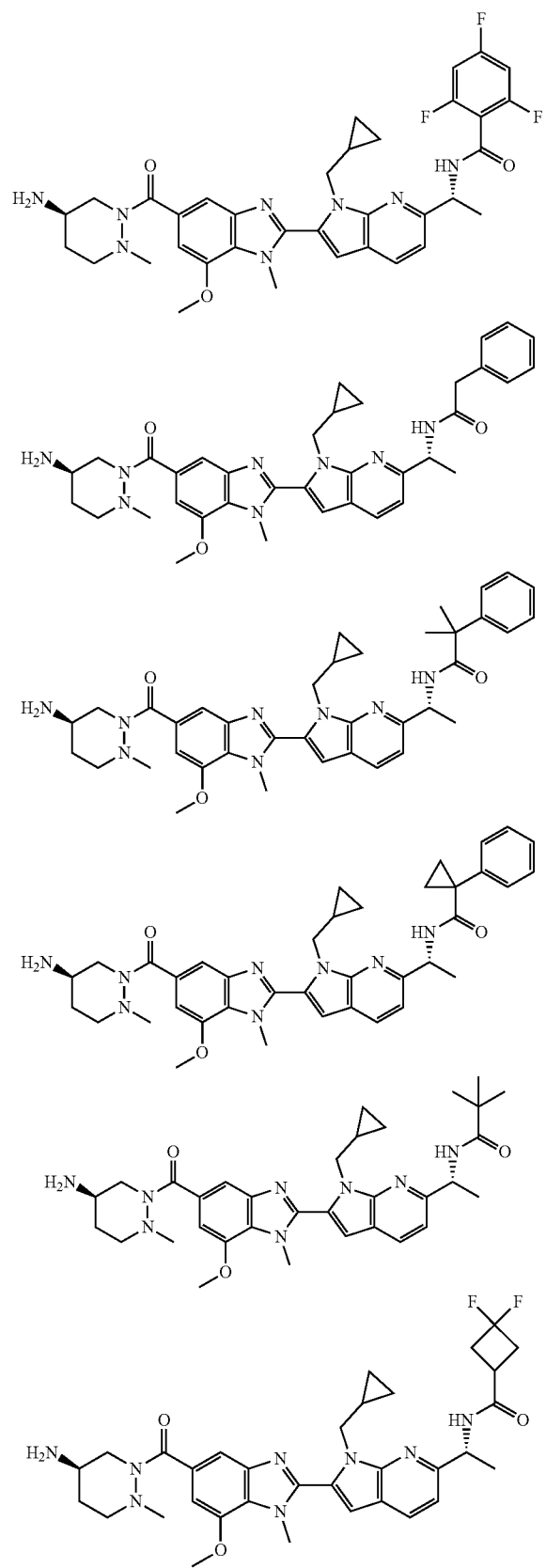
450
-continued
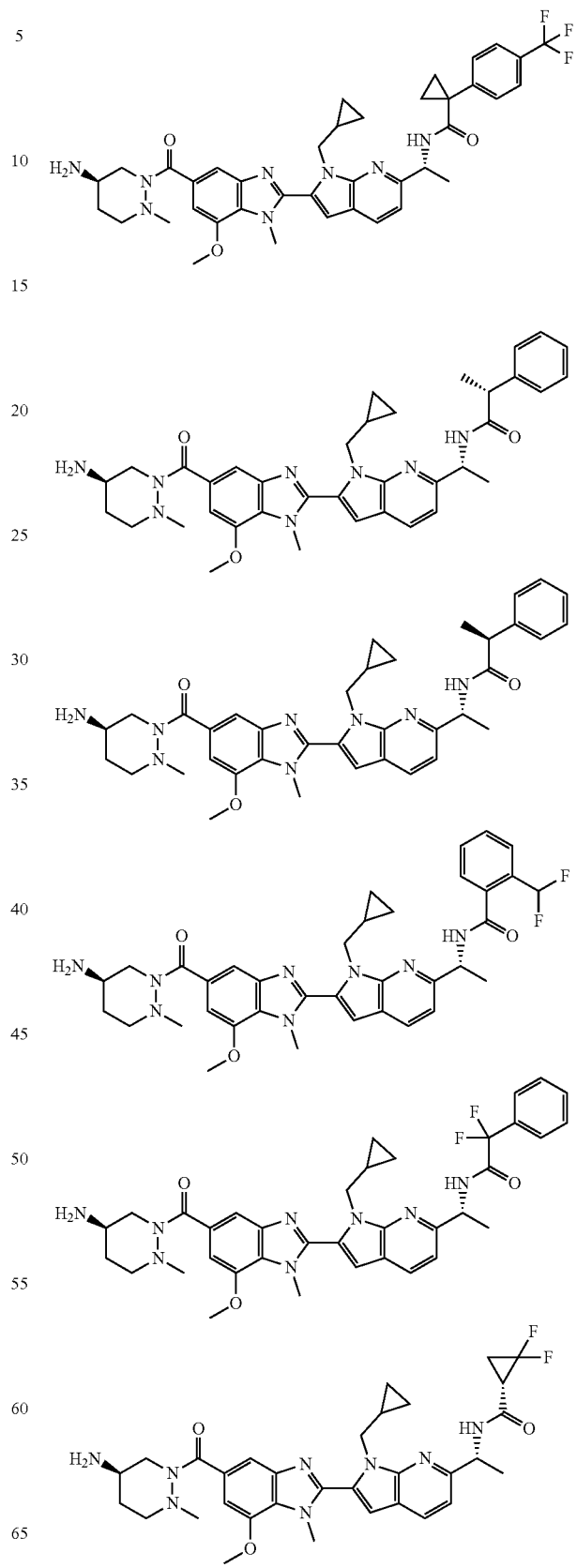

451
-continued
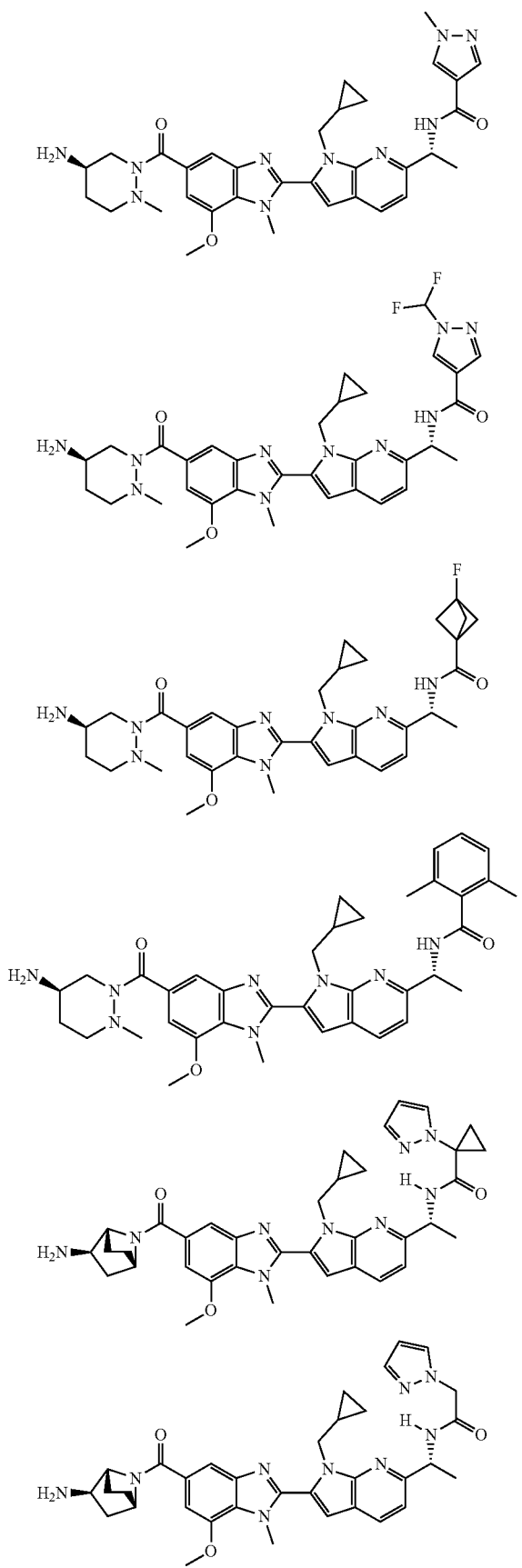
452
-continued
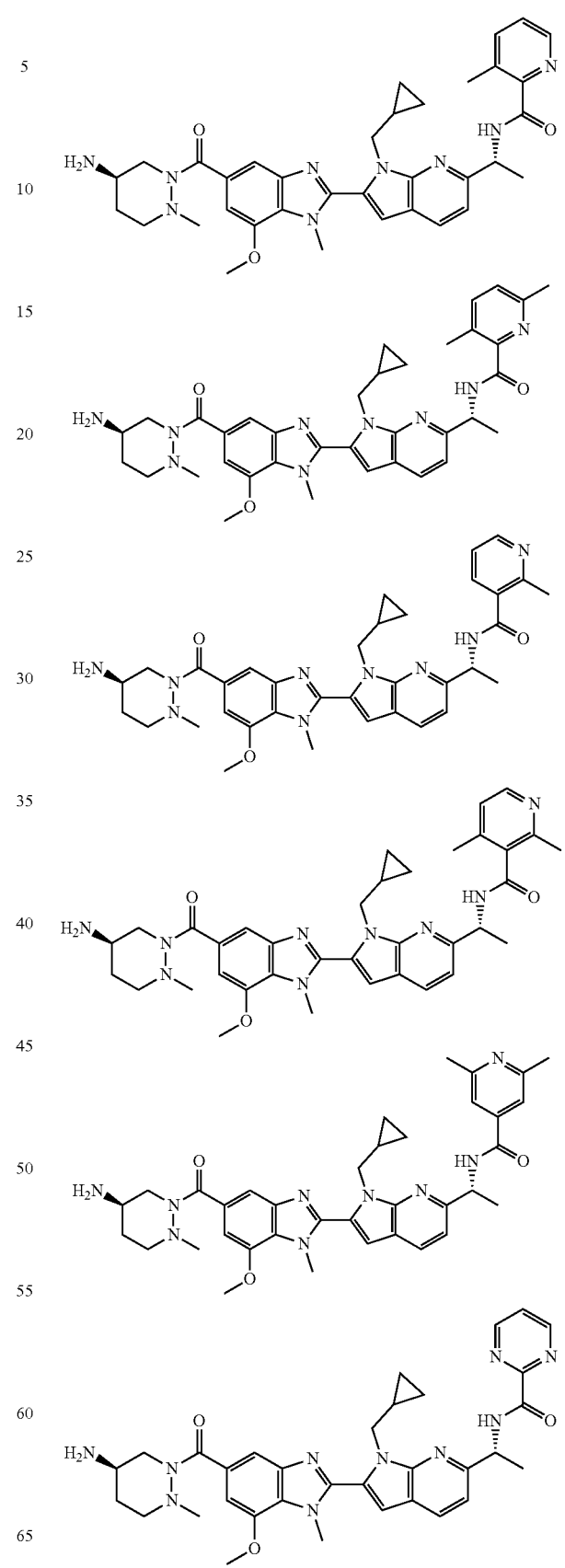

453
-continued
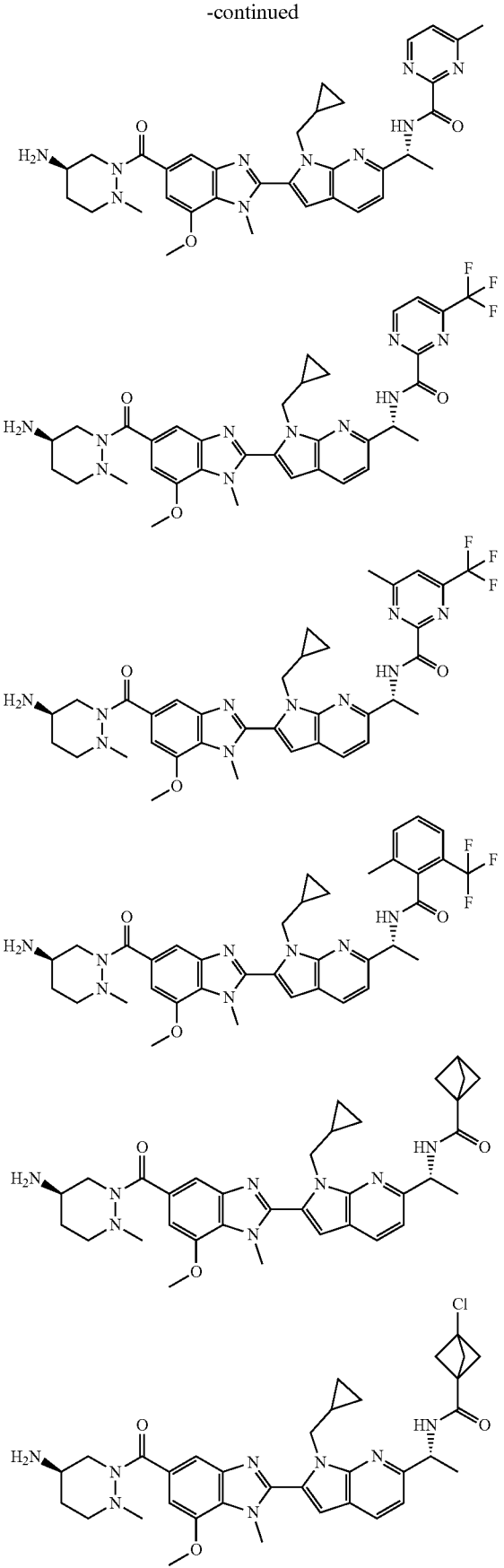
454
-continued
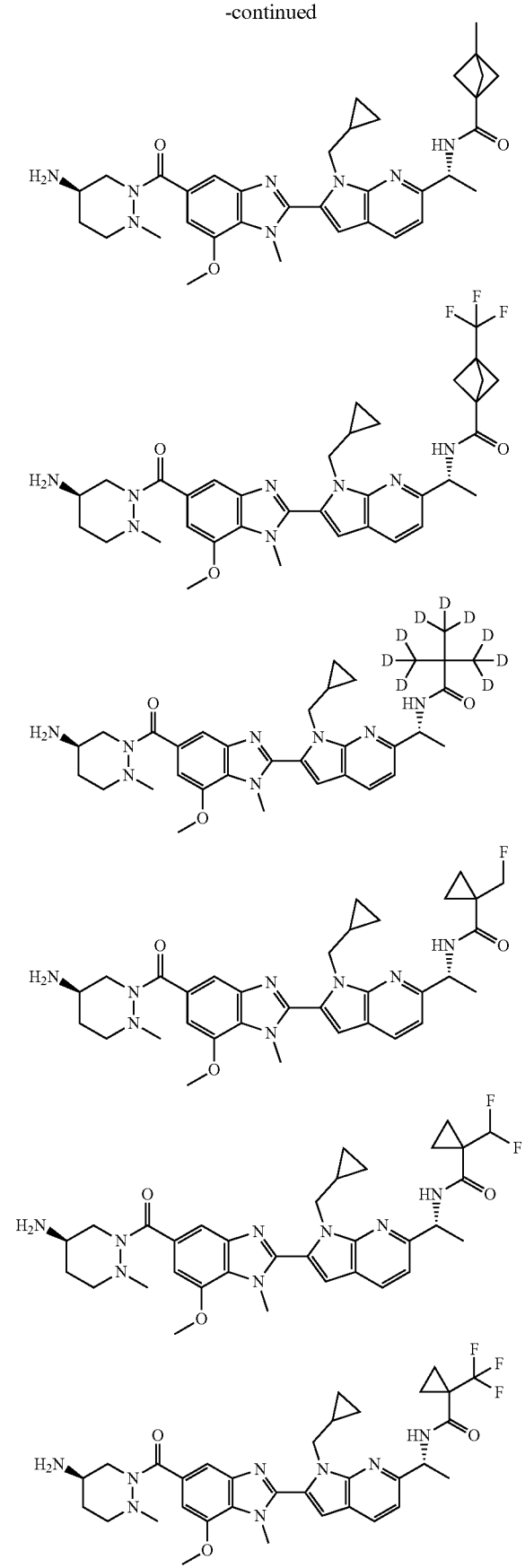

455
-continued
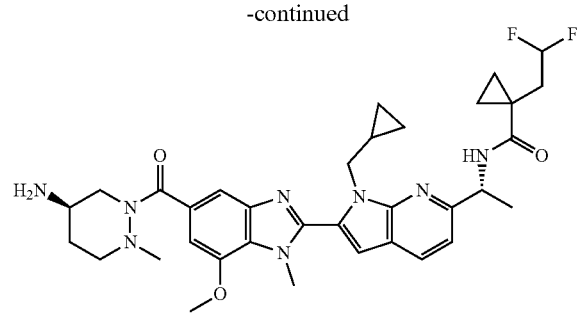
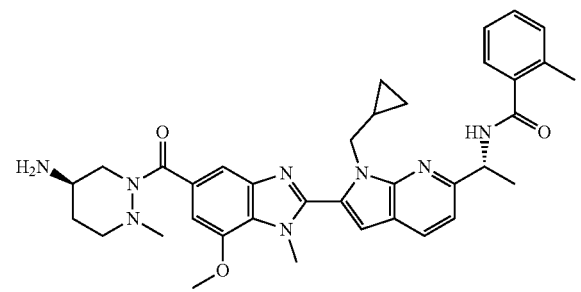
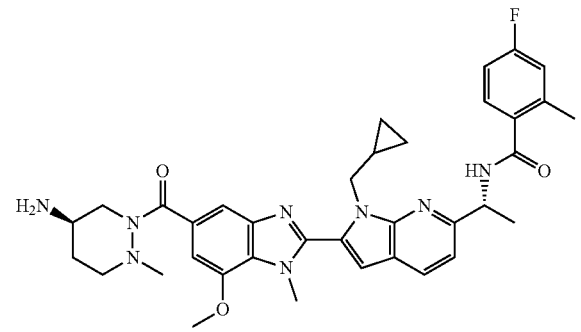
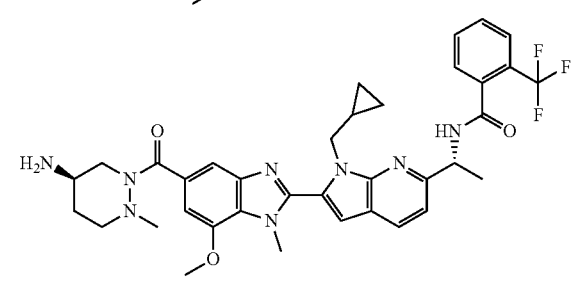
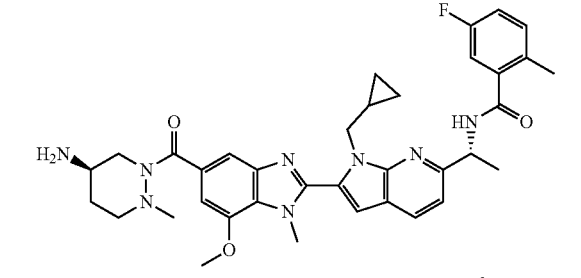
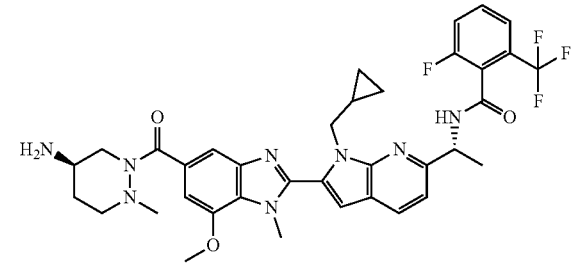
456
-continued
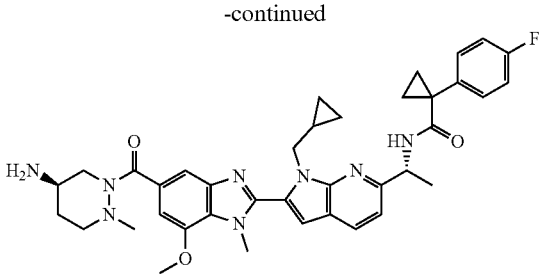
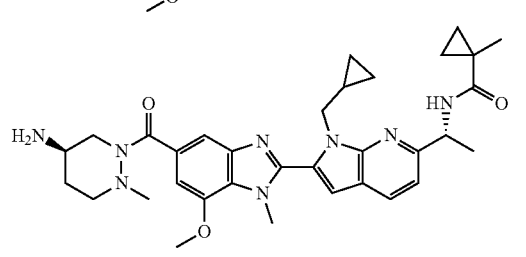
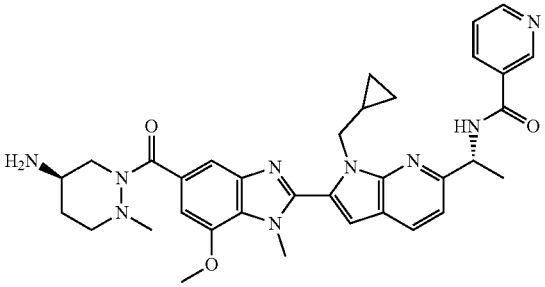
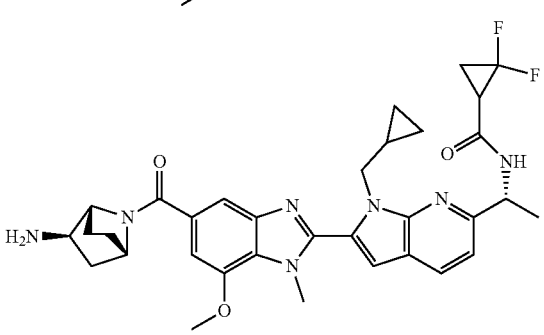
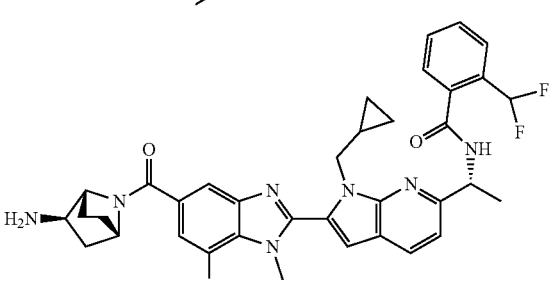
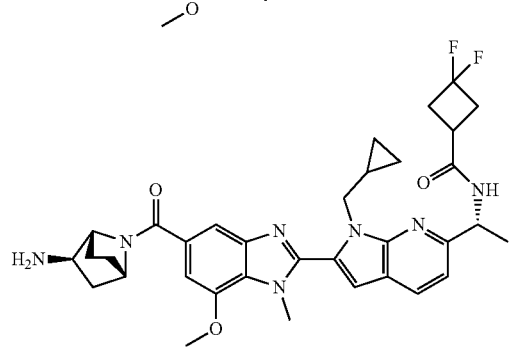

457
-continued
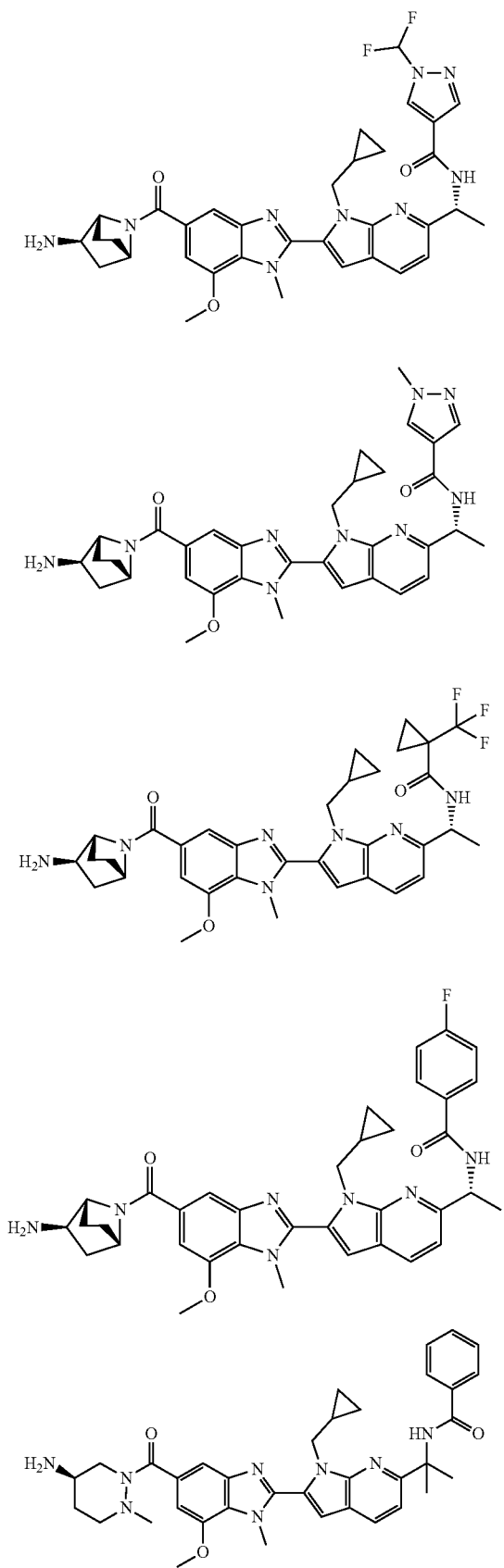
458
-continued
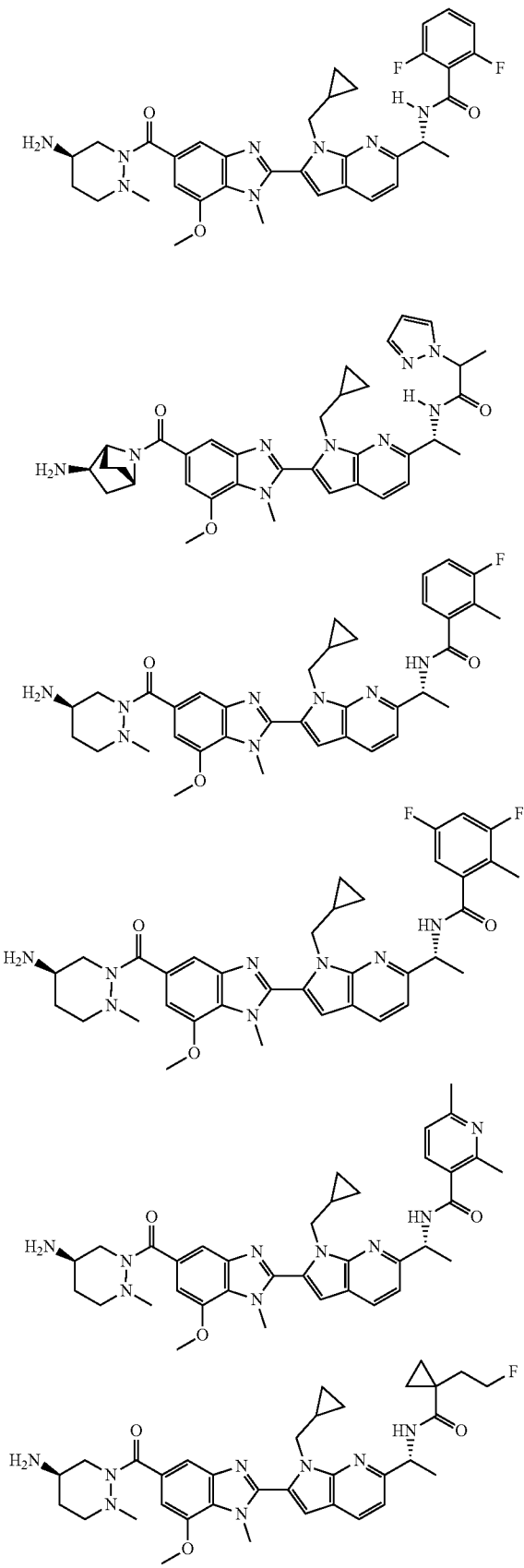

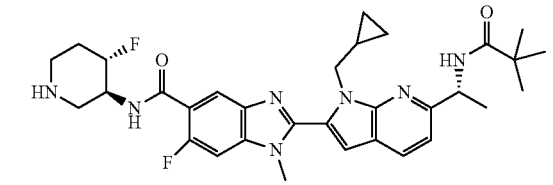
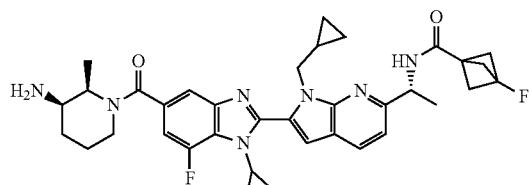
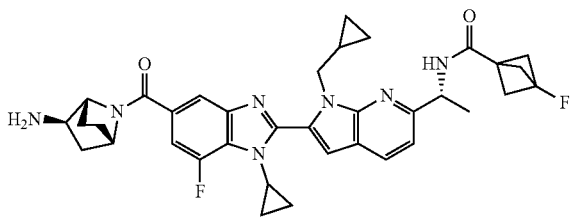
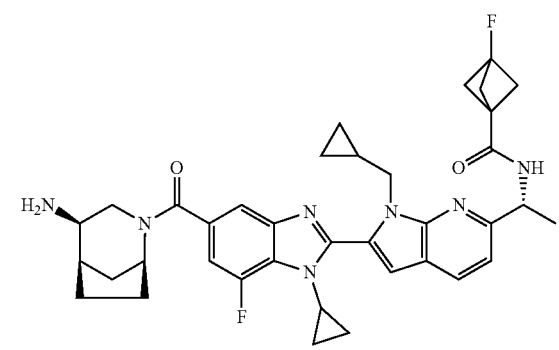
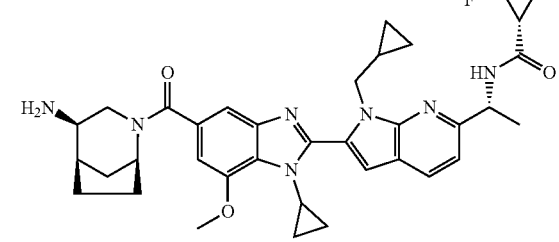
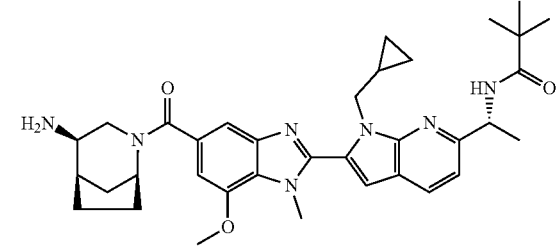
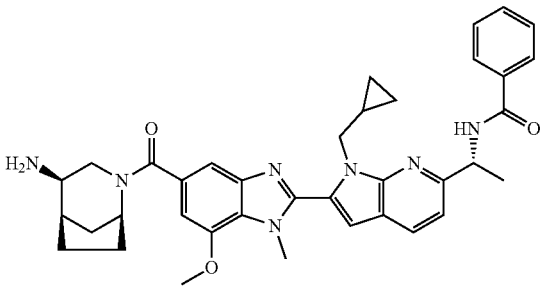
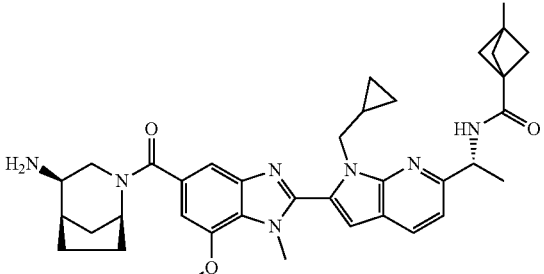
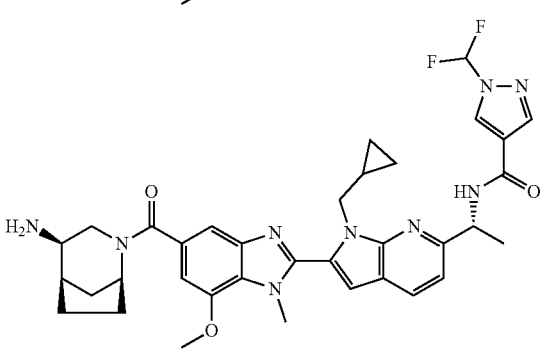
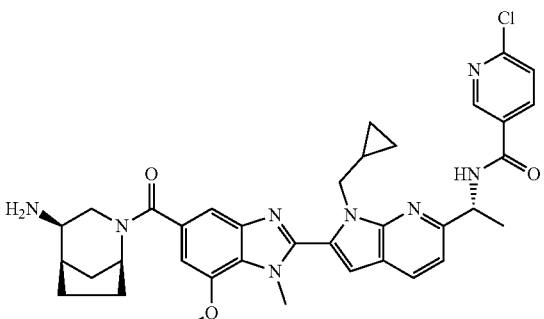
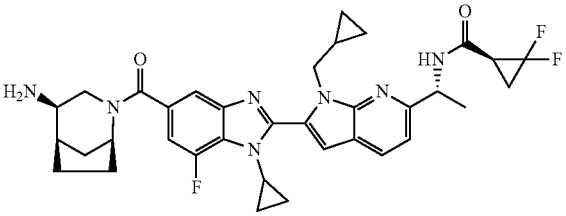
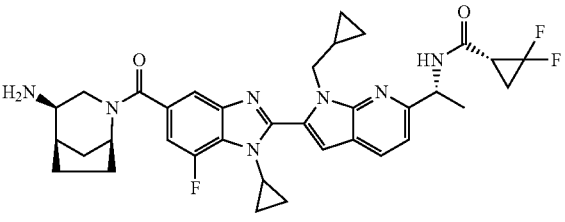

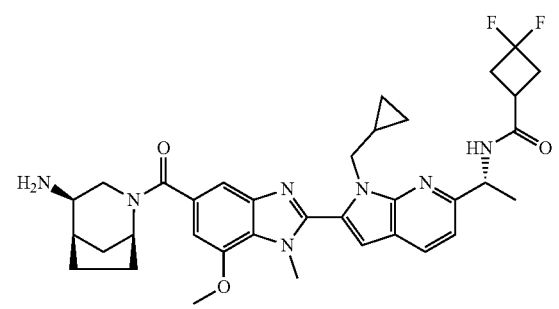
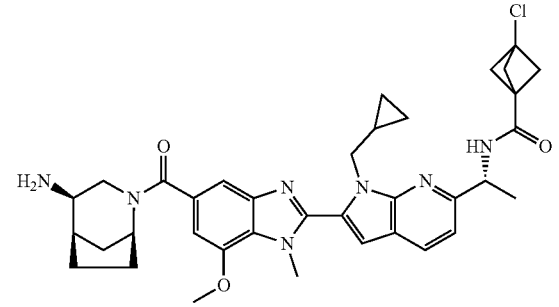
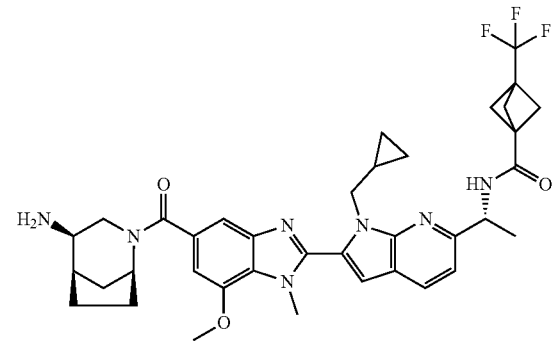
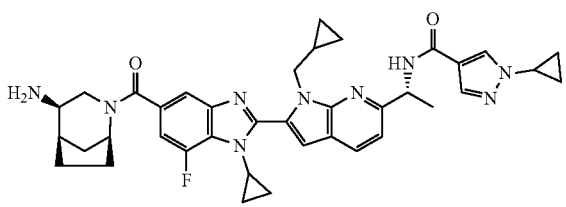
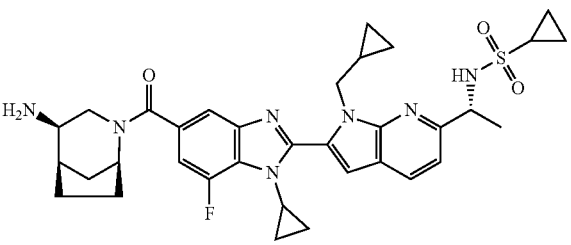
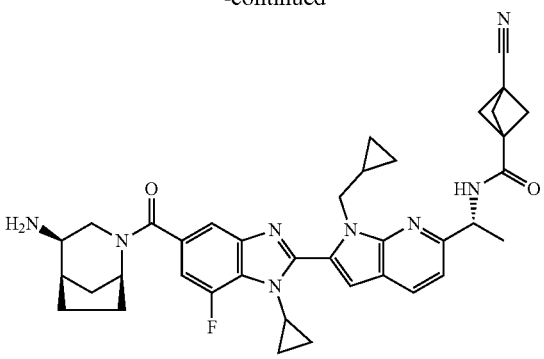
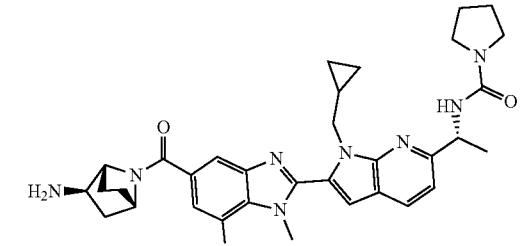
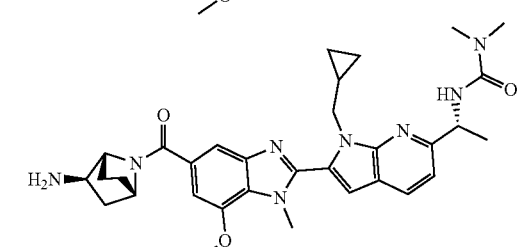
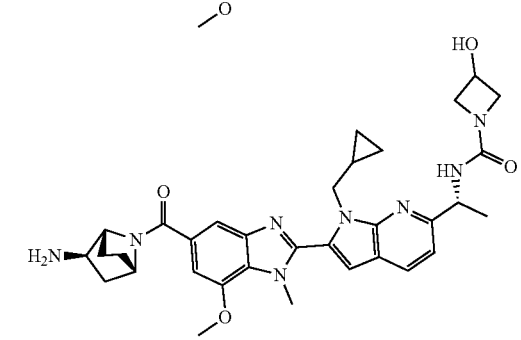
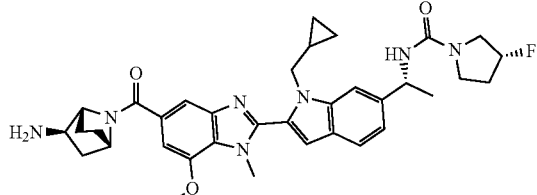
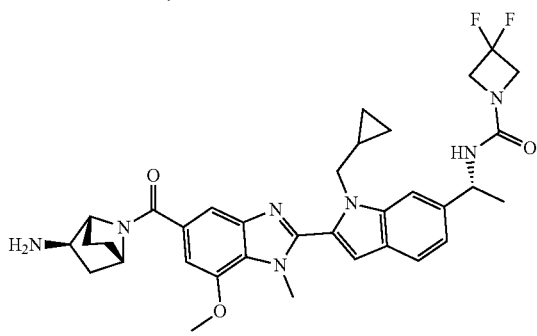

463
-continued
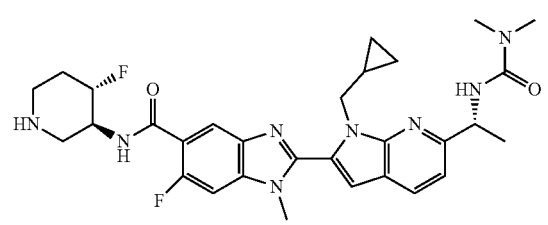
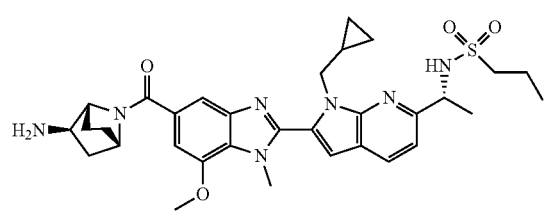
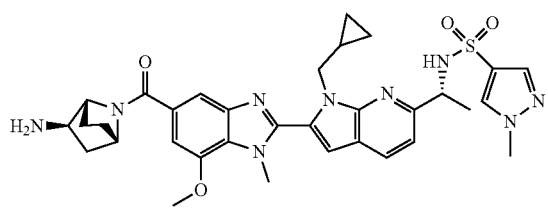
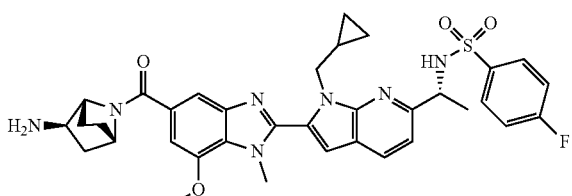
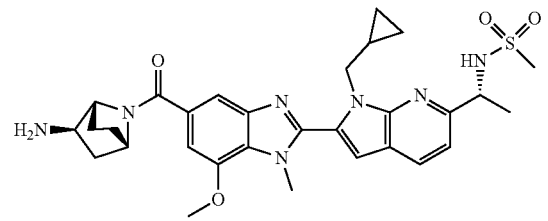
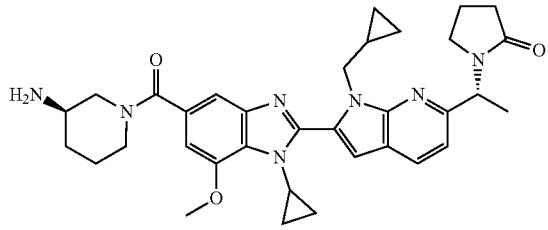
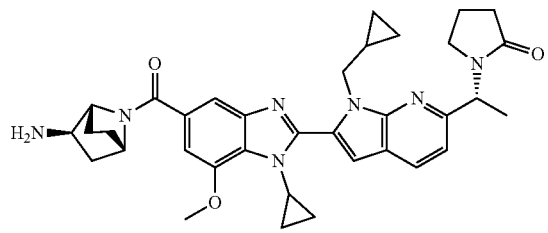
464
-continued
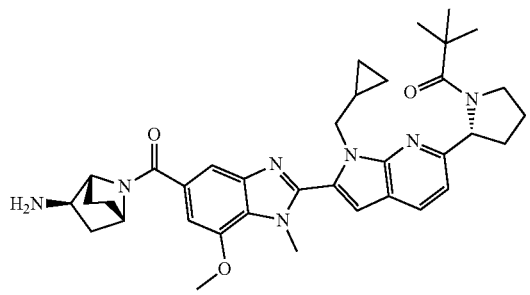
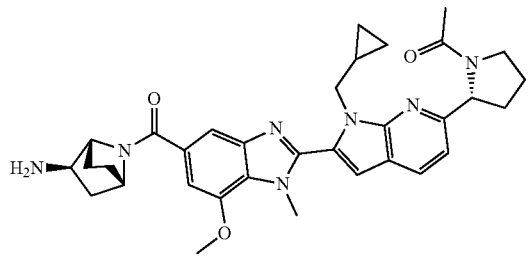
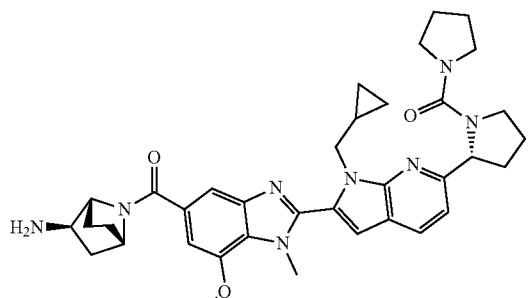
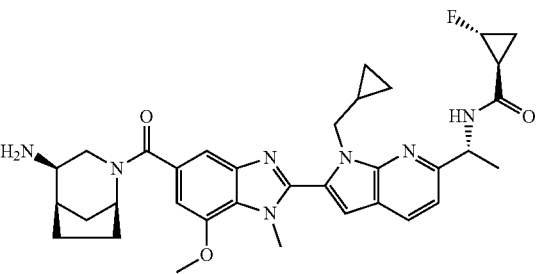
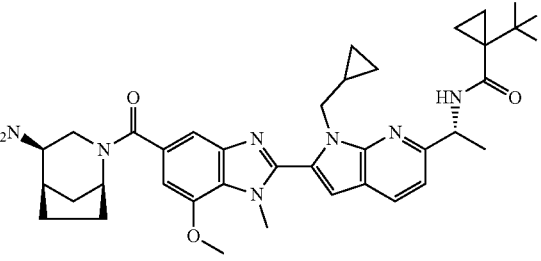
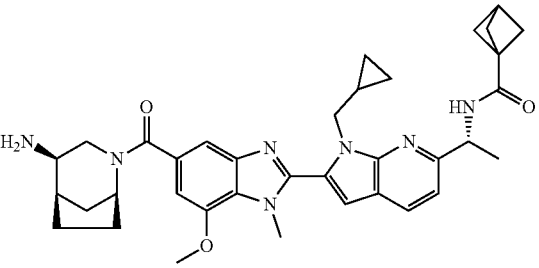

465
-continued
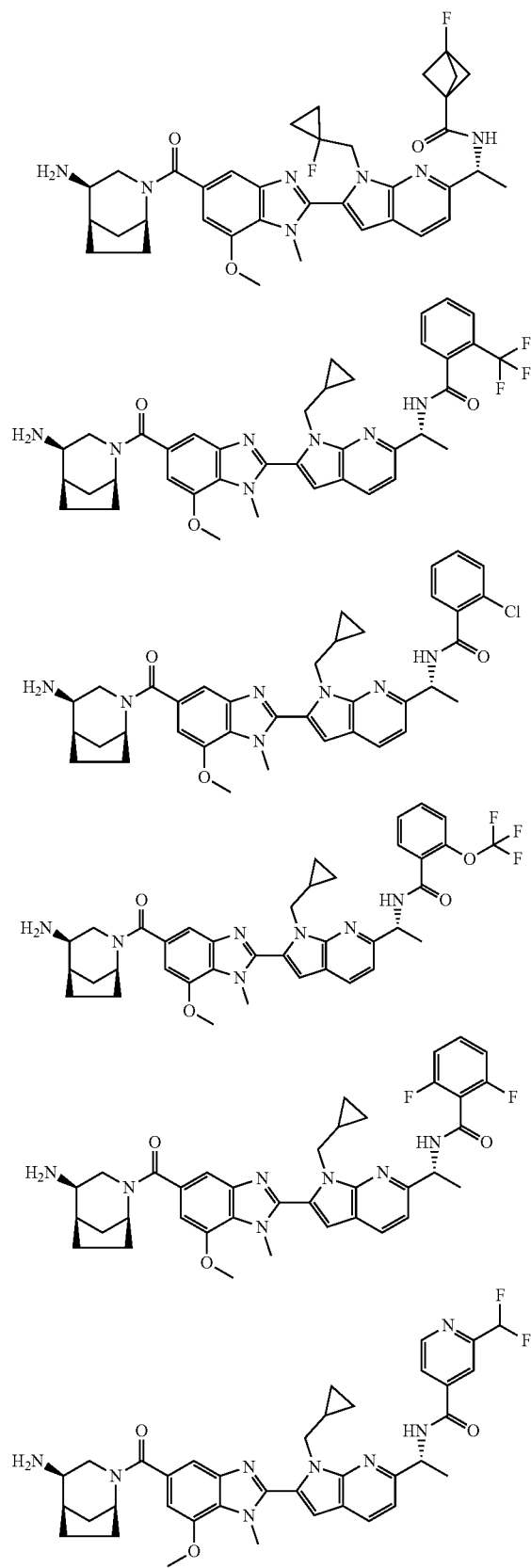
466
-continued
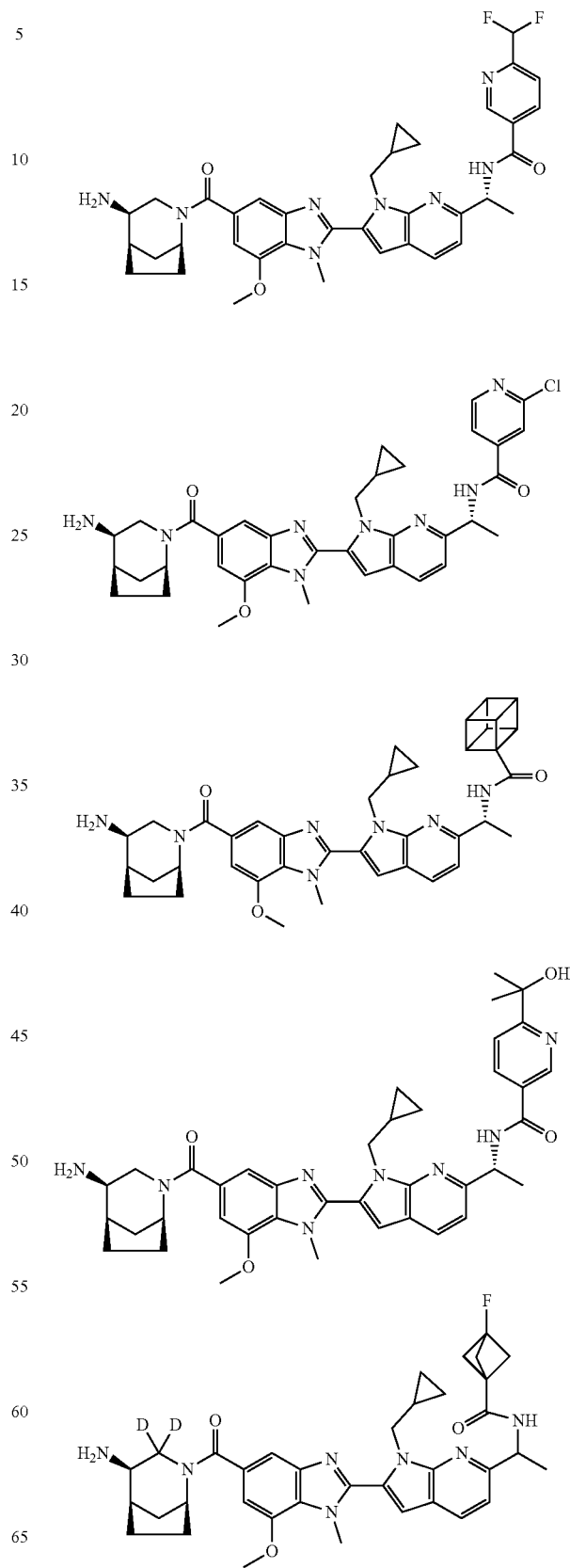

467
-continued
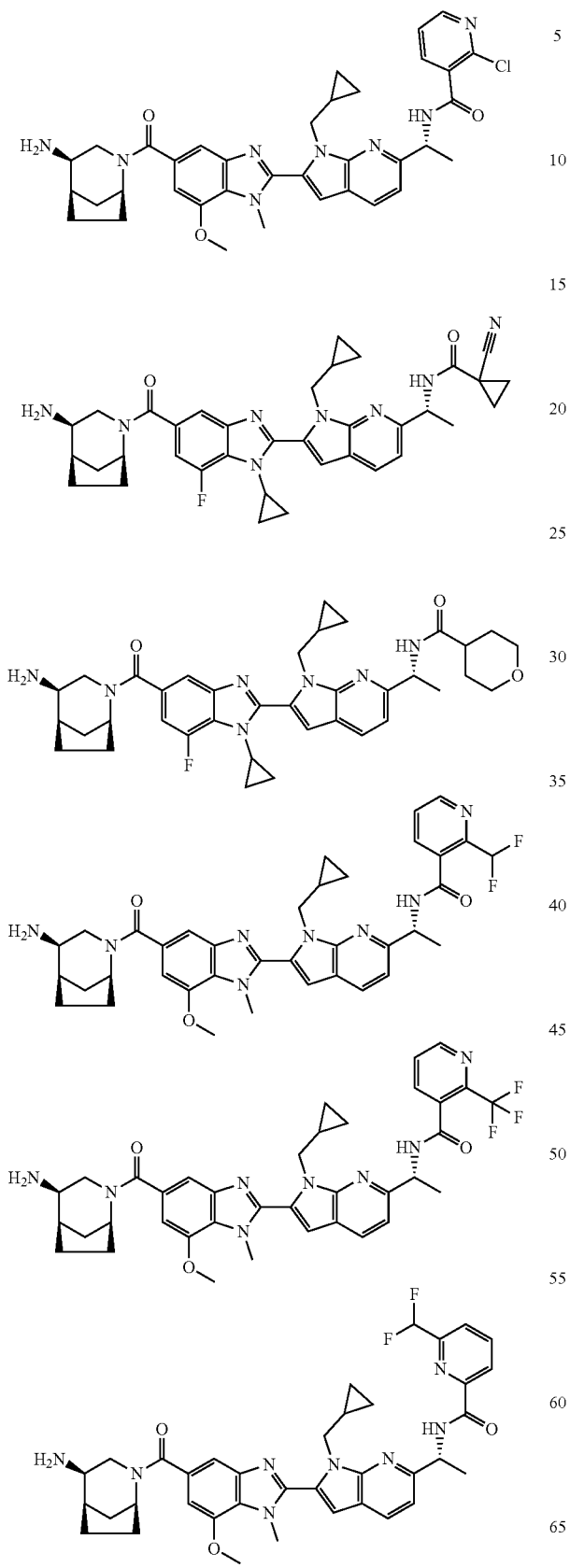
468
-continued
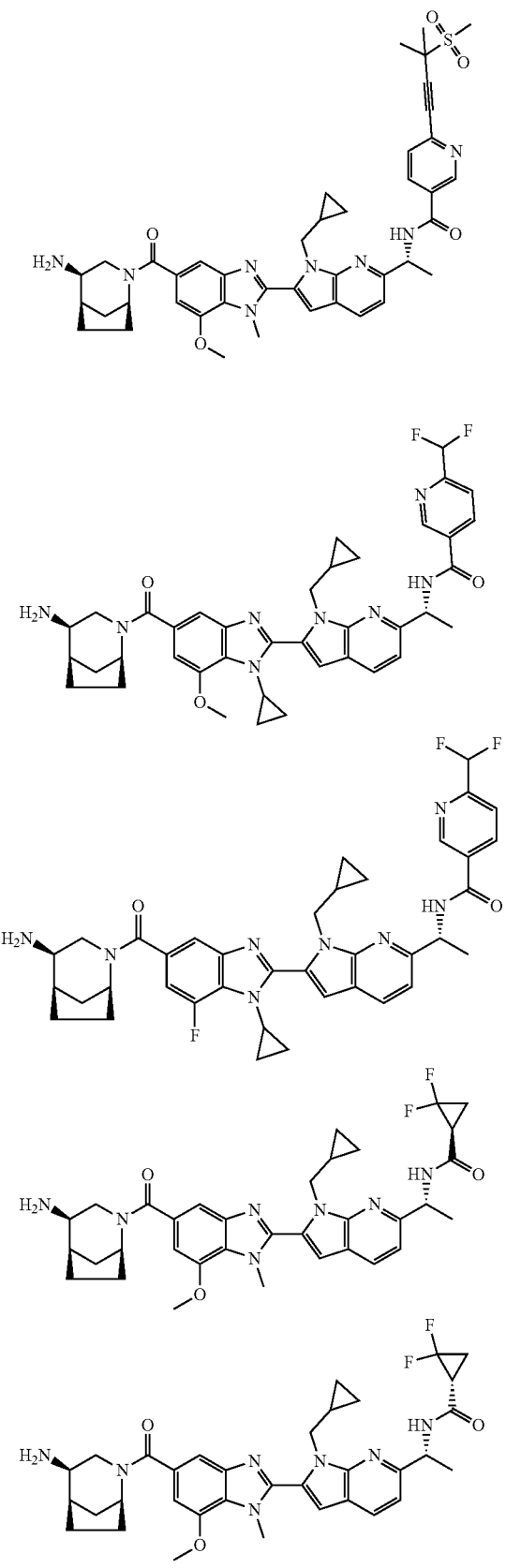

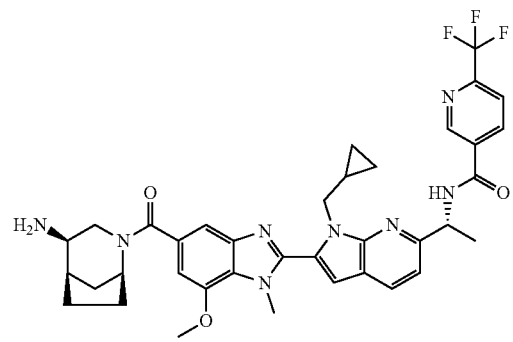
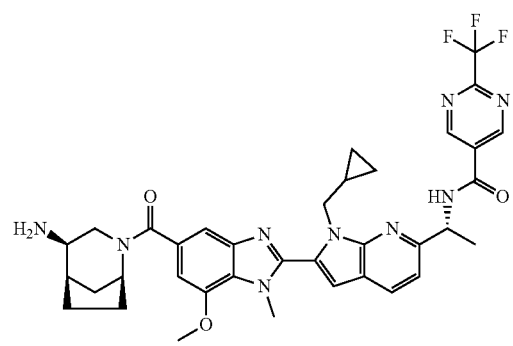
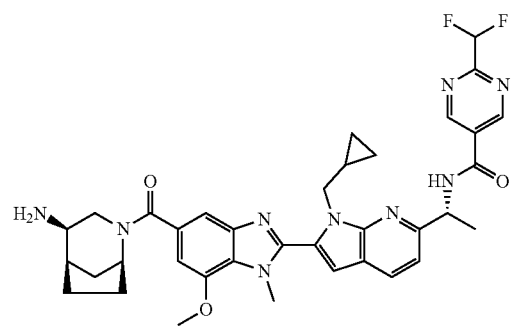
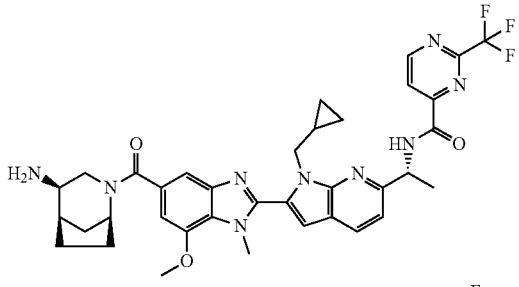
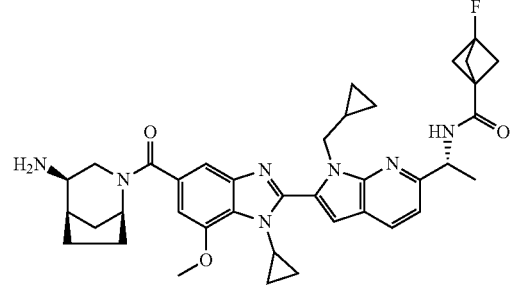
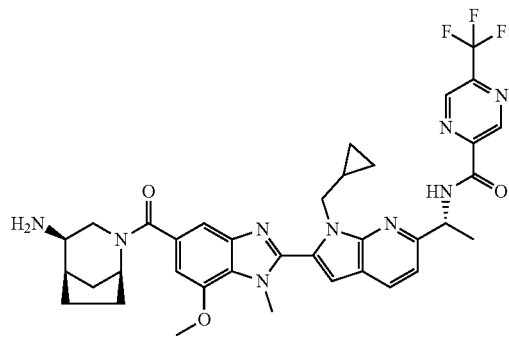
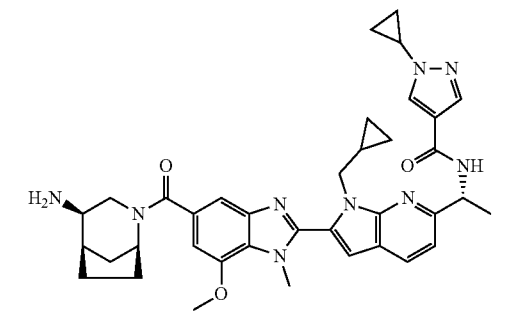
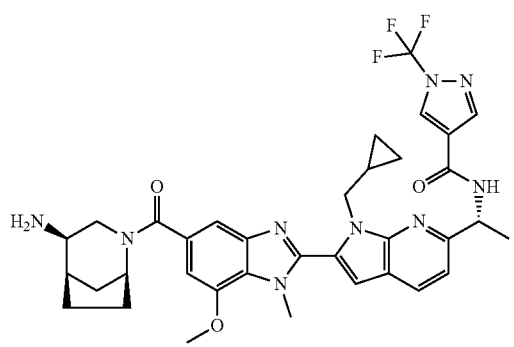
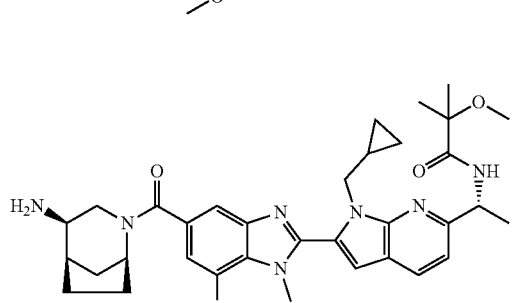

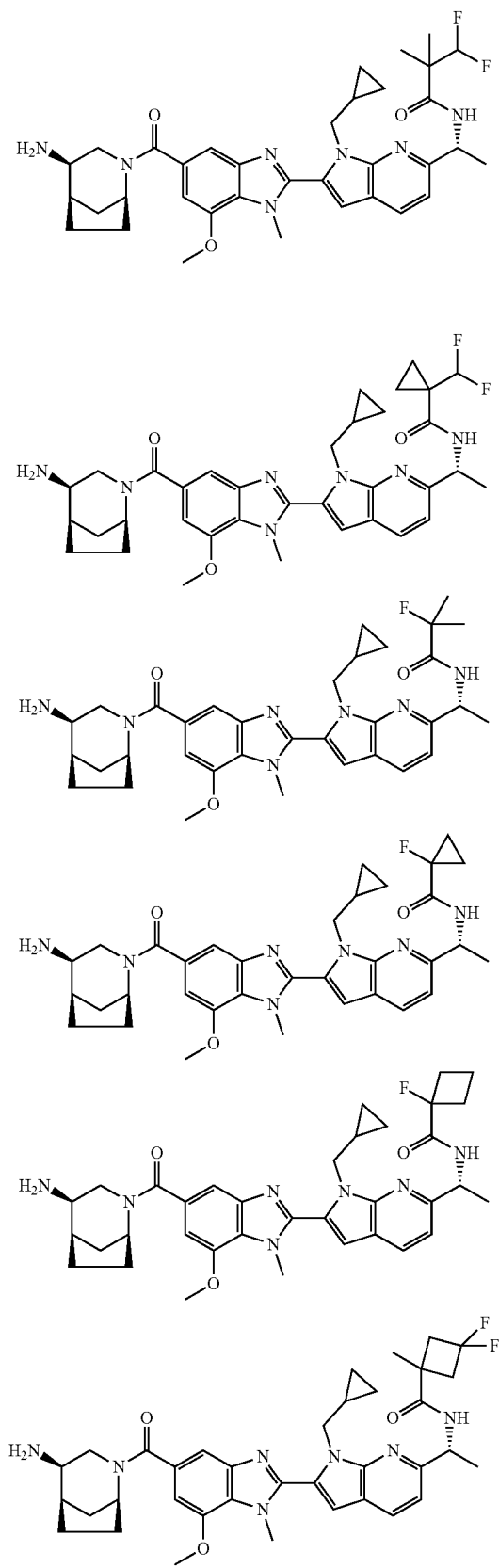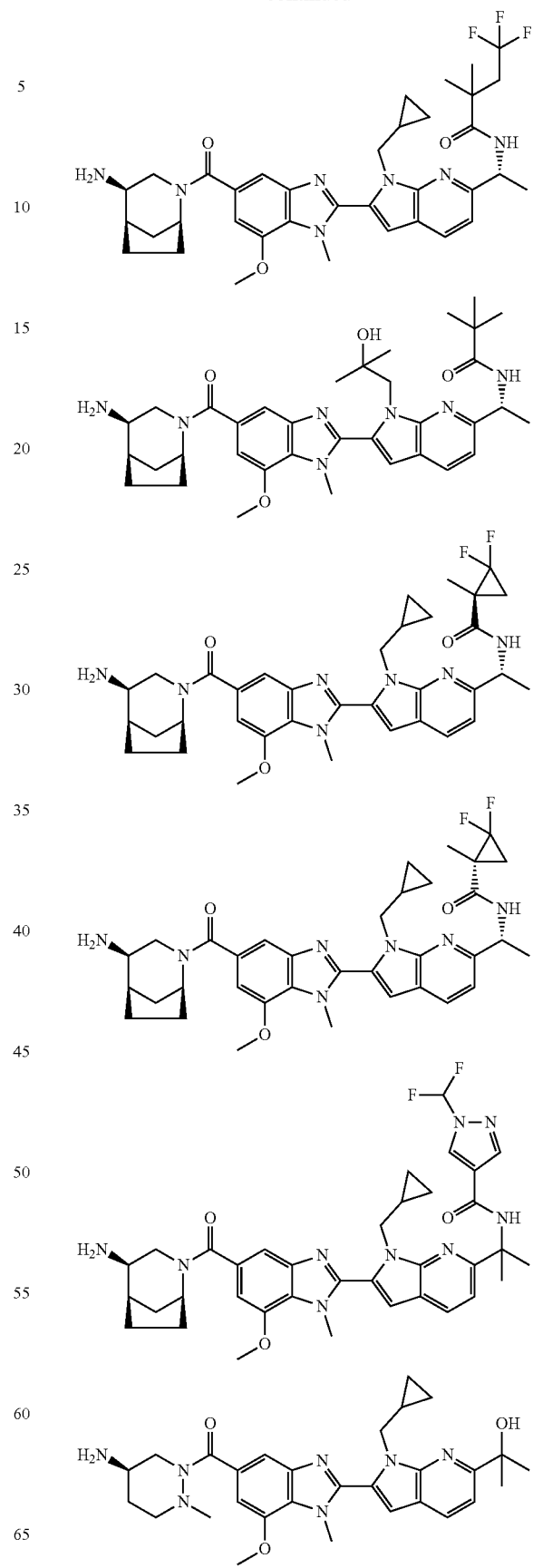

473
-continued
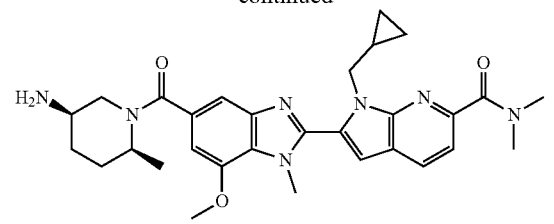
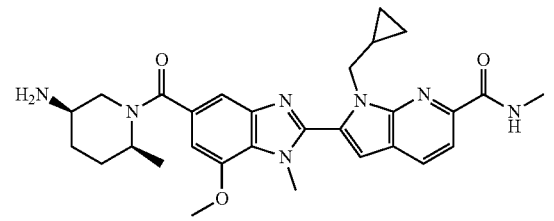
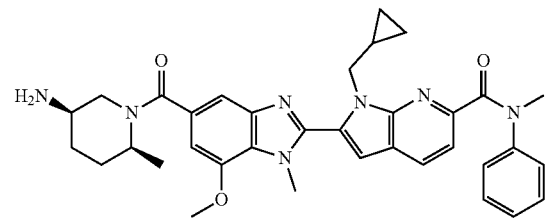
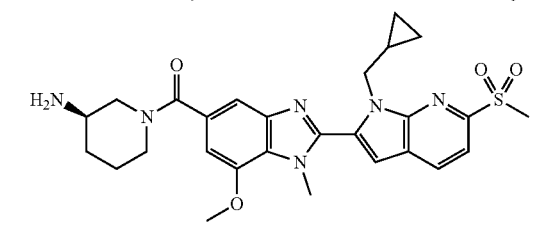
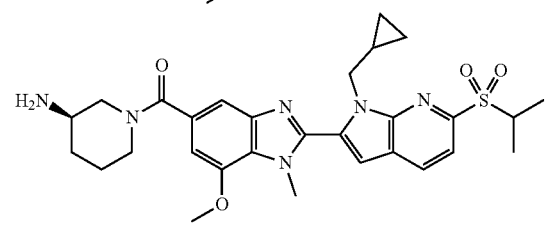
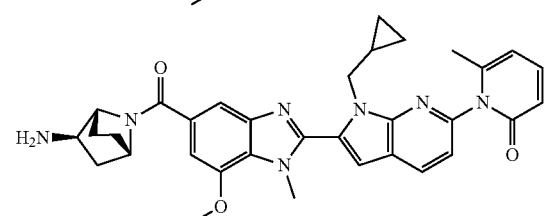
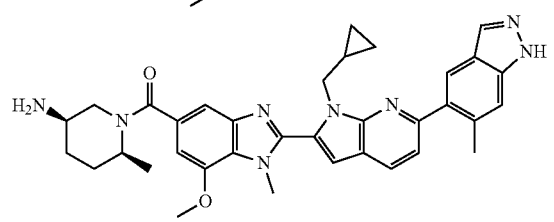
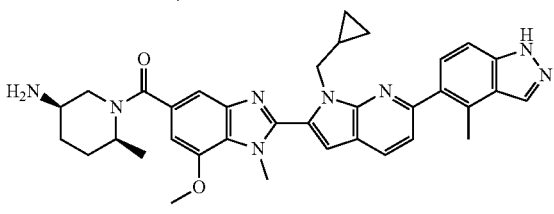
474
-continued
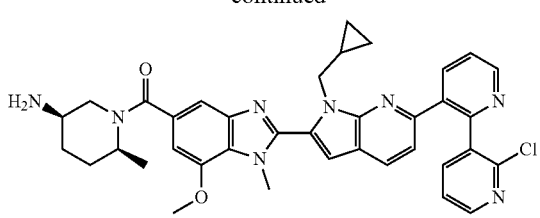
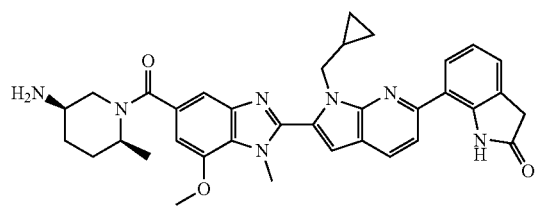
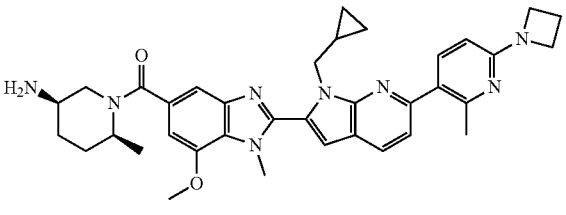
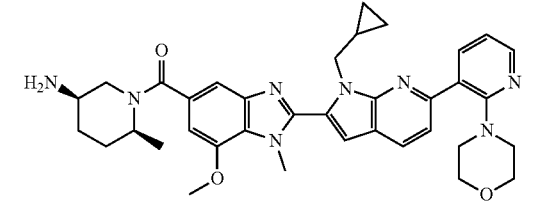
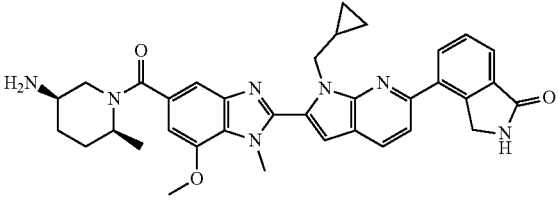
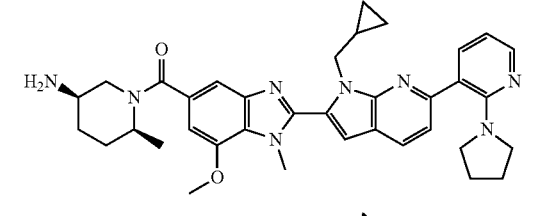
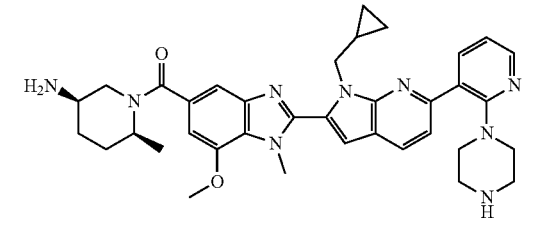
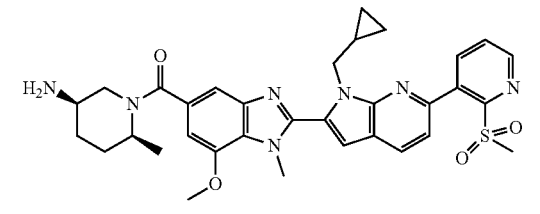

475
-continued
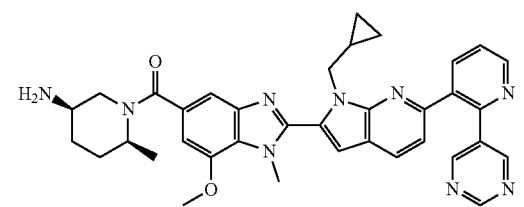
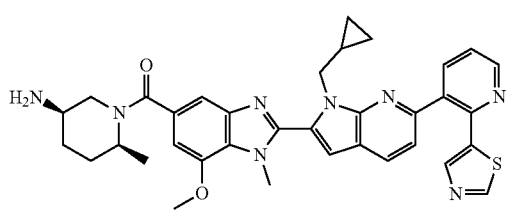
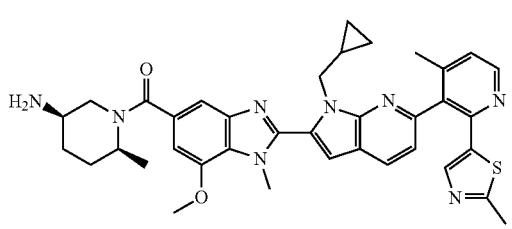
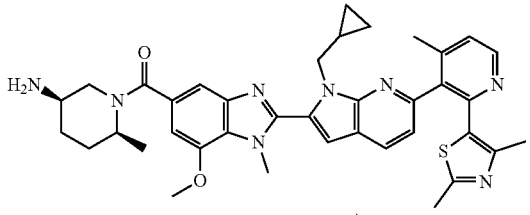
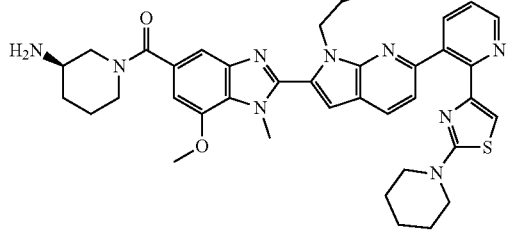
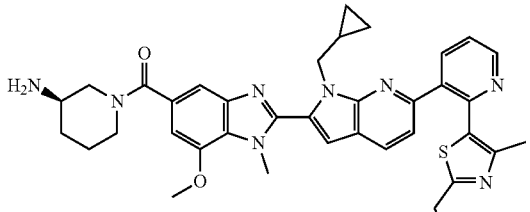
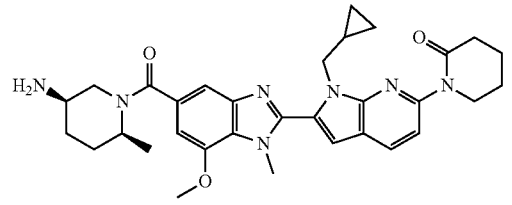
476
-continued
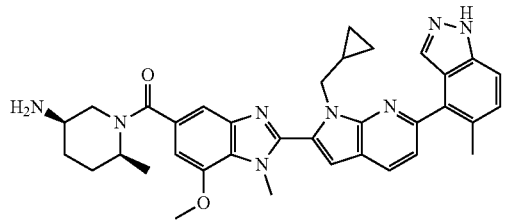
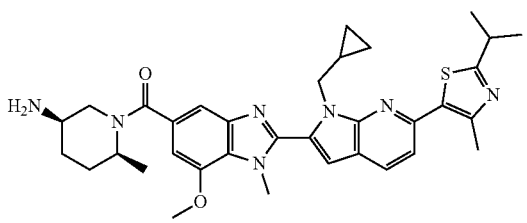
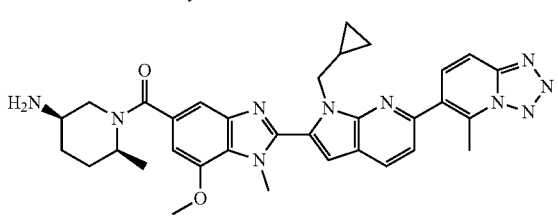
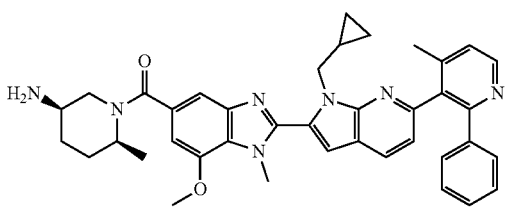
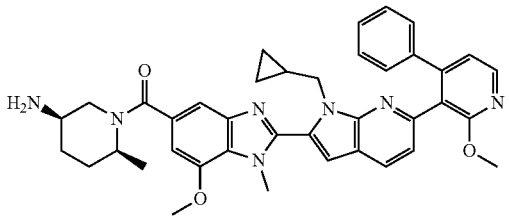
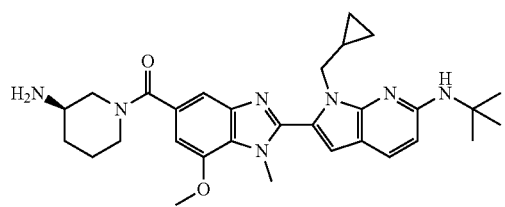
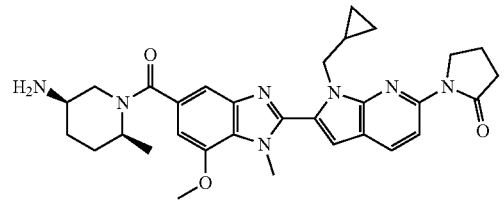
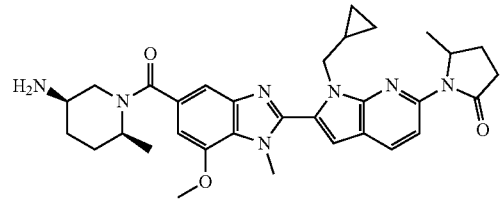

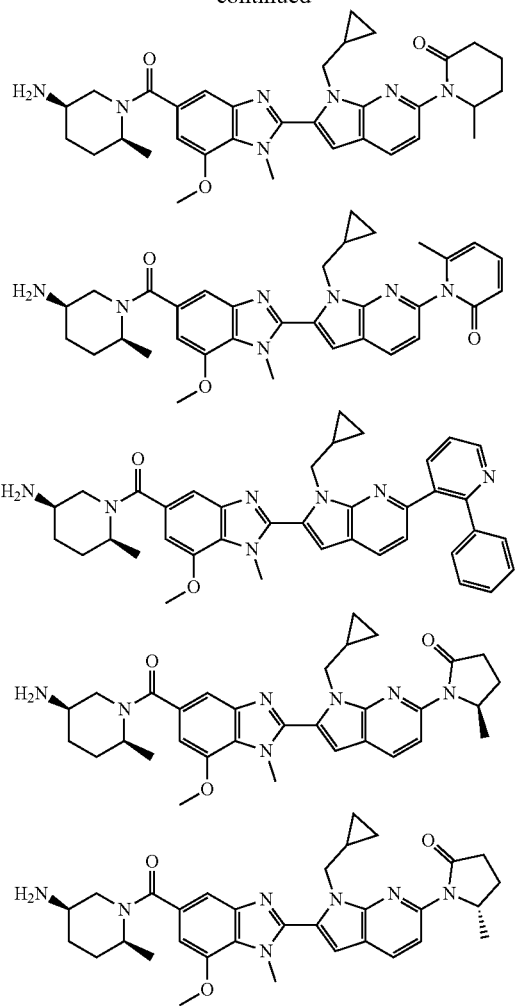

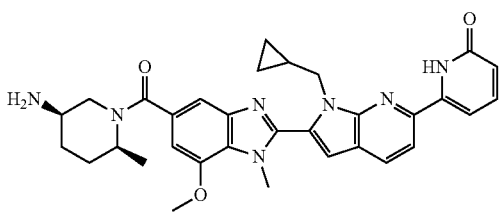

or a pharmaceutically acceptable salt thereof.

17. A pharmaceutical composition comprising a compound according to claim 1 or a pharmaceutically acceptable salt thereof, and at least one pharmaceutically acceptable excipient.

18. A method for inhibiting peptidylarginine deiminase type 4 (PAD4), comprising administering a therapeutically effective amount of a compound of claim 1 or a pharmaceutically acceptable salt thereof, to a patient in need thereof.

19. A method of treating a disease or disorder mediated by peptidylarginine deiminase type 4 (PAD4), comprising administering a therapeutically effective amount of a compound of claim 1 or a pharmaceutically acceptable salt thereof, to a patient in need thereof.

20. A kit for treating rheumatoid arthritis or a disease or condition that is amenable to treatment by inhibiting peptidylarginine deiminase type 4 (PAD4) in a patient in need thereof, comprising:

a) a compound according to claim 1, or a pharmaceutically acceptable salt thereof;

b) an additional therapeutic agent; and optionally c) a label or instructions for use.

* * * * *